(12) United States Patent
Sugimoto et al.

(10) Patent No.: US 8,293,715 B2
(45) Date of Patent: Oct. 23, 2012

(54) 10A-AZALIDE COMPOUND CROSSLINKED AT 10A- AND 12-POSITIONS

(75) Inventors: Tomohiro Sugimoto, Saitama (JP); Kanako Yamamoto, Saitama (JP); Jun Kurosaka, Saitama (JP); Naoki Sasamoto, Saitama (JP); Masato Kashimura, Saitama (JP); Tomoaki Miura, Kanagawa (JP); Kenichi Kanemoto, Kanagawa (JP); Tomohiro Ozawa, Saitama (JP); Ken Chikauchi, Kanagawa (JP); Eiki Shitara, Kanagawa (JP)

(73) Assignees: Taisho Pharmaceutical Co., Ltd., Tokyo (JP); Meiji Seika Pharma Co., Ltd., Tokyo (JP)

(*) Notice: Subject to any disclaimer, the term of this patent is extended or adjusted under 35 U.S.C. 154(b) by 180 days.

(21) Appl. No.: 12/671,813

(22) PCT Filed: Aug. 6, 2008

(86) PCT No.: PCT/JP2008/002129
§ 371 (c)(1),
(2), (4) Date: May 10, 2010

(87) PCT Pub. No.: WO2009/019868
PCT Pub. Date: Feb. 12, 2009

(65) Prior Publication Data
US 2011/0237784 A1   Sep. 29, 2011

(30) Foreign Application Priority Data
Aug. 6, 2007 (JP) .................. 2007-203769

(51) Int. Cl.
*A61K 31/70* (2006.01)
*C07H 17/08* (2006.01)
(52) U.S. Cl. .......................... 514/29; 536/7.4
(58) Field of Classification Search ............. 536/7.4
See application file for complete search history.

(56) References Cited

U.S. PATENT DOCUMENTS

| 4,474,768 A | 10/1984 | Bright |
| 4,517,359 A | 5/1985 | Kobrehel et al. |
| 5,523,399 A | 6/1996 | Asaka et al. |
| 5,635,485 A | 6/1997 | Agouridas et al. |
| 6,100,404 A | 8/2000 | Agouridas et al. |
| 6,191,118 B1 | 2/2001 | Asaka et al. |
| 6,420,535 B1 | 7/2002 | Phan et al. |
| 2006/0142214 A1 | 6/2006 | Or et al. |
| 2007/0042974 A1 | 2/2007 | Miura et al. |
| 2009/0281292 A1 | 11/2009 | Sugimoto et al. |
| 2011/0152239 A1 | 6/2011 | Sugimoto et al. |

FOREIGN PATENT DOCUMENTS

| CA | 1 661 904 A1 | 5/2006 |
| EP | 0 508 726 A1 | 10/1992 |
| EP | 0 680 967 A1 | 11/1995 |
| JP | 2002-530422 A | 9/2002 |
| WO | 98/09978 A1 | 3/1998 |
| WO | 00/31097 A1 | 6/2000 |
| WO | 02/32919 A2 | 4/2002 |
| WO | 03/014136 A1 | 2/2003 |
| WO | 2005/019238 A1 | 3/2005 |
| WO | 2007/091393 A1 | 8/2007 |
| WO | 2009/139181 | 11/2009 |

OTHER PUBLICATIONS

International Search Report that issued with respect to PCT/JP2008/002129, mailed Oct. 28, 2008.
International Preliminary Report on Patentability that issued with respect to PCT/JP2008/002129, mailed Mar. 4, 2010.
Extended European Search Report issued with respect to patent family member EP 08790393.6, dated Jul. 23, 2012.

*Primary Examiner* — Elli Peselev
(74) *Attorney, Agent, or Firm* — Greenblum & Bernstein, P.L.C.

(57) ABSTRACT

A novel 10a-azalide compound crosslinked at the 10a- and 12-positions, which is represented by the following formula, and is effective on even *Hemophilus influenzae*, or erythromycin resistant bacteria (e.g., resistant pneumococci and streptococci).

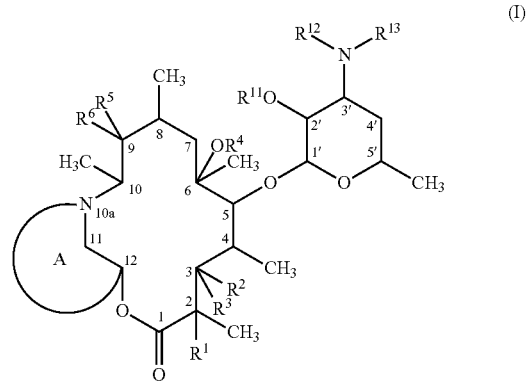

27 Claims, No Drawings

10A-AZALIDE COMPOUND CROSSLINKED AT 10A- AND 12-POSITIONS

TECHNICAL FIELD

The present invention relates to a novel antibiotic having an erythromycin-like structure. More specifically, the present invention relates to a novel 10a-azalide compound crosslinked at the 10a- and 12-positions.

BACKGROUND ART

Erythromycin A is an antibiotic which has been widely used as a therapeutic agent for infectious diseases caused by Gram-positive bacteria, mycoplasmas, and the like. However, due to decomposition by gastric acid, erythromycin has a drawback of inconstant pharmacokinetics. Therefore, derivatives of erythromycin having increased stability to acids were researched. As a result, macrolides having stable pharmacokinetics such as clarithromycin, azithromycin (Patent documents 1 and 2) and roxithromycin have been developed. These macrolide agents have been applied in a therapeutic field of respiratory infectious diseases of ambulatory patients, and therefore, they are required to have a potent antibacterial activity especially against pneumococci, streptococci, and Hemophilus influenzae which are frequently isolated clinically. Furthermore, since macrolide-resistant pneumococci have been highly frequently isolated from community acquired pneumonia patients, it has been considered important that they are effective against the resistant pneumococci.

As a result of various researches in recent years, Agouridas et al. found HMR3647 (telithromycin, Patent document 3) in 1995, and successively Or et al. found ABT-773 (cethromycin, Patent document 4) in 1998 as macrolides that are effective both against erythromycin resistant pneumococci and erythromycin resistant streptococci. Then, 2-fluoroketolide (Patent document 5) of which efficacy was further enhanced was reported.

From a structural viewpoint, marketed macrolides are mainly classified into 14-membered or 15-membered ring type macrolides which are erythromycin derivatives, and 16-membered ring type macrolides which are leucomycin derivatives. Among the erythromycin derivatives, the 15-membered ring macrolides include azithromycin mentioned above. Azithromycin, unlike the other 14-membered ring macrolides, possesses a structural feature of having a nitrogen atom in the lactone ring, and therefore the macrolide is called azalide. Nomenclature of azalides is based on the position number of a carbon atom substituted with a nitrogen atom when the carbonyl group of the lactone is assumed to be in the 1-position. In the case of azithromycin mentioned above, since the nitrogen atom is introduced in the position of the ninth carbon atom from the carbonyl group, the compound is called 9a-azalide.

In addition to the 9a-azalides, 8a-azalides (Patent document 6) and 11a-azalides (Patent document 7) are known as examples of reported azalides obtainable by chemical conversion of 14-membered ring macrolides.

As for 10a-azalides, those derived from 16-membered ring macrolides as leucomycin derivatives have recently been reported (Patent document 8). However, no 10a-azalides derived from 14-membered ring macrolides have been reported. Although 10a-azalides are disclosed in Patent document 9, which was published after the priority date of the present international application (Aug. 6, 2007), this publication does not constitute a prior art of the present invention.

Patent document 1: U.S. Pat. No. 4,474,768
Patent document 2: U.S. Pat. No. 4,517,359
Patent document 3: EP680967
Patent document 4: WO98/09978
Patent document 5: WO02/32919
Patent document 6: EP508726
Patent document 7: WO2003/014136
Patent document 8: WO2005/019238
Patent document 9: WO2007/091393

DISCLOSURE OF THE INVENTION

Object to be Achieved by the Invention

An object of the present invention is to provide a compound having a novel structure which is effective against Hemophilus influenzae and erythromycin resistant bacteria (for example, resistant pneumococci and streptococci) as well as against conventional erythromycin sensitive bacteria.

Means for Achieving the Object

The inventors of the present invention conducted various researches on azalide compounds, and as a result, succeeded in synthesis of novel azalides derived from 14-membered ring macrolides.

More specifically, the inventors of the present invention used 14-membered ring macrolides as starting materials, and oxidized 11-oxo compounds, which were obtained by oxidative cleavage of the diol moieties in the 11- and 12-positions, to derive into carboxyl compounds. Then, they performed rearrangement reactions by using the carboxyl compounds as starting materials to synthesize compounds having 10-amino group which were not reported so far. Further, by performing partial structural conversion, then intramolecular cyclization and further macrocyclization of those compounds, or by successively forming two rings in the inverse order, they succeeded in providing 10a-azalide compounds crosslinked at the 10a- and 12-positions having a novel skeleton. Further, as a result of evaluation of antibacterial activity of these compounds, the inventors found that the 10a-azalide compounds crosslinked at the 10a- and 12-positions had activities superior to those of the erythromycin derivatives as the starting materials, and accomplished the present invention.

The present invention provides a 10a-azalide compound represented by the following formula (I)

[Formula 1]

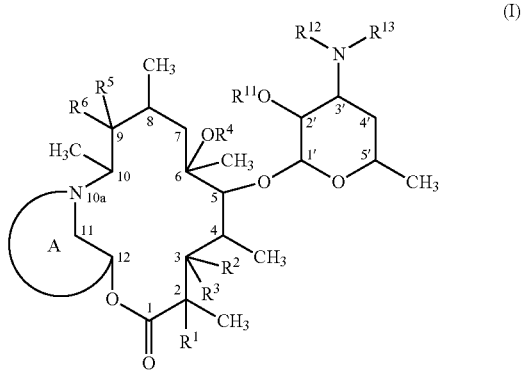

wherein, in the formula, $R^1$ is:
hydrogen atom, or
a halogen atom, $R^2$ and $R^3$ combine together to represent oxo group, or one of them is hydrogen atom, and the other is:
hydroxyl group,
a protected hydroxyl group,
a group represented by the formula $—X^{031}—R^{031}$, or a group represented by the formula (II)

[Formula 2]

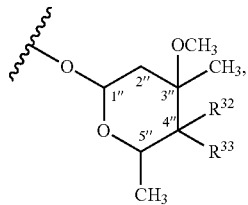

wherein $X^{031}$ is:
a group represented by the formula $—O—$,
a group represented by the formula $—OCO—$, or
a group represented by the formula $—OCON(R^{20})—$,
$R^{031}$ is
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or a biaryl group which may be substituted with 1 to 3 groups selected from the group A,
the group A is a group consisting of hydroxyl group, a halogen atom, a $C_{1-6}$ alkyl group, a $C_{1-6}$ haloalkyl group, a $C_{1-6}$ alkoxy group, a $C_{2-7}$ alkoxycarbonyl group, nitro group, a saturated heterocyclic group and a $C_{1-11}$ acyl group, one of $R^{32}$ and $R^{33}$ is hydrogen atom, and the other is:
hydrogen atom,
hydroxyl group,
a protected hydroxyl group,
amino group,
a protected amino group,
a group represented by the formula $—X^{331}—R^{331}$,
a group represented by the formula $—X^{331}$-$A^{331}$-$X^{332}—R^{331}$,
a group represented by the formula $—X^{331}$-$A^{331}$-$X^{332}$-$A^{332}$-$X^{333}—R^{331}$, or
a group represented by the formula $—X^{331}$-$A^{331}$-$X^{332}$-$A^{332}$-$X^{333}$-$A^{333}$-$X^{334}—R^{331}$,
wherein $X^{331}$ is:
a group represented by the formula $—O—$,
a group represented by the formula $—OCO—$,
a group represented by the formula $—OCON(R^{20})—$,
a group represented by the formula $—N(R^{20})—$, or
a group represented by the formula $—N(R^{20})CO—$,
$R^{331}$ is
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or
one of $R^{32}$ and $R^{33}$ is hydroxyl group, and the other is:
a group represented by the formula $—X^{335}—R^{332}$,
a group represented by the formula $—X^{335}$-$A^{334}$-$X^{336}—R^{332}$, or
a group represented by the formula $—X^{335}$-$A^{334}$-$X^{336}$-$A^{335}$-$X^{337}—R^{332}$,
wherein $X^{335}$ is:
a single bond,
a group represented by the formula $—CH_2N(R^{20})—$,
a group represented by the formula $—CH_2N(R^{20})CO—$,
a group represented by the formula $—CH_2N(R^{20})CO_2—$,
a group represented by the formula $—CH_2N(R^{20})CON(R^{21})—$,
a group represented by the formula $—CH_2O—$, or
a group represented by the formula $—CH_2S(O)_p—$,
$R^{332}$ is:
a $C_{1-6}$ alkyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 substituents selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A,
p is an integer of 0 to 2, or
$R^{32}$ and $R^{33}$ combine together to represent oxo group, oxime group,
a protected oxime group, a group represented by the formula (III):

[Formula 3]

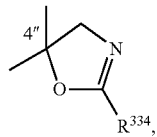
(III)

or
a group represented by the formula (IV):

[Formula 4]

(IV)

wherein $R^{334}$ is:
a group represented by the formula —OH, or
a group represented by the formula —SH, or one of $R^2$ and $R^3$ is hydrogen atom, and the other may combine with $R^4$ to represent a group represented by the formula (V):

[Formula 5]

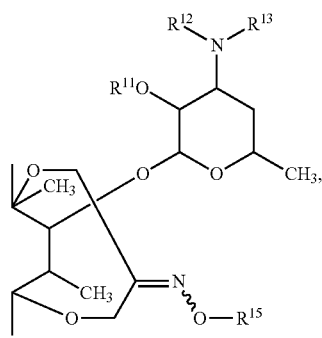
(V)

wherein $R^{15}$ is a $C_{1-6}$ alkyl group substituted with one biaryl group which may be substituted with 1 to 3 groups selected from the group A,
$R^4$ is:
hydrogen atom,
a group represented by the formula —$R^{041}$,
a group represented by the formula —$CH_2$—CH(OH)—$CH_2$—$NHR^{041}$, or
a group represented by the formula —$CH_2$—CH(OH)—$CH_2$—NH-$A^{041}$-$X^{042}$—$R^{041}$,
wherein $A^{041}$ is:
a divalent $C_{1-6}$ aliphatic hydrocarbon group, or
a divalent heterocyclic group, and
$R^{041}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or
$R^4$ may combine with $R^6$ to form cyclic carbonate [—$CO_2$—],
one of $R^5$ and $R^6$ is hydrogen atom, and the other is:
hydrogen atom,
hydroxyl group,
a protected hydroxyl group,
amino group,
a protected amino group,
a group represented by the formula —$X^{051}$—$R^{051}$, or
a group represented by the formula —$X^{051}$-$A^{051}$-$X^{052}$—$R^{051}$,
wherein $X^{051}$ is:
a group represented by the formula —O—,
a group represented by the formula —OCON($R^{22}$)—,
a group represented by the formula —N($R^{22}$)—, or
a group represented by the formula —N($R^{22}$)CO—, and
$R^{051}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or
$R^5$ and $R^6$ combine together to represent
oxo group,
oxime group,
a protected oxime group,
a group represented by the formula =N—$X^{053}$—$R^{052}$, or,
a group represented by the formula =N—$X^{053}$-$A^{052}$-$X^{054}$—$R^{052}$,
wherein $X^{053}$ is:
a group represented by the formula —O—, or
a group represented by the formula —CO—, and
$R^{052}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, the ring A is a group represented by the formula (VI):

[Formula 6]

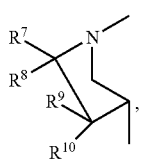

(VI)

or a group represented by the formula (VII):

[Formula 7]

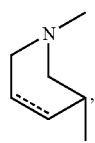

(VII)

wherein $R^7$ and $R^8$, which are the same or different, represent hydrogen atom, or a group represented by the formula —$X^{071}$—$R^{071}$, wherein $X^{071}$ is:

a single bond, a group represented by the formula -$A^{072}$-N($R^{27}$)—, a group represented by the formula -$A^{072}$-N($R^{27}$)CO—, a group represented by the formula -$A^{072}$-N($R^{27}$)CO$_2$—, a group represented by the formula -$A^{072}$-N($R^{27}$)CON($R^{28}$)—, a group represented by the formula -$A^{072}$-OCON($R^{27}$)—, a group represented by the formula -$A^{072}$-O—, a group represented by the formula -$A^{072}$-CO$_2$—, a group represented by the formula —CO$_2$—, a group represented by the formula -$A^{072}$-OCO—, a group represented by the formula -$A^{072}$-OCO$_2$—, a group represented by the formula -$A^{072}$-S(O)$_t$—, a group represented by the formula -$A^{072}$-N($R^{27}$)SO$_2$—, a group represented by the formula -$A^{072}$-SO$_2$N($R^{27}$)—, a group represented by the formula -$A^{072}$-CON($R^{27}$)—, or a group represented by the formula —CON($R^{27}$)—, $A^{072}$ is:

a divalent $C_{1-10}$ aliphatic hydrocarbon group, t is an integer of 0 to 2, and $R^{071}$ is:

a $C_{1-6}$ alkyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "amino group, hydroxyl group, an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, and $R^9$ and $R^{10}$, which are the same or different, represent hydrogen atom, hydroxyl group, a protected hydroxyl group, amino group, a protected amino group, azido group a halogen atom, a group represented by the formula —$X^{091}$—$R^{091}$, a group represented by the formula —$X^{091}$-$A^{091}$-$X^{092}$—$R^{091}$, a group represented by the formula —$X^{091}$-$A^{091}$-$X^{092}$-$A^{092}$-$X^{093}$—$R^{091}$, or a group represented by the formula —$X^{091}$-$A^{091}$-$X^{092}$-$A^{092}$-$X^{093}$-$A^{093}$-$X^{094}$—$R^{091}$, wherein $X^{091}$ is:

a single bond, a group represented by the formula -$A^{094}$-N($R^{23}$)—, a group represented by the formula -$A^{094}$-N($R^{23}$)CO—, a group represented by the formula -$A^{094}$-N($R^{23}$)CO$_2$—, a group represented by the formula -$A^{094}$-N($R^{23}$)CON($R^{24}$)—, a group represented by the formula -$A^{094}$-OCON($R^{23}$)—, a group represented by the formula -$A^{094}$-O—, a group represented by the formula -$A^{094}$-CO$_2$—, a group represented by the formula -$A^{094}$-OCO—, a group represented by the formula -$A^{094}$-OCO$_2$—, a group represented by the formula -$A^{094}$-S(O)$_q$—, a group represented by the formula -$A^{094}$-N($R^{23}$)SO$_2$—, a group represented by the formula -$A^{094}$-SO$_2$N($R^{23}$)—, or a group represented by the formula -$A^{094}$-CON($R^{23}$)—, $A^{094}$ is:

a single bond, a divalent $C_{1-10}$ aliphatic hydrocarbon group, an arylene group, or a divalent heterocyclic group, $R^{091}$ is:

a $C_{1-6}$ alkyl group which may be substituted with 1 to 3 groups selected from the group consisting of "amino group, hydroxyl group, a $C_{3-8}$ cycloalkyl group, a $C_{3-8}$ cycloalkylidene group, a $C_{1-6}$ alkoxy group, a $C_{1-11}$ acyloxy group, a $C_{2-7}$ alkoxycarbonyl group, a $C_{1-11}$ acyl group, cyano group, an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "amino group, hydroxyl group, a $C_{3-8}$ cycloalkyl group, a $C_{1-6}$ alkoxy group, a $C_{1-11}$ acyloxy group, a $C_{2-7}$ alkoxycarbonyl group, cyano group, an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "amino group, hydroxyl group, a $C_{3-8}$ cycloalkyl group, a $C_{1-6}$ alkoxy group, a $C_{1-11}$ acyloxy group, a $C_{2-7}$ alkoxycarbonyl group, cyano group, an aryl group, a heterocyclic group, and a biaryl group (the aryl group, the heterocyclic group, and the biaryl group may be substituted with 1 to 3 groups selected from the group A)", a $C_{3-8}$ cycloalkyl group which may be substituted with a $C_{1-6}$ alkyl group, an aryl group which may be substituted with 1 to 5 groups selected from the group B, a heterocyclic group which may be substituted with 1 to 5 groups selected from the group B, or a biaryl group which may be substituted with 1 to 5 groups selected from the group B, the group B is a group consisting of "hydroxyl group, a halogen atom, cyano group, a $C_{1-6}$ alkyl group, a $C_{1-6}$ hydroxyalkyl group, a $C_{2-6}$ alkynyl group, a $C_{3-8}$ cycloalkyl group, a $C_{1-6}$ haloalkyl group, a $C_{7-11}$ aralkyl group, a $C_{1-10}$ alkoxy group, a $C_{3-8}$ cycloalkoxy group, a $C_{1-6}$ haloalkoxy group, a $C_{7-11}$ aralkyloxy group, an aryloxy group, a $C_{1-11}$ acyloxy group, a $C_{1-6}$ alkylthio group, a $C_{1-6}$ haloalkylthio group, adamantyl group, carboxy group, a $C_{2-7}$ alkoxycarbonyl group, a $C_{2-7}$ alkylaminocarbonyl group, an aryloxycarbonyl group, a $C_{8-12}$ aralkyloxycarbonyl group, a $C_{1-11}$ acyl group, a $C_{1-11}$ haloacyl group, amino group, a $C_{1-6}$ alkylamino group, nitro group, a saturated heterocyclic group, and a $C_{1-11}$ acylamino group", and q is an integer of 0 to 2, and the bond indicated with lines including a broken line is a single bond or a double bond, $R^{11}$ is:

hydrogen atom, or a protective group of hydroxyl group, $R^{12}$ and $R^{13}$, which are the same or different, represent hydrogen atom, a $C_{1-6}$ alkyl group, or a protective group of amino group, $X^{332}, X^{333}, X^{334}, X^{336}, X^{337}, X^{042}, X^{052}, X^{054}, X^{092}, X^{093}$, and $X^{094}$ mentioned above, which are the same or different, represent a single bond, a group represented by the formula —O—, a group represented by the formula —OCO—, a group represented by the formula —OCO$_2$— a group represented by the formula —OCON($R^{25}$)—, a group represented by the formula —S(O)$_r$— a group represented by the formula —SO$_2$N($R^{25}$)—, a group represented by the formula —OCS—, a group represented by the formula —CO—, a group represented by the formula —CO$_2$—, a group represented by the formula —CON($R^{25}$)—, a group represented by the formula —CH=N—, a group represented by the formula —CH=N—O—, a group represented by the formula —C($R^{25}$)=N—, a group represented by the formula —C($R^{25}$)=N—O—, a group represented by the formula —C($R^{25}$)=N—N($R^{26}$)—, a group represented by the formula —CH=N—N($R^{25}$)—, a group represented by the formula —CS—, a group represented by the formula —C(S)O—, a group represented by the formula —CSN($R^{25}$)—, a group represented by the formula —O—N=C($R^{25}$)—, a group represented by the formula —N=CH—, a group represented by the formula —N($R^{25}$)—, a group represented by the formula —N($R^{25}$)CO—, a group represented by the formula —N($R^{25}$)CS—, a group represented by the formula —N($R^{25}$)SO$_2$—, a group represented by the formula —N($R^{25}$)CO$_2$—, or a group represented by the formula —N($R^{25}$)CON($R^{26}$)—, r is an integer of 0 to 2, $A^{331}, A^{332}, A^{333}, A^{334}, A^{335}, A^{051}, A^{052}, A^{091}, A^{092}$ and $A^{093}$ mentioned above, which are the same or different, represent a divalent $C_{1-10}$ aliphatic hydrocarbon group which may be substituted with hydroxyl group or a $C_{1-6}$ alkoxy group, an arylene group which may be substituted with hydroxyl group or a $C_{1-6}$ alkoxy group, or a divalent heterocyclic group which may be substituted with hydroxyl group or a $C_{1-6}$ alkoxy group, and $R^{20}, R^{21}, R^{22}, R^{23}, R^{24}, R^{25}, R^{26}, R^{27}$ and $R^{28}$ mentioned above, which are the same or different, represent hydrogen atom, or a $C_{1-6}$ alkyl group, a salt thereof, or a hydrate or solvate thereof.

According to preferred embodiments of the aforementioned invention, there are provided:

(1) The aforementioned 10a-azalide compound, a salt thereof, or a hydrate or solvate thereof, wherein $R^2$ and $R^3$ combine together to represent oxo group, or one of them is hydrogen atom, and the other is:

hydroxyl group, a protected hydroxyl group, a group represented by the formula —$X^{031}$—$R^{031}$, or a group represented by the formula (II), the ring A is a group represented by the formula (VI), and $R^9$ and $R^{10}$, which are the same or different, represent:

hydrogen atom, hydroxyl group, a protected hydroxyl group, amino group, a protected amino group, azido group a halogen atom, a group represented by the formula —$X^{091}$—$R^{091}$, a group represented by the formula —$X^{091}$-$A^{091}$-$X^{092}$—$R^{091}$, a group represented by the formula —$X^{091}$-$A^{091}$-$X^{092}$-$A^{092}$-$X^{093}$—$R^{091}$, or a group represented by the formula —$X^{091}$-$A^{091}$-$X^{092}$-$A^{092}$-$X^{093}$-$A^{093}$-$X^{094}$—$R^{091}$, wherein $X^{091}$ is:

a single bond, a group represented by the formula -$A^{094}$-N($R^{23}$)—, a group represented by the formula -$A^{094}$-N($R^{23}$)CO—, a group represented by the formula -$A^{094}$-N($R^{23}$)CO$_2$—, a group represented by the formula -$A^{094}$-N($R^{23}$)CON($R^{24}$)—, a group represented by the formula -$A^{094}$-OCON($R^{23}$)—, a group represented by the formula -A$^{094}$-O—,
a group represented by the formula -A$^{094}$-CO$_2$—,
a group represented by the formula -A$^{094}$-OCO—,
a group represented by the formula -A$^{094}$-OCO$_2$—,
a group represented by the formula -A$^{094}$-S(O)$_q$—,
a group represented by the formula -A$^{094}$-N(R$^{23}$)SO$_2$—,
a group represented by the formula -A$^{094}$-SO$_2$N(R$^{23}$)—, or
a group represented by the formula -A$^{094}$-CON(R$^{23}$)—,
A$^{094}$ is:
a single bond,
a divalent C$_{1-10}$ aliphatic hydrocarbon group,
an arylene group, or
a divalent heterocyclic group,
R$^{091}$ is:
a C$_{1-6}$ alkyl group which may be substituted with 1 to 3 groups selected from the group consisting of "amino group, hydroxyl group, a C$_{1-6}$ alkoxy group, a C$_{2-7}$ alkoxycarbonyl group, a C$_{1-11}$ acyl group, cyano group, an aryl group, a heterocyclic group, and a biaryl group (the aryl group, the heterocyclic group, and the biaryl group may be substituted with 1 to 3 groups selected from the group A)",
a C$_{2-6}$ alkenyl group which may be substituted with 1 to 3 groups selected from the group consisting of "amino group, hydroxyl group, a C$_{1-6}$ alkoxy group, a C$_{2-7}$ alkoxycarbonyl group, cyano group, an aryl group, a heterocyclic group, and a biaryl group (the aryl group, the heterocyclic group, and the biaryl group may be substituted with 1 to 3 groups selected from the group A)",
a C$_{2-6}$ alkynyl group which may be substituted with 1 to 3 groups selected from the group consisting of "amino group, hydroxyl group, a C$_{1-6}$ alkoxy group, a C$_{2-7}$ alkoxycarbonyl group, cyano group, an aryl group, a heterocyclic group, and a biaryl group (the aryl group, the heterocyclic group, and the biaryl group may be substituted with 1 to 3 groups selected from the group A)",
a C$_{3-8}$ cycloalkyl group which may be substituted with a C$_{1-6}$ alkyl group,
an aryl group which may be substituted with 1 to 5 groups selected from the group B',
a heterocyclic group which may be substituted with 1 to 5 groups selected from the group B', or
a biaryl group which may be substituted with 1 to 5 groups selected from the group B',
the group B' is a group consisting of "hydroxyl group, a halogen atom, cyano group, a C$_{1-6}$ alkyl group, a C$_{3-8}$ cycloalkyl group, a C$_{1-6}$ haloalkyl group, a C$_{7-11}$ aralkyl group, a C$_{1-10}$ alkoxy group, a C$_{3-8}$ cycloalkoxy group, a C$_{1-6}$ haloalkoxy group, a C$_{7-11}$ aralkyloxy group, an aryloxy group, a C$_{1-11}$ acyloxy group, a C$_{1-6}$ alkylthio group, a C$_{1-6}$ haloalkylthio group, adamantyl group, a C$_{2-7}$ alkoxycarbonyl group, a C$_{2-7}$ alkylaminocarbonyl group, an aryloxycarbonyl group, a C$_{1-11}$ acyl group, a C$_{1-11}$ haloacyl group, amino group, a C$_{1-6}$ alkylamino group, nitro group, a saturated heterocyclic group, and a C$_{1-11}$ acylamino group", and
q is an integer of 0 to 2;
(2) The aforementioned 10a-azalide compound, a salt thereof, or a hydrate or solvate thereof, wherein one of R$^9$ and R$^{19}$ is hydrogen atom, and the other is:
hydrogen atom,
hydroxyl group,
a protected hydroxyl group,
amino group,
a protected amino group,
azido group
a halogen atom,
a group represented by the formula —X$^{091}$—R$^{091}$, or
a group represented by the formula —X$^{091}$-A$^{091}$-X$^{092}$—R$^{091}$;
(3) The aforementioned 10a-azalide compound, a salt thereof, or a hydrate or solvate thereof, wherein one of R$^9$ and R$^{10}$ is hydrogen atom, and the other is:
hydrogen atom, or
a group represented by the formula —X$^{091}$—R$^{091}$;
(4) The aforementioned 10a-azalide compound, a salt thereof, or a hydrate or solvate thereof, wherein both R$^9$ and R$^{10}$ represent hydrogen atom;
(5) The aforementioned 10a-azalide compound, a salt thereof, or a hydrate or solvate thereof, wherein X$^{091}$ is:
a single bond,
a group represented by the formula -A$^{094}$-N(R$^{23}$)—,
a group represented by the formula -A$^{094}$-N(R$^{23}$)CO—,
a group represented by the formula -A$^{094}$-N(R$^{23}$)CO$_2$—,
a group represented by the formula -A$^{094}$-O—, or
a group represented by the formula -A$^{094}$-S(O)$_q$—, and
A$^{094}$ is:
a single bond, or
a divalent C$_{1-10}$ aliphatic hydrocarbon group;
(6) The aforementioned 10a-azalide compound, a salt thereof, or a hydrate or solvate thereof, wherein X$^{091}$ is:
a single bond,
a group represented by the formula -A$^{094}$-N(H)—,
a group represented by the formula -A$^{094}$-N(H)CO—,
a group represented by the formula -A$^{094}$-N(H)CO$_2$—,
a group represented by the formula -A$^{094}$-O—, or
a group represented by the formula -A$^{094}$-S—, and
A$^{094}$ is;
a single bond, or
methylene group;
(7) The aforementioned 10a-azalide compound, a salt thereof, or a hydrate or solvate thereof, wherein X$^{091}$ is:
a single bond,
a group represented by the formula —CH$_2$—O—, or
a group represented by the formula —CH$_2$—S—;
(8) The aforementioned 10a-azalide compound, a salt thereof, or a hydrate or solvate thereof, wherein R$^{091}$ is:
a C$_{1-6}$ alkyl group which may be substituted with 1 to 3 groups selected from the group consisting of "hydroxyl group, a C$_{3-8}$ cycloalkyl group, a C$_{3-8}$ cycloalkylidene group, a C$_{1-6}$ alkoxy group, cyano group, an aryl group, a heterocyclic group, and a biaryl group (the aryl group may be substituted with 1 to 3 C$_{1-6}$ alkyl groups)",
a C$_{2-6}$ alkenyl group which may be substituted with 1 to 3 groups selected from the group consisting of "hydroxyl group, a C$_{1-11}$ acyloxy group, cyano group, an aryl group, a heterocyclic group, and a biaryl group",
a C$_{2-6}$ alkynyl group which may be substituted with 1 to 3 groups selected from the group consisting of "an aryl group, a heterocyclic group, and a biaryl group",
an aryl group which may be substituted with 1 to 3 groups selected from the group consisting of the group C,
a heterocyclic group which may be substituted with 1 to 3 groups selected from the group consisting of the group C, or
a biaryl group which may be substituted with 1 to 3 groups selected from the group consisting of the group C, and
the group C is a group consisting of "hydroxyl group, a halogen atom, cyano group, a C$_{1-6}$ alkyl group, a C$_{1-6}$ hydroxyalkyl group, a C$_{2-6}$ alkynyl group, a C$_{3-8}$ cycloalkyl group, a C$_{1-6}$ haloalkyl group, a C$_{7-11}$ aralkyl group, a C$_{1-10}$ alkoxy group, a C$_{3-8}$ cycloalkoxy group, a C$_{1-6}$ haloalkoxy group, a C$_{7-11}$ aralkyloxy group, an aryloxy group, a C$_{1-6}$ alkylthio group, a C$_{1-6}$ haloalkylthio group, adamantyl group, carboxy group, a C$_{2-7}$ alkoxycarbonyl group, an aryloxycarbonyl group, a C$_{1-11}$ acyl group, amino group, a $C_{1-6}$ alkylamino group, a saturated heterocyclic group, and a $C_{1-11}$ acylamino group";

(9) The aforementioned 10a-azalide compound, a salt thereof, or a hydrate or solvate thereof, wherein $R^{091}$ is:
a $C_{1-6}$ alkyl group which may be substituted with 1 to 3 groups selected from the group consisting of "hydroxyl group, cyano group, an aryl group, a heterocyclic group, and a biaryl group",
a $C_{2-6}$ alkenyl group which may be substituted with 1 to 3 groups selected from the group consisting of "an aryl group, a heterocyclic group, and a biaryl group",
a $C_{2-6}$ alkynyl group which may be substituted with 1 to 3 groups selected from the group consisting of "an aryl group, a heterocyclic group, and a biaryl group",
an aryl group which may be substituted with 1 to 3 groups selected from the group C',
a heterocyclic group which may be substituted with 1 to 3 groups selected from the group C', or
a biaryl group which may be substituted with 1 to 3 groups selected from the group C', and
the group C' is a group consisting of "hydroxyl group, a halogen atom, a $C_{1-6}$ alkyl group, a $C_{3-8}$ cycloalkyl group, a $C_{7-11}$ aralkyl group, a $C_{1-10}$ alkoxy group, a $C_{3-8}$ cycloalkoxy group, a $C_{7-11}$ aralkyloxy group, an aryloxy group, a $C_{1-6}$ alkylthio group, adamantyl group, an aryloxycarbonyl group, a $C_{1-11}$ acyl group, amino group, a $C_{1-6}$ alkylamino group, and a $C_{1-11}$ acylamino group";

(10) The aforementioned 10a-azalide compound, a salt thereof, or a hydrate or solvate thereof, wherein $R^{091}$ is:
a $C_{1-6}$ alkyl group which may be substituted with one group selected from the group consisting of "an aryl group, and a biaryl group",
a $C_{2-6}$ alkenyl group which may be substituted with one group selected from the group consisting of "an aryl group, and a biaryl group",
a $C_{2-6}$ alkynyl group which may be substituted with one aryl group,
an aryl group which may be substituted with 1 to 3 groups selected from the group consisting of "hydroxyl group, a halogen atom, a $C_{1-6}$ alkyl group, a $C_{3-8}$ cycloalkyl group, a $C_{7-11}$ aralkyl group, a $C_{1-10}$ alkoxy group, a $C_{3-8}$ cycloalkoxy group, a $C_{7-11}$ aralkyloxy group, an aryloxy group, a $C_{1-6}$ alkylthio group, adamantyl group, an aryloxycarbonyl group, a $C_{1-11}$ acyl group, amino group, a $C_{1-6}$ alkylamino group, and a $C_{1-11}$ acylamino group",
a heterocyclic group which may be substituted with one $C_{1-6}$ alkyl group, or
a biaryl group which may be substituted with one group selected from the group consisting of "hydroxyl group, a halogen atom, and a $C_{7-11}$ aralkyloxy group";

(11) The aforementioned 10a-azalide compound, a salt thereof, or a hydrate or solvate thereof, wherein $R^{091}$ is:
a $C_{1-6}$ alkyl group substituted with one biaryl group,
a $C_{2-6}$ alkenyl group substituted with one aryl group,
a $C_{2-6}$ alkynyl group substituted with one aryl group,
an aryl group which may be substituted with one group selected from the group consisting of "a halogen atom, a $C_{1-6}$ alkyl group, a $C_{1-10}$ alkoxy group, a $C_{1-6}$ alkylamino group, and a $C_{7-11}$ aralkyloxy group", or
a biaryl group;

(12) The aforementioned 10a-azalide compound, a salt thereof, or a hydrate or solvate thereof, wherein one of $R^9$ and $R^{10}$ is hydrogen atom, and the other is:
a group represented by the formula —$X^{091}$-$A^{091}$-$X^{092}$— $R^{091}$,
$X^{091}$ is:
a group represented by the formula -$A^{094}$-O—,
$A^{094}$ is a divalent $C_{1-10}$ aliphatic hydrocarbon group,
$A^{091}$ is an arylene group, and
$X^{092}$ is a single bond, or
a group represented by the formula —N($R^{25}$)—;

(13) The aforementioned 10a-azalide compound, a salt thereof, or a hydrate or solvate thereof, wherein one of $R^9$ and $R^{10}$ is hydrogen atom, and the other is:
a group represented by the formula —$X^{091}$-$A^{091}$-$X^{092}$— $R^{091}$,
$X^{091}$ is:
a group represented by the formula —$CH_2$—O—,
$A^{091}$ is a phenylene group, and
$X^{092}$ is a single bond, or
a group represented by the formula —N($R^{25}$)—;

(14) The aforementioned 10a-azalide compound, a salt thereof, or a hydrate or solvate thereof, wherein $R^{091}$ is:
a $C_{1-6}$ alkyl group which may be substituted with 1 to 3 groups selected from the group consisting of "hydroxyl group, a $C_{3-8}$ cycloalkyl group, and an aryl group (the aryl group may be substituted with 1 to 3 $C_{1-6}$ alkyl groups)",
a $C_{2-6}$ alkenyl group which may be substituted with 1 to 3 aryl groups,
an aryl group, or
a heterocyclic group which may be substituted with 1 to 3 groups selected from the group consisting of "a $C_{1-6}$ alkyl group, and a $C_{8-12}$ aralkyloxycarbonyl group";

(15) The aforementioned 10a-azalide compound, a salt thereof, or a hydrate or solvate thereof, wherein $R^{091}$ is:
a $C_{1-6}$ alkyl group which may be substituted with 1 to 3 groups selected from the group consisting of "hydroxyl group, a $C_{3-8}$ cycloalkyl group, and an aryl group (the aryl group may be substituted with 1 to 3 $C_{1-6}$ alkyl groups)",
a $C_{2-6}$ alkenyl group which may be substituted with 1 to 3 aryl groups, or
an aryl group;

(16) The aforementioned 10a-azalide compound, a salt thereof, or a hydrate or solvate thereof, wherein one of $R^2$ and $R^3$ is hydrogen atom, and the other is:
a group represented by the formula (II);

(17) The aforementioned 10a-azalide compound, a salt thereof, or a hydrate or solvate thereof, wherein one of $R^{32}$ and $R^{33}$ is hydrogen atom, and the other is:
hydroxyl group,
amino group, or,
a group represented by the formula —$X^{331}$-$A^{331}$-$X^{332}$— $R^{331}$, or
one of $R^{32}$ and $R^{33}$ is hydroxyl group, and the other is:
a group represented by the formula —$X^{335}$—$R^{332}$, or
a group represented by the formula —$X^{335}$-$A^{334}$-$X^{336}$— $R^{332}$;

(18) The aforementioned 10a-azalide compound, a salt thereof, or a hydrate or solvate thereof, wherein one of $R^{32}$ and $R^{33}$ is hydrogen atom, and the other is hydroxyl group;

(19) The aforementioned 10a-azalide compound, a salt thereof, or a hydrate or solvate thereof, wherein $X^{331}$ is:
a group represented by the formula —OCON(H)—,
$A^{331}$ is:
a divalent $C_{1-10}$ aliphatic hydrocarbon group, or,
a divalent heterocyclic group,
$X^{332}$ is:
a single bond, or
a group represented by the formula —N($R^{25}$)—,
$X^{335}$ is:
a group represented by the formula —$CH_2$N($R^{20}$)—, $A^{334}$ is:
  a divalent $C_{1-10}$ aliphatic hydrocarbon group which may be substituted with hydroxyl group, or
  a divalent heterocyclic group, and
$X^{336}$ is:
  a single bond,
  a group represented by the formula $-N(R^{25})-$, or
  a group represented by the formula $-N(R^{25})CO_2-$; and
(20) The aforementioned 10a-azalide compound, a salt thereof, or a hydrate or solvate thereof, wherein $R^{331}$ is:
  a $C_{1-6}$ alkyl group substituted with one group selected from the group consisting of "an aryl group, and a heterocyclic group (the aryl group and the heterocyclic group may be substituted with one group selected from the group A)", and $R^{332}$ is:
  a $C_{1-6}$ alkyl group which may be substituted with one group selected from the group consisting of "hydroxyl group, an aryl group, and a heterocyclic group (the aryl group and the heterocyclic group may be substituted with one group selected from the group A)", or
  the aforementioned aryl group which may be substituted with one group selected from the group A.

As another aspect of the present invention, there is provided a macrolide antibiotic comprising a substance selected from the group consisting of a 10a-azalide compound represented by the aforementioned formula (I), a pharmaceutically acceptable salt thereof, a hydrate thereof, and a solvate thereof as an active ingredient. The present invention also provides a medicament, preferably a medicament for prophylactic and/or therapeutic treatment of an infectious disease, comprising a substance selected from the group consisting of a 10a-azalide compound represented by the aforementioned formula (I), a pharmaceutically acceptable salt thereof, a hydrate thereof, and a solvate thereof as an active ingredient.

The present invention further provides an antimicrobial agent comprising a substance selected from the group consisting of a 10a-azalide compound represented by the aforementioned formula (I), a pharmaceutically acceptable salt thereof, a hydrate thereof, and a solvate thereof as an active ingredient, and a prophylactic and/or therapeutic agent for an infectious disease, which comprises a substance selected from the group consisting of a 10a-azalide compound represented by the aforementioned formula (I), a pharmaceutically acceptable salt thereof, a hydrate thereof, and a solvate thereof as an active ingredient.

In addition to these, the present invention also provides use of a substance selected from the group consisting of a 10a-azalide compound represented by the aforementioned formula (I), a pharmaceutically acceptable salt thereof, a hydrate thereof, and a solvate thereof for manufacture of the aforementioned medicament, and a method for prophylactic and/or therapeutic treatment of an infectious disease, which comprises the step of administering an effective amount of a substance selected from the group consisting of a 10a-azalide compound represented by the aforementioned formula (I), a pharmaceutically acceptable salt thereof, a hydrate thereof, and a solvate thereof to a mammal including human.

Effect of the Invention

The 10a-azalide compounds of the present invention, salts thereof, hydrates thereof, and solvates thereof have an antibacterial activity against a wide variety of microorganisms, preferably aerobic or anaerobic bacteria such as Gram-positive or Gram-negative bacteria, mycoplasmas, chlamydiae, and the like, and they are characterized in, in particular, that they have superior antibacterial activity also against *Hemophilus influenzae*, erythromycin resistant pneumococci, and the like, against which sufficient antibacterial activity cannot be obtained with conventional macrolide antibiotics.

BEST MODE FOR CARRYING OUT THE INVENTION

In the present invention, the symbol "$C_{x-y}$" means that the group mentioned after that has x to y of carbon atoms.

The "halogen atom" is fluorine, chlorine, bromine, or iodine.

The "alkyl group" is a linear or branched alkyl group, and examples include, for example, methyl group, ethyl group, n-propyl group, isopropyl group, n-butyl group, 2-butyl group, t-butyl group, n-pentyl group, isopentyl group, 1,1-dimethylpropyl group, n-hexyl group, 1,1,3,3-tetramethylbutyl group, n-nonyl group, n-decyl group, and the like.

The "alkenyl group" is a linear or branched alkenyl group corresponding to the aforementioned "alkyl group" having one or more double bonds at arbitrary positions, and examples include, for example, vinyl group, 1-propenyl group, 2-propenyl group, 1-butenyl group, 1,3-butadienyl group, 2-pentenyl group, 3-pentenyl group, 2-hexenyl group, and the like.

The "alkynyl group" means a linear or branched alkynyl group corresponding to the aforementioned "alkyl group" having one or more triple bonds at arbitrary positions, and examples include, for example, ethynyl group, 1-propynyl group, 2-propynyl group, and the like.

The "alkoxy group" is a linear or branched alkoxy group, and examples include, for example, methoxy group, ethoxy group, 1-propoxy group, isopropoxy group, 1-butoxy group, 1-methyl-1-propoxy group, t-butoxy group, 1-pentyloxy group, 1,1,3,3-tetramethylbutoxy group, n-decyloxy group, and the like.

The "alkoxycarbonyl group" means a group formed by bonding the aforementioned "alkoxy group" and carbonyl group, and examples include, for example, methoxycarbonyl group, ethoxycarbonyl group, t-butoxycarbonyl group, and the like.

The "haloalkyl group" is an alkyl group corresponding to the aforementioned "alkyl group" of which arbitrary one or two or more hydrogen atoms are substituted with one or two or more halogen atoms, and examples of include, for example, fluoromethyl group, difluoromethyl group, trifluoromethyl group, 2,2,2-trifluoroethyl group, 2,2,2-trichloroethyl group, pentafluoroethyl group, 3,3,3-trifluoropropyl group, perfluoropropyl group, 4-fluorobutyl group, 4-chlorobutyl group, 4-bromobutyl group, perfluorohexyl group, and the like.

The "alkylamino group" is a group formed by bonding one or two of the aforementioned "alkyl groups" and amino group, and examples include, for example, methylamino group, dimethylamino group, diethylamino group, N-ethyl-N-methylamino group, and the like.

The "alkylaminocarbonyl group" is a group formed by bonding the aforementioned "alkylamino group" and carbonyl group, and examples include, for example, methylaminocarbonyl group, dimethylaminocarbonyl group, diethylaminocarbonyl group, and the like.

The "hydroxyalkyl group" is a group corresponding to the aforementioned "alkyl group" of which arbitrary one hydrogen atom is substituted with hydroxyl group, and examples include, for example, hydroxymethyl group, hydroxyethyl group, 1-hydroxy-1-methylethyl group, 1-hydroxy-1-methylpropyl group, and the like.

The "haloalkoxy group" is an alkoxy group corresponding to the aforementioned "alkoxy group" substituted with one or two or more halogen atoms, and examples include, for example, fluoromethoxy group, difluoromethoxy group, trifluoromethoxy group, 2,2,2-trifluoroethoxy group, 2,2,2-trichloroethoxy group, pentafluoroethoxy group, perfluoropropoxy group, 4-fluorobutoxy group, 4-chlorobutoxy group, 4-bromobutoxy group, perfluorohexyloxy group, and the like.

The "aryl group" is a monocyclic to tetracyclic aromatic carbon ring group having 6 to 18 carbon atoms, this aromatic carbon ring group may condense with a cycloalkyl ring, and this cycloalkyl ring may be substituted with oxo group. Examples of the aromatic carbon ring group include, for example, phenyl group, naphthyl group, anthryl group, phenanthrenyl group, tetracenyl group, pyrenyl group, and the like. Examples of the aromatic carbon ring group condensed with a cycloalkyl ring include fluorenyl group, oxofluorenyl group, indanyl group, oxoindanyl group, tetrahydronaphthyl group, oxotetrahydronaphthyl group, and the like.

The "heterocyclic group" is a monocyclic heterocyclic group, or a condensed ring type heterocyclic group containing 1 to 5 of atoms arbitrarily selected from nitrogen atom, oxygen atom and sulfur atom as ring constituting atoms, and includes a saturated heterocyclic group, an aromatic heterocyclic group, a partially saturated monocyclic aromatic heterocyclic group and a condensed ring type heterocyclic group comprising an aromatic heterocyclic group having a single partially saturated ring. The condensed ring type heterocyclic group having a single partially saturated ring may be substituted with oxo group. When the hetero atom is sulfur atom, dioxide compounds also fall within the scope of the present invention.

As the heterocyclic group, a heterocyclic group having 2 to 10 carbon atoms in the ring system is preferred.

In this specification, an "aromatic heterocyclic group" is also referred to as "heteroaryl group" for convenience, and the aromatic heterocyclic group and the heteroaryl group have the same meaning.

Examples of the saturated heterocyclic group include, for example, aziridinyl group, azetidinyl group, pyrrolidinyl group, imidazolidinyl group, pyrazolidinyl group, oxolanyl group, thiolanyl group, piperidinyl group, piperazinyl group, morpholinyl group, and the like.

Examples of the aromatic heterocyclic group include, for example, pyridyl group, pyridazinyl group, pyrimidinyl group, pyrazinyl group, quinolyl group (e.g., 2-quinolyl, 3-quinolyl group, 4-quinolyl group, 5-quinolyl group), isoquinolyl group, thienyl group (e.g., 2-thienyl group, 3-thienyl group), pyrrolyl group (e.g., 1-pyrrolyl group, 2-pyrrolyl group, 3-pyrrolyl group), thiazolyl group (e.g., 2-thiazolyl group, 4-thiazolyl group, 5-thiazolyl group), isothiazolyl group (e.g., 3-isothiazolyl group, 4-isothiazolyl group, 5-isothiazolyl group), pyrazolyl group (e.g., 1-pyrazolyl group, 3-pyrazolyl group, 4-pyrazolyl group), imidazolyl group (e.g., limidazolyl group, 2-imidazolyl group, 3-imidazolyl group), furyl group (e.g., 2-furyl group, 3-furyl group), oxazolyl group (e.g., 2-oxazolyl group, 4-oxazolyl group, 5-oxazolyl group), isoxazolyl group (e.g., 3-isoxazolyl group, 4-isoxazolyl group, 5-isoxazolyl group), oxadiazolyl group (e.g., 1,2,3-oxadiazolyl group, 1,3,4-oxadiazolyl group), thiadiazolyl group (e.g., 1,2,3-thiadiazolyl group, 1,3,4-thiadiazolyl group), triazolyl group (e.g., 1,2,4-triazolyl group), benzofuranyl group (e.g., 2-benzofuranyl group, 3-benzofuranyl group, 4-benzofuranyl group, 5-benzofuranyl group), benzothienyl group (e.g., 2-benzothienyl group, 3-benzothienyl group, 4-benzothienyl group, 5-benzothienyl group), indolyl group (e.g., 2-indolyl group, 3-indolyl group, 4-indolyl group, 5-indolyl group), benzoxazolyl group (e.g., 2-benzoxazolyl group, 4-benzoxazolyl group, 5-benzoxazolyl group, 6-benzoxazolyl group), benzisoxazolyl group (e.g., 3-benzo[c]isoxazolyl group, 4-benzo[c]isoxazolyl group, 5-benzo[c]isoxazolyl group, 6-benzo[c]isoxazolyl group, 3-benzo[d]isoxazolyl group, 4-benzo[d]isoxazolyl group, 5-benzo[d]isoxazolyl group, 6-benzo[d]isoxazolyl group), indazolyl group (e.g., 3-indazolyl group, 4-indazolyl group, 5-indazolyl group, 6-indazolyl group), benzimidazolyl group (e.g., 2-benzimidazolyl group, 4-benzimidazolyl group, 5-benzimidazolyl group, 6-benzimidazolyl group), benzooxadiazolyl group (e.g. 4-benzo[1,2,5]oxadiazolyl group, 5-benzo[1,2,5]oxadiazolyl group, 4-benzo[1,2,3]oxadiazolyl group, 5-benzo[1,2,3]oxadiazolyl group), benzothiadiazolyl group (e.g., 4-benzo[1,2,5]thiadiazolyl group, 5-benzo[1,2,5]thiadiazolyl group, 4-benzo[1,2,3]thiadiazolyl group, 5-benzo[1,2,3]thiadiazolyl group), indolidinyl group (e.g., 1-indolidinyl group, 2-indolidinyl group, 3-indolidinyl group, 5-indolidinyl group), thienopyridyl group (e.g., 2-thieno[2,3-b]pyridyl group, 3-thieno[2,3-b]pyridyl group, 5-thieno[2,3-b]pyridyl group, 6-thieno[2,3-b]pyridyl group, 2-thieno[3,2-b]pyridyl group, 3-thieno[3,2-b]pyridyl group, 5-thieno[3,2-b]pyridyl group, 6-thieno[3,2-b]pyridyl group), pyrazolopyridyl group (e.g., 2-pyrazolopyridyl group, 3-pyrazolopyridyl group, 5-pyrazolopyridyl group, 6-pyrazolopyridyl group), imidazopyridyl group (e.g., 1-imidazo[1,5-a]pyridyl group, 3-imidazo[1,5-a]pyridyl group, 5-imidazo[1,5-a]pyridyl group, 7-imidazo[1,5-a]pyridyl group, 2-imidazo[1,2-a]pyridyl group, 3-imidazo[1,2-a]pyridyl group, 5-imidazo[1,2-a]pyridyl group, 7-imidazo[1,2-a]pyridyl group), imidazopyrazyl group (e.g., 1-imidazo[1,5-a]pyrazyl group, 3-imidazo[1,5-a]pyrazyl group, 5-imidazo[1,5-a]pyrazyl group, 8-imidazo[1,5-a]pyrazyl group, 2-imidazo[1,2-a]pyrazyl group, 3-imidazo[1,2-a]pyrazyl group, 5-imidazo[1,2-a]pyrazyl group, 8-imidazo[1,2-a]pyrazyl group), pyrazolopyrimidyl group (e.g., 2-pyrazolo[1,5-a]pyrimidyl group, 3-pyrazolo[1,5-a]pyrimidyl group, 5-pyrazolo[1,5-a]pyrinaidyl group, 6-pyrazolo[1,5-a]pyrimidyl group, 2-pyrazolo[1,5-c]pyrimidyl group, 3-pyrazolo[1,5-c]pyrimidyl group, 4-pyrazolo[1,5-c]pyrimidyl group, 5-pyrazolo[1,5-c]pyrimidyl group), triazolopyrimidyl group (e.g., 3-[1,2,3]triazolo[1,5-a]pyrimidyl group, 5-[1,2,3]triazolo[1,5-a]pyrimidyl group, 6-[1,2,3]triazolo[1,5-a]pyrimidyl group, 3-[1,2,3]triazolo[1,5-c]pyrimidyl group, 4-[1,2,3]triazolo[1,5-c]pyrimidyl group, 5-[1,2,3]triazolo[1,5-c]pyrimidyl group, 2-[1,2,4]triazolo[1,5-a]pyrimidyl group, 5-[1,2,4]triazolo[1,5-a]pyrimidyl group, 6-[1,2,4]triazolo[1,5-a]pyrimidyl group, 7-[1,2,4]triazolo[1,5-a]pyrimidyl group, 2-[1,2,4]-triazolo[1,5-c]pyrimidyl group, 5-[1,2,4]triazolo[1,5-c]pyrimidyl group, 7-[1,2,4]triazolo[1,5-c]pyrimidyl group, 8-[1,2,4]triazolo[1,5-c]pyrimidyl group), thienothienyl group (e.g., 2-thieno[2,3-b]thienyl group, 3-thieno[2,3-b]thienyl group, 2-thieno[3,2-b]thienyl group, 3-thieno[3,2-b]thienyl group), imidazothiazolyl group (e.g., 2-imidazo[2,1-b]thiazolyl group, 3-imidazo[2,1-b]thiazolyl group, 5-imidazo[2,1-b]thiazolyl group, 2-imidazo[5,1-b]thiazolyl group, 3-imidazo[5,1-b]thiazolyl group, 5-imidazo[5,1-b]thiazolyl group), and the like.

Examples of the partially saturated monocyclic aromatic heterocyclic group and condensed ring type heterocyclic group comprising an aromatic heterocyclic group having a single partially saturated ring include, for example, maleimido group, tetrahydrobenzofuranyl group, tetrahydrobenzothienyl group, tetrahydrobenzopyrrolyl group, 2,3-dihydro-1H-benzofuranyl group, 2,3-dihydro-1H-benzothienyl group, 2,3-dihydro-1H-indolyl group, 2,3-dihydro-1H-indazolyl group, 2,3-dihydro-1H-benzotriazolyl group, 2,3-dihydro-1H-benzoxazolyl group, 2,3-dihydro-1H-benzothiazolyl group, benzo[1,3]oxathioly group, benzo[1,3]dioxolyl group, 2H-chromenyl group, chromanyl group, indolinyl group, isoindolinyl group, and the like.

Examples of the condensed ring type heterocyclic group having a partially saturated monocyclic ring and substituted with oxo group include, for example, 2-oxo-1,3-dihydro-1H-indolyl ring, 3-oxo-1,2-dihydro-1H-indazolyl ring, 2-oxo-3H-benzoxazolyl ring, 2-oxo-3H-benzothiazolyl ring, 2-oxo-benzo[1,3]oxathiolyl ring, 2-oxo-benzo[1,3]dioxolyl ring, 2-oxo-chromenyl ring, and the like.

The "biaryl group" is a group formed by bonding two groups selected from the aforementioned aryl groups and/or the heteroaryl groups, and examples include, for example, biphenyl group, pyridylphenyl group (e.g., 4-(pyridin-3-yl)phenyl group), furylphenyl group (e.g., 3-(furan-2-yl)phenyl group, 4-(furan-3-yl)phenyl group), pyridylimidazole group (e.g., 4-(pyridin-3-yl)imidazole group), and the like.

The "cycloalkyl group" is a cyclic alkyl group, and examples include, for example, cyclopropyl group, cyclobutyl group, cyclopentyl group, cyclohexyl group, cycloheptyl group, and the like.

The "cyclo alkylidene group" is a group formed by eliminating two hydrogen atoms on one arbitrary carbon atom of the aforementioned "cycloalkyl group", and examples include, for example, cyclopropylidene group, cyclobutylidene group, cyclopentylidene group, cyclohexylidene group, cycloheptylidene group, and the like.

The "cycloalkoxy group" is a group corresponding to the aforementioned "cycloalkyl group" substituting via oxygen atom, and examples include, for example, cyclopropoxy group, cyclobutoxy group, cyclopentyloxy group, cyclohexyloxy group, cycloheptyloxy group, and the like.

The "acyl group" is a group formed by eliminating hydroxyl group from a carboxylic acid, and examples include, for example, acetyl group, propionyl group, butyryl group, isobutyryl group, pivaloyl group, cyclopentylcarbonyl group, benzoyl group, nicotinoyl group, and the like.

The "acyloxy group" is a group corresponding to the aforementioned "acyl group" substituting via oxygen atom, and examples include, for example, acetyloxy group, propionyloxy group, butyryloxy group, isobutyryloxy group, pivaloyloxy group, cyclopentylcarbonyloxy group, benzoyloxy group, nicotinoyloxy group, and the like.

The "acylamino group" is a group formed by bonding the aforementioned "acyl group" and amino group, and examples include, for example, acetylamino group, propionylamino group, butyrylamino group, isobutylylamino group, pivaloylamino group, cyclopentylcarbonylamino group, benzoylamino group, nicotinoylamino group, and the like.

The "aryloxy group" is a group corresponding to the aforementioned "aryl group" substituting via oxygen atom, and examples include, for example, phenoxy group, naphthoxy group, and the like.

The "aryloxycarbonyl group" is a group formed by bonding the aforementioned "aryloxy group" and carbonyl group, and examples include, for example, phenoxycarbonyl group, naphthoxycarbonyl group, and the like.

The "aralkyl group" is a group formed by binding the aforementioned "aryl group" and "alkyl group", and examples include, for example, benzyl group, phenethyl group, naphthylmethyl group, and the like.

The "aralkyloxy group" is a group corresponding to the aforementioned "aralkyl group" substituting via oxygen atom, and examples include, for example, benzyloxy group, phenethyloxy group, naphthylmethyloxy group, and the like.

The "alkylthio group" is a group corresponding to the aforementioned "alkyl group" substituting via sulfur atom, and examples include, for example, methylthio group, ethylthio group, n-propylthio group, isopropylthio group, n-butylthio group, 2-butylthio group, t-butylthio group, n-pentylthio group, isopentylthio group, 1,1-dimethylpropylthio group, n-hexylthio group, and the like.

The "haloalkylthio group" is a group corresponding to the aforementioned "haloalkyl group" substituting via sulfur atom, and examples include, for example, fluoromethylthio group, difluoromethylthio group, trifluoromethylthio group, 2,2,2-trifluoroethylthio group, 2,2,2-trichloroethylthio group, pentafluoroethylthio group, 3,3,3-trifluoropropylthio group, perfluoropropylthio group, 4-fluorobutylthio group, 4-chlorobutylthio group, 4-bromobutylthio group, perfluorohexylthio group, and the like.

The "haloacyl group" is an acyl group corresponding to the aforementioned "acyl group" substituted with one or more halogen atoms, and examples include, for example, fluoroacetyl group, trifluoroacetyl group, 2,2,2-trifluoropropionyl group, 2,2,2-trichloropropionyl group, 4-fluorobutyryl group, 4-chlorobutyryl group, 4-bromobutyryl group, and the like.

The "divalent aliphatic hydrocarbon group" means an alkylene group, an alkenylene group, an alkynylene group, a cycloalkylene group, or a cycloalkenylene group.

The "alkylene group" is a linear or branched alkylene group, and examples include, for example, —CH$_2$—, —(CH$_2$)$_2$—, —(CH$_2$)$_3$—, —CH(CH$_3$)—, —(CH$_2$)$_3$—, —(CH(CH$_3$))$_2$—, —(CH$_2$)$_2$—CH(CH$_3$)—, —(CH$_2$)$_3$—CH(CH$_3$)—, —(CH$_2$)$_2$—CH(C$_2$H$_5$)—, —(CH$_2$)$_6$—, —(CH$_2$)$_2$—C(C$_2$H$_5$)$_2$—, —(CH$_2$)$_3$C(CH$_3$)$_2$CH$_2$—, —(CH$_2$)$_8$—, —(CH$_2$)$_3$C(CH$_3$)$_2$(CH$_2$)$_3$—, —(CH$_2$)$_{10}$—, and the like.

The "alkenylene group" is a linear or branched alkenylene group having one or two or more double bonds in the chain, and examples include, for example, a divalent group having a double bond formed by eliminating 2 to 6 hydrogen atoms on adjacent carbon atoms of the aforementioned alkylene group.

The "alkynylene group" is a linear or branched alkynylene group having one or two or more triple bonds in the chain, and examples include, for example, a divalent group having a triple bond formed by further eliminating hydrogen atoms from carbon atoms at the double bond moiety of the aforementioned alkenylene group.

Further, the "divalent aliphatic hydrocarbon group" may contain a double bond and triple bond.

The "cycloalkylene group" is a divalent group formed by eliminating arbitrary 2 of hydrogen atoms from a cycloalkane, and examples include, for example, 1,2-cyclopentylene group, 1,2-cyclohexylene group, 1,3-cyclohexylene group, 1,4-cyclohexylene group, 1,3-cycloheptylene group, and the like.

The "cycloalkenylene group" is a divalent group formed by eliminating arbitrary 2 of hydrogen atoms from a cycloalkene, and examples include, for example, 3-cyclohexen-1,2-ylene group, 2,5-cyclohexadien-1,4-ylene group, and the like.

The "arylene group" is a divalent group formed by eliminating arbitrary 2 of hydrogen atoms from a mono- to tetracyclic aromatic hydrocarbon having 6 to 18 carbon atoms, and examples include, for example, divalent groups formed by eliminating arbitrary 2 of hydrogen atoms from benzene, naphthalene, azulene, fluorene, phenanthrene, anthracene, pyrene, and the like.

The "divalent heterocyclic group" is a divalent group formed by further eliminating arbitrary 1 of hydrogen atom from the aforementioned "heterocyclic group", and examples include, for example, divalent groups formed by eliminating arbitrary 1 of hydrogen atom from pyrazolidinyl group, oxolanyl group, thiolanyl group, piperidinyl group, piperazinyl group, morpholinyl group, pyridyl group, pyridazinyl group, pyrimidinyl group, pyrazinyl group, quinolyl group, isoquinolyl group, thienyl group, pyrrolyl group, thiazolyl group, isothiazolyl group, pyrazolyl group, imidazolyl group, furyl group, oxazolyl group, isoxazolyl group, oxadiazolyl group, thiadiazolyl group, triazolyl group, benzofuranyl group, benzothienyl group, indolyl group, benzoxazolyl group, benzisoxazolyl group, indazolyl group, benzimidazolyl group, benzoxadiazolyl group, benzothiadiazolyl group, indolidinyl group, or thienopyridyl group, and the like.

The "protected hydroxyl group" means hydroxyl group protected with "a protective group of hydroxyl group".

The "protected amino group" means amino group protected with "a protective group of amino group".

The "protected oxime group" means oxime group protected with "a protective group of oxime group".

Examples of the "protective group of hydroxyl group", "protective group of amino group" and "protective group of oxime group" include a silyl type protective group such as trimethylsilyl group, triethylsilyl group and tert-butyldimethylsilyl group, an acyl type protective group such as acetyl group and benzoyl group, an ether type protective group such as benzyl group, p-methoxybenzyl group and 2-chlorobenzyl group, an acetal type protective group such as tetrahydropyranyl group, tetrahydrofuranyl group and 1-ethoxyethyl group, protective groups such as benzyloxycarbonyl group, t-butyloxy carbonyl group and ((9-9H-fluorenyl)methoxy) carbonyl group, and the like.

In the aforementioned formula (I), the preferred embodiments of $R^1$ to $R^{13}$ and $R^{15}$ are as follows. The compounds one of which $R^1$ to $R^{13}$ and $R^{15}$ corresponds to any one of the preferred examples of $R^1$ to $R^{13}$ explained below are preferred compounds, and the compounds having two or more of the preferred examples of $R^1$ to $R^{13}$ are more preferred compounds. However, the scope of the present invention is not limited to the following preferred embodiments.

It is preferred that $R^1$ is hydrogen atom. It is preferred that $R^2$ is hydrogen atom, and it is preferred that $R^3$ is a group represented by the formula (II) at the same time. It is also preferred that $R^2$ and $R^3$ combine to form oxo group.

When $R^2$ is hydrogen atom, and $R^3$ is a group represented by the formula (II), it is preferred that $R^{32}$ is hydrogen atom, and $R^{33}$ is hydroxyl group, amino group, or a group represented by the formula —$X^{331}$-$A^{331}$-$X^{332}$—$R^{331}$. It is also preferred that $R^{32}$ is hydroxyl group, and $R^{33}$ is a group represented by the formula —$X^{335}$—$R^{332}$, or a group represented by the formula —$X^{335}$-$A^{334}$-$X^{336}$—$R^{332}$.

In this case, it is preferred that $X^{331}$ is a group represented by the formula —OCON(H)—, $A^{331}$ is a divalent $C_{1-10}$ aliphatic hydrocarbon group, or a divalent heterocyclic group, $X^{332}$ is a single bond or a group represented by the formula —N($R^{25}$)—, $X^{335}$ is a group represented by the formula —CH$_2$N($R^{20}$)—, $A^{334}$ is a divalent $C_{1-10}$ aliphatic hydrocarbon group which may be substituted with hydroxyl group, or a divalent heterocyclic group, and $X^{336}$ is a group represented by the formula —N($R^{25}$)—, or a group represented by the formula —N($R^{25}$)CO$_2$—. It is also preferred that $R^{331}$ is a $C_{1-6}$ alkyl group substituted with one group selected from the group consisting of "an aryl group, and a heterocyclic group (the aryl group and the heterocyclic group may be substituted with one group selected from the group A)", and $R^{332}$ is a $C_{1-6}$ alkyl group which may be substituted with one group selected from the group consisting of "hydroxyl group, an aryl group, and a heterocyclic group (the aryl group and the heterocyclic group may be substituted with one group selected from the group A)", or an aryl group which may be substituted with one group selected from the group A.

It is preferred that $R^4$ is an unsubstituted $C_{1-6}$ alkyl group, and it is further preferred that $R^4$ is methyl group.

It is preferred that $R^5$ is hydrogen atom, and it is preferred that $R^6$ is hydroxyl group at the same time. It is also preferred that $R^5$ and $R^6$ combine to form oxo group, oxime group, or a protected oxime group.

It is preferred that the ring A is a group represented by the formula (VI).

It is preferred that $R^7$ is hydrogen atom, and it is preferred that $R^8$ is hydrogen atom, or a group represented by —$X^{071}$—$R^{071}$ at the same time. When $R^8$ is a group represented by the formula —$X^{071}$—$R^{071}$, it is preferred that —$X^{071}$ is a group represented by the formula -$A^{072}$-O—, and it is preferred that $A^{072}$ is methylene (—CH$_2$—). In this case, it is also preferred that $R^{071}$ is a $C_{1-6}$ alkyl group substituted with an aryl group, or a biaryl group.

It is preferred that $R^9$ is hydrogen atom, and it is preferred that, at the same time, $R^{10}$ is hydrogen atom, or is hydroxyl group, a protected hydroxyl group, amino group, a protected amino group, azido group, a halogen atom, a group represented by the formula —$X^{091}$—$R^{091}$, or a group represented by the formula —$X^{091}$-$A^{091}$-$X^{092}$—$R^{091}$, and it is further preferred that $R^{10}$ is hydrogen atom, or a group represented by the formula —$X^{091}$—$R^{091}$.

When $R^{10}$ is a group represented by the formula —$X^{091}$—$R^{091}$, it is preferred that $X^{091}$ is a single bond, a group represented by the formula -$A^{094}$-N($R^{23}$)—, a group represented by the formula -$A^{094}$-N($R^{23}$)CO—, a group represented by the formula -$A^{094}$-N($R^{23}$)CO$_2$—, a group represented by the formula -$A^{094}$-O—, or a group represented by the formula -$A^{094}$-S(O)$_q$—, and in this case, it is preferred that $A^{094}$ is a single bond or a divalent $C_{1-10}$ aliphatic hydrocarbon group. It is more preferred that $X^{091}$ is a single bond, a group represented by the formula -$A^{094}$-N(H)—, a group represented by the formula -$A^{094}$-N(H)CO—, a group represented by the formula -$A^{094}$-N(H)CO$_2$—, a group represented by the formula -$A^{094}$-O—, or a group represented by the formula -$A^{094}$-S—, and $A^{094}$ is a single bond or methylene group, and it is particularly preferred that $X^{091}$ is a single bond, a group represented by the formula —CH$_2$—N(H)CO—, a group represented by the formula —CH$_2$—N(H)CO$_2$—, a group represented by the formula —CH$_2$—O—, or a group represented by the formula —CH$_2$—S—.

Further, when $R^{10}$ is a group represented by the formula —$X^{091}$—$R^{091}$, it is preferred that $R^{091}$ is a $C_{1-6}$ alkyl group which may be substituted with 1 to 3 groups selected from the group consisting of "hydroxyl group, cyano group, an aryl group, a heterocyclic group, and a biaryl group", a $C_{2-6}$ alkenyl group which may be substituted with 1 to 3 groups selected from the group consisting of "an aryl group, a heterocyclic group, and a biaryl group", a $C_{2-6}$ alkynyl group which may be substituted with 1 to 3 groups selected from the group consisting of "an aryl group, a heterocyclic group, and a biaryl group", an aryl group which may be substituted with 1 to 3 groups selected from the group C', a heterocyclic group which may be substituted with 1 to 3 groups selected from the group C', or a biaryl group which may be substituted with 1 to 3 groups selected from the group C', where the group C' is a group consisting "hydroxyl group, a halogen atom, a $C_{1-6}$ alkyl group, a $C_{3-8}$ cycloalkyl group, a $C_{7-11}$ aralkyl group, a $C_{1-10}$ alkoxy group, a $C_{3-8}$ cycloalkoxy group, a $C_{7-11}$ aralkyloxy group, an aryloxy group, a $C_{1-6}$ alkylthio group, adamantyl group, an aryloxycarbonyl group, a $C_{1-11}$ acyl group, amino group, a $C_{1-6}$ alkylamino group, and a $C_{1-11}$ acylamino group", it is further preferred that $R^{091}$ is a $C_{1-6}$ alkyl group which may be substituted with one group selected from the group consisting of "an aryl group, and a biaryl group", a $C_{2-6}$ alkenyl group which may be substituted with one group selected from the group consisting of "an aryl group, and a biaryl group", a $C_{2-6}$ alkynyl group which may be substituted with one aryl group, an aryl group which may be substituted with 1 to 3 groups selected from the group consisting of "hydroxyl group, a halogen atom, a $C_{1-6}$ alkyl group, a $C_{3-8}$ cycloalkyl group, a $C_{7-11}$ aralkyl group, a $C_{1-10}$ alkoxy group, a $C_{3-8}$ cycloalkoxy group, a $C_{7-11}$ aralkyloxy group, an aryloxy group, a $C_{1-6}$ alkylthio group, adamantyl group, an aryloxycarbonyl group, a $C_{1-11}$ acyl group, amino group, a $C_{1-6}$ alkylamino group, and a $C_{1-11}$ acylamino group", a heterocyclic group which may be substituted with one $C_{1-6}$ alkyl group, or a biaryl group which may be substituted with one group selected from the group consisting of "hydroxyl group, a halogen atom, and a $C_{7-11}$ aralkyloxy group", and it is particularly preferred that $R^{091}$ is a $C_{1-6}$ alkyl group substituted with one biaryl group, a $C_{2-6}$ alkenyl group substituted with one aryl group, a $C_{2-6}$ alkynyl group substituted with one aryl group, an aryl group which may be substituted with one group selected from the group consisting of "a halogen atom, a $C_{1-6}$ alkyl group, a $C_{1-6}$ alkylamino group, and a $C_{7-11}$ aralkyloxy group", or a biaryl group.

When $R^{10}$ is a group represented by the formula —$X^{091}$-$A^{091}$-$X^{092}$—$R^{091}$, it is preferred that $X^{091}$ is a group represented by the formula -$A^{094}$-O—, and in this case, it is preferred that $A^{094}$ is a divalent $C_{1-10}$ aliphatic hydrocarbon group. It is more preferred that $X^{091}$ is a group represented by the formula —$CH_2$—O—. Further, it is preferred that $A^{091}$ is an arylene group, more preferably phenylene group. It is preferred that $X^{092}$ is a single bond, or a group represented by the formula —$N(R^{25})$—.

Further, when $R^{10}$ is a group represented by the formula —$X^{091}$-$A^{091}$-$X^{092}$—$R^{091}$, it is preferred that $R^{091}$ is a $C_{1-6}$ alkyl group which may be substituted with 1 to 3 groups selected from the group consisting of "hydroxyl group, a $C_{3-8}$ cycloalkyl group, and an aryl group (the aryl group may be substituted with 1 to 3 $C_{1-6}$ alkyl groups)", a $C_{2-6}$ alkenyl group which may be substituted with 1 to 3 aryl groups, an aryl group, or a heterocyclic group which may be substituted with 1 to 3 groups selected from the group consisting of "a $C_{1-6}$ alkyl group, and a $C_{8-12}$ aralkyloxycarbonyl group", and it is further preferred that $R^{091}$ is a $C_{1-6}$ alkyl group which may be substituted with 1 to 3 groups selected from the group consisting of "hydroxyl group, a $C_{3-8}$ cycloalkyl group, and an aryl group (the aryl group may be substituted with 1 to 3 $C_{1-6}$ alkyl groups)", a $C_{2-6}$ alkenyl group which may be substituted with 1 to 3 aryl groups, or an aryl group.

It is preferred that $R^{11}$ is hydrogen atom.

It is preferred that $R^{12}$ and $R^{13}$ independently represent $C_{1-6}$ alkyl groups, and it is more preferred that both $R^{12}$ and $R^{13}$ represent methyl groups.

It is preferred that $R^{15}$ is a $C_{1-6}$ alkyl group substituted with a biaryl group.

The salt of the 10a-azalide compound represented by the aforementioned formula (I) may be an acid addition salt or a base addition salt. Examples of the acid addition salt include, for example, salts with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid, laurylsulfuric acid, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer, and carboxyvinyl polymer, and examples of the base addition salt include salts with an inorganic base such as sodium salts, potassium salts and calcium salts, salts with an organic amine such as morpholine and piperidine, and salts with an amino acid, but the salt is not limited to these. Among these, pharmaceutically acceptable salts are preferred.

The 10a-azalide compounds of the present invention represented by the aforementioned formula (I) and salts thereof may exist as hydrates or arbitrary solvates, and these hydrates and solvates also fall within the scope of the present invention. Further, the 10a-azalide compounds of the present invention represented by the aforementioned formula (I) have two or more asymmetric carbons, and these asymmetric carbons may be in arbitrary configurations. Stereoisomers such as optical isomers and diastereoisomers in pure forms based on these asymmetric carbons, arbitrary mixtures of stereoisomers, racemates, and the like are all encompassed within the scope of the present invention. Moreover, the 10a-azalide compounds of the present invention represented by the aforementioned formula (I) may have one or more double bonds, and geometrical isomers thereof originating in a double bond or a ring structure may also exist. It should be understood that arbitrary geometrical isomers of pure forms or arbitrary mixtures of geometrical isomers fall within the scope of the present invention. One of the preferred stereoisomers of the 10a-azalide compound in which the ring A is represented by the formula (VI) is represented by the formula (VIII), and one of the preferred stereoisomers of the 10a-azalide compound in which the ring A is represented by the formula (VII) is represented by the formula (IX), as follows. However, the compounds of the present invention are not limited to the following specific stereoisomers. The configurations shown in the following structural formulas are absolute configurations, and represented with usual indications.

[Formula 8]

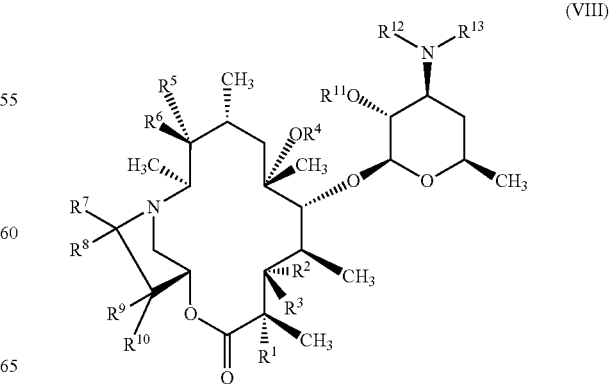

(VIII)

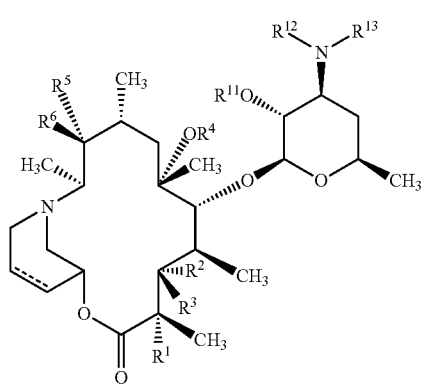

(IX)

The 10a-azalide compounds of the present invention can be synthesized by, for example, the following methods. However, the preparation methods of the 10a-azalide compounds of the present invention are not limited to these methods.

Although all of the 10a-azalide compounds of the present invention are novel compounds not having been described in literatures, they can be prepared by known methods described in literatures, or similar methods. Examples of such literatures include S. R. Sandler et al., Organic Functional Group Preparations, Academic Press Inc., New York and London, 1968; S. R. Wagner et al., Synthetic Organic Chemistry, John Wiley, 1961; R. C. Larock, Comprehensive Organic Transformations, 1989; L. A. Paquette et al., Encyclopedia of Reagents for Organic Synthesis, 1995; Compendium of Organic Synthetic Methods, and the like.

In the text of the specification, the term base means, unless specifically indicated, for example, an organic base (e.g., an amine such as triethylamine, diisopropylethylamine, pyridine and 4-dimethylaminopyridine, a metal alkoxide such as sodium methoxide, and the like), or an inorganic base (e.g., an alkali metal carbonate such as sodium carbonate and potassium carbonate, an alkaline earth metal carbonate such as calcium carbonate, a metal hydroxide such as sodium hydroxide and potassium hydroxide, and the like), but the base is not limited to these.

The term solvent means, unless specifically indicated, for example, a polar solvent (e.g., water, an alcohol type solvent such as methanol, and the like), an inert solvent (e.g., a halogenated hydrocarbon type solvent such as chloroform and methylene chloride, an ether type solvent such as diethyl ether, tetrahydrofuran and 1,4-dioxane, an aprotic solvent such as dimethylformamide, dimethyl sulfoxide and acetonitrile, an aromatic hydrocarbon type solvent such as toluene, a hydrocarbon such as cyclohexane, and the like), or a mixed solvent thereof, but the solvent is not limited to these.

The condensing agent means, unless specifically indicated, for example, a chloroformic acid ester (e.g., isobutyl chloroformate, ethyl chloroformate, methyl chloroformate and the like), an acid chloride (e.g., pivaloyl chloride, oxalyl chloride, 2,4,6-trichlorobenzoyl chloride and the like), a dehydration condensing agent (e.g., a carbodiimide reagent such as 1-ethyl-3-[3-(dimethylamino)propyl]carbodiimide hydrochloride and dicyclohexylcarbodiimide), carbonyldiimidazole, 2-chloro-1-methylpyridinium iodide salt, and the like), and the like, but the condensing agent is not limited to these.

In the following schemes, Me represents methyl group, and the same shall apply to the following text in this specification.

<Scheme 1>

[Formula 9]

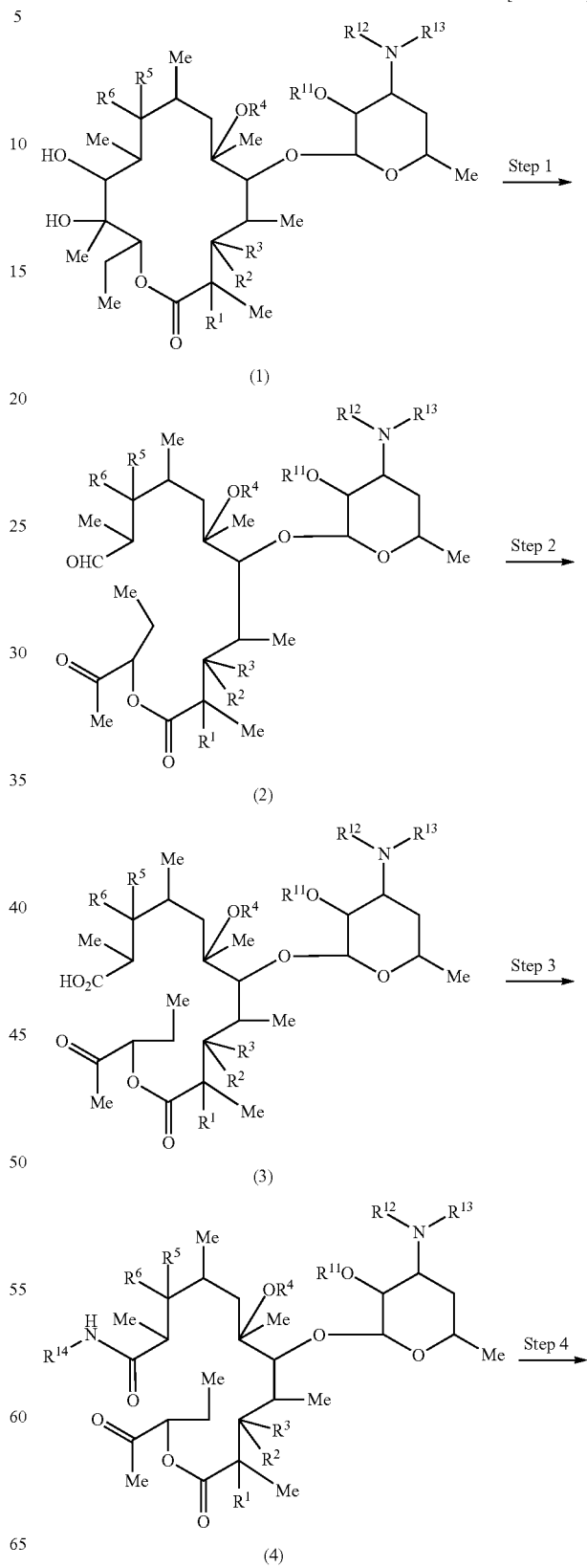

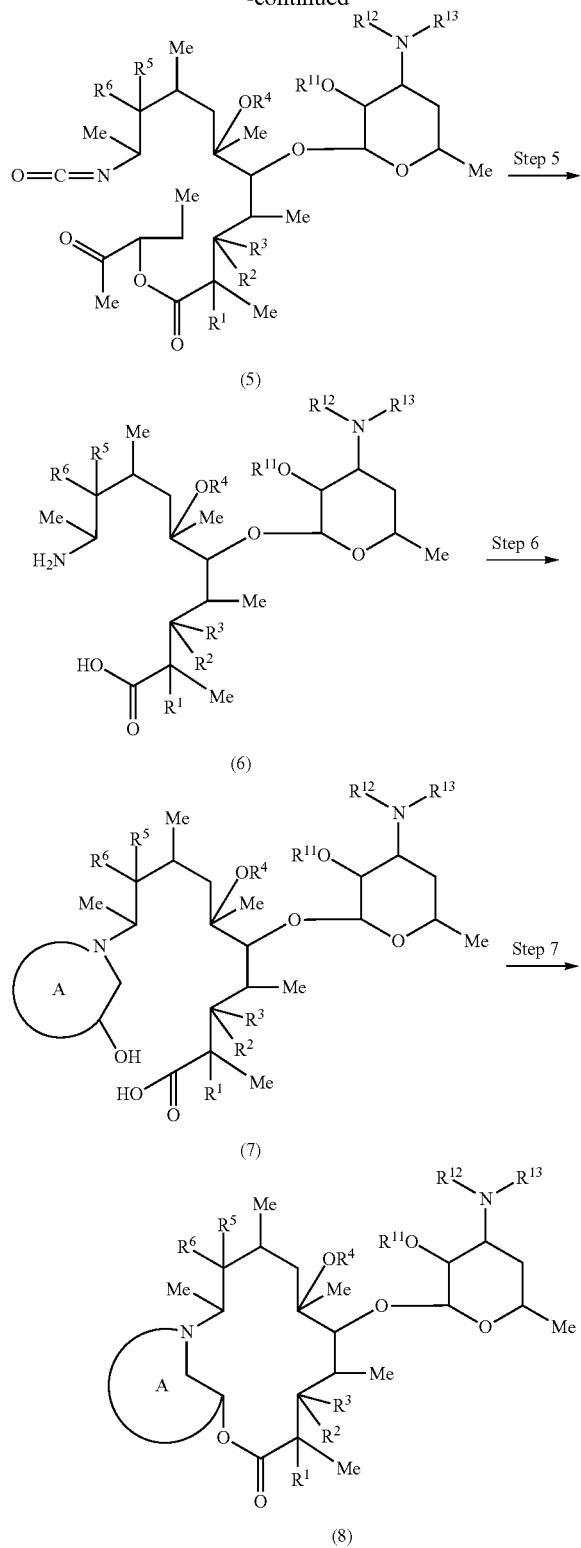

(In the formula, $R^{14}$ represents hydrogen atom, or hydroxyl group, and the other symbols have the same meanings as those defined above.)

[Step 1]

The erythromycin analogue compounds represented by the formula (1) can be synthesized by, for example, the methods described in the publications (WO99/28332, WO02/096922, U.S. Pat. No. 6,420,535, WO01/077134, WO00/069875, WO05/030786, WO04/078770, US2006/0142214, and the like), or obtained by reducing any of the compounds wherein $R^5$ and $R^6$ combine together to form oxo group with a hydride reducing agent (for example, sodium borohydride, and lithium triethylborohydride are preferred) or the like, and then converting hydroxyl groups into other substituents defined as $R^5$ and $R^6$ according to a generally used functional group conversion method. The compounds represented by the formula (2) can be prepared according to the methods described in the publications (e.g., WO03/014136 and the like) by using a compound represented by the formula (1) (a compound wherein $R^5$ is a protected hydroxyl group, and $R^6$ is hydrogen atom is preferred) as a starting material, specifically, by stirring a compound represented by the formula (1) with an oxidizing agent (examples include, for example, lead tetraacetate, periodic acid salts and the like, and among them, lead tetraacetate is preferred) in a solvent (e.g., chloroform is preferred). The reaction temperature is chosen from the range of, for example, from −20° C. to the boiling point of the solvent, and within that range, a temperature of from 0° C. to room temperature is preferred. The compounds represented by the formula (2) can be used in the following step 2 without isolation from the reaction system.

[Step 2]

The compounds represented by the formula (3) can be obtained by stirring a compound represented by the formula (2) with an oxidizing agent (examples include, for example, sodium chlorite, sodium perchlorate, potassium permanganate, and the like, and among them, sodium chlorite is preferred) in a solvent (for example, a mixed solvent of chloroform, tetrahydrofuran, or tert-butyl alcohol and water is preferred). The reaction temperature is selected from the range of, for example, −20° C. to the boiling temperature of the solvent, and a temperature of from 0° C. to room temperature is especially preferred.

[Step 3]

The compounds represented by the formula (4) can be obtained by stirring a compound represented by the formula (3) with a condensing agent (for example, a chloroformic acid ester is preferred) in a solvent (for example, chloroform is preferred) in the presence or absence of an organic base (for example, an amine such as triethylamine is preferred), adding ammonia when $R^{14}$ is hydrogen atom, or adding hydroxylamine when $R^{14}$ is hydroxyl group, and then stirring the mixture. Although ammonia is preferably added as ammonia gas, it may also be added as a solution in a solvent (for example, water, alcohol, dioxane and the like). Hydroxylamine can be used in a state of a solution in a solvent (examples of the solvent include, for example, water, alcohol, dioxane and the like, and water is especially preferred). The reaction temperature is selected from the range of, for example, −20° C. to room temperature, and a temperature of from −5° C. to 5° C. is especially preferred.

[Step 4]

The compounds represented by the formula (5) can be obtained by stirring a compound represented by the formula (4) wherein $R^{14}$ is hydrogen atom in a solvent (e.g., ethyl acetate and the like) in the presence of iodobenzene diacetate, iodobenzene bistrifluoroacetate or the like. Further, the compounds represented by the formula (5) can also be obtained by stirring a compound represented by the formula (4) wherein $R^{14}$ is hydroxyl group in a solvent (for example, tetrahydrofuran is especially preferred) in the presence of a sulfonyl chloride (examples include, for example, p-toluenesulfonyl chloride, methanesulfonyl chloride and the like, and among them, p-toluenesulfonyl chloride is especially preferred). The reaction temperature is chosen from the range of, for example, from −20° C. to the boiling point of the solvent, and within that range, a temperature of from 0° C. to room temperature is preferred. The compounds of the formula (5) can be used for the following step 5 without isolation from the reaction system.

[Step 5]

The compounds represented by the formula (6) can be obtained by stirring a compound represented by the formula (5) in an aqueous solution of a metal hydroxide (examples include, for example, lithium hydroxide, sodium hydroxide and the like, and among them, lithium hydroxide is preferred), or in a mixed solvent of such an aqueous solution and an alcohol solvent such as methanol and ethanol, tetrahydrofuran, or the like. The reaction temperature is selected from the range of, for example, from 0° C. to the boiling temperature of the solvent, and a temperature of from 0° C. to room temperature is especially preferred.

[Step 6]

In the step 6, a compound represented by the formula (9) can be used for the reaction.

[Formula 10]

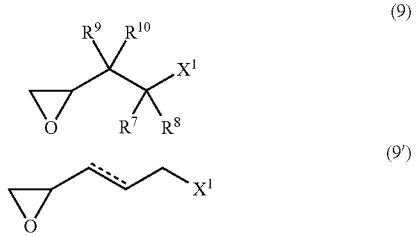

[In the formulas, $X^1$ represents a leaving group (e.g., chloro group, bromo group, iodo group, methanesulfonyloxy group, p-toluenesulfonyloxy group, and the like), and the other symbols have the same meanings as those defined above.]

The compounds represented by the formula (7) wherein the ring A is a group represented by the formula (VI) or (VII) can be obtained by reacting a compound represented by the formula (6) with an epoxide represented by the formula (9) or (9') in an inert solvent (for example, tetrahydrofuran is preferred) in the presence or absence of a Lewis acid (for example, ytterbium triflate and the like) and in the presence or absence of a base (examples include, for example, an amine such as triethylamine, diisopropylethylamine, and pyridine, and among these, triethylamine is preferred) with heating. The reaction temperature of the aforementioned reaction is chosen from the range of, for example, from room temperature to 120° C., and within that range, a temperature of from 50 to 100° C. is preferred.

[Step 7]

The compounds represented by the formula (8) wherein the ring A is a group represented by the formula (VI) or (VII) can also be obtained by a method of reacting a compound represented by the formula (7) with a condensing agent (for example, 2,4,6-trichlorobenzoyl chloride is preferred) in a solvent (for example, tetrahydrofuran is preferred) in the presence of an organic base (an amine such as triethylamine is preferred), and performing a reaction using the resulting reaction solution and a solution of a base (for example, 4-dimethylaminopyridine is preferred) in an inert solvent (for example, toluene or acetonitrile is preferred), or a method of reacting a compound represented by the formula (7) with a solution of an acid anhydride (for example, 2-nitro-6-methylbenzoic anhydride is preferred) and a base (for example, 4-dimethylaminopyridine is preferred) in an inert solvent (examples include, for example, a mixed solution of dichloromethane, chloroform, toluene, and acetonitrile, and dichloromethane, or chloroform is preferred). The reaction temperature of the aforementioned reaction is preferably a temperature in the range of from room temperature to the boiling temperature of the solvent.

<Scheme 2>

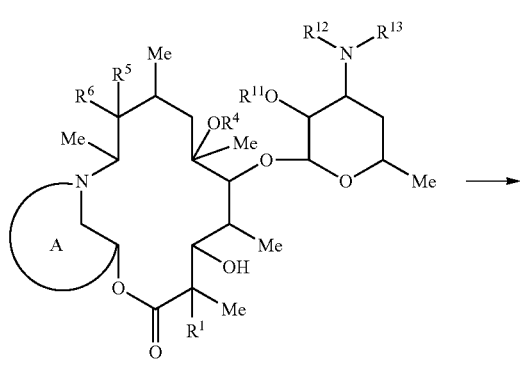

(10)

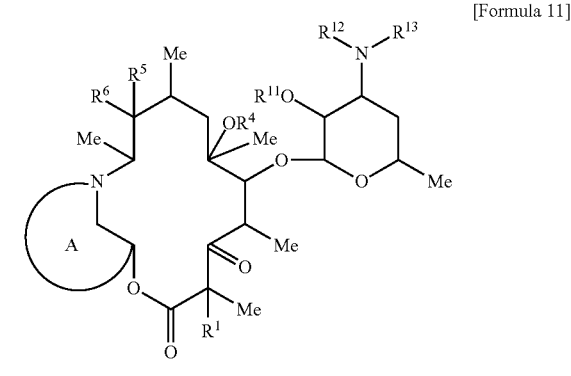

[Formula 11]

(11)

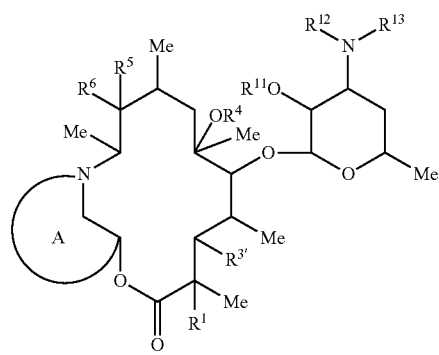

(12)

(In the formulas, $R^{3'}$ is:
a group represented by the formula $—X^{031}—R^{031}$,
$X^{031}$, and $R^{031}$ have the same meanings as those defined above, and
the other symbols have the same meanings as those defined above.)

The compounds represented by the formula (11) can be obtained by using a compound represented by the formula (10) as a starting material and oxidizing it by a method similar to the methods described in the literatures (Tetrahedron, 1978, vol. 34, p. 1651; Journal of American Chemical Society, 1972, vol. 94, p. 7586), i.e., Swern oxidation, Corey-Kim Oxidation, or the like.

The compounds represented by the formula (12) wherein $X^{031}$ is a group represented by the formula —O— can be obtained by a method similar to the methods described in the publications (for example, WO94/17088 and the like), i.e., by a method of reacting a compound represented by the formula (10) and a corresponding alkyl halide or the like in an inert solvent in the presence of a base.

The compounds represented by the formula (12) wherein $X^{031}$ is a group represented by the formula —OCO— can be obtained by a method similar to the methods described in the publications (U.S. Pat. No. 6,191,118, WO04/101584, WO05/030786 and the like), specifically, by a method of reacting a compound represented by the formula (10) in an inert solvent in the presence of a corresponding carboxylic acid and a condensing agent, or with a corresponding acid anhydride or a corresponding acid chloride in an inert solvent in the presence or absence of a base. The reaction temperature is selected from the range of, for example, from 0° C. to the boiling temperature of the solvent. Further, the compounds represented by the formula (12) wherein $X^{031}$ is a group represented by the formula —OCON($R^{20}$)— can be obtained by a method similar to the method described in the publication (U.S. Pat. No. 5,523,399), specifically, by a method of reacting a compound represented by the formula (10) and carbonyldiimidazole in an inert solvent, and then adding a corresponding amine, a method of reacting triphosgene in an inert solvent in the presence of a base, and then adding a corresponding amine, or a method of reacting a compound represented by the formula (10) and a corresponding isocyanate in an inert solvent. The reaction temperature of the aforementioned reactions is preferably in the range of from room temperature to the boiling temperature of the solvent.

Further, among the compounds represented by the formula (8) shown in Scheme 1, those compounds shown in Scheme 3 can also be obtained by the steps shown in Scheme 3, as well as the steps shown in Scheme 1.

<Scheme 3>

[Formula 12]

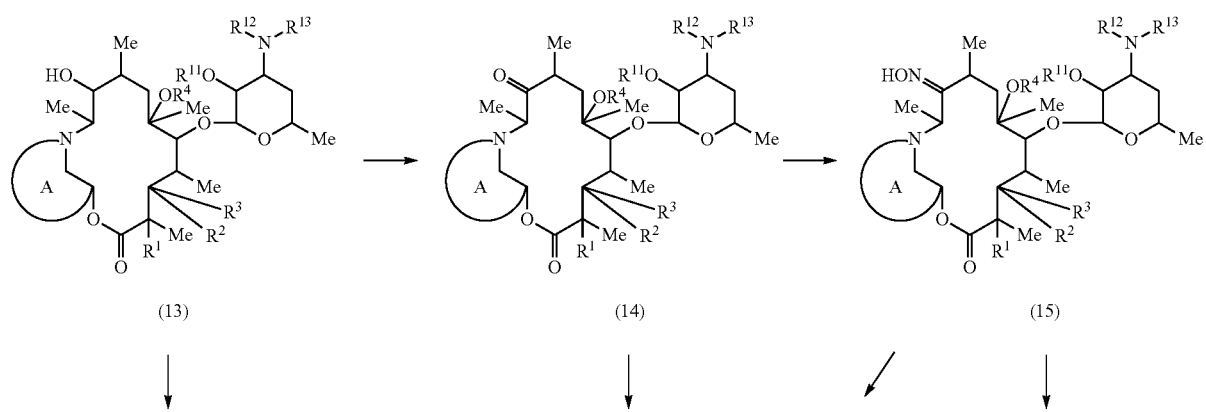

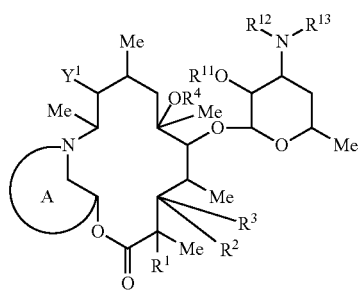 (16)

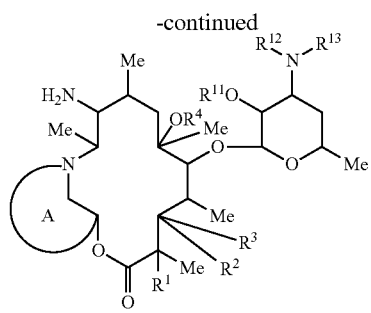 (18)

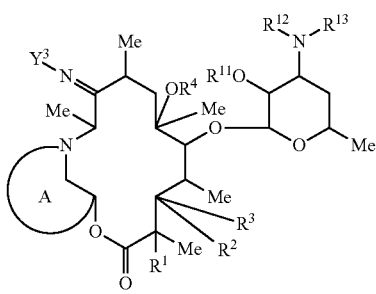 (17)

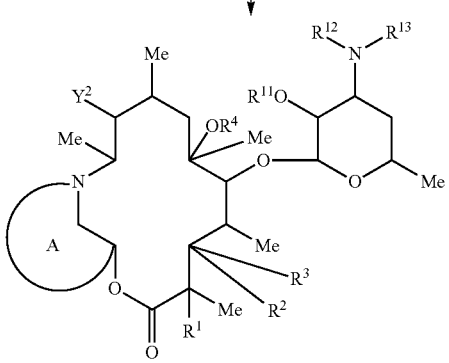 (19)

(In the formulas, $Y^1$ is:
a group represented by the formula —$X^{051'}$—$R^{051}$, or
a group represented by the formula —$X^{051'}$-$A^{051}$-$X^{052}$—$R^{051}$,
  wherein $X^{051'}$ is:
  a group represented by the formula —O—, or
  a group represented by the formula —OCON($R^{22}$)—, and
  $A^{051}$, $X^{052}$, $R^{051}$, and $R^{22}$ have the same meanings as those defined above,
$Y^2$ is:
a group represented by the formula —$X^{051''}$—$R^{051}$, or
a group represented by the formula —$X^{051''}$-$A^{051}$-$X^{052}$—$R^{051}$,
  wherein $X^{051''}$ is:
  a group represented by the formula —N($R^{22}$)—, or
  a group represented by the formula —N($R^{22}$)CO—, and
  $A^{051}$, $X^{052}$, $R^{051}$ and $R^{22}$ have the same meanings as those defined above, and
$Y^3$ is:
a group represented by the formula —$X^{053}$—$R^{052}$, or
a group represented by the formula —$X^{053}$-$A^{052}$-$X^{054}$—$R^{052}$,
  $X^{053}$, $A^{052}$, $X^{054}$ and $R^{052}$ have the same meanings as those defined above, and
the other symbols have the same meanings as those defined above.)

The compounds represented by the formula (14) can be obtained by using a compound represented by the formula (13) as a starting material and oxidizing it by a method similar to the methods described in the literatures (Tetrahedron, 1978, vol. 34, p. 1651; Journal of American Chemical Society, 1972, vol. 94, p. 7586), i.e., Swern oxidation, Corey-Kim Oxidation, or the like.

The compounds represented by the formula (15) can be obtained by reacting a compound represented by the formula (14) and a hydroxylamine salt such as hydroxylamine hydrochloride or hydroxylamine in a solvent (for example, methanol is preferred) in the presence or absence of a base (for example, imidazole is preferred). The reaction temperature of the aforementioned reaction is preferably in the range of from room temperature to the boiling temperature of the solvent.

The compounds represented by the formula (16) wherein $X^{051'}$ is a group represented by the formula —O— can be obtained by using a compound represented by the formula (13) as a starting material, and reacting the compound with an alkyl halide or the like in an inert solvent (for example, tetrahydrofuran is preferred) in the presence or absence of a crown ether (for example, 18-crown-6-ether and the like) and in the presence of a base (for example, potassium hydroxide is preferred). The reaction temperature of the aforementioned reaction is preferably room temperature.

The compounds represented by the formula (16) wherein $X^{051'}$ is a group represented by the formula —OCON($R^{22}$)— can be obtained by a method of using a compound represented by the formula (13) as a starting material, reacting the compound with carbonyldiimidazole in the presence of a base (for example, pyridine is preferred) at a temperature in the range of from room temperature to 100° C., and reacting the resulting imidazocarbonyl compound with a corresponding amine in the presence of a base (for example, pyridine is preferred) at a temperature in the range of from room temperature to 50° C., or the compounds can also be obtained by a method of reacting a compound represented by the formula (13) with a corresponding isocyanate in a solvent (examples include, for example, toluene, pyridine, and the like, and pyridine is preferred) in the presence or absence of a base (for example, 1,4-diazabicyclo[2.2.2]octane is preferred). The reaction temperature of the aforementioned reactions is preferably in the range of from room temperature to the boiling temperature of the solvent.

The compounds represented by the formula (18) can be obtained by using a compound represented by the formula (14) as a starting material according to a method similar to the methods described in the literatures (Tetrahedron Letters, 1971, vol. 2, p. 195; Tetrahedron Letters, 1972, vol. 1, p. 29), specifically, by reacting the carbonyl group with hydrazine in a polar solvent to convert it into hydrazono group, and then reacting the resultant with sodium nitrite or the like, or by using a compound represented by the formula (15) as a starting material, reacting the compound with titanium chloride or the like to obtain an imino compound, and reducing the imino compound with a hydride reducing agent or the like.

The compounds represented by the formula (17) wherein $X^{053}$ is a group represented by the formula —O— can be obtained by using a compound represented by the formula (15) as a starting material according to a method similar to the method described in the publication (European Patent No. 284203 or WO93/13116), specifically, by reacting the compound with a corresponding alkyl halide or the like in an inert solvent in the presence or absence of crown ether (for example, 18-crown-6-ether and the like) and in the presence or absence of a base.

The compounds represented by the formula (17) wherein $X^{053}$ is a group represented by the formula —CO— can be obtained by using a compound represented by the formula (15) as a starting material, reacting the compound with titanium chloride or the like to obtain an imino compound, and reacting the imino compound with a corresponding acid chloride, acid anhydride, or the like in an inert solvent in the presence or absence of a base.

The compounds represented by the formula (19) wherein $X^{051''}$ is a group represented by the formula —N($R^{22}$)CO— can be obtained by reacting a compound represented by the formula (18) with a corresponding acid chloride or acid anhydride in a solvent (for example, a mixed solvent of ether and water is preferred) in the presence or absence of a base (examples include, for example, an amine such as pyridine and triethylamine, sodium carbonate, and the like, and sodium carbonate is preferred). The reaction temperature of the aforementioned reaction is preferably a temperature in the range of from 0° C. to room temperature.

The compounds represented by the formula (19) wherein $X^{051''}$ is a group represented by the formula —N($R^{22}$)— can be obtained by reacting a compound represented by the formula (18) with a corresponding aldehyde reagent in a solvent (for example, methanol is preferred) in the presence of a hydride reducing agent (for example, sodium triacetoxyborohydride, sodium cyanoborohydride, and the like). The reaction temperature of the aforementioned reaction is preferably room temperature.

Further, among the compounds represented by the formula (8) shown in Scheme 1, those compounds shown in Scheme 4 can also be obtained by the steps shown in Scheme 4, as well as the steps shown in Scheme 1.

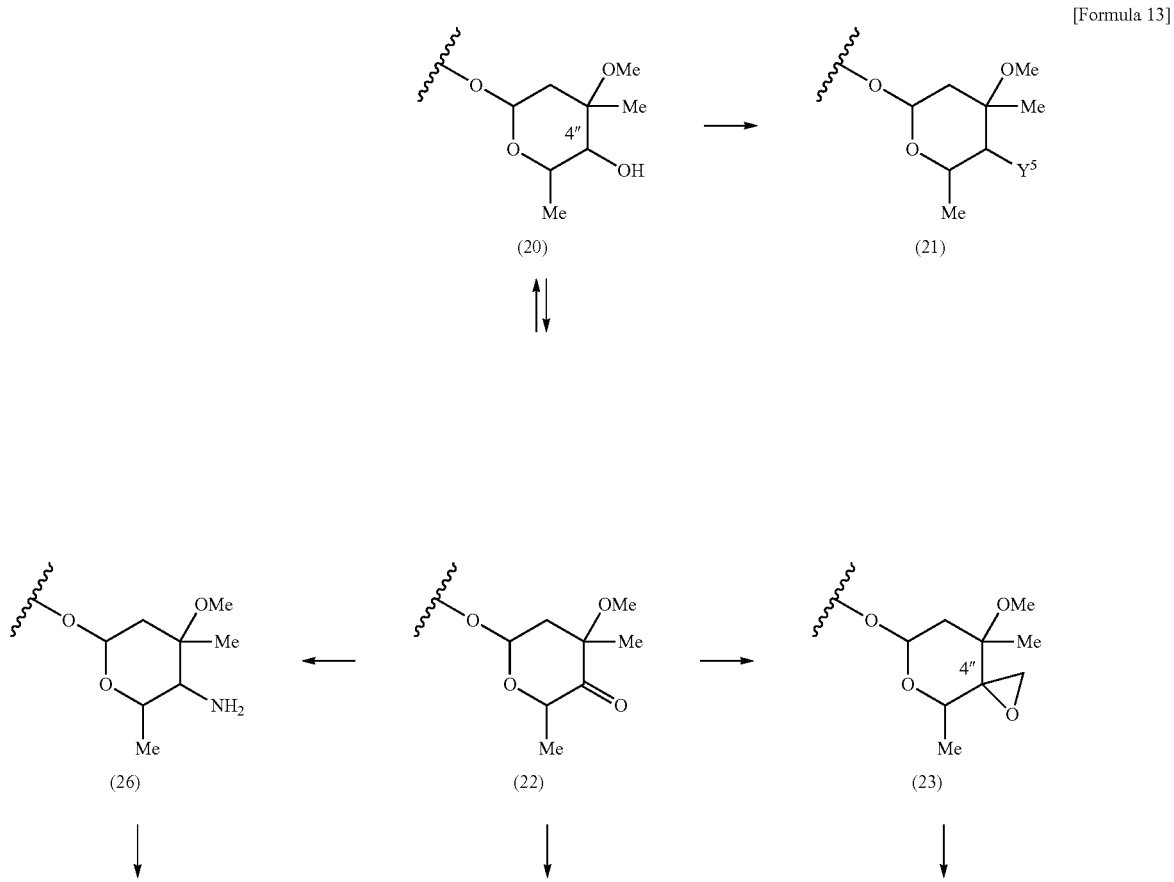

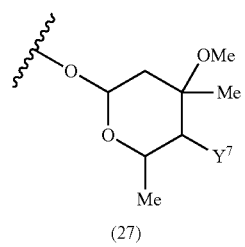

(27)

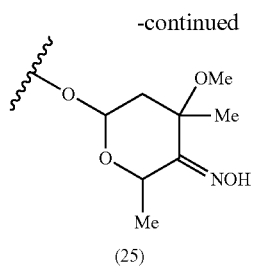

(25)

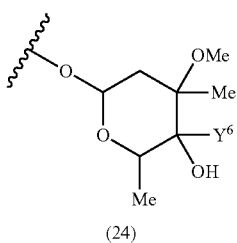

(24)

(The formulas (20) to (27) show conversion at the 4"-position of the compounds of the formula (I) wherein $R^2$ or $R^3$ is a group represented by the formula (II),
wherein, in the formulas, $Y^5$ is:
a group represented by the formula $—X^{331'}—R^{331}$,
a group represented by the formula $—X^{331'}\text{-}A^{331}\text{-}X^{332}—R^{331}$,
a group represented by the formula $—X^{331'}\text{-}A^{331}\text{-}X^{332}\text{-}A^{332}\text{-}X^{333}—R^{331}$, or
a group represented by the formula $—X^{331'}\text{-}A^{331}\text{-}X^{332}\text{-}A^{332}\text{-}X^{333}\text{-}A^{333}\text{-}X^{334}—R^{331}$,
wherein $X^{331'}$ is:
a group represented by the formula —O—,
a group represented by the formula —OCO—, or
a group represented by the formula $—OCON(R^{20})—$, and
$A^{331}$, $X^{332}$, $A^{332}$, $X^{333}$, $A^{333}$, $X^{334}$, $R^{331}$, and $R^{20}$ have the same meanings as those defined above,
$Y^6$ is:
a group represented by the formula $—X^{335'}—R^{332}$
a group represented by the formula $—X^{335'}\text{-}A^{334}\text{-}X^{336}—R^{332}$, or
a group represented by the formula $—X^{335'}\text{-}A^{334}\text{-}X^{336}\text{-}A^{335}\text{-}X^{337}—R^{332}$,
wherein $X^{335'}$ is:
a single bond,
a group represented by the formula $—CH_2N(R^{20})—$,
a group represented by the formula $—CH_2O—$, or
a group represented by the formula $—CH_2S(O)_p—$, and
$A^{334}$, $X^{336}$, $A^{335}$, $X^{337}$, $R^{332}$, $R^{20}$, and p have the same meanings as those defined above, and
$Y^7$ is:
a group represented by the formula $—X^{331''}—R^{331}$,
a group represented by the formula $—X^{331''}\text{-}A^{331}\text{-}X^{332}—R^{331}$,
a group represented by the formula $—X^{331''}\text{-}A^{331}\text{-}X^{332}\text{-}A^{332}\text{-}X^{333}—R^{331}$, or
a group represented by the formula $—X^{331''}\text{-}A^{331}\text{-}X^{332}\text{-}A^{332}\text{-}X^{333}\text{-}A^{333}\text{-}X^{334}—R^{331}$,
wherein $X^{331''}$ is:
a group represented by the formula $—N(R^{20})—$, or
a group represented by the formula $—N(R^{20})CO—$, and
$A^{331}$, $X^{332}$, $A^{332}$, $X^{333}$, $A^{333}$, $X^{334}$, $R^{331}$, and $R^{20}$ have the same meanings as those defined above.)

The compounds represented by the formula (21) wherein $X^{331'}$ is a group represented by the formula —OCO— can be obtained by a method similar to the methods described in the publications (for example, European Patent No. 895999) by using a compound represented by the formula (20) as a starting material, specifically, by reacting the compound with a corresponding carboxylic acid in the presence of a condensing agent.

The compounds represented by the formula (21) wherein $X^{331'}$ is a group represented by the formula —O— can be obtained by using a compound represented by the formula (20) as a starting material, and reacting the compound with a corresponding alkyl halide or the like in a solvent (for example, tetrahydrofuran is preferred) in the presence or absence of a crown ether (for example, 18-crown-6-ether and the like) and in the presence of a base (for example, potassium hydroxide is preferred).

The compounds represented by the formula (21) wherein $X^{331'}$ is a group represented by the formula $—OCON(R^{20})—$ can be obtained by a method similar to the methods described in the publications (for example, European Patent No. 895999) by using a compound represented by the formula (20) as a starting material, specifically, by reacting the compound, via an imidazocarbonyl compound, with a corresponding amine.

The compounds represented by the formula (22) can be obtained by using a compound represented by the formula (20) as a starting material and oxidizing it by a method similar to the methods described in the literatures (Tetrahedron, 1978, vol. 34, p. 1651; Journal of American Chemical Society, 1972, vol. 94, p. 7586), i.e., Swern oxidation, Corey-Kim Oxidation, or the like.

The compounds represented by the formula (23) wherein the steric configuration of the 4"-position is the (R)-configuration can be obtained by a method similar to the methods described in the publications (for example, WO98/56801), specifically, by reacting a compound represented by the formula (22) with $(CH_3)_3SX^2$ (examples of $X^2$ include, for example, a halogen, $—BF_4$ and $—PF_6$, and iodine is preferred) in a solvent (examples include, for example, tetrahydrofuran, ether, dimethylformamide, dimethyl sulfoxide, and the like, and two or more kinds of these may be used as a mixture) in the presence of an organic base or an inorganic base (NaH is preferred). The reaction temperature of the aforementioned reaction is chosen from the range of 0 to 60° C., and it is preferably in the range of from 0° C. to room temperature.

The compounds represented by the formula (23) wherein the steric configuration of the 4"-position is the (S)-configuration can be obtained by a method similar to the methods described in the publications (for example, WO98/56801), specifically, by reacting a compound represented by the formula (22) with $(CH_3)_3SX^3$ (examples of $X^3$ include, for example, a halogen, $—BF_4$ and $—PF_6$, and $—BF_4$ is preferred) in a solvent (examples include, for example, tetrahydrofuran, ether, dimethylformamide, dimethyl sulfoxide, and the like, and two or more kinds of these may be used as a mixture) in the presence of an organic base or an inorganic base. The reaction temperature of the aforementioned reaction is chosen from the range of −30 to 60° C., and it is preferably in the range of from −30° C. to room temperature.

The compounds represented by the formula (24) wherein $X^{335'}$ is a group represented by the formula $—CH_2N(R^{20})—$ can be obtained by a method similar to the methods described in the publications (for example, WO98/56801), specifically, by reacting a compound represented by the formula (23) with a corresponding amine or the like in the presence or absence of a salt containing a halogen ion (examples include, for example, potassium iodide, ammonium chloride, pyridine hydrochloride, and the like) and in the presence or absence of a solvent (for example, water, methanol, ethanol, tetrahydrofuran, and the like are preferred). Further, the compounds represented by the formula (24) wherein $X^{335'}$ is a group represented by the formula —$CH_2O$—, or a group represented by the formula —$CH_2S$— can be obtained by using a corresponding alcohol reagent or thiol reagent instead of the amine reagent in the aforementioned reaction. The resulting sulfide compound wherein $X^{335'}$ is a group represented by the formula —$CH_2S$— can be converted into a sulfoxide or sulfone by oxidization with an oxidizing agent.

The compounds represented by the formula (25) can be obtained by reacting a compound represented by the formula (22) and a hydroxylamine salt such as hydroxylamine hydrochloride or hydroxylamine in a solvent (for example, methanol is preferred) in the presence or absence of a base (for example, imidazole is preferred). The reaction temperature of the aforementioned reaction is preferably in the range of from room temperature to the boiling temperature of the solvent.

The compounds represented by the formula (26) can be obtained by reacting a compound represented by the formula (22) with a reducing agent (examples include, for example, sodium triacetoxyborohydride, sodium cyanoborohydride, and sodium borohydride, and sodium cyanoborohydride is preferred) in a solvent (for example, methanol is preferred) in the presence of an ammonium salt (examples include, for example, ammonium acetate, ammonium carbonate, ammonium chloride, and the like, and ammonium acetate is preferred). The reaction temperature of the aforementioned reaction is preferably in the range of from room temperature to 50° C.

The compounds represented by the formula (27) wherein $X^{331'''}$ is a group represented by the formula —$N(R^{20})CO$— can be obtained by reacting a compound represented by the formula (26) with a corresponding acid chloride, acid anhydride, or the like in an inert solvent in the presence or absence of a base. Those compounds wherein $X^{331'''}$ is a group represented by the formula —$N(R^{20})$— can be obtained by stirring a corresponding aldehyde reagent in the presence of a hydride reducing agent (for example, sodium triacetoxyborohydride, sodium cyanoborohydride, and the like) in a solvent. The reaction temperature of the aforementioned reaction is preferably in the range of from 0 to 50° C.

Further, among the compounds represented by the formula (8) shown in Scheme 1, those compounds shown in Scheme 5 can also be obtained by the steps shown in Scheme 5, as well as the steps shown in Scheme 1.

(The formulas (28) to (30) show conversion at the 4''-position of the compounds of the formula (I) wherein $R^2$ or $R^3$ is a group represented by the formula (II), wherein $Y^8$ is:

a group represented by the formula —$X^{335'''}$—$R^{332}$, a group represented by the formula —$X^{335'''}$-$A^{334}$-$X^{336}$—$R^{332}$, or a group represented by the formula —$X^{335'''}$-$A^{334}$-$X^{336}$-$A^{335}$-$X^{337}$—$R^{332}$, wherein $X^{335'''}$ is:

a group represented by the formula —$CH_2N(R^{20})CO$—, a group represented by the formula —$CH_2N(R^{20})CO_2$—, or a group represented by the formula —$CH_2N(R^{20})CON(R^{21})$—, and $A^{334}$, $X^{336}$, $A^{335}$, $X^{337}$, $R^{332}$, $R^{20}$, and $R^{21}$ have the same meanings as those defined above.)

The compounds represented by the formula (29) can be obtained by reacting a compound represented by the formula (28) and a corresponding acid chloride, a corresponding acid anhydride, a corresponding isocyanate, a corresponding chloroformate, or the like in an inert solvent in the presence or absence of a base. The reaction temperature of the aforementioned reaction is preferably in the range of from 0° C. to the boiling temperature of the solvent. Among the compounds represented by the formula (29), those compounds wherein $R^{20}$ is a $C_{1-6}$ alkyl group which may be substituted with 1 to 3 groups selected from the group A can be obtained by monoalkylating the amino group of a compound represented by the formula (28) and then acylating the monoalkylated group.

The compounds represented by the formula (30) can be obtained by reacting a compound represented by the formula (28) with triphosgene or thiocarbonyldiimidazole in an inert solvent (for example, chloroform or dichloromethane is preferred) in the presence or absence of a base (for example, pyridine is preferred). The reaction temperature of the aforementioned reaction is preferably room temperature.

Further, among the compounds represented by the formula (8) shown in Scheme 1, those compounds shown in Scheme 6 can also be obtained by the steps shown in Scheme 6, as well as the steps shown in Scheme 1.

<Scheme 5>

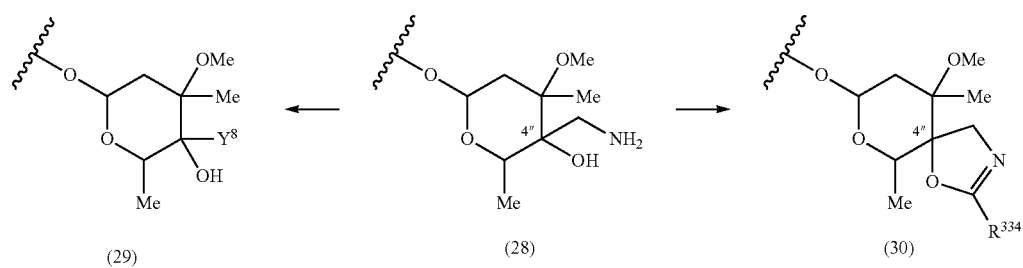

[Formula 14]

<Scheme 6>

[Formula 15]

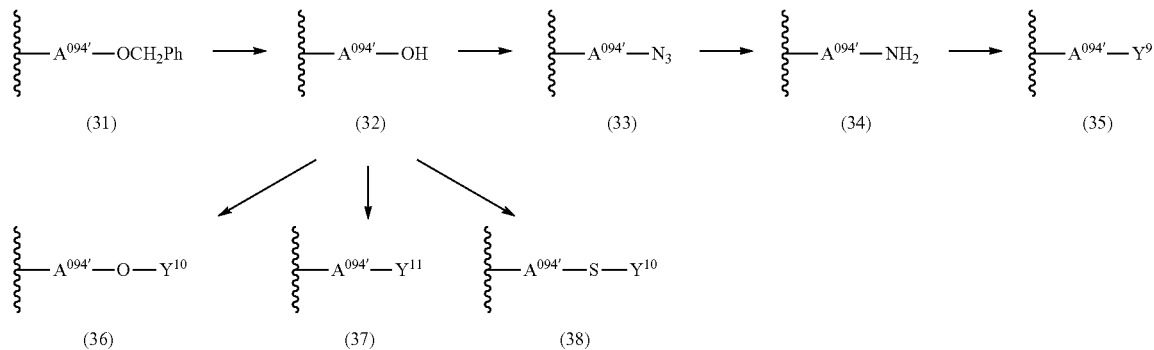

(The formulas (31) to (38) show conversion of $R^9$ and $R^{10}$ of the compounds of the formula (I),
wherein $A^{094'}$ is a divalent aliphatic hydrocarbon group,
$Y^9$ is:
a group represented by the formula $-X^{091'}-R^{091}$,
a group represented by the formula $-X^{091'}-A^{091}-X^{092}-R^{091}$,
a group represented by the formula $-X^{091'}-A^{091}-X^{092}-A^{092}-X^{093}-R^{091}$, or
a group represented by the formula $-X^{091'}-A^{091}-X^{092}-A^{092}-X^{093}-A^{093}-X^{094}-R^{091}$,
wherein $X^{091'}$ is:
a group represented by the formula $-N(R^{23})-$,
a group represented by the formula $-N(R^{23})CO-$,
a group represented by the formula $-N(R^{23})CO_2-$,
a group represented by the formula $-N(R^{23})CON(R^{24})-$, or
a group represented by the formula $-N(R^{23})SO_2-$, and
$A^{091}, X^{092}, A^{092}, X^{093}, A^{093}, X^{094}, R^{091}, R^{23}$, and $R^{24}$ have the same meanings as those defined above.
$Y^{10}$ is:
a group represented by the formula $-R^{091'}$,
$R^{091'}$ is an aryl group which may be substituted with 1 to 5 groups selected from the group B, a heterocyclic group which may be substituted with 1 to 5 groups selected from the group B, or a biaryl group which may be substituted with 1 to 5 groups selected from the group B,
the group B has the same meaning as that defined above, and
$Y^{11}$ is:
a group represented by the formula $-X^{091''}-R^{091}$,
a group represented by the formula $-X^{091''}-A^{091}-X^{092}-R^{091}$,
a group represented by the formula $-X^{091''}-A^{091}-X^{092}-A^{092}-X^{093}-R^{091}$, or
a group represented by the formula $-X^{091''}-A^{091}-X^{092}-A^{092}-X^{093}-A^{093}-X^{094}-R^{091}$,
wherein $X^{091''}$ is:
a group represented by the formula $-OCON(R^{23})-$,
a group represented by the formula $-OCO-$, or
a group represented by the formula $-OCO_2-$, and
$A^{091}, X^{092}, A^{092}, X^{093}, A^{093}, X^{094}, R^{091}$, and $R^{23}$ have the same meanings as those defined above.)

The compounds represented by the formula (32) can be obtained by reacting a compound represented by the formula (31) in a solvent (examples include, for example, methanol, ethanol, tetrahydrofuran, ethyl acetate, water, 1,4-dioxane, and acetic acid, and two or more kinds of these solvents may be used as a mixture) in the presence of a palladium catalyst (for example, palladium hydroxide, palladium/carbon, and the like are preferred) and in the presence of a hydrogen source (examples include, for example, formic acid, ammonium formate, and hydrogen, and hydrogen is preferred). The reaction temperature of the aforementioned reaction is preferably in the range of from room temperature to 50° C.

The compounds represented by the formula (33) can be obtained by reacting a compound represented by the formula (32) with methanesulfonyl chloride, p-toluenesulfonyl chloride, or the like in a solvent in the presence of a base to obtain a sulfonate, and reacting the resulting sulfonate with sodium azide in a solvent (for example, dimethylformamide, dimethyl sulfoxide and the like are preferred). The reaction temperature of the aforementioned reaction is preferably in the range of from room temperature to 80° C.

The compounds represented by the formula (34) can be obtained by reacting a compound represented by the formula (33) in a solvent (examples include, for example, methanol, ethanol, tetrahydrofuran, and ethyl acetate, and two or more kinds of these solvents may be used as a mixture) in the presence of a palladium catalyst (for example, palladium/carbon, and the like are preferred) and in the presence of a hydrogen source (for example, hydrogen and the like are preferred).

The compounds represented by the formula (35) wherein $X^{091'}$ is a group represented by the formula $-N(R^{23})CO-$, the formula $-N(R^{23})CO_2-$, the formula $-N(R^{23})CON(R^{24})-$, or the formula $-N(R^{23})SO_2-$ can be obtained by using a compound represented by the formula (34) as a starting material, and reacting the compound with a corresponding acid chloride, a corresponding acid anhydride, a corresponding chloroformate, a corresponding isocyanate, a corresponding sulfonyl chloride, or the like in an inert solvent in the presence or absence of a base. Further, the compounds wherein $X^{091'}$ is a group represented by the formula $-N(R^{23})-$ can be obtained by stirring a corresponding aldehyde reagent in a solvent in the presence of a hydride reducing agent (for example, sodium triacetoxyborohydride, sodium cyanoborohydride, and the like are preferred). The reaction temperature of the aforementioned reaction is preferably in the range of from 0° C. to the boiling temperature of the solvent.

The compounds represented by the formula (36) can be obtained by reacting a compound represented by the formula (32) and a corresponding alcohol with a phosphine reagent (for example, triphenylphosphine, and the like are preferred)

in an inert solvent (for example, toluene, tetrahydrofuran, and the like are preferred) in the presence of an azodicarboxylate (for example, diethyl azodicarboxylate, 1,1'-azobis(N,N'-dimethylformamide), and the like are preferred). The reaction temperature of the aforementioned reaction is preferably in range of from room temperature to the boiling point of the solvent.

The compounds represented by the formula (37) can be obtained by reacting a compound represented by the formula (32) as a starting material, and reacting the compound with a corresponding isocyanate, a corresponding acid chloride, a corresponding acid anhydride, a corresponding chloroformate or the like in an inert solvent in the presence or absence of a base.

The compounds represented by the formula (38) can be obtained by reacting a compound represented by the formula (32) with methanesulfonyl chloride or p-toluenesulfonyl chloride in a solvent in the presence of a base to obtain a sulfonate, and reacting the resulting sulfonate with a corresponding thiol in a solvent (for example, dimethylformamide, and the like are preferred) in the presence of a base (for example, potassium carbonate, and the like are preferred). The reaction temperature of the aforementioned reaction is preferably room temperature.

Further, among the compounds represented by the formula (8) shown in Scheme 1, those compounds shown in Scheme 7 can also be obtained by the steps shown in Scheme 7, as well as the steps shown in Scheme 1.

phosphine reagent (for example, t-butylphosphine, and the like are preferred), and base (for example, dicyclohexylmethylamine, silver carbonate, and the like are preferred) in a solvent (for example, 1,4-dioxane, dimethylformamide, and the like are preferred) in the presence of a palladium catalyst (for example, trisdibenzylideneacetonedipalladium(0), and the like are preferred). The reaction temperature of the aforementioned reaction is preferably in the range of from room temperature to the boiling point of the solvent. Alternatively, the compounds represented by the formula (42) can be obtained as a cis-isomer by reacting a compound represented by the formula (40) and a Lindlar catalyst in a solvent (examples include, for example, benzene, 1,4-dioxane, tetrahydrofuran, and ethyl acetate, and two or more kinds of these solvents may be used as a mixture) in the presence of a hydrogen source (for example, hydrogen, and the like are preferred). The reaction temperature of the aforementioned reaction is preferably room temperature.

The compounds represented by the formula (43) can be obtained by reacting a compound represented by the formula (40) or the formula (42) and a palladium catalyst (for example, palladium/carbon, and the like are preferred) in a solvent (examples include, for example, methanol, ethanol, tetrahydrofuran, and ethyl acetate, and two or more kinds of these solvents may be used as a mixture) in the presence of a hydrogen source (for example, hydrogen, and the like are preferred).

<Scheme 7>

[Formula 16]

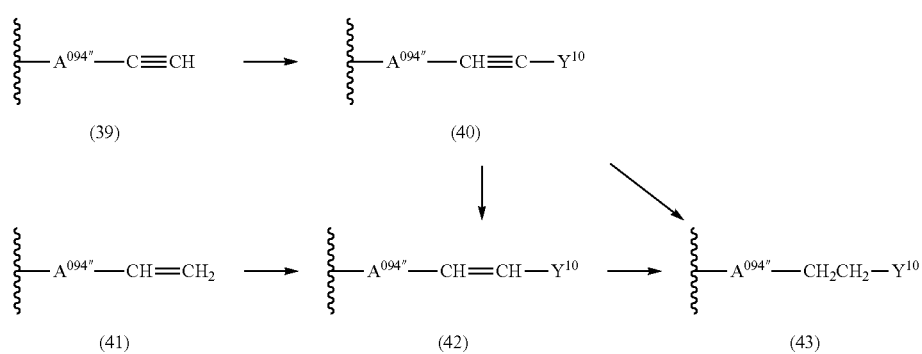

(The formulas (39) to (43) show conversion of $R^9$ and $R^{10}$ of the compounds of the formula (I),
wherein $A^{094''}$ is a single bond, or a divalent aliphatic hydrocarbon group, and
$Y^{10}$ has the same meaning as that defined above.)

The compounds represented by the formula (40) can be obtained by reacting a compound represented by the formula (39) and a corresponding halide (for example, bromide, iodide and the like are preferred) with a base (for example, tetrabutylammonium acetate, and the like are preferred) and in a solvent (for example, dimethylformamide, and the like are preferred) in the presence of a palladium catalyst (for example, palladium acetate, and the like are preferred). The reaction temperature of the aforementioned reaction is preferably room temperature.

The compounds represented by the formula (42) can be obtained as a trans-isomer by reacting a compound represented by the formula (41) and a corresponding halide (for example, bromide, iodide, and the like are preferred) with a Further, among the compounds represented by the formula (8) shown in Scheme 1, those compounds shown in Scheme 8 can also be obtained by the steps shown in Scheme 8, as well as the steps shown in Scheme 1.

<Scheme 8>

[Formula 17]

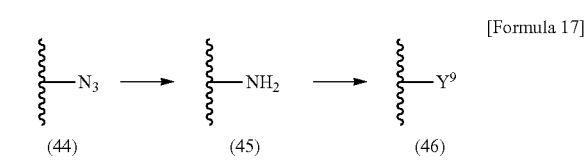

(The formulas (44) to (46) show conversion of $R^9$ and $R^{10}$ of the compounds of the formula (I), and
$Y^9$ has the same meaning as that defined above.)

The compounds represented by the formula (45) can be obtained from a compound represented by the formula (44) in the same manner as that for obtaining a compound of the formula (34) from a compound of the formula (33) shown in Scheme 6.

The compounds represented by the formula (46) wherein $X^{091'}$ is a group represented by the formula —N($R^{23}$)CO—, the formula —N($R^{23}$)CO$_2$—, the formula —N($R^{23}$)CON ($R^{24}$)—, or the formula —N($R^{23}$)SO$_2$— can be obtained by using a compound of the formula (45) as a starting material in the same manner as that for obtaining a compound of the formula (35) from a compound of the formula (34) shown in Scheme 6. Further, the compounds represented by the formula (46) wherein $X^{091'}$ is a group represented by the formula —N($R^{23}$)CO$_2$— can be obtained by using a compound of the formula (45) as a starting material, and reacting the compound with carbonyldiimidazole in a solvent (for example, methylene chloride, dimethylformamide, and the like are preferred) in the presence or absence of a base (for example, pyridine is preferred) at a temperature in the range of from room temperature to 50° C., and reacting the resulting imidazocarbonyl compound with a corresponding alcohol in the presence of a base (for example, sodium hydride is preferred). The reaction temperature of the aforementioned reaction is preferably room temperature.

Schemes 6 to 8 mentioned above show conversion of $R^9$ and $R^{10}$, and similar conversion can also be applied to $R^7$ and $R^8$.

<Scheme 9>

[Formula 18]

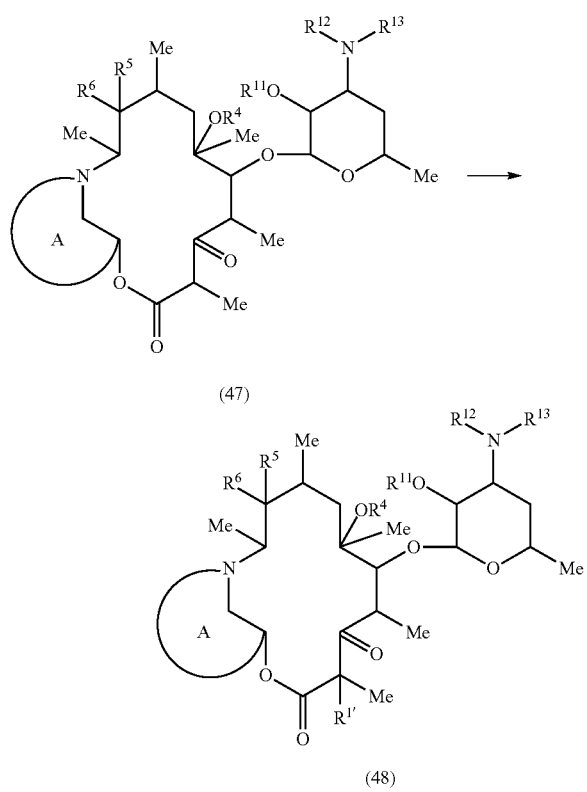

(In the formulas, $R^{1'}$ represents a halogen atom, and the other symbols have the same meanings as those defined above.)

The compounds represented by the formula (48) can be obtained by reacting a compound represented by the formula (47) according to a method similar to the methods described in the publications (for example, WO00/069875), specifically, by a reaction with a corresponding halogenating reagent or the like (for example, N-fluorobenzenesulfonimide and the like) in an inert solvent in the presence or absence of a base.

<Scheme 10>

[Formula 19]

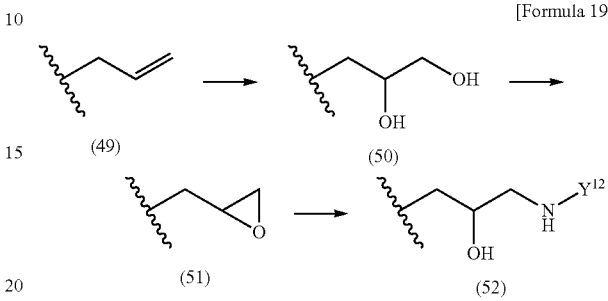

(The formulas (49) to (52) show conversion of $R^4$ of the compounds of the formula (I), wherein $Y^{12}$ is:

a group represented by the formula —$R^{041}$, or a group represented by the formula -$A^{041}$-$X^{042}$—$R^{041}$, and $A^{041}$, $X^{042}$, and $R^{041}$ have the same meanings as those defined above.)

The compounds represented by the formula (50) can be obtained from a compound represented by the formula (49) by a method similar to the methods described in the publications (for example, WO97/42204), specifically, by reacting the compound in a solvent (for example, a mixed solvent of tetrahydrofuran and water, and the like) in the presence of osmium tetroxide and N-methylmorpholine N-oxide.

The compounds represented by the formula (51) can be obtained by using a compound represented by the formula (50) as a starting material, reacting the compound with p-toluenesulfonyl chloride in an inert solvent (for example, chloroform is preferred) in the presence of a base (for example, triethylamine, 4-dimethylaminopyridine and the like) to obtain a sulfonate, and epoxylating the resulting sulfonate in a solvent (for example, methanol is preferred) in the presence of base (for example, potassium carbonate is preferred). The reaction temperature of the aforementioned reaction is preferably in the range of from 0° C. to room temperature.

The compounds represented by the formula (52) can be obtained by reacting a compound represented by the formula (51) and a corresponding amine reagent in a polar solvent (for example, ethanol is preferred) in the presence or absence of a perchlorate or an alkali metal salt (for example, lithium perchlorate and potassium iodide are preferred). The reaction temperature of the aforementioned reaction is chosen from the range of, for example, from room temperature to the boiling point of the solvent, and it is preferably in the range of from 50° C. to the boiling temperature of the solvent.

Further, among the compounds represented by the formula (8) shown in Scheme 1, the compounds where the ring A is a group of the formula (VII) in which the bond indicated with lines including broken line is a double bond can also be obtained by the steps shown in Scheme 11, as well as the steps shown in Scheme 1.

Scheme 11

[Formula 20]

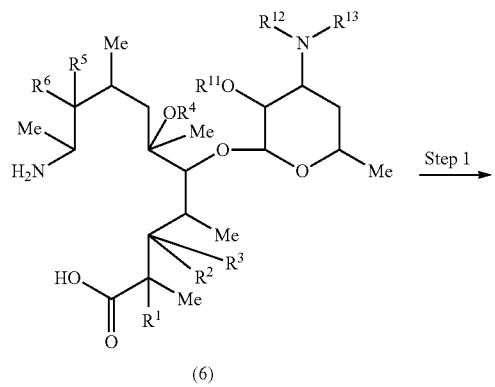

(6)

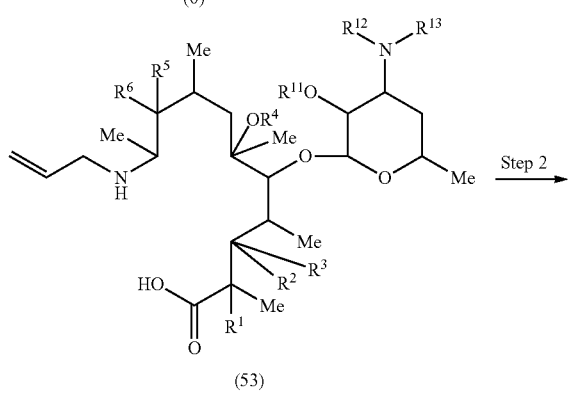

(53)

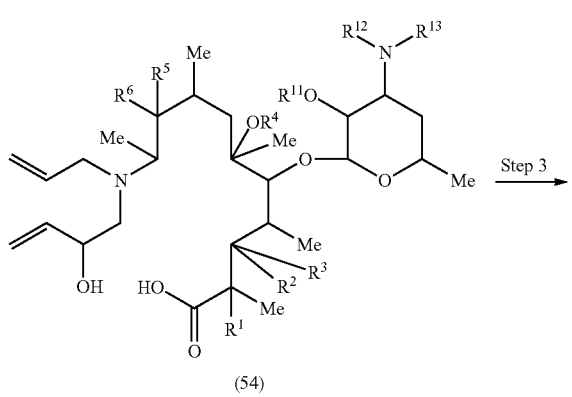

(54)

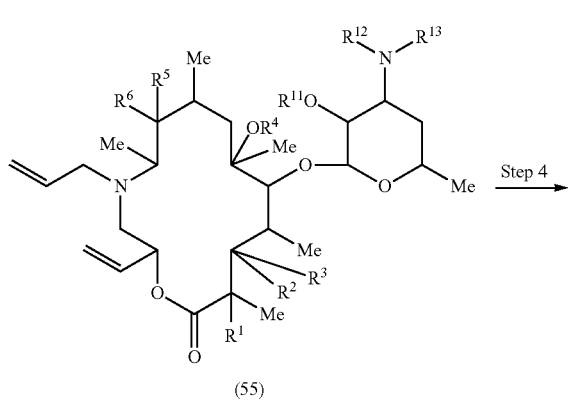

(55)

-continued

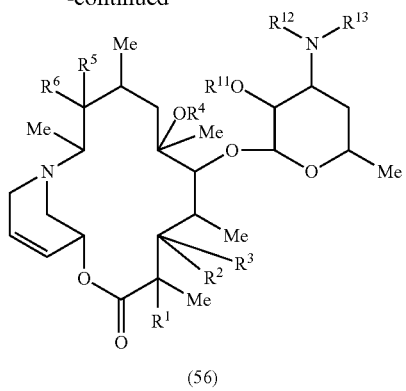

(56)

(The symbols used in the formulas have the same meanings as those defined above.)

[Step 1]

The compounds represented by the formula (53) can be obtained by reacting a compound represented by the formula (6) with an allyl halide in a solvent (for example, a bilayer system solvent of chloroform or methylene chloride and water, and the like are preferred) in the presence of a base (for example, sodium hydroxide, and the like are preferred). The reaction temperature of the aforementioned reaction is preferably room temperature.

[Step 2]

The compounds represented by the formula (54) can be obtained by reacting a compound represented by the formula (53) with epoxybutene in an inert solvent (for example, tetrahydrofuran is preferred) with heating in the presence or absence of a Lewis acid (for example, ytterbium triflate, and the like) and in the presence or absence of a base (examples include, for example, an amine such as triethylamine, diisopropylethylamine, or pyridine, and among these, triethylamine is preferred). The reaction temperature of the aforementioned reaction is chosen from the range of from room temperature to 120° C., and it is preferably in the range of 50 to 100° C.

[Step 3]

The compounds represented by the formula (55) can be obtained in the same manner as that of the step 7 of Scheme 1 by using a compound represented by the formula (54) as a starting material, specifically, reacting the compound in the presence of a condensing agent. Alternatively, the compound can also be obtained by using a compound represented by the formula (54) as a starting material, and reacting the compound in the presence of an acid anhydride.

[Step 4]

The compounds represented by the formula (56) can be obtained by reacting a compound represented by the formula (55) in an inert solvent (for example, methylene chloride is preferred) in the presence of tricyclohexylphosphine[1,3-bis (2,4,6-trimethylphenyl)-4,5-dihydroimidazol-2-ylidene] [benzylidene]ruthenium(IV) dichloride (second generation Grubbs catalyst). The reaction temperature of the aforementioned reaction is preferably in range of from room temperature to the boiling temperature of the solvent.

Further, among the compounds represented by the formula (8) shown in Scheme 1, the compounds where one of $R^2$ or $R^3$ is hydrogen atom, and the other combines with $R^4$ to form a group represented by the formula (V) can also be obtained by the steps shown in Scheme 12, as well as the steps shown in Scheme 1.

<Scheme 12>

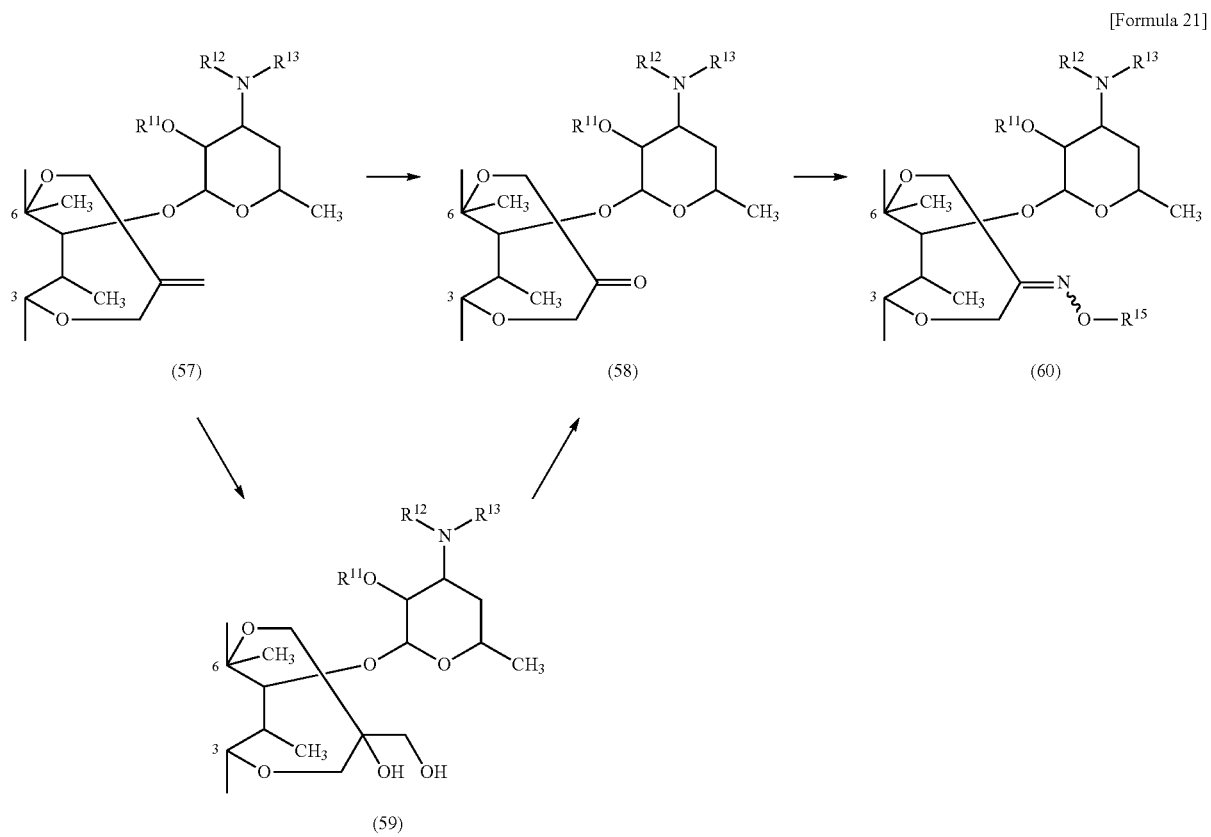

[Formula 21]

(The formulas (57) to (60) show conversion of the moieties at the 3- to 6-positions of the compounds of the formula (I), wherein the symbols used in the formulas have the same meanings as those defined above.)

The compounds represented by the formula (58) can be obtained by a method similar to the method described in the publication (US2006/0142214), specifically, by stirring a compound represented by the formula (57) with osmium tetroxide in a solvent (for example, a mixed solvent of acetone and water is preferred) in the presence of N-methylmorpholine N-oxide and an oxidizing agent (for example, periodate and the like are preferred). Alternatively, the compounds can also be obtained by reacting a compound represented by the formula (57) with osmium tetroxide in a solvent (for example, a mixed solvent of tetrahydrofuran and water and the like) in the presence of N-methylmorpholine N-oxide to obtain a compound represented by the formula (59), and stirring the resulting compound represented by the formula (59) in a solvent (for example, chloroform is preferred) in the presence of an oxidizing agent (examples include, for example, lead tetraacetate, periodate, and the like, and among these, lead tetraacetate is preferred).

The compounds represented by the formula (60) can be obtained by a method similar to the method described in the publication (US2006/0142214), specifically, by reacting a compound represented by the formula (58) and a corresponding hydroxylamine in a solvent (for example, a mixed solvent of ethanol, acetonitrile or the like is preferred) in the presence of an acid (for example, hydrochloric acid, and the like are preferred).

Hydroxyl groups, amino groups, carboxyl groups and oxime groups contained in the compounds represented by the formulas (1) to (60) mentioned in these synthesis methods may be protected with selectively removable protective groups known in this field, and by removing them at a desired stage, intermediates for the synthesis of the 10a-azalide compounds represented by the formula (I) can be provided. Examples of the known protective group include a silyl type protective group such as trimethylsilyl group, triethylsilyl group and tert-butyldimethylsilyl group, an acyl type protective group such as acetyl group and benzoyl group, an ether type protective group such as benzyl group, p-methoxybenzyl group and 2-chlorobenzyl group, an acetal type protective group such as tetrahydropyranyl group, tetrahydrofuranyl group and 1-ethoxyethyl group, a carbonate type protective group such as benzyloxycarbonyl group and tert-butyloxycarbonyl group, and the like. However, besides those mentioned above, protective groups described in Protective Groups in Organic Syntheses (Third Edition, 1999, Ed. by P. G. M. Wuts, T. Green), and the like can also be used. Further, the substituents of the compounds represented by the formulas (1) to (52) mentioned in these synthesis methods can be interchangeably converted by known methods.

The intermediates and the objective compounds mentioned in the aforementioned preparation methods can be isolated and purified by purification methods commonly used in organic synthetic chemistry, for example, neutralization, filtration, extraction, washing, drying, concentration, recrystallization using a solvent such as ethyl acetate, ethyl acetate-hexane, isopropyl alcohol, ethanol, hydrated ethanol, acetone and hydrated acetone, various chromatography techniques, and the like. The intermediates can also be used in subsequent reactions without particular purification.

A substance selected from the group consisting of the 10a-azalide compounds represented by the aforementioned formula (I), physiologically acceptable salts thereof, and hydrates and solvates thereof can be used as a medicament for prophylactic and/or therapeutic treatment of a microbial infectious disease as a novel macrolide antibiotic. Preferably, a pharmaceutical composition containing the aforementioned substance together with one or more kinds of usually used pharmaceutical additives can be prepared and administered for prophylactic and/or therapeutic treatment of a microbial infectious disease of a mammal including human. The administration route is not particularly limited, and administration route of oral administration, or parenteral administration may be chosen. Examples of the pharmaceutical composition suitable for oral administration include, for example, tablets, capsules, powders, granules, syrups, and the like, and examples of the pharmaceutical composition suitable for parenteral administration include, for example, injections for subcutaneous injection, intramuscular injection, or intravenous injection, drip infusions, suppositories, and the like, but the pharmaceutical composition is not limited to these examples. Injections or drip infusions can also be prepared as a pharmaceutical composition in the form of a lyophilized preparation. For manufacture of solid preparations such as tablets and capsules, usually used excipients, stabilizers, binders, coating agents, and the like can be suitably used, for manufacture of injections, drip infusions, and the like, usually used pharmaceutical additives, for example, excipients, pH modifiers, soothing agents, stabilizers, dissolving aids, and the like, can be suitably used, and these can be suitably chosen by those skilled in the art.

Although type of microbial infectious disease as the application object of the medicament of the present invention is not particularly limited, preferred examples include bacterial infectious diseases, mycoplasmal infectious diseases, chlamydial infectious diseases, and the like. Examples of the bacterial infectious diseases include Gram-positive or Gram-negative bacterial infectious diseases, and the medicament of the present invention can be used for them in a similar manner as that used for conventionally used macrolides. However, the medicament of the present invention is characterized by showing superior antibacterial activities even against, in particular, *Hemophilus influenzae*, erythromycin resistant pneumococci, and the like, against which the conventional macrolides cannot show sufficient antibacterial activity, and has an extremely wide antibacterial spectrum. Therefore, it is usable even for an infectious disease of which etiologic bacterium is not specified.

The medicament of the present invention can be used for prophylactic and/or therapeutic treatment of infectious diseases caused by, for example, microorganisms of the genera *Staphylococcus*, and *Streptococcus*, pneumococci, *Moraxella* (*Branhamella*) *catarrhalis*, *Hemophilus influenzae*, microorganisms of the genera *Legionella*, *Campylobacter*, *Peptostreptococcus*, *Prevotella*, *Chlamydia*, and *Mycoplasma*, and the like, and can be used for, but not limited to, superficial skin infection, profound skin infection, lymphangitis and lymphadenitis, chronic pyoderma, secondary infection after traumatic injury, thermal burn, operative wound, and the like, perirectal abscess, pharyngitis and laryngitis (laryngopharyngitis), tonsillitis, acute bronchitis, pneumonia, lung abscess, secondary infection in chronic respiratory diseases (including chronic bronchitis and diffuse panbronchiolitis), bronchiectasis, urethritis, cervicitis, enteritis infectious, otitis media, sinusitis, scarlet fever, pertussis, periodontitis, pericoronitis, jaw inflammation, disseminated *Mycobacterium avium* complex (MAC) disease accompanying acquired immunodeficiency syndrome (AIDS), *Helicobacter Pylori* infectious disease in gastric ulcer and duodenal ulcer, and the like.

Dose of the medicament of the present invention is not particularly limited, and it can be suitably chosen depending on type of infectious disease, purpose of administration (prophylactic or therapeutic treatment), age, weight and the like of patient, severity of infectious disease, and the like. For example, in the case of oral administration, 100 to 1,000 mg as a daily dose can be administered at one time or several times as divided portions. Moreover, the medicament of the present invention can be administered together with one or more kinds of other antibacterial agents or antibiotics.

EXAMPLES

The present invention will be more specifically explained with reference to reference examples, examples and test example. However, the scope of the present invention is not limited to these examples.

[Formula 22]

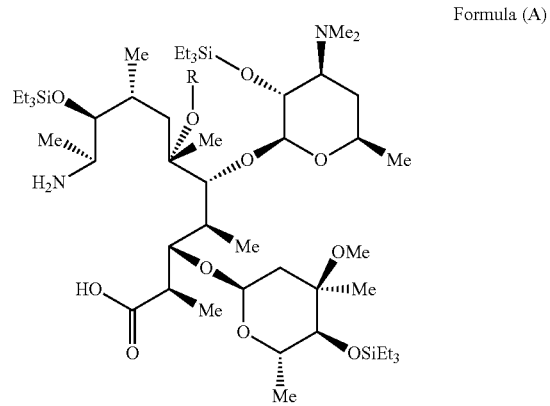

Formula (A)

(In the formula, Et represents ethyl group.)

Reference Example 1

Synthesis of Compound of the Formula (A) Wherein R is Methyl Group (1) (9S)-9-Dihydro-6-O-methylerythromycin A (84.5 g, 112.7 mmol) obtained by the method described in the literature (The Journal of Antibiotics, 1990, vol. 43, 10, p. 1334) and imidazole (80.6 g, 1183 mmol) were dissolved in dimethylformamide (1000 ml), and the solution was cooled to 0° C., and added dropwise with triethylsilyl chloride (59.4 g, 394.4 mmol). After the addition, the mixture was stirred at room temperature for 16 hours, and then added with ethyl acetate (500 ml), hexane (500 ml), and distilled water (1000 ml), and the layers were separated. The organic layer was washed successively with saturated aqueous ammonium chloride (300 ml) and saturated brine, and dried over anhydrous magnesium sulfate, and then the solvent was evaporated under reduced pressure. The resulting residue was purified by silica gel column chromatography (hexane:ethyl acetate=100:1 to 5:1) to obtain a protected compound (107.9 g).

(2) A compound obtained in the same manner as that of (1) mentioned above (200 g) was dissolved in chloroform (400 ml), the solution was added with 90% lead tetraacetate (90.2 g) under ice cooling, and the mixture was stirred for 10 minutes. The mixture was further added successively with a solution of 2-methyl-2-butene (51.3 g) in tetrahydrofuran (800 ml), t-butyl alcohol (400 ml), and an aqueous solution (400 ml) of sodium chlorite (33.1 g), and the mixture was stirred at room temperature for 18 hours. The reaction mixture was added with saturated aqueous sodium hydrogencarbonate (700 ml), the mixture was stirred, and then added with ethyl acetate (1000 ml), and the layers were separated. The organic layer was washed successively with saturated aqueous sodium hydrogencarbonate (500 ml), and saturated brine (500 ml), then dried over anhydrous magnesium sulfate, and filtered. The resulting filtrate was concentrated under reduced pressure to obtain a 10-carboxy compound (218.9 g).

(3) A solution of the compound obtained in (2) mentioned above (218.9 g) in toluene (500 ml) was concentrated under reduced pressure, the resulting residue was dissolved in chloroform (500 ml), and the solution was added with triethylamine (28.1 ml). Then, the mixture was added dropwise with isobutyl chloroformate (25.0 g) under ice cooling, and the mixture was stirred at the same temperature for 30 minutes. Then, the mixture was added with a 50% aqueous solution of hydroxylamine (12.1 g) under ice cooling, and the mixture was stirred at the same temperature for 1 hour. The reaction mixture was added with saturated aqueous ammonium chloride (500 ml), the layers were separated, and the organic layer was washed with saturated brine (500 ml), then dried over anhydrous magnesium sulfate, and filtered. The filtrate was concentrated under reduced pressure to obtain a 10-hydroxamic acid compound (219.9 g).

(4) A solution of the compound obtained in (3) mentioned above (219.9 g) in toluene (500 ml) was concentrated under reduced pressure, the resulting residue was dissolved in tetrahydrofuran (800 ml), the mixture was successively added with triethylamine (77.0 ml), and p-toluenesulfonyl chloride (38.4 g), the mixture was stirred at room temperature for 40 minutes, and then further added with an aqueous solution (260 ml) of lithium hydroxide (38.4 g), and the mixture was stirred at room temperature for 1 hour. The reaction mixture was added with saturated aqueous ammonium chloride (500 ml) and thereby neutralized, then the mixture was concentrated under reduced pressure, the resulting residue was added with chloroform (1000 ml), and the layers were separated. The organic layer was washed with saturated aqueous sodium hydrogencarbonate (500 ml), then dried over anhydrous magnesium sulfate, and filtered. The filtrate was concentrated under reduced pressure, and the resulting residue was purified by silica gel column chromatography (chloroform:methanol: 28% aqueous ammonia=40:1:0.1 to 15:1:0.1) to obtain the title compound (44.3 g).

MS (ESI) m/z=993.8 [M+H]$^+$ $^1$H-NMR (500 MHz, CDCl$_3$) δ (ppm): 0.51-0.70 (m, 18H), 0.84-1.00 (m, J=7.84, 7.84 Hz, 30H), 1.06-1.12 (m, 6H), 1.13-1.17 (m, 7H), 1.22 (d, J=6.50 Hz, 3H), 1.24 (d, J=6.88 Hz, 3H), 1.30 (s, 3H), 1.30-1.35 (m, 1H), 1.42 (dd, J=14.72, 4.78 Hz, 1H), 1.55-1.72 (m, 3H), 2.15-2.19 (m, 1H), 2.18 (s, 6H), 2.31-2.38 (m, 1H), 2.43-2.52 (m, 1H), 2.52-2.60 (m, 1H), 3.12 (dd, J=9.75, 7.07 Hz, 1H), 3.18 (d, J=9.17 Hz, 1H), 3.28 (s, 3H), 3.29 (s, 3H), 3.32-3.43 (m, 2H), 3.51-3.60 (m, 1H), 3.72 (d, J=7.65 Hz, 1H), 3.83-3.88 (m, 1H), 4.19-4.29 (m, 1H), 4.43 (d, J=7.26 Hz, 1H), 4.85 (d, J=4.59 Hz, 1H)

Reference Example 2

Synthesis of 2-(2-bromoethyl)oxirane

4-Bromo-1-butene (55.4 g) was dissolved in chloroform (554 ml), the solution was added with m-chloroperbenzoic acid (108.9 g) under ice cooling, and the mixture was stirred for 18 hours with warming to room temperature. The reaction mixture was ice-cooled, added with 10% aqueous sodium thiosulfate (500 ml), and 5 N aqueous sodium hydroxide (100 ml), and the layers were separated. The organic layer was dried over anhydrous magnesium sulfate, and filtered, and then the filtrate was concentrated under reduced pressure to obtain the title compound (85.58 g).

MS (EI) m/z=150 [M]$^+$ $^1$H-NMR (400 MHz, CDCl$_3$) δ (ppm): 2.00-1.10 (m, 1H), 2.13-2.22 (m, 1H), 2.58 (dd, J=4.8, 2.6 Hz, 1H), 2.84 (dd, J=4.6, 4.1 Hz, 1H), 3.07-3.12 (m, 1H), 3.52 (dd, J=7.3, 5.9 Hz, 2H)

Reference Example 3

Synthesis of (2R)-2-[(2S)-oxiran-2-yl]-2-phenoxyethyl methanesulfonate (1) (L)-Diethyl tartrate (30 g) was dissolved in toluene (300 ml), the solution was added with benzaldehyde (18.5 g), and p-toluenesulfonic acid (2.5 g), and the mixture was stirred for 8 hours under reflux by heating. The reaction mixture was cooled, and then added with saturated aqueous sodium hydrogencarbonate, and ethyl acetate, and the layers were separated. The resulting organic layer was dried over anhydrous magnesium sulfate, and filtered, and then the filtrate was concentrated under reduced pressure to obtain a crude product (43.8 g).

(2) Lithium aluminum hydride (8.47 g) was suspended in tetrahydrofuran (300 ml), the suspension was added with a solution of the crude product obtained in (1) mentioned above (43.8 g) in tetrahydrofuran (200 ml) under ice cooling, and then the mixture was stirred at room temperature for 2 hours. Under ice cooling, the reaction mixture was added with distilled water, 1 N sodium hydroxide, and distilled water in this order, and the mixture was stirred overnight. The reaction mixture was filtered through Celite, then the filtrate was concentrated under reduced pressure, and the resulting residue was purified by silica gel column chromatography (hexane:ethyl acetate=1:1 to ethyl acetate) to obtain a diol compound (15.47 g).

(3) The compound obtained in (2) mentioned above (8 g) was dissolved in chloroform (200 ml), then the solution was added with a 0.99 M solution of diisobutylaluminum hydride in toluene (193 ml) under ice cooling, and the mixture was stirred under ice cooling for 30 minutes and at room temperature for 4 hours. The reaction mixture was added with 1 N hydrochloric acid under ice cooling, and the mixture was extracted with chloroform. The organic layer was dried over anhydrous magnesium sulfate, and filtered, then the filtrate was concentrated under reduced pressure, and the resulting residue was purified by silica gel column chromatography (chloroform:methanol=30:1) to obtain a triol compound (2.2 g).

(4) The compound obtained in (3) mentioned above (2.2 g) was dissolved in dimethylformamide (20 ml), the solution was added with imidazole (4.45 g), and t-butyldimethylsilyl chloride (3.3 g), and the mixture was stirred at room temperature for 6 hours. The reaction mixture was added with distilled water and ethyl acetate, the layers were separated, and the organic layer was further washed three times with distilled water. The organic layer was dried over anhydrous magnesium sulfate, and filtered, then the filtrate was concentrated under reduced pressure, and the resulting residue was purified by silica gel column chromatography (hexane:ethyl acetate=20:1) to obtain a protected compound (3.5 g).

(5) The compound obtained in (4) mentioned above (500 mg) was dissolved in toluene (5 ml), the solution was added with phenol (214 mg), triphenylphosphine (595 mg), and 1,1'-azobis(N,N-dimethylformamide) (293 mg) at room temperature, and the mixture was stirred at 100° C. for 10 minutes. The reaction mixture was concentrated under reduced pressure, and the resulting residue was roughly purified by silica gel column chromatography (hexane: ethyl acetate=10:1) to obtain a crude product of ether compound. The resulting crude product was dissolved in tetrahydrofuran (10 ml), the solution was added with tetrabutylammonium fluoride (886 mg), and the mixture was stirred at room temperature for 14 hours. The reaction mixture was concentrated under reduced pressure, and the resulting residue was purified by silica gel column chromatography (hexane:chloroform=1:1, chloroform, chloroform:methanol=30:1) to obtain a diol compound (246 mg).

(6) The compound obtained in (5) mentioned above (240 mg) was dissolved in tetrahydrofuran (1.0 ml), the solution was added with 20% palladium hydroxide-carbon (240 mg), and the mixture was stirred at 50° C. for 1 hour under a hydrogen atmosphere of 1 atm. The reaction mixture was filtered, and then the filtrate was concentrated under reduced pressure to obtain a triol compound (151 mg).

(7) The compound obtained in (6) mentioned above (50 mg) was dissolved in chloroform (1 ml), the solution was added with triethylamine (176 μl), the mixture was added dropwise with a solution of methanesulfonyl chloride (48.4 μl) in chloroform (5 ml) over 40 minutes under ice cooling, and then the mixture was stirred for 15 minutes. The reaction mixture was added with saturated aqueous sodium hydrogencarbonate, and chloroform, the layers were separated, and the organic layer was dried over anhydrous magnesium sulfate, and filtered. The filtrate was concentrated under reduced pressure, the resulting residue was dissolved in methanol (2 ml), the solution was added with potassium carbonate (69 mg), and the mixture was stirred at room temperature for 2 hours. The reaction mixture was added with distilled water, the mixture was extracted with ethyl acetate, and the organic layer was dried over anhydrous magnesium sulfate, and filtered. The filtrate was concentrated under reduced pressure, and the resulting residue was purified by silica gel column chromatography (hexane:ethyl acetate=10:1) to obtain the title compound (20 mg).

MS (ESI) m/z=259.2 [M+H]$^+$
$^1$H-NMR (600 MHz, CDCl$_3$) δ (ppm): 2.76-2.80 (m, 1H), 2.84-2.88 (m, 1H), 3.03 (s, 3H), 3.18-3.22 (m, 1H), 4.34-4.39 (m, 1H), 4.46-4.54 (m, 2H), 6.95-6.98 (m, 2H), 7.00-7.05 (m, 1H) 7.27-7.32 (m, 2H)

Reference Example 4

Synthesis of (2R)-2-(biphenyl-3-yloxy)-2-[(2S)-oxiran-2-yl]ethyl methanesulfonate By using 3-phenylphenol (289.4 mg) and the compound obtained in Reference Example 3, (4) (500 mg) as starting materials, the title compound (56 mg) was obtained in the same manners as those of Reference Example 3, (5), (6) and (7).

MS (ESI) m/z=335.3 [M+H]$^+$
$^1$H-NMR (600 MHz, CDCl$_3$) δ (ppm): 2.81-2.91 (m, 2H), 3.04 (s, 3H), 3.22-3.25 (m, 1H), 4.42-4.56 (m, 3H), 6.93-6.96 (m, 1H), 7.19-7.20 (m, 1H), 7.25-7.27 (m, 1H), 7.36 (t, J=8.02 Hz, 2H), 7.41-7.47 (m, 2H), 7.53-7.59 (m, 2H)

Reference Example 5

Synthesis of (2R)-2-(naphthalen-1-yloxy)-2-[(2S)-oxiran-2-yl]ethyl methanesulfonate By using 1-naphthol (327.1 mg) and the compound obtained in Reference Example 3, (4) (500 mg) as starting materials, the title compound (118 mg) was obtained in the same manners as those of Reference Example 3, (5), (6) and (7).

MS (ESI) m/z=309.1 [M+H]$^+$
$^1$H-NMR (600 MHz, CDCl$_3$) δ (ppm): 2.82-2.91 (m, 2H), 2.97 (s, 3H), 3.30-3.35 (m, 1H), 4.55-4.65 (m, 3H), 6.95 (d, J=7.34 Hz, 1H), 7.37 (t, J=8.02 Hz, 1H), 7.46-7.55 (m, 3H), 7.78-7.85 (m, 1H), 8.20-8.28 (m, 1H)

Reference Example 6

Synthesis of (2R)-2-(naphthalen-2-yloxy)-2-[(2S)-oxiran-2-yl]ethyl methanesulfonate By using 2-naphthol (327.1 mg) and the compound obtained in Reference Example 3, (4) (500 mg) as starting materials, the title compound (51 mg) was obtained in the same manners as those of Reference Example 3, (5), (6) and (7).

MS (ESI) m/z=308.9 [M+H]$^+$
$^1$H-NMR (600 MHz, CDCl$_3$) δ (ppm): 2.82-2.91 (m, 2H), 3.04 (s, 3H), 3.25-3.29 (m, 1H), 4.52-4.60 (m, 3H), 7.17-7.20 (m, 1H), 7.26-7.28 (m, 1H), 7.36-7.40 (m, 1H), 7.43-7.48 (m, 1H), 7.69-7.80 (m, 3H)

Reference Example 7

Synthesis of (R)-2-azido-2-((R)-oxiran-2-yl)ethyl 4-methylbenzenesulfonate (1) (2R,3R)-3-Azidobutane-1,2,4-triol (1.56 g) obtained by the method described in the literature (Journal of Organic Chemistry, 2006, vol. 71, p. 6258) was dissolved in chloroform (16 ml) and tetrahydrofuran (16 ml), the solution was added with pyridine (6 ml) and p-toluenesulfonyl chloride (4.44 g) under ice cooling, and the mixture was stirred for 16 hours with warming to room temperature. The reaction mixture was added with 1 N hydrochloric acid and chloroform, the layers were separated, and the organic layer was washed with saturated brine, then dried over anhydrous sodium sulfate, and filtered. The filtrate was concentrated under reduced pressure, and the resulting residue was purified by silica gel column chromatography (chloroform:methanol=50:1) to obtain a ditoluenesulfonyl compound (2.50 g).

(2) The compound obtained in (1) mentioned above (2.50 g) was dissolved in methanol (50 ml), the solution was added with potassium carbonate (1.14 g), and the mixture was stirred at room temperature for 0.5 hour. The reaction mixture was concentrated under reduced pressure, the resulting residue was added with ethyl acetate and distilled water, the layers were separated, and the organic layer was washed with saturated brine, then dried over anhydrous sodium sulfate, and filtered. The filtrate was concentrated under reduced pressure to obtain the title compound (1.52 g).

$^1$H-NMR (300 MHz, CDCl$_3$) δ (ppm): 2.46 (s, 3H), 2.76-2.82 (m, 2H), 3.02-3.06 (m, 1H), 3.59-3.65 (m, 1H), 4.05-4.19 (m, 2H), 7.37 (d, J=8.7 Hz, 2H), 7.81 (d, J=8.7 Hz, 2H)

Reference Example 8

Synthesis of (R)-2-((R)-oxiran-2-yl)propyl 4-methylbenzenesulfonate (1) By using (2R,3R)-3-methylbutane-1,2,4-triol (39 mg) obtained by the method described in Tetrahedron, 1980, vol. 36, p. 87 as a starting material, a ditoluenesulfonyl compound (48 mg) was obtained in the same manner as that of Reference Example 7, (1).
(2) By using the compound obtained in (1) mentioned above (43 mg) as a starting material, the title compound (23 mg) was obtained in the same manner as that of Reference Example 7, (2).
MS (ESI) m/z=257 [M+H]$^+$
$^1$H-NMR (300 MHz, CDCl$_3$) δ (ppm): 1.00 (d, J=7.2 Hz, 3H), 1.63-1.73 (m, 1H), 2.45 (s, 3H), 2.49 (dd, J=4.8 Hz, J=2.4 Hz, 1H), 2.74 (dd, J=5.0 Hz, J=4.8 Hz, 1H), 2.76-2.81 (m, 1H), 3.98-4.08 (m, 2H), 7.34 (d, J=8.4 Hz, 2H), 7.79 (d, J=8.4 Hz, 2H)

Reference Example 9

Synthesis of (R)-3-(naphthalen-2-yl)-2-[(R)-oxiran-2-yl]propyl 4-methylbenzenesulfonate (1) Diethyl (D)-malate (1.65 g) and 2-bromomethylnaphthalene (2.5 g) were dissolved in tetrahydrofuran, the solution was cooled to −78° C., and then added with a 1 N solution of lithium bis(trimethylsilyl)amide in tetrahydrofuran (18.27 ml), and the mixture was stirred for 1 hour and 30 minutes. The reaction mixture was stirred for 15 hours with warming to room temperature, and then added with saturated aqueous ammonium chloride, the mixture was added with ethyl acetate, and the layers were separated. The organic layer was dried over anhydrous magnesium sulfate, and filtered, then the filtrate was concentrated under reduced pressure, and the resulting residue was purified by silica gel column chromatography (hexane:ethyl acetate=7:1) to obtain a naphthylmethyl compound (1.52 g).
(2) Lithium aluminum hydride (349 mg) was dissolved in tetrahydrofuran (20 ml), and the solution was added dropwise with a solution of the compound obtained in (1) mentioned above (1.52 g) in tetrahydrofuran (10 ml) under ice cooling. The reaction mixture was stirred at room temperature for 3 hours, and then added successively with distilled water, 15% aqueous sodium hydroxide and distilled water under ice cooling, and the mixture was stirred at room temperature for 0.5 hour. The insoluble matter was taken by filtration, and washed with a 5:1 mixed solvent of tetrahydrofuran and distilled water, and then the filtrate was concentrated under reduced pressure. The resulting residue was purified by silica gel column chromatography (hexane:ethyl acetate=1:1 to 1:3) to obtain a triol compound (409 mg).
(3) By using the compound obtained in (2) mentioned above (389 mg) as a starting material, a ditoluenesulfonyl compound (912.6 mg) was obtained as a crude product in the same manner as that of Reference Example 7, (1).
(4) By using the compound obtained in (3) mentioned above (912.6 mg) as a starting material, the title compound (279.2 mg) was obtained in the same manner as that of Reference Example 7, (2).
MS (FAB) m/z=382 [M]$^+$
$^1$H-NMR (300 MHz, CDCl$_3$) δ (ppm): 1.78-1.90 (m, 1H), 2.30 (dd, J=4.9, 2.7 Hz, 1H), 2.43 (s, 3H), 2.66 (t, J=4.1 Hz, 1H), 2.82-3.01 (m, 3H), 4.03-4.15 (m, 2H), 7.18-7.32 (m, 2H), 7.42-7.50 (m, 2H), 7.54 (s, 1H), 7.70-7.82 (m, 6H)

Reference Example 10

Synthesis of (2R)-3-(benzyloxy)-2-[(2R)-oxiran-2-yl]propyl methanesulfonate (1) Diisopropylamine (71 ml) was dissolved in tetrahydrofuran (540 ml), the solution was added with a 2.44 M solution of n-butyllithium in hexane (200 ml) at −78° C., and the mixture was stirred for 30 minutes. The reaction mixture was added with a solution of diethyl (D)-malate (37.1 g) in tetrahydrofuran (40 ml), and the mixture was stirred for 30 minutes, and then further stirred at −20° C. for 1 hour. The reaction mixture was cooled to −78° C., and added with a solution of benzyl chloromethyl ether (88.6 g) in 1,3-dimethyl-3,4,5,6-tetrahydro-2(1H)-pyrimidinone (120 ml), and the mixture was stirred for 18 hours with gradually warming to room temperature. The reaction mixture was added with a solution of acetic acid (55 ml) in tetrahydrofuran (60 ml) under ice cooling, the mixture was added with diethyl ether and distilled water, and the layers were separated. The organic layer was washed successively with saturated aqueous sodium hydrogencarbonate and saturated brine, then dried over anhydrous magnesium sulfate, and filtered. The filtrate was concentrated under reduced pressure, and the resulting residue was purified by silica gel column chromatography (hexane:ethyl acetate=8:1 to 2:1) to obtain an adduct compound (58.7 g).
(2) Lithium aluminum hydride (10.3 g) was suspended in diethyl ether (350 ml), the suspension was added with a solution of the compound obtained in (1) mentioned above (58.7 g) in diethyl ether (350 ml), and the mixture was stirred at room temperature for 3 hours. The reaction mixture was added dropwise with distilled water by small and small, and added with 1 N hydrochloric acid and chloroform, and the mixture was stirred for 20 minutes. The reaction mixture was added with chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=2:1 to 1:3) to obtain a diol compound (22.3 g).
(3) The compound obtained in (2) mentioned above (22.3 g) was dissolved in methanol (220 ml), the solution was added with 1 N hydrochloric acid (110 ml), and the mixture was stirred for 3 hours under reflux by heating. The reaction mixture was added with sodium hydrogencarbonate under ice cooling until foaming ceased, and then filtered. The filtrate was concentrated under reduced pressure, and the resulting residue was purified by silica gel column chromatography (ethyl acetate to ethyl acetate:methanol=10:1) to obtain a deprotected compound (11.2 g).
(4) Methanesulfonyl chloride (11.3 g) was dissolved in chloroform (340 ml), and the solution was added with triethylamine (14.4 ml). The mixture was added dropwise with a solution of the compound obtained in (3) mentioned above (11.2 g) in chloroform (170 ml) over 90 minutes under ice cooling, and then the mixture was stirred for 5 minutes. The reaction mixture was added dropwise with distilled water by small and small, and added with 1 N hydrochloric acid and chloroform, and the mixture was stirred for 20 minutes. The reaction mixture was added with saturated aqueous ammonium chloride and chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=2:1 to 1:2) to obtain a methanesulfonyl compound (17.1 g).

(5) The compound obtained in (4) mentioned above (17.1 g) was dissolved in methanol (300 ml), the solution was added with potassium carbonate (9.27 g), and the mixture was stirred at room temperature for 1 hour. The reaction mixture was added with saturated aqueous sodium hydrogencarbonate and ethyl acetate, the layers were separated, and the organic layer was dried over anhydrous magnesium sulfate, and filtered. The filtrate was concentrated under reduced pressure, and the resulting residue was purified by silica gel column chromatography (hexane:ethyl acetate=1:1) to obtain the title compound (8.20 g).
MS (ESI) m/z=286.9 [M+H]$^+$
$^1$H-NMR (200 MHz, CDCl$_3$) δ (ppm): 1.80-1.99 (m, 1H), 2.60-2.73 (m, 1H), 2.83 (t, J=4.61 Hz, 1H), 2.98-3.07 (m, 1H), 3.00 (s, 3H), 3.60 (d, J=4.83 Hz, 2H), 4.42 (d, J=5.27 Hz, 2H), 4.52 (s, 2H), 7.28-7.49 (m, 5H)

Reference Example 11

Synthesis of (2S)-3-(benzyloxy)-2-[(2R)-oxiran-2-yl]propyl methanesulfonate (1) By using diethyl (L)-malate (37.12 g) as a starting material, a triol compound (13.9 g) was obtained in the same manners as those of Reference Example 10, (1), (2) and (3).
(2) The compound obtained in (1) mentioned above (13.9 g) was dissolved in dimethylformamide (150 ml), the solution was added with t-butyldimethylsilyl chloride (18.5 g) and imidazole (25.1 g) under ice cooling, and the mixture was stirred at room temperature for 1.5 hours. The reaction mixture was further added with t-butyldimethylsilyl chloride (1.85 g) and imidazole (2.51 g) under ice cooling, and the mixture was stirred for 30 minutes. The reaction mixture was added with saturated aqueous ammonium chloride, the mixture was extracted with a 2:1 mixed solvent of hexane and ethyl acetate, and the organic layer was washed with saturated brine, dried over anhydrous magnesium sulfate, and filtered. The filtrate was concentrated under reduced pressure to obtain a disilyl compound (31.0 g).
(3) The compound obtained in (2) mentioned above (31.0 g) was dissolved in chloroform (300 ml), the solution was added successively with methanesulfonyl chloride (7.9 ml) and triethylamine (15.3 ml) under ice cooling, and the mixture was stirred at room temperature for 14 hours. The mixture was further added with methanesulfonyl chloride (0.8 ml) and triethylamine (1.5 ml), and the mixture was stirred for 3 hours. The reaction mixture was added with saturated aqueous sodium hydrogencarbonate and chloroform, the layers were separated, and the organic layer was washed with saturated brine, then dried over anhydrous magnesium sulfate, and filtered. The filtrate was concentrated under reduced pressure to obtain a methanesulfonyl compound (44.1 g).
(4) A solution of the compound obtained in (3) mentioned above (44.1 g) in tetrahydrofuran (200 ml) was added with tetrabutylammonium fluoride (64.9 g), and the mixture was stirred at room temperature for 2 hours. The reaction mixture was added with saturated aqueous sodium hydrogencarbonate and chloroform, the layers were separated, and the organic layer was dried over anhydrous magnesium sulfate, and filtered. The filtrate was concentrated under reduced pressure, and the resulting residue was dissolved in methanol (200 ml), the solution was added with potassium carbonate (8.5 g), and the mixture was stirred at room temperature for 2 hours. The reaction mixture was added with distilled water and chloroform, the layers were separated, and the organic layer was washed with saturated brine, then dried over anhydrous magnesium sulfate, and filtered. The filtrate was concentrated under reduced pressure, the resulting residue was dissolved in chloroform (200 ml), the solution was added successively with methanesulfonyl chloride (7.1 ml) and triethylamine (13.8 ml) under ice cooling, and the mixture was stirred at room temperature for 1.5 hours. The reaction mixture was added with saturated aqueous sodium hydrogencarbonate and chloroform, the layers were separated, and the organic layer was dried over anhydrous magnesium sulfate, and filtered. The filtrate was concentrated under reduced pressure, and the resulting residue was purified by silica gel column chromatography (chloroform) to obtain the title compound (9.43 g).
MS (ESI) m/z=287.2 [M+H]$^+$
$^1$H-NMR (200 MHz, CDCl$_3$) δ (ppm): 2.61-2.68 (m, 1H), 2.80-2.89 (m, 1H), 2.95-3.08 (m, 2H), 2.98 (s, 3H), 3.58-3.78 (m, 2H), 4.22-4.46 (m, 2H), 4.53 (s, 2H), 7.27-7.40 (m, 5H)

Reference Example 12

Synthesis of 1-(benzyloxy)naphthalen-2-ol 1,2-Dihydroxynaphthalene (70 mg) was dissolved in acetone (1 ml), the solution was added with benzyl bromide (74.7 mg) and potassium carbonate (72.5 mg), and the mixture was stirred at 70° C. for 1 hour. The reaction mixture was added with distilled water and ethyl acetate, the layers were separated, and the organic layer was dried over anhydrous magnesium sulfate, and filtered. The filtrate was concentrated under reduced pressure, and the resulting residue was purified by silica gel column chromatography (hexane:acetone:triethylamine=50:10:0.2) to obtain the title compound (20.7 mg).
$^1$H-NMR (200 MHz, CDCl$_3$) δ (ppm): 5.11 (s, 2H), 5.56 (s, 1H), 7.13-7.23 (m, 1H), 7.29-7.63 (m, 8H), 7.76-7.86 (m, 1H), 7.97-8.06 (m, 1H)

Reference Example 13

Synthesis of 2-(benzyloxy)naphthalen-1-ol

By using 1,2-dihydroxynaphthalene (70 mg) as a starting material, the title compound (11.6 mg) was obtained in the same manner as that of Reference Example 12.
$^1$H-NMR (200 MHz, CDCl$_3$) δ (ppm): 5.23 (s, 2H), 6.03 (s, 1H), 7.22-7.62 (m, 10H), 7.66-7.81 (m, 1H)

Reference Example 14

Synthesis of 2-(benzyloxy)-5-bromophenol

By using 4-bromocathecol (500 mg) as a starting material, the title compound (61.2 mg) was obtained in the same manner as that of Reference Example 12.
MS (ESI) m/z=277.0 [M+H]$^+$ $^1$H-NMR (200 MHz, CDCl$_3$) δ (ppm): 5.09 (s, 2H), 5.68 (s, 1H), 6.73-6.83 (m, 1H), 6.89-6.99 (m, 1H), 7.05-7.11 (m, 1H), 7.35-7.44 (m, 5H)

Reference Example 15

Synthesis of 3-(1-methylethoxy)phenol (1) 3-Hydroxyphenyl benzoate (100 mg) obtained by the method described in the literature (Journal of Organic Chemistry, 1976, vol. 41, 21, p. 3419) was dissolved in toluene (4 ml), the solution was added with triphenylphosphine (146.9 mg), isopropyl alcohol (53.6 μl), and 1,1'-azobis(N,N-dimethylformamide) (98.7 mg), and the mixture was stirred at 100° C. for 1 hour. The reaction mixture was concentrated under reduced pressure, and the resulting residue was roughly purified by silica gel column chromatography (hexane:ethyl acetate=10:1) to obtain an ether compound.
(2) The compound obtained in (1) mentioned above was dissolved in ethanol (2 ml), the solution was added with 1 N aqueous sodium hydroxide (0.5 ml), and the mixture was stirred at room temperature for 1 hour. The reaction mixture was added with 2 N hydrochloric acid and ethyl acetate, the layers were separated, and the organic layer was dried over anhydrous magnesium sulfate, and filtered. The filtrate was concentrated under reduced pressure, and the resulting residue was purified by silica gel column chromatography (hexane:ethyl acetate=5:1 to 3:1) to obtain the title compound (59.4 mg).
$^1$H-NMR (200 MHz, CDCl$_3$) δ (ppm): 1.33 (d, J=6.15 Hz, 6H), 4.51 (ddd, J=11.98, 6.15, 6.04 Hz, 1H), 6.33-6.52 (m, 3H), 7.11 (t, J=8.57 Hz, 1H)

Reference Example 16

Synthesis of 3-(cyclopentyloxy)phenol

By using 3-hydroxyphenyl benzoate (50 mg) and cyclopentanol (23.5 μl) as starting materials, the title compound (50 mg) was obtained in the same manner as that of Reference Example 15.
MS (ESI) m/z=179.0 [M+H]$^+$
$^1$H-NMR (200 MHz, CDCl$_3$) δ (ppm): 1.33-1.95 (m, 8H), 4.64-4.77 (m, 2H), 6.34-6.50 (m, 3H), 7.08 (t, 1H)

Reference Example 17

Synthesis of 3-(cyclohexyloxy)phenol

By using 3-hydroxyphenyl benzoate (100 mg) and cyclohexanol (54.3 μl) as starting materials, the title compound (29 mg) was obtained in the same manner as that of Reference Example 15.
MS (ESI) m/z=193.0 [M+H]$^+$
$^1$H-NMR (200 MHz, CDCl$_3$) δ (ppm): 1.22-1.64 (m, 6H), 1.70-2.07 (m, 4H), 4.05-4.27 (m, 1H), 4.66-4.72 (m, 1H), 6.34-6.54 (m, 3H), 7.04-7.16 (m, 1H)

Reference Example 18

Synthesis of N-(3-hydroxyphenyl)-2-methylpropanamide

3-Aminophenol (1.0 g) was dissolved in acetonitrile (10 ml), the solution was added with isobutyryl chloride (488 mg) under ice cooling, and the mixture was stirred for 1 hour. The reaction mixture was filtered, then the filtrate was concentrated under reduced pressure, and the resulting residue was crystallized from hexane-ethyl acetate to obtain the title compound (392 mg).
$^1$H-NMR (200 MHz, DMSO-d6) δ (ppm): 1.08 (d, J=7.03 Hz, 6H), 2.53-2.64 (m, 1H), 6.41 (ddd, J=7.69, 2.42, 1.32 Hz, 1H), 6.91-6.99 (m, 1H), 6.99-7.09 (m, 1H), 7.18 (t, J=2.20 Hz, 1H) 9.30 (s, 1H), 9.65 (s, 1H)

Reference Example 19

Synthesis of N-(3-hydroxyphenyl)acetamide

By using 3-aminophenol (1.0 g) and acetyl chloride (359 mg) as starting materials, the title compound (392 mg) was obtained in the same manner as that of Reference Example 18.
$^1$H-NMR (200 MHz, DMSO-d6) δ (ppm): 2.00 (s, 3H), 6.38-6.45 (m, 1H), 6.87-6.94 (m, 1H), 7.04 (t, J=7.91 Hz, 1H), 7.17 (s, 1H), 9.31 (s, 1H), 9.77 (s, 1H)

Reference Example 20

Synthesis of N-(3-hydroxyphenyl)benzamide

By using 3-aminophenol (1.0 g) and benzoyl chloride (644 mg) as starting materials, the title compound (573 mg) was obtained in the same manner as that of Reference Example 18.
$^1$H-NMR (200 MHz, DMSO-d6) δ (ppm): 7.12-7.17 (m, 1H), 7.34-7.37 (m, 1H), 7.46-7.59 (m, 4H), 7.88-7.97 (m, 3H), 9.39 (s, 1H), 10.10 (s, 1H)

Reference Example 21

Synthesis of N-(3-hydroxyphenyl)cyclopentanecarboxamide

By using 3-aminophenol (1.0 g) and cyclopentanecarbonyl chloride (607 mg) as starting materials, the title compound (531 mg) was obtained in the same manner as that of Reference Example 18.
$^1$H-NMR (200 MHz, DMSO-d6) δ (ppm): 1.42-1.92 (m, 8H), 2.62-2.86 (m, 1H), 6.37-6.44 (m, 1H), 6.91-6.99 (m, 1H), 6.99-7.09 (m, 1H), 7.18 (t, J=1.98 Hz, 1H), 9.29 (brs, 1H), 9.69 (s, 1H)

Reference Example 22

Synthesis of 2-hydroxybenzyl acetate

2-Hydroxybenzyl alcohol (1.0 g) was dissolved in methylene chloride (20 ml), the solution was slowly added dropwise with pyridine (0.65 ml) and acetyl chloride (0.57 ml) under ice cooling, and the mixture was stirred for 30 minutes. The reaction mixture was added with saturated aqueous ammonium chloride, the mixture was extracted with chloroform, and the organic layer was dried over anhydrous magnesium sulfate, and filtered. The filtrate was concentrated under reduced pressure, and the resulting residue was purified by silica gel column chromatography (hexane:ethyl acetate=5:1) to obtain the title compound (1.22 g).
$^1$H-NMR (200 MHz, CDCl$_3$) δ (ppm): 2.11 (s, 3H), 5.12 (s, 2H), 6.84-7.00 (m, 2H), 7.22-7.31 (m, 1H), 7.76 (s, 1H)

Reference Example 23

Synthesis of 3-hydroxybenzyl acetate

By using 3-hydroxybenzyl alcohol (1.0 g) as a starting material, the title compound (855 mg) was obtained in the same manner as that of Reference Example 22.

$^1$H-NMR (200 MHz, CDCl$_3$) δ (ppm): 2.11 (s, 3H), 4.78-4.85 (m, 1H), 5.06 (s, 2H), 6.73-6.97 (m, 3H), 7.17-7.30 (m, 1H)

Reference Example 24

Synthesis of (3-hydroxynaphthalen-2-yl)methyl acetate (1) Lithium aluminum hydride (140.8 mg) was suspended in tetrahydrofuran (10 ml), the suspension was slowly added with methyl 3-hydroxy-2-naphthylate (500 mg) under ice cooling, and the mixture was stirred at room temperature for 1 hour. The reaction mixture was added with distilled water and 2 N hydrochloric acid, the mixture was extracted with ethyl acetate, and the organic layer was dried over anhydrous magnesium sulfate, and filtered. The filtrate was concentrated under reduced pressure, and the resulting residue was purified by silica gel column chromatography (hexane:ethyl acetate=1:1 to ethyl acetate) to obtain a diol compound (405 mg).

(2) The compound obtained in (1) mentioned above (100 mg) was dissolved in chloroform (3 ml), the solution was added with pyridine (47 µl) and acetyl chloride (41 µl), and the mixture was stirred at room temperature for 3 hours. The reaction mixture was added with distilled water and chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=10:1 to 1:1) to obtain the title compound (40.7 mg).

$^1$H-NMR (200 MHz, CDCl$_3$) δ (ppm): 2.13 (s, 3H), 5.31 (s, 2H), 7.27-7.49 (m, 4H), 7.63-7.84 (m, 3H)

Reference Example 25

Synthesis of (2S)-2-[4-(benzyloxy)butoxy]-2-[(2S)-oxiran-2-yl]ethyl methanesulfonate (1) Diethyl (L)-tartrate (5.0 g) was dissolved in dimethylformamide (30 ml), the solution was added with benzyl 4-bromobutyl ether (5.9 g) and tetrabutylammonium iodide (9.0 g), and the mixture was stirred at room temperature for 15 minutes. The reaction mixture was added with silver oxide (6.0 g), the reaction mixture was further stirred for 4 hours, and then added with distilled water and ethyl acetate, and the layers were separated. The organic layer was dried over anhydrous magnesium sulfate, and filtered, then the filtrate was concentrated under reduced pressure, and the resulting residue was purified by silica gel column chromatography (hexane:ethyl acetate=3:1) to obtain a monoalkyl compound (2.15 g).

(2) By using the compound obtained in (1) mentioned above (2.35 g) as a starting material, the title compound (456 mg) was obtained in the same manners as those of Reference Example 10, (2), (4) and (5).

MS (ESI) m/z=345.1 [M+H]$^+$ $^1$H-NMR (600 MHz, CDCl$_3$) δ (ppm): 1.65-1.70 (m, 4H), 2.62 (dd, J=4.58, 2.75 Hz, 1H), 2.79-2.82 (m, 1H), 3.02-3.06 (m, 1H), 3.03 (s, 3H), 3.30-3.34 (m, 1H), 3.46-3.50 (m, 2H), 3.54-3.60 (m, 1H), 3.72-3.77 (m, 1H), 4.23-4.32 (m, 2H), 4.49 (s, 2H), 7.25-7.37 (m, 5H)

Reference Example 26

Synthesis of (2S)-2-[3-(benzyloxy)propoxy]-2-[(2S)-oxiran-2-yl]ethyl methanesulfonate By using diethyl (L)-tartrate (5 g) and benzyl 3-bromopropyl ether (5.55 g) as starting materials, the title compound (100 mg) was obtained in the same manners as those of Reference Example 25, (1), Reference Example 10, (2), (4) and (5).

MS (ESI) m/z=353.1 [M+Na]$^+$ $^1$H-NMR (200 MHz, CDCl$_3$) δ (ppm): 1.83-1.98 (m, 2H), 2.63 (dd, J=4.83, 2.64 Hz, 1H), 2.82 (d, J=4.83 Hz, 1H), 3.01 (s, 3H), 3.02-3.08 (m, 1H), 3.29-3.41 (m, 1H), 3.56 (t, J=6.15 Hz, 2H), 3.61-3.90 (m, 2H), 4.18-4.35 (m, 2H), 4.50 (s, 2H), 7.33 (d, J=7.03 Hz, 5H)

Reference Example 27

Synthesis of (S)-2-(benzyloxycarbonylamino)-2-[(R)-oxiran-2-yl]ethyl methanesulfonate By using benzyl (S)-2-hydroxy-1-[(R)-oxiran-2-yl]ethylcarbamate (43 mg) obtained by the method described in the literature (Tetrahedron Letters, 1984, vol. 25, p. 1587) as a starting material, the title compound (53 mg) was obtained in the same manner as that of Reference Example 10, (4).

$^1$H-NMR (400 MHz, CDCl$_3$) δ (ppm): 2.62-2.69 (m, 1H), 2.80 (t, J=4.2 Hz, 1H), 3.03 (s, 3H), 3.18-3.23 (m, 1H), 4.24-4.33 (m, 1H), 4.33-4.39 (m, 2H), 4.90-4.99 (m, 1H) 5.11 (s, 2H), 7.32-7.40 (m, 5H)

Reference Example 28

Synthesis of (E)-3-(quinolin-4-yl)acrylic acid (1) 4-Quinolinecarboxyaldehyde (5.0 g) and ethyl (triphenylphosphoranylidene)acetate (11.1 g) were dissolved in toluene (100 ml), the solution was added with benzoic acid (388 mg), and the mixture was stirred for 5 hours under reflux by heating. The reaction mixture was returned to room temperature, and then added with saturated aqueous sodium hydrogencarbonate, the layers were separated, and the organic layer was washed with saturated brine. The organic layer was dried over anhydrous sodium sulfate and filtered, then the filtrate was concentrated under reduced pressure, and the resulting residue was purified by silica gel column chromatography (hexane:ethyl acetate=10:1 to 4:1) to obtain ethyl (E)-3-(quinolin-4-yl)acrylate (7.30 g).

(2) The compound obtained in (1) mentioned above (7.0 g) was dissolved in ethanol (100 ml), the solution was added with 1 N aqueous sodium hydroxide (35.8 ml), and the mixture was stirred at room temperature for 3 hours. The reaction mixture was concentrated under reduced pressure, the resulting residue was added with distilled water, and the mixture was adjusted to pH 5 with 1 N hydrochloric acid. The deposited solid was taken by filtration, washed with distilled water, and then dried by heating to obtain the title compound (3.9 g).

MS (GC) m/z=139 [M+H]$^+$ $^1$H-NMR (400 MHz, DMSO-d6) δ (ppm): 6.82 (d, J=16.0 Hz, D), 7.73 (t, J=8.00 Hz, 1H), 7.82 (t, J=8.00 Hz, 1H), 7.87

(d, J=4.40 Hz, 1H), 8.09 (d, J=8.40 Hz, 1H), 8.27 (d, J=8.00 Hz, 1H), 8.33 (d, J=16.0 Hz, 1H), 8.94 (d, J=4.40 Hz, 1H)

Reference Example 29

Synthesis of (E)-3-(quinolin-6-yl)acrylic acid (1) By using 6-quinolinecarboxyaldehyde (1.0 g) as a starting material, ethyl (E)-3-(quinolin-6-yl)acrylate (1.3 g) was obtained in the same manner as that of Reference Example 28, (1).
(2) By using the compound obtained in (1) mentioned above (500 mg) as a starting material, the title compound (350 mg) was obtained in the same manner as that of Reference Example 28, (2).
MS (GC) m/z=103 [M+H]$^+$
$^1$H-NMR (400 MHz, DMSO-d6) δ (ppm): 6.72 (d, J=16.1 Hz, 1H), 7.56 (dd, J=4.14 Hz, J=8.28 Hz, 1H), 7.77 (d, J=16.1 Hz, 1H), 8.02 (d, J=8.77 Hz, 1H), 8.13 (dd, J=1.95 Hz, J=8.77 Hz, 1H), 8.27 (s, 1H), 8.38 (d, J=7.06 Hz, 1H), 8.93 (dd, J=1.70 Hz, J=4.14 Hz, 1H)

Reference Example 30

Synthesis of (E)-4-(quinolin-6-yl)-3-butenoic acid (1) 6-Bromoquinoline (21 mg) and methyl 3-butenoate (12 mg) were dissolved in 1,4-dioxane (1 ml), the solution was added with tris(dibenzylideneacetone)dipalladium(0) (9.2 mg), dicyclohexylmethylamine (43 μl), and a 0.44 N solution of tri-t-butylphosphine in dioxane (5 μl), and the mixture was stirred at 80° C. for 5 minutes under microwave irradiation. The reaction mixture was added with ethyl acetate and saturated aqueous ammonium chloride, the layers were separated, and the organic layer was washed with saturated brine. The organic layer was dried over anhydrous sodium sulfate and filtered, then the filtrate was concentrated under reduced pressure, and the resulting residue was purified twice by preparative thin layer chromatography (hexane:ethyl acetate=2:1) to obtain a methyl ester compound (20 mg) as a mixture of isomers.
(2) The compound obtained in (1) mentioned above (35 mg) was suspended in a mixed solvent of methanol and distilled water (1:1, 1.2 ml), the suspension was added with lithium hydroxide hydrate (6.4 mg), and the mixture was stirred at room temperature for 1.5 hours. The reaction mixture was added with a solution of saturated ammonium chloride, the mixture was concentrated under reduced pressure, and the resulting residue was roughly purified by preparative thin layer chromatography (chloroform:methanol:28% aqueous ammonia=5:1:0.1) to obtain the title compound (23 mg) as a mixture containing isomers.
MS (ESI) m/z=214 [M+H]$^+$ Reference Example 31

Synthesis of (E)-5-(quinolin-6-yl)-4-pentenoic acid (1) By using 6-bromoquinoline (21 mg) and ethyl 4-pentenoate (15 mg) as starting materials, an ethyl ester compound (21 mg) was obtained as a mixture of isomers in the same manner as that of Reference Example 30, (1).
(2) By using the compound obtained in (1) mentioned above (44 mg) as a starting material, the title compound (10 mg) was obtained as a mixture containing isomers in the same manner as that of Reference Example 30, (2).
MS (ESI) m/z=228 [M+H]$^+$ Reference Example 32

Synthesis of 3-[4-(pyridin-3-yl)phenyl]propionic acid (1) 3-(4-Bromophenyl)propionic acid (495 mg) was dissolved in a mixed solvent of ethanol and toluene (1:1, 10 ml), the solution was added with 10-camphorsulfonic acid (120 mg), and the mixture was stirred for 20 hours under reflux by heating. The reaction mixture was concentrated under reduced pressure, and then added with toluene, and the mixture was washed twice with saturated aqueous sodium hydrogencarbonate (1 ml). The organic layer was dried over anhydrous sodium sulfate and filtered, then the filtrate was concentrated under reduced pressure, and the resulting residue was purified by silica gel column chromatography (hexane:ethyl acetate=9:1) to obtain an ethyl ester compound (512 mg).
(2) The compound obtained in (1) mentioned above (294 mg) and 3-pyridineboronic acid (408 mg) were dissolved in 1,2-dimethoxyethane (6 ml), the solution was added with distilled water (2 ml), sodium carbonate (378 mg), and tetrakis(triphenylphosphine)palladium(0) (100 mg), and the mixture was stirred at 80° C. for 7 hours. The 1,2-dimethoxyethane was evaporated under reduced pressure, and the residue was extracted twice with toluene (10 ml). The organic layer was concentrated under reduced pressure, and the resulting residue was purified by silica gel column chromatography (hexane:ethyl acetate=1:1) to obtain a coupled compound (327 mg).
(3) The compound obtained in (2) mentioned above (324 mg) was dissolved in ethanol (900 μl), the solution was added with distilled water (900 μl), and 4 N aqueous lithium hydroxide (340 μl), and the mixture was stirred at room temperature for 2 hours. The ethanol was evaporated under reduced pressure, the residue was added with distilled water and hexane, and the layers were separated. The aqueous layer was added with 5 N hydrochloric acid (250 μl) and thereby adjusted to pH 7, and then the deposited solid was taken by filtration. The solid was washed with water and vacuum-dried to obtain the title compound (243 mg).
$^1$H-NMR (400 MHz, DMSO-d6) δ (ppm): 2.58 (t, J=7.6 Hz, 2H), 2.88 (t, J=7.5 Hz, 2H), 7.33-7.39 (m, 2H), 7.44-7.49 (m, 1H), 7.62-7.67 (m, 2H), 8.03-8.07 (m, 1H), 8.530-8.87 (m, 1H), 8.85-8.89 (m, 1H)

Reference Example 33

Synthesis of 4-bromoquinoline

By using 4-hydroxyquinoline (5.0 g) as a starting material, the title compound (6.87 g) was obtained in the same manner as that of the method described in the literature (Journal of Heterocyclic Chemistry, 1975, vol. 12, p. 1723).

Reference Example 34

Synthesis of 3-[4-(pyridin-3-yl)phenyl]propanal (1) The compound obtained in Reference Example 32 (50 mg) was dissolved in a mixed solvent of dimethylformamide and methylene chloride (1:1, 3 ml), the solution was added with N,O-dimethylhydroxylamine hydrochloride (35 mg) and N-methylmorpholine (27 μl), and the solution was added with N-ethyl-N'-(3-dimethylaminopropyl)carbodiimide hydrochloride (71 mg) at −15° C. The reaction mixture was stirred for 2 hours with warming to room temperature, and then added with distilled water, and the layers were separated. After 5 times of extraction with chloroform, the organic layer was dried over anhydrous sodium sulfate, and filtered. The filtrate was concentrated under reduced pressure to obtain an amide compound (59 mg) as a crude product.

(2) The compound obtained in (1) mentioned above (55 mg) was dissolved in tetrahydrofuran (1 ml), and the solution was added dropwise with a 1 M solution of lithium aluminum hydride in tetrahydrofuran (100 μl) under ice cooling. The reaction mixture was stirred for 30 minutes under ice cooling, and then added with saturated aqueous potassium hydrogensulfate (1 ml) and diethyl ether (4 ml) at −15° C., and the mixture was stirred. The mixture was added with saturated aqueous sodium hydrogencarbonate (3 ml) under ice cooling, the mixture was extracted with diethyl ether, and then the organic layer was washed with saturated brine. The organic layer was dried over anhydrous sodium sulfate and filtered, then the filtrate was concentrated under reduced pressure, and the resulting residue was purified by preparative thin layer chromatography (hexane:ethyl acetate=1:4) to obtain the title compound (36 mg).

$^1$H-NMR (400 MHz, CDCl$_3$) δ (ppm): 2.82-2.87 (m, 2H), 3.00-3.06 (m, 2H), 7.30-7.38 (m, 3H), 7.50-7.54 (m, 2H), 7.83-7.88 (m, 1H), 8.57-8.60 (m, 1H), 8.82-8.85 (m, 1H), 9.86 (t, J=1.2 Hz, 1H)

Reference Example 35

Synthesis of 3-[4-(pyridin-3-yl)phenyl]butanal (1) By using 4-(4-bromophenyl)butanoic acid (214 mg) as a starting material, an amide compound (237 mg) was obtained in the same manner as that of Reference Example 34, (1).
(2) By using the compound obtained in (1) mentioned above (140 mg) as a starting material, a coupled compound (150 mg) was obtained in the same manner as that of Reference Example 32, (2).
(3) By using the compound obtained in (2) mentioned above (135 g) as a starting material, the title compound (150 mg) was obtained in the same manner as that of Reference Example 34, (2).

$^1$H-NMR (400 MHz, CDCl$_3$) δ (ppm): 1.97-2.05 (m, 2H), 2.47-2.58 (m, 2H), 2.69-2.76 (m, 2H), 7.28-7.32 (m, 2H), 7.34-7.38 (m, 1H), 7.50-7.54 (m, 2H), 7.84-7.88 (m, 1H), 8.56-8.60 (m, 1H), 8.82-8.86 (m, 1H), 9.79 (t, J=1.2 Hz, 1H)

Reference Example 36

Synthesis of 3-(quinolin-6-yl)propanal (1) The compound obtained in Reference Example 29, (1) (400 mg) was dissolved in dioxane (4 ml), the solution was added with 5% palladium-carbon (480 mg) under an argon atmosphere, and the mixture was stirred at room temperature for 4 hours under a hydrogen atmosphere of 1 atm. The reaction mixture was filtered through Celite, then the filtrate was concentrated under reduced pressure, and the resulting residue was purified by silica gel column chromatography (hexane:ethyl acetate=8:1 to 2:1) to obtain a reduced compound (131.3 mg).
(2) The compound obtained in (1) mentioned above (50 mg) was dissolved in toluene (2.0 ml), the solution was cooled to −78° C., and then added with a 1 N solution of diisobu-tylaluminum hydride in toluene (436 μl), and the mixture was stirred for 1 hour and 30 minutes. The reaction mixture was added successively with a solution of acetic acid (37.5 μl) in diethyl ether (125 μl) and distilled water (11.7 μl), and the mixture was further stirred for 5 minutes, then warmed to room temperature, and stirred for 30 minutes. The reaction mixture was added with ethyl acetate, the mixture was filtered, then the filtrate was concentrated under reduced pressure, and the resulting residue was purified by silica gel column chromatography (hexane:ethyl acetate=2:1) to obtain the title compound (33.2 mg).

MS (FAB) m/z=186 [M+H]$^+$ $^1$H-NMR (400 MHz, CDCl$_3$) δ (ppm): 2.91 (dt, J=7.6, 1.2 Hz, 2H), 3.16 (t, J=7.5 Hz, 2H), 7.39 (dd, J=8.3, 4.2 Hz, 1H), 7.57 (dd, J=8.6, 2.0 Hz, 1H), 7.61-7.63 (m, 1H), 8.05 (d, J=8.8 Hz, 1H), 8.08-8.13 (m, 1H), 8.88 (dd, J=4.4, 1.7 Hz, 1H), 9.87 (s, 1H)

Reference Example 37

Synthesis of 2-(naphthalen-2-yl)acetaldehyde

By using 2-naphthaleneethanol (34 mg) as a starting material, the title compound (23 mg) was obtained in the same manner as that of method described in the patent document (WO05/019238).

Reference Example 38

Synthesis of 3-(naphthalen-2-yl)propanal

By using ethyl 3-(naphthalen-2-yl)propionate (228 mg) as a starting material, the title compound (151 mg) was obtained in the same manner as that of Reference Example 36, (2).

Reference Example 39

Synthesis of 4-(quinolin-6-yl)butanal (1) By using the compound obtained in Reference Example 30, (1) (168.5 mg) as a starting material, and using ethyl acetate as the solvent instead of dioxane, a reduced compound (105.1 mg) was obtained in the same manner as that of Reference Example 36, (1).
(2) By using the compound obtained in (1) mentioned above (50 mg) as a starting material, the title compound (33.8 mg) was obtained in the same manner as that of Reference Example 36, (2).

MS (FAB) m/z=200 [M+H]$^+$ $^1$H-NMR (400 MHz, CDCl$_3$) δ (ppm): 2.03-2.12 (m, 2H), 2.52 (dt, J=7.1, 1.4 Hz, 2H), 2.86 (t, J=7.8 Hz, 2H), 7.39 (dd, J=8.3, 4.2 Hz, 1H), 7.55-7.61 (m, 2H), 8.05 (d, J=8.5 Hz, 1H), 8.08-8.13 (m, 1H), 8.88 (dd, J=4.2, 1.7 Hz, 1H), 9.79 (s, 1H)

Reference Example 40

Synthesis of (R)-2-((R)-oxiran-2-yl)-4-pentenyl 4-methylbenzenesulfonate (1) (2R,3R)-3-Allylbutane-1,2,4-triol (2.44 g) obtained by the method described in the literature (Tetrahedron Asymmetry, 1996, vol. 7, p. 3371) was dissolved in chloroform (75 ml), the solution was added with pyridine (10 ml) and p-toluenesulfonyl chloride (7.40 g) under ice cooling, and the mixture was stirred for 18 hours with warming to room temperature. The reaction mixture was added with 1 N hydrochloric acid, the layers were separated, the organic layer was washed successively with 1 N hydrochloric acid, saturated aqueous sodium hydrogencarbonate, and saturated brine, then dried over anhydrous magnesium sulfate, and filtered. The filtrate was concentrated under reduced pressure to obtain a 1,4-ditoluenesulfonyl compound (9.30 g).

(2) By using the compound obtained in (1) mentioned above (9.30 g) as a starting material, the title compound (2.70 g) was obtained in the same manner as that of Reference Example 7, (2).

MS (GC) m/z=283 [M+H]$^+$ $^1$H-NMR (400 MHz, CDCl$_3$) δ (ppm): 1.50-1.62 (m, 1H) 2.15-2.30 (m, 2H), 2.46 (s, 3H) 2.51 (dd, J=2.75 Hz, 4.95 Hz, 1H) 2.75-2.87 (m, 2H), 4.08 (d, J=4.95 Hz, 2H) 4.98-5.09 (m, 2H), 5.60-5.75 (m, 1H), 7.36 (d, J=8.24 Hz, 2H) 7.80 (t, J=8.24 Hz, 2H)

Reference Example 41

Synthesis of (E)-5-(quinolin-4-yl)-4-pentenoic acid (1) By using the compound obtained in Reference Example 33 (21 mg) and ethyl 4-pentenoate (15 mg) as starting materials, an ethyl ester compound (9.4 mg) was obtained as a mixture of isomers in the same manner as that of Reference Example 30, (1).

(2) By using the compound obtained in (1) mentioned above (17 mg) as a starting material, the title compound (7.1 mg) was obtained as a mixture containing isomers in the same manner as that of Reference Example 30, (2).

MS (ESI) m/z=228 [M+H]$^+$

Reference Example 42

Synthesis of 2-(3-bromophenyl)furan

1-Bromo-3-iodobenzene (3.0 g), tris(dibenzylideneacetone)dipalladium(0) (1.22 g), tributyl(furan-2-yl)tin (3.34 ml), and tri(o-tolyl)phosphine (807 mg) were dissolved in dioxane (30 ml), and the solution was stirred at room temperature for 20 hours, at 35° C. for 6 hours, at 45° C. for 19 hours, and at 55° C. for 5 hours and 30 minutes. The reaction mixture was filtered through Celite, the filtrate was concentrated under reduced pressure, and the resulting residue was purified by silica gel column chromatography (NH-form, hexane) to obtain the title compound (1.40 g).

MS (EI) m/z=222 [M+H]$^+$ $^1$H-NMR (400 MHz, CDCl$_3$) δ (ppm): 6.48 (dd, J=3.5, 1.8 Hz, 1H), 6.67 (dd, J=3.4, 0.7 Hz, 1H), 7.22-7.26 (m, 1H), 7.36-7.39 (m, 1H), 7.48 (dd, J=2.2, 0.8 Hz, 1H), 7.57-7.60 (m, 1H), 7.82 (t, J=1.7 Hz, 1H)

Reference Example 43

Synthesis of (R)-2-[(R)-oxiran-2-yl]4-pentynyl 4-methylbenzenesulfonate (1) Diisopropylamine (10.2 ml) was dissolved in tetrahydrofuran (50 ml), the solution was added dropwise with a L57 M solution of n-butyllithium in hexane (42 ml) under ice cooling, and the mixture was stirred for 10 minutes. The reaction mixture was cooled to −78° C., and added dropwise with a solution of diethyl (D)-malate (5 g) in tetrahydrofuran (20 ml), and then the reaction mixture was warmed to −18° C. over 1 hour. The reaction mixture was cooled to −60° C., added dropwise with propargyl bromide (7.1 ml), and then the mixture was stirred for 2 hours. The reaction mixture was further stirred for 15.5 hours with gradually warming to 0° C., then cooled to −50° C., and added with a mixed solvent of acetic acid and diethyl ether (2:3, 40 ml), and the mixture was warmed to room temperature. The reaction mixture was added with distilled water and diethyl ether, the layers were separated, and the organic layer was washed with saturated brine, then dried over anhydrous sodium sulfate, and filtered. The filtrate was concentrated under reduced pressure, and the resulting residue was purified by silica gel column chromatography (hexane:ethyl acetate=8:1) to obtain a propargyl compound (6.0 g).

(2) Lithium borohydride (611 mg) was dissolved in tetrahydrofuran (34 ml), and the solution was added dropwise with a solution of the compound obtained in (1) mentioned above (3.2 g) in tetrahydrofuran (44 ml) under ice cooling. The reaction mixture was stirred at room temperature for 5 hours, and then added with 1 N hydrochloric acid under ice cooling, and tetrahydrofuran was evaporated under reduced pressure. The aqueous layer was extracted 5 times with ethyl acetate, the organic layer was dried over anhydrous sodium sulfate and filtered, and then the filtrate was concentrated under reduced pressure to obtain a triol compound (1.68 g) as a crude product.

(3) By using the compound obtained in (2) mentioned above (188 mg) as a starting material, the title compound (87 mg) was obtained in the same manners as those of Reference Example 40, (1) and Reference Example 7, (2).

$^1$H-NMR (400 MHz, CDCl$_3$) δ (ppm): 1.68-1.79 (m, 1H), 1.94 (t, J=2.6 Hz, 1H), 2.38 (dd, J=2.6, 6.3 Hz, 2H), 2.46 (s, 3H), 2.61 (dd, J=4.6, 2.4 Hz, 1H), 2.81 (dd, J=4.6, 3.9 Hz, 1H), 2.89-2.94 (m, 1H), 4.17-4.21 (m, 2H), 7.34-7.38 (m, 2H), 7.78-7.83 (m, 2H)

Reference Example 44

Synthesis of (2S)-1-[2-(benzyloxy)ethoxy]-3-(oxiran-2-yl)propan-2-yl methanesulfonate (1) Sodium hydride (1.78 g) was suspended in dimethylformamide (40 ml), the suspension was added with a solution of (R)-glycidol (3.0 g) in dimethylformamide (10 ml) under ice cooling, and the mixture was stirred for 90 minutes. The reaction mixture was added with a solution of benzyl 2-bromoethyl ether (10.5 g) in dimethylformamide (10 ml), and the mixture was stirred at room temperature for 2 hours. The reaction mixture was added with saturated aqueous ammonium chloride and ethyl acetate, the layers were separated, and the organic layer was dried over anhydrous sodium sulfate, and filtered. The filtrate was concentrated under reduced pressure, and the resulting residue was purified by silica gel column chromatography (hexane:ethyl acetate=6:1 to 1:2) to obtain an ether compound (2.45 g).

(2) Copper iodide (1.62 g) was suspended in tetrahydrofuran (50 ml), the suspension was added with a 1 M solution of vinylmagnesium bromide in tetrahydrofuran (34 ml) on a sodium chloride-ice bath, and the mixture was stirred for 15 minutes. The reaction mixture was added with a solution of the compound obtained in (1) mentioned above (1.77 g) in tetrahydrofuran (10 ml), and the mixture was stirred for 1 hour. The reaction mixture was added with saturated aqueous ammonium chloride and chloroform, the layers were separated, and the organic layer was dried over anhydrous sodium sulfate, and filtered. The filtrate was concentrated under reduced pressure, and the resulting residue was purified by silica gel column chromatography (hexane:ethyl acetate=10:1 to 2:1) to obtain an adduct compound (1.39 g).
(3) The compound obtained in (2) mentioned above (1.10 g) was dissolved in chloroform (20 ml), the solution was added with m-chloroperbenzoic acid (1.48 g) under ice cooling, and the mixture was stirred at room temperature for 18 hours. The reaction mixture was added with saturated aqueous sodium hydrogencarbonate and ethyl acetate, the layers were separated, and the organic layer was washed successively with saturated aqueous sodium hydrogencarbonate and saturated aqueous sodium thiosulfate, then dried over anhydrous magnesium sulfate, and filtered. The filtrate was concentrated under reduced pressure, and the resulting residue was purified by silica gel column chromatography (hexane:ethyl acetate=3:1 to 1:2) to obtain an epoxy compound (1.11 g).
(4) The compound obtained in (3) mentioned above (1.10 g) was dissolved in chloroform (15 ml), the solution was added with triethylamine (1.83 ml) and methanesulfonyl chloride (506 μl), and the mixture was stirred at room temperature for 18 hours. The reaction mixture was added with saturated brine and chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=2:1 to 1:2) to obtain the title compound (1.27 g).
MS (ESI) m/z=331.2 [M+H]$^+$
$^1$H-NMR (600 MHz, CDCl$_3$) δ (ppm): 1.68-1.80 (m, 1H) 1.96-2.12 (m, 1H), 2.47-2.55 (m, 1H), 2.76-2.85 (m, 1H), 3.03 (s, 3H), 3.04-3.12 (m, 1H), 3.57-3.81 (m, 6H), 4.52 (s, 2H), 4.90-4.99 (m, 1H), 7.26-7.37 (m, 5H)

Reference Example 45

Synthesis of (2S)-1-[3-(benzyloxy)propoxy]-3-(oxiran-2-yl)propan-2-yl methanesulfonate By using benzyl 3-bromopropyl ether (9.28 g) as a starting material, the title compound (1.17 g) was obtained in the same manner as that of Reference Example 44.
MS (ESI) m/z=345.1 [M+H]$^+$
$^1$H-NMR (600 MHz, CDCl$_3$) δ (ppm): 1.68-1.79 (m, 1H), 1.84-1.90 (m, 2H), 1.97-2.12 (m, 1H), 2.47-2.54 (m, 1H), 2.76-2.86 (m, 1H), 3.02 (s, 3H), 3.03-3.09 (m, 1H), 3.49-3.55 (m, 2H), 3.55-3.74 (m, 4H), 4.49 (s, 210, 4.88-4.95 (m, 1H), 7.25-7.36 (m, 5H)

Reference Example 46

Synthesis of (2S)-1-[4-(benzyloxy)butoxy]-3-(propoxy)propan-2-yl)methanesulfonate By using benzyl 4-bromobutyl ether (4.44 g) as a starting material, the title compound (3.49 g) was obtained in the same manner as that of Reference Example 44.
MS (ESI) m/z=359.2 [M+H]$^+$
$^1$H-NMR (600 MHz, CDCl$_3$) δ (ppm): 1.61-1.68 (m, 4H), 1.68-1.80 (m, 1H), 1.98-2.13 (m, 1H), 2.47-2.55 (m, 1H), 2.76-2.86 (m, 1H), 3.03-3.11 (m, 1H), 3.06 (s, 3H), 3.43-3.74 (m, 6H), 4.49 (s, 2H), 4.89-4.96 (m, 1H), 7.26-7.36 (m, 5H)

Reference Example 47

Synthesis of (2S)-1-[3-(3-naphthalen-1-yl)propoxy]-3-(propoxy)propan-2-yl methanesulfonate (1) Lithium aluminum hydride (1.99 g) was suspended in tetrahydrofuran (50 ml), the suspension was added with a solution of 3-(1-naphthyl)-propionic acid (7 g) in tetrahydrofuran (10 ml) under ice cooling, and the mixture was stirred for 1 hour. The reaction mixture was added dropwise with distilled water by small and small under ice cooling, and added with 1 N hydrochloric acid and chloroform, and the mixture was stirred for 20 minutes. The reaction mixture was added with chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=2:1 to 1:2) to obtain an alcohol compound (6.81 g).
(2) By using the compound obtained in (1) mentioned above (7.2 g) as a starting material, a methanesulfonyl compound (9.11 g) was obtained in the same manner as that of Reference Example 44, (4).
(3) The compound obtained in (2) mentioned above (3.8 g) was dissolved in acetone (60 ml), the solution was added with lithium bromide (1.88 g), and the mixture was stirred at 50° C. for 2 hours. The reaction mixture was added with lithium bromide (0.13 g), and the mixture was further stirred at 50° C. for 1 hour. The reaction mixture was added with saturated brine and chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=5:1) to obtain a bromo compound (3.7 g).
(4) By using the compound obtained in (3) mentioned above (3.7 g) as a starting material, the title compound (1.5 g) was obtained in the same manner as that of Reference Example 44.
MS (ESI) m/z=387.1 [M+Na]$^+$
$^1$H-NMR (600 MHz, CDCl$_3$) δ (ppm): 1.71-1.82 (m, 1H), 2.00-2.06 (m, 2H), 2.05-2.18 (m, 1H), 2.49-2.57 (m, 1H), 2.74-2.91 (m, 1H), 3.04-3.11 (m, 1H), 3.08 (s, 3H), 3.11-3.18 (m, 2H), 3.48-3.77 (m, 4H), 4.91-4.99 (m, 1H), 7.30 (d, J=6.88 Hz, 1H), 7.39 (t, J=7.79 Hz, 1H), 7.49 (dd, J=15.59, 6.88 Hz, 2H), 7.72 (d, J=8.25 Hz, 1H), 7.85 (d, J=8.25 Hz, 1H), 8.02 (d, J=8.25 Hz, 1H)

Reference Example 48

Synthesis of (2R)-2-(benzyloxy)-2-[(2R)-oxiran-2-yl]ethyl methanesulfonate (1) By using (+)-2,3-O-benzylidene-D-threitol (3.5 g) as a starting material, a methanesulfonyl compound (5.63 g) was obtained in the same manner as that of Reference Example 44, (4).
(2) The compound obtained in (1) mentioned above (2.10 g) was dissolved in chloroform (60 ml), the solution was added with a 0.99 M solution of diisobutylaluminum hydride in toluene (17.4 ml) under ice cooling, and the mixture was stirred for 2 hours. The reaction mixture was added dropwise with distilled water, the mixture was added with 0.5 N hydrochloric acid and chloroform, and the layers were separated. The organic layer was dried over anhydrous magnesium sulfate, and filtered, and then the filtrate was concentrated under reduced pressure to obtain an alcohol compound (2.16 g).
(3) By using the compound obtained in (2) mentioned above (2.16 g) as a starting material, the title compound (1.02 g) was obtained in the same manner as that of Reference Example 10, (5).
MS (ESI) m/z=295.1 [M+Na]$^+$ $^1$H-NMR (200 MHz, CDCl$_3$) δ (ppm): 2.64 (dd, J=4.83, 2.64 Hz, 1H), 2.85 (t, J=4.40 Hz, 1H), 3.01 (s, 3H), 3.09-3.20 (m, 1H), 3.39-3.52 (m, 1H), 4.33 (dd, J=5.05, 4.18 Hz, 2H), 4.60-4.71 (m, 1H), 4.78-4.89 (m, 1H), 7.27-7.44 (m, 5H)

Reference Example 49

Synthesis of (2S)-3-(benzyloxy)-2-[(2S)-oxiran-2-yl] propyl methanesulfonate

By using diethyl (L)-malate (8 g) as a starting material, the title compound (197 mg) was obtained in the same manners as those of Reference Example 10, (1), (2), (4), (3) and (5).

MS (ESI) m/z=308.9 [M+Na]$^+$ $^1$H-NMR (200 MHz, CDCl$_3$) δ (ppm): 1.80-1.99 (m, 1H), 2.63 (dd, J=4.83, 2.64 Hz, 1H), 2.83 (t, J=4.61 Hz, 1H), 2.95-3.04 (m, 1H), 3.00 (s, 3H), 3.60 (dd, J=5.93, 1.10 Hz, 2H), 4.42 (d, J=5.27 Hz, 2H), 4.52 (s, 2H), 7.00-7.57 (m, 5H)

Reference Example 50

Synthesis of 1-[(1S)-1-(2-methoxyphenyl)ethyl]azetidin-3-amine (1) Epichlorohydrin (200 mg) and (1S)-1-(2-methoxyphenyl) ethylamine (326.9 mg) obtained by the method described in the patent document (Japanese Patent Unexamined Publication No. 54/154724) were dissolved in isopropanol (2 ml), and the solution was stirred at room temperature for 2 days. The reaction mixture was concentrated under reduced pressure, and the resulting residue was purified by silica gel column chromatography (chloroform:methanol: 28% aqueous ammonia=10:1:0.1) to obtain a chloro compound (482 mg).

(2) The compound obtained in (1) mentioned above (480 mg) was dissolved in acetonitrile (4 ml), the solution was added with triethylamine (0.83 ml), and the mixture was stirred for 5 hours under reflux by heating. The reaction mixture was concentrated under reduced pressure, and the resulting residue was purified by silica gel column chromatography (chloroform:methanol:28% aqueous ammonia=10:1:0.1) to obtain an azetidine compound (359 mg).

(3) The compound obtained in (2) mentioned above (100 mg) was dissolved in tetrahydrofuran (5 ml), the solution was added with a 2.2 M solution of diethyl azodicarboxylate in toluene (0.33 ml), triphenylphosphine (190 mg), and phthalimide (106.5 mg), and the mixture was stirred at room temperature for 14 hours. The reaction mixture was concentrated under reduced pressure, and the resulting residue was purified by silica gel column chromatography (chloroform:methanol:28% aqueous ammonia=50:1:0.1) to obtain a crude product of phthalimide compound (403.6 mg).

(4) The compound obtained in (3) mentioned above was dissolved in ethanol (3 ml), the solution was added with hydrazine monohydrate, and the mixture was stirred at room temperature for 14 hours. The reaction mixture was filtered, then the filtrate was concentrated under reduced pressure, the resulting residue was added with 1 N hydrochloric acid, and the mixture was washed with chloroform. The aqueous layer was made alkaline with 1 N aqueous sodium hydroxide, and extracted with chloroform. The organic layer was dried over anhydrous sodium sulfate and filtered, and then the filtrate was concentrated under reduced pressure to obtain the title compound (25 mg).

MS (ESI) m/z=207.2 [M+H]$^+$ $^1$H-NMR (600 MHz, CDCl$_3$) δ (ppm): 1.15 (d, J=6.42 Hz, 3H), 2.48-2.57 (m, 1H), 2.67-2.74 (m, 1H) 3.45-3.52 (m, 1H), 3.54-3.61 (m, 1H), 3.70-3.76 (m, 2H), 3.82 (s, 3H), 6.82-6.86 (m, 1H), 6.91-6.96 (m, 1H) 7.16-7.21 (m, 1H), 7.39-7.43 (m, 1H)

Reference Example 51

Synthesis of N-[1-(3-hydroxyphenyl)ethyl]ethane-1,2-diamine

3'-Hydroxyacetophenone (1.0 g) and ethylenediamine (1.47 ml) were dissolved in methanol (10 ml), and the solution was stirred at room temperature for 16 hours. The reaction mixture was added with sodium borohydride (277.9 mg), the mixture was stirred at room temperature for 5 hours, and then was added with 1 N hydrochloric acid, and the solvent was evaporated. The resulting residue was added with potassium carbonate and distilled water, and thereby made alkaline, then the mixture was extracted with a 10:1 mixed solvent of chloroform and ethanol, and the organic layer was dried over anhydrous sodium sulfate, and filtered. The filtrate was concentrated under reduced pressure, and the resulting residue was purified by silica gel column chromatography (chloroform:methanol:28% aqueous ammonia=10:1:0.1 to 5:1:0.1) to obtain the title compound (59.1 mg).

MS (ESI) m/z=181.0 [M+H]$^+$ $^1$H-NMR (200 MHz, CDCl$_3$) δ (ppm): 1.36 (d, J=6.59 Hz, 3H), 2.44-2.85 (m, 4H), 3.72 (q, J=6.45 Hz, 1H), 6.63-6.91 (m, 3H), 7.09-7.21 (m, 1H)

Reference Example 52

Synthesis of N-ethyl-N-[(1S)-1-(2-methoxyphenyl) ethyl]ethane-1,2-diamine (1) (1S)-1-(2-Methoxyphenyl)ethylamine (8.86 g) obtained by the method described in the publication (Japanese Patent Unexamined Publication No. 54/154724) was dissolved in chloroform (100 ml), the solution was added with acetic anhydride (12.0 g) and 4-dimethylaminopyridine (14.3 g), and the mixture was stirred at 70° C. for 30 minutes. The reaction mixture was left to cool, and then washed successively with 1 N hydrochloric acid, and 10% aqueous sodium hydroxide. The organic layer was dried over anhydrous magnesium sulfate, and filtered, and then the filtrate was concentrated under reduced pressure to obtain an acetyl compound (11.23 g).

(2) Lithium aluminum hydride (3.3 g) was suspended in tetrahydrofuran (200 ml), and the suspension was added with the compound obtained in (1) mentioned above (11.2 g) over 15 minutes under reflux by heating. The reaction mixture was stirred for 3 hours under reflux by heating, then left to cool, and added successively with distilled water (3.3 ml), 15% aqueous sodium hydroxide (3.3 ml), and distilled water (3.3 ml), and the mixture was stirred for 2 hours. The reaction mixture was filtered, the resulting filtrate was further washed with tetrahydrofuran, and then the filtrate was concentrated under reduced pressure to obtain an N-ethyl compound (10.86 g).

(3) Phthalimidoacetaldehyde (125 mg) obtained by the method described in the literature (Tetrahedron Letters, 2001, vol. 42, p. 315) was dissolved in chloroform (20 ml), the solution was added with the compound obtained in (2) mentioned above (0.6 g) and sodium triacetoxyborohydride (1.06 g), and the mixture was stirred at room temperature for 2 hours. The reaction mixture was added with saturated aqueous sodium hydrogencarbonate and chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=2:1) to obtain a phthalimide compound (0.93 g).

(4) The compound obtained in (3) mentioned above (0.93 g) was dissolved in ethanol (20 ml), the solution was added with hydrazine monohydrate (0.38 ml), and the mixture was stirred under reflux by heating for 3 hours and at room temperature for 18 hours. The reaction mixture was concentrated under reduced pressure, the resulting residue was added with 1 N hydrochloric acid and thereby made acidic, and the deposited solid was removed by filtration. The filtrate was neutralized with potassium carbonate, and then added with chloroform, the layers were separated, and the organic layer was dried over anhydrous magnesium sulfate, and filtered. The filtrate was concentrated under reduced pressure, and the resulting residue was purified by silica gel column chromatography (chloroform:methanol:28% aqueous ammonia=10:1:0.1) to obtain the title compound (484 mg).

MS (ESI) m/z=223.2 [M+H]$^+$ $^1$H-NMR (200 MHz, CDCl$_3$) δ (ppm): 0.98 (t, J=7.03 Hz, 3H), 1.29 (d, J=7.03 Hz, 3H), 2.38-2.72 (m, 6H), 3.82 (s, 3H), 4.37 (q, J=7.03 Hz, 1H), 6.83-6.97 (m, 2H), 7.15-7.25 (m, 1H), 7.36 (dd, J=7.47, 1.76 Hz, 1H)

Reference Example 53

Synthesis of benzyl 2-(methylamino)ethylcarbamate

N-Methylethylenediamine (2.0 g) was dissolved in dioxane (20 ml), the solution was added with N-carbobenzoxysuccinimide (8.07 g), and the mixture was stirred at room temperature for 4 days. The reaction mixture was added with distilled water and chloroform, the layers were separated, and the organic layer was dried over anhydrous magnesium sulfate, and filtered. The filtrate was concentrated under reduced pressure, and the resulting residue was purified by silica gel column chromatography (hexane:ethyl acetate=3:1 to 2:1), and then purified again by silica gel column chromatography (chloroform:methanol:28% aqueous ammonia=30:1:0.1) to obtain the title compound (243 mg).

MS (ESI) m/z=209 [M+H]$^+$ $^1$H-NMR (400 MHz, CDCl$_3$) δ (ppm): 2.41 (s, 3H), 2.71 (t, J=5.6 Hz, 2H), 3.26-3.33 (m, 2H), 5.10 (s, 2H), 5.25-5.35 (m, 1H), 7.28-7.37 (m, 5H)

Reference Example 54

Synthesis of (1S)-1-(2-methoxyphenyl)ethylamine (1) 2'-Methoxyacetophenone (200 g) and ammonium formate (272 g) were mixed, and the mixture was stirred at 200° C. for 2 hours. The reaction mixture was left to cool to room temperature, and then added with distilled water and chloroform, the layers were separated, and the organic layer was dried over anhydrous potassium carbonate, and filtered. The filtrate was concentrated under reduced pressure, the resulting residue was added with concentrated hydrochloric acid (310 ml), and the mixture was stirred at 100° C. for 1 hour, and then left to cool to room temperature. The reaction mixture was added with distilled water and toluene, the layers were separated, and the aqueous layer was washed with toluene. The aqueous layer was added with 5 N aqueous sodium hydroxide, thereby adjusted to pH 11, and then extracted 5 times with chloroform. The organic layer was dried over anhydrous potassium carbonate, and filtered, then the filtrate was concentrated under reduced pressure, and the resulting residue was purified by silica gel column chromatography (chloroform to chloroform:methanol:28% aqueous ammonia=5:1:0.1) to obtain an amino compound (81.9 g).

(2) By using the compound obtained in (1) mentioned above (81.9 g) as a starting material, the title compound (33.7 g) was obtained in the same manner as that of the patent document (Japanese Patent Unexamined Publication No. 54/154724).

Reference Example 55

Synthesis of 3-(quinolin-4-yl)propylamine (1) 4-Quinolinecarboxyaldehyde (4.46 g) was dissolved in toluene (50 ml), the solution was added with (carboethoxymethylene)triphenylphosphorane (9.85 g) and benzoic acid (0.345 g), and the mixture was stirred for 5 hours under reflux by heating. The reaction mixture was cooled, and then added with saturated aqueous sodium hydrogencarbonate and ethyl acetate, and the layers were separated. The organic layer was washed with saturated brine, dried over anhydrous magnesium sulfate, and filtered. The filtrate was concentrated under reduced pressure, and the resulting residue was purified by silica gel column chromatography (hexane:ethyl acetate=1:1) to obtain an ester compound (6.6 g).

(2) The compound obtained in (1) mentioned above (6.6 g) was dissolved in toluene (300 ml), and the solution was cooled to −78° C., and then added with a 0.99 M solution of diisobutylaluminum hydride in toluene (64.5 ml), and the mixture was stirred for 1 hour. The reaction mixture was added with 1 N hydrochloric acid and thereby made acidic, and then the mixture was stirred overnight. The organic layer was separated, the aqueous layer was extracted with chloroform, and then the organic layer was dried over anhydrous magnesium sulfate, and filtered. The filtrate was concentrated under reduced pressure, and the resulting residue was purified by silica gel column chromatography (chloroform to chloroform:methanol=9:1) to obtain an alcohol compound (3.3 g).

(3) The compound obtained in (2) mentioned above (1.0 g) was dissolved in tetrahydrofuran (20 ml), the solution was added with triphenylphosphine (2.1 g) and phthalimide (1.19 g), and then added with a 40% solution of diethyl azodicarboxylate in toluene (3.5 ml) under ice cooling, and the mixture was stirred for 30 minutes. The reaction mixture was further stirred at room temperature for 1 hour, and then added with saturated aqueous sodium hydrogencarbonate and ethyl acetate, and the layers were separated. The organic layer was washed with saturated brine, dried over anhydrous magnesium sulfate, and filtered. The filtrate was concentrated under reduced pressure, and the resulting residue was roughly purified by silica gel column chromatography (hexane:ethyl acetate=2:1 to 1:1) to obtain a phthalimide compound.

(4) The compound obtained in (3) mentioned above was dissolved in ethanol (30 ml), the solution was added with hydrazine monohydrate (5 ml), and the mixture was stirred at room temperature for 18 hours. The reaction mixture was filtered, and then concentrated under reduced pressure, and the resulting residue was roughly purified by silica gel column chromatography (chloroform:methanol:28% aqueous ammonia=20:1:0.1 to 10:1:0.1). The resulting crude product was added with 1 N hydrochloric acid and chloroform, the layers were separated, and the aqueous layer was made basic with 4 N aqueous sodium hydroxide, and then extracted with chloroform. The organic layer was dried over anhydrous magnesium sulfate, and filtered, and then the filtrate was concentrated under reduced pressure to obtain the title compound (180 mg).
MS (ESI) m/z=187.2 [M+H]$^+$
$^1$H-NMR (200 MHz, CDCl$_3$)δ (ppm): 1.89-1.95 (m, 2H), 2.84 (t, J=6.88 Hz, 2H), 3.11-3.16 (m, 2H), 7.24 (d, J=4.58 Hz, 1H), 7.53-7.58 (m, 1H), 7.67-7.72 (m, 1H), 8.02-8.13 (m, 2H), 8.80 (d, J=4.13 Hz, 1H)

Reference Example 56

Synthesis of [3-(furan-3-yl)phenyl]methylamine (1) 3-Bromobenzylamine (2 g) was dissolved in methylene chloride (25 ml), the solution was added with a solution of di-t-butyl dicarbonate (2.23 g) in methylene chloride (5 ml), and the mixture was stirred at room temperature for 16 hours. The reaction mixture was added with distilled water and 1 N hydrochloric acid, the layers were separated, and the organic layer was washed successively with saturated aqueous sodium hydrogencarbonate and saturated brine. The organic layer was dried over anhydrous magnesium sulfate, and filtered, and then the filtrate was concentrated under reduced pressure to obtain a protected compound (2.80 g).
(2) The compound obtained in (1) mentioned above (2.80 g) was dissolved in toluene (22 ml), the solution was added with tetrakis(triphenylphosphine)palladium(0) (1.7 g), 2 M aqueous sodium carbonate (10.8 ml), and a solution of 3-furanboronic acid (1.64 g) in methanol (6.5 ml), and the mixture was stirred at 80° C. for 16 hours. The reaction mixture was added with 2 M aqueous sodium carbonate (20 ml) and ethyl acetate, the layers were separated, and the organic layer was washed with saturated brine, then dried over anhydrous sodium sulfate, and filtered. The filtrate was concentrated under reduced pressure, and the resulting residue was purified by silica gel column chromatography (hexane:ethyl acetate=5:1) to obtain a furanyl compound (2.65 g).
(3) The compound obtained in (2) mentioned above (1.0 g) was added with an ice-cooled 4 N solution of hydrochloric acid in dioxane, and the mixture was stirred for 1 hour and 30 minutes. The reaction mixture was concentrated under reduced pressure, and the resulting residue was dissolved in a mixed solvent of methylene chloride and methanol (4:1, 25 ml), and purified by silica gel column chromatography (NH-form, chloroform:methanol=7:1) to obtain the title compound (687 mg).
MS (FAB) m/z=174 [M+H]$^+$
$^1$H-NMR (400 MHz, CDCl$_3$) δ (ppm): 3.90 (s, 2H), 6.71-6.74 (m, 1H), 7.20-7.24 (m, 1H), 7.32-7.40 (m, 2H), 7.44-7.46 (m, 1H), 7.48 (t, J=1.7 Hz, 1H), 7.73-7.77 (m, 1H)

Reference Example 57

Synthesis of 2-[3-(furan-3-yl)phenyl]ethylamine

By using 2-(3-bromophenyl)ethylamine (5.0 g) as a starting material, the title compound (1.70 g) was obtained in the same manner as that of Reference Example 56.
MS (FAB) m/z=188 [M+H]$^+$
$^1$H-NMR (400 MHz, CDCl$_3$) δ (ppm): 2.78 (t, J=6.8 Hz, 2H), 3.00 (t, J=6.8 Hz, 2H), 6.69-6.72 (m, 1H) 7.09-7.13 (m, 1H) 7.29-7.37 (m, 3H), 7.48 (t, J=1.7 Hz, 1-H), 7.72-7.76 (m, 1H)

Reference Example 58

Synthesis of Compound of the Formula (A) wherein R=Allyl (1) By using 6-O-alkylerythromycin A (33.0 g) obtained by the method described in the patent document (WO98/18807) as a starting material, (9S)-9-dihydro-6-β-allylerythromycin A (8.15 g) was obtained in the same manner as that described in the literature (The Journal of Antibiotics, 1990, vol. 43, 10, p. 1334).
(2) By using the compound obtained in (1) mentioned above (8.15 g) as a starting material, the title compound (3.9 g) was obtained in the same manner as that of Reference Example 1.
MS (ESI) m/z=1019.9 [M+H]$^+$ Reference Example 59

Synthesis of N-(quinolin-6-yl)ethane-1,2-diamine (1) 6-Aminoquinoline (0.5 g) was dissolved in chloroform (10 ml), the solution was added with phthalimideacetaldehyde (984 mg) obtained by the method described in the literature (Tetrahedron Letters, 2001, vol. 42, p. 315), and the mixture was stirred at room temperature for 2 hours, and then added with sodium triacetoxyborohydride (1.47 g), and the mixture was stirred at room temperature for 12 hours. The reaction mixture was added with saturated aqueous sodium hydrogencarbonate and chloroform, the layers were separated, and the organic layer was dried over anhydrous sodium sulfate, and filtered. The filtrate was concentrated under reduced pressure, and the resulting residue was washed with ethyl acetate to obtain a phthalimide compound (913 mg).
(2) The compound obtained in (1) mentioned above (297 mg) was dissolved in ethanol (4 ml), the solution was added with hydrazine monohydrate (68 μl), and the mixture was stirred for 2 hours under reflux by heating. The reaction mixture was filtered, the filtrate was concentrated under reduced pressure, and the resulting residue was purified by silica gel column chromatography (chloroform to chloroform:methanol:28% aqueous ammonia=40:1:0.1) to obtain the title compound (107 mg).
MS (ESI) m/z=188.1 [M+H]$^+$
$^1$H-NMR (600 MHz, CD$_3$OD) δ (ppm): 2.90 (t, J=6.19 Hz, 1-H), 3.28-3.31 (m, 1H), 3.42-3.48 (m, 1H) 3.51-3.57 (m, 1H), 6.78 (dd, J=13.07, 2.52 Hz, 1H), 7.20 (ddd, J=9.17, 5.50, 2.75 Hz, 1H), 7.30 (ddd, J=6.19, 4.13, 2.06 Hz, 1H), 7.70 (d, J=9.17 Hz, 1H), 7.99-8.07 (m, 1H), 8.41 (dd, J=4.36, 1.60 Hz, 1H)

Reference Example 60

Synthesis of (R)-2-(oxiran-2-yl)ethyl methanesulfonate (1) (D)-Malic acid (151 g) was dissolved in ethanol (1000 ml), the solution was added with concentrated sulfuric acid (5 ml), and the mixture was stirred for 2 hours under reflux by heating. The reaction mixture was concentrated under reduced pressure, then the residue was added with saturated aqueous sodium hydrogencarbonate and chloroform, and the layers were separated. The organic layer was dried over anhydrous magnesium sulfate, and filtered, and then the filtrate was concentrated under reduced pressure to obtain a crude product.
(2) Lithium aluminum hydride (85.5 g) was suspended in tetrahydrofuran (2000 ml), the suspension was added with a solution of the compound obtained in (1) mentioned above in tetrahydrofuran (1000 ml), and the mixture was stirred at room temperature for 2 hours. The reaction mixture was added with distilled water, 1 N aqueous sodium hydroxide, and distilled water in this order under ice cooling, and the mixture was stirred overnight. The mixture was filtered through Celite, then the filtrate was concentrated under reduced pressure, and the resulting residue was purified by silica gel column chromatography (chloroform:methanol:28% aqueous ammonia=10:1:0.1) to obtain a triol compound (31.0 g).
(3) The compound obtained in (2) mentioned above (30.3 g) was dissolved in chloroform (1000 ml), and the solution was added with ice-cooled triethylamine (120 ml). The mixture was added with a solution of methanesulfonyl chloride (46.4 ml) in tetrahydrofuran (100 ml), and the mixture was stirred for 1 hour under ice cooling. The reaction mixture was added with saturated aqueous sodium hydrogencarbonate and chloroform, the layers were separated, and the organic layer was dried over anhydrous magnesium sulfate, and filtered. The filtrate was concentrated under reduced pressure to obtain a crude product of methanesulfonyl compound.
(4) The compound obtained in (3) mentioned above was dissolved in methanol (285 ml), the solution was added with potassium carbonate 11.8 g), and the mixture was stirred at room temperature for 2 hours. The reaction mixture was added with distilled water and ethyl acetate, the layers were separated, and the organic layer was dried over anhydrous magnesium sulfate, and filtered. The filtrate was concentrated under reduced pressure, and the resulting residue was purified by silica gel column chromatography (hexane:ethyl acetate=10:1) to obtain the title compound (25.5 g).
MS (ESI) m/z=167.1 [M+H]$^+$
$^1$H-NMR (600 MHz, CD$_3$OD) δ (ppm): 1.80-1.88 (m, 1H), 2.08-2.16 (m, 1H), 2.54-2.57 (m, 1H), 2.80-2.85 (m, 1H), 3.03 (s, 3H), 3.04-3.08 (m, 1H), 4.34-4.39 (m, 2H)

Reference Example 61

Synthesis of 2-(benzyloxy)-5-tert-butylphenol

A solution (20 ml) of 4-t-butylcathecol (3.0 g) in acetone was added with benzyl bromide (2.2 ml) and potassium carbonate (3.0 g), and the mixture was stirred for 3 hours under reflux by heating. The mixture was added with distilled water and ethyl acetate, the layers were separated, and the organic layer was concentrated under reduced pressure. The resulting residue was purified by silica gel column chromatography (chloroform) to obtain the title compound (43.2 mg).
$^1$H-NMR (200 MHz, CDCl$_3$) δ (ppm): 1.28 (s, 9H), 5.09 (s, 2H), 6.81-6.88 (m, 2H), 6.97-7.05 (m, 1H), 7.29-7.47 (m, 5H)

Reference Example 62

Synthesis of 2-(benzyloxy)-4-tert-butylphenol

By using 4-t-butylcathecol (3.0 g) as a starting material, the title compound (61.2 mg) was obtained in the same manner as that of Reference Example 61.

$^1$H-NMR (200 MHz, CDCl$_3$) δ (ppm): 1.28 (s, 9H), 5.11 (s, 2H), 6.86-6.91 (m, 2H), 6.94-6.99 (m, 1H), 7.32-7.47 (m, 5H)

Reference Example 63

Synthesis of 1-methyl-1H-indol-7-ol (1) 7-Hydroxyindole (300 mg) was dissolved in dimethylformamide (2.0 ml), the solution was added with potassium carbonate (622.6 mg) and benzyl bromide (295 μl) at room temperature, and the mixture was stirred overnight at room temperature. The reaction mixture was added with distilled water and ethyl acetate for extraction, and the organic layer was washed twice with distilled water, then dried over anhydrous magnesium sulfate, and filtered. The filtrate was concentrated under reduced pressure, and the resulting residue was purified by silica gel column chromatography (hexane:ethyl acetate=10:1) to obtain a benzyl compound (384 mg).
(2) The compound obtained in (1) mentioned above (380 mg) was dissolved in dimethylformamide (5.0 ml), the solution was added with sodium hydride (136 mg) under ice cooling, and the mixture was stirred for 10 minutes. The reaction mixture was added with methyl iodide (116.4 μl), and the mixture was stirred for 1 hour under ice cooling. The reaction mixture was added with distilled water and ethyl acetate for extraction, and the organic layer was washed twice with distilled water, then dried over anhydrous magnesium sulfate, and filtered. The filtrate was concentrated under reduced pressure, and the resulting residue was purified by silica gel column chromatography (hexane:ethyl acetate=10:1) to obtain an N-methyl compound (363 mg).
(3) The compound obtained in (2) mentioned above (180 mg) was dissolved in methanol (2.0 ml), the solution was added with 5% palladium-carbon (90 mg), and the mixture was stirred overnight at room temperature under a hydrogen atmosphere of 1 atm. The reaction mixture was filtered through Celite, then the filtrate was concentrated under reduced pressure, and the resulting residue was purified by silica gel column chromatography (hexane:ethyl acetate=10:1) to obtain the title compound (91.0 mg).
MS (ESI) m/z=148.1 [M+H]$^+$
$^1$H-NMR (600 MHz, CDCl$_3$) δ (ppm): 4.08 (s, 3H), 6.41 (d, J=3.21 Hz, 1H), 6.46-6.49 (m, 1H), 6.84-6.88 (m, 1H), 6.94 (d, J=3.21 Hz, 1H), 7.16-7.19 (m, 1H)

Reference Example 64

Synthesis of benzyl 4-(3-hydroxyphenyl)piperazine-1-carboxylate 1-(3-Hydroxyphenyl)piperazine (200 mg) was dissolved in tetrahydrofuran (10 ml), the solution was added with saturated aqueous sodium hydrogencarbonate (10 ml) and benzyl chloroformate (176 μl) at room temperature, and the mixture was stirred for 14 hours. The reaction mixture was added with ethyl acetate for extraction, and the organic layer was dried over anhydrous magnesium sulfate, and filtered. The filtrate was concentrated under reduced pressure, and the resulting residue was purified by silica gel column chromatography (hexane:ethyl acetate=3:1) to obtain the title compound (342 mg).
MS (ESI) m/z=313.1 [M+H]$^+$
$^1$H-NMR (600 MHz, CDCl$_3$) δ (ppm): 3.13 (br. s., 4H), 3.63-3.67 (m, 4H), 5.16 (s, 2H), 6.34-6.37 (m, 1H), 6.40 (t, J=2.29 Hz, 1H), 6.49 (dd, J=8.02, 2.06 Hz, 1H), 7.11 (t, J=8.25 Hz, 1H), 7.30-7.39 (m, 5H)

Reference Example 65

Synthesis of 2-(benzyloxy)-5-ethylphenol

By using 4-ethylcathecol (500 mg) as a starting material, the title compound (29.4 mg) was obtained in the same manner as that of Reference Example 61.
$^1$H-NMR (200 MHz, CDCl$_3$) δ (ppm): 1.20 (t, J=7.47 Hz, 3H), 2.56 (q, J=7.76 Hz, 2H), 5.08 (s, 2H), 6.59-6.70 (m, 1H), 6.77-6.85 (m, 2H), 7.31-7.47 (m, 5H)

Reference Example 66

Synthesis of benzyl 4-(3-hydroxyphenyl)piperidine-1-carboxylate

By using 4-(3-hydroxyphenyl)piperidine (200 mg) as a starting material, the title compound (354.2 mg) was obtained in the same manner as that of Reference Example 64.
MS (ESI) m/z=312.1 [M+H]$^+$
$^1$H-NMR (600 MHz, CDCl$_3$) δ (ppm): 1.55-1.67 (m, 2H), 1.78-1.89 (m, 2H), 2.58-2.67 (m, 1H), 2.79-2.95 (m, 2H), 4.23-4.41 (m, 2H), 5.16 (br, s, 2H), 6.64-6.78 (m, 3H), 7.16 (t, J=8.02 Hz, 1H), 7.29-7.40 (m, 5H)

Reference Example 67

Synthesis of 3-(2-hydroxypropan-2-yl)phenol

3'-Hydroxyacetophenone (500 mg) was dissolved in tetrahydrofuran (10 ml), and the solution was slowly added dropwise with a 3 M solution of methylmagnesium bromide in diethyl ether (3.7 ml) under ice cooling. The mixture was stirred at the same temperature for 2 hours, and then added with saturated aqueous ammonium chloride, the mixture was extracted with ethyl acetate, and the organic layer was concentrated under reduced pressure. The resulting residue was purified by silica gel column chromatography (hexane:ethyl acetate=5:1 to 1:1) to obtain the title compound (224.3 mg).
MS (ESI) m/z=151.0 [M+H]$^+$
$^1$H-NMR (600 MHz, DMSO-d6) δ (ppm): 1.34 (s, 6H), 6.50-6.55 (m, 1H), 6.80 (d, J=8.25 Hz, 1H), 6.86 (s, 1H), 7.03 (t, J=7.79 Hz, 1H)

Reference Example 68

Synthesis of 3-(piperidin-1-yl)phenol

3-Aminophenol (500 mg) was dissolved in toluene (5.0 ml), the solution was added with sodium hydrogencarbonate (846.5 mg) and 1,5-dibromopentane (686.3 µl) at room temperature, and the mixture was stirred for 16 hours under reflux by heating. The reaction mixture was cooled, and then added with distilled water and ethyl acetate for extraction, and the organic layer was dried over anhydrous magnesium sulfate, and filtered. The filtrate was concentrated under reduced pressure to obtain the title compound (513 mg).
MS (ESI) m/z=178.1 [M+H]$^+$
$^1$H-NMR (600 MHz, CDCl$_3$) δ (ppm): 1.54-1.60 (m, 2H), 1.66-1.71 (m, 4H), 3.13-3.16 (m, 4H), 6.27 (dd, J=7.79, 2.29 Hz, 1H), 6.40 (t, J=2.29 Hz, 1H), 6.52 (dd, J=8.25, 2.29 Hz, 1H), 7.09 (t, J=8.02 Hz, 1H)

Reference Example 69

Synthesis of 3-(1-hydroxy-1-phenylethyl)phenol

3'-Hydroxyacetophenone (5.0 g) was dissolved in tetrahydrofuran (100 ml), and the solution was added dropwise with a 1 M solution of phenylmagnesium bromide in tetrahydrofuran (100 ml) at −30° C. Then mixture was further added with tetrahydrofuran (100 ml), and the mixture was stirred for 3 hours with gradually warming it. The mixture was added with saturated aqueous ammonium chloride under ice cooling, the mixture was extracted with ethyl acetate, and the organic layer was concentrated under reduced pressure. The resulting residue was purified by silica gel column chromatography (hexane:ethyl acetate=2:1 to 1:1) to obtain the title compound (7.55 g).
$^1$H-NMR (200 MHz, CDCl$_3$) δ (ppm): 1.93 (s, 3H), 6.65-6.77 (m, 1H), 6.87-7.01 (m, 2H), 7.12-7.20 (m, 1H), 7.20-7.47 (m, 5H)

Reference Example 70

Synthesis of 3-(1-phenylethenyl)phenol

The compound obtained in Reference Example 69 (500 mg) was dissolved in acetonitrile (11 ml), the solution was added with 2.5 N sulfuric acid (0.3 ml) and distilled water (1.1 ml), and the mixture was stirred for 2 hours under reflux by heating. The reaction mixture was added with saturated brine, the mixture was extracted with chloroform, and the organic layer was dried over anhydrous magnesium sulfate, and filtered. The filtrate was concentrated under reduced pressure, and the resulting residue was purified by silica gel column chromatography (hexane:ethyl acetate=5:1) to obtain the title compound (424.8 mg).
$^1$H-NMR (200 MHz, CDCl$_3$) δ (ppm): 5.41-5.49 (m, 2H), 6.74-6.84 (m, 2H), 6.88-6.98 (m, 1H) 7.13-7.41 (m, 6H)

Reference Example 71

Synthesis of 3-[hydroxy(diphenyl)methyl]phenol

By using 3-hydroxybenzophenone (200 mg) as a starting material, the title compound (334.1 mg) was obtained in the same manner as that of Reference Example 69.
$^1$H-NMR (600 MHz, CDCl$_3$) δ (ppm): 6.68-6.89 (m, 4H), 7.09-7.47 (m, 10H)

Reference Example 72

Synthesis of 3-(1-cyclopropyl-1-hydroxyethyl)phenol

By using 3'-hydroxyacetophenone (200 mg) and a 0.5 M solution of cyclopropylmagnesium bromide in tetrahydrofuran (8.8 ml) as starting materials, the title compound (176.6 mg) was obtained in the same manner as that of Reference Example 69.
$^1$H-NMR (200 MHz, CDCl$_3$) δ (ppm): 0.30-0.64 (m, 4H), 1.18-1.33 (m, 1H), 1.47 (s, 3H), 6.65-6.78 (m, 1H), 7.00-7.13 (m, 2H), 7.15-7.26 (m, 1H)

Reference Example 73

Synthesis of 3-(2-hydroxybutan-2-yl)phenol

By using 3'-hydroxyacetophenone (200 mg) and a 3 M solution of ethylmagnesium bromide in diethyl ether (1.5 ml)

as starting materials, the title compound (124.9 mg) was obtained in the same manner as that of Reference Example 69.

¹H-NMR (200 MHz, CDCl₃) δ (ppm): 0.80 (t, J=7.47 Hz, 3H), 1.53 (s, 3H), 1.73-1.90 (m, 2H), 6.64-6.76 (m, 1H), 6.89-7.01 (m, 2H), 7.15-7.26 (m, 1H)

Reference Example 74

Synthesis of 3-(1-cyclohexyl-1-hydroxyethyl)phenol

By using 3'-hydroxyacetophenone (200 mg) and a 2 M solution of cyclohexylmagnesium chloride in diethyl ether (2.2 ml) as starting materials, the title compound (69.6 mg) was obtained in the same manner as that of Reference Example 69.

¹H-NMR (200 MHz, CDCl₃) δ (ppm): 0.84-1.31 (m, 6H), 1.46-1.86 (m, 5H), 1.50 (s, 3H), 6.66-6.74 (m, 1H), 6.88-6.99 (m, 2H), 7.19 (t, J=8.13 Hz, 1H)

Reference Example 75

Synthesis of 3-[1-hydroxy-1-(3-methylphenyl)ethyl]phenol

By using 3'-hydroxyacetophenone (200 mg) and a 1 M solution of m-tolylmagnesium chloride in tetrahydrofuran (4.4 ml) as starting materials, the title compound (329.0 mg) was obtained in the same manner as that of Reference Example 69.

¹H-NMR (200 MHz, CDCl₃) δ (ppm): 1.92 (s, 3H), 2.33 (s, 3H), 6.66-6.76 (m, 1H), 6.86-7.12 (m, 3H), 7.19 (s, 4H)

Reference Example 76

Synthesis of 3-[1-hydroxy-1-(4-methylphenyl)ethyl]phenol

By using 3'-hydroxyacetophenone (200 mg) and a 1 M solution of p-tolylmagnesium bromide in tetrahydrofuran (4.4 ml) as starting materials, the title compound (346.8 mg) was obtained in the same manner as that of Reference Example 69.

¹H-NMR (200 MHz, CDCl₃) δ (ppm): 1.91 (s, 3H), 2.33 (s, 3H), 6.65-6.76 (m, 1H), 6.86-7.00 (m, 2H), 7.06-7.24 (m, 3H), 7.25-7.36 (m, 2H)

Reference Example 77

Synthesis of 3-[1-hydroxy-1-(2-methylphenyl)ethyl]phenol

By using 3'-hydroxyacetophenone (200 mg) and a 1 M solution of o-tolylmagnesium chloride in tetrahydrofuran (4.4 ml) as starting materials, the title compound (119.3 mg) was obtained in the same manner as that of Reference Example 69.

¹H-NMR (600 MHz, CDCl₃) δ (ppm): 1.91 (s, 3H), 2.02 (s, 3H), 6.64-6.74 (m, 1H), 6.76-6.91 (m, 2H), 7.05-7.30 (m, 4H), 7.61-7.73 (m, 1H)

Reference Example 78

Synthesis of 3-(pentan-3-yl)phenol (1) Methyl 3-hydroxybenzoate (1.50 g), t-butyldimethylsilyl chloride (1.78 g), and imidazole (1.00 g) were dissolved in dimethylformamide (3 ml), and the solution was stirred at room temperature for 40 minutes. The reaction mixture was concentrated under reduced pressure, and added with ethyl acetate, and the mixture was washed with distilled water, then dried over anhydrous sodium sulfate, and filtered. The filtrate was concentrated under reduced pressure to obtain a silyl ether compound (2.61 g).

(2) The compound obtained in (1) mentioned above (2.61 g) was dissolved in tetrahydrofuran (10 ml), the solution was added with a 1 M solution of ethylmagnesium bromide in tetrahydrofuran (19.7 ml), and the mixture was stirred for 2 hours and 30 minutes under reflux by heating. The reaction mixture was added to saturated aqueous ammonium chloride, the mixture was extracted with ethyl acetate, and the organic layer was dried over anhydrous sodium sulfate, and filtered. The filtrate was concentrated under reduced pressure to obtain an alcohol compound (2.86 g).

(3) The compound obtained in (2) mentioned above (1.65 g) was dissolved in ethanol (25 ml), the solution was added with concentrated hydrochloric acid (25 ml), and the mixture was stirred at 100° C. for 40 minutes. The reaction mixture was concentrated to an about half volume under reduced pressure, and then extracted with diethyl ether, and the organic layer was washed with saturated brine. The organic layer was dried over anhydrous sodium sulfate and filtered, and then the filtrate was concentrated under reduced pressure to obtain an olefin (942 mg).

(4) The compound obtained in (3) mentioned above (942 mg) was added with methanol (50 ml), water (5 ml) and 10% palladium-carbon (94 mg) under an argon atmosphere, and the mixture was stirred at room temperature for 2 hours under a hydrogen atmosphere of 1 atm. The reaction mixture was filtered through Celite, then the filtrate was concentrated under reduced pressure, and the resulting residue was purified by silica gel column chromatography (hexane:ethyl acetate=100:0 to 94:6) to obtain the title compound (652 mg).

MS (EI) m/z=164 [M+H]⁺

¹H-NMR (400 MHz, CDCl₃) δ (ppm): 0.77 (t, J=7.6 Hz, 6H), 1.44-1.59 (m, 2H), 1.61-1.74 (m, 2H), 2.22-2.30 (m, 1H), 4.70 (s, 1H), 6.60-6.68 (m, 1H), 6.73 (d, J=7.6 Hz, 1-H), 7.15 (t, J=7.8 Hz, 1H)

Reference Example 79

Synthesis of 3-butylphenol (1) Propyltriphenylphosphonium bromide (2.18 g) was added with tetrahydrofuran (10 ml) under an argon atmosphere, the mixture was added with a 1.57 M solution of n-butyllithium in hexane (3.30 ml) under ice cooling, the mixture was stirred at room temperature for 20 minutes, and then added with a solution of 3-(benzyloxy)benzaldehyde (1.00 g) in tetrahydrofuran (5 ml) under ice cooling, and the mixture was stirred for 30 minutes. The reaction mixture was added with saturated aqueous ammonium chloride, and the mixture was extracted with ethyl acetate. The organic layer was dried over anhydrous sodium sulfate and filtered, and then concentrated under reduced pressure, and the resulting residue was purified by silica gel column chromatography (hexane:ethyl acetate=90:10) to obtain an olefin compound (1.08 g).

(2) The compound obtained in (1) mentioned above (1.08 g) was added with methanol (15 ml) and 10% palladium-carbon (94 mg) under an argon atmosphere, and the mixture was stirred at room temperature for 2 hours under a hydrogen atmosphere of 1 atm. The reaction mixture was filtered through Celite, and then the filtrate was concentrated under reduced pressure to obtain the title compound (687 mg).
MS (FAB) m/z=150 [M+H]$^+$
$^1$H-NMR (400 MHz, CDCl$_3$) δ (ppm): 0.93 (t, J=7.3 Hz, 3H), 1.30-1.40 (m, 2H), 1.54-1.63 (m, 2H), 2.56 (t, J=7.8 Hz, 1H), 4.74 (s, 1H), 6.62-6.68 (m, 2H), 6.75 (d, J=7.6 Hz, 1H), 7.14 (t, J=7.6 Hz, 1H)

Reference Example 80

Synthesis of 3-pentylphenol

By using butyltriphenylphosphonium bromide (1.13 g) as a starting material, the title compound (207 mg) was obtained in the same manner as that of Reference Example 79.
MS (FAB) m/z=164 [M+H]$^+$
$^1$H-NMR (400 MHz, CDCl$_3$) δ (ppm): 0.89 (t, J=7.2 Hz, 3H), 1.25-1.40 (m, 2H), 1.54-1.69 (m, 2H), 2.51-2.59 (m, 2H), 4.72 (s, 1H), 6.61-6.68 (m, 2H), 6.75 (d, J=7.6 Hz, 1-H), 7.14 (t, J=7.6 Hz, 1H)

Reference Example 81

Synthesis of 3-cyclopropylphenol (1) By using methyltriphenylphosphonium bromide (2.02 g) as a starting material, an olefin compound (959 mg) was obtained in the same manner as that of Reference Example 79, (1).
(2) Methylene chloride (5 ml) was added with a 1 M solution of diethylzinc in hexane (4.76 ml) under an argon atmosphere, the mixture was added dropwise with a solution of trifluoroacetic acid (354 μl) in methylene chloride (2.5 ml) under ice cooling, and then the mixture was stirred at the same temperature for 20 minutes. The reaction mixture was added with a solution of diiodomethane (383 μl) in methylene chloride (2.5 ml), the reaction mixture was further stirred for 20 minutes, and then added with a solution of the compound obtained in (1) mentioned above (500 mg) in methylene chloride (2.5 ml), and the mixture was stirred at room temperature for 1 hour. The reaction mixture was added with saturated aqueous ammonium chloride, the mixture was extracted with ethyl acetate, and the organic layer was dried over anhydrous sodium sulfate, and filtered. The filtrate was concentrated under reduced pressure, and the resulting residue was purified by silica gel column chromatography (hexane:ethyl acetate=90:10) to obtain a benzyl ether compound (262 mg).
(3) By using the compound obtained in (2) mentioned above (90 mg) as a starting material, the title compound (18.7 mg) was obtained in the same manner as that of Reference Example 79, (2).
$^1$H-NMR (400 MHz, CDCl$_3$) δ (ppm): 0.65-0.70 (m, 2H), 0.91-0.97 (m, 2H), 1.80-1.88 (m, 1H), 5.00 (s, 1H), 6.51-6.55 (m, 1H), 6.60 (ddd, J=8.3, 2.4, 0.7 Hz, 1H), 6.64-6.68 (m, 1H), 7.11 (t, J=7.8 Hz, 1H)

Reference Example 82

Synthesis of (2R)-3-methoxy-2-[(2R)-oxiran-2-yl] propyl methanesulfonate

By using diethyl (D)-malate (5.0 g) and methoxymethyl chloride (6.14 g) as starting materials, the title compound (158 mg) was obtained in the same manner as that of Reference Example 10.
MS (ESI) m/z=211.0 [M+H]$^+$
$^1$H-NMR (200 MHz, CDCl$_3$) δ (ppm): 1.78-1.95 (m, 1H), 2.64 (dd, J=4.83, 2.64 Hz, 1H), 2.84 (dd, J=4.83, 3.96 Hz, 1H), 2.94-3.03 (m, 1H), 3.04 (s, 3H), 3.36 (s, 3H), 3.51 (d, J=4.83 Hz, 2H), 4.40 (d, J=5.71 Hz, 2H)

Reference Example 83

Synthesis of benzyl 4-hydroxy-2-methylbenzoate

A solution of 4-hydroxy-2-methylbenzoic acid (300 mg) in dimethylformamide (3 ml) was added with potassium hydrogencarbonate (236.9 mg), the mixture was stirred for 10 minutes, and then added with benzyl bromide (0.35 ml), and the mixture was stirred at 40° C. for 2 hours. The mixture was added with distilled water, the mixture was extracted with ethyl acetate, and the organic layer was concentrated under reduced pressure. The resulting residue was purified by silica gel column chromatography (hexane to hexane ethyl acetate=50:1 to 20:1 to 2:1) to obtain the title compound (351.8 mg).
$^1$H-NMR (200 MHz, DMSO-d6) δ (ppm): 2.47 (s, 3H), 5.25 (s, 2H), 6.60-6.73 (m, 2H), 7.29-7.50 (m, 5H), 7.80 (d, J=9.23 Hz, 1H)

Reference Example 84

Synthesis of (R)-2-((R)-oxiran-2-yl)-3-butenyl 4-methylbenzenesulfonate

By using (2R,3R)-3-vinylbutane-1,2,4-triol (2.0 g) obtained by the method described in the literature (Tetrahedron Letters, 2000, vol. 41, p. 2659) as a starting material, the title compound (912.6 mg) was obtained in the same manners as those of Reference Example 7, (1) and (2) as a crude product.
MS (ESI) m/z=269 [M+H]$^+$
$^1$H-NMR (300 MHz, CDCl$_3$) δ (ppm): 2.20-29 (m, 1H), 2.46 (s, 3H), 2.53 (dd, J=4.94, 2.75 Hz, 1H), 2.77 (dd, J=4.67, 3.85 Hz, 1H), 2.90-2.95 (m, 1H), 4.15 (d, J=5.50 Hz, 2H), 5.14-5.22 (m, 2H), 5.64-5.76 (m, 2H), 7.35 (d, J=7.97 Hz, 2H), 7.80 (d, J=8.51 Hz, 2H)

Reference Example 85

Synthesis of 3-ethylbenzenethiol (1) 1-Bromo-3-ethylbenzene (300 mg), methyl 3-mercaptopropionate (216 μl), tris(dibenzylideneacetone)dipalladium(0) (37 mg), and 9,9-dimethyl-4,5-bis(diphenylphosphino)xanthene (47 mg) were added with dioxane (5 ml) and diisopropylethylamine (564 μl), and the mixture was stirred at 100° C. for 9 hours. The reaction mixture was concentrated under reduced pressure, the residue was added with ethyl acetate, and the organic layer was washed with saturated aqueous sodium hydrogencarbonate, then dried over anhydrous sodium sulfate, and filtered. The filtrate was concentrated under reduced pressure, and the resulting residue was purified by silica gel column chromatography (hexane:ethyl acetate=100:0 to 97:3) to obtain a sulfide compound (369 mg).
(2) The compound obtained in (1) mentioned above (171.9 mg) was dissolved in tetrahydrofuran (3 ml), the solution was added with potassium t-butoxide (86 mg), and the mixture was stirred at room temperature for 1 hour. The mixture was further added with potassium t-butoxide (86 mg), the reaction mixture was stirred for 10 minutes, and then added with saturated aqueous ammonium chloride and distilled water, the mixture was extracted with ethyl acetate, the organic layer was dried over anhydrous sodium sulfate and filtered, and then the filtrate was concentrated under reduced pressure to obtain the title compound (102 mg).

$^1$H-NMR (400 MHz, CDCl$_3$) δ (ppm): 1.50 (t, J=7.6 Hz, 3H), 2.60 (q, J=7.6 Hz, 2H), 3.41 (s, 1H), 6.99 (d, J=7.6 Hz, 1H), 7.07-7.18 (m, 3H)

Reference Example 86

Synthesis of (R)-2-((R)-oxidran-2-yl)-butyn-3-yl p-toluenesulfonate (1) Trimethylsilylacetylene (0.9 ml) was dissolved in a mixed solvent of hexane (90 ml) and toluene (45 ml) under an argon atmosphere, and the solution was slowly added with a 1.58 M solution of n-butyllithium in hexane (24.4 ml) at −78° C. The mixture was stirred at the same temperature for 30 minutes, then warmed to −40° C., and slowly added with a solution of (2S,3S)-2,3-bis(benzyloxymethyl)oxirane (4.38 g) obtained by the method described in the literature (Journal of Organic Chemistry, 1985, vol. 50, p. 1440) in toluene (20 ml) at the same temperature. The mixture was slowly warmed to 5° C., and stirred at the same temperature for about 3 hours. The reaction mixture was diluted with diethyl ether, and added with saturated aqueous sodium hydrogencarbonate, and the layers were separated. The organic layer was washed with saturated brine, and dried over anhydrous magnesium sulfate, and then the solvent was evaporated under reduced pressure. The residue was dissolved in tetrahydrofuran (23 ml), the solution was added with a 1 M solution of tetrabutylammonium fluoride in tetrahydrofuran (23 ml) at room temperature, the mixture was stirred at the same temperature for 3 hours, and then added with diethyl ether and saturated aqueous sodium hydrogencarbonate, and the layers were separated. The aqueous layer was extracted with diethyl ether, the organic layers were combined, and washed with saturated brine. The organic layer was dried over anhydrous magnesium sulfate, the filtrate was concentrated under reduced pressure, and the resulting residue was purified by silica gel column chromatography (ethyl acetate:hexane=1:3) to obtain an acetylene alcohol (3.7 g).

(2) The compound obtained in (1) mentioned above (3.7 g) was dissolved in methylene chloride (50 ml) under an argon atmosphere, the solution was added with a 1 M solution of boron trichloride in heptane (47 ml) at −78° C., and the mixture was stirred at the same temperature for 2 hours. The reaction mixture was added with 5 N aqueous sodium hydroxide, and then the solvent was evaporated under reduced pressure. The residue was suspended in tetrahydrofuran and methanol (1:1), the insoluble matter was removed by filtration, and then the filtrate was concentrated under reduced pressure. The resulting residue was purified by silica gel column chromatography (chloroform:methanol=10:1) to obtain a triol compound (1.2 g).

(3) The compound obtained in (2) mentioned above (1.2 g) was dissolved in methylene chloride (20 ml), the solution was added with pyridine (5.3 ml) and p-toluenesulfonyl chloride (4.8 g) under ice cooling, the mixture was stirred overnight at room temperature, and then added with diethyl ether and saturated aqueous sodium hydrogencarbonate, the layers were separated, and the aqueous layer was extracted with diethyl ether. The organic layers were combined, washed with saturated brine, dried over anhydrous magnesium sulfate, and filtered. The filtrate was concentrated under reduced pressure, and the resulting residue was purified by silica gel column chromatography (ethyl acetate:hexane=1:2) to obtain a bistosyl compound (1.4 g).

(4) The compound obtained in (3) mentioned above (1.4 g) was dissolved in methanol (20 ml), the solution was added with potassium carbonate (0.54 g) under ice cooling, and the mixture was stirred at the same temperature for 3 hours. The reaction mixture was added with diethyl ether, the insoluble matter was removed by filtration, and then the filtrate was washed with saturated aqueous sodium hydrogencarbonate and saturated brine, dried over anhydrous magnesium sulfate, and filtered. The filtrate was concentrated under reduced pressure, and the resulting residue was purified by silica gel column chromatography (ethyl acetate:hexane=1:2) to obtain the title compound (1.4 g).

MS (FAB) m/z=267 [M+H]$^+$ $^1$H-NMR (400 MHz, CDCl$_3$) δ (ppm): 1.60 (s, 1H), 2.16 (dd, J=2.43, 0.73 Hz, 1H), 2.73 (dd, J=4.38, 2.19 Hz, 1H), 2.75 (ddd, J=14.5, 5.60, 2.44 Hz, 1H), 2.79 (dd, J=4.63, 4.63 Hz, 1H), 3.06 (m, 1H), 4.18 (ddd, J=18.0, 9.74, 5.60 Hz, 1H), 7.35 (d, J=8.28 Hz, 2H), 7.82 (d, J=8.28 Hz, 2H)

Reference Example 87

Synthesis of (2R)-2-[(2R)-oxiran-2-yl]pent-4-en-1-yl methanesulfonate (1) (R)-Malic acid (25 g) was dissolved in ethanol (250 ml), the solution was added with concentrated sulfuric acid (2.5 ml), and the mixture was refluxed by heating for 3 hours. The mixture was cooled to room temperature, then concentrated under reduced pressure, and added with saturated aqueous sodium hydrogencarbonate and chloroform, and the layers were separated. The organic layer was dried over anhydrous magnesium sulfate, and filtered. The filtrate was concentrated under reduced pressure, and the resulting residue was purified by silica gel column chromatography (hexane: acetone=2:1) to obtain a diester (32.6 g).

(2) Diisopropylamine (46.6 ml) was dissolved in tetrahydrofuran (300 ml), the solution was cooled to −78° C., and then added with a 2.77 M solution of n-butyllithium in hexane (100 ml), and the mixture was stirred for 30 minutes. The reaction mixture was added with a solution of the diester (26.3 g) obtained in (1) mentioned above in tetrahydrofuran (20 ml), and then the mixture was warmed to −20° C., and cooled again to −78° C. The reaction mixture was added with allyl bromide (28.8 ml), and the mixture was stirred at −78° C. for 2 hours. The mixture was added with saturated aqueous ammonium chloride and ethyl acetate, the layers were separated, and the organic layer was washed with saturated brine, then dried over anhydrous magnesium sulfate, and filtered. The filtrate was concentrated under reduced pressure, and the resulting residue was purified by silica gel column chromatography (hexane:ethyl acetate=10:1) to obtain a crude product (13.6 g).

(3) Lithium aluminum hydride (4.5 g) was suspended in tetrahydrofuran (50 ml), and the suspension was added dropwise with a solution of the compound obtained in (2) mentioned above (13.5 g) in tetrahydrofuran (20 ml). The mixture was stirred for 2 hours under reflux by heating, then left to cool, and added successively with distilled water (4.5 ml), 15% aqueous sodium hydroxide (4.5 ml), and distilled water (13.5 ml), and the mixture was stirred overnight. The reaction mixture was filtered, the filtrate was concentrated under reduced pressure, and the resulting residue was purified by silica gel column chromatography (chloroform to chloroform:methanol=20:1 to 10:1) to obtain a triol compound (2.84 g).

(4) The compound obtained in (3) mentioned above (2.16 g) was dissolved in pyridine (25 ml), the solution was added with methanesulfonyl chloride (2.29 ml) under ice cooling, and the mixture was stirred for 2 hours. The mixture was added with distilled water, the layers were separated, and the resulting organic layer was concentrated under reduced pressure to obtain a residue. This residue was dissolved in methanol (20 ml), the solution was added with potassium carbonate (3.06 g) at room temperature, and the mixture was stirred overnight. The reaction mixture was added with diethyl ether, the mixture was filtered, the filtrate was concentrated under reduced pressure, and the resulting residue was purified by silica gel column chromatography (chloroform to chloroform:methanol=20:1) to obtain the title compound (400 mg).
MS (ESI) m/z=207.0 [M+H]$^+$
$^1$H-NMR (600 MHz, CDCl$_3$) δ (ppm): 1.61-1.68 (m, 1H), 2.23-2.34 (m, 2H), 2.57-2.61 (m, 1H), 2.83-2.86 (m, 1H), 2.89-2.93 (m, 1H), 3.04 (s, 3H), 4.27-4.35 (m, 2H), 5.09-5.17 (m, 2H), 5.72-5.81 (m, 1H)

Reference Example 88

Synthesis of (2S)-1-(benzyloxy)-3-(oxiran-2-yl)propan-2-yl methanesulfonate

By using benzyl-(S)-glycidyl ether (4.1 g) as a starting material, the title compound (3.4 g) was obtained in the same manners as those of Reference Example 44, (2), (3) and (4).
MS (ESI) m/z=308.9 [M+Na]$^+$
$^1$H-NMR (600 MHz, CDCl$_3$) δ (ppm): 1.70-1.82 (m, 1H), 2.02-2.15 (m, 1H), 2.47-2.55 (m, 1H), 2.77-2.86 (m, 1H), 3.02-3.04 (m, 3H), 3.05-3.10 (m, 1H), 3.61-3.79 (m, 2H), 4.52-4.60 (m, 2H), 4.95-5.01 (m, 1H), 7.27-7.38 (m, 5H)

Reference Example 89

Synthesis of (2R)-1-(benzyloxy)-3-(oxiran-2-yl)propan-2-yl methanesulfonate

By using benzyl-(R)-glycidyl ether (4.1 g) as a starting material, the title compound (5.3 g) was obtained in the same manners as those of Reference Example 44, (2), (3) and (4).
MS (ESI) m/z=308.9 [M+Na]$^+$
$^1$H-NMR (600 MHz, CDCl$_3$) δ (ppm): 1.69-1.83 (m, 1H), 2.00-2.17 (m, 1H), 2.43-2.56 (m, 1H), 2.72-2.87 (m, 1H), 3.01-3.06 (m, 3H), 3.04-3.11 (m, 1H), 3.58-3.81 (m, 2H), 4.50-4.63 (m, 2H), 4.91-5.06 (m, 1H), 7.27-7.43 (m, 5H)

Reference Example 90

Synthesis of 6-[(aminooxy)methyl]-2,2'-bipyridine (1) (6-Bromopyridin-2-yl)methanol (2.0 g) and triethylamine (1.14 g) were dissolved in chloroform (20 ml), the solution was added with methanesulfonyl chloride (1.22 g), and the mixture was stirred at room temperature for 2 hours. The reaction mixture was added with saturated aqueous ammonium chloride, the layers were separated, and then the organic layer was dried over anhydrous magnesium sulfate, and filtered. The filtrate was concentrated under reduced pressure to obtain a methanesulfonyl compound (3.04 g).
(2) The compound obtained in (1) mentioned above (2.0 g) and sodium iodide (1.80 g) were dissolved in acetone, and the solution was stirred at room temperature for 2 hours. The reaction mixture was added with distilled water and ethyl acetate, the layers were separated, and then the organic layer was washed with saturated aqueous sodium hydrogencarbonate, dried over anhydrous magnesium sulfate, and filtered. The filtrate was concentrated under reduced pressure to obtain an iodo compound (1.94 g).
(3) The compound obtained in (2) mentioned above (1.82 g) and N-hydroxyphthalimide (997 mg) were dissolved in dimethylformamide (40 ml), the solution was added with silver(I) oxide (1.42 g), and the mixture was stirred at room temperature for 30 minutes. The reaction mixture was added with distilled water and ethyl acetate, the layers were separated, and then the organic layer was washed with saturated aqueous sodium hydrogencarbonate, dried over anhydrous magnesium sulfate, and filtered. The filtrate was concentrated under reduced pressure, and the deposited solid was washed with a solution of hexane:ethyl acetate=1:5 to obtain an adduct compound (1.32 g).
(4) The compound obtained in (3) mentioned above (300 mg), tris(dibenzylideneacetone)dipalladium(0) (83 mg), 2-tributylstanylpyridine (332 mg), and tri(o-tolyl)phosphine (110 mg) were dissolved in toluene (3 ml) and dimethylformamide (1.5 ml), and the solution was stirred at 120° C. for 10 minutes under microwave irradiation. The reaction mixture was added with cesium fluoride (274 mg), and the mixture was stirred and then filtered. The filtrate was added with distilled water and ethyl acetate, the layers were separated, and then the organic layer was washed with saturated aqueous sodium hydrogencarbonate, dried over anhydrous magnesium sulfate, and filtered. The filtrate was concentrated under reduced pressure, and the resulting residue was recrystallized from ethyl acetate to obtain a bipyridine compound (56.7 mg).
(5) By using the compound obtained in (4) mentioned above (55 mg) as a starting material, the title compound (22.4 mg) was obtained in the same manner as that of Reference Example 52, (4).
MS (ESI) m/z=202.1 [M+H]$^+$
$^1$H-NMR (600 MHz, CDCl$_3$) δ (ppm): 4.92 (s, 2H), 7.25-7.45 (m, 2H), 7.75-7.89 (m, 2H), 8.28-8.48 (m, 2H), 8.64-8.72 (m, 1H)

Reference Example 91

Synthesis of Compound of the Formula (A) wherein R=Hydrogen Atom (1) Erythromycin A (10.0 g) was dissolved in methanol (30 ml), the solution was cooled to 0° C., and added with sodium borohydride (2.58 g), and the mixture was stirred for 1 hour. The reaction mixture was added with ethyl acetate (150 ml), distilled water (50 ml) and saturated brine (150 ml), and the layers were separated. The organic layer was dried over anhydrous magnesium sulfate, and filtered, and then the filtrate was cooled to 0° C., and added dropwise with a solution obtained by diluting a 4 N solution of hydrochloric acid in ethyl acetate (3.5 ml) with ethyl acetate (30 ml) with stirring. The mixture was stirred at room temperature for 15 hours, and then the deposited solid was taken by filtration, and washed with ethyl acetate. The resulting solid was suspended in ethyl acetate (200 ml), the suspension was added with sodium carbonate (1.18 g) and distilled water (50 ml), and the layers were separated. The organic layer was dried over anhydrous magnesium sulfate, and filtered. The solvent was evaporated under reduced pressure to obtain (9S)-9-dihydroerythromycin A (7.45 g).

(2) By using the compound obtained in (1) mentioned above (1174 g) as a starting material, (9S)-9,2',4"-O-tris(triethylsilyl)-9-dihydroerythromycin A (574.8 g) was obtained in the same manner as that of Reference Example 1, (1).

(3) By using the compound obtained in (2) mentioned above (200 g) as a starting material, the title compound (53.0 g) was obtained in the same manners as those of Reference Example 1, (2), (3) and (4).

MS (ESI) m/z=979.9 [M+H]$^+$ $^1$H-NMR (300 MHz, CDCl$_3$) δ (ppm): 0.49-0.76 (m, 18H) 0.84-1.04 (m, 30H) 1.03-1.37 (m, 23H) 1.37-1.72 (m, 3H) 1.77-1.93 (m, 1H) 2.01-2.18 (m, 1H) 2.19 (s, 6H) 2.32 (d, J=15.23 Hz, 1H), 2.38-2.56 (m, 2H), 3.13-3.29 (m, 3H) 3.30 (s, 3H) 3.37-3.54 (m, 1H) 3.56 (d, J=6.84 Hz, 1H), 3.62 (s, 1H) 3.64-3.80 (m, 1H) 4.13 (d, J=4.97 Hz, 1H), 4.17-4.30 (m, 1H), 4.60 (d, J=6.68 Hz, 1H), 4.64 (d, J=4.35 Hz, 1H)

Reference Example 92

Synthesis of 2-(3-bromopropyl)oxirane

By using 5-bromo-1-pentene (29.5 g) as a starting material, the title compound (35.3 g) was obtained in the same manner as that of Reference Example 2.

MS (EI) m/z=165 [M+H]$^+$ $^1$H-NMR (300 MHz, CDCl$_3$) δ (ppm): 1.52-1.66 (m, 1H), 1.76-1.89 (m, 2H), 1.93-2.15 (m, 2H), 2.51 (dd, J=5.1, 2.7 Hz, 1H), 2.78 (dd, J=5.1, 0.6 Hz, 1H), 2.90-2.98 (m, 1H), 3.40-3.54 (m, 2H)

Examples 1 to 158

Preparation methods of the compounds represented by the formula (B) having R defined in Table 1 are shown below.

[Formula 23]

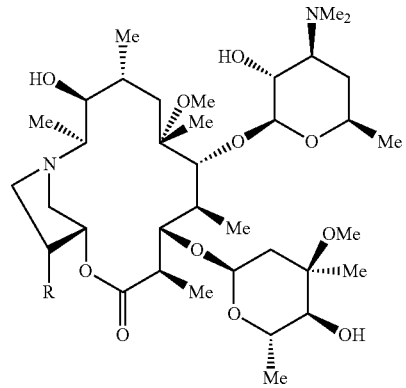

Formula (B)

TABLE 1

| Example | Reference Example | R | ESI MS (M + H) | $^1$H-NMR, CDCl$_3$, δ (ppm) |
|---|---|---|---|---|
| 1 | | —H | 703.0 | (400 MHz): 0.96 (d, J = 7.3 Hz, 3H) 0.98 (d, J = 6.6 Hz, 3H)1.10 (d, J = 7.4 Hz, 3H) 1.15 (d, J = 7.1 Hz, 3H) 1.18-1.27 (m, 1H) 1.23 (d, J = 5.9 Hz, 3H) 1.25 (s, 3H) 1.30 (d, J = 6.1 Hz, 3H) 1.38 (s, 3H) 1.47 (d, J = 14.6 Hz, 1H) 1.57 (dd, J = 15.1, 4.9 Hz, 1H) 1.62-1.69 (m, 1H) 1.75-1.85 (m, 1H) 1.97-2.04 (m, 1H) 2.22-2.32 (m, 1H) 2.29 (s, 6H) 2.35-2.59 (m, 5H) 2.78-3.08 (m, 5 H) 3.17-3.23 (m, 3H) 3.30 (s, 3H) 3.33 (s, 3H) 3.43-3.52 (m, 1H) 3.63 (d, J = 9.5 Hz, 1H) 3.74 (d, J = 8.1 Hz, 1H) 4.00-4.07 (m, 1H) 4.42 (d, J = 7.1 Hz, 1H) 4.90 (d, J = 4.6 Hz, 1H) 4.93-4.98 (m, 1H) |
| 2 | 3 | PhO— | 795.6 | (600 MHz): 0.95 (d, J = 7.34 Hz, 3H)1.01-1.09 (m, 9H) 1.18-1.26 (m, 7H) 1.28 (d, J = 5.96 Hz, 3H) 1.36 (s, 3H) 1.44 (d, J = 14.21 Hz, 1H) 1.51-1.70 (m, 2H) 2.19-2.27 (m, 1H) 2.30 (s, 6H) 2.34 (d, J = 15.13 Hz, 1H) 2.42-2.49 (m, 1H) 2.55-2.63 (m, 1H) 2.67-2.74 (m, 1H) 2.85-2.90 (m, 1H) 2.94-3.06 (m, 4H) 3.14-3.27 (m, 4H) 3.28 (s, 3 H) 3.30 (s, 3H) 3.43-3.52 (m, 1H) 3.61 (d, J = 9.63 Hz, 1H) 3.76 (d, J = 7.34 Hz, 1H) 3.98-4.07 (m,1H) 4.47 (d, J = 7.34 Hz, 1H) 4.65-4.73 (m, 1H) 4.85 (d, J = 4.58 Hz, 1H) 5.16-5.21 (m, 1H) 6.87 (d, J = 7.79 Hz, 2H) 6.92 (t, J = 7.34 Hz, 1H) 7.21-7.26 (m, 2H) |

TABLE 1-continued

| Example | Reference Example | R | ESI MS (M + H) | $^1$H-NMR, CDCl$_3$, δ (ppm) |
|---|---|---|---|---|
| 3 | 4 | 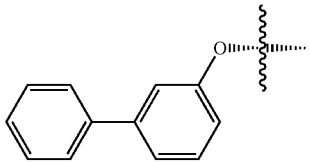 | 871.7 | (600 MHz): 0.94-1.10 (m, 12H) 1.17-1.31 (m, 10H) 1.37 (s, 3H) 1.46 (d, J = 13.75 Hz, 1H) 1.50-1.70 (m, 2H) 2.18-2.27 (m, 1H) 2.29 (s, 6H) 2.33 (d, J = 15.13 Hz, 1H) 2.38-2.47 (m, 1H) 2.56-2.64 (m, 1H) 2.69-2.78 (m, 1H) 2.86-3.08 (m, 5H) 3.14-3.31 (m, 4H) 3.29 (s, 3H) 3.29 (s, 3H) 3.43-3.52 (m, 1H) 3.62 (d, J = 9.63 Hz, 1H) 3.76 (d, J = 7.34 Hz, 1H) 3.98-4.06 (m, 1H) 4.46 (d, J = 6.88 Hz, 1H) 4.71-4.78 (m, 1H) 4.84 (d, J = 4.13 Hz, 1H) 5.21-5.26 (m, 1H) 6.82-6.88 (m, 1H) 7.07-7.10 (m, 1H) 7.13-7.18 (m, 1H) 7.28-7.35 (m, 2H) 7.41 (t, J = 7.79 Hz, 2H) 7.53-7.58 (m, 2H) |
| 4 | 5 | 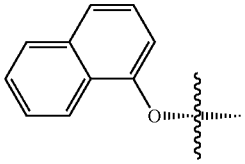 | 845.7 | (600 MHz): 0.88-1.00 (m, 9H) 1.07 (d, J = 6.88 Hz, 3H) 1.18-1.29 (m, 10H) 1.37 (s, 3H) 1.44-1.55 (m, 2H) 1.66-1.73 (m, 1H) 2.18-2.30 (m, 2H) 2.32 (s, 6H) 2.41-2.60 (m, 3H) 2.89-3.13 (m, 5H) 3.15-3.38 (m, 4H) 3.26 (s, 3H) 3.28 (s, 3H) 3.41-3.51 (m, 1H) 3.58 (d, J = 9.17 Hz, 1H) 3.74 (d, J = 7.34 Hz, 1H) 3.93-4.07 (m, 1H) 4.44 (d, J = 6.88 Hz, 1H) 4.80 (d, J = 4.58 Hz, 1H) 4.90-4.98 (m, 1H) 5.27-5.34 (m, 1H) 6.76 (d, J = 7.79 Hz, 1H) 7.27-7.35 (m, 1H) 7.40 (d, J = 8.25 Hz, 1H) 7.43-7.51 (m, 2H) 7.70-7.81 (m, 1H) 8.24-8.37 (m, 1H) |
| 5 | 6 | 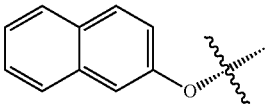 | 845.6 | (600 MHz): 0.94-0.99 (m, 6H) 1.08 (d, J = 7.79 Hz, 6H) 1.20-1.30 (m, 10H) 1.37 (s, 3H) 1.44-1.62 (m, 3H) 2.17-2.37 (m, 8H) 2.38-2.52 (m, 1H) 2.57-2.73 (m, 2H) 2.89-3.09 (m, 5H) 3.15-3.34 (m, 4H) 3.28 (s, 3H) 3.29 (s, 3H) 3.44-3.51 (m, 1H) 3.59-3.62 (m, 1H) 3.75-3.78 (m, 1H) 3.99-4.05 (m, 1H) 4.45-4.48 (m, 1H) 4.81-4.86 (m, 2H) 5.27-5.31 (m, 1H) 7.06-7.08 (m, 1H) 7.15-7.18 (m, 1H) 7.30-7.34 (m, 1H) 7.39-7.43 (m, 1H) 7.66-7.77 (m, 3H) |
| 6 | 9 | 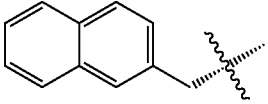 | 843 FAB MASS | (300 MHz): 0.96 (d, J = 7.4 Hz, 3H) 0.99 (d, J = 8.5 Hz, 3H) 1.16-1.25 (m, 1H) 1.18 (d, J = 7.4 Hz, 3H) 1.21 (d, J = 8.8 Hz, 3H) 1.24 (d, J = 6.6 Hz, 3H) 1.27 (s, 3H) 1.31 (d, J = 6.0 Hz, 3H) 1.38 (s, 3H) 1.45 (d, J = 15.1 Hz, 1H) 1.60 (dd, J = 15.1, 4.9 Hz, 1H) 1.63-1.71 (m, 1H) 2.16-2.64 (m, 5H) 2.31 (s, 6H) 2.74 (t, J = 8.8 Hz, 1H) 2.81-3.14 (m, 9H) 3.17-3.29 (m, 2H) 3.29 (s, 3H) 3.36 (s, 3H) 3.45-3.56 (m, 1H) 3.64 (d, J = 9.9 Hz, 1H) 3.80 (d, J = 6.9 Hz, 1H) 4.01-4.12 (m, 1H) 4.52 (d, J = 7.1 Hz, 1H) 4.84-4.89 (m, 1H) 4.94 (d, J = 4.7 Hz, 1H) 7.26-7.32 (m, 1H) 7.38-7.48 (m, 2H) 7.58 (s, 1H) 7.72-7.82 (m, 3H) |
| 7 | 8 |  | 717 FAB MASS | (300 MHz): 0.94 (d, J = 7.1 Hz, 3H) 1.00-1.03 (m, 6H) 1.11 (d, J = 7.3 Hz, 3H) 1.16-1.21 (m, 4H) 1.23 (d, J = 6.1 Hz, 3H) 1.26 (s, 3H) 1.30 (d, J = 6.3 Hz, 3H) 1.36 (s, 3H) 1.41 (d, J = 14.8 Hz, 1H) 1.56-1.67 (m, 3H) 2.18-2.25 (m, 4H) 2.29 (s, 6H) 2.37-2.54 (m, 3H) 2.69-2.80 (m, 3H) 2.86-3.04 (m, 4H) 3.11-3.24 (m, 3H) 3.28 (s, 3H) 3.34 (s, 3H) 3.46-3.52 (m, 1H) 3.61 (d, J = 9.7 Hz, 1H) 3.77 (d, J = 7.3 Hz, 1H) 4.05 (dq, J = 9.3 Hz, J = 6.3 Hz, 1H) 4.46 (d, J = 7.3 Hz, 1H) 4.86 (dd, J = 5.6 Hz, J = 4.4 Hz, 1H) 4.92 (d, J = 4.4 Hz, 1H) |

TABLE 1-continued

| Example | Reference Example | R | ESI MS (M + H) | 1H-NMR, CDCl3, δ (ppm) |
|---|---|---|---|---|
| 8 | |  | 744.2 | (300 MHz): 0.95 (d, J = 7.2 Hz, 3H) 1.00 (d, J = 6.6 Hz, 3H) 1.12 (d, J = 7.5 Hz, 3H) 1.18-1.23 (m, 7H) 1.25 (s, 3H) 1.29 (d, J = 6.3 Hz, 3H) 1.37 (s, 3H) 1.48 (d, J = 15.3 Hz, 1H) 1.55-1.67 (m, 2H) 2.21-2.28 (m, 8H) 2.37-2.56 (m, 3H) 2.79-2.92 (m, 3H) 2.98-3.06 (m, 3H) 3.10-3.25 (m, 4H) 3.29 (s, 3H) 3.36 (s, 3H) 3.44-3.51 (m, 1H) 3.56-3.66 (m, 2H) 3.76 (d, J = 7.5 Hz, 1H) 4.04 (dq, J = 9.3 Hz, J = 6.3 Hz, 1H) 4.47 (d, J = 7.2 Hz, 1H) 4.84-4.92 (m, 2H) 5.04 (dd, J = 5.1 Hz, J = 5.1 Hz, 1H) |
| 9 | | 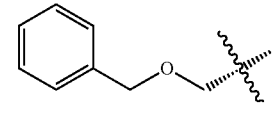 | 823.6 | (600 MHz): 0.92 (d, J = 7.34 Hz, 3H) 1.00 (d, J = 6.88 Hz, 3H) 1.07 (d, J = 7.34 Hz, 3H) 1.14 (d, J = 6.88 Hz, 3H) 1.19-1.25 (m, 1H) 1.22-1.24 (m, 3H) 1.26 (s, 3H) 1.30 (d, J = 5.96 Hz, 3H) 1.36 (s, 3H) 1.40 (d, J = 15.59 Hz, 1H) 1.56-1.59 (m, 1H) 1.63-1.69 (m, 1H) 2.19-2.25 (m, 1H) 2.23 (d, J = 10.09 Hz, 1H) 2.30 (s, 6H) 2.38 (d, J = 14.21 Hz, 1H) 2.42-2.52 (m, 3H) 2.74 (t, J = 9.17 Hz, 1H) 2.77-2.83 (m, 2H) 2.84-2.88 (m, 1H) 2.89-2.95 (m, 1H) 2.95-2.99 (m, 1H) 3.02 (t, J = 9.63 Hz, 1H) 3.11-3.15 (m, 1H) 3.18 (d, J = 11.46 Hz, 1H) 3.22 (dd, J = 10.09, 7.34 Hz, 1H) 3.28 (s, 3H) 3.33 (s, 3H) 3.46-3.51 (m, 2H) 3.59 (d, J = 9.17 Hz, 1H) 3.63 (dd, J = 8.71, 6.88 Hz, 1H) 3.75 (d, J = 7.34 Hz, 1H) 3.99-4.07 (m, 1H) 4.44-4.57 (m, 3H) 4.90 (d, J = 5.04 Hz, 1H) 5.04 (dd, J = 5.96, 4.58 Hz, 1H) 7.27-7.37 (m, 5H) |
| 10 | | 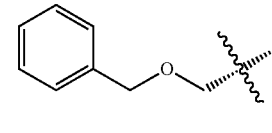 | 823.5 | (600 MHz): 0.93 (d, J = 6.88 Hz, 3H) 0.96 (d, J = 6.88 Hz, 3H) 1.08 (d, J = 7.34 Hz, 3H) 1.14 (d, J = 6.88 Hz, 3H) 1.16-1.21 (m, 1H) 1.22 (d, J = 5.96 Hz, 3H) 1.23 (s, 3H) 1.29 (d, J = 6.42 Hz, 3H) 1.36 (s, 3H) 1.46 (d, J = 14.67 Hz, 1H) 1.55 (dd, J = 15.13, 5.04 Hz, 1H) 1.60-1.68 (m, 1H) 2.21-2.32 (m, 2H) 2.28 (s, 6H) 2.35-2.57 (m, 4H) 2.58-2.65 (m, 1H) 2.80-2.94 (m, 2H) 2.96-3.08 (m, 3H) 3.12-3.22 (m, 3H) 3.28 (s, 3H) 3.31 (s, 3H) 3.35-3.50 (m, 3H) 3.61 (d, J = 9.63 Hz, 1H) 3.72 (d, J = 7.79 Hz, 1H) 3.98-4.06 (m, 1H) 4.42 (d, J = 7.34 Hz, 1H) 4.50 (s, 2H) 4.66-4.72 (m, 1H) 4.88 (d, J = 4.58 Hz, 1H) 7.23-7.36 (m, 5H) |
| 11 | | 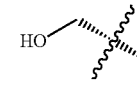 | 733.4 | (600 MHz): 0.95 (d, J = 7.34 Hz, 3H) 1.01 (d, J = 6.42 Hz, 3H) 1.11 (d, J = 7.79 Hz, 3H) 1.17 (d, J = 6.88 Hz, 3H) 1.20-1.25 (m, 1H) 1.23 (d, J = 5.96 Hz, 3H) 1.25 (s, 3H) 1.30 (d, J = 5.96 Hz, 3H) 1.37 (s, 3H) 1.47 (d, J = 14.21 Hz, 1H) 1.58 (dd, J = 15.13, 4.58 Hz, 1H) 1.63-1.68 (m, 1H) 2.22-2.27 (m, 2H) 2.29 (s, 6H) 2.39 (d, J = 15.13 Hz, 1H) 2.38-2.46 (m, 2H) 2.49 (t, J = 7.57 Hz, 1H) 2.71 (t, 1H) 2.78 (dd, J = 12.15, 4.81 Hz, 1H) 2.80-2.92 (m, 3H) 2.97-3.04 (m, 2H) 3.17-3.23 (m, 3H) 3.29 (s, 3H) 3.33 (s, 3H) 3.45-3.52 (m, 1H) 3.64 (d, J = 10.09 Hz, 1H) 3.70 (dd, J = 10.55, 5.96 Hz, 1H) 3.76 (d, J = 7.34 Hz, 1H) 3.81 (dd, J = 11.00, 7.34 Hz, 1H) 4.00-4.08 (m, 1H) 4.46 (d, J = 7.34 Hz, 1H) 4.90 (d, J = 4.58 Hz, 1H) 5.06 (dd, J = 6.88, 5.04 Hz, 1H) |

TABLE 1-continued

| Example | Reference Example | R | ESI MS (M + H) | ¹H-NMR, CDCl₃, δ (ppm) |
|---|---|---|---|---|
| 12 | | HO–(CH(CH₃))– | 733.4 | (600 MHz): 0.94 (d, J = 7.34 Hz, 3H) 0.98 (d, J = 6.42 Hz, 3H) 1.08 (d, J = 7.34 Hz, 3H) 1.15-1.25 (m, 1H) 1.18 (d, J = 6.88 Hz, 3H) 1.22 (d, J = 5.96 Hz, 3H) 1.23 (s, 3H) 1.29 (d, J = 6.42 Hz, 3H) 1.36 (s, 3H) 1.45 (d, J = 14.67 Hz, 1H) 1.56 (dd, J = 15.13, 5.04 Hz, 1H) 1.61-1.67 (m, 1H) 2.17-2.30 (m, 2H) 2.27 (s, 6H) 2.31-2.47 (m, 3H) 2.54-2.63 (m, 2H) 2.78-2.86 (m, 1H) 2.93-3.06 (m, 4H) 3.12-3.26 (m, 3H) 3.29-3.32 (m, 6H) 3.42-3.50 (m, 1H) 3.57-3.61 (m, 2H) 3.66 (d, J = 9.63 Hz, 1H) 3.75 (d, J = 8.25 Hz, 1H) 3.98-4.06 (m, 1H) 4.42 (d, J = 6.88 Hz, 1H) 4.66-4.72 (m, 1H) 4.86 (d, J = 5.04 Hz, 1H) |
| 13 | | H₂N–(CH(CH₃))– | 732.4 | (600 MHz): 0.94 (d, J = 5.50 Hz, 3H) 1.01 (d, J = 6.88 Hz, 3H) 1.09-1.13 (m, 3H) 1.15-1.18 (m, 3H) 1.19-1.25 (m, 1H) 1.23 (d, J = 5.96 Hz, 3H) 1.26 (s, 3H) 1.30 (d, J = 6.42 Hz, 3H) 1.36 (s, 3H) 1.41-1.46 (m, 1H) 1.55-1.61 (m, 1H) 1.63-1.68 (m, 1H) 2.15-2.25 (m, 2H) 2.29 (s, 6H) 2.38 (d, J = 15.13 Hz, 1H) 2.41-2.46 (m, 1H) 2.46-2.55 (m, 1H) 2.72-2.78 (m, 1H) 2.77-3.07 (m, 6H) 3.11-3.17 (m, 1H) 3.17-3.26 (m, 2H) 3.29 (s, 3H) 3.33 (s, 3H) 3.36-3.49 (m, 2H) 3.58-3.67 (m, 2H) 3.76 (d, J = 7.34 Hz, 1H) 4.00-4.09 (m, 1H) 4.44-4.51 (m, 1H) 4.91 (t, J = 3.90 Hz, 1H) 4.99-5.05 (m, 1H) |
| 14 | | Me₂N–CH(CH₃)– | 760.5 | (600 MHz): 0.94 (d, J = 6.88 Hz, 3H) 1.02 (d, J = 6.88 Hz, 3H) 1.11 (d, J = 7.34 Hz, 3H) 1.17 (d, J = 6.88 Hz, 3H) 1.18-1.23 (m, 1H) 1.23 (d, J = 6.42 Hz, 3H) 1.26 (s, 3H) 1.30 (d, J = 6.42 Hz, 3H) 1.36 (s, 3H) 1.40 (d, J = 14.21 Hz, 1H) 1.59 (dd, J = 15.13, 5.04 Hz, 1H) 1.65 (d, J = 12.38 Hz, 1H) 2.17-2.22 (m, 2H) 2.22 (s, 6H) 2.29 (s, 6H) 2.34-2.41 (m, 2H) 2.41-2.46 (m, 1H) 2.50 (t, J = 7.57 Hz, 1H) 2.80 (t, J = 9.40 Hz, 1H) 2.85-2.95 (m, 3H) 2.95-3.00 (m, 2H) 3.02 (t, J = 9.40 Hz, 1H) 3.11 (d, J = 4.58 Hz, 1H) 3.18 (d, J = 11.92 Hz, 1H) 3.21-3.24 (m, 1H) 3.28 (s, 3H) 3.33 (s, 3H) 3.36-3.41 (m, 1H) 3.44-3.53 (m, 1H) 3.61 (d, J = 9.17 Hz, 1H) 3.60-3.65 (m, 1H) 3.76 (d, J = 6.88 Hz, 1H) 4.00-4.08 (m, 1H) 4.49 (d, J = 7.34 Hz, 1H) 4.92 (d, J = 4.58 Hz, 1H) 4.98 (d, J = 4.13 Hz, 1H) |
| 15 | | N≡C–CH(CH₃)– | 742.6 | (600 MHz): 0.93 (d, J = 6.88 Hz, 3H) 0.99 (d, J = 6.88 Hz, 3H) 1.12 (d, J = 7.79 Hz, 3H) 1.17 (d, J = 6.88 Hz, 3H) 1.18-1.26 (m, 7H) 1.29 (d, J = 6.42 Hz, 3H) 1.36 (s, 3H) 1.47-1.69 (m, 3H) 2.18-2.33 (m, 2H) 2.29 (s, 6H) 2.33-2.62 (m, 4H) 2.70-2.85 (m, 5H) 2.90-3.04 (m, 3H) 3.13-3.25 (m, 3H) 3.28 (s, 3H) 3.32 (s, 3H) 3.43-3.51 (m, 1H) 3.55-3.61 (m, 1H) 3.75 (d, J = 7.79 Hz, 1H) 3.98-4.06 (m, 1H) 4.46 (d, J = 7.34 Hz, 1H) 4.90 (d, J = 4.58 Hz, 1H) 4.95-5.01 (m, 1H) |

TABLE 1-continued

| Example | Reference Example | R | ESI MS (M + H) | $^1$H-NMR, CDCl$_3$, δ (ppm) |
|---|---|---|---|---|
| 16 | | naphthalene-1-C(=O)-NH-CH$_2$- | 886.6 | (600 MHz): 0.81 (d, J = 7.34 Hz, 3H) 1.01 (d, J = 6.88 Hz, 3H) 1.07 (d, J = 7.34 Hz, 3H) 1.12 (d, J = 6.88 Hz, 3H) 1.21-1.24 (m, 1H) 1.23 (d, J = 5.96 Hz, 3H) 1.24 (s, 3H) 1.29 (d, J = 5.96 Hz, 3H) 1.35 (s, 3H) 1.42 (d, J = 14.67 Hz, 1H) 1.56 (dd, J = 15.13, 5.04 Hz, 1H) 1.67 (d, J = 12.84 Hz, 1H) 2.17-2.26 (m, 2H) 2.31 (s, 6H) 2.37 (d, J = 15.13 Hz, 1H) 2.41-2.48 (m, 2H) 2.58-2.67 (m, 1H) 2.79-2.89 (m, 4H) 2.95-3.04 (m, 2H) 3.13-3.18 (m, 1H) 3.19-3.25 (m, 2H) 3.29 (s, 3H) 3.30 (s, 3H) 3.33-3.42 (m, 1H) 3.44-3.51 (m, 1H) 3.60 (ddd, J = 13.64, 5.62, 5.50 Hz, 1H) 3.64 (d, J = 9.63 Hz, 1H) 3.75 (d, J = 7.79 Hz, 1H) 3.84 (ddd, J = 14.10, 6.99, 6.88 Hz, 1H) 4.02 (dd, J = 9.40, 6.19 Hz, 1H) 4.45 (d, J = 6.88 Hz, 1H) 4.87 (d, J = 4.58 Hz, 1H) 5.11 (dd, J = 6.42, 4.58 Hz, 1H) 6.25 (t, J = 5.73 Hz, 1H) 7.49-7.61 (m, 4H) 7.86 (d, J = 8.25 Hz, 1H) 7.91 (d, J = 8.25 Hz, 1H) 8.26 (d, J = 8.71 Hz, 1H) |
| 17 | | naphthalene-1-CH$_2$-C(=O)-NH-CH$_2$- | 900.6 | (600 MHz): 0.79 (d, J = 7.79 Hz, 3H) 0.85 (d, J = 7.34 Hz, 3H) 0.91 (d, J = 6.42 Hz, 3H) 0.96 (d, J = 6.88 Hz, 3H) 1.19-1.23 (m, 1H) 1.21 (d, J = 5.96 Hz, 3H) 1.26-1.28 (m, 6H) 1.30 (s, 3H) 1.35 (d, J = 15.13 Hz, 1H) 1.58 (dd, J = 15.13, 4.58 Hz, 1H) 1.66 (d, J = 11.92 Hz, 1H) 2.13-2.29 (m, 6H) 2.30 (s, 6H) 2.38 (d, J = 15.13 Hz, 1H) 2.40-2.46 (m, 1H) 2.47-2.51 (m, 1H) 2.63 (dd, J = 11.69, 4.36 Hz, 1H) 2.67-2.74 (m, 1H) 2.80-2.89 (m, 1H) 2.97-3.04 (m, 2H) 3.07-3.11 (m, 1H) 3.12-3.20 (m, 2H) 3.21 (s, 3H) 3.36 (s, 3H) 3.41-3.51 (m, 3H) 3.65 (d, J = 7.34 Hz, 1H) 3.94-4.01 (m, 1H) 4.02 (s, 2H) 4.40 (d, J = 7.34 Hz, 1H) 4.60 (t, J = 5.73 Hz, 1H) 4.83 (d, J = 4.58 Hz, 1H) 5.46 (t, J = 5.96 Hz, 1H) 7.36-7.41 (m, 1H) 7.43 (t, J = 7.57 Hz, 1H) 7.48-7.52 (m, 1H) 7.52-7.57 (m, 1H) 7.80 (d, J = 8.25 Hz, 1H) 7.85 (d, J = 7.79 Hz, 1H) 7.92 (d, J = 8.25 Hz, 1H) |
| 18 | | naphthalene-1-CH$_2$CH$_2$-C(=O)-NH-CH$_2$- | 914.7 | (600 MHz): 0.88 (d, J = 6.88 Hz, 3H) 0.98 (d, J = 6.42 Hz, 3H) 1.08 (d, J = 7.79 Hz, 3H) 1.11 (d, J = 6.88 Hz, 3H) 1.17-1.23 (m, 1H) 1.22 (d, J = 5.96 Hz, 4H) 1.25 (s, 3H) 1.29 (d, J = 6.42 Hz, 3H) 1.35 (s, 3H) 1.44 (d, J = 14.67 Hz, 1H) 1.57 (dd, J = 15.13, 5.04 Hz, 1H) 1.62-1.69 (m, 1H) 2.17-2.26 (m, 3H) 2.29 (s, 6H) 2.37 (d, J = 15.13 Hz, 1H) 2.39-2.46 (m, 2H) 2.55-2.63 (m, 4H) 2.69-2.74 (m, 1H) 2.77-2.85 (m, 1H) 2.93 (q, J = 6.72 Hz, 1H) 3.01 (t, J = 9.40 Hz, 1H) 3.14 (d, J = 11.92 Hz, 1H) 3.14-3.18 (m, 1H) 3.17 (dd, J = 10.09, 7.34 Hz, 1H) 3.27 (s, 3H) 3.28-3.31 (m, 1H) 3.32 (s, 3H) 3.34-3.40 (m, 1H) 3.41-3.50 (m, 3H) 3.60 (d, J = 9.63 Hz, 1H) 3.74 (d, J = 7.34 Hz, 1H) 3.97-4.05 (m, 1H) 4.44 (d, J = 7.34 Hz, 1H) 4.79-4.83 (m, 1H) 4.87 (d, J = 4.59 Hz, 1H) 5.51 (t, J = 5.73 Hz, 1H) 7.34-7.41 (m, 2H) 7.46-7.50 (m, 1H) 7.50-7.55 (m, 1H) 7.72 (d, J = 7.79 Hz, 1H) 7.85 (d, J = 7.79 Hz, 1H) 8.07 (d, J = 8.25 Hz, 1H) |

TABLE 1-continued

| Example | Reference Example | R | ESI MS (M + H) | $^1$H-NMR, CDCl$_3$, δ (ppm) |
|---|---|---|---|---|
| 19 | | 3-(furan-2-yl)phenyl-CH$_2$-C(O)-NH- | 916.7 | (600 MHz): 0.89 (d, J = 7.34 Hz, 3H) 0.95 (d, J = 6.88 Hz, 3H) 0.97 (d, J = 7.79 Hz, 3H) 1.00 (d, J = 6.88 Hz, 3H) 1.18-1.24 (m, 1H) 1.22 (d, J = 5.96 Hz, 3H) 1.26 (s, 3H) 1.28 (d, J = 6.42 Hz, 3H) 1.34 (s, 3H) 1.42 (d, J = 14.67 Hz, 1H) 1.56 (dd, J = 14.90, Hz, 1H) 1.66 (d, J = 12.84 Hz, 1H) 2.18-2.25 (m, 2H) 2.30 (s, 6H) 2.34 (d, J = 15.13 Hz, 1H) 2.36-2.41 (m, 2H) 2.41-2.47 (m, 1H) 2.50-2.58 (m, 1H) 2.60-2.68 (m, 2H) 2.70-2.76 (m, 1H) 2.76-2.82 (m, 1H) 2.88-2.97 (m, 1H) 2.97-3.03 (m, 1H) 3.12 (d, J = 12.38 Hz, 1H) 3.12-3.15 (m, 1H) 3.18 (dd, J = 10.09, 7.34 Hz, 1H) 3.25 (s, 3H) 3.28-3.36 (m, 1H) 3.31 (s, 3H) 3.41-3.51 (m, 2H) 3.52 (d, J = 9.63 Hz, 1H) 3.60 (s, 2H) 3.70 (d, J = 7.34 Hz, 1H) 3.96-4.04 (m, 1H) 4.42 (d, J = 7.34 Hz, 1H) 4.84 (d, J = 4.58 Hz, 1H) 4.87-4.89 (m, 1H) 5.63 (t, J = 6.19 Hz, 1H) 6.47 (dd, J = 3.21, 1.83 Hz, 1H) 6.67 (d, J = 3.21 Hz, 1H) 7.14 (d, J = 7.79 Hz, 1H) 7.36 (t, J = 7.79 Hz, 1H) 7.47 (s, 1H) 7.56 (s, 1H) 7.58 (d, J = 9.17 Hz, 1H) |
| 20 | | 3-(furan-2-yl)phenyl-C(O)-NH- | 902.6 | (600 MHz): 0.90 (d, J = 6.88 Hz, 3H) 1.01 (d, J = 6.42 Hz, 3H) 1.13 (d, J = 7.34 Hz, 3H) 1.18 (d, J = 7.34 Hz, 3H) 1.20-1.26 (m, 1H) 1.23 (d, J = 5.96 Hz, 3H) 1.25 (s, 3H) 1.30 (d, J = 5.96 Hz, 3H) 1.37 (s, 3H) 1.48 (d, J = 14.67 Hz, 1H) 1.58 (dd, J = 15.13, 4.58 Hz, 1H) 1.66 (d, J = 12.84 Hz, 1H) 2.19-2.28 (m, 2H) 2.30 (s, 6H) 2.39 (d, J = 15.13 Hz, 1H) 2.41-2.53 (m, 2H) 2.54-2.62 (m, 1H) 2.75-2.86 (m, 3H) 2.86-2.95 (m, 2H) 3.01 (d, J = 2H) 3.16-3.20 (m, 1H) 3.19-3.24 (m, 1H) 3.24 (d, J = 11.46 Hz, 1H) 3.30 (s, 3H) 3.32 (s, 3H) 3.46-3.52 (m, 1H) 3.59 (ddd, J = 13.53, 5.96, 5.73 Hz, 1H) 3.67-3.74 (m, 2H) 3.77 (d, J = 7.79 Hz, 1H) 4.00-4.07 (m, 1H) 4.47 (d, J = 7.34 Hz, 1H) 4.89 (d, J = 4.58 Hz, 1H) 5.10 (dd, J = 6.42, 4.58 Hz, 1H) 6.41 (t, J = 5.50 Hz, 1H) 6.49 (dd, J = 3.21, 1.83 Hz, 1H) 6.74 (d, J = 3.21 Hz, 1H) 7.49 (d, J = 0.92 Hz, 1H) 7.51 (t, J = 7.79 Hz, 1H) 7.59 (d, J = 7.79 Hz, 1H) 7.79 (d, J = 7.79 Hz, 1H) 8.06 (t, J = 1.60 Hz, 1H) |
| 21 | | 3-(furan-2-yl)phenyl-CH$_2$CH$_2$-C(O)-NH- | 930.7 | (600 MHz): 0.91 (d, J = 7.34 Hz, 3H) 0.95 (d, J = 6.42 Hz, 3H) 1.09 (d, J = 7.79 Hz, 3H) 1.14 (d, J = 7.34 Hz, 3H) 1.19 (d, J = 11.0 Hz, 1H) 1.22 (d, J = 5.96 Hz, 3H) 1.25 (s, 3H) 1.29 (d, J = 5.96 Hz, 3H) 1.36 (s, 3H) 1.46 (d, J = 15.13 Hz, 1H) 1.57 (dd, J = 15.13, 5.04 Hz, 1H) 1.64 (d, J = 11.92 Hz, 1H) 2.17-2.24 (m, 2H) 2.26 (s, 6H) 2.28-2.33 (m, 1H) 2.38 (d, J = 15.13 Hz, 1H) 2.39-2.45 (m, 2H) 2.51 (t, J = 7.57 Hz, 2H) 2.58 (t, J = 9.17 Hz, 1H) 2.61-2.64 (m, 1H) 2.69 (dd, J = 11.92, 4.59 Hz, 1H) 2.79-2.86 (m, 2H) 2.89-2.95 (m, 1H) 2.96-3.03 (m, 3H) 3.11-3.19 (m, 3H) 3.28 (s, 3H) 3.29-3.33 (m, 1H) 3.31 (s, 3H) 3.38-3.44 (m, 1H) 3.44-3.50 (m, 1H) 3.61 (d, J = 9.63 Hz, 1H) 3.74 (d, J = 7.34 Hz, 1H) 4.02 (d, J = 3.21 Hz, 1H) 4.44 (d, J = 7.34 Hz, 1H) 4.84-4.90 (m, 2H) 5.60 (t, J = 5.50 Hz, 1H) 6.46 (dd, J = 3.44, 1.60 Hz, 1H) 6.64 (d, J = 3.21 Hz, 1H) 7.11 (d, J = 7.79 Hz, 1H) 7.29 (t, J = 7.57 Hz, 1H) 7.45 (d, J = 1.38 Hz, 1H) 7.51 (d, J = 7.79 Hz, 1H) 7.53 (s, 1H) |

TABLE 1-continued

| Example | Reference Example | R | ESI MS (M + H) | ¹H-NMR, CDCl₃, δ (ppm) |
|---|---|---|---|---|
| 22 | | 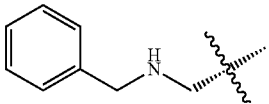 | 822.5 | (600 MHz): 0.93 (d, J = 7.34 Hz, 3H) 1.00 (d, J = 6.88 Hz, 3H) 1.07 (d, J = 7.79 Hz, 3H) 1.14 (d, J = 6.88 Hz, 3H) 1.21-1.23 (m, 1H) 1.23 (d, J = 5.96 Hz, 3H) 1.26 (s, 3H) 1.29 (d, J = 6.42 Hz, 3H) 1.36 (s, 3H) 1.39 (d, J = 14.67 Hz, 1H) 1.59 (dd, J = 15.13, 5.04 Hz, 1H) 1.66 (d, J = 12.84 Hz, 1H) 2.19-2.23 (m, 2H) 2.30 (s, 6H) 2.31-2.35 (m, 1H) 2.38 (d, J = 14.67 Hz, 1H) 2.41-2.51 (m, 2H) 2.65 (dd, J = 11.69, 7.11 Hz, 1H) 2.75-2.87 (m, 5H) 2.92-2.99 (m, 2H) 3.00-3.03 (m, 1H) 3.12 (d, J = 4.13 Hz, 1H) 3.19 (d, J = 11.92 Hz, 1H) 3.20-3.24 (m, 1H) 3.28 (s, 3H) 3.34 (s, 3H) 3.46-3.51 (m, 1H) 3.60 (d, J = 10.09 Hz, 1H) 3.74-3.77 (m, 2H) 3.79-3.83 (m, 1H) 4.01-4.07 (m, 1H) 4.47 (d, J = 7.34 Hz, 1H) 4.90 (d, J = 4.58 Hz, 1H) 5.00 (d, J = 4.58 Hz, 1H) 7.22-7.34 (m, 5H) |
| 23 | | 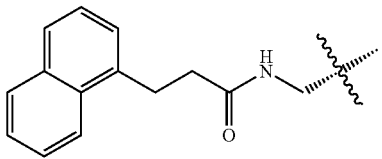 | 914.6 | (600 MHz): 0.93 (d, J = 7.34 Hz, 3H) 0.97 (d, J = 6.88 Hz, 3H) 1.04 (d, J = 7.79 Hz, 3H) 1.16 (d, J = 7.34 Hz, 3H) 1.17-1.40 (m, 2H) 1.22 (d, J = 5.96 Hz, 3H) 1.23 (s, 3H) 1.29 (d, J = 5.96 Hz, 3H) 1.36 (s, 3H) 1.55 (dd, J = 15.13, 5.04 Hz, 1H) 1.61-1.70 (m, 1H) 2.04 (t, J = 8.71 Hz, 1H) 2.12-2.66 (m, 8H) 2.28 (s, 6H) 2.67-2.76 (m, 1H) 2.83-3.03 (m, 3H) 3.05-3.26 (m, 6H) 3.29 (s, 3H) 3.31 (s, 3H) 3.39-3.50 (m, 3H) 3.68 (d, J = 8.71 Hz, 1H) 3.74 (d, J = 7.79 Hz, 1H) 3.96-4.05 (m, 1H) 4.30-4.36 (m, 1H) 4.40 (d, J = 7.34 Hz, 1H) 4.83 (d, J = 4.58 Hz, 1H) 6.14-6.22 (m, 1H) 7.32-7.41 (m, 2H) 7.43-7.55 (m, 2H) 7.71 (d, J = 7.79 Hz, 1H) 7.84 (d, J = 8.25 Hz, 1H) 8.07 (d, J = 8.25 Hz, 1H) |
| 24 | | 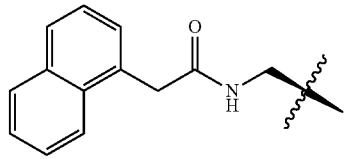 | 900.5 | (600 MHz): 0.83 (d, J = 6.42 Hz, 3H) 0.87 (d, J = 7.34 Hz, 3H) 1.00 (d, J = 7.34 Hz, 3H) 1.11 (d, J = 7.34 Hz, 3H) 1.14-1.30 (m, 1H) 1.21 (d, J = 5.96 Hz, 3H) 1.24 (s, 3H) 1.28 (d, J = 5.96 Hz, 3H) 1.33 (s, 3H) 1.35-1.40 (m, 1H) 1.56 (dd, J = 15.13, 5.04 Hz, 1H) 1.61-1.69 (m, 1H) 1.89 (t, J = 8.94 Hz, 1H) 2.05-2.12 (m, 1H) 2.18-2.25 (m, 1H) 2.28 (s, 6H) 2.33-2.47 (m, 4H) 2.56-2.69 (m, 2H) 2.74-2.85 (m, 2H) 2.95-3.35 (m, 6H) 3.25 (s, 3H) 3.32 (s, 3H) 3.41-3.50 (m, 1H) 3.57 (d, J = 9.63 Hz, 1H) 3.70 (d, J = 8.25 Hz, 1H) 3.95-4.07 (m, 3H) 4.29-4.34 (m, 1H) 4.39 (d, J = 7.34 Hz, 1H) 4.83 (d, J = 4.58 Hz, 1H) 5.57-5.65 (m, 1H) 7.39 (d, J = 6.42 Hz, 1H) 7.44 (d, J = 8.25 Hz, 1H) 7.48-7.58 (m, 2H) 7.82 (d, J = 8.25 Hz, 1H) 7.86 (d, J = 7.34 Hz, 1H) 7.95 (d, J = 8.25 Hz, 1H) |
| 25 | | 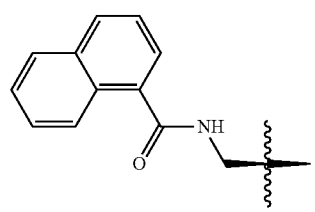 | 886.6 | (600 MHz): 0.95 (d, J = 7.34 Hz, 3H) 1.02 (d, J = 6.88 Hz, 3H) 1.07 (d, J = 7.34 Hz, 3H) 1.11 (d, J = 7.34 Hz, 3H) 1.16-1.26 (m, 7H) 1.29 (d, J = 6.42 Hz, 3H) 1.37 (s, 3H) 1.44 (d, J = 14.67 Hz, 1H) 1.54 (dd, J = 15.13, 5.04 Hz, 1H) 1.62-1.68 (m, 1H) 2.17-2.38 (m, 3H) 2.28 (s, 6H) 2.39-2.47 (m, 1H) 2.48-2.61 (m, 2H) 2.64-2.72 (m, 1H) 2.73-2.80 (m, 1H) 2.90-3.05 (m, 3H) 3.08-3.15 (m, 1H) 3.16-3.22 (m, 2H) 3.24-3.33 (m, 1H) 3.29 (s, 3H) 3.31 (s, 3H) 3.42-3.49 (m, 1H) 3.52-3.58 (m, 2H) 3.66 (d, J = 9.17 Hz, 1H) 3.74 (dd, J = 8.25 Hz, 1H) 3.97-4.05 (m, 1H) 4.41 (d, J = 6.88 Hz, 1H) 4.67-4.73 (m, 1H) 4.84 (d, J = 4.58 Hz, 1H) 6.55-6.63 (m, 1H) 7.41-7.61 (m, 4H) 7.85 (d, J = 7.79 Hz, 1H) 7.90 (d, J = 8.25 Hz, 1H) 8.31 (d, J = 8.25 Hz, 1H) |

TABLE 1-continued

| Example | Reference Example | R | ESI MS (M + H) | 1H-NMR, CDCl3, δ (ppm) |
|---|---|---|---|---|
| 26 | | | 930.5 | (600 MHz): 0.92 (d, J = 7.34 Hz, 3H) 0.94 (d, J = 6.42 Hz, 3H) 1.05 (d, J = 7.34 Hz, 3H) 1.15-1.26 (m, 2H) 1.17 (d, J = 6.88 Hz, 3H) 1.22 (d, J = 5.96 Hz, 3H) 1.23 (s, 3H) 1.29 (d, J = 6.42 Hz, 3H) 1.35 (s, 6H) 1.55 (dd, J = 15.13, 4.58 Hz, 1H) 1.61-1.67 (m, 1H) 2.06 (t, J = 8.94 Hz, 1H) 2.17-2.25 (m, 2H) 2.27 (s, 6H) 2.32-2.61 (m, 5H) 2.69-2.78 (m, 1H) 2.87-3.02 (m, 7H) 3.09-3.34 (m, 5H) 3.29 (s, 3H) 3.31 (s, 3H) 3.42-3.49 (m, 1H) 3.68 (d, J = 8.71 Hz, 1H) 3.74 (d, J = 7.79 Hz, 1H) 3.97-4.05 (m, 1H) 4.37-4.43 (m, 2H) 4.83 (d, J = 4.58 Hz, 1H) 6.19-6.25 (m, 1H) 6.43-6.48 (m, 1H) 6.60-6.65 (m, 1H) 7.10 (d, J = 7.79 Hz, 1H) 7.28 (t, J = 7.57 Hz, 1H) 7.42-7.54 (m, 3H) |
| 27 | | | 902.5 | (600 MHz): 0.95 (d, J = 7.34 Hz, 3H) 1.02 (d, J = 6.42 Hz, 3H) 1.08 (d, J = 7.34 Hz, 3H) 1.18-1.28 (m, 10H) 1.30 (d, J = 5.96 Hz, 3H) 1.35-1.44 (m, 1H) 1.38 (s, 3H) 1.57 (dd, J = 15.13, 5.04 Hz, 1H) 1.62-1.69 (m, 1H) 2.17-2.31 (m, 2H) 2.28 (s, 3H) 2.37 (d, J = 15.13 Hz, 1H) 2.40-2.48 (m, 2H) 2.59-2.69 (m, 2H) 2.78-2.86 (m, 1H) 2.95-3.23 (m, 6H) 3.26-3.39 (m, 2H) 3.31 (s, 3H) 3.34 (s, 3H) 3.43-3.56 (m, 2H) 3.73-3.81 (m, 2H) 3.98-4.07 (m, 1H) 4.42 (d, J = 6.88 Hz, 1H) 4.65-4.70 (m, 1H) 4.85 (d, J = 4.58 Hz, 1H) 6.43-6.51 (m, 1H) 6.72-6.79 (m, 1H) 7.42-7.49 (m, 2H) 7.70-7.81 (m, 2H) 8.16 (s, 1H) |
| 28 | | | 916.7 | (600 MHz): 0.85-0.95 (m, 6H) 1.03 (d, J = 7.79 Hz, 3H) 1.13 (d, J = 7.34 Hz, 3H) 1.17-1.27 (m, 1H) 1.22 (d, 3H) 1.24 (s, 3H) 1.29 (d, J = 5.96 Hz, 3H) 1.35 (s, 3H) 1.40 (d, J = 15.13 Hz, 1H) 1.50-1.68 (m, 2H) 2.10 (t, J = 8.71 Hz, 1H) 2.19-2.31 (m, 2H) 2.27 (s, 6H) 2.33-2.46 (m, 2H) 2.47-2.56 (m, 2H) 2.67-2.75 (m, 1H) 2.83-2.95 (m, 3H) 2.99 (t, J = 9.86 Hz, 1H) 3.09-3.22 (m, 4H) 3.23-3.35 (m, 1H) 3.28 (s, 3H) 3.32 (s, 3H) 3.41-3.50 (m, 1H) 3.59 (s, 2H) 3.63 (d, J = 8.71 Hz, 1H) 3.72 (d, J = 7.79 Hz, 1H) 3.97-4.06 (m, 1H) 4.40 (d, J = 6.88 Hz, 1H) 4.45-4.49 (m, 1H) 4.84 (d, J = 5.04 Hz, 1H) 5.92-5.99 (m, 1H) 6.43-6.48 (m, 1H) 6.63-6.68 (m, 1H) 7.15 (d, J = 7.34 Hz, 1H) 7.36 (t, J = 7.57 Hz, 1H) 7.43-7.48 (m, 1H) 7.54-7.60 (m, 2H) |
| 29 | | | 885.4 | (600 MHz): 0.93 (d, J = 7.34 Hz, 3H) 0.98 (d, J = 6.88 Hz, 3H) 1.05-1.10 (m, 6H) 1.17-1.26 (m, 7H) 1.28 (d, J = 5.96 Hz, 3H) 1.35 (s, 3H) 1.41 (d, J = 14.67 Hz, 1H) 1.54-1.70 (m, 2H) 2.17-2.37 (m, 2H) 2.30 (s, 6H) 2.40-2.59 (m, 2H) 2.70 (t, J = 9.40 Hz, 1H) 2.75-3.03 (m, 7H) 3.09-3.24 (m, 3H) 3.27 (s, 3H) 3.30 (s, 3H) 3.44-3.51 (m, 1H) 3.58 (d, J = 9.63 Hz, 1H) 3.74 (d, J = 7.34 Hz, 1H) 3.96-4.05 (m, 2H) 4.09-4.13 (m, 1H) 4.44-4.47 (m, 1H) 4.88-4.90 (m, 1H) 4.97-5.01 (m, 1H) 6.96-7.03 (m, 2H) 7.27-7.33 (m, 3H) 7.37 (t, J = 7.79 Hz, 2H) 7.44 (d, J = 6.88 Hz, 2H) |

TABLE 1-continued

| Example | Reference Example | R | ESI MS (M + H) | ¹H-NMR, CDCl₃, δ (ppm) |
|---|---|---|---|---|
| 30 | | phenyl-O-CH< | 809.5 | (600 MHz): 0.94 (d, J = 7.34 Hz, 3H) 1.03 (d, J = 6.88 Hz, 3H) 1.07 (d, J = 7.34 Hz, 3H) 1.09 (d, J = 6.88 Hz, 3H) 1.20-1.26 (m, 1H) 1.22 (d, J = 5.96 Hz, 3H) 1.25 (s, 3H) 1.29 (d, J = 6.42 Hz, 3H) 1.37 (s, 3H) 1.44 (d, J = 14.67 Hz, 1H) 1.57 (dd, J = 15.13, 5.04 Hz, 1H) 1.63-1.69 (m, 1H) 2.21 (d, J = 10.09 Hz, 1H) 2.23-2.27 (m, 1H) 2.29 (s, 6H) 2.36 (d, J = 15.13 Hz, 1H) 2.39-2.47 (m, 1H) 2.49-2.55 (m, 1H) 2.62-2.70 (m, 1H) 2.72-2.79 (m, 1H) 2.79-2.86 (m, 2H) 2.93 (dd, J = 9.40, 5.73 Hz, 1H) 2.95-3.03 (m, 3H) 3.14-3.18 (m, 1H) 3.20 (dd, J = 10.32, 7.11 Hz, 1H) 3.24 (d, J = 11.92 Hz, 1H) 3.29 (s, 3H) 3.31 (s, 3H) 3.45-3.52 (m, 1H) 3.59 (d, J = 9.63 Hz, 1H) 3.75 (d, J = 7.34 Hz, 1H) 3.96-4.00 (m, 1H) 4.00-4.06 (m, 1H) 4.13 (dd, J = 9.17, 7.34 Hz, 1H) 4.46 (d, J = 7.34 Hz, 1H) 4.89 (d, J = 4.58 Hz, 1H) 5.14 (dd, J = 6.42, 4.13 Hz, 1H) 6.88 (d, J = 8.71 Hz, 2H) 6.91-6.95 (m, 1H) 7.24-7.29 (m, 2H) |
| 31 | | naphthyl-O-CH< | 859.4 | (600 MHz): 0.88-0.96 (m, 5H) 0.99-1.07 (m, 6H) 1.18-1.23 (m, 7H) 1.27 (d, J = 5.96 Hz, 3H) 1.35 (s, 3H) 1.42-1.47 (m, 1H) 1.50-1.55 (m, 1H) 1.60-1.69 (m, 1H) 2.17-2.33 (m, 2H) 2.29 (s, 6H) 2.39-2.63 (m, 3H) 2.80-3.06 (m, 8H) 3.15-3.29 (m, 3H) 3.27 (s, 3H) 3.27 (s, 3H) 3.42-3.50 (m, 1H) 3.53-3.57 (m, 1H) 3.73 (d, J = 7.34 Hz, 1H) 3.96-4.04 (m, 1H) 4.16-4.22 (m, 1H) 4.27-4.34 (m, 1H) 4.44 (d, J = 7.34 Hz, 1H) 4.81-4.85 (m, 1H) 5.21-5.27 (m, 1H) 6.82 (d, J = 6.88 Hz, 1H) 7.32-7.49 (m, 4H) 7.75-7.79 (m, 1H) 8.15-8.20 (m, 1H) |
| 32 | | 2-MeO-phenyl-O-CH< | 839.4 | (600 MHz): 0.93 (d, J = 7.34 Hz, 3H) 1.00-1.11 (m, 9H) 1.19-1.30 (m, 10H) 1.35 (s, 3H) 1.39-1.43 (m, 1H) 1.54-1.63 (m, 2H) 2.18-2.37 (m, 2H) 2.31 (s, 6H) 2.39-2.53 (m, 2H) 2.69-3.04 (m, 8H) 3.11-3.25 (m, 3H) 3.27 (s, 3H) 3.30 (s, 3H) 3.44-3.51 (m, 1H) 3.55-3.60 (m, 1H) 3.75 (d, J = 7.34 Hz, 1H) 3.83 (s, 3H) 3.98-4.06 (m, 2H) 4.14-4.19 (m, 1H) 4.45 (d, J = 7.34 Hz, 1H) 4.88 (d, J = 4.58 Hz, 1H) 5.11-5.15 (m, 1H) 6.84-6.94 (m, 4H) |
| 33 | | 3-MeO-phenyl-O-CH< | 839.4 | (600 MHz): 0.93 (d, J = 7.34 Hz, 3H) 1.00-1.12 (m, 9H) 1.19-1.31 (m, 10H) 1.35 (s, 3H) 1.39-1.44 (m, 1H) 1.52-1.77 (m, 2H) 2.19-2.38 (m, 2H) 2.31-2.33 (m, 6H) 2.39-2.54 (m, 2H) 2.60-3.04 (m, 8H) 3.13-3.25 (m, 3H) 3.27 (s, 3H) 3.30 (s, 3H) 3.45-3.52 (m, 1H) 3.58 (d, J = 9.63 Hz, 1H) 3.75 (d, J = 7.79 Hz, 1H) 3.78 (s, 3H) 3.93-4.05 (m, 2H) 4.08-4.14 (m, 1H) 4.43-4.49 (m, 1H) 4.86-4.90 (m, 1H) 5.09-5.15 (m, 1H) 6.41-6.52 (m, 3H) 7.15 (s, 1H) |
| 34 | | 4-MeO-phenyl-O-CH< | 839.4 | (600 MHz): 0.93 (d, J = 6.88 Hz, 3H) 1.00-1.11 (m, 9H) 1.17-1.30 (m, 10H) 1.35 (s, 3H) 1.41 (d, J = 15.13 Hz, 1H) 1.53-1.68 (m, 2H) 2.18-2.25 (m, 1H) 2.28 (s, 6H) 2.36 (d, J = 15.13 Hz, 1H) 2.38-2.53 (m, 2H) 2.58-2.66 (m, 1H) 2.72-3.02 (m, 7H) 3.12-3.24 (m, 3H) 3.27 (s, 3H) 3.30 (s, 3H) 3.44-3.51 (m, 1H) 3.57 (d, J = 9.63 Hz, 1H) 3.71-3.77 (m, 1H) 3.75 (s, 3H) 3.90-3.95 (m, 1H) 3.98-4.09 (m, 2H) 4.45 (d, J = 6.88 Hz, 1H) 4.88 (d, J = 4.58 Hz, 1H) 5.09-5.13 (m, 1H) 6.81 (s, 4H) |

TABLE 1-continued

| Example | Reference Example | R | ESI MS (M + H) | ¹H-NMR, CDCl₃, δ (ppm) |
|---|---|---|---|---|
| 35 | | 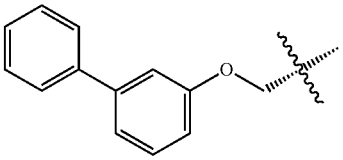 | 885.7 | (600 MHz): 0.94 (d, J = 7.34 Hz, 3H), 1.01-1.10 (m, 9H) 1.16-1.31 (m, 10H) 1.36 (s, 3H) 1.39-1.68 (m, 3H) 2.18-2.37 (m, 2H) 2.29 (s, 6H) 2.37-2.55 (m, 2H) 2.63-3.05 (m, 8H) 3.13-3.26 (m, 3H) 3.28 (s, 3H) 3.30 (s, 3H) 3.44-3.51 (m, 1H) 3.55-3.60 (m, 1H) 3.72-3.77 (m, 1H) 3.98-4.07 (m, 2H) 4.15-4.21 (m, 1H) 4.43-4.48 (m, 1H) 4.86-4.89 (m, 1H) 5.13-5.17 (m, 1H) 6.84-6.89 (m, 1H) 7.09-7.12 (m, 1H) 7.14-7.18 (m, 1H) 7.30-7.35 (m, 2H) 7.39-7.44 (m, 2H) 7.55-7.61 (m, 2H) |
| 36 | | 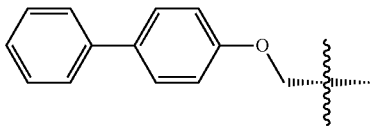 | 885.7 | (600 MHz): 0.93 (d, J = 7.34 Hz, 3H) 1.00-1.10 (m, 9H) 1.16-1.32 (m, 10H) 1.36 (s, 3H) 1.40-1.47 (m, 1H) 1.51-1.70 (m, 2H) 2.17-2.37 (m, 2H) 2.29 (s, 6H) 2.38-2.55 (m, 2H) 2.64-3.05 (m, 8H) 3.13-3.26 (m, 3H) 3.28 (s, 6H) 3.43-3.51 (m, 1H) 3.55-3.59 (m, 1H) 3.74 (d, J = 7.34 Hz, 1H) 3.99-4.05 (m, 2H) 4.14-4.21 (m, 1H) 4.55 (d, J = 6.88 Hz, 1H) 4.87 (d, J = 5.04 Hz, 1H) 5.12-5.16 (m, 1H) 6.94 (d, J = 8.71 Hz, 2H) 7.27-7.31 (m, 1H) 7.40 (t, J = 7.79 Hz, 2H) 7.47-7.56 (m, 4H) |
| 37 | | 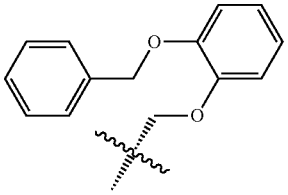 | 915.5 | (600 MHz): 0.93 (d, J = 7.34 Hz, 3H) 1.01 (d, J = 6.88 Hz, 3H) 1.04-1.10 (m, 6H) 1.15-1.26 (m, 1H) 1.21 (d, J = 5.96 Hz, 3H) 1.24 (s, 3H) 1.28 (d, J = 5.96 Hz, 3H) 1.35 (s, 3H) 1.42 (d, J = 14.67 Hz, 1H) 1.53-1.67 (m, 2H) 2.16-2.26 (m, 1H) 2.28 (s, 6H) 2.35 (d, J = 14.21 Hz, 1H) 2.38-2.45 (m, 1H) 2.45-2.54 (m, 1H) 2.65-2.87 (m, 4H) 2.90-3.04 (m, 4H) 3.11-3.25 (m, 3H) 3.28 (s, 3H) 3.30 (s, 3H) 3.42-3.51 (m, 1H) 3.58 (d, J = 9.17 Hz, 1H) 3.74 (d, J = 7.34 Hz, 1H) 3.99-4.07 (m, 2H) 4.17-4.23 (m, 1H) 4.45 (d, J = 6.88 Hz, 1H) 4.88 (d, J = 4.58 Hz, 1H) 5.08 (s, 2H) 5.10-5.14 (m, 1H) 6.83-6.95 (m, 4H) 7.26-7.32 (m, 1H) 7.33-7.38 (m, 2H) 7.39-7.45 (m, 2H) |
| 38 | | 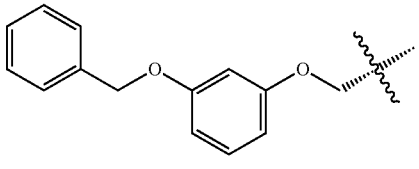 | 915.4 | (600 MHz): 0.93 (d, J = 7.34 Hz, 3H) 1.02 (d, J = 6.88 Hz, 3H) 1.05-1.13 (m, 6H) 1.15-1.25 (m, 1H) 1.21 (d, J = 5.96 Hz, 3H) 1.24 (s, 3H) 1.28 (d, J = 6.42 Hz, 3H) 1.35 (s, 3H) 1.43 (d, J = 14.67 Hz, 1H) 1.54 (s, 2H) 2.17-2.31 (m, 1H) 2.27 (s, 6H) 2.32-2.44 (m, 2H) 2.46-2.55 (m, 1H) 2.59-2.67 (m, 1H) 2.74-2.86 (m, 3H) 2.89-3.04 (m, 4H) 3.10-3.25 (m, 3H) 3.28 (s, 3H) 3.30 (s, 3H) 3.42-3.51 (m, 1H) 3.58 (d, J = 10.09 Hz, 1H) 3.75 (d, J = 7.34 Hz, 1H) 3.96 (d, J = 7.79 Hz, 1H) 3.99-4.06 (m, 1H) 4.08-4.13 (m, 1H) 4.45 (d, J = 7.34 Hz, 1H) 4.89 (d, J = 4.58 Hz, 1H) 5.03 (s, 2H) 5.09-5.14 (m, 1H) 6.47-6.59 (m, 3H) 7.15 (t, J = 8.02 Hz, 1H) 7.28-7.33 (m, 1H) 7.34-7.40 (m, 2H) 7.40-7.45 (m, 2H) |
| 39 | | 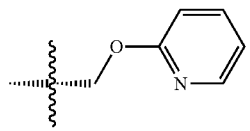 | 810.5 | (600 MHz): 0.94 (d, J = 6.88 Hz, 3H) 1.00-1.10 (m, 9H) 1.19-1.30 (m, 10H) 1.35 (s, 3H) 1.41 (d, J = 14.67 Hz, 1H) 1.53-1.70 (m, 2H) 2.17-2.38 (m, 2H) 2.29 (s, 6H) 2.40-2.52 (m, 2H) 2.60-2.68 (m, 1H) 2.75-3.04 (m, 7H) 3.11-3.25 (m, 3H) 3.27 (s, 3H) 3.30 (s, 3H) 3.44-3.50 (m, 1H) 3.58 (d, J = 10.09 Hz, 1H) 3.75 (d, J = 6.88 Hz, 1H) 3.98-4.06 (m, 1H) 4.23-4.28 (m, 1H) 4.46 (d, J = 7.34 Hz, 1H) 4.50-4.56 (m, 1H) 4.88 (d, J = 4.58 Hz, 1H) 5.09-5.14 (m, 1H) 6.68 (d, J = 8.25 Hz, 1H) 6.80-6.86 (m, 1H) 7.50-7.57 (m, 1H) 8.09-8.16 (m, 1H) |

TABLE 1-continued

| Example | Reference Example | R | ESI MS (M + H) | ¹H-NMR, CDCl₃, δ (ppm) |
|---|---|---|---|---|
| 40 | | *pyridin-2(1H)-one-N-CH2-* | 810.5 | (600 MHz): 0.93-1.00 (m, 6H) 1.11-1.31 (m, 16H) 1.36 (s, 3H) 1.42-1.75 (m, 3H) 2.16-2.54 (m, 4H) 2.29 (s, 6H) 2.66-3.05 (m, 8H) 3.09-3.25 (m, 3H) 3.28 (s, 3H) 3.33 (s, 3H) 3.45-3.53 (m, 1H) 3.61 (d, J = 9.63 Hz, 1H) 3.77 (d, J = 6.88 Hz, 1H) 3.83-3.90 (m, 1H) 3.99-4.07 (m, 1H) 4.11-4.17 (m, 1H) 4.48 (d, J = 6.88 Hz, 1H) 4.89-4.94 (m, 2H) 6.07-6.14 (m, 1H) 6.54 (d, J = 8.71 Hz, 1H) 7.17-7.21 (m, 1H) 7.29-7.33 (m, 1H) |
| 41 | | *4-benzyloxyphenoxy-CH2-* | 915.6 | (600 MHz): 0.93 (d, J = 7.34 Hz, 3H) 1.02 (d, J = 6.88 Hz, 3H) 1.07 (d, J = 7.34 Hz, 3H) 1.09 (d, J = 7.34 Hz, 3H) 1.18-1.26 (m, 1H) 1.22 (d, J = 5.96 Hz, 3H) 1.24 (s, 3H) 1.28 (d, J = 6.42 Hz, 3H) 1.35 (s, 3H) 1.43 (d, J = 14.67 Hz, 1H) 1.53-1.59 (m, 1H) 1.61-1.66 (m, 1H) 2.18-2.25 (m, 1H) 2.28 (s, 6H) 2.31-2.46 (m, 2H) 2.47-2.54 (m, 1H) 2.58-2.66 (m, 1H) 2.72-2.85 (m, 3H) 2.88-3.04 (m, 4H) 3.11-3.24 (m, 3H) 3.28 (s, 3H) 3.30 (s, 3H) 3.43-3.51 (m, 1H) 3.58 (d, J = 10.09 Hz, 1H) 3.74 (d, J = 7.34 Hz, 1H) 3.92 (t, J = 8.25 Hz, 1H) 3.99-4.09 (m, 2H) 4.45 (d, J = 7.34 Hz, 1 H) 4.88 (d, J = 4.13 Hz, 1H) 5.00 (s, 2H) 5.08-5.14 (m, 1H) 6.78-6.82 (m, 2H) 6.86-6.91 (m, 2H) 7.28-7.33 (m, 1H) 7.34-7.39 (m, 2H) 7.40-7.44 (m, 2H) |
| 42 | | *quinolin-8-yloxy-C(CH3)2-* | 860.6 | (600 MHz): 0.92 (d, J = 7.34 Hz, 3H) 1.00 (d, J = 7.34 Hz, 3H) 1.04 (d, J = 6.88 Hz, 3H) 1.08 (d, J = 7.34 Hz, 3H) 1.19-1.24 (m, 1H) 1.22 (d, J = 5.96 Hz, 3H) 1.24 (s, 3H) 1.29 (d, J = 6.42 Hz, 3H) 1.37 (s, 3H) 1.45 (d, J = 15.13 Hz, 1H) 1.56 (dd, J = 14.90, 4.81 Hz, 1 H) 1.63-1.68 (m, 1H) 2.20-2.27 (m, 2H) 2.30 (s, 6H) 2.34 (d, J = 14.67 Hz, 1H) 2.41-2.47 (m, 1H) 2.51-2.56 (m, 1H) 2.68-2.73 (m, 1H) 2.84-3.08 (m, 7H) 3.15-3.18 (m, 1H) 3.21 (dd, J = 10.09, 6.88 Hz, 1H) 3.26 (d, J = 11.46 Hz, 1H) 3.28 (s, 3H) 3.31 (s, 3H) 3.45-3.51 (m, 1H) 3.58 (d, J = 9.63 Hz, 1H) 3.75 (d, J = 7.34 Hz, 1H) 4.00-4.06 (m, 1H) 4.27 (t, J = 8.48 Hz, 1H) 4.43 (dd, J = 9.40, 6.65 Hz, 1H) 4.46 (d, J = 7.34 Hz, 1H) 4.87 (d, J = 4.58 Hz, 1H) 5.23 (dd, J = 5.96, 5.04 Hz, 1H) 7.10 (d, J = 7.34 Hz, 1H) 7.37-7.43 (m, 2H) 7.46 (t, J = 8.02 Hz, 1H) 8.12 (dd, J = 8.25, 1.83 Hz, 1H) 8.94 (dd, J = 4.13, 1.83 Hz, 1H) |
| 43 | | *quinolin-6-yloxy-CH2-* | 860.3 | (500 MHz): 0.92 (d, J = 7.40 Hz, 3H) 1.05 (d, J = 6.86 Hz, 3H) 1.08 (d, 7.13 Hz, 3H) 1.10 (d, J = 7.40 Hz, 3H) 1.17-1.22 (m, 1H) 1.23 (d, J = 6.03 Hz, 3H) 1.24 (s, 3H) 1.29 (d, J = 6.03 Hz, 3H) 1.37 (s, 3H) 1.47 (d, J = 14.53 Hz, 1H) 1.56 (dd, J = 15.08, 5.21 Hz, 1H) 1.63-1.68 (m, 1H) 2.21-2.27 (m, 2H) 2.29 (s, 6H) 2.35 (d, J = 15.08 Hz, 1H) 2.39-2.46 (m, 1H) 2.53-2.59 (m, 1H) 2.72-2.79 (m, 2H) 2.81-2.89 (m, 2H) 2.93-3.07 (m, 4H) 3.15-3.28 (m, 3H) 3.28 (s, 3H) 3.30 (s, 3H) 3.44-3.51 (m, 1H) 3.59 (d, J = 9.60 Hz, 1H) 3.76 (d, J = 7.40 Hz, 1H) 3.99-4.05 (m, 1H) 4.13 (t, J = 8.36 Hz, 1H) 4.26 (dd, J = 8.91, 7.27 Hz, 1H) 4.46 (d, J = 7.13 Hz, 1H) 4.88 (d, J = 4.66 Hz, 1H) 5.18 (dd, J = 6.44, 4.52 Hz, 1H) 7.09 (d, J = 2.74 Hz, 1H) 7.32-7.36 (m, 2H) 7.99 (d, J = 9.32 Hz, 1H) 8.08 (dd, J = 8.36, 0.96 Hz, 1H) 8.76 (dd, J = 4.11, 1.65 Hz, 1H) |

TABLE 1-continued

| Example | Reference Example R | ESI MS (M + H) | ¹H-NMR, CDCl₃, δ (ppm) |
|---|---|---|---|
| 44 | quinoline-7-yloxy-CH₂- | 860.4 | (600 MHz): 0.89 (d, J = 6.88 Hz, 3H) 1.05 (d, J = 6.88 Hz, 3H) 1.13 (d, J = 7.34 Hz, 3H) 1.15 (d, J = 7.34 Hz, 3H) 1.22 (d, J = 5.96 Hz, 3H) 1.21-1.27 (m, 1H) 1.25 (s, 3H) 1.30 (d, J = 6.42 Hz, 3H) 1.37 (s, 3H) 1.47 (d, J = 14.21 Hz, 1H) 1.57 (dd, J = 15.13, 5.04 Hz, 1H) 1.63-1.68 (m, 1H) 2.20-2.27 (m, 2H) 2.31 (s, 6H) 2.38 (d, J = 14.67 Hz, 1H) 2.43-2.50 (m, 1H) 2.52-2.57 (m, 1H) 2.72-2.78 (m, 1H) 2.83-2.91 (m, 3H) 2.94-3.05 (m, 4H) 3.15-3.18 (m, 1H) 3.22-3.27 (m, 2H) 3.30 (s, 3H) 3.32 (s, 3H) 3.45-3.51 (m, 1H) 3.61 (d, J = 9.63 Hz, 1H) 3.77 (d, J = 7.79 Hz, 1H) 4.01-4.07 (m, 1H) 4.21 (t, J = 8.94 Hz, 1H) 4.31 (dd, J = 9.40, 6.19 Hz, 1H) 4.47 (d, J = 7.34 Hz, 1H) 4.91 (d, J = 4.58 Hz, 1H) 5.16 (dd, J = 5.96, 4.58 Hz, 1H) 7.18 (dd, J = 8.94, 2.52 Hz, 1H) 7.25-7.28 (m, 1H) 7.43 (d, J = 2.29 Hz, 1H) 7.70 (d, J = 9.17 Hz, 1H) 8.07 (dd, J = 8.25, 1.38 Hz, 1H) 8.84 (dd, J = 4.36, 1.60 Hz, 1H) |
| 45 | isoquinolin-3-yloxy-CH₂- | 860.4 | (600 MHz): 0.94 (d, J = 6.88 Hz, 3H) 1.04 (d, J = 6.88 Hz, 3H) 1.07 (d, J = 6.88 Hz, 3H) 1.10 (d, J = 7.34 Hz, 3H) 1.19-1.25 (m, 1H) 1.22 (d, J = 5.96 Hz, 3H) 1.24 (s, 3H) 1.29 (d, J = 5.96 Hz, 3H) 1.37 (s, 3H) 1.45 (d, J = 14.67 Hz, 1H) 1.56 (dd, J = 15.13, 5.04 Hz, 1H) 1.63-1.68 (m, 1H) 2.20-2.26 (m, 2H) 2.29 (s, 6H) 2.35 (d, J = 14.67 Hz, 1H) 2.40-2.47 (m, 1H) 2.51-2.57 (m, 1H) 2.70-2.89 (m, 4H) 2.97-3.06 (m, 4H) 3.15-3.17 (m, 1H) 3.21 (dd, J = 10.09, 7.34 Hz, 1H) 3.25 (d, J = 11.46 Hz, 1H) 3.29 (s, 3H) 3.30 (s, 3H) 3.45-3.51 (m, 1H) 3.60 (d, J = 9.63 Hz, 1H) 3.76 (d, J = 7.34 Hz, 1H) 4.01-4.06 (m, 1H) 4.34 (dd, J = 9.86, 8.02 Hz, 1H) 4.47 (d, J = 7.34 Hz, 1H) 4.58 (dd, J = 10.09, 7.34 Hz, 1H) 4.89 (d, J = 4.13 Hz, 1H) 5.17 (dd, J = 5.96, 4.58 Hz, 1H) 6.98 (s, 1H) 7.35-7.38 (m, 1H) 7.54-7.58 (m, 1H) 7.69 (d, J = 7.79 Hz, 1H) 7.87 (d, J = 7.79 Hz, 1H) 8.94 (s, 1H) |
| 46 | isoquinolin-7-yloxy-CH₂- | 860.3 | (600 MHz): 0.93 (d, J = 7.34 Hz, 3H) 1.05 (d, J = 6.88 Hz, 3H) 1.09 (d, J = 6.88 Hz, 3H) 1.13 (d, J = 7.34 Hz, 3H) 1.19-1.22 (m, 1H) 1.22 (d, J = 6.42 Hz, 3H) 1.24 (s, 3H) 1.30 (d, J = 6.42 Hz, 3H) 1.37 (s, 3H) 1.48 (d, J = 14.67 Hz, 1H) 1.57 (dd, J = 15.13, 5.04 Hz, 1H) 1.63-1.67 (m, 1H) 2.21-2.27 (m, 2H) 2.28 (s, 6H) 2.35 (d, J = 15.13 Hz, 1H) 2.39-2.45 (m, 1H) 2.53-2.59 (m, 1H) 2.72-2.89 (m, 4H) 2.96-3.06 (m, 4H) 3.16-3.21 (m, 2H) 3.27 (d, J = 11.92 Hz, 1H) 3.30 (s, 3H) 3.30 (s, 3H) 3.44-3.51 (m, 1H) 3.60 (d, J = 10.09 Hz, 1H) 3.76 (d, J = 7.34 Hz, 1H) 4.01-4.06 (m, 1H) 4.14 (t, J = 8.48 Hz, 1H) 4.28 (dd, J = 8.94, 7.11 Hz, 1H) 4.46 (d, J = 7.34 Hz, 1H) 4.89 (d, J = 4.58 Hz, 1H) 5.18 (dd, J = 6.42, 4.58 Hz, 1H) 7.24 (d, J = 2.29 Hz, 1H) 7.32 (dd, J = 8.94, 2.52 Hz, 1H) 7.57 (d, J = 5.50 Hz, 1H) 7.72 (d, J = 9.17 Hz, 1H) 8.40 (d, J = 5.50 Hz, 1H) 9.16 (s, 1H) |

TABLE 1-continued

| Example | Reference Example | R | ESI MS (M + H) | $^1$H-NMR, CDCl$_3$, δ (ppm) |
|---|---|---|---|---|
| 47 | | 5-indolyloxy-methyl group | 848.5 | (600 MHz): 0.94 (d, J = 6.88 Hz, 3H) 1.04 (d, J = 6.88 Hz, 3H) 1.07-1.11 (m, 6H) 1.20-1.24 (m, 1H) 1.22 (d, J = 5.96 Hz, 3H) 1.24 (s, 3 H) 1.29 (d, J = 5.96 Hz, 1H) 1.37 (s, 3H) 1.43 (d, J = 15.13 Hz, 1H) 1.54-1.68 (m, 2H) 2.20-2.26 (m, 2H) 2.29 (s, 6H) 2.36 (d, J = 14.67 Hz, 1H) 2.40-2.48 (m, 1H) 2.50-2.55 (m, 1 H) 2.65-2.72 (m, 1H) 2.77-2.89 (m, 3H) 2.96-3.05 (m, 4H) 3.15-3.17 (m, 1H) 3.19-3.25 (m, 2H) 3.29 (s, 3H) 3.30 (s, 3H) 3.45-3.51 (m, 1H) 3.60 (d, J = 9.17 Hz, 1H) 3.76 (d, J = 7.34 Hz, 1H) 4.00-4.06 (m, 2H) 4.17 (dd, J = 8.71, 7.34 Hz, 1H) 4.47 (d, J = 6.88 Hz, 1H) 4.89 (d, J = 4.58 Hz, 1H) 5.16 (dd, J = 5.96, 4.13 Hz, 1H) 6.47 (t, J = 2.29 Hz, 1H) 6.83 (dd, J = 8.94, 2.52 Hz, 1H) 7.10 (d, J = 2.29 Hz, 1H) 7.18 (t, J = 2.75 Hz, 1H) 7.26-7.28 (m, 1H) 8.06 (br. s., 1H) |
| 48 | | 6-indolyloxy-methyl group | 848.4 | (600 MHz): 0.66 (d, J = 6.88 Hz, 3H) 1.00 (d, J = 6.88 Hz, 3H) 1.12 (d, J = 7.34 Hz, 3H) 1.24 (d, J = 6.42 Hz, 3H) 1.25-1.27 (m, 7H) 1.31 (d, J = 5.96 Hz, 3H) 1.35 (s, 3H) 1.46 (d, J = 15.13 Hz, 1H) 1.55-1.71 (m, 2H) 2.17-2.27 (m, 2H) 2.34 (s, 6H) 2.39 (d, J = 15.13 Hz, 1H) 2.45-2.51 (m, 1H) 2.64-2.76 (m, 3H) 2.78-3.04 (m, 6H) 3.12-3.18 (m, 2H) 3.28 (dd, J = 10.32, 7.11 Hz, 1H) 3.30 (s, 3H) 3.32 (s, 3 H) 3.47-3.53 (m, 1H) 3.62 (d, J = 10.09 Hz, 1H) 3.78 (d, J = 8.25 Hz, 1H) 4.01-4.07 (m, 1 H) 4.14 (dd, J = 9.17, 5.96 Hz, 1H) 4.24 (t, J = 9.17 Hz, 1H) 4.49 (d, J = 7.34 Hz, 1H) 4.89 (d, J = 4.58 Hz, 1H) 5.10 (t, J = 6.42 Hz, 1H) 6.44 (t, J = 2.06 Hz, 1H) 6.75 (dd, J = 8.71, 2.29 Hz, 1H) 6.97 (d, J = 1.83 Hz, 1H) 7.04 (dd, J = 3.21, 2.29 Hz, 1H) 7.46 (d, J = 8.25 Hz, 1H) 9.12 (br. s., 1H) |
| 49 | | 3-hydroxy-2-naphthyloxy-methyl group | 875.4 | (600 MHz): 0.93 (d, J = 6.88 Hz, 3H) 1.04 (d, J = 6.88 Hz, 3H) 1.06-1.10 (m, 6H) 1.17-1.26 (m, 1H) 1.22 (d, J = 5.96 Hz, 3H) 1.23 (s, 3 H) 1.28 (d, J = 6.42 Hz, 3H) 1.36 (s, 3H) 1.47 (d, J = 14.67 Hz, 1H) 1.55 (dd, J = 15.13, 5.04 Hz, 1H) 1.61-1.67 (m, 1H) 2.17-2.23 (m, 1H) 2.28 (s, 6H) 2.34 (d, J = 15.13 Hz, 1H) 2.38-2.46 (m, 1H) 2.49-2.56 (m, 1H) 2.70-2.88 (m, 4H) 2.90-3.06 (m, 4H) 3.16-3.23 (m, 2H) 3.24-3.31 (m, 1H) 3.27 (s, 3H) 3.29 (s, 3H) 3.43-3.50 (m, 1H) 3.61 (d, J = 9.63 Hz, 1H) 3.75 (d, J = 7.79 Hz, 1H) 3.98-4.04 (m, 1H) 4.21-4.26 (m, 1H) 4.29-4.34 (m, 1H) 4.44 (d, J = 7.34 Hz, 1H) 4.85 (d, J = 4.58 Hz, 1H) 5.20-5.24 (m, 1H) 7.14 (s, 1H) 7.22-7.33 (m, 3H) 7.61-7.70 (m, 2H) |
| 50 | | 7-hydroxy-2-naphthyloxy-methyl group | 875.4 | (600 MHz): 0.76 (d, J = 6.88 Hz, 3H) 1.01 (d, J = 6.88 Hz, 3H) 1.11 (d, J = 6.88 Hz, 3H) 1.16-1.27 (m, 10H) 1.30 (d, J = 5.96 Hz, 3 H) 1.36 (s, 3H) 1.46 (d, J = 14.67 Hz, 1H) 1.56 (dd, J = 15.13, 5.04 Hz, 1H) 1.59-1.67 (m, 1H) 2.17-2.27 (m, 1H) 2.29 (s, 6H) 2.36 (d, J = 15.59 Hz, 1H) 2.42-2.51 (m, 1H) 2.56-2.64 (m, 1H) 2.69-2.77 (m, 2H) 2.77-2.86 (m, 2H) 2.88-3.05 (m, 4H) 3.12-3.27 (m, 3H) 3.29 (s, 3H) 3.30 (s, 3H) 3.44-3.53 (m, 1H) 3.60 (d, J = 10.09 Hz, 1H) 3.78 (d, J = 7.34 Hz, 1H) 3.99-4.07 (m, 1H) 4.16-4.25 (m, 2H) 4.48 (d, J = 7.34 Hz, 1H) 4.89 (d, J = 4.58 Hz, 1H) 5.10-5.16 (m, 1H) 6.89-6.96 (m, 2H) 6.98-7.02 (m, 1H) 7.11-7.15 (m, 1 H) 7.61 (dd, 2H) |

TABLE 1-continued

| Example | Reference Example | R | ESI MS (M + H) | $^1$H-NMR, CDCl$_3$, δ (ppm) |
|---|---|---|---|---|
| 51 | | (6-hydroxynaphthalen-2-yl)oxymethyl | 875.3 | (600 MHz): 0.92 (d, J = 6.88 Hz, 3H) 1.04 (d, J = 6.88 Hz, 3H) 1.07 (d, J = 7.34 Hz, 3H) 1.09 (d, J = 7.34 Hz, 3H) 1.15-1.26 (m, 1H) 1.21 (d, J = 5.96 Hz, 3H) 1.23 (s, 3H) 1.28 (d, J = 5.96 Hz, 3H) 1.36 (s, 3H) 1.45 (d, J = 14.67 Hz, 1H) 1.55 (dd, J = 15.13, 5.04 Hz, 1H)1.60-1.67 (m, 1H) 2.20-2.27 (m, 1H) 2.28 (s, 6H) 2.34 (d, J = 14.67 Hz, 1H) 2.39-2.48 (m, 1H) 2.49-2.57 (m, 1H) 2.65-2.89 (m, 4H) 2.93-3.06 (m, 4H) 3.15-3.27 (m, 3H) 3.27-3.31 (m, 6H) 3.43-3.50 (m, 1H) 3.58 (d, J = 9.63 Hz, 1H) 3.75 (d, J = 7.34 Hz, 1H) 3.98-4.09 (m, 2H) 4.16-4.23 (m, 1H) 4.45 (d, J = 7.34 Hz, 1H) 4.88 (d, J = 4.58 Hz, 1H) 5.13-5.19 (m, 1H) 7.01-7.10 (m, 4H) 7.53-7.65 (m, 2H) |
| 52 | | (3-bromophenoxy)methyl | 887.4 | (600 MHz): 0.94 (d, J = 6.88 Hz, 3H) 1.03 (d, J = 7.34 Hz, 3H) 1.08 (d, J = 7.34 Hz, 3H) 1.11 (d, J = 7.34 Hz, 3H) 1.16-1.21 (m, 1H) 1.22 (d, J = 5.96 Hz, 3H) 1.25 (s, 3H) 1.29 (d, J = 6.42 Hz, 3H) 1.37 (s, 3H) 1.45 (d, J = 14.67 Hz, 1H) 1.55-1.67 (m, 2H) 2.20-2.27 (m, 2H) 2.29 (s, 6H) 2.35-2.53 (m, 3H) 2.62-2.67 (m, 1H) 2.73-2.86 (m, 3H) 2.89-3.04 (m, 4H) 3.14-3.26 (m, 3H) 3.29 (s, 3H) 3.32 (s, 3H) 3.45-3.51 (m, 1H) 3.59 (d, J = 10.09 Hz, 1H) 3.75 (d, J = 7.34 Hz, 1H) 3.94-3.99 (m, 1H) 4.01-4.06 (m, 1H) 4.11 (dd, J = 8.71, 7.34 Hz, 1H) 4.46 (d, J = 7.34 Hz, 1H) 4.89 (d, J = 5.04 Hz, 1H) 5.12 (dd, J = 6.42, 4.58 Hz, 1H) 6.80-6.82 (m, 1H) 7.03-7.05 (m, 1H) 7.05-7.09 (m, 1H) 7.13 (t, J = 8.02 Hz, 1H) |
| 53 | 12 | (1-benzyloxynaphthalen-2-yl)oxymethyl | 965.6 | (600 MHz): 0.93 (d, J = 7.34 Hz, 3H) 0.99-1.07 (m, 9H) 1.18-1.26 (m, 7H) 1.28 (d, J = 6.42 Hz, 3H) 1.35 (s, 3H) 1.44 (d, J = 14.67 Hz, 1H) 1.49-1.67 (m, 2H) 2.17-2.55 (m, 4H) 2.28 (s, 6H) 2.66-2.88 (m, 4H) 2.91-3.03 (m, 3H) 3.10-3.32 (m, 4H) 3.27 (s, 3H) 3.27 (s, 3H) 3.42-3.51 (m, 1H) 3.56 (d, J = 9.63 Hz, 1H) 3.73 (d, J = 7.79 Hz, 1H) 3.97-4.06 (m, 1H) 4.15-4.21 (m, 1H) 4.30-4.36 (m, 1H) 4.44 (d, J = 7.34 Hz, 1H) 4.86 (d, J = 4.58 Hz, 1H) 5.10-5.19 (m, 1H) 5.12 (s, 2H) 7.26-7.44 (m, 6H) 7.50-7.56 (m, 2H) 7.56-7.61 (m, 1H) 7.76 (d, J = 8.25 Hz, 1H) 8.10 (d, J = 8.25 Hz, 1H) |
| 54 | 13 | (2-benzyloxynaphthalen-1-yl)oxymethyl | 965.9 | (600 MHz): 0.93 (d, J = 7.34 Hz, 3H) 0.97 (d, J = 6.88 Hz, 3H) 1.00 (d, J = 6.88 Hz, 3H) 1.02 (d, J = 6.88 Hz, 3H) 1.14-1.29 (m, 1H) 1.21 (d, J = 6.42 Hz, 3H) 1.23 (s, 3H) 1.27 (d, J = 6.42 Hz, 3H) 1.34 (s, 3H) 1.39 (d, J = 14.67 Hz, 1H) 1.55 (dd, J = 15.13, 5.04 Hz, 1H) 1.62-1.70 (m, 1H) 2.14-2.49 (m, 3H) 2.29 (s, 6H) 2.60-2.69 (m, 1H) 2.69-2.78 (m, 1H) 2.81-3.07 (m, 7H) 3.10-3.24 (m, 3H) 3.26 (s, 3H) 3.28 (s, 3H) 3.43-3.51 (m, 1H) 3.54 (dd, J = 10.09, 7.34 Hz, 1H) 3.72 (d, J = 7.34 Hz, 1H) 3.95-4.04 (m, 1H) 4.23-4.35 (m, 2H) 4.44 (d, J = 7.34 Hz, 1H) 4.86 (d, J = 4.58 Hz, 1H) 5.11-5.18 (m, 1H) 5.20-5.25 (m, 2H) 7.23-7.47 (m, 8H) 7.51 (d, J = 8.71 Hz, 1H) 7.74 (d, J = 7.79 Hz, 1H) 8.05 (d, J = 8.71 Hz, 1H) |

TABLE 1-continued

| Example | Reference Example | R | ESI MS (M + H) | ¹H-NMR, CDCl₃, δ (ppm) |
|---|---|---|---|---|
| 55 | | 3-acetylphenyl-O-CH< | 851.8 | (600 MHz): 0.92 (d, J = 7.34 Hz, 3H) 1.03 (d, J = 6.88 Hz, 3H) 1.08 (d, J = 7.34 Hz, 3H) 1.10 (d, J = 6.88 Hz, 3H) 1.15-1.26 (m, 1H) 1.21 (d, J = 5.96 Hz, 3H) 1.24 (s, 3H) 1.28 (d, J = 5.96 Hz, 3H) 1.36 (s, 3H) 1.45 (d, J = 14.21 Hz, 1H) 1.49-1.68 (m, 2H) 2.17-2.54 (m, 4H) 2.28 (s, 6H) 2.58 (s, 3H) 2.62-2.72 (m, 1H) 2.74-2.88 (m, 3H) 2.89-3.07 (m, 4H) 3.11-3.26 (m, 3H) 3.28 (s, 3H) 3.30 (s, 3H) 3.42-3.51 (m, 1H) 3.58 (d, J = 9.17 Hz, 1H) 3.75 (d, J = 7.34 Hz, 1H) 3.95-4.08 (m, 2H) 4.13-4.21 (m, 1H) 4.45 (d, J = 6.88 Hz, 1H) 4.89 (d, J = 4.58 Hz, 1H) 5.09-5.16 (m, 1H) 7.04-7.12 (m, 1H) 7.35 (t, J = 7.79 Hz, 1H) 7.44-7.48 (m, 1H) 7.50-7.54 (m, 1H) |
| 56 | | 3,4-dimethylphenyl-O-CH< | 837 | (400 MHz): 0.94 (d, J = 7.1 Hz, 3H) 1.03 (d, J = 6.6 Hz, 3H) 1.08 (d, J = 7.8 Hz, 3H) 1.10 (d, J = 8.1 Hz, 3H) 1.16-1.26 (m, 1H) 1.23 (d, J = 6.1 Hz, 3H) 1.25 (s, 3H) 1.30 (d, J = 6.4 Hz, 3H) 1.36 (s, 3H) 1.43 (d, J = 14.9 Hz, 1H) 1.57 (dd, J = 15.1, 5.1 Hz, 1H) 1.62-1.71 (m, 1H) 2.18 (s, 3H) 2.19-2.56 (m, 7H) 2.22 (s, 3H) 2.30 (s, 6H) 2.57-2.69 (m, 1H) 2.72-2.87 (m, 3H) 2.89-3.06 (m, 4H) 3.14-3.24 (m, 3H) 3.29 (s, 3H) 3.32 (s, 3H) 3.43-3.53 (m, 1H) 3.58 (d, J = 9.8 Hz, 1H) 3.75 (d, J = 7.3 Hz, 1H) 3.91-4.12 (m, 3H) 4.46 (d, J = 7.3 Hz, 1H) 4.89 (d, J = 4.4 Hz, 1H) 5.12 (dd, J = 6.1, 4.4 Hz, 1H) 6.63 (dd, J = 8.3, 2.7 Hz, 1H) 6.69 (d, J = 2.4 Hz, 1H) 7.01 (d, J = 8.3 Hz, 1H) |
| 57 | | 3,4-dimethoxyphenyl-O-CH< | 869.6 | (600 MHz): 0.93 (d, J = 7.34 Hz, 3H) 1.02 (d, J = 6.42 Hz, 3H) 1.07 (d, J = 7.34 Hz, 3H) 1.09 (d, J = 6.88 Hz, 3H) 1.14-1.20 (m, 1H) 1.21 (d, J = 5.96 Hz, 3H) 1.23 (s, 3H) 1.28 (d, J = 6.42 Hz, 3H) 1.35 (s, 3H) 1.43 (d, J = 14.67 Hz, 1H) 1.56 (dd, J = 15.13, 5.04 Hz, 1H) 1.64 (d, J = 12.38 Hz, 1H) 2.18-2.25 (m, 1H) 2.28 (s, 6H) 2.35 (d, J = 15.13 Hz, 1H) 2.38-2.45 (m, 1H) 2.47-2.55 (m, 1H) 2.59-2.67 (m, 1H) 2.79 (d, J = 9.17 Hz, 3H) 2.87-3.04 (m, 4H) 3.13-3.24 (m, 3H) 3.28 (s, 3H) 3.30 (s, 3H) 3.42-3.50 (m, 1H) 3.57 (d, J = 10.09 Hz, 1H) 3.74 (d, J = 7.34 Hz, 1H) 3.82 (s, 3H) 3.84 (s, 3H) 3.93 (t, J = 8.25 Hz, 1H) 4.06 (d, 2H) 4.45 (d, J = 7.34 Hz, 1H) 4.88 (d, J = 4.58 Hz, 1H) 5.12 (d, 1H) 6.38 (dd, J = 8.71, 2.75 Hz, 1H) 6.47 (d, J = 2.75 Hz, 1H) 6.76 (d, 1H) |
| 58 | | 3,4-dichlorophenyl-O-CH< | 877.5 | (600 MHz): 0.92 (d, J = 7.34 Hz, 3H) 1.02 (d, J = 6.88 Hz, 3H) 1.07 (d, J = 7.34 Hz, 3H) 1.10 (d, J = 7.34 Hz, 3H) 1.15-1.20 (m, 1H) 1.21 (d, 3H) 1.24 (s, 3H) 1.28 (d, J = 5.96 Hz, 3H) 1.35 (s, 3H) 1.44 (d, J = 14.67 Hz, 1H) 1.56 (dd, J = 15.13, 5.04 Hz, 1H) 1.61-1.68 (m, 1H) 2.21 (d, J = 10.09 Hz, 1H) 2.28 (s, 6H) 2.33-2.52 (m, 3H) 2.59-2.67 (m, 1H) 2.70-2.96 (m, 5H) 2.97-3.03 (m, 2H) 3.13-3.25 (m, 3H) 3.28 (s, 3H) 3.31 (s, 3H) 3.43-3.51 (m, 1H) 3.58 (d, J = 9.17 Hz, 1H) 3.74 (d, J = 7.34 Hz, 1H) 3.91-3.96 (m, 1H) 3.98-4.05 (m, 1H) 4.08 (d, 1H) 4.45 (d, 1H) 4.88 (d, J = 4.58 Hz, 1H) 5.10 (dd, 1H) 6.73 (dd, J = 9.17, 2.75 Hz, 1H) 6.97 (d, 1H) 7.30 (d, J = 9.17 Hz, 1H) |

TABLE 1-continued

| Example | Reference Example | R | ESI MS (M + H) | $^1$H-NMR, CDCl$_3$, δ (ppm) |
|---|---|---|---|---|
| 59 | | 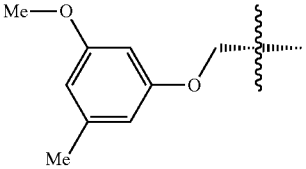 | 853.6 | (600 MHz): 0.93 (d, J = 6.88 Hz, 3H) 1.02 (d, J = 6.88 Hz, 3H) 1.07 (d, J = 7.79 Hz, 3H) 1.10 (d, J = 7.34 Hz, 3H) 1.14-1.21 (m, 1H) 1.21 (d, J = 5.96 Hz, 3H) 1.24 (s, 3H) 1.28 (d, J = 6.42 Hz, 3H) 1.35 (s, 3H) 1.43 (d, J = 15.13 Hz, 1H) 1.56 (dd, J = 15.13, 5.04 Hz, 1H) 1.61-1.67 (m, 1H) 2.18-2.25 (m, 1H) 2.26-2.29 (m, 9H) 2.36 (d, J = 15.13 Hz, 1H) 2.38-2.45 (m, 1H) 2.47-2.54 (m, 1H) 2.58-2.67 (m, 1H) 2.73-2.86 (m, 3H) 2.88-3.03 (m, 4H) 3.12-3.24 (m, 3H) 3.28 (s, 3H) 3.30 (s, 3H) 3.43-3.50 (m, 1H) 3.58 (d, J = 9.63 Hz, 1H) 3.72-3.75 (m, 1H) 3.75 (s, 3H) 3.94 (t, J = 8.48 Hz, 1H) 3.98-4.05 (m, 1H) 4.06-4.11 (m, 1H) 4.45 (d, J = 7.34 Hz, 1H) 4.88 (d, J = 4.58 Hz, 1H) 5.09-5.14 (m, 1H) 6.23-6.26 (m, 1H) 6.28-6.34 (m, 2H) |
| 60 | | 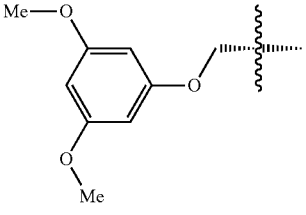 | 869.6 | (600 MHz): 0.93 (d, J = 7.34 Hz, 3H) 1.02 (d, J = 6.88 Hz, 3H) 1.07 (d, J = 7.79 Hz, 3H) 1.10 (d, J = 6.88 Hz, 3H) 1.14-1.21 (m, 1H) 1.21 (d, J = 5.96 Hz, 3H) 1.24 (s, 3H) 1.28 (d, J = 5.98 Hz, 3H) 1.35 (s, 3H) 1.43 (d, J = 14.67 Hz, 1H) 1.56 (dd, J = 15.13, 5.04 Hz, 1H) 1.60-1.67 (m, 1H) 2.18-2.26 (m, 1H) 2.28 (s, 6H) 2.36 (d, J = 14.67 Hz, 1H) 2.38-2.46 (m, 1H) 2.46-2.54 (m, 1H) 2.58-2.66 (m, 1H) 2.75-2.86 (m, 3H) 2.89-3.05 (m, 4H) 3.12-3.25 (m, 3H) 3.28 (s, 3H) 3.30 (s, 3H) 3.43-3.50 (m, 1H) 3.58 (d, J = 9.63 Hz, 1H) 3.71-3.75 (m, 1H) 3.75 (s, 6H) 3.94 (t, J = 8.48 Hz, 1H) 3.98-4.05 (m, 1H) 4.05-4.10 (m, 1H) 4.45 (d, J = 6.88 Hz, 1H) 4.89 (d, J = 4.58 Hz, 1H) 5.09-5.13 (m, 1H) 6.03-6.08 (m, 3H) |
| 61 | | 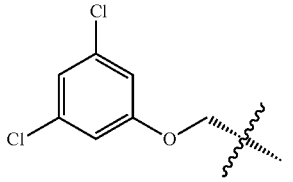 | 877.5 | (600 MHz): 0.93 (d, J = 6.88 Hz, 3H) 1.02 (d, J = 6.88 Hz, 3H) 1.08 (d, J = 7.34 Hz, 3H) 1.11 (d, J = 6.88 Hz, 3H) 1.15-1.20 (m, 1H) 1.21 (d, J = 6.42 Hz, 3H) 1.24 (s, 3H) 1.28 (d, J = 6.42 Hz, 3H) 1.36 (s, 3H) 1.44 (d, J = 15.13 Hz, 1H) 1.56 (dd, J = 15.13, 5.04 Hz, 1H) 1.61-1.68 (m, 1H) 2.19-2.26 (m, 1H) 2.28 (s, 6H) 2.36 (br. s., 3H) 2.57-2.67 (m, 1H) 2.73-2.95 (m, 5H) 2.97-3.03 (m, 2H) 3.12-3.25 (m, 3H) 3.28 (s, 3H) 3.31 (s, 3H) 3.43-3.50 (m, 1H) 3.58 (d, J = 10.09 Hz, 1H) 3.75 (d, J = 7.34 Hz, 1H) 3.92-3.97 (m, 1H) 3.99-4.05 (m, 1H) 4.06-4.11 (m, 1H) 4.45 (d, J = 7.34 Hz, 1H) 4.89 (d, J = 4.58 Hz, 1H) 5.07-5.12 (m, 1H) 6.76-6.78 (m, 2H) 6.92-6.94 (m, 1H) |
| 62 | 15 | 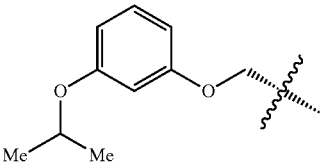 | 867.7 | (600 MHz): 0.93 (d, J = 7.34 Hz, 3H) 1.02 (d, J = 6.88 Hz, 3H) 1.06 (d, J = 7.34 Hz, 3H) 1.09 (d, J = 6.88 Hz, 3H) 1.15-1.26 (m, 1H) 1.21 (d, J = 5.96 Hz, 3H) 1.24 (s, 3H) 1.28 (d, J = 5.96 Hz, 3H) 1.31 (d, J = 6.42 Hz, 6H) 1.35 (s, 3H) 1.42 (d, J = 14.67 Hz, 1H) 1.56 (dd, J = 15.13, 5.04 Hz, 1H) 1.62-1.68 (m, 1H) 2.19-2.26 (m, 1H) 2.29 (s, 6H) 2.35 (d, J = 15.13 Hz, 1H) 2.38-2.54 (m, 2H) 2.59-2.68 (m, 1H) 2.73-2.87 (m, 3H) 2.88-3.04 (m, 4H) 3.11-3.24 (m, 3H) 3.27 (s, 3H) 3.30 (s, 3H) 3.43-3.51 (m, 1H) 3.58 (d, J = 9.63 Hz, 1H) 3.74 (d, 1H) 3.91-3.97 (m, 1H) 3.98-4.05 (m, 1H) 4.07-4.12 (m, 1H) 4.45 (d, J = 7.34 Hz, 1H) 4.47-4.54 (m, 1H) 4.88 (d, J = 4.58 Hz, 1H) 5.09-5.15 (m, 1H) 6.38-6.49 (m, 3H) 7.13 (t, J = 8.25 Hz, 1H) |

TABLE 1-continued

| Example | Reference Example | R | ESI MS (M+H) | ¹H-NMR, CDCl₃, δ (ppm) |
|---|---|---|---|---|
| 63 | 16 | (3-cyclopentyloxyphenoxy-methyl group) | 893.7 | (600 MHz): 0.93 (d, J = 7.34 Hz, 3H) 1.01-1.11 (m, 9H) 1.19-1.29 (m, 10H) 1.35 (s, 3H) 1.41 (d, J = 14.67 Hz, 1H) 1.53-1.93 (m, 11H) 2.17-2.26 (m, 1H) 2.29 (s, 6H) 2.35 (d, J = 15.59 Hz, 1H) 2.40-2.52 (m, 2H) 2.59-2.67 (m, 1H) 2.72-3.03 (m, 7H) 3.12-3.24 (m, 3H) 3.27 (s, 3H) 3.30 (s, 3H) 3.44-3.50 (m, 1H) 3.57 (d, J = 9.63 Hz, 1H) 3.74 (d, J = 7.34 Hz, 1H) 3.91-3.96 (m, 1H) 3.98-4.05 (m, 1H) 4.07-4.12 (m, 1H) 4.69-4.74 (m, 1H) 4.88 (d, J = 4.58 Hz, 1H) 5.10-5.14 (m, 1H) 6.38-6.47 (m, 3H) 7.12 (t, J = 8.25 Hz, 1H) |
| 64 | 17 | (3-cyclohexyloxyphenoxy-methyl group) | 907.7 | (600 MHz): 0.93 (d, J = 7.34 Hz, 3H) 1.09 (d, J = 6.88 Hz, 9H) 1.18-1.39 (m, 14H) 1.77 (d, J = 4.13 Hz, 8H) 1.92-2.01 (m, 2H) 2.18-2.38 (m, 2H) 2.30 (s, 6H) 2.38-2.52 (m, 2H) 2.59-2.67 (m, 1H) 2.73-3.06 (m, 8H) 3.12-3.24 (m, 3H) 3.27 (s, 3H) 3.30 (s, 3H) 3.44-3.51 (m, 1H) 3.57 (d, J = 9.63 Hz, 1H) 3.74 (d, J = 7.34 Hz, 1H) 3.91-3.96 (m, 1H) 3.99-4.05 (m, 1H) 4.07-4.12 (m, 1H) 4.16-4.23 (m, 1H) 4.45 (d, J = 7.34 Hz, 1H) 4.88 (d, J = 4.58 Hz, 1H) 5.09-5.14 (m, 1H) 6.38-6.52 (m, 3H) 7.12 (t, J = 8.25 Hz, 1H) |
| 65 | 18 | (3-isobutyramidophenoxy-methyl group) | 894.7 | (600 MHz): 0.93 (d, J = 7.34 Hz, 3H) 1.01 (d, J = 6.88 Hz, 3H) 1.07 (d, J = 7.79 Hz, 3H) 1.09 (d, J = 7.34 Hz, 3H) 1.14-1.26 (m, 13H) 1.28 (d, J = 6.42 Hz, 3H) 1.35 (s, 3H) 1.43 (d, J = 14.21 Hz, 1H) 1.56 (dd, J = 15.13, 5.04 Hz, 1H) 1.61-1.68 (m, 1H) 2.19-2.26 (m, 1H) 2.28 (s, 6H) 2.35 (d, J = 15.13 Hz, 1H) 2.38-2.45 (m, 1H) 2.45-2.54 (m, 1H) 2.59-2.67 (m, 1H) 2.74-2.85 (m, 3H) 2.88-3.03 (m, 4H) 3.12-3.24 (m, 3H) 3.27 (s, 3H) 3.29 (s, 3H) 3.43-3.50 (m, 1H) 3.57 (d, J = 9.63 Hz, 1H) 3.74 (d, J = 7.79 Hz, 1H) 3.94-4.05 (m, 2H) 4.09-4.14 (m, 1H) 4.45 (d, J = 6.88 Hz, 1H) 4.88 (d, J = 4.58 Hz, 1H) 5.08-5.13 (m, 1H) 6.59-6.64 (m, 1H) 7.05-7.09 (m, 1H) 7.12-7.21 (m, 2H) |
| 66 | 19 | (3-acetamidophenoxy-methyl group) | 866.6 | (600 MHz): 0.92 (d, J = 6.88 Hz, 3H) 1.01 (d, J = 6.42 Hz, 3H) 1.07 (d, J = 7.79 Hz, 3H) 1.09 (d, J = 6.88 Hz, 3H) 1.17-1.26 (m, 1H) 1.22 (d, J = 5.96 Hz, 3H) 1.23 (s, 3H) 1.28 (d, J = 6.42 Hz, 3H) 1.35 (s, 3H) 1.45 (d, J = 14.67 Hz, 1H) 1.56 (dd, J = 15.36, 4.81 Hz, 1H) 1.62-1.68 (m, 1H) 2.15 (s, 3H) 2.19-2.27 (m, 1H) 2.29 (s, 6H) 2.36 (d, J = 15.13 Hz, 1H) 2.38-2.47 (m, 1H) 2.47-2.55 (m, 1H) 2.60-2.68 (m, 1H) 2.73-2.84 (m, 3H) 2.86-3.04 (m, 4H) 3.13-3.24 (m, 3H) 3.28 (s, 3H) 3.30 (s, 3H) 3.43-3.51 (m, 1H) 3.57 (d, J = 10.09 Hz, 1H) 3.74 (d, J = 7.34 Hz, 1H) 3.95-4.06 (m, 2H) 4.08-4.14 (m, 1H) 4.45 (d, J = 6.88 Hz, 1H) 4.88 (d, J = 4.58 Hz, 1H) 5.08-5.13 (m, 1H) 6.59-6.66 (m, 1H) 7.01-7.12 (m, 2H) 7.15-7.21 (m, 1H) |
| 67 | 20 | (3-benzamidophenoxy-methyl group) | 928.6 | (600 MHz): 0.93 (d, J = 7.34 Hz, 3H) 1.02 (d, J = 6.88 Hz, 3H) 1.07-1.13 (m, 6H) 1.13-1.26 (m, 1H) 1.21 (d, J = 5.96 Hz, 3H) 1.23 (s, 3H) 1.28 (d, J = 5.96 Hz, 3H) 1.35 (s, 3H) 1.44 (d, J = 15.13 Hz, 1H) 1.52-1.67 (m, 2H) 2.17-2.30 (m, 1H) 2.25 (s, 6H) 2.32-2.46 (m, 2H) 2.49-2.57 (m, 1H) 2.61-2.72 (m, 1H) 2.75-2.86 (m, 3H) 2.90-3.05 (m, 4H) 3.12-3.25 (m, 3H) 3.28 (s, 3H) 3.29 (s, 3H) 3.42-3.50 (m, 1H) 3.58 (d, J = 10.09 Hz, 1H) 3.74 (d, J = 7.79 Hz, 1H) 3.97-4.06 (m, 2H) 4.12-4.19 (m, 1H) 4.44 (d, J = 7.34 Hz, 1H) 4.88 (d, J = 4.58 Hz, 1H) 5.10-5.15 (m, 1H) 6.65-6.71 (m, 1H) 7.20-7.27 (m, 2H) 7.45-7.57 (m, 3H) 7.79-7.89 (m, 3H) |

TABLE 1-continued

| Example | Reference Example | R | ESI MS (M + H) | $^1$H-NMR, CDCl$_3$, δ (ppm) |
|---|---|---|---|---|
| 68 | 21 | (3-cyclopentanecarboxamido-phenoxymethyl group) | 920.7 | (600 MHz): 0.93 (d, J = 7.34 Hz, 3H) 1.02 (d, J = 6.88 Hz, 3H) 1.05-1.12 (m, 6H) 1.14-1.26 (m, 1H) 1.21 (d, J = 6.42 Hz, 3H) 1.23 (s, 3H) 1.28 (d, J = 5.96 Hz, 3H) 1.35 (s, 3H) 1.43 (d, J = 14.21 Hz, 1H) 1.52-1.68 (m, 4H) 1.73-1.82 (m, 2H) 1.83-1.97 (m, 4H) 2.18-2.27 (m, 1H) 2.28 (s, 6H) 2.35 (d, J = 14.67 Hz, 1H) 2.38-2.45 (m, 1H) 2.46-2.55 (m, 1H) 2.59-2.69 (m, 2H) 2.74-2.86 (m, 3H) 2.87-3.04 (m, 4H) 3.12-3.24 (m, 3H) 3.28 (s, 3H) 3.30 (s, 3H) 3.42-3.51 (m, 1H) 3.58 (d, J = 9.63 Hz, 1H) 3.74 (d, J = 7.79 Hz, 1H) 3.96 (t, J = 8.25 Hz, 1H) 3.99-4.06 (m, 1H) 4.08-4.15 (m, 1H) 4.45 (d, J = 6.88 Hz, 1H) 4.88 (d, J = 4.58 Hz, 1H) 5.08-5.13 (m, 1H) 6.61 (d, J = 7.79 Hz, 1H) 7.05-7.10 (m, 1H) 7.11-7.21 (m, 2H) |
| 69 | | (2,6-dimethylphenoxymethyl group) | 837.6 | (600 MHz): 0.96 (d, J = 6.88 Hz, 3H) 1.06 (d, J = 7.34 Hz, 3H) 1.07 (d, J = 6.42 Hz, 3H) 1.14 (d, J = 6.88 Hz, 3H) 1.16-1.22 (m, 1H) 1.23 (d, J = 5.96 Hz, 3H) 1.25 (s, 3H) 1.30 (d, J = 5.96 Hz, 3H) 1.37 (s, 3H) 1.40 (d, J = 13.30 Hz, 1H) 1.59 (dd, J = 15.13, 5.04 Hz, 1H) 1.63-1.67 (m, 1H) 2.17-2.27 (m, 2H) 2.27 (s, 6H) 2.29 (s, 6H) 2.37 (d, J = 14.67 Hz, 1H) 2.40-2.44 (m, 1H) 2.44-2.50 (m, 1H) 2.64-2.73 (m, 1H) 2.81-2.87 (m, 1H) 2.90 (t, J = 9.40 Hz, 1H) 2.93-2.97 (m, 1H) 2.93-3.09 (m, 4H) 3.13-3.16 (m, 1H) 3.20 (dd, J = 10.55, 7.34 Hz, 1H) 3.26 (d, J = 11.92 Hz, 1H) 3.29 (s, 3H) 3.32 (s, 3H) 3.46-3.52 (m, 1H) 3.60 (d, J = 8.71 Hz, 1H) 3.76 (d, J = 7.34 Hz, 2H) 3.93 (dd, J = 8.94, 7.11 Hz, 1H) 4.01-4.07 (m, 1H) 4.48 (d, J = 7.34 Hz, 1H) 4.92 (d, J = 4.58 Hz, 1H) 5.17 (dd, J = 5.50, 3.67 Hz, 1H) 6.89-6.92 (m, 1H) 7.00 (d, J = 7.79 Hz, 2H) |
| 70 | | (4-(1H-imidazol-1-yl)phenoxymethyl group) | 875.7 | (600 MHz): 0.93 (d, J = 7.34 Hz, 3H) 1.04 (d, J = 6.88 Hz, 3H) 1.09 (d, J = 7.79 Hz, 3H) 1.10 (d, J = 6.88 Hz, 3H) 1.17-1.22 (m, 1H) 1.23 (d, J = 5.96 Hz, 3H) 1.25 (s, 3H) 1.30 (d, J = 5.96 Hz, 3H) 1.37 (s, 3H) 1.46 (d, J = 14.21 Hz, 1H) 1.57 (dd, J = 15.13, 5.04 Hz, 1H) 1.63-1.67 (m, 1H) 2.21-2.23 (m, 1H) 2.22-2.27 (m, 1H) 2.28 (s, 6H) 2.36 (d, J = 15.13 Hz, 1H) 2.39-2.46 (m, 1H) 2.52 (t, J = 7.34 Hz, 1H) 2.67-2.72 (m, 1H) 2.72-2.78 (m, 1H) 2.79-2.88 (m, 2H) 2.90-2.96 (m, 2H) 2.98-3.05 (m, 2H) 3.15-3.22 (m, 2H) 3.25 (d, J = 11.92 Hz, 1H) 3.29 (s, 3H) 3.30 (s, 3H) 3.44-3.51 (m, 1H) 3.59 (d, J = 10.09 Hz, 1H) 3.75 (d, J = 7.34 Hz, 1H) 3.99-4.07 (m, 2H) 4.14-4.20 (m, 1H) 4.46 (d, J = 7.34 Hz, 1H) 4.89 (d, J = 5.04 Hz, 1H) 5.14 (dd, J = 6.42, 4.58 Hz, 1H) 6.97 (d, J = 8.71 Hz, 2H) 7.19 (d, J = 11.46 Hz, 2H) 7.29 (d, J = 8.71 Hz, 2H) 7.75 (s, 1H) |

TABLE 1-continued

| Example | Reference Example | R | ESI MS (M + H) | $^1$H-NMR, CDCl$_3$, δ (ppm) |
|---|---|---|---|---|
| 71 | | 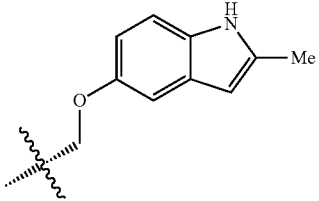 | 862.7 | (600 MHz): 0.94 (d, J = 7.34 Hz, 3H) 1.03 (d, J = 6.88 Hz, 3H) 1.08 (d, J = 7.34 Hz, 3H) 1.10 (d, J = 7.34 Hz, 3H) 1.16-1.21 (m, 1H) 1.22 (d, J = 5.96 Hz, 3H) 1.24 (s, 3H) 1.29 (d, J = 6.42 Hz, 3H) 1.36 (s, 3H) 1.43 (d, J = 14.21 Hz, 1H) 1.57 (dd, J = 15.13, 5.04 Hz, 1H) 1.62-1.67 (m, 1H) 2.22 (d, J = 9.63 Hz, 1H) 2.22-2.26 (m, 1H) 2.29 (s, 6H) 2.36 (d, J = 15.13 Hz, 1H) 2.42 (s, 3H) 2.43-2.47 (m, 1H) 2.52 (t, J = 7.34 Hz, 1H) 2.62-2.71 (m, 1H) 2.77-2.90 (m, 3H) 2.95-3.07 (m, 4H) 3.13-3.17 (m, 1H) 3.18-3.25 (m, 2H) 3.29 (s, 3H) 3.31 (s, 3H) 3.43-3.50 (m, 1H) 3.59 (d, J = 10.55 Hz, 1H) 3.76 (d, J = 7.34 Hz, 1H) 3.96-4.06 (m, 2H) 4.15 (dd, J = 9.17, 7.34 Hz, 1H) 4.47 (d, J = 7.34 Hz, 1H) 4.89 (d, J = 4.13 Hz, 1H) 5.14-5.18 (m, 1H) 6.13 (s, 1H) 6.73 (dd, J = 8.71, 2.29 Hz, 1H) 6.99 (d, J = 2.29 Hz, 1H) 7.15 (d, J = 8.71 Hz, 1H) 7.75 (br. s., 1H) |
| 72 | | 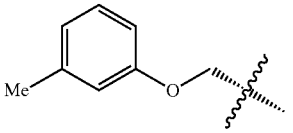 | 823 | (400 MHz): 0.94 (d, J = 7.1 Hz, 3H) 1.03 (d, J = 6.6 Hz, 3H) 1.08 (d, J = 7.8 Hz, 3H) 1.10 (d, J = 7.6 Hz, 3H) 1.19-1.25 (m, 1H) 1.23 (d, J = 6.1 Hz, 3H) 1.25 (s, 3H) 1.30 (d, J = 6.1 Hz, 3H) 1.36 (s, 3H) 1.44 (d, J = 14.9 Hz, 1H) 1.57 (dd, J = 15.1, 4.9 Hz, 1H) 1.62-1.70 (m, 1H) 2.20-2.56 (m, 5H) 2.29 (s, 6H) 2.32 (s, 3H) 2.59-2.87 (m, 4H) 2.89-3.05 (m, 4H) 3.12-3.39 (m, 4H) 3.28 (s, 3H) 3.32 (s, 3H) 3.43-3.53 (m, 1H) 3.59 (d, J = 9.8 Hz, 1H) 3.75 (d, J = 7.6 Hz, 1H) 3.93-4.15 (m, 3H) 4.46 (d, J = 7.3 Hz, 1H) 4.76-4.95 (m, 1H) 4.89 (d, J = 4.4 Hz, 1H) 5.14 (dd, J = 6.3, 4.4 Hz, 1H) 6.66-6.72 (m, 2H) 6.75 (d, J = 7.6 Hz, 1H) 7.15 (t, J = 7.8 Hz, 1H) |
| 73 | | 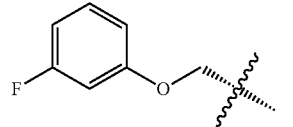 | 827 | (400 MHz): 0.94 (d, J = 7.3 Hz, 3H) 1.03 (d, J = 6.6 Hz, 3H) 1.07 (d, J = 7.3 Hz, 3H) 1.11 (d, J = 7.1 Hz, 3H) 1.16-1.25 (m, 1H) 1.23 (d, J = 6.1 Hz, 3H) 1.25 (s, 3H) 1.29 (d, J = 6.1 Hz, 3H) 1.36 (s, 3H) 1.45 (d, J = 14.9 Hz, 1H) 1.57 (dd, J = 15.1, 4.9 Hz, 1H) 1.61-1.70 (m, 1H) 2.20-2.55 (m, 5H) 2.29 (s, 6H) 2.60-3.06 (m, 8H) 3.13-3.43 (m, 4H) 3.29 (s, 3H) 3.31 (s, 3H) 3.43-3.53 (m, 1H) 3.59 (d, J = 9.5 Hz, 1H) 3.75 (d, J = 7.6 Hz, 1H) 3.88-4.15 (m, 3H) 4.46 (d, J = 7.3 Hz, 1H) 4.78-4.95 (m, 1H) 4.89 (d, J = 4.6 Hz, 1H) 5.13 (dd, J = 6.3, 4.4 Hz, 1H) 6.56-6.70 (m, 3H) 7.21 (dd, J = 15.1, 8.3 Hz, 1H) |
| 74 | | 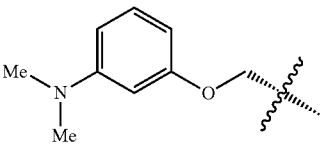 | 852 | (300 MHz): 0.94 (d, J = 7.1 Hz, 3H) 1.03 (d, J = 6.6 Hz, 3H) 1.07 (d, J = 7.7 Hz, 3H) 1.10 (d, J = 8.8 Hz, 3H) 1.16-1.25 (m, 1H) 1.23 (d, J = 6.0 Hz, 3H) 1.25 (s, 3H) 1.29 (d, J = 6.3 Hz, 3H) 1.36 (s, 3H) 1.43 (d, J = 15.1 Hz, 1H) 1.57 (dd, J = 15.8, 4.9 Hz, 1H) 1.61-1.70 (m, 1H) 2.17-2.58 (m, 5H) 2.30 (s, 6H) 2.58-3.07 (m, 8H) 2.92 (s, 6H) 3.10-3.34 (m, 4H) 3.28 (s, 3H) 3.31 (s, 3H) 3.42-3.54 (m, 1H) 3.58 (d, J = 9.6 Hz, 1H) 3.75 (d, J = 7.4 Hz, 1H) 3.93-4.16 (m, 3H) 4.46 (d, J = 6.9 Hz, 1H) 4.75-4.93 (m, 1H) 4.89 (d, J = 4.4 Hz, 1H) 5.10-5.16 (m, 1H) 6.23-6.30 (m, 2H) 6.32-6.38 (m, 1H) 7.21 (t, J = 8.0 Hz, 1H) |

TABLE 1-continued

| Example | Reference Example | R | ESI MS (M + H) | ¹H-NMR, CDCl₃, δ (ppm) |
|---|---|---|---|---|
| 75 | | 3-ethylphenoxy group | 837 | (400 MHz): 0.94 (d, J = 7.3 Hz, 3H) 1.03 (d, J = 6.6 Hz, 3H) 1.07 (d, J = 7.3 Hz, 3H) 1.10 (d, J = 7.1 Hz, 3H) 1.19-1.27 (m, 7H) 1.27 (s, 3H) 1.29 (d, J = 6.1 Hz, 3H) 1.36 (s, 3H) 1.43 (d, J = 14.7 Hz, 1H) 1.57 (dd, J = 15.1, 4.9 Hz, 1H) 1.63-1.70 (m, 1H) 2.19-2.52 (m, 7H) 2.30 (s, 6H) 2.59-2.70 (m, 1H) 2.62 (q, J = 7.6 Hz, 2H) 2.73-2.89 (m, 3H) 2.90-3.07 (m, 4H) 3.14-3.25 (m, 3H) 3.29 (s, 3H) 3.31 (s, 3H) 3.44-3.53 (m, 1H) 3.59 (d, J = 9.8 Hz, 1H) 3.75 (d, J = 7.6 Hz, 1H) 3.94-4.07 (m, 2H) 4.12 (dd, J = 8.8, 7.3 Hz, 1H) 4.46 (d, J = 7.3 Hz, 1H) 4.89 (d, J = 4.4 Hz, 1H) 5.14 (dd, J = 6.4, 4.4 Hz, 1H) 6.68-6.74 (m, 2H) 6.78 (d, J = 7.8 Hz, 1H) 7.18 (t, 7.8 Hz, 1H) |
| 76 | | 4-chlorophenoxy group | 843 | (400 MHz): 0.93 (d, J = 7.1 Hz, 3H) 1.03 (d, J = 6.6 Hz, 3H) 1.07 (d, J = 7.6 Hz, 3H) 1.10 (d, J = 8.6 Hz, 3H) 1.17-1.25 (m, 1H) 1.23 (d, J = 5.9 Hz, 3H) 1.25 (s, 3H) 1.30 (d, J = 6.4 Hz, 3H) 1.36 (s, 3H) 1.45 (d, J = 14.9 Hz, 1H) 1.57 (dd, J = 15.1, 5.1 Hz, 1H) 1.63-1.71 (m, 1H) 2.18-2.55 (m, 5H) 2.30 (s, 6H) 2.60-3.06 (m, 7H) 3.14-3.25 (m, 3H) 3.29 (s, 3H) 3.32 (s, 3H) 3.43-3.53 (m, 1H) 3.58 (d, J = 9.8 Hz, 1H) 3.75 (d, J = 7.6 Hz, 1H) 3.92-4.12 (m, 3H) 4.46 (d, J = 7.1 Hz, 1H) 4.89 (d, J = 4.6 Hz, 1H) 6.78-6.84 (m, 2H) 7.20-7.23 (m, 2H) |
| 77 | | 4-chloro-2,3-dimethylphenoxy group | 871 | (400 MHz): 0.94 (d, J = 7.1 Hz, 3H) 1.02-1.09 (m, 9H) 1.16-1.25 (m, 1H) 1.23 (d, J = 6.1 Hz, 3H) 1.25 (s, 3H) 1.29 (d, J = 6.1 Hz, 3H) 1.36 (s, 3H) 1.44 (d, J = 14.6 Hz, 1H) 1.57 (dd, J = 15.1, 4.9 Hz, 1H) 1.63-1.70 (m, 1H) 2.12 (s, 3H) 2.20-2.54 (m, 5H) 2.30 (s, 3H) 2.31 (s, 6H) 2.64-2.75 (m, 2H) 2.79-3.05 (m, 6H) 3.14-3.26 (m, 3H) 3.28 (s, 3H) 3.31 (s, 3H) 3.44-3.53 (m, 1H) 3.58 (d, J = 9.7 Hz, 1H) 3.74 (d, J = 7.3 Hz, 1H) 3.94-4.12 (m, 3H) 4.46 (d, J = 7.1 Hz, 1H) 4.88 (d, J = 4.4 Hz, 1H) 5.13 (dd, J = 6.3, 4.4 Hz, 1H) 6.67 (d, J = 8.8 Hz, 1H) 7.14 (d, J = 8.8 Hz, 1H) |
| 78 | | 3-tert-butylphenoxy group | 865 | (400 MHz): 0.95 (d, J = 7.3 Hz, 3H) 1.04 (d, J = 7.3 Hz, 3H) 1.06 (d, J = 8.1 Hz, 3H) 1.10 (d, J = 7.1 Hz, 3H) 1.16-1.25 (m, 1H) 1.23 (d, J = 6.1 Hz, 3H) 1.24 (s, 3H) 1.29 (d, J = 7.3 Hz, 3H) 1.30 (s, 9H) 1.36 (s, 3H) 1.43 (d, J = 14.9 Hz, 1H) 1.57 (dd, J = 15.1, 4.9 Hz, 1H) 1.63-1.72 (m, 1H) 2.18-2.57 (m, 7H) 2.30 (s, 6H) 2.60-2.72 (m, 1H) 2.73-2.89 (m, 3H) 2.91-3.07 (m, 4H) 3.14-3.26 (m, 3H) 3.29 (s, 3H) 3.31 (s, 3H) 3.43-3.53 (m, 1H) 3.58 (d, J = 9.8 Hz, 1H) 3.75 (d, J = 7.3 Hz, 1H) 3.95-4.07 (m, 2H) 4.13 (dd, J = 8.8, 7.3 Hz, 1H) 4.46 (d, J = 7.1 Hz, 1H) 4.89 (d, J = 4.6 Hz, 1H) 5.15 (dd, J = 6.1, 4.2 Hz, 1H) 6.70 (dd, J = 8.1, 2.0 Hz, 1H) 6.91 (t, J = 2.0 Hz, 1H) 6.95-7.00 (m, 1H) 7.21 (t, J = 7.8 Hz, 1H) |

TABLE 1-continued

| Example | Reference Example | R | ESI MS (M + H) | ¹H-NMR, CDCl₃, δ (ppm) |
|---|---|---|---|---|
| 79 | | (4-benzyloxy-3-oxy-biphenyl group) | 991.8 | (600 MHz): 0.94 (d, J = 7.34 Hz, 3H) 1.02 (d, J = 6.88 Hz, 3H) 1.06 (d, J = 7.34 Hz, 3H) 1.09 (d, J = 7.34 Hz, 3H) 1.15-1.26 (m, 1H) 1.21 (d, J = 6.42 Hz, 3H) 1.23 (s, 3H) 1.28 (d, J = 5.96 Hz, 3H) 1.35 (s, 3H) 1.43 (d, J = 15.13 Hz, 1H) 1.51-1.67 (m, 2H) 2.16-2.25 (m, 1H) 2.27 (s, 6H) 2.34 (d, J = 14.67 Hz, 1H) 2.37-2.44 (m, 1H) 2.46-2.55 (m, 1H) 2.67-2.89 (m, 4H) 2.94-3.04 (m, 4H) 3.10-3.27 (m, 3H) 3.28 (s, 3H) 3.30 (s, 3H) 3.42-3.51 (m, 1H) 3.57 (d, J = 9.63 Hz, 1H) 3.74 (d, J = 7.34 Hz, 1H) 3.98-4.07 (m, 1H) 4.09-4.15 (m, 1H) 4.24-4.29 (m, 1H) 4.45 (d, J = 7.34 Hz, 1H) 4.88 (d, J = 7.34 Hz, 1H) 4.88 (d, J = 504 Hz, 1H) 5.10-5.16 (m, 1H) 5.13 (s, 2H) 6.95-7.00 (m, 1H) 7.07-7.11 (m, 1H) 7.14-7.17 (m, 1H) 7.27-7.33 (m, 2H) 7.35-7.47 (m, 6H) 7.51-7.57 (m, 2H) |
| 80 | | (3-(diethylamino)phenoxy group) | 880.8 | (600 MHz): 0.93 (d, J = 7.34 Hz, 3H) 1.01-1.16 (m, 15H) 1.19-1.25 (m, 6H) 1.27-1.30 (m, 3H) 1.35 (s, 3H) 1.40-1.44 (m, 1H) 1.47-1.59 (m, 2H) 1.60-1.67 (m, 1H) 2.17-2.53 (m, 4H) 2.28 (s, 6H) 2.59-2.67 (m, 1H) 2.75-2.86 (m, 3H) 2.89-3.04 (m, 4H) 3.12-3.24 (m, 3H) 3.28 (s, 3H) 3.28-3.34 (m, 4H) 3.30 (s, 3H) 3.43-3.50 (m, 1H) 3.56-3.60 (m, 1H) 3.73-3.76 (m, 1H) 3.93-3.98 (m, 1H) 3.99-4.06 (m, 1H) 4.08-4.13 (m, 1H) 4.46 (d, J = 7.34 Hz, 1H) 4.87-4.91 (m, 1H) 5.11-5.15 (m, 1H) 6.15-6.21 (m, 2H) 6.26-6.31 (m, 1H) 7.05-7.11 (m, 1H) |
| 81 | | (naphthalen-2-yloxy group) | 859.3 | (600 MHz): 0.92 (d, J = 7.34 Hz, 3H) 1.00-1.13 (m, 9H) 1.17-1.30 (m, 10H) 1.36 (s, 3H) 1.41-1.47 (m, 1H) 1.52-1.58 (m, 1H) 1.59-1.70 (m, 1H) 2.18-2.37 (m, 2H) 2.29 (s, 6H) 2.38-2.49 (m, 1H) 2.50-2.59 (m, 1H) 2.69-2.89 (m, 4H) 2.93-3.06 (m, 4H) 3.14-3.30 (m, 3H) 3.28 (s, 3H) 3.28 (s, 3H) 3.44-3.51 (m, 1H) 3.56-3.61 (m, 1H) 3.75 (d, J = 7.34 Hz, 1H) 3.98-4.05 (m, 1H) 4.08-4.13 (m, 1H) 4.21-4.27 (m, 1H) 4.46 (d, J = 7.34 Hz, 1H) 4.88 (d, J = 4.58 Hz, 1H) 5.14-5.20 (m, 1H) 7.08-7.15 (m, 2H) 7.29-7.34 (m, 1H) 7.38-7.44 (m, 1H) 7.68-7.78 (m, 3H) |
| 82 | | (2-bromophenoxy group) | 887.5 | (600 MHz): 0.94 (d, J = 7.34 Hz, 3H) 1.02 (d, J = 7.34 Hz, 3H) 1.04 (d, J = 6.88 Hz, 3H) 1.10 (d, J = 7.34 Hz, 3H) 1.16-1.20 (m, 1H) 1.22 (d, J = 5.96 Hz, 3H) 1.24 (s, 3H) 1.29 (d, J = 6.42 Hz, 3H) 1.36 (s, 3H) 1.44 (d, J = 14.21 Hz, 1H) 1.57 (dd, J = 15.13, 5.04 Hz, 1H) 1.63-1.67 (m, 1H) 2.19-2.23 (m, 1H) 2.22-2.26 (m, 1H) 2.28 (s, 6H) 2.36 (d, J = 15.13 Hz, 1H) 2.39-2.46 (m, 1H) 2.49 (t, J = 7.34 Hz, 1H) 2.63-2.70 (m, 1H) 2.73-2.80 (m, 1H) 2.80-2.85 (m, 2H) 2.90-2.97 (m, 2H) 2.99-3.03 (m, 2H) 3.13-3.22 (m, 2H) 3.25 (d, J = 11.46 Hz, 1H) 3.28 (s, 3H) 3.30 (s, 3H) 3.44-3.50 (m, 1H) 3.57 (d, J = 9.17 Hz, 1H) 3.74 (d, J = 7.79 Hz, 1H) 3.99-4.05 (m, 1H) 4.06-4.11 (m, 1H) 4.17 (t, J = 8.25 Hz, 1H) 4.44 (d, J = 7.34 Hz, 1H) 4.89 (d, J = 4.58 Hz, 1H) 5.16 (dd, J = 6.65, 4.36 Hz, 1H) 6.82 (td, J = 7.57, 1.38 Hz, 1H) 6.91 (dd, J = 8.25, 1.38 Hz, 1H) 7.24 (d, J = 8.25 Hz, 1H) 7.51 (dd, J = 7.79, 1.38 Hz, 1H) |

TABLE 1-continued

| Example | Reference Example | R | ESI MS (M + H) | $^1$H-NMR, CDCl$_3$, δ (ppm) |
|---|---|---|---|---|
| 83 | | 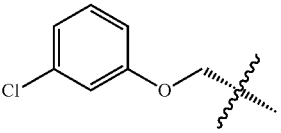 | 843 | (400 MHz): 0.94 (d, J = 7.1 Hz, 3H) 1.03 (d, J = 6.6 Hz, 3H) 1.08 (d, J = 7.6 Hz, 3H) 1.11 (d, J = 7.1 Hz, 3H) 1.16-1.25 (m, 1H) 1.23 (d, J = 6.1 Hz, 3H) 1.25 (s, 3H) 1.29 (d, J = 6.1 Hz, 3H) 1.37 (s, 3H) 1.45 (d, J = 14.9 Hz, 1H) 1.57 (dd, J = 15.1, 4.9 Hz, 1H) 1.62-1.70 (m, 1H) 2.21-2.56 (m, 5H) 2.29 (s, 6H) 2.60-3.06 (m, 8H) 3.12-3.43 (m, 4H) 3.29 (s, 3H) 3.32 (s, 3H) 3.43-3.52 (m, 1H) 3.59 (d, J = 9.7 Hz, 1H) 3.75 (d, J = 7.6 Hz, 1H) 3.89-4.14 (m, 3H) 4.46 (d, J = 7.1 Hz, 1H) 4.80-4.92 (m, 1H) 4.89 (d, J = 4.4 Hz, 1H) 5.12 (dd, J = 6.3, 4.4 Hz, 1H) 6.77 (dd, J = 7.3, 1.7 Hz, 1H) 6.86-6.94 (m, 2H) 7.18 (t, 8.0 Hz, 1H) |
| 84 | | 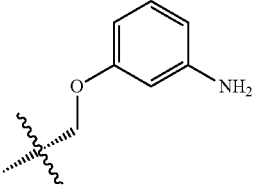 | 824.4 | (600 MHz): 0.91 (d, J = 7.34 Hz, 3H) 1.01 (d, J = 6.88 Hz, 3H) 1.07-1.14 (m, 6H) 1.16-1.26 (m, 1H) 1.22 (d, J = 5.96 Hz, 3H) 1.24 (s, 3H) 1.29 (d, J = 5.96 Hz, 3H) 1.36 (s, 3H) 1.44 (d, J = 15.13 Hz, 1H) 1.53-1.68 (m, 2H) 2.17-2.31 (m, 1H) 2.28 (s, 6H) 2.33-2.46 (m, 2H) 2.49-2.57 (m, 1H) 2.58-2.66 (m, 1H) 2.72-2.85 (m, 3H) 2.86-3.03 (m, 4H) 3.11-3.23 (m, 3H) 3.28 (s, 3H) 3.31 (s, 3H) 3.43-3.50 (m, 1H) 3.58 (d, J = 10.09 Hz, 1H) 3.75 (d, J = 7.34 Hz, 1H) 3.96 (t, J = 8.48 Hz, 1H) 3.99-4.10 (m, 2H) 4.45 (d, J = 7.34 Hz, 1H) 4.88 (d, J = 4.58 Hz, 1H) 5.07-5.14 (m, 1H) 6.20-6.31 (m, 3H) 7.02 (t, J = 8.02 Hz, 1H) |
| 85 | | 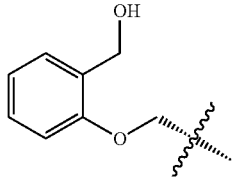 | 839.4 | (600 MHz): 0.94 (d, J = 7.34 Hz, 3H) 1.00-1.05 (m, 6H) 1.07 (d, J = 7.34 Hz, 3H) 1.16-1.26 (m, 1H) 1.22 (d, J = 5.96 Hz, 3H) 1.23 (s, 3H) 1.28 (d, J = 5.96 Hz, 3H) 1.36 (s, 3H) 1.45 (d, J = 15.13 Hz, 1H) 1.51-1.67 (m, 2H) 2.18-2.31 (m, 1H) 2.28 (s, 6H) 2.34 (d, J = 15.59 Hz, 1H) 2.37-2.44 (m, 1H) 2.46-2.54 (m, 1H) 2.67-2.76 (m, 2H) 2.79-2.86 (m, 2H) 2.88-3.04 (m, 4H) 3.13-3.26 (m, 3H) 3.28 (s, 3H) 3.29 (s, 3H) 3.42-3.50 (m, 1H) 3.58 (d, J = 10.55 Hz, 1H) 3.74 (d, J = 7.79 Hz, 1H) 3.97-4.08 (m, 2H) 4.16-4.22 (m, 1H) 4.44 (d, J = 7.34 Hz, 1H) 4.58-4.69 (m, 2H) 4.86 (d, J = 4.58 Hz, 1H) 5.13-5.18 (m, 1H) 6.88 (d, J = 7.79 Hz, 1H) 6.93 (t, J = 7.11 Hz, 1H) 7.22-7.29 (m, 2H) |
| 86 | | 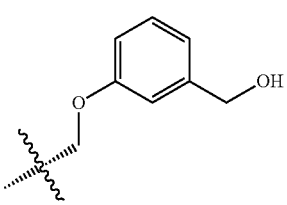 | 839.3 | (600 MHz): 0.89 (d, J = 6.88 Hz, 3H) 1.01 (d, J = 6.88 Hz, 3H) 1.08 (d, J = 7.79 Hz, 3H) 1.11 (d, J = 6.88 Hz, 3H) 1.15-1.26 (m, 1H) 1.22 (d, J = 5.96 Hz, 3H) 1.24 (s, 3H) 1.29 (d, J = 5.96 Hz, 3H) 1.35 (s, 3H) 1.48 (d, J = 15.13 Hz, 1H) 1.54-1.69 (m, 2H) 2.17-2.31 (m, 1H) 2.28 (s, 6H) 2.33-2.45 (m, 2H) 2.50-2.58 (m, 1H) 2.62-2.71 (m, 1H) 2.71-2.84 (m, 3H) 2.87-3.04 (m, 4H) 3.13-3.22 (m, 3H) 3.28 (s, 3H) 3.30 (s, 3H) 3.43-3.50 (m, 1H) 3.57 (d, J = 9.63 Hz, 1H) 3.74 (d, J = 7.79 Hz, 1H) 3.97-4.16 (m, 3H) 4.44 (d, J = 6.88 Hz, 1H) 4.66 (s, 2H) 4.88 (d, J = 4.58 Hz, 1H) 5.07-5.13 (m, 1H) 6.77-6.82 (m, 1H) 6.87 (d, J = 7.79 Hz, 1H) 7.01 (s, 1H) 7.22 (t, J = 7.79 Hz, 1H) |

TABLE 1-continued

| Example | Reference Example | R | ESI MS (M + H) | ¹H-NMR, CDCl₃, δ (ppm) |
|---|---|---|---|---|
| 87 | | 2-hydroxyphenoxymethyl | 825.3 | (600 MHz): 0.93 (d, J = 7.34 Hz, 3H) 1.00-1.05 (m, 6H) 1.10 (d, J = 6.88 Hz, 3H) 1.16-1.25 (m, 1H) 1.22 (d, J = 5.96 Hz, 3H) 1.23 (s, 3H) 1.28 (d, J = 5.96 Hz, 3H) 1.36 (s, 3H) 1.45 (d, J = 14.21 Hz, 1H) 1.55 (dd, J = 15.13, 5.04 Hz, 1H) 1.61-1.67 (m, 1H) 2.18-2.26 (m, 1H) 2.28 (s, 6H) 2.36 (d, J = 14.67 Hz, 1H) 2.39-2.45 (m, 1H) 2.45-2.51 (m, 1H) 2.65-2.94 (m, 6H) 2.95-3.05 (m, 2H) 3.14-3.26 (m, 3H) 3.28 (s, 3H) 3.30 (s, 3H) 3.43-3.51 (m, 1H) 3.60 (d, J = 8.71 Hz, 1H) 3.74 (d, J = 7.79 Hz, 1H) 3.97-4.05 (m, 1H) 4.07-4.12 (m, 1H) 4.14-4.20 (m, 1H) 4.44 (d, J = 6.88 Hz, 1H) 4.86 (d, J = 4.59 Hz, 1H) 5.15-5.20 (m, 1H) 6.78-6.93 (m, 4H) |
| 88 | | 3-hydroxyphenoxymethyl | 825.4 | (600 MHz): 0.79 (d, J = 6.88 Hz, 3H) 0.99 (d, J = 6.42 Hz, 3H) 1.12 (d, J = 6.88 Hz, 3H) 1.17-1.27 (m, 1H) 1.20 (d, J = 7.34 Hz, 3H) 1.23 (d, J = 5.96 Hz, 3H) 1.24 (s, 3H) 1.30 (s, 3H) 1.36 (s, 3H) 1.50 (d, J = 15.13 Hz, 1H) 1.56 (dd, J = 15.13, 5.04 Hz, 1H) 1.64-1.70 (m, 1H) 2.19-2.26 (m, 1H) 2.29 (s, 6H) 2.38 (d, J = 15.13 Hz, 1H) 2.41-2.48 (m, 1H) 2.60-2.69 (m, 3H) 2.76-2.90 (m, 3H) 2.93-3.03 (m, 3H) 3.13 (d, J = 11.92 Hz, 1H) 3.14-3.18 (m, 1H) 3.20-3.26 (m, 1H) 3.30 (s, 3H) 3.31 (s, 3H) 3.43-3.51 (m, 1H) 3.58 (d, J = 10.09 Hz, 1H) 3.77 (d, J = 7.79 Hz, 1H) 3.97-4.05 (m, 1H) 4.06-4.14 (m, 2H) 4.44 (d, J = 7.34 Hz, 1H) 4.87 (d, J = 4.58 Hz, 1H) 5.03-5.08 (m, 1H) 6.39-6.47 (m, 3H) 7.06-7.11 (m, 1H) |
| 89 | | 4-hydroxyphenoxymethyl | 825.5 | (600 MHz): 0.92 (d, J = 6.88 Hz, 3H) 1.02 (d, J = 6.88 Hz, 3H) 1.06 (d, J = 7.34 Hz, 3H) 1.09 (d, J = 6.88 Hz, 3H) 1.15-1.26 (m, 1H) 1.22 (d, J = 6.42 Hz, 3H) 1.24 (s, 3H) 1.28 (d, J = 6.42 Hz, 3H) 1.35 (s, 3H) 1.42 (d, J = 14.67 Hz, 1H) 1.56 (dd, J = 15.13, 5.04 Hz, 1H) 1.62-1.68 (m, 1H) 2.16-2.26 (m, 1H) 2.29 (s, 6H) 2.36 (d, J = 15.13 Hz, 1H) 2.39-2.55 (m, 2H) 2.58-2.66 (m, 1H) 2.72-2.85 (m, 3H) 2.87-3.04 (m, 4H) 3.12-3.24 (m, 3H) 3.28 (s, 3H) 3.30 (s, 3H) 3.43-3.51 (m, 1H) 3.58 (d, J = 9.63 Hz, 1H) 3.74 (d, J = 7.34 Hz, 1H) 3.92 (d, J = 8.25 Hz, 1H) 3.98-4.08 (m, 2H) 4.45 (d, J = 7.34 Hz, 1H) 4.88 (d, J = 4.58 Hz, 1H) 5.08-5.13 (m, 1H) 6.75 (d, J = 4.58 Hz, 4H) |
| 90 | | naphthalen-2-yloxymethyl (1-hydroxy) | 875.4 | (600 MHz): 0.94 (d, J = 7.34 Hz, 3H) 1.00 (d, J = 7.34 Hz, 3H) 1.03 (d, J = 6.88 Hz, 3H) 1.06 (d, J = 6.88 Hz, 3H) 1.14-1.31 (m, 1H) 1.21 (d, J = 6.42 Hz, 3H) 1.22 (s, 3H) 1.27 (d, J = 6.42 Hz, 3H) 1.35 (s, 3H) 1.45 (d, J = 14.21 Hz, 1H) 1.53 (dd, J = 15.13, 4.58 Hz, 1H) 1.60-1.69 (m, 1H) 2.16-2.50 (m, 3H) 2.28 (s, 6H) 2.60-3.05 (m, 9H) 3.15-3.33 (m, 3H) 3.25 (s, 3H) 3.28 (s, 3H) 3.42-3.51 (m, 1H) 3.60 (d, J = 9.17 Hz, 1H) 3.74 (d, J = 7.34 Hz, 1H) 3.93-4.07 (m, 1H) 4.19-4.30 (m, 2H) 4.43 (d, J = 7.34 Hz, 1H) 4.83 (d, J = 4.58 Hz, 1H) 5.20-5.25 (m, 1H) 7.19-7.45 (m, 4H) 7.72 (d, J = 8.25 Hz, 1H) 8.13 (d, J = 8.71 Hz, 1H) |

TABLE 1-continued

| Example | Reference Example | R | ESI MS (M + H) | $^1$H-NMR, CDCl$_3$, δ (ppm) |
|---|---|---|---|---|
| 91 | | (2-hydroxymethyl-3-naphthyloxymethyl group) | 889.4 | (600 MHz): 0.94 (d, J = 6.88 Hz, 3H) 1.01-1.08 (m, 9H) 1.17-1.26 (m, 7H) 1.28 (d, J = 6.42 Hz, 3H) 1.36 (s, 3H) 1.47 (d, J = 14.67 Hz, 1H) 1.54 (dd, J = 15.13, 5.04 Hz, 1H) 1.57-1.71 (m, 1H) 2.15-2.59 (m, 4H) 2.29 (s, 6H) 2.68-2.90 (m, 4H) 2.93-3.08 (m, 3H) 3.14-3.24 (m, 3H) 3.26 (s, 3H) 3.29 (s, 3H) 3.42-3.50 (m, 1H) 3.59 (d, J = 9.63 Hz, 1H) 3.75 (d, J = 7.34 Hz, 1H) 3.97-4.04 (m, 1H) 4.15-4.25 (m, 2H) 4.28 (d, J = 8.25 Hz, 1H) 4.44 (d, J = 6.88 Hz, 1H) 4.79 (s, 2H) 4.85 (d, J = 4.58 Hz, 1H) 5.15-5.23 (m, 1H) 7.14 (s, 1H) 7.30-7.36 (m, 1H) 7.38-7.44 (m, 1H) 7.71-7.78 (m, 3H) |
| 92 | | (4-hydroxy-3-biphenyloxymethyl group) | 901.6 | (600 MHz): 0.94 (d, J = 6.88 Hz, 3H) 1.03 (d, J = 6.88 Hz, 3H) 1.07-1.12 (m, 6H) 1.16-1.21 (m, 1H) 1.22 (d, J = 5.96 Hz, 3H) 1.24 (s, 3H) 1.28 (d, J = 6.42 Hz, 3H) 1.36 (s, 3H) 1.45 (d, J = 14.21 Hz, 1H) 1.52-1.68 (m, 2H) 2.17-2.23 (m, 1H) 2.27 (s, 6H) 2.35 (d, J = 15.13 Hz, 1H) 2.38-2.45 (m, 1H) 2.47-2.55 (m, 1H) 2.68-2.87 (m, 4H) 2.89-3.06 (m, 4H) 3.14-3.28 (m, 3H) 3.29 (s, 3H) 3.29 (s, 3H) 3.43-3.51 (m, 1H) 3.61 (d, J = 9.63 Hz, 1H) 3.75 (d, J = 7.34 Hz, 1H) 3.99-4.05 (m, 1H) 4.17 (t, J = 8.48 Hz, 1H) 4.21-4.26 (m, 1H) 4.45 (d, J = 7.34 Hz, 1H) 4.86 (d, J = 4.58 Hz, 1H) 5.17-5.22 (m, 1H) 6.97 (d, J = 8.71 Hz, 1H) 7.07-7.12 (m, 2H) 7.28 (t, J = 7.34 Hz, 1H) 7.39 (t, J = 7.79 Hz, 2H) 7.51-7.55 (m, 2H) |
| 93 | | (3-(pyridin-2-yl)phenyloxymethyl group) | 886.4 | (600 MHz): 0.95 (d, J = 7.34 Hz, 3H) 1.04 (d, J = 6.88 Hz, 3H) 1.08 (d, J = 7.34 Hz, 3H) 1.09 (d, J = 7.34 Hz, 3H) 1.16-1.21 (m, 1H) 1.22 (d, J = 5.96 Hz, 3H) 1.24 (s, 3H) 1.29 (d, J = 5.96 Hz, 3H) 1.37 (s, 3H) 1.44 (d, J = 14.21 Hz, 1H) 1.56 (dd, J = 15.13, 5.04 Hz, 1H) 1.63-1.67 (m, 1H) 2.21-2.27 (m, 2H) 2.29 (s, 6H) 2.35 (d, J = 14.67 Hz, 1H) 2.38-2.54 (m, 2H) 2.66-2.72 (m, 1H) 2.78-2.89 (m, 3H) 2.95-3.06 (m, 4H) 3.15-3.18 (m, 1H) 3.20 (dd, J = 10.55, 7.34 Hz, 1H) 3.25 (d, J = 11.46 Hz, 1H) 3.29 (s, 3H) 3.30 (s, 3H) 3.45-3.51 (m, 1H) 3.59 (d, J = 10.09 Hz, 1H) 3.76 (d, J = 7.34 Hz, 1H) 4.00-4.06 (m, 1H) 4.08 (dd, J = 9.17, 7.79 Hz, 1H) 4.23 (dd, J = 8.94, 7.57 Hz, 1H) 4.46 (d, J = 6.88 Hz, 1H) 4.89 (d, J = 4.58 Hz, 1H) 5.16 (dd, J = 6.19, 4.36 Hz, 1H) 6.94 (ddd, J = 8.14, 2.64, 1.15 Hz, 1H) 7.22 (ddd, J = 6.88, 5.04, 1.83 Hz, 1H) 7.37 (t, J = 8.25 Hz, 1H) 7.54-7.56 (m, 2H) 7.70-7.76 (m, 2H) 8.67-8.69 (m, 1H) |

TABLE 1-continued

| Example | Reference Example | R | ESI MS (M + H) | ¹H-NMR, CDCl₃, δ (ppm) |
|---|---|---|---|---|
| 94 | | 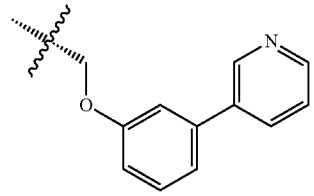 | 886.4 | (600 MHz): 0.92 (d, J = 6.88 Hz, 3H) 1.04 (d, J = 6.88 Hz, 3H) 1.10 (d, J = 7.79 Hz, 6H) 1.16-1.22 (m, 1H) 1.22 (d, J = 5.96 Hz, 3H) 1.25 (s, 3H) 1.29 (d, J = 5.96 Hz, 3H) 1.37 (s, 3H) 1.45 (d, J = 14.67 Hz, 1H) 1.55-1.70 (m, 2H) 2.20-2.27 (m, 2H) 2.29-2.31 (m, 6H) 2.34-2.49 (m, 2H) 2.50-2.56 (m, 1H) 2.66-2.74 (m, 1H) 2.75-2.87 (m, 3H) 2.93-3.07 (m, 4H) 3.14-3.28 (m, 3H) 3.29 (s, 3H) 3.31 (s, 3H) 3.45-3.51 (m, 1H) 3.59 (dd, J = 9.63 Hz, 1H) 3.76 (d, J = 7.34 Hz, 1H) 4.00-4.06 (m, 1H) 4.08 (t, J = 8.71 Hz, 1H) 4.20 (dd, J = 8.94, 7.11 Hz, 1H) 4.46 (d, J = 7.34 Hz, 1H) 4.89 (d, J = 5.04 Hz, 1H) 5.15 (dd, J = 6.42, 4.58 Hz, 1H) 6.93-6.95 (m, 1H) 7.09-7.11 (m, 1H) 7.15-7.18 (m, 1H) 7.34-7.37 (m, 1H) 7.38 (t, J = 8.02 Hz, 1H) 7.88 (ddd, J = 7.57, 2.29, 2.06 Hz, 1H) 8.58 (dd, J = 4.81, 1.60 Hz, 1H) 8.84 (d, J = 1.83 Hz, 1H) |
| 95 | | 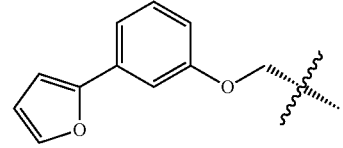 | 875.4 | (600 MHz): 0.94 (d, J = 7.34 Hz, 3H) 1.04 (d, J = 6.42 Hz, 3H) 1.09 (d, J = 7.34 Hz, 3H) 1.09 (d, J = 7.34 Hz, 3H) 1.16-1.21 (m, 1H) 1.22 (d, J = 5.96 Hz, 3H) 1.24 (s, 3H) 1.29 (d, J = 5.96 Hz, 3H) 1.37 (s, 3H) 1.45 (d, J = 14.67 Hz, 1H) 1.54-1.67 (m, 2H) 2.20-2.27 (m, 2H) 2.29 (s, 6H) 2.33-2.48 (m, 2H) 2.50-2.56 (m, 1H) 2.65-2.71 (m, 1H) 2.77-2.87 (m, 3H) 2.93-3.03 (m, 4H) 3.15-3.18 (m, 1H) 3.20 (dd, J = 10.32, 7.11 Hz, 1H) 3.25 (d, J = 11.92 Hz, 1H) 3.29 (s, 3H) 3.30 (s, 3H) 3.45-3.50 (m, 1H) 3.59 (d, J = 9.63 Hz, 1H) 3.76 (d, J = 7.34 Hz, 1H) 4.01-4.06 (m, 2H) 4.17 (dd, J = 9.17, 7.34 Hz, 1H) 4.46 (d, J = 7.34 Hz, 1H) 4.89 (d, J = 4.58 Hz, 1H) 5.15 (dd, J = 6.42, 4.58 Hz, 1H) 6.46 (dd, J = 3.21, 1.83 Hz, 1H) 6.64 (d, J = 3.21 Hz, 1H) 6.78-6.81 (m, 1H) 7.20-7.21 (m, 1H) 7.24-7.26 (m, 1H) 7.27-7.29 (m, 1H) 7.46 (d, J = 0.92 Hz, 1H) |
| 96 | | 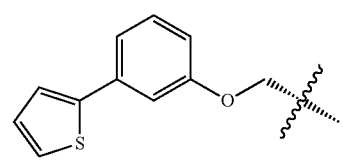 | 891.4 | (600 MHz): 0.95 (d, J = 6.88 Hz, 3H) 1.04 (d, J = 6.88 Hz, 3H) 1.07-1.10 (m, 6H) 1.17-1.22 (m, 1H) 1.23 (s, 3H) 1.24 (s, 3H) 1.29 (d, J = 6.42 Hz, 3H) 1.37 (s, 3H) 1.45 (d, J = 14.21 Hz, 1H) 1.56 (dd, J = 15.13, 5.04 Hz, 1H) 1.63-1.67 (m, 1H) 2.21-2.27 (m, 2H) 2.29 (s, 6H) 2.35 (d, J = 14.67 Hz, 1H) 2.39-2.46 (m, 1H) 2.49-2.55 (m, 1H) 2.65-2.87 (m, 4H) 2.93-3.05 (m, 4H) 3.15-3.18 (m, 1H) 3.20 (dd, J = 10.32, 7.11 Hz, 1H) 3.25 (d, J = 11.46 Hz, 1H) 3.29 (s, 3H) 3.30 (s, 3H) 3.45-3.51 (m, 1H) 3.59 (d, J = 9.17 Hz, 1H) 3.75 (d, J = 7.34 Hz, 1H) 4.00-4.06 (m, 2H) 4.17 (dd, J = 8.94, 7.57 Hz, 1H) 4.46 (d, J = 7.34 Hz, 1H) 4.89 (d, J = 4.58 Hz, 1H) 5.15 (dd, J = 6.42, 4.58 Hz, 1H) 6.81 (ddd, J = 8.25, 2.75, 0.92 Hz, 1H) 7.06 (dd, J = 5.04, 3.67 Hz, 1H) 7.13 (d, J = 1.83 Hz, 1H) 7.18-7.21 (m, 1H) 7.25-7.29 (m, 2H) 7.30 (dd, J = 3.67, 0.92 Hz, 1H) |

TABLE 1-continued

| Example | Reference Example | R | ESI MS (M + H) | $^1$H-NMR, CDCl$_3$, δ (ppm) |
|---|---|---|---|---|
| 97 | | 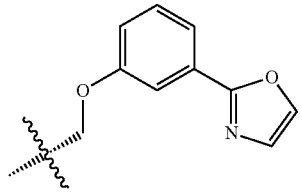 | 876.7 | (600 MHz): 0.93 (d, J = 7.34 Hz, 3H) 1.07 (t, J = 6.65 Hz, 9H) 1.18-1.30 (m, 10H) 1.35 (s, 3H) 1.43 (d, J = 14.67 Hz, 1H) 1.53-1.67 (m, 2H) 2.19-2.25 (m, 1H) 2.28 (s, 6H) 2.34 (d, J = 14.67 Hz, 1H) 2.38-2.53 (m, 2H) 2.63-3.05 (m, 8H) 3.14-3.26 (m, 3H) 3.28 (s, 3H) 3.29 (s, 3H) 3.43-3.50 (m, 1H) 3.58 (d, J = 9.63 Hz, 1H) 3.74 (d, J = 7.34 Hz, 1H) 3.97-4.08 (m, 2H) 4.17-4.22 (m, 1H) 4.45 (d, J = 6.88 Hz, 1H) 4.88 (d, J = 4.58 Hz, 1H) 5.12-5.16 (m, 1H) 6.93-6.99 (m, 1H) 7.22 (s, 1H) 7.35 (t, J = 8.02 Hz, 1H) 7.54-7.58 (m, 1H) 7.62 (d, J = 7.79 Hz, 1H) 7.70 (s, 1H) |
| 98 | | 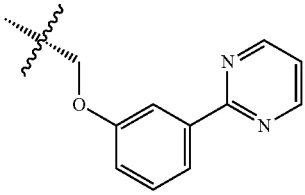 | 887.7 | (600 MHz): 0.93 (d, J = 7.34 Hz, 3H) 1.03 (d, J = 6.88 Hz, 3H) 1.05-1.09 (m, 6H) 1.21 (d, J = 5.96 Hz, 7H) 1.28 (d, J = 5.96 Hz, 3H) 1.35 (s, 3H) 1.42 (d, J = 14.67 Hz, 1H) 1.52-1.67 (m, 2H) 2.19-2.26 (m, 2H) 2.28 (s, 6H) 2.34 (d, J = 14.67 Hz, 1H) 2.37-2.54 (m, 2H) 2.64-3.04 (m, 7H) 3.13-3.26 (m, 3H) 3.28 (s, 3H) 3.29 (s, 3H) 3.43-3.51 (m, 1H) 3.58 (d, J = 9.63 Hz, 1H) 3.75 (d, J = 7.34 Hz, 1H) 3.98-4.13 (m, 2H) 4.18-4.27 (m, 1H) 4.45 (d, J = 7.34 Hz, 1H) 4.88 (d, J = 4.58 Hz, 1H) 5.14-5.18 (m, 1H) 6.98-7.03 (m, 1H) 7.17 (t, J = 4.81 Hz, 1H) 7.38 (t, J = 7.79 Hz, 1H) 7.98-8.04 (m, 2H) 8.79 (d, J = 5.04 Hz, 2H) |
| 99 | | 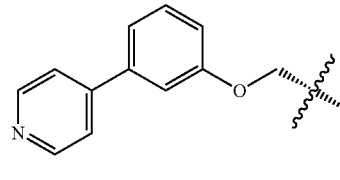 | 886.4 | (600 MHz): 0.94 (d, J = 6.88 Hz, 3H) 1.04 (d, J = 6.88 Hz, 3H) 1.09 (d, J = 6.88 Hz, 3H) 1.12 (d, J = 7.34 Hz, 3H) 1.16-1.21 (m, 1H) 1.23 (d, J = 5.96 Hz, 3H) 1.25 (s, 3H) 1.30 (d, J = 5.96 Hz, 3H) 1.37 (s, 3H) 1.46 (d, J = 14.67 Hz, 1H) 1.55-1.68 (m, 2H) 2.19-2.27 (m, 2H) 2.28 (s, 6H) 2.33-2.44 (m, 2H) 2.52-2.59 (m, 1H) 2.67-2.74 (m, 1H) 2.76-2.87 (m, 3H) 2.93-3.06 (m, 4H) 3.14-3.28 (m, 3H) 3.30 (s, 3H) 3.31 (s, 3H) 3.45-3.51 (m, 1H) 3.59 (d, J = 10.09 Hz, 1H) 3.76 (d, J = 7.79 Hz, 1H) 4.00-4.09 (m, 2H) 4.19 (dd, J = 8.71, 7.34 Hz, 1H) 4.47 (d, J = 7.34 Hz, 1H) 4.89 (d, J = 4.58 Hz, 1H) 5.15 (dd, J = 6.42, 4.58 Hz, 1H) 6.97 (dd, J = 8.25, 2.29 Hz, 1H) 7.14-7.16 (m, 1H) 7.21 (d, J = 8.25 Hz, 1H) 7.39 (t, J = 8.02 Hz, 1H) 7.51 (d, J = 5.96 Hz, 2H) 8.64 (d, J = 6.42 Hz, 2H) |
| 100 | | 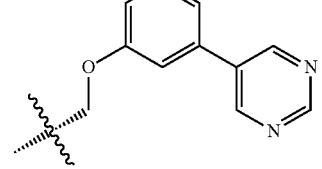 | 887.7 | (600 MHz): 0.92 (d, J = 7.34 Hz, 3H) 1.01-1.11 (m, 9H) 1.18-1.30 (m, 10H) 1.36 (s, 3H) 1.44 (d, J = 14.67 Hz, 1H) 1.53-1.69 (m, 2H) 2.19-2.26 (m, 1H) 2.28 (s, 6H) 2.35 (d, J = 15.13 Hz, 1H) 2.38-2.55 (m, 2H) 2.64-3.04 (m, 8H) 3.14-3.27 (m, 3H) 3.28 (s, 3H) 3.30 (s, 3H) 3.43-3.50 (m, 1H) 3.58 (d, J = 9.63 Hz, 1H) 3.75 (d, J = 7.34 Hz, 1H) 3.98-4.09 (m, 2H) 4.17-4.21 (m, 1H) 4.44 (d, J = 7.34 Hz, 1H) 4.88 (d, J = 4.58 Hz, 1H) 5.12-5.16 (m, 1H) 6.96-7.00 (m, 1H) 7.06-7.08 (m, 1H) 7.12-7.15 (m, 1H) 7.41 (t, J = 7.79 Hz, 1H) 8.93 (s, 2H) 9.18 (s, 1H) |

TABLE 1-continued

| Example | Reference Example | R | ESI MS (M + H) | ¹H-NMR, CDCl₃, δ (ppm) |
|---|---|---|---|---|
| 101 | | (3-(furan-3-yl)phenyl)methoxy group | 875.7 | (600 MHz): 0.93 (d, J = 7.34 Hz, 3H) 1.00-1.11 (m, 9H) 1.17-1.30 (m, 10H) 1.36 (s, 3H) 1.44 (d, J = 14.67 Hz, 1H) 1.53-1.71 (m, 2H) 2.19-2.25 (m, 1H) 2.29 (s, 6H) 2.35 (d, J = 15.13 Hz, 1H) 2.39-2.55 (m, 2H) 2.62-3.04 (m, 8H) 3.13-3.26 (m, 3H) 3.28 (s, 3H) 3.30 (s, 3H) 3.44-3.51 (m, 1H) 3.58 (d, J = 9.63 Hz, 1H) 3.75 (d, J = 7.34 Hz, 1H) 3.98-4.05 (m, 2H) 4.13-4.17 (m, 1H) 4.45 (d, J = 6.88 Hz, 1H) 4.88 (d, J = 4.58 Hz, 1H) 5.11-5.16 (m, 1H) 6.67-6.69 (m, 1H) 6.76-6.81 (m, 1H) 6.98-7.01 (m, 1H) 7.06 (d, J = 7.79 Hz, 1H) 7.24-7.28 (m, 1H) 7.43-7.47 (m, 1H) 7.71-7.73 (m, 1H) |
| 102 | | (3-(thiophen-3-yl)phenyl)methoxy group | 891.6 | (600 MHz): 0.93 (d, J = 7.34 Hz, 3H) 1.01-1.11 (m, 9H) 1.17-1.26 (m, 7H) 1.28 (d, J = 5.96 Hz, 3H) 1.36 (s, 3H) 1.44 (d, J = 14.67 Hz, 1H) 1.53-1.68 (m, 2H) 2.19-2.26 (m, 1H) 2.29 (s, 6H) 2.34 (d, J = 15.13 Hz, 1H) 2.39-2.56 (m, 2H) 2.64-2.71 (m, 1H) 2.74-3.04 (m, 7H) 3.14-3.26 (m, 3H) 3.28 (s, 3H) 3.30 (s, 3H) 3.44-3.51 (m, 1H) 3.58 (d, J = 10.09 Hz, 1H) 3.75 (d, J = 7.34 Hz, 1H) 3.99-4.05 (m, 2H) 4.14-4.19 (m, 1H) 4.46 (d, J = 7.34 Hz, 1H) 4.88 (d, J = 4.58 Hz, 1H) 5.12-5.16 (m, 1H) 6.80-6.83 (m, 1H) 7.09-7.11 (m, 1H) 7.15-7.18 (m, 1H) 7.28 (t, J = 8.02 Hz, 1H) 7.34-7.38 (m, 2H) 7.43-7.46 (m, 1H) |
| 103 | | (5-phenylpyridin-3-yl)methoxy group | 886.3 | (600 MHz): 0.94 (d, J = 7.34 Hz, 3H) 1.05 (d, J = 6.42 Hz, 3H) 1.10-1.13 (m, 6H) 1.17-1.21 (m, 1H) 1.22 (d, J = 5.96 Hz, 3H) 1.25 (s, 3H) 1.30 (d, J = 6.42 Hz, 3H) 1.37 (s, 3H) 1.46 (d, J = 14.67 Hz, 1H) 1.50-1.68 (m, 2H) 2.20-2.27 (m, 2H) 2.28 (s, 6H) 2.34-2.49 (m, 2H) 2.50-2.56 (m, 1H) 2.68-2.74 (m, 1H) 2.78-2.89 (m, 3H) 2.92-3.08 (m, 4H) 3.13-3.23 (m, 2H) 3.26-3.28 (m, 1H) 3.29 (s, 3H) 3.31 (s, 3H) 3.45-3.50 (m, 1H) 3.60 (d, J = 9.17 Hz, 1H) 3.76 (d, J = 7.34 Hz, 1H) 4.01-4.06 (m, 1H) 4.11 (t, J = 8.25 Hz, 1H) 4.24 (dd, J = 8.94, 7.11 Hz, 1H) 4.46 (d, J = 6.88 Hz, 1H) 4.89 (d, J = 4.58 Hz, 1H) 5.15 (dd, J = 6.42, 4.58 Hz, 1H) 7.36-7.38 (m, 1H) 7.39-7.42 (m, 1H) 7.45-7.49 (m, 2H) 7.57-7.60 (m, 2H) 8.27-8.29 (m, 1H) 8.45-8.46 (m, 1H) |
| 104 | | (5-(furan-2-yl)pyridin-3-yl)methoxy group | 876.3 | (600 MHz): 0.94 (d, J = 6.88 Hz, 3H) 1.04 (d, J = 6.42 Hz, 3H) 1.09 (d, J = 7.34 Hz, 3H) 1.09 (d, J = 7.79 Hz, 3H) 1.16-1.22 (m, 1H) 1.22 (d, J = 5.96 Hz, 3H) 1.24 (s, 3H) 1.29 (d, J = 5.96 Hz, 3H) 1.37 (s, 3H) 1.45 (d, J = 14.67 Hz, 1H) 1.54-1.67 (m, 2H) 2.19-2.26 (m, 2H) 2.29 (s, 6H) 2.33-2.48 (m, 2H) 2.49-2.56 (m, 1H) 2.65-2.71 (m, 1H) 2.76-2.87 (m, 3H) 2.93-3.04 (m, 4H) 3.13-3.27 (m, 3H) 3.29 (s, 3H) 3.30 (s, 3H) 3.45-3.51 (m, 1H) 3.59 (d, J = 9.63 Hz, 1H) 3.76 (d, J = 7.34 Hz, 1H) 4.01-4.06 (m, 2H) 4.17 (dd, J = 9.17, 7.34 Hz, 1H) 4.46 (d, J = 7.34 Hz, 1H) 4.89 (d, J = 4.58 Hz, 1H) 5.15 (dd, J = 6.42, 4.58 Hz, 1H) 6.46 (dd, J = 3.21, 1.83 Hz, 1H) 6.64 (d, J = 2.75 Hz, 1H) 6.78-6.80 (m, 1H) 7.19-7.21 (m, 1H) 7.24-7.29 (m, 1H) 7.45-7.46 (m, 1H) |

| Reference Example | Reference Example | R | ESI MS (M + H) | 1H-NMR, CDCl3, δ (ppm) |
|---|---|---|---|---|
| 105 | | 3-methylphenyl-triazole-CH group | 874.4 | (600 MHz): 0.98 (d, J = 6.88 Hz, 3H) 1.00 (d, J = 6.42 Hz, 3H) 1.13-1.17 (m, 1H) 1.17 (d, J = 7.34 Hz, 3H) 1.18 (d, J = 7.79 Hz, 3H) 1.24 (d, J = 5.96 Hz, 3H) 1.26 (s, 3H) 1.31 (d, J = 5.96 Hz, 3H) 1.39 (s, 3H) 1.53 (d, J = 15.13 Hz, 1H) 1.59 (dd, J = 15.13, 5.04 Hz, 1H) 1.67 (d, J = 12.38 Hz, 1H) 2.22-2.25 (m, 1H) 2.26-2.30 (m, 1H) 2.30 (s, 6H) 2.38-2.40 (m, 1H) 2.41 (s, 3H) 2.42-2.48 (m, 1H) 2.50-2.55 (m, 1H) 2.74 (t, J = 8.94 Hz, 1H) 2.78-2.83 (m, 1H) 2.84-2.90 (m, 2H) 2.89-2.95 (m, 2H) 2.98-3.04 (m, 2H) 3.15-3.20 (m, 1H) 3.20-3.24 (m, 1H) 3.28 (d, J = 11.92 Hz, 1H) 3.30 (s, 3H) 3.34 (s, 3H) 3.46-3.54 (m, 1H) 3.62-3.66 (m, 1H) 3.78 (d, J = 7.34 Hz, 1H) 3.99-4.08 (m, 1H) 4.38-4.44 (m, 1H) 4.49 (d, J = 6.88 Hz, 1H) 4.64 (dd, J = 13.75, 6.42 Hz, 1H) 4.92 (d, J = 4.58 Hz, 1H) 4.99-5.04 (m, 1H) 7.15 (d, J = 7.79 Hz, 1H) 7.31 (t, J = 7.57 Hz, 1H) 7.59 (d, J = 7.79 Hz, 1H) 7.67-7.71 (m, 1H) 7.70 (s, 1H) |
| 106 | | phenyl-triazole-CH group | 860.7 | (600 MHz): 0.98 (d, J = 7.34 Hz, 3H) 1.00 (d, J = 6.42 Hz, 3H) 1.17 (d, J = 6.88 Hz, 3H) 1.17 (d, J = 7.34 Hz, 3H) 1.21-1.24 (m, 1H) 1.24 (d, J = 5.96 Hz, 3H) 1.26 (s, 3H) 1.31 (d, J = 6.42 Hz, 3H) 1.39 (s, 3H) 1.53 (d, J = 14.67 Hz, 1H) 1.59 (dd, J = 15.13, 4.58 Hz, 1H) 1.67 (d, J = 12.38 Hz, 1H) 2.23-2.29 (m, 2H) 2.30 (s, 6H) 2.39 (d, J = 14.21 Hz, 1H) 2.42-2.47 (m, 1H) 2.51-2.54 (m, 1H) 2.75 (t, J = 8.94 Hz, 1H) 2.83-2.89 (m, 2H) 2.89-2.95 (m, 3H) 2.97-3.05 (m, 2H) 3.17-3.20 (m, 1H) 3.19-3.24 (m, 1H) 3.28 (d, J = 11.92 Hz, 1H) 3.30 (s, 3H) 3.34 (s, 3H) 3.46-3.53 (m, 1H) 3.63 (d, J = 10.09 Hz, 1H) 3.78 (d, J = 7.34 Hz, 1H) 4.01-4.08 (m, 1H) 4.42 (dd, J = 13.53, 8.48 Hz, 1H) 4.49 (d, J = 7.34 Hz, 1H) 4.64 (dd, J = 13.75, 6.88 Hz, 1H) 4.91 (d, J = 4.58 Hz, 1H) 5.00-5.04 (m, 1H) 7.31-7.36 (m, 1H) 7.43 (t, J = 7.79 Hz, 2H) 7.71 (s, 1H) 7.81-7.85 (m, 2H) |
| 107 | | O-(CH2)4-triazole-pyridin-3-yl group | 918.5 | (600 MHz): 0.92 (d, J = 7.34 Hz, 3H) 1.00 (d, J = 6.88 Hz, 3H) 1.10 (d, J = 7.34 Hz, 3H) 1.15 (d, J = 7.34 Hz, 3H) 1.18-1.27 (m, 1H) 1.22 (d, J = 5.96 Hz, 3H) 1.24 (s, 3H) 1.29 (d, J = 6.42 Hz, 3H) 1.35 (s, 3H) 1.46 (d, J = 15.13 Hz, 1H) 1.52-1.73 (m, 4H) 1.87-1.96 (m, 2H) 2.17-2.27 (m, 1H) 2.28 (s, 6H) 2.35-2.53 (m, 4H) 2.73-3.23 (m, 9H) 3.28 (s, 3H) 3.31 (s, 3H) 3.38-3.52 (m, 3H) 3.60 (s, 1H) 3.73 (d, J = 7.79 Hz, 1H) 3.87-3.92 (m, 1H) 3.96-4.04 (m, 3H) 4.43 (d, J = 7.34 Hz, 1H) 4.67-4.72 (m, 1H) 4.87 (d, J = 4.58 Hz, 1H) 7.26-7.32 (m, 2H) 7.51-7.55 (m, 1H) 8.04-8.10 (m, 1H) 8.42-8.49 (m, 1H) 8.92-8.99 (m, 1H) |

TABLE 1-continued

| Example | Reference Example | R | ESI MS (M + H) | ¹H-NMR, CDCl₃, δ (ppm) |
|---|---|---|---|---|
| 108 | | (pyridinyl-imidazole-propyloxy group) | 904.7 | (600 MHz): 0.93 (d, J = 6.88 Hz, 3H) 1.03 (d, J = 6.88 Hz, 3H) 1.10 (d, J = 7.34 Hz, 3H) 1.16 (d, J = 7.34 Hz, 3H) 1.18-1.27 (m, 1H) 1.23 (d, J = 5.96 Hz, 3H) 1.25 (s, 3H) 1.30 (d, J = 6.42 Hz, 3H) 1.37 (s, 3H) 1.47 (d, J = 15.59 Hz, 1H) 1.55-1.60 (m, 1H) 1.63-1.67 (m, 1H) 2.03-2.09 (m, 2H) 2.23 (d, J = 10.55 Hz, 1H) 2.25-2.31 (m, 7H) 2.36-2.52 (m, 4H) 2.76-2.90 (m, 3H) 2.95-2.99 (m, 1H) 3.01 (t, J = 9.86 Hz, 1H) 3.14-3.22 (m, 3H) 3.29 (s, 3H) 3.32 (s, 3H) 3.38-3.50 (m, 4H) 3.62 (d, J = 9.17 Hz, 1H) 3.74 (d, J = 8.25 Hz, 1H) 3.88-3.93 (m, 1H) 4.00-4.05 (m, 1H) 4.08-4.12 (m, 2H) 4.44 (d, J = 7.34 Hz, 1H) 4.73 (dd, J = 5.96, 1.83 Hz, 1H) 4.88 (d, J = 4.58 Hz, 1H) 7.28 (d, J = 1.38 Hz, 1H) 7.28-7.31 (m, 1H) 7.54 (d, J = 1.38 Hz, 1H) 8.08 (ddd, J = 8.02, 2.06, 1.83 Hz, 1H) 8.47 (dd, J = 4.81, 1.60 Hz, 1H) 8.97 (dd, J = 2.29, 0.92 Hz, 1H) |
| 109 | | H₂N— | 718 FAB MASS | (300 MHz): 0.94 (d, J = 6.9 Hz, 3H) 1.00 (d, J = 6.6 Hz, 3H) 1.12 (d, J = 7.5 Hz, 3H) 1.17-1.26 (m, 10H) 1.29 (d, J = 6.3 Hz, 3H) 1.37 (s, 3H) 1.45 (d, J = 14.7 Hz, 1H) 1.56-1.68 (m, 2H) 2.20-2.30 (m, 7H) 2.36-2.52 (m, 3H) 2.73-3.03 (m, 7H) 3.12-3.24 (m, 3H) 3.28-3.43 (m, 7H) 3.46-3.52 (m, 1H) 3.62 (d, J = 10.2 Hz, 1H) 3.77 (d, J = 7.2 Hz, 1H) 4.04 (dq, J = 9.0 Hz, J = 6.3 Hz, 1H) 4.48 (d, J = 7.5 Hz, 1H) 4.77 (dd, J = 4.8 Hz, J = 4.8 Hz, 1H) 4.93 (d, J = 4.5 Hz, 1H) |
| 110 | | allyloxycarbonylamino group | 802.2 | (300 MHz): 0.94 (d, J = 7.2 Hz, 3H) 1.02 (d, J = 6.9 Hz, 3H) 1.12 (d, J = 7.5 Hz, 3H) 1.20-1.67 (m, 4H) 1.22 (d, J = 6.0 Hz, 3H) 1.26 (s, 3H) 1.29 (d, J = 6.0 Hz, 3H) 1.37 (s, 3H) 1.43-1.67 (m, 3H) 2.21-2.24 (s, 2H) 2.29 (s, 6H) 2.36-2.47 (m, 3H) 2.77-3.06 (m, 7H) 3.13-3.24 (m, 3H) 3.29 (s, 3H) 3.33 (s, 3H) 3.45-3.52 (m, 1H) 3.59-3.62 (m, 1H) 3.77 (d, J = 7.5 Hz, 1H) 4.03 (dq, J = 9.6 Hz, J = 6.6 Hz, 1H) 4.24-4.31 (m, 1H) 4.48 (d, J = 7.2 Hz, 1H) 4.55-4.58 (m, 2H) 4.78-4.84 (m, 1H) 4.90-4.94 (m, 2H) 5.03 (d, J = 9.3 Hz, 1H) 5.23 (dd, J = 10.5 Hz, J = 1.5 Hz, 1H) 5.28-5.35 (m, 1H) 5.87-6.00 (m, 1H) |
| 111 | | naphthylmethyloxycarbonylamino group | 902.2 | (300 MHz): 0.92 (d, J = 7.2 Hz, 3H) 0.98 (d, J = 7.2 Hz, 3H) 1.03 (d, J = 6.6 Hz, 3H) 1.10 (d, J = 6.6 Hz, 3H) 1.19-1.23 (m, 4H) 1.25 (s, 3H) 1.28 (d, J = 6.3 Hz, 3H) 1.35 (s, 3H) 1.39-1.44 (m, 1H) 1.54-1.68 (m, 2H) 2.16-2.46 (m, 11H) 2.76-3.02 (m, 7H) 3.11-3.23 (m, 3H) 3.26 (s, 3H) 3.31 (s, 3H) 3.45-3.51 (m, 1H) 3.57 (d, J = 9.6 Hz, 1H) 3.73 (d, J = 7.5 Hz, 1H) 3.97-4.04 (m, 1H) 4.27-4.34 (m, 1H) 4.44 (d, J = 6.9 Hz, 1H) 4.88-4.94 (m, 2H) 5.04 (d, J = 9.3 Hz, 1H) 5.52-5.64 (m, 2H) 7.43-7.59 (m, 4H) 7.83-7.88 (m, 2H) 8.07 (d, J = 8.1 Hz, 1H) |

TABLE 1-continued

| Example | Reference Example | R | ESI MS (M + H) | $^1$H-NMR, CDCl$_3$, δ (ppm) |
|---|---|---|---|---|
| 112 | | naphthalen-1-yl-ethyl-O-C(=O)-NH- | 916.2 | (300 MHz): 0.96 (d, J = 6.6 Hz, 3H) 1.02 (d, J = 6.9 Hz, 3H) 1.12-1.20 (m, 4H) 1.22-1.26 (m, 6H) 1.30 (d, J = 6.3 Hz, 3H) 1.38 (s, 3H) 1.46-1.69 (m, 3 H) 2.22-2.48 (m, 11H) 2.77-3.04 (m, 7 H) 3.15-3.25 (m, 3H) 3.29 (s, 3H) 3.30 (s, 3H) 3.41-3.53 (m, 3H) 3.60 (d, J = 9.6 Hz, 1H) 3.78 (d, J = 7.2 Hz, 1H) 4.04 (dq, J = 8.1H, J = 6.6 Hz, 1H) 4.25-4.50 (m, 4H) 4.76-4.81 (m, 1H) 4.90-4.94 (m, 2H) 5.01 (d, J = 9.0 Hz, 1H) 7.36-7.56 (m, 4H) 7.73-7.77 (m, 1H) 7.84-7.87 (m, 1H) 8.14 (d, J = 8.7 Hz, 1H) |
| 113 | | naphthalen-2-yl-methyl-NH- | 858 FAB MASS | (300 MHz): 0.94 (d, J = 6.9 Hz, 3H) 1.01 (d, J = 6.6 Hz, 3H) 1.10 (t, J = 7.5 Hz, 3H) 1.17-1.31 (m, 13H) 1.36 (s, 3H) 1.40-1.63 (m, 3H) 2.15-2.50 (m, 11H) 2.92-3.10 (m, 7H) 3.20-3.32 (m, 10H) 3.47-3.54 (m, 1H) 3.64 (d, J = 9.9 Hz, 1H) 3.78 (d, J = 7.8 Hz, 1 H) 3.91 (s, 2H) 4.04 (dq, J = 9.3 Hz, J = 6.3 Hz, 1H) 4.49 (d, J = 7.5 Hz, 1 H) 4.93 (d, J = 5.4 Hz, 1H) 5.03-5.06 (m, 1H) 7.44-7.47 (m, 3H) 7.75 (m, 1 H) 7.80-7.83 (m, 3H) |
| 114 | | naphthalen-2-yl-ethyl-NH- | 872 FAB MASS | (300 MHz): 0.66 (d, J = 7.2 Hz, 3H) 0.86-0.90 (m, 6H) 1.00 (d, J = 6.6 Hz, 3H) 1.20 (d, J = 6.0 Hz, 3H) 1.24-1.27 (m, 7H) 1.30 (s, 3H) 1.52-1.72 (m, 3 H) 2.08-2.50 (m, 11H) 2.78-3.06 (m, 11H) 3.13-3.32 (m, 10H) 3.40-3.50 (m, 2H) 3.64 (d, J = 7.2 Hz, 1H) 3.97 (dq, J = 9.3 Hz, J = 6.9 Hz, 1H) 4.41 (d, J = 6.9 Hz, 1H) 4.80 (d, J = 4.2 Hz, 1H) 4.89-4.93 (m, 1H) 7.30-7.45 (m, 3H) 7.64 (brs, 1H) 7.75-7.80 (m, 3H) |
| 115 | | naphthalen-2-yl-methyl-N(Me)- | 872.5 | (300 MHz): 0.95 (d, J = 6.9 Hz, 3H) 1.06 (d, J = 6.9 Hz, 3H) 1.13-1.17 (m, 6H) 1.22-1.26 (m, 7H) 1.30 (d, J = 6.3 Hz, 3H) 1.38-1.44 (m, 4H) 1.56-1.72 (m, 2H) 2.19 (s, 3H) 2.33-2.35 (m, 11 H) 2.90-3.09 (m, 7H) 3.14-3.30 (m, 7 H) 3.35 (s, 3H) 3.48-3.61 (m, 2H) 3.67 (d, J = 9.3 Hz, 1H) 3.78-3.85 (m, 2H) 4.05 (dq, J = 9.6 Hz, J = 6.9 Hz, 1 H) 4.51 (d, J = 7.5 Hz, 1H) 4.91 (d, J = 3.9 Hz, 1H) 5.09 (m, 1H) 7.41-7.49 (m, 3H) 7.72 (m, 1H) 7.78-7.83 (m, 3 H) |
| 116 | | naphthalen-2-yl-ethyl-N(Me)- | 886.5 | (300 MHz): 0.94 (d, J = 7.2 Hz, 3H) 1.02-1.09 (m, 6H) 1.16-1.30 (m, 10H) 1.35-1.41 (m, 4H) 1.54-1.69 (m, 2H) 2.22-2.50 (m, 14H) 2.70-3.02 (m, 11H) 3.13-3.27 (m, 7H) 3.33 (s, 3H) 3.46-3.52 (m, 1H) 3.62 (d, J = 9.6 Hz, 1H) 3.74 (d, J = 6.9 Hz, 1H) 4.02 (dq, J = 9.0 Hz, J = 6.3 Hz, 1H) 4.56 (d, J = 7.2 Hz, 1H) 4.89 (d, J = 4.5 Hz, 1H) 5.07-5.09 (m, 1H) 7.32 (d, J = 8.1 Hz, 1H) 7.38-7.46 (m, 2H) 7.61 (brs, 1H) 7.75-7.80 (m, 3H) |

TABLE 1-continued

| Example | Reference Example | R | ESI MS (M + H) | $^1$H-NMR, CDCl$_3$, δ (ppm) |
|---|---|---|---|---|
| 117 | | benzyl carbamate group | 852.2 | (400 MHz): 0.94 (d, J = 7.0 Hz, 3H) 1.00 (d, J = 6.6 Hz, 3H) 1.10 (d, J = 7.3 Hz, 3H) 1.13-1.26 (m, 9H) 1.30 (d, J = 6.1 Hz, 3H) 1.37 (s, 3H) 1.49 (m, 1H) 1.56 (dd, J = 4.9, 15.2 Hz, 1H) 1.63-1.67 (m, 3H) 2.24-2.52 (m, 12H) 2.77 (m, 1H) 2.91 (m, 1H) 3.01 (m, 1H) 3.15-3.40 (m, 11H) 3.47 (m, 1H) 3.60 (m, 1H) 3.74 (d, J = 8.1 Hz, 1H) 4.03 (m, 1H) 4.16 (m, 1H) 4.43 (d, J = 7.1 Hz, 1H) 4.68 (m, 1H) 4.82 (m, 1H) 4.88 (m, 1H) 5.10 (m, 2H) 7.30-7.39 (m, 5H) |
| 118 | | H$_2$N– | 718 | (CD3OD, 400 MHz): 0.97 (d, J = 7.0 Hz, 3H) 1.05 (d, J = 6.6 Hz, 3H) 1.11 (d, J = 7.5 Hz, 3H) 1.19 (d, J = 7.1 Hz, 3H) 1.25-1.09 (m, 9H) 1.36 (s, 3H) 1.40-1.51 (m, 2H) 1.60 (dd, J = 4.9, 15.2 Hz, 1H) 1.96 (m, 1H) 2.24 (m, 1H) 2.40-2.51 (m, 3H) 2.77 (s, 6H) 2.78-2.96 (m, 3H) 3.07-3.18 (m, 3H) 3.27-3.43 (m, 10H) 3.50 (m, 1H) 3.63 (m, 1H) 3.79-3.87 (m, 2H) 4.12 (m, 1 H) 4.60-4.64 (m, 2H) 4.70 (m, 1H) |
| 119 | | allyl carbamate group | 802.2 | (400 MHz): 0.94 (d, J = 7.4 Hz, 3H) 1.01 (d, J = 6.6 Hz, 3H) 1.10 (d, J = 7.3 Hz, 3H) 1.15 (d, J = 7.0 Hz, 3H) 1.21 (m, 1H) 1.23 (d, J = 6.1 Hz, 3H) 1.25 (s, 3H) 1.30 (d, J = 6.1 Hz, 3H) 1.38 (s, 3H) 1.50 (m, 1H) 1.56 (dd, J = 4.9, 15.2 Hz, 1H) 1.65 (m, 1H) 2.24-2.55 (m, 12H) 2.72-2.84 (m, 2H) 2.90 (m, 1H) 2.98-3.05 (m, 2H) 3.16-3.51 (m, 12H) 3.60 (m, 1H) 3.74 (m, 1H) 4.03 (m, 1H) 4.14 (m, 1H) 4.43 (d, J = 7.1 Hz, 1H) 4.50-5.00 (m, 6H) 5.22 (dd, J = 1.2, 10.5 Hz, 1H) 5.31 (dd, J = 1.2, 17.3 Hz, 1H) 5.92 (m, 1H) |
| 120 | | Me$_2$N– (dimethylamino) | 746 | (400 MHz): 0.95 (d, J = 6.9 Hz, 3H) 1.00 (d, J = 6.6 Hz, 3H) 1.12-1.21 (m, 7H) 1.24 (d, J = 6.1 Hz, 3H) 1.25 (s, 3H) 1.30 (d, J = 6.3 Hz, 3H) 1.37 (s, 3H) 1.50-1.60 (m, 2H) 1.66 (m, 1H) 2.21 (s, 6H) 2.26-2.34 (m, 7H) 2.36-2.50 (m, 3H) 2.55 (dq, J = 7.7, 7.7 Hz, 1H) 2.70-3.04 (m, 7H) 3.12-3.26 (m, 3H) 3.29 (s, 3H) 3.32 (s, 3H) 3.39-3.52 (m, 2H) 3.60 (m, 1H) 3.74 (d, J = 8.3 Hz, 1H) 4.03 (m, 1H) 4.44 (d, J = 7.3 Hz, 1 H) 4.72 (m, 1H) 4.85-4.95 (m, 2H) |
| 121 | | naphthylmethyl carbamate group | 902 | (400 MHz): 0.94 (d, J = 6.4 Hz, 3H) 0.99 (d, J = 6.1 Hz, 3H) 1.11 (d, J = 6.8 Hz, 3H) 1.16 (d, J = 6.9 Hz, 3H) 1.22 (m, 1H)1.23 (d, J = 6.9 Hz, 3H) 1.25 (s, 3H)1.30 (d, J = 6.1 Hz, 3H) 1.37 (s, 3H)1.49 (m, 1H) 1.56 (dd, J = 4.8, 15.3 Hz, 1H) 1.66 (m, 1H) 2.21-2.56 (m, 14H) 2.65-3.05 (m, 5H) 3.15-3.35 (m, 10H) 3.47 (m, 1H) 3.60 (m, 1H) 3.74 (m, 1H) 4.03 (m, 1H) 4.18 (m, 1H) 4.44 (m, 1H) 4.55-4.95 (m, 2H) 5.53 (d, J = 12.2 Hz, 1H) 5.59 (d, J = 12.2 Hz, 1H) 7.45 (d, J = 7.1, 8.3 Hz, 1H) 7.49-7.59 (m, 3H) 7.82-7.90 (m, 2H) 8.04 (m, 1H) |

TABLE 1-continued

| Example | Reference Example | R | ESI MS (M + H) | $^1$H-NMR, CDCl$_3$, δ (ppm) |
|---|---|---|---|---|
| 122 | | 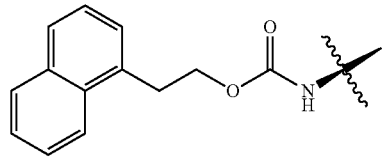 | 916 | (400 MHz): 0.95 (d, J = 7.1 Hz, 3H) 1.00 (d, J = 6.4 Hz, 3H) 1.09-1.38 (m, 20H) 1.49 (m, 1H) 1.56 (dd, J = 4.8, 15.3 Hz, 1H) 1.66 (m, 1H) 2.21-2.56 (m, 13H) 2.71-3.06 (m, 5H) 3.15-3.53 (m, 13H) 3.60 (m, 1H) 3.74 (m, 1H) 4.03 (m, 1H) 4.15 (m, 1H) 4.36-4.46 (m, 3H) 4.66 (m, 1H) 4.74 (m, 1H) 4.88 (m, 1H) 7.34-7.57 (m, 4H) 7.76 (m, 1H) 7.86 (m, 1H) 8.09 (m, 1H) |
| 123 | | 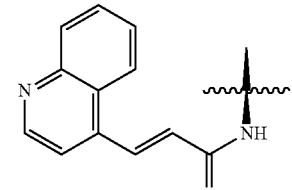 | 899 FAB MASS | (300 MHz): 0.97 (d, J = 7.14 Hz, 3H) 1.04 (d, J = 6.87 Hz, 3H) 1.13 (d, J = 7.42 Hz, 3H) 1.17 (d, J = 7.14 Hz, 3H) 1.19-1.27 (m, 7H) 1.30 (d, J = 6.32 Hz, 3H) 1.39 (s, 3H) 1.47-1.61 (m, 2H) 1.61-1.71 (m, 1H) 2.20-2.34 (m, 8H) 2.39 (d, J = 15.4 Hz, 1H) 2.41-2.59 (m, 3H) 2.71-3.12 (m, 6H) 3.16-3.26 (m, 2H) 3.30 (s, 3H) 3.33 (s, 3H) 3.35-3.52 (m, 2H) 3.63 (d, J = 9.07 Hz, 1H) 3.75 (d, J = 7.97 Hz, 1H) 3.97-4.09 (m, 1H) 4.45 (d, J = 7.14 Hz, 1H) 4.47-4.58 (m, 1H) 4.76-4.84 (m, 1H) 4.88 (d, J = 4.12 Hz, 1H) 6.01 (br s, 1H) 6.58 (d, J = 15.4 Hz, 1H) 7.48 (d, J = 4.40 Hz, 1H) 7.61 (t, J = 7.42 Hz, 1H) 7.76 (d, J = 6.87 Hz, 1H) 8.16 (d, J = 9.34 Hz, 1H) 8.38 (d, J = 15.4 Hz, 1H) 8.91 (d, J = 4.40 Hz, 1H) |
| 124 | | 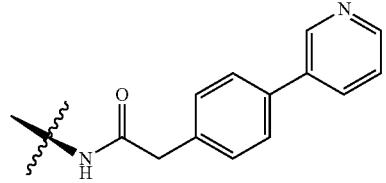 | 913 FAB MASS | (300 MHz): 0.89 (d, J = 6.87 Hz, 3H) 0.92 (d, J = 7.14 Hz, 3H) 1.09 (d, J = 7.14 Hz, 3H) 1.12-1.19 (m, 3H) 1.22 (d, J = 7.04 Hz, 3H) 1.25 (s, 3H) 1.29 (d, J = 6.32 Hz, 3H) 1.36 (s, 3H) 1.46 (d, J = 15.4 Hz, 1 H) 1.66 (dd, J = 4.40 Hz, J = 14.6, 1H) 1.61-1.69 (m, 1H) 2.17-2.33 (m, 9H) 2.39 (d, J = 14.6 Hz, 1H) 2.38-2.52 (m, 2H) 2.67-2.81 (m, 2H) 2.83-3.05 (m, 3H) 3.11-3.23 (m, 3H) 3.27 (s, 3H) 3.32 (s, 3 H) 3.40-3.53 (m, 1H) 3.54-3.64 (m, 3H) 3.72 (d, J = 7.97 Hz, 1H) 3.96-4.09 (m, 1 H) 4.27-4.39 (m, 1H) 4.43 (d, J = 7.14 Hz, 1H) 4.58-4.65 (m, 1H) 4.88 (d, J = 4.40 Hz, 1H) 5.42-5.52 (m, 1H) 7.32-7.42 (m, 3H) 7.59 (d, J = 7.97 Hz, 2H) 7.84-7.91 (m, 1H) 8.60 (dd, J = 1.37 Hz, J = 4.67 Hz, 1H) 8.85 (d, J = 1.92 Hz, 1H) |
| 125 | | 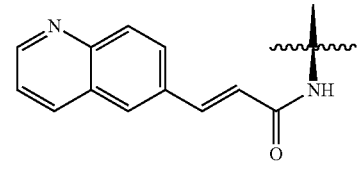 | 899 FAB MASS | (300 MHz): 0.97 (d, J = 6.87 Hz, 3H) 1.05 (d, J = 6.32 Hz, 3H) 1.13 (d, J = 7.42 Hz, 3H) 1.17 (d, J = 7.14 Hz, 3H) 1.19-1.27 (m, 7H) 1.30 (d, J = 6.32 Hz, 3H) 1.39 (s, 3H) 1.52 (d, J = 16.2 Hz, 1H) 1.57 (d, J = 4.95 Hz, J = 15.1 Hz, 1H) 1.61-1.71 (m, 1H) 2.21-2.34 (m, 8H) 2.40 (d, J = 15.1 Hz, 1H) 2.41-2.57 (m, 3H) 2.73-3.12 (m, 5H) 3.16-3.26 (m, 2H) 3.30 (s, 3H) 3.33 (s, 3H) 3.34-3.54 (m, 2H) 3.63 (d, J = 9.62 Hz, 1H) 3.75 (d, J = 7.97 Hz, 1H) 3.96-4.09 (m, 1H) 4.45 (d, J = 7.42 Hz, 1H) 4.47-4.58 (m, 1H) 4.76-4.82 (m, 1H) 4.89 (d, J = 4.40 Hz, 1H) 5.83 (br s, 1H) 6.52 (d, J = 15.7 Hz, 1H) 7.43 (dd, J = 4.40 Hz, J = 8.24 Hz, 1H) 7.81 (d, J = 15.7 Hz, 1H) 7.84-7.92 (m, 2H) 8.08 (d, J = 9.34 Hz, 1H) 8.17 (d, J = 7.14 Hz, 1H) 8.92 (dd, J = 1.65 Hz, J = 4.40 Hz, 1H) |

TABLE 1-continued

| Example | Reference Example | R | ESI MS (M + H) | $^1$H-NMR, CDCl$_3$, δ (ppm) |
|---|---|---|---|---|
| 126 | | (quinoline-6-yl connected via CH=CH-CH$_2$-C(=O)-NH) | 913 FAB MASS | (300 MHz): 0.93 (d, J = 6.9 Hz, 3H) 0.98 (d, J = 6.0 Hz, 3H) 1.10 (d, J = 7.5 Hz, 3H) 1.15 (d, J = 7.2 Hz, 3H) 1.19-1.24 (m, 7H) 1.29 (d, J = 6.3 Hz, 3H) 1.36 (s, 3H) 1.36 (s, 3H) 1.45-1.68 (m, 3H) 2.22-2.50 (m, 11H) 2.76-3.03 (m, 5H) 3.17-3.23 (m, 7H) 3.27 (s, 3H) 3.31 (s, 3H) 3.42-3.51 (m, 1H) 3.60 (d, J = 9.9 Hz, 1H) 3.72 (d, J = 8.1 Hz, 1H) 4.02 (dq, J = 9.0H, J = 6.0 Hz, 1H) 4.35-4.44 (m, 2H) 4.67-4.71 (m, 1H) 4.87 (d, J = 4.5 Hz, 1H) 5.71 (br, 1H) 6.45 (dt, J = 15.9 Hz, J = 6.9 Hz, 1H) 6.70 (d, J = 15.9 Hz, 1H) 7.39 (dd, J = 8.1 Hz, 4.2 Hz, 1H) 7.70 (m, 1H) 7.82 (dd, J = 8.7 Hz, J = 1.8 Hz, 1H) 8.04 (d, J = 8.7 Hz, 1H) 8.10-8.13 (m, 1H) |
| 127 | | (quinoline-6-yl connected via CH=CH-CH$_2$-CH$_2$-C(=O)-NH) | 927 FAB MASS | (300 MHz): 0.90-0.96 (m, 6H) 1.08-1.14 (m, 6H) 1.20-1.25 (m, 7H) 1.29 (d, J = 6.3 Hz, 3H) 1.36 (s, 3H) 1.44-1.69 (m, 3H) 2.91-2.48 (m, 13H) 2.58-3.02 (m, 7H) 3.16-3.32 (m, 11H) 3.43-3.49 (m, 1H) 3.59 (d, J = 9.6 Hz, 1H) 3.71 (d, J = 7.5 Hz, 1H) 4.01 (dq, J = 9.3H, J = 6.3 Hz, 1H) 4.35-4.44 (m, 2H) 4.66-4.70 (m, 1H) 4.87 (d, J = 4.5 Hz, 1H) 5.57 (br, 1H) 6.32-6.41 (m, 1H) 6.60 (d, J = 15.6 Hz, 1H) 7.36 (dd, J = 8.7 Hz, 3.9 Hz, 1H) 7.65 (m, 1H) 7.78-7.80 (m, 1H) 8.01 (d, J = 8.7 Hz, 1H) 8.09-8.11 (m, 1H) 8.82-8.84 (m, 1H) |
| 128 | | (3-pyridyl-phenyl-CH$_2$-CH$_2$-C(=O)-NH) | 927.5 | (400 MHz): 0.91-0.98 (m, 6H) 1.10 (d, J = 7.3 Hz, 3H) 1.15 (d, J = 7.1 Hz, 3H) 1.20-1.27 (m, 7H) 1.30 (d, J = 6.1 Hz, 3H) 1.36 (s, 3H) 1.48 (m, 1H) 1.56 (dd, J = 4.8, 15.3 Hz, 1H) 1.65 (m, 1H) 2.16-2.54 (m, 14H) 2.64-2.82 (m, 2H) 2.90 (m, 1H) 2.95-3.06 (m, 4H) 3.13-3.42 (m, 11H) 3.47 (m, 1H) 3.60 (m, 1H) 3.73 (m, 1H) 4.03 (m, 1H) 4.34 (m, 1H) 4.44 (m, 1H) 4.60 (m, 1H) 4.85-5.00 (m, 2H) 5.53 (m, 1H) 7.28-7.39 (m, 3H) 7.51 (m, 2H) 7.86 (m, 1H) 8.57 (m, 1H) 8.82 (m, 1H) |
| 129 | | (3-pyridyl-phenyl-C(=O)-NH) | 899 FAB MASS | (300 MHz): 0.98 (d, J = 6.87 Hz, 3H) 1.06 (d, J = 6.59 Hz, 3H) 1.13 (d, J = 7.42 Hz, 3H) 1.17 (d, J = 6.87 Hz, 3H) 1.19-1.27 (m, 7H) 1.31 (d, J = 6.04 Hz, 3H) 1.39 (s, 3H) 1.48-1.61 (m, 2H) 1.62-1.70 (m, 1H) 2.20-2.34 (m, 8H) 2.40 (d, J = 15.1 Hz, 1H) 2.42-2.59 (m, 3H) 2.75-3.12 (m, 5H) 3.16-3.27 (m, 2H) 3.31 (s, 3H) 3.33 (s, 3H) 3.40-3.52 (m, 2H) 3.64 (d, J = 9.62 Hz, 1H) 3.76 (d, J = 7.97 Hz, 1H) 3.98-4.10 (m, 1H) 4.45 (d, J = 6.87 Hz, 1H) 4.52-4.62 (m, 1H) 4.80-4.87 (m, 1H) 4.89 (d, J = 4.67 Hz, 1H) 6.30 (br s, 1H) 7.40 (dd, J = 4.95 Hz, J = 7.97 Hz, 2H) 7.66 (d, J = 8.24 Hz, 2H) 7.84-7.94 (m, 3H) 8.64 (dd, J = 1.37 Hz, J = 4.95 Hz, 1H) 8.87 (d, J = 1.92 Hz, 1H) |

TABLE 1-continued

| Example | Reference Example | R | ESI MS (M + H) | $^1$H-NMR, CDCl$_3$, δ (ppm) |
|---|---|---|---|---|
| 130 | | (quinolin-4-yl CH=CH-CH$_2$-C(=O)-NH-) | 927.5 | (300 MHz): 0.91-0.99 (m, 6H) 1.08-1.13 (m, 6H) 1.21-1.25 (m, 7H) 1.29 (d, J = 6.0 Hz, 3H) 1.36 (s, 3H) 1.44-1.69 (m, 3H) 2.25-2.49 (m, 14H) 2.67-3.02 (m, 6H) 3.17-3.26 (m, 8H) 3.32 (s, 3H) 3.42-3.50 (m, 1H) 3.60 (d, J = 9.9 Hz, 1H) 3.72 (d, J = 8.4 Hz, 1H) 4.01 (dq, J = 9.3H, J = 6.6 Hz, 1H) 4.34-4.37 (m, 2H) 4.67-4.69 (m, 1H) 4.86 (d, J = 4.5 Hz, 1H) 6.41-6.51 (m, 1H) 7.14 (d, J = 15.6 Hz, 1H) 7.41 (d, J = 4.5 Hz, 1H) 7.53-7.58 (m, 1H) 7.67-7.73 (m, 1H) 8.07-8.10 (m, 1H) 8.82 (d, J = 4.5 Hz, 1H) |
| 131 | | (HN-C(=O)-CH$_2$CH$_2$CH$_2$-quinolin-6-yl) | 915 FAB MASS | (300 MHz): 0.91-1.17 (m, 12H) 1.22-1.25 (m, 7H) 1.28 (d, J = 6.3 Hz, 3H) 1.37 (s, 3H) 1.56 (dd, J = 15 Hz, J = 4.8 Hz, 1H) 1.76-1.82 (m, 1H) 2.01-3.03 (m, 25H) 3.17-3.31 (m, 9H) 3.45-3.52 (m, 1H) 3.60-3.74 (m, 2H) 4.01 (dq, J = 9.6H, J = 6.0 Hz, 1H) 4.36-4.45 (m, 2H) 4.70 (br, 1H) 4.87 (d, J = 4.2 Hz, 1H) 7.37 (dd, J = 8.4 Hz, 4.5 Hz, 1H) 7.55-7.59 (m, 2H) 8.02 (d, J = 8.7 Hz, 1H) 8.08-8.11 (m, 1H) 8.85 (dd, J = 5.6 Hz, J = 1.2 Hz, 1H) |
| 132 | | (NH-C(=O)-CH$_2$CH$_2$CH$_2$CH$_2$-quinolin-6-yl) | 929 FAB MASS | (300 MHz): 0.93 (d, J = 6.9 Hz, 3H) 1.00 (d, J = 6.9 Hz, 3H) 1.10 (d, J = 7.8 Hz, 3H) 1.14 (d, J = 6.9 Hz, 3H) 1.19-1.25 (m, 7H) 1.29 (d, J = 6.0 Hz, 3H) 1.37 (s, 3H) 1.45-1.74 (m, 7H) 2.18-2.50 (m, 13H) 2.70-3.01 (m, 9H) 3.17-3.23 (m, 3H) 3.28 (s, 3H) 3.32 (s, 3H) 3.43-3.51 (m, 1H) 3.60 (d, J = 10.2 Hz, 1H) 3.72 (d, J = 8.4 Hz, 1H) 4.02 (dq, J = 9.9H, J = 6.3 Hz, 1H) 4.30-4.37 (m, 1H) 4.43 (d, J = 7.2 Hz, 1H) 4.64-4.67 (m, 1H) 4.87 (d, J = 4.5 Hz, 1H) 5.49 (br, 1H) 7.37 (dd, J = 8.1 Hz, 4.2 Hz, 1H) 7.54-7.58 (m, 2H) 8.02 (d, J = 8.7 Hz, 1H) 8.08-8.11 (m, 1H) 8.85 (dd, J = 4.2 Hz, J = 1.5 Hz, 1H) |
| 133 | | (quinolin-4-yl-CH$_2$CH$_2$-C(=O)-NH-) | 901 FAB MASS | (300 MHz): 0.94 (d, J = 7.14 Hz, 3H) 0.96 (d, J = 6.59 Hz, 3H) 1.11 (d, J = 7.42 Hz, 3H) 1.16 (d, J = 7.14 Hz, 3H) 1.19-1.27 (m, 7H) 1.30 (d, J = 6.04 Hz, 3H) 1.37 (s, 3H) 1.48 (d, J = 15.1 Hz, 1H) 1.56 (d, J = 10.2 Hz, 1H) 1.61-1.71 (m, 1H) 2.14-2.34 (m, 9H) 2.39 (d, J = 15.1 Hz, 1H) 2.42-2.54 (m, 2H) 2.54-2.65 (m, 2H) 2.65-2.80 (m, 2H) 2.84-3.05 (m, 3H) 3.11-3.25 (m, 3H) 3.28 (s, 3H) 3.33 (s, 3H) 3.38-3.53 (m, 3H) 3.61 (d, J = 9.62 Hz, 1H) 3.73 (d, J = 7.69 Hz, 1H) 3.96-4.08 (m, 1H) 4.24-4.36 (m, 1H) 4.44 (d, J = 7.14 Hz, 1H) 4.57-4.63 (m, 1H) 4.88 (d, J = 4.40 Hz, 1H) 5.44 (br s, 1H) 7.25 (d, J = 4.40 Hz, 1H) 7.59 (t, J = 8.24 Hz, 1H) 7.69 (t, J = 8.24 Hz, 1H) 8.06 (d, J = 8.24 Hz, 1H) 8.12 (d, J = 8.24 Hz, 1H) 8.81 (d, J = 4.40 Hz, 1H) |

TABLE 1-continued

| Example | Reference Example | R | ESI MS (M + H) | ¹H-NMR, CDCl₃, δ (ppm) |
|---|---|---|---|---|
| 134 | | | 901 FAB MASS | (300 MHz): 0.90 (d, J = 6.04 Hz, 3H) 0.91 (d, J = 6.59 Hz, 3H) 1.09 (d, J = 7.42 Hz, 3H) 1.14 (d, J = 7.14 Hz, 3H) 1.18-1.27 (m, 7H) 1.29 (d, J = 6.32 Hz, 3H) 1.36 (s, 3H) 1.46 (d, J = 15.1 Hz, 1H) 1.56 (d, J = 10.4 Hz, 1H) 1.61-1.71 (m, 1H) 2.06-2.18 (m, 1H) 2.19-2.34 (m, 8H) 2.39 (d, J = 15.7 Hz, 1H) 2.39-2.50 (m, 2H) 2.50-2.60 (m, 2H) 2.60-2.78 (m, 2H) 2.81-3.05 (m, 3H) 3.07-3.24 (m, 5H) 3.27 (s, 3H) 3.32 (s, 3H) 3.40-3.52 (m, 1H) 3.59 (d, J = 9.34 Hz, 1H) 3.72 (d, J = 8.24 Hz, 1H) 3.96-4.08 (m, 1H) 4.24-4.36 (m, 1H) 4.43 (d, J = 7.14 Hz, 1H) 4.55-4.62 (m, 1H) 4.87 (d, J = 4.67 Hz, 1H) 5.43 (br s, 1H) 7.38 (d, J = 4.40 Hz, J = 8.24 Hz, 1H) 7.56 (d, J = 1.65 Hz, J = 8.52 Hz, 1H) 7.62 (s, 1H) 8.03 (d, J = 8.79 Hz, 1H) 8.10 (d, J = 7.42 Hz, 1H) 8.87 (dd, J = 1.37 Hz, J = 4.4.40 Hz, 1H) |
| 135 | | | 913.6 | (400 MHz): 0.94 (d, J = 7.1 Hz, 3H) 1.01 (d, J = 6.6 Hz, 3H) 1.11 (d, J = 7.3 Hz, 3H) 1.16 (d, J = 7.1 Hz, 3H) 1.20-1.28 (m, 7H) 1.30 (d, J = 6.1 Hz, 3H) 1.37 (s, 3H) 1.48 (m, 1H) 1.57 (dd, J = 4.9, 15.1 Hz, 1H) 1.67 (m, 1H) 1.80-1.90 (m, 2H) 2.12-2.50 (m, 11H) 2.56 (m, 1H) 2.63 (m, 2H) 2.72 (m, 2H) 2.76-2.94 (m, 3H) 2.96-3.05 (m, 2H) 3.08-3.28 (m, 5H) 3.31 (s, 3H) 3.32 (s, 3H) 3.47 (m, 1H) 3.64 (m, 1H) 3.75 (d, J = 8.3 Hz, 1H) 4.03 (m, 1H) 4.43 (d, J = 7.3 Hz, 1H) 4.55 (m, 1H) 4.80-4.96 (m, 2H) 7.28-7.38 (m, 3H) 7.51 (m, 2H) 7.87 (m, 1H) 8.57 (m, 1H) 8.84 (m, 1H) |
| 136 | 35 | | 927.6 | (400 MHz): 0.94 (d, J = 7.1 Hz, 3H) 1.00 (d, J = 6.6 Hz, 3H) 1.11 (d, J = 7.5 Hz, 3H) 1.17 (d, J = 7.0 Hz, 3H) 1.20-1.27 (m, 7H) 1.31 (d, J = 6.3 Hz, 3H) 1.37 (s, 3H) 1.42-1.75 (m, 8H) 2.25-2.50 (m, 12H) 2.52-2.65 (m, 3H) 2.68 (m, 2H) 2.75-3.05 (m, 5H) 3.07-3.25 (m, 5H) 3.30 (s, 3H) 3.32 (s, 3H) 3.47 (m, 1H) 3.64 (m, 1H) 3.70 (d, J = 8.1 Hz, 1H) 4.03 (m, 1H) 4.43 (d, J = 7.1 Hz, 1H) 4.54 (m, 1H) 4.70-5.10 (m, 2H) 7.27-7.38 (m, 3H) 7.50 (m, 2H) 7.86 (m, 1H) 8.57 (m, 1H) 8.84 (m, 1H) |
| 137 | 38 | | 886 FAB MASS | (300 MHz): 0.93 (d, J = 6.9 Hz, 3H) 0.99 (d, J = 6.6 Hz, 3H) 1.08-1.15 (m, 6H) 1.22-1.25 (m, 7H) 1.30 (d, J = 6.3 Hz, 3H) 1.37 (s, 3H) 1.46 (d, J = 15.3 Hz, 1H) 1.56 (dd, J = 15.0 Hz, J = 4.8 Hz, 1H) 1.65-1.72 (m, 1H) 1.86-1.95 (m, 2H) 2.23-2.56 (m, 12H) 2.63 (t, J = 7.2 Hz, 2H) 2.75-2.88 (m, 5H) 2.97-3.02 (m, 2H) 3.09-3.24 (m, 5H) 3.30 (s, 3H) 3.32 (s, 3H) 3.43-3.50 (m, 1H) 3.62 (d, J = 9.6 Hz, 1H) 3.74 (d, J = 8.7 Hz, 1H) 4.02 (dq, J = 9.9 Hz, J = 6.3 Hz, 1H) 4.43 (d, J = 7.2 Hz, 1H) 4.54-4.57 (m, 1H) 4.87 (d, J = 4.2 Hz, 1H) 7.32 (dd, J = 8.4 Hz, J = 1.5 Hz, 1H) 7.38-7.46 (m, 2H) 7.61 (m, 1H) 7.75-7.81 (m, 3H) |

TABLE 1-continued

| Example | Reference Example | R | ESI MS (M + H) | $^1$H-NMR, CDCl$_3$, δ (ppm) |
|---|---|---|---|---|
| 138 | 37 | (2-naphthylethyl-NH-) | 872 FAB MASS | (300 MHz): 0.92-0.99 (m, 6H) 1.10-1.16 (m, 6H) 1.19-1.24 (m, 7H) 1.29 (d, J = 6.0 Hz, 3H) 1.36 (s, 3H) 1.46-1.67 (m, 5H) 2.23-2.57 (m, 11H) 2.74-3.02 (m, 9H) 3.11-3.32 (m, 10H) 3.42-3.49 (m, 1H) 3.61 (d, J = 9.9 Hz, 1H) 3.74 (d, J = 7.8 Hz, 1H) 3.99-4.06 (m, 1H) 4.42 (d, J = 6.9 Hz, 1H) 4.54-4.56 (m, 1H) 4.87 (d, J = 4.5 Hz, 1H) 7.33-7.36 (m, 1H) 7.42-7.48 (m, 2H) 7.65 (m, 1H) 7.78-7.81 (m, 3H) |
| 139 | | (quinolin-6-ylmethyl-NH-) | 859 FAB MASS | (400 MHz): 0.94 (d, J = 7.3 Hz, 3H) 1.02 (d, J = 6.8 Hz, 3H) 1.08 (d, J = 7.3 Hz, 3H) 1.16 (d, J = 7.3 Hz, 3H) 1.19-1.25 (m, 1H) 1.23 (d, J = 5.9 Hz, 3H) 1.25 (s, 3H) 1.30 (d, J = 6.3 Hz, 3H) 1.37 (s, 3H) 1.47 (d, J = 14.9 Hz, 1H) 1.57 (dd, J = 15.1, 4.9 Hz, 1H) 1.66-1.75 (m, 1H) 2.24-2.58 (m, 6H) 2.29 (s, 6H) 2.78-2.93 (m, 3H) 2.95-3.05 (m, 2H) 3.13-3.22 (m, 4H) 3.33 (s, 3H) 3.35 (s, 3H) 3.35-3.40 (m, 1H) 3.41-3.52 (m, 1H) 3.64 (d, J = 9.7 Hz, 1H) 3.74 (d, J = 8.2 Hz, 1H) 3.95 (s, 2H) 3.98-4.07 (m, 1H) 4.42 (d, J = 7.1 Hz, 1H) 4.64-4.69 (m, 1H) 4.84-4.99 (m, 1H) 4.88 (d, J = 4.4 Hz, 1H) 7.39 (dd, J = 8.3, 4.1 Hz, 1H) 7.69 (dd, J = 8.5, 1.7 Hz, 1H) 7.74-7.77 (m, 1H) 8.07 (d, J = 8.5 Hz, 1H) 8.13 (dd, J = 8.3, 1.0 Hz, 1H) 8.89 (dd, J = 4.4, 1.7 Hz, 1H) |
| 140 | 36 | (3-(quinolin-6-yl)propyl-NH-) | 887 FAB MASS | (300 MHz): 0.93 (d, J = 7.1 Hz, 3H) 1.00 (d, J = 6.9 Hz, 3H) 1.10 (d, J = 7.1 Hz, 3H) 1.14 (d, J = 7.1 Hz, 3H) 1.18-1.28 (m, 1H) 1.23 (d, J = 6.0 Hz, 3H) 1.24 (s, 3H) 1.30 (d, J = 6.3 Hz, 3H) 1.37 (s, 3H) 1.47 (d, J = 15.4 Hz, 1H) 1.56 (dd, J = 15.1, 4.9 Hz, 1H) 1.58-1.72 (m, 1H) 1.85-1.97 (m, 2H) 2.18-2.67 (m, 8H) 2.28 (s, 6H) 2.73-3.34 (m, 12H) 3.30 (s, 3H) 3.31 (s, 3H) 3.38-3.53 (m, 1H) 3.63 (d, J = 9.3 Hz, 1H) 3.74 (d, J = 8.0 Hz, 1H) 3.96-4.08 (m, 1H) 4.42 (d, J = 7.1 Hz, 1H) 4.51-4.57 (m, 1H) 4.83-4.99 (m, 1H) 4.87 (d, J = 4.7 Hz, 1H) 7.36 (dd, J = 8.2, 4.1 Hz, 1H) 7.54-7.62 (m, 2H) 8.02 (d, J = 8.5 Hz, 1H) 8.09 (d, J = 7.7 Hz, 1H) 8.85 (dd, J = 4.4, 1.6 Hz, 1H) |
| 141 | 39 | (4-(quinolin-6-yl)butyl-NH-X) | 901 FAB MASS | (400 MHz): 0.93 (d, J = 7.1 Hz, 3H) 1.00 (d, J = 6.8 Hz, 3H) 1.11 (d, J = 7.3 Hz, 3H) 1.16 (d, J = 7.1 Hz, 3H) 1.19-1.26 (m, 1H) 1.23 (d, J = 6.1 Hz, 3H) 1.25 (s, 3H) 1.30 (d, J = 6.1 Hz, 3H) 1.37 (s, 3H) 1.48 (d, J = 14.9 Hz, 1H) 1.52-1.81 (m, 6H) 2.22-2.64 (m, 8H) 2.29 (s, 6H) 2.73-3.05 (m, 7H) 3.07-3.25 (m, 5H) 3.30 (s, 3H) 3.32 (s, 3H) 3.41-3.52 (m, 1H) 3.63 (d, J = 9.5 Hz, 1H) 3.75 (d, J = 8.3 Hz, 1H) 3.98-4.08 (m, 1H) 4.43 (d, J = 7.1 Hz, 1H) 4.52-4.56 (m, 1H) 4.83-4.99 (m, 1H) 4.88 (d, J = 4.6 Hz, 1H) 7.37 (dd, J = 8.3, 4.1 Hz, 1H) 7.55-7.60 (m, 2H) 8.02 (d, J = 8.5 Hz, 1H) 8.10 (dd, J = 8.3, 1.0 Hz, 1H) 8.86 (dd, J = 4.1, 1.7 Hz, 1H) |

TABLE 1-continued

| Reference Example | Reference Example | R | ESI MS (M + H) | 1H-NMR, CDCl3, δ (ppm) |
|---|---|---|---|---|
| 142 | | | 743 | (400 MHz): 0.94 (d, J = 8.00 Hz, 3H) 1.02 (d, J = 6.60 Hz, 3H) 1.12 (d, J = 7.30 Hz, 3H) 1.17 (d, J = 7.00 Hz, 3H) 1.21-1.44 (m, 14H) 1.59 (dd, J = 4.90 Hz, J = 15.1 Hz, 1H) 1.63-1.70 (m, 1H) 2.10-2.58 (m, 12H) 2.72-3.07 (m, 7H) 3.10-3.25 (m, 3H) 3.29 (s, 3H) 3.34 (s, 3H) 3.44-3.55 (m, 1H) 3.62 (d, J = 9.80 Hz, 1H) 3.78 (q, J = 7.30 Hz, 1H) 3.99-4.12 (m, 1H) 4.50 (d, J = 7.00 Hz, 1H) 4.88-5.10 (m, 4H) 5.68-5.84 (m, 1H) 6.77 (d, J = 8.24 Hz, 1H) 7.09 (d, J = 7.97 Hz, 1H) 7.27-7.29 (m, 1H) |
| 143 | | | 745 FAB MASS | (400 MHz): 0.90 (t, J = 7.40 Hz, 3H) 0.94 (d, J = 7.10 Hz, 3H) 1.02 (d, J = 6.60 Hz, 3H) 1.11 (d, J = 7.50 Hz, 3H) 1.18 (d, J = 7.10 Hz, 3H) 1.20-1.32 (m, 12H) 1.32-1.40 (m, 5H) 1.41-1.52 (m, 1H) 1.60 (dd, J = 4.90 Hz, J = 15.1 Hz, 1H) 1.63-1.69 (m, 1H) 2.00-2.10 (m, 1H) 2.15-2.34 (m, 8H) 2.39 (d, J = 15.1 Hz, 1H) 2.42-2.54 (m, 2H) 2.75-3.07 (m, 7H) 3.08-3.12 (m, 1H) 3.17 (d, J = 11.7 Hz, 1H) 3.21 (dd, J = 7.30 Hz, J = 10.5 Hz, 1H) 3.28 (s, 3H) 3.33 (s, 3H) 3.44-3.53 (m, 1H) 3.61 (d, J = 9.80 Hz, 1H) 3.77 (d, J = 7.10 Hz, 1H) 4.00-4.09 (m, 1H) 4.49 (d, J = 7.00 Hz, 1H) 4.88-4.95 (m, 2H) |
| 144 | | | 819 FAB MASS | (300 MHz): 0.94 (d, J = 7.14 Hz, 3H) 1.02 (d, J = 6.59 Hz, 3H) 1.15 (d, J = 7.14 Hz, 3H) 1.17 (d, J = 5.49 Hz, 3H) 1.19-1.28 (m, 7H) 1.30 (d, J = 6.04 Hz, 3H) 1.37 (s, 3H) 1.43 (d, J = 15.4 Hz, 3H) 1.59 (dd, J = 4.67 Hz, J = 14.8 Hz, 1H) 1.62-1.70 (m, 1H) 2.14-2.34 (m, 9H) 2.34-2.59 (m, 5H) 2.74-3.07 (m, 5H) 3.08-3.26 (m, 2H) 3.29 (s, 3H) 3.34 (s, 3H) 3.43-3.56 (m, 1H) 3.63 (d, J = 9.62 Hz, 1H) 3.78 (d, J = 7.14 Hz, 1H) 3.99-4.11 (m, 1H) 4.50 (d, J = 7.14 Hz, 1H) 4.92 (d, J = 4.67 Hz, 1H) 4.95-5.00 (m, 1H) 6.14 (dt, J = 6.87 Hz, J = 15.9 Hz, 1H) 6.39 (d, J = 15.9 Hz, 1H) 7.14-7.36 (m, 5H) |
| 145 | | | 869 FAB MASS | (300 MHz): 0.96 (d, J = 7.14 Hz, 3H) 1.03 (d, J = 6.59 Hz, 3H) 1.16 (d, J = 6.59 Hz, 3H) 1.17 (d, J = 7.42 Hz, 3H) 1.19-1.27 (m, 7H) 1.31 (d, J = 6.04 Hz, 3H) 1.38 (s, 3H) 1.45 (d, J = 14.6 Hz, 3H) 1.59 (dd, J = 4.67 Hz, J = 15.1 Hz, 1H) 1.62-1.72 (m, 1H) 2.15-2.35 (m, 9H) 2.35-2.63 (m, 5H) 2.80-3.09 (m, 4H) 3.10-3.27 (m, 3H) 3.30 (s, 3H) 3.34 (s, 3H) 3.43-3.56 (m, 1H) 3.65 (d, J = 9.62 Hz, 1H) 3.79 (d, J = 7.14 Hz, 1H) 3.97-4.11 (m, 1H) 4.50 (d, J = 7.14 Hz, 1H) 4.93 (d, J = 4.40 Hz, 1H) 5.00-5.08 (m, 1H) 6.17 (dt, J = 7.14 Hz, J = 15.4 Hz, 1H) 7.14 (d, J = 15.4 Hz, 1H) 7.38-7.56 (m, 4H) 7.75 (d, J = 7.97 Hz, 1H) 7.79-7.88 (m, 1H) 8.05-8.13 (m, 1H) |

TABLE 1-continued

| Example | Reference Example | R | ESI MS (M + H) | $^1$H-NMR, CDCl$_3$, δ (ppm) |
|---|---|---|---|---|
| 146 | | 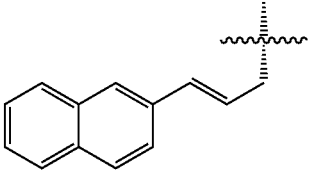 | 869 FAB MASS | (300 MHz): 0.95 (d, J = 7.14 Hz, 3H) 1.03 (d, J = 6.59 Hz, 3H) 1.16 (d, J = 7.41 Hz, 3H) 1.17 (d, J = 6.87 Hz, 3H) 1.19-1.28 (m, 7H) 1.30 (d, J = 6.32 Hz, 3H) 1.38 (s, 3H) 1.44 (d, J = 14.8 Hz, 3H) 1.59 (dd, J = 4.67 Hz, J = 15.4 Hz, 1H) 2.14-2.62 (m, 14H) 2.76-3.07 (m, 4H) 3.17-3.32 (m, 6H) 3.34 (s, 3H) 3.43-3.56 (m, 1H) 3.64 (d, J = 9.34 Hz, 1H) 3.79 (d, J = 7.14 Hz, 1H) 3.98-4.12 (m, 1H) 4.50 (d, J = 7.14 Hz, 1H) 4.93 (d, J = 4.40 Hz, 1H) 4.97-5.04 (m, 1H) 6.27 (dt, J = 6.87 Hz, J = 15.9 Hz, 1H) 7.14 (d, J = 15.4 Hz, 1H) 7.36-7.48 (m, 2H) 7.55 (dd, J = 1.37 Hz, J = 8.42 Hz, 1H) 7.66 (s, 1H) 7.72-7.84 (m, 3H) |
| 147 | 33 | 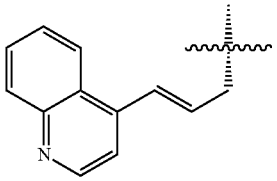 | 870 | (300 MHz): 0.94 (d, J = 7.1 Hz, 3H) 1.03 (d, J = 6.6 Hz, 3H) 1.15 (d, J = 5.2 Hz, 3H) 1.15-1.30 (m, 1H) 1.17 (d, J = 7.4 Hz, 3H) 1.23 (d, J = 6.0 Hz, 3H) 1.26 (s, 3H) 1.30 (d, J = 6.0 Hz, 3H) 1.38 (s, 3H) 1.46 (d, J = 15.4 Hz, 1H) 1.59 (dd, J = 15.4, 4.9 Hz, 1H) 1.63-1.72 (m, 1H) 2.15-2.67 (m, 9H) 2.30 (s, 6H) 2.77-3.02 (m, 6H) 3.10-3.32 (m, 3H) 3.30 (s, 3H) 3.33 (s, 3H) 3.43-3.57 (m, 1H) 3.65 (d, J = 9.6 Hz, 1H) 3.79 (d, J = 7.4 Hz, 1H) 3.99-4.12 (m, 1H) 4.50 (d, J = 7.1 Hz, 1H) 4.92 (d, J = 4.4 Hz, 1H) 5.00-5.07 (m, 1H) 6.36-6.48 (m, 1H) 7.12 (d, J = 15.7 Hz, 1H) 7.41 (d, J = 4.4 Hz, 1H) 7.52-7.60 (m, 1H) 7.67-7.75 (m, 1H) |
| 148 | | 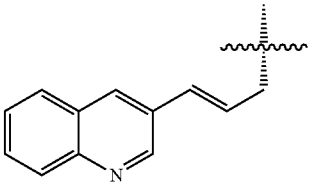 | 870 FAB MASS | (400 MHz): 0.70 (d, J = 7.1 Hz, 3H) 1.00 (d, J = 6.6 Hz, 3H) 1.18 (d, J = 7.1 Hz, 3H) 1.22-1.29 (m, 7H) 1.26 (s, 3H) 1.32 (d, J = 6.3 Hz, 3H) 1.36 (s, 3H) 1.47 (d, J = 14.9 Hz, 1H) 1.59 (dd, J = 15.1, 4.9 Hz, 1H) 1.67-1.75 (m, 1H) 2.15-2.65 (m, 9H) 2.40 (s, 6H) 2.71-3.07 (m, 7H) 3.09-3.15 (m, 1H) 3.22 (d, J = 11.7 Hz, 1H) 3.28-3.35 (m, 1H) 3.30 (s, 3H) 3.34 (s, 3H) 3.45-3.57 (m, 1H) 3.70 (d, J = 9.5 Hz, 1H) 3.80 (d, J = 7.8 Hz, 1H) 4.01-4.11 (m, 1H) 4.49 (d, J = 7.1 Hz, 1H) 4.52-4.85 (m, 2H) 4.92 (d, J = 4.4 Hz, 1H) 5.01-5.06 (m, 1H) 6.51-6.55 (m, 2H) 7.49-7.55 (m, 1H) 7.62-7.68 (m, 1H) 7.78 (d, J = 8.0 Hz, 1H) 7.93-7.96 (m, 1H) 8.12 (d, J = 8.3 Hz, 1H) 9.01-9.04 (m, 1H) |
| 149 | 42 | 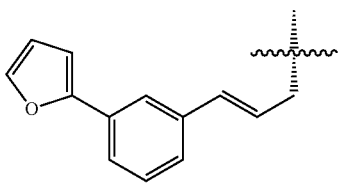 | 885 FAB MASS | (300 MHz): 0.95 (d, J = 6.9 Hz, 3H) 1.02 (d, J = 6.3 Hz, 3H) 1.07-1.28 (m, 13H) 1.26 (s, 3H) 1.37 (s, 3H) 1.43 (d, J = 14.6 Hz, 1H) 1.59 (dd, J = 15.1, 4.4 Hz, 1H) 1.62-1.72 (m, 1H) 2.13-2.62 (m, 9H) 2.31 (s, 6H) 2.74-3.42 (m, 9H) 3.29 (s, 3H) 3.34 (s, 3H) 3.43-3.56 (m, 1H) 3.63 (m, J = 9.9 Hz, 1H) 3.78 (d, J = 6.9 Hz, 1H) 3.98-4.12 (m, 1H) 4.50 (d, J = 7.4 Hz, 1H) 4.92 (d, J = 4.4 Hz, 1H) 4.95-5.01 (m, 1H) 6.14-6.25 (m, 1H) 6.43 (d, J = 15.9 Hz, 1H) 6.45-6.49 (m, 1H) 6.61-6.67 (m, 1H) 7.19-7.34 (m, 2H) 7.44-7.55 (m, 2H) 7.62 (s, 1H) |

TABLE 1-continued

| Example | Reference Example | R | ESI MS (M + H) | ¹H-NMR, CDCl₃, δ (ppm) |
|---|---|---|---|---|
| 150 | | 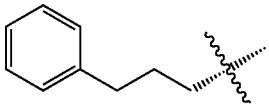 | 821 FAB MASS | (300 MHz): 0.93 (d, J = 6.87 Hz, 3H) 1.01 (d, J = 6.59 Hz, 3H) 1.08 (d, J = 7.42 Hz, 3H) 1.15 (d, J = 6.87 Hz, 3H) 1.18-1.46 (m, 16H) 1.47-1.70 (m, 4H) 2.00-2.12 (m, 1H) 2.13-2.34 (m, 8H) 2.39 (d, J = 14.8 Hz, 1H) 2.41-2.53 (m, 2H) 2.54-2.68 (m, 2H) 2.72-3.06 (m, 6H) 3.07-3.12 (m, 1H) 3.16 (d, J = 12.1 Hz, 1H) 3.23 (dd, J = 2.75 Hz, J = 10.2 Hz, 1H) 3.27 (s, 3H) 3.34 (s, 3H) 3.43-3.55 (m, 1H) 3.59 (d, J = 9.07 Hz, 1H) 3.76 (d, J = 7.14 Hz, 1H) 3.98-4.10 (m, 1H) 4.49 (d, J = 7.14 Hz, 1H) 4.87-4.95 (m, 2H) 7.11-7.21 (m, 3H) 7.23-7.31 (m, 2H) |
| 151 | | 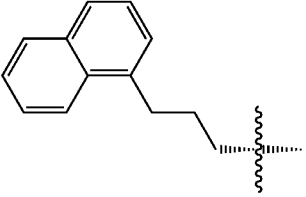 | 871 FAB MASS | (300 MHz): 0.93 (d, J = 6.87 Hz, 3H) 100 (d, J = 6.32 Hz, 3H) 1.03-1.10 (m, 6H) 1.13-1.41 (m, 14H) 1.44-1.77 (m, 6H) 2.04-2.27 (m, 3H) 2.31 (s, 6H) 2.39 (d, J = 15.4 Hz, 1H) 2.40-2.54 (m, 3H) 2.66-3.30 (m, 15H) 3.36 (s, 3H) 3.42-3.55 (m, 1H) 3.57 (d, J = 9.89 Hz, 1H) 3.75 (d, J = 7.69 Hz, 1H) 3.97-4.10 (m, 1H) 4.49 (d, J = 6.87 Hz, 1H) 4.85-4.94 (m, 2H) 7.30 (d, J = 6.87 Hz, 1H) 7.35-7.54 (m, 3H) 7.69 (d, J = 7.69 Hz, 1H) 7.79-7.87 (m, 1H) 8.01 (d, J = 7.97 Hz, 1H) |
| 152 | | 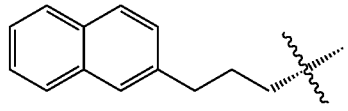 | 871 FAB MASS | (300 MHz): 0.91 (d, J = 7.14 Hz, 3H) 0.96-1.05 (m, 6H) 108 (d, J = 6.87 Hz, 3H) 1.17-1.51 (m, 16H) 1.52-1.72 (m, 4H) 2.00-2.26 (m, 3H) 2.31 (s, 6H) 2.36 (d, J = 15.1 Hz, 1H) 2.38-2.52 (m, 2H) 2.65-3.06 (m, 7H) 3.06-3.12 (m, 1H) 3.16 (d, J = 11.8 Hz, 1H) 3.20 (dd, J = 3.30 Hz, J = 10.2 Hz, 1H) 3.26 (s, 3H) 3.33 (s, 3H) 3.42-3.60 (m, 2H) 3.74 (d, J = 6.87 Hz, 1H) 3.96-4.08 (m, 1H) 4.47 (d, J = 7.14 Hz, 1H) 4.85-4.95 (m, 2H) 7.30 (dd, J = 1.37 Hz, J = 8.52 Hz, 1H) 7.35-7.47 (m, 2H) 7.59 (s, 1H) 7.73-7.82 (m, 3H) |
| 153 | | 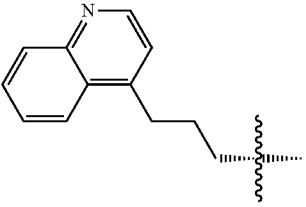 | 872 FAB MASS | (300 MHz): 0.91 (d, J = 6.9 Hz, 3H) 1.00 (d, J = 6.0 Hz, 3H) 1.03-1.13 (m, 6H) 1.22-1.25 (m, 1H) 1.23 (d, J = 6.0 Hz, 3H) 1.26 (s, 3H) 1.29 (d, J = 6.3 Hz, 3H) 1.35 (s, 3H) 1.35-1.42 (m, 1H) 1.49-1.83 (m, 6H) 2.02-2.54 (m, 7H) 2.30 (s, 6H) 2.67-3.28 (m, 10H) 3.27 (s, 3H) 3.35 (s, 3H) 3.42-3.53 (m, 1H) 3.57 (d, J = 9.9 Hz, 1H) 3.75 (d, J = 7.1 Hz, 1H) 3.98-4.10 (m, 1H) 4.48 (d, J = 7.1 Hz, 1H) 4.86-4.94 (m, 2H) 7.22 (d, J = 4.4 Hz, 1H) 7.52-7.59 (m, 1H) 7.66-7.73 (m, 1H) 8.01 (d, J = 8.2 Hz, 1H) 8.10 (d, J = 8.2 Hz, 1H) 8.81 (d, J = 4.4 Hz, 1H) |

TABLE 1-continued

| Example | Reference Example | R | ESI MS (M + H) | $^1$H-NMR, CDCl$_3$, δ (ppm) |
|---|---|---|---|---|
| 154 | | (3-quinolinyl propyl group) | 872 FAB MASS | (400 MHz): 0.70 (d, J = 6.8 Hz, 3H) 0.98 (d, J = 6.6 Hz, 3H) 1.09 (d, J = 7.6 Hz, 3H) 1.12 (d, J = 7.1 Hz, 3H) 1.23 (d, J = 5.8 Hz, 3H) 1.22-1.25 (m, 1H) 1.26 (s, 3H) 1.30 (d, J = 6.1 Hz, 3H) 1.33 (s, 3H) 1.40-1.85 (m, 7H) 2.05-2.54 (m, 7H) 2.34 (s, 6H) 2.69-2.95 (m, 7H) 2.98-3.09 (m, 2H) 3.13 (d, J = 11.7 Hz, 1H) 3.26-3.33 (m, 1H) 3.26 (s, 3H) 3.34 (s, 3H) 3.45-3.54 (m, 1H) 3.57 (d, J = 9.7 Hz, 1H) 3.75 (d, J = 7.3 Hz, 1H) 3.83-3.96 (m, 1H) 4.00-4.08 (m, 1H) 4.47 (d, J = 7.3 Hz, 1H) 4.87-4.93 (m, 2H) 7.48-7.55 (m, 1H) 7.62-7.67 (m, 1H) 7.78 (d, J = 8.3 Hz, 1H) 7.92 (s, 1H) 8.06 (d, J = 8.3 Hz, 1H) 8.76 (d, J = 2.2 Hz, 1H) |
| 155 | | (3-(tetrahydrofuran-2-yl)phenyl propyl group) | 891 | mixture of diastereomers, (400 MHz): 0.93 (d, J = 6.8 Hz, 3H) 1.01 (d, J = 6.3 Hz, 3H) 1.09 (d, J = 7.3 Hz, 3H) 1.16 (d, J = 7.1 Hz, 3H) 1.20-1.26 (m, 1H) 1.23 (d, J = 6.1 Hz, 3H) 1.26 (s, 3H) 1.30 (d, J = 6.3 Hz, 3H) 1.36 (s, 3H) 1.37-1.74 (m, 7H) 1.75-1.85 (m, 1H) 1.94-2.10 (m, 3H) 2.13-2.53 (m, 5H) 2.31 (s, 6H) 2.55-2.66 (m, 2H) 2.73-3.38 (m, 10H) 3.28 (s, 3H) 3.34 (s, 3H) 3.45-3.55 (m, 1H) 3.60 (d, J = 10.0 Hz, 1H) 3.77 (d, J = 7.1 Hz, 1H) 3.89-3.96 (m, 1H) 4.00-4.13 (m, 2H) 4.49 (d, J = 7.1 Hz, 1H) 4.86 (t, J = 7.1 Hz, 1H) 4.89-4.95 (m, 2H) 7.05 (d, J = 7.6 Hz, 1H) 7.11-7.16 (m, 2H) 7.23 (d, J = 7.8 Hz, 1H) |
| 156 | | (propargyl group) | 741 | (400 MHz): 0.94 (d, J = 7.1 Hz, 3H) 1.02 (d, J = 6.9 Hz, 3H) 1.11 (d, J = 7.6 Hz, 3H) 1.17 (d, J = 7.3 Hz, 3H) 1.20-1.27 (m, 7H) 1.30 (d, J = 6.3 Hz, 3H) 1.37 (s, 3H) 1.43 (m, 1H) 1.59 (dd, J = 4.9, 15.1 Hz, 1H) 1.67 (m, 1H) 1.91 (t, J = 2.3 Hz, 1H) 1.92-2.55 (m, 14H) 2.78-3.08 (m, 8H) 3.12-3.25 (m, 3H) 3.28 (m, 3H) 3.33 (s, 3H) 3.49 (m, 1H) 3.60 (m, 1H) 3.76 (m, 1H) 4.04 (m, 1H) 4.48 (d, J = 7.3 Hz, 1H) 4.66 (m, 1H) 4.92 (m, 1H) 4.98 (m, 1H) |
| 157 | | (3-phenyl-2-propynyl group) | 817 | (400 MHz): 0.94 (d, J = 7.1 Hz, 3H) 1.02 (d, J = 6.9 Hz, 3H) 1.11 (d, J = 7.6 Hz, 3H) 1.17 (d, J = 7.3 Hz, 3H) 1.20-1.27 (m, 7H) 1.30 (d, J = 6.3 Hz, 3H) 1.37 (s, 3H) 1.43 (m, 1H) 1.59 (dd, J = 4.9, 15.1 Hz, 1H) 1.67 (m, 1H) 1.91 (t, J = 2.3 Hz, 1H) 1.92-2.55 (m, 14H) 2.78-3.08 (m, 8H) 3.12-3.25 (m, 3H) 3.28 (m, 3H) 3.33 (s, 3H) 3.49 (m, 1H) 3.60 (m, 1H) 3.76 (m, 1H) 4.04 (m, 1H) 4.48 (d, J = 7.3 Hz, 1H) 4.66 (m, 1H) 4.92 (m, 1H) 4.98 (m, 1H) |
| 158 | | (naphthalen-2-ylthiomethyl group) | 875 FAB MASS | (300 MHz): 0.93 (d, J = 7.2 Hz, 3H) 0.99 (d, J = 6.9 Hz, 3H) 1.19-1.30 (m, 10H) 1.36-1.43 (m, 4H) 1.58 (dd, J = 15.3 Hz, J = 5.1 Hz, 1H) 1.71-1.76 (m, 1H) 2.03 (d, J = 5.7 Hz, 1H) 2.35-2.54 (m, 10H) 2.84-3.12 (m, 9H) 3.19-3.28 (m, 7H) 3.32 (s, 3H) 3.47-3.51 (m, 1H) 3.60 (d, J = 10.2 Hz, 1H) 3.77 (d, J = 7.2 Hz, 1H) 4.03 (dq, J = 9.0 Hz, J = 6.3 Hz, 1H) 4.49 (d, J = 7.2 Hz, 1H) 4.91 (d, J = 4.5 Hz, 1H) 5.02-5.05 (m, 1H) 7.40-7.50 (m, 3H) 7.74-7.78 (m, 4H) |

Example 1

(1) The compound obtained in Reference Example 1 (1 g), the compound obtained in Reference Example 2 (2.28 g), and ytterbium triflate monohydrate (62.4 mg) were dissolved in tetrahydrofuran (120 ml), and the solution was stirred at 80° C. for 20 minutes under microwave irradiation. The reaction mixture was concentrated under reduced pressure, and the resulting residue was purified by silica gel column chromatography (chloroform:methanol:28% aqueous ammonia=70:1:0.1 to 8:1:0.1) to obtain a lactonization precursor where the steric configuration of the asymmetric carbon atom on the pyrrolidine ring is R (237 mg), and a lactonization precursor where the steric configuration of the asymmetric carbon atom on the pyrrolidine ring is S (225 mg). As another method different from the aforementioned method, the compound obtained in Reference Example 1 (50.8 g), the compound obtained in Reference Example 60 (25.5 g), and ytterbium triflate monohydrate (6.53 g) were dissolved in tetrahydrofuran (190 ml), the solution was added with triethylamine (21.4 ml), and the mixture was stirred at 90° C. for 2 hours. The reaction mixture was concentrated under reduced pressure, and the resulting residue was purified by silica gel column chromatography (chloroform:methanol:28% aqueous ammonia=10:1:0.1) to also obtain a lactonization precursor (30.0 g) where the steric configuration of the asymmetric carbon atom on the pyrrolidine ring is R.

(2) 4-Dimethylaminopyridine (6.42 g) and 2-methyl-6-nitrobenzoic anhydride (9.05 g) were dissolved in methylene chloride (1664 ml), the solution was added dropwise with a solution of the lactonization precursor obtained in (1) mentioned above (9.32 g) where the steric configuration of the asymmetric carbon atom on the pyrrolidine ring is R in methylene chloride (200 ml) at room temperature over 4 hours and 30 minutes, and then the mixture was further stirred at room temperature for 3 hours. The reaction mixture was added with saturated aqueous sodium hydrogencarbonate, the layers were separated, and the organic layer was dried over anhydrous magnesium sulfate, and filtered. The filtrate was concentrated under reduced pressure, and the resulting residue was purified by silica gel column chromatography (hexane:acetone=70:1 to 20:1) to obtain a cyclized compound (4.25 g).

(3) The compound obtained in (2) mentioned above (48.3 mg) was dissolved in tetrahydrofuran (966 µl), the solution was added with hydrogen fluoride-pyridine complex (12 µl), and the mixture was stirred at room temperature for 23 hours. The reaction mixture was added with saturated aqueous sodium hydrogencarbonate and methylene chloride, the layers were separated, then the organic layer was concentrated under reduced pressure, and the resulting residue was purified by preparative thin layer chromatography (chloroform:methanol:28% aqueous ammonia=5:1:0.1) to obtain the compound shown in Table 1 (30.6 mg).

In Examples 2 to 7, synthesis was performed in the same manner as that of Example 1 by using corresponding epoxide reagents.

Example 8

(1) By using the compound obtained in Reference Example 1 (123 mg), and the compound obtained in Reference Example 7 (176 mg) as starting materials, a lactonization precursor (69.6 mg) was obtained in the same manner as that of Example 1, (1).

(2) By using the compound obtained in (1) mentioned above (69.6 mg) as a starting material, a cyclized compound (30.3 mg) was obtained in the same manner as that of Example 1, (2).

(3) By using the compound obtained in (2) mentioned above (30.3 mg) as a starting material, the compound shown in Table 1 (17.9 mg) was obtained in the same manner as that of Example 1, (3).

Example 9

(1) By using the compound obtained in Reference Example 1 (43.4 g), the compound obtained in Reference Example 10 (25 g) as a starting material, a cyclized compound (27 g) was obtained in the same manners as those of Example 1, (1) and (2).

(2) By using the compound obtained in (1) mentioned above (100 mg) as a starting material, the compound shown in Table 1 (65 mg) was obtained in the same manner as that of Example 1, (3).

Example 10

(1) By using the compound obtained in Reference Example 1 ((5.8 g), and the compound obtained in Reference Example 11 (5.0 g) as starting materials, a cyclized compound (3.12 g) was obtained in the same manners as those of Example 1, (1) and (2).

(2) By using the compound obtained in (1) mentioned above (100 mg) as a starting material, the compound shown in Table 1 (67.5 mg) was obtained in the same manner as that of Example 1, (3).

Example 11

The compound obtained in Example 9, (2) (56.3 mg) was dissolved in methanol (1 ml), the solution was added with 5% palladium-carbon (56 mg), and the mixture was stirred at room temperature for 1 hour under a hydrogen atmosphere of 1 atm. The reaction mixture was filtered, then the filtrate was concentrated under reduced pressure, the resulting residue was dissolved in methanol (1 ml), the solution was added with 20% palladium hydroxide-carbon (112 mg), and the mixture was stirred at room temperature for 2 hours under a hydrogen atmosphere of 1 atm. The reaction mixture was filtered, then the filtrate was concentrated under reduced pressure, the resulting residue was dissolved in methanol (1 ml), the solution was added with 20% palladium hydroxide-carbon (120 mg), and the mixture was stirred at room temperature for 2 hours under a hydrogen atmosphere of 1 atm. The reaction mixture was filtered, then the filtrate was concentrated under reduced pressure, and the resulting residue was purified by preparative thin layer chromatography (chloroform:methanol:28% aqueous ammonia=10:1:0.1) to obtain the compound shown in Table 1 (15 mg).

Example 12

By using the compound obtained in Example 10, (2) (50 mg) as a starting material, the compound shown in Table 1 (11.0 mg) was obtained in the same manner as that of Example 11.

Example 13

(1) By using the compound obtained in Example 9, (1) (230 mg) as a starting material, a debenzylated compound (163 mg) was obtained in the same manner as that of Example 11.

(2) The compound obtained in (1) mentioned above (106 mg) was dissolved in chloroform (1 ml), the solution was added with triethylamine (41.2 µl), p-toluenesulfonyl chloride (28.2 mg), and 4-dimethylaminopyridine (6.0 mg), and the mixture was stirred for 18 hours under reflux by heating. The mixture was added with saturated aqueous sodium hydrogencarbonate and chloroform, the layers were separated, and then the organic layer was dried over anhydrous magnesium sulfate, and filtered. The filtrate was concentrated under reduced pressure, and the resulting residue was purified by silica gel column chromatography (hexane:ethyl acetate=10:1 to 4:1) to obtain a p-toluenesulfonyl compound (89 mg).

(3) The compound obtained in (2) mentioned above (99 mg) was dissolved in dimethylformamide (2 ml), the solution was added with sodium azide (7.9 mg), and the mixture was stirred at 80° C. for 20 hours. The reaction mixture was added with ethyl acetate, the mixture was washed with saturated brine, and then the organic layer was dried over anhydrous magnesium sulfate, and filtered. The filtrate was concentrated under reduced pressure, and the resulting residue was purified by silica gel column chromatography (hexane:ethyl acetate=15:1 to 4:1) to obtain an azide compound (57 mg).

(4) By using the compound obtained in (3) mentioned above (55 mg) as a starting material, a deprotected compound (30 mg) was obtained in the same manner as that of Example 1, (3).

(5) The compound obtained in (4) mentioned above (10 mg) was dissolved in methanol (0.5 ml), the solution was added with 5% palladium-carbon (10 mg), and the mixture was stirred at room temperature for 2 hours under a hydrogen atmosphere of 1 atm. The reaction mixture was filtered through Celite, and then the filtrate was concentrated under reduced pressure to obtain the compound shown in Table 1 (9 mg).

Example 14

The compound obtained in Example 13 (11.0 mg) was dissolved in chloroform (1 ml), the solution was added with 36% aqueous formaldehyde (26 μl), and sodium triacetoxyborohydride (9.8 mg), and the mixture was stirred at room temperature for 30 minutes. The reaction mixture was added with saturated aqueous sodium hydrogencarbonate and chloroform, the layers were separated, and then the organic layer was dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 1 (5.3 mg).

Example 15

The compound obtained in Example 13, (2) (43 mg) was added with dimethylformamide (0.5 ml), and potassium cyanide (26.5 mg), and the mixture was stirred at 100° C. for 8 hours. The reaction mixture was added with saturated aqueous sodium hydrogencarbonate and ethyl acetate, the layers were separated, and the organic layer was washed twice with distilled water. The organic layer was dried over anhydrous magnesium sulfate, and filtered. The filtrate was concentrated under reduced pressure, and the resulting residue was purified by preparative thin layer chromatography (hexane:acetone:triethylamine=30:10:0.2) to obtain the compound shown in Table 1 (13 mg).

Example 16

(1) By using the compound obtained in Example 13, (3) (433 mg) as a starting material, an amine compound (414 mg) was obtained in the same manner as that of Example 13, (5).

(2) The compound obtained in (1) mentioned above (82 mg) was dissolved in chloroform (2 ml), the solution was added with 1-naphthoic acid (40.6 mg) and 1-ethyl-3-(3-dimethylaminopropyl)carbodiimide hydrochloride (45.1 mg), and the mixture was stirred at room temperature for 1 hour. The reaction mixture was concentrated under reduced pressure, and the resulting residue was purified by silica gel column chromatography (hexane:ethyl acetate=10:1 to hexane:acetone:triethylamine=60:10:0.2) to obtain an amide compound (79 mg).

(3) By using the compound obtained in (2) mentioned above (76 mg) as a starting material, the compound shown in Table 1 (26 mg) was obtained in the same manner as that of Example 1, (3).

Example 17

By using the compound obtained in Example 16, (1) (82 mg) and 1-naphthaleneacetic acid (43.9 mg) as starting materials, the compound shown in Table 1 (20 mg) was obtained in the same manners as those of Example 16, (2) and Example 1, (3).

Example 18

By using the compound obtained in Example 16, (1) (82 mg) and 3-(1-naphthyl)propionic acid (47.3 mg) as starting materials, the compound shown in Table 1 (22 mg) was obtained in the same manners as those of Example 16, (2) and Example 1, (3).

Example 19

(1) By using the compound obtained in Example 16, (1) (60 mg) and 3-bromophenylacetic acid (35.2 mg) as starting materials, an amide compound (32 mg) was obtained in the same manner as that of Example 16, (2).

(2) Tri(o-tolyl)phosphine (1.4 mg) was dissolved in toluene (1 ml), the solution was successively added with tris(dibenzylideneacetone)dipalladium(0) (2.1 mg), tri-n-butyl(2-furyl)tin (16.6 mg), and a solution of the compound obtained in (1) mentioned above (29 mg) in toluene (0.5 ml), and the mixture was stirred for 1.5 hours under reflux by heating. The reaction mixture was concentrated under reduced pressure, and the resulting residue was purified by silica gel column chromatography (hexane:ethyl acetate=10:1 to hexane:acetone:triethylamine=100:10:0.2) to obtain a biaryl compound (29 mg).

(3) By using the compound obtained in (2) mentioned above (26 mg) as a starting material, the compound shown in Table 1 (11 mg) was obtained in the same manner as that of Example 1, (3).

Example 20

By using the compound obtained in Example 16, (1) (82 mg) and 3-bromobenzoic acid (47.5 mg) as starting materials, the compound shown in Table 1 (17 mg) was obtained in the same manners as those of Example 16, (2), Example 19, (2), and Example 1, (3).

Example 21

By using the compound obtained in Example 16, (1) (82 mg) and 3-(3-bromophenyl)propionic acid (54.1 mg) as starting materials, the compound shown in Table 1 (16 mg) was obtained in the same manners as those of Example 16, (2), Example 19, (2), Example 1, (3).

Example 22

By using the compound obtained in Example 13, (3) (40 mg) as a starting material, an amine compound was obtained in the same manner as that of Example 13, (5). By using the resulting amine compound and benzaldehyde (4.4 µl) as starting materials, the compound shown in Table 1 (2.1 mg) was obtained in the same manners as those of Example 14 and Example 1, (3).

Example 23

(1) The compound obtained in Example 10, (1) (1.0 g) was dissolved in a mixed solvent of methanol and tetrahydrofuran (2:1, 21 ml), the solution was added with 20% palladium hydroxide (1.0 g), and the mixture was stirred at 40° C. for 8 hours, and at room temperature for 2 days under a hydrogen atmosphere of 1 atm. The reaction mixture was filtered, and then the filtrate was concentrated under reduced pressure to obtain a debenzylated compound (1.01 g).
(2) By using the compound obtained in (1) mentioned above (1.0 g) as a starting material, an azide compound (536 mg) was obtained in the same manners as those of Example 13, (2) and (3).
(3) The compound obtained in (2) mentioned above (100 mg) was dissolved in tetrahydrofuran (2 ml), the solution was added with 5% palladium-carbon (100 mg), and the mixture was stirred at room temperature for 1 hour under a hydrogen atmosphere of 1 atm. The reaction mixture was filtered, and then the filtrate was concentrated under reduced pressure to obtain an amine compound (107.2 mg).
(4) By using the compound obtained in (3) mentioned above (30 mg) and 3-(1-naphthyl)propionic acid (16.8 mg) as starting materials, the compound shown in Table 1 (6.7 mg) was obtained in the same manners as those of Example 16, (2) and Example 1, (3).

Example 24

By using the compound obtained in Example 23, (3) (35 mg) and 1-naphthaleneacetic acid (18.2 mg) as starting materials, the compound shown in Table 1 (20.3 mg) was obtained in the same manners as those of Example 16, (2) and Example 1, (3).

Example 25

By using the compound obtained in Example 23, (3) (35 mg) and 1-naphthoic acid (16.8 mg) as starting materials, the compound shown in Table 1 (17.9 mg) was obtained in the same manners as those of Example 16, (2) and Example 1, (3).

Example 26

(1) By using the compound obtained in Example 23, (3) (30 mg) and 3-bromophenylpropionic acid (19.2 mg) as starting materials, an amide compound (27.4 mg) was obtained in the same manner as that of Example 16, (2).
(2) By using the compound obtained in (1) mentioned above (25 mg) as a starting material, a biaryl compound (22.0 mg) was obtained in the same manner as that of Example 19, (2).
(3) By using the compound obtained in (2) mentioned above (20 mg) as a starting material, the compound shown in Table 1 (14.8 mg) was obtained in the same manner as that of Example 1, (3).

Example 27

By using the compound obtained in Example 23, (3) (35 mg) and 3-bromobenzoic acid (19.6 mg) as starting materials, the compound shown in Table 1 (12.0 mg) was obtained in the same manners as those of Example 16, (2), Example 19, (2), and Example 1, (3).

Example 28

By using the compound obtained in Example 23, (3) (30 mg) and 3-bromophenylacetic acid (16.0 mg) as starting materials, the compound shown in Table 1 (7.4 mg) was obtained in the same manners as those of Example 16, (2), Example 19, (2), and Example 1, (3).

Example 29

(1) The compound obtained in Example 13, (1) (20 mg) was dissolved in toluene (400 µl), the solution was added with 2-phenylphenol (15.8 mg), triphenylphosphine (9.8 mg), and 1,1'-azobis(N,N-dimethylformamide) (6.4 mg), and the mixture was stirred at 100° C. for 2 hours. The reaction mixture was concentrated under reduced pressure, and the resulting residue was purified by silica gel column chromatography (hexane:acetone:triethylamine=30:10:0.2) to obtain an ether compound (15 mg).
(2) The compound obtained in (1) mentioned above (15 mg) was dissolved in tetrahydrofuran (0.15 ml), the solution was added with hydrogen fluoride-pyridine complex (13.7 µl, and the mixture was stirred at room temperature for 18 hours. The reaction mixture was neutralized with saturated aqueous sodium hydrogencarbonate, and then added with 10% aqueous sodium hydroxide and ethyl acetate, the layers were separated, and the organic layer was dried over anhydrous magnesium sulfate, and filtered. The filtrate was concentrated under reduced pressure, and the resulting residue was purified by silica gel column chromatography (chloroform:methanol:28% aqueous ammonia=20:1:0.1 to 10:1:0.1) to obtain the compound shown in Table 1 (11 mg).

In Example 30 to Example 78, the compounds shown in Table 1 were synthesized in the same manner as that of Example 29 by using corresponding phenol reagents.

Example 79

(1) By using the compound obtained in Example 13, (1) (50 mg) and the compound obtained in Reference Example 14 (25.9 mg) as starting materials, an ether compound (61.9 mg) was obtained in the same manner as that of Example 29, (1).
(2) A solution of palladium acetate (1.0 mg) and triphenylphosphine (5.9 mg) in 1,2-dimethoxyethane (1 ml) was successively added with phenylboronic acid (8.2 mg), aqueous sodium carbonate (0.5 ml), and a solution of the compound obtained in (1) mentioned above (60 mg) in 1,2-dimethoxyethane (1 ml) under a nitrogen atmosphere, and the mixture was stirred at 80° C. for 1.5 hours. The reaction mixture was added with distilled water and ethyl acetate for extraction, and the organic layer was dried over anhydrous magnesium sulfate, and filtered. The filtrate was concentrated under reduced pressure, and the resulting residue was purified by silica gel column chromatography (hexane:acetone:triethylamine=30:10:0.2) to obtain a biaryl compound (46.7 mg).
(3) By using the compound obtained in (2) mentioned above (43 mg) as a starting material, the compound shown in Table 1 (26.9 mg) was obtained in the same manner as that of Example 1, (3).

Example 80

(1) By using the compound obtained in Example 13, (1) (50 mg) and N,N-diethyl-3-aminophenol (15.4 mg) as starting materials, an ether compound (56 mg) was obtained in the same manner as that of Example 29, (1).
(2) The compound obtained in (1) mentioned above (56 mg) was dissolved in tetrahydrofuran (1 ml), the solution was added with tetrabutylammonium fluoride (43 mg), and the mixture was stirred at room temperature for 16 hours, and at 50° C. for 4 hours. The reaction mixture was concentrated under reduced pressure, and the resulting residue was purified by preparative thin layer chromatography (chloroform:methanol:28% aqueous ammonia=10:1:0.1) to obtain the compound shown in Table 1 (4.5 mg).

Example 81

(1) The compound obtained in Example 13, (1) (20 mg) was dissolved in tetrahydrofuran (200 µl), the solution was added with β-naphthol (8 mg), triphenylphosphine (14.6 mg) and a 40% solution of diethyl azodicarboxylate in toluene (24.3 µl), and the mixture was stirred at room temperature for 24 hours. The reaction mixture was concentrated under reduced pressure, and the resulting residue was purified by preparative thin layer chromatography (hexane:acetone:triethylamine=30:10:0.2) to obtain an ether compound (8 mg).
(2) By using the compound obtained in (1) mentioned above (9 mg) as a starting material, the compound shown in Table 1 (7 mg) was obtained in the same manner as that of Example 1, (3).

Example 82

(1) By using the compound obtained in Example 13, (1) (2 g) and 2-bromophenol (650 µl) as starting materials, an ether compound (1.15 g) was obtained in the same manner as that of Example 29, (1).
(2) By using the compound obtained in (1) mentioned above (240 mg) as a starting material, the compound shown in Table 1 (181 mg) was obtained in the same manner as that of Example 1, (3).

Example 83

(1) By using the compound obtained in Example 13, (1) (25 mg) and 3-chlorophenol (6.0 mg) as starting materials, an ether compound (21.7 mg) was obtained in the same manner as that of Example 29, (1).
(2) By using the compound obtained in (1) mentioned above (21.7 mg) as a starting material, the compound shown in Table 1 (13.5 mg) was obtained in the same manner as that of Example 1, (3).

Example 84

(1) The compound obtained in Example 13, (1) (30 mg), 3-nitrophenol (11.6 mg), triphenylphosphine (21.9 mg), and a 40% solution of diethyl azodicarboxylate in toluene (38 µl) was dissolved in toluene (1 ml), and the mixture was stirred at 60° C. for 3 hours. The reaction mixture was concentrated under reduced pressure, and the resulting residue was purified by silica gel column chromatography (hexane:acetone:triethylamine=70:10:0.2) to obtain an ether compound (26.6 mg).
(2) By using the compound obtained in (1) mentioned above (26 mg) as a starting material, the compound shown in Table 1 (6.6 mg) was obtained in the same manners as those of Example 23, (3) and Example 1, (3).

Example 85

(1) By using the compound obtained in Example 13, (1) (30 mg) and the compound obtained in Reference Example 22 (13.9 mg) as starting materials, an ether compound (23.2 mg) was obtained in the same manner as that of Example 84, (1).
(2) The compound obtained in (1) mentioned above (23 mg) was dissolved in a mixed solvent of methanol and tetrahydrofuran (3:1, 1 ml), the solution was added with sodium methoxide (5.1 mg), and the mixture was stirred at room temperature for 5 hours. The reaction mixture was added with distilled water, the mixture was extracted with ethyl acetate, and the organic layer was dried over anhydrous magnesium sulfate. The organic layer was filtered, and the resulting filtrate was concentrated under reduced pressure to obtain a hydroxymethyl compound (20.4 mg).
(3) By using the compound obtained in (2) mentioned above (18 mg) as a starting material, the compound shown in Table 1 (8.3 mg) was obtained in the same manner as that of Example 1, (3).

Example 86

By using the compound obtained in Example 13, (1) (30 mg) and the compound obtained in Reference Example 23 (13.9 mg) as starting materials, the compound shown in Table 1 (8.9 mg) was obtained in the same manners as those of Example 84, (1), Example 85, (2), and Example 1, (3).

Example 87

The compound obtained in Example 37 (15 mg) was dissolved in tetrahydrofuran (1 mg), the solution was added with 20% palladium hydroxide (8 mg), and the mixture was stirred at room temperature for 4 hours under a hydrogen atmosphere of 1 atm. The reaction mixture was filtered, then the filtrate was concentrated under reduced pressure, and the resulting residue was purified by preparative thin layer chromatography (chloroform:methanol:28% aqueous ammonia=10:1:0.1) to obtain the compound shown in Table 1 (9.1 mg).

Example 88

By using the compound obtained in Example 38 (15 mg) as a starting material, the compound shown in Table 1 (4.5 mg) was obtained in the same manner as that of Example 87.

Example 89

By using the compound obtained in Example 41 (10 mg) as a starting material, the compound shown in Table 1 (3.2 mg) was obtained in the same manner as that of Example 87.

Example 90

By using the compound obtained in Example 53 (11 mg) as a starting material, the compound shown in Table 1 (4.6 mg) was obtained in the same manner as that of Example 87.

Example 91

By using the compound obtained in Example 13, (1) (30 mg) and the compound obtained in Reference Example 24 (18.1 mg) as starting materials, the compound shown in Table 1 (5.0 mg) was obtained in the same manners as those of Example 84, (1), Example 85, (2), and Example 1, (3).

Example 92

By using the compound obtained in Example 79 (18 mg) as a starting material, the compound shown in Table 1 (11.0 mg) was obtained in the same manner as that of Example 87.

Example 93

The compound obtained in Example 52 (30 mg), tri(o-tolyl)phosphine (2.1 mg), tris(dibenzylideneacetone)dipalladium(0) (3.1 mg), and tri-n-butyl(2-pyridyl)tin (25 mg) were dissolved in toluene (1 ml), and the mixture was stirred for 5 hours under reflux by heating. The reaction mixture was concentrated under reduced pressure, and the resulting residue was purified by silica gel column chromatography (chloroform:methanol:28% aqueous ammonia=20:1:0.1) to obtain the compound shown in Table 1 (19.2 mg).

In Examples 94 to 98, the compounds shown in Table 1 were synthesized in the same manner as that of Example 93 by using corresponding tin reagents.

Example 99

The compound obtained in Example 52 (30 mg), 4-pyridineboronic acid (8.3 mg), tri(o-tolyl)phosphine (2.1 mg), tris(dibenzylideneacetone)dipalladium(0) (3.1 mg), and sodium carbonate (36 mg) were dissolved in dimethoxyethane (1 ml) and distilled water (1 ml), and the solution was stirred for 5 hours under reflux by heating. The reaction mixture was concentrated under reduced pressure, and the resulting residue was purified by silica gel column chromatography (chloroform:methanol:28% aqueous ammonia=20:1:0.1) to obtain the compound shown in Table 1 (3.3 mg).

In Examples 100 to 102, the compounds shown in Table 1 were synthesized in the same manner as that of Example 99 by using corresponding boronic acid reagents.

Example 103

(1) By using the compound obtained in Example 13, (1) (200 mg) and 5-bromo-3-pyridinol (65 mg) as starting materials, a bromo compound (180 mg) was obtained in the same manner as that of Example 29, (1).
(2) By using the compound obtained in (1) mentioned above (30 mg) and tri-n-butylphenyltin (18 mg) as starting materials, the compound shown in Table 1 (3.5 mg) was obtained in the same manners as those of Example 19, (2) and Example 1, (3).

Example 104

By using the compound obtained in Example 103, (1) (30 mg) and tri-n-butyl(2-furanyl)tin (18 mg) as starting materials, the compound shown in Table 1 (4.2 mg) was obtained in the same manners as those of Example 93 and Example 1, (3).

Example 105

The compound obtained in Example 13, (4) (14 mg) was dissolved in distilled water (0.2 ml), the solution was added with m-tolylacetylene (6.6 mg) and copper iodide (3.6 mg), and the mixture was stirred at room temperature for 4 hours. The reaction mixture was added with saturated aqueous sodium hydrogencarbonate and chloroform, the layers were separated, and then the organic layer was dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 1 (7.1 mg).

Example 106

By using the compound obtained in Example 13, (4) (11 mg) and phenylacetylene (4.7 mg) as starting materials, the compound shown in Table 1 (9.2 mg) was obtained in the same manner as that of Example 105.

Example 107

(1) By using the compound obtained in Reference Example 1 (432 mg) and the compound obtained in Reference Example 25 (450 mg) as starting materials, a cyclized compound (428 mg) was obtained in the same manners as those of Example 1, (1) and (2).
(2) By using the compound obtained in (1) mentioned above (200 mg) as a starting material, a p-toluenesulfonyl compound (151 mg) was obtained in the same manners as those of Example 87 and Example 13, (2).
(3) 3-(1H-Imidazol-4-yl)pyridine (163.3 mg) obtained by the method described in the literature (Journal of Medicinal Chemistry, 2005, vol. 48, p. 224) was dissolved in dimethylformamide (1 ml), the solution was added with sodium hydride (27 mg) under ice cooling, and the mixture was stirred for 5 minutes. The reaction mixture was added with a solution of the compound obtained in (2) mentioned above (145 mg) in dimethylformamide (2 ml), and the mixture was stirred at 60° C. for 1.5 hours. The reaction mixture was added with distilled water, the mixture was extracted with ethyl acetate, and the organic layer was dried over anhydrous magnesium sulfate, and filtered. The filtrate was concentrated under reduced pressure, and the resulting residue was purified by silica gel column chromatography (hexane:acetone:triethylamine=10:10:0.2) to obtain an adduct compound (67 mg).
(4) By using the compound obtained in (3) mentioned above (15 mg) as a starting material, the compound shown in Table 1 (10.9 mg) was obtained in the same manner as that of Example 1, (3).

Example 108

(1) By using the compound obtained in Reference Example 1 (300 mg) and the compound obtained in Reference Example 26 (100 mg) as starting materials, a cyclized compound (77 mg) was obtained in the same manners as those of Example 1, (1) and (2).
(2) By using the compound obtained in (1) mentioned above (77 mg) as a starting material, the compound shown in Table 1 (34 mg) was obtained in the same manners as those of Example 87, Example 13, (2), Example 107, (3), and Example 1, (3).

Example 109

The compound obtained in Example 8 (8.5 mg) was dissolved in ethanol, the solution was added with 5% palladium-carbon (8.5 mg), and the mixture was stirred at room temperature for 2 hours under a hydrogen atmosphere of 1 atm. The reaction mixture was filtered, and then the filtrate was concentrated under reduced pressure to obtain the compound shown in Table 1 (6.8 mg).

Example 110

(1) By using the compound obtained in Example 8 (7.0 mg) as a starting material, an amine compound was obtained as an ethanol solution in the same manner as that of Example 109.
(2) The ethanol solution of the compound obtained in (1) mentioned above was added with pyridine (1.0 µl) and allyloxycarbonyl chloride (1.0 µl) under ice cooling, and the mixture was stirred at room temperature for 30 minutes. The reaction mixture was added with saturated aqueous ammonium chloride, then saturated with potassium carbonate, and extracted with chloroform, and the organic layer was dried over anhydrous sodium sulfate, and filtered. The filtrate was concentrated under reduced pressure, and the resulting residue was purified by silica gel column chromatography (chloroform:methanol:28% aqueous ammonia=20:1:0.1) to obtain the compound shown in Table 1 (2.7 mg).

Example 111

(1) By using the compound obtained in Example 8, (2) (30 mg) as a starting material, an amine compound was obtained as an ethanol solution in the same manner as that of Example 109.
(2) The ethanol solution obtained in (1) mentioned above was concentrated by substitution with 1,2-dichloroethane, the solution was added with 1,1-carbonyldiimidazole (6.7 mg), and the mixture was stirred at room temperature for 5 hours. The reaction mixture was added with chloroform, the mixture was washed with saturated brine, and the organic layer was dried over anhydrous sodium sulfate, and filtered. The filtrate was concentrated under reduced pressure to obtain a solution of imidazolamide compound.
(3) The solution obtained in (2) mentioned above was concentrated with substitution with tetrahydrofuran, the solution was added with sodium hydride (2.4 mg) and 1-naphthalenemethanol (6.5 mg), and the mixture was stirred at room temperature for 1 hour. The mixture was added with 1-naphthalenemethanol (2.1 mg), and the mixture was further stirred at room temperature for 1 hour. The reaction mixture was added with saturated ammonium chloride, the mixture was added with chloroform, the layers were separated, and the organic layer was washed with saturated brine, then dried over anhydrous sodium sulfate, and filtered. The filtrate was concentrated under reduced pressure, and the resulting residue was purified twice by preparative thin layer chromatography (toluene:ethyl acetate=3:1) to obtain a carbamate compound (8.8 mg).
(4) By using the compound obtained in (3) mentioned above (13.5 mg) as a starting material, the compound shown in Table 1 (6.3 mg) was obtained in the same manner as that of Example 1, (3).

Example 112

(1) By using the solution obtained in Example 111, (2) and 1-naphthaleneethanol (9.5 mg) as starting materials, a carbamate compound (7.8 mg) was obtained in the same manner as that of Example 111, (3).
(2) By using the compound obtained in (1) mentioned above (7.8 mg) as a starting material, the compound shown in Table 1 (4.3 mg) was obtained in the same manner as that of Example 1, (3).

Example 113

(1) By using the compound obtained in Example 8, (2) (30 mg) as a starting material, an amine compound was obtained as an ethanol solution in the same manner as that of Example 109.
(2) The solution obtained in (1) mentioned above was concentrated by substitution with 1,2-dichloroethane, the solution was added with 2-naphthalenealdehyde (5.6 mg) and sodium triacetoxyborohydride (7.6 mg) under ice cooling, and the mixture was stirred at room temperature for 2 hours. The reaction mixture was added with saturated aqueous sodium hydrogencarbonate and chloroform, the layers were separated, and the organic layer was washed with saturated brine. The organic layer was dried over anhydrous sodium sulfate and filtered, then the filtrate was concentrated under reduced pressure, and the resulting residue was purified by preparative thin layer chromatography (chloroform:methanol=30:1) to obtain an amine compound (7.5 mg).
(3) By using the compound obtained in (2) mentioned above (7.5 mg) as a starting material, the compound shown in Table 1 (2.7 mg) was obtained in the same manner as that of Example 1, (3).

Example 114

(1) By using the compound obtained in Example 8, (2) (40 mg) as a starting material, an amine compound was obtained as an ethanol solution in the same manner as that of Example 109.
(2) By using the solution obtained in (1) mentioned above and 2-(naphthalen-2-yl)acetaldehyde (8.2 mg) obtained by the method described in the patent document (International Patent Publication WO05/019238) as starting materials, an amine compound (10.2 mg) was obtained in the same manner as that of Example 113, (2).
(3) By using the compound obtained in (2) mentioned above (10.2 mg) as a starting material, the compound shown in Table 1 (3.5 mg) was obtained in the same manner as that of Example 1, (3).

Example 115

(1) By using the compound obtained in Example 113, (2) (9.8 mg) as a starting material, a methyl compound (9.8 mg) was obtained in the same manner as that of Example 14.
(2) By using the compound obtained in (1) mentioned above (9.8 mg) as a starting material, the compound shown in Table 1 (4.4 mg) was obtained in the same manner as that of Example 1, (3).

Example 116

(1) By using the compound obtained in Example 114, (2) (19.2 mg) as a starting material, a methyl compound (18.6 mg) was obtained in the same manner as that of Example 14.
(2) By using the compound obtained in (1) mentioned above (18.6 mg) as a starting material, the compound shown in Table 1 (8.0 mg) was obtained in the same manner as that of Example 1, (3).

Example 117

(1) By using the compound obtained in Reference Example 1 (56 mg) and the compound obtained in Reference Example 27 (53 mg) as starting materials, a cyclized compound (21 mg) was obtained in the same manners as those of Example 1, (1) and (2).
(2) By using the compound obtained in (1) mentioned above (21 mg) as a starting material, the compound shown in Table 1 (11 mg) was obtained in the same manner as that of Example 1, (3).

Example 118

By using the compound obtained in Example 117 (8 mg) as a starting material, the compound shown in Table 1 (5 mg) was obtained in the same manner as that of Example 109.

Example 119

(1) By using the compound obtained in Example 117, (1) (96 mg) as a starting material, an amino compound (49 mg) was obtained in the same manner as that of Example 109.
(2) The compound obtained in (1) mentioned above (49 mg) was dissolved in tetrahydrofuran (1.2 ml), the solution was added with pyridine (8 µl) and allyloxycarbonyl chloride (5 µl), and the mixture was stirred at room temperature for 1 hour. The reaction mixture was added with saturated aqueous sodium hydrogencarbonate (500 µl), and tetrahydrofuran was evaporated under reduced pressure. The resulting aqueous layer was extracted twice with ethyl acetate, then the organic layer was concentrated under reduced pressure, and the resulting residue was purified by silica gel column chromatography (hexane:ethyl acetate=5:1) to obtain an allyloxycarbonyl compound (40 mg).
(3) By using the compound obtained in (2) mentioned above (36 mg) as a starting material, the compound shown in Table 1 (23 mg) was obtained in the same manner as that of Example 1, (3).

Example 120

(1) By using the compound obtained in Example 119, (1) (36 mg) as a starting material, the compound shown in Table 1 (22 mg) was obtained in the same manners as those of Example 14 and Example 1, (3).

Example 121

(1) The compound obtained in Example 119, (1) (21 mg) was dissolved in methylene chloride (600 µl), the solution was added with 1,1-carbonyldiimidazole (4.3 mg), and the mixture was stirred at room temperature for 2 hours. The mixture was added with distilled water (0.2 ml) and methylene chloride (1 ml), the layers were separated, and the organic layer was washed with distilled water (0.2 ml). The organic layer was dried over anhydrous sodium sulfate and filtered, and then the filtrate was concentrated under reduced pressure to obtain an imidazolamide compound (24 mg) as a crude product.
(2) By using the compound obtained in (1) mentioned above (24 mg) and 1-naphthalenemethanol (8.5 mg) as starting materials, a carbamate compound (18 mg) was obtained in the same manner as that of Example 111, (3).
(3) By using the compound obtained in (2) mentioned above (14 mg) as a starting material, the compound shown in Table 1 (10 mg) was obtained in the same manner as that of Example 1, (3).

Example 122

(1) By using the compound obtained in Example 119, (1) (25 mg) as a starting material, an imidazolamide compound (20 mg) was obtained as a crude product in the same manner as that of Example 121, (1).
(2) By using the compound obtained in (1) mentioned above (27 mg) and 1-naphthaleneethanol (12 mg) as starting materials, a carbamate compound (20 mg) was obtained in the same manner as that of Example 111, (3).
(3) By using the compound obtained in (2) mentioned above (20 mg) as a starting material, the compound shown in Table 1 (13 mg) was obtained in the same manner as that of Example 1, (3).

Example 123

(1) By using the compound obtained in Example 119, (1) (15 mg) and the compound obtained in Reference Example 28 (4.2 mg) as starting materials, an amide compound (13.8 mg) was obtained in the same manner as that of Example 16, (2).
(2) By using the compound obtained in (1) mentioned above (13.8 mg) as a starting material, the compound shown in Table 1 (9.0 mg) was obtained in the same manner as that of Example 1, (3).

Example 124

(1) By using the compound obtained in Example 119, (1) (15 mg) and 2-(4-(pyridin-3-yl)phenyl)acetic acid (4.5 mg) as starting materials, an amide compound (13.5 mg) was obtained in the same manner as that of Example 16, (2).
(2) By using the compound obtained in (1) mentioned above (13.5 mg) as a starting material, the compound shown in Table 1 (9.5 mg) was obtained in the same manner as that of Example 1, (3).

Example 125

(1) By using the compound obtained in Example 119, (1) (90 mg) and the compound obtained in Reference Example 29 (26 mg) as starting materials, an amide compound (89 mg) was obtained in the same manner as that of Example 16, (2).
(2) By using the compound obtained in (1) mentioned above (11 mg) as a starting material, the compound shown in Table 1 (9.5 mg) was obtained in the same manner as that of Example 1, (3).

Example 126

(1) By using the compound obtained in Example 119, (1) (96.7 mg) and the compound obtained in Reference Example 30 (21.4 mg) as starting materials, an amide compound (15.2 mg) was obtained in the same manner as that of Example 16, (2).
(2) By using the compound obtained in (1) mentioned above (15.2 mg) as a starting material, the compound shown in Table 1 (10.2 mg) was obtained in the same manner as that of Example 1, (3).

Example 127

(1) By using the compound obtained in Example 119, (1) (43.2 mg) and the compound obtained in Reference Example 31 (10.2 mg) as starting materials, an amide compound (9.2 mg) was obtained in the same manner as that of Example 16, (2).
(2) By using the compound obtained in (1) mentioned above (9.2 mg) as a starting material, the compound shown in Table 1 (5.8 mg) was obtained in the same manner as that of Example 1, (3).

Example 128

(1) By using the compound obtained in Example 119, (1) (50 mg) and the compound obtained in Reference Example 32 (14 mg) as starting materials, an amide compound (32 mg) was obtained in the same manner as that of Example 16, (2).
(2) By using the compound obtained in (1) mentioned above (25 mg) as a starting material, the compound shown in Table 1 (19 mg) was obtained in the same manner as that of Example 1, (3).

Example 129

(1) By using the compound obtained in Example 119, (1) (90 mg) and 4-(pyridin-3-yl)benzoic acid (25 mg) as starting materials, an amide compound (70 mg) was obtained in the same manner as that of Example 16, (2).
(2) By using the compound obtained in (1) mentioned above (20 mg) as a starting material, the compound shown in Table 1 (13 mg) was obtained in the same manner as that of Example 1, (3).

Example 130

(1) By using the compound obtained in Example 119, (1) (43.6 mg) and the compound obtained in Reference Example 41 (18.7 mg) as starting materials, an amide compound (14.1 mg) was obtained in the same manner as that of Example 16, (2).
(2) By using the compound obtained in (1) mentioned above (14.1 mg) as a starting material, the compound shown in Table 1 (8.1 mg) was obtained in the same manner as that of Example 1, (3).

Example 131

By using the compound obtained in Example 126 (9.1 mg) as a starting material, the compound shown in Table 1 (7.8 mg) was obtained in the same manner as that of Example 109.

Example 132

By using the compound obtained in Example 127 (4.6 mg) as a starting material, the compound shown in Table 1 (3.5 mg) was obtained in the same manner as that of Example 109.

Example 133

By using the compound obtained in Example 123 (6.9 mg) as a starting material, the compound shown in Table 1 (4.1 mg) was obtained in the same manner as that of Example 109.

Example 134

By using the compound obtained in Example 125 (6.4 mg) as a starting material, the compound shown in Table 1 (5.0 mg) was obtained in the same manner as that of Example 109.

Example 135

(1) By using the compound obtained in Example 119, (1) (23 mg) and the compound obtained in Reference Example 34 (5 mg) as starting materials, an amino compound (14 mg) was obtained in the same manner as that of Example 113, (2).
(2) By using the compound obtained in (1) mentioned above (14 mg) as a starting material, the compound shown in Table 1 (10 mg) was obtained in the same manner as that of Example 1, (3).

In Examples 136 to 141, the compounds shown in Table 1 were synthesized in the same manner as that of Example 135 by using corresponding aldehyde reagents.

Example 142

(1) By using the compound obtained in Reference Example 1 (1.90 g) and the compound obtained in Reference Example 40 (2.7 g) as starting materials, a lactonization precursor (1.24 g) was obtained in the same manner as that of Example 1, (1).
(2) By using the compound obtained in (1) mentioned above (1.81 g) as a starting material, a cyclized compound (890 mg) was obtained in the same manner as that of Example 1, (2).
(3) By using the compound obtained in (2) mentioned above (20 mg) as a starting material, the compound shown in Table 1 (13 mg) was obtained in the same manner as that of Example 1, (3).

Example 143

By using the compound obtained in Example 142 (12 mg) as a starting material, the compound shown in Table 1 (13 mg) was obtained in the same manner as that of Example 109.

Example 144

(1) The compound obtained in Example 142, (2) (30 mg) and tris(dibenzylideneacetone)dipalladium(0) (3.8 mg) were dissolved in 1,4-dioxane (0.21 µl), the solution was added with bromobenzene (5.8 µl), dicyclohexylmethylamine (16 µl), and a 0.44 N solution of tri-t-butylphosphine in dioxane (19 µl), and the mixture was stirred at 50° C. for 5 hours. The reaction mixture was filtered, then the filtrate was concentrated under reduced pressure, and the resulting residue was purified by preparative thin layer chromatography (hexane:acetone=9:1) to obtain a coupled compound (5.8 mg).
(2) By using the compound obtained in (1) mentioned above (22 mg) as a starting material, the compound shown in Table 1 (15 mg) was obtained in the same manner as that of Example 1, (3).

Example 145

By using the compound obtained in Example 142, (2) (30 mg) and 1-bromonaphthalene (9 μl) as starting materials, the compound shown in Table 1 (9.8 mg) was obtained in the same manners as those of Example 144, (1) and Example 1, (3).

Example 146

(1) The compound obtained in Example 142, (2) (20 mg) and tris(dibenzylideneacetone)dipalladium(0) (2.5 mg) were dissolved in dimethylformamide (200 μl), the solution was added with 2-bromonaphthalene (11.5 mg), silver carbonate (15.7 mg), and a 0.44 N solution of tri-t-butylphosphine in dioxane (13 μl), and the mixture was stirred at 100° C. for 15 minutes under microwave irradiation. The reaction mixture was filtered, then the filtrate was concentrated under reduced pressure, and the resulting residue was purified by preparative thin layer chromatography (hexane:acetone=7:1) to obtain a coupled compound (16.3 mg).

(2) By using the compound obtained in (1) mentioned above (21 mg) as a starting material, the compound shown in Table 1 (12.5 mg) was obtained in the same manner as that of Example 1, (3).

In Examples 147 to 149, the compounds shown in Table 1 were synthesized in the same manner as that of Example 146 by using corresponding bromoaryl reagents.

Example 150

By using the compound obtained in Example 144 (12.2 mg) as a starting material, the compound shown in Table 1 (9.6 mg) was obtained in the same manner as that of Example 109.

Example 151

By using the compound obtained in Example 145 (7.1 mg) as a starting material, the compound shown in Table 1 (6.1 mg) was obtained in the same manner as that of Example 109.

Example 152

By using the compound obtained in Example 146 (9.9 mg) as a starting material, the compound shown in Table 1 (7.7 mg) was obtained in the same manner as that of Example 109.

Example 153

By using the compound obtained in Example 147 (13.3 mg) as a starting material, the compound shown in Table 1 (6.6 mg) was obtained in the same manner as that of Example 109.

Example 154

By using the compound obtained in Example 148 (15.4 mg) as a starting material, the compound shown in Table 1 (10.7 mg) was obtained in the same manner as that of Example 109.

Example 155

By using the compound obtained in Example 149 (9.8 mg) as a starting material, the compound shown in Table 1 (3.4 mg) was obtained in the same manner as that of Example 109.

Example 156

(1) By using the compound obtained in Reference Example 1 (1.31 g) and the compound obtained in Reference Example 43 (1.47 g) as starting materials, a cyclized compound (289 mg) was obtained in the same manners as those of Example 1, (1) and (2).

(2) By using the compound obtained in (2) mentioned above (8 mg) as a starting material, the compound shown in Table 1 (6 mg) was obtained in the same manner as that of Example 1, (3).

Example 157

(1) Tetrabutylammonium acetate (16 mg) and palladium acetate (1.1 mg) were dissolved in dimethylformamide (400 μl), the solution was added with iodobenzene (20 μl) and the compound obtained in Example 156, (1) (20 mg), and the mixture was stirred at room temperature for 24 hours. The reaction mixture was added with diethyl ether and distilled water, the layers were separated, and the aqueous layer was extracted three times with diethyl ether. The combined organic layer was dried over anhydrous sodium sulfate and filtered, then the filtrate was concentrated under reduced pressure, and the resulting residue was purified by preparative thin layer chromatography (chloroform:ethyl acetate:triethylamine=6:1:0.1) to obtain a phenylethynyl compound (8 mg).

(2) By using the compound obtained in (1) mentioned above (8 mg) as a starting material, the compound shown in Table 1 (4 mg) was obtained in the same manner as that of Example 1, (3).

Example 158

(1) The compound obtained in Example 13, (2) (16.2 mg) was dissolved in dimethylformamide (0.5 ml), the solution was added with 2-naphthalenethiol (3.2 mg) and potassium carbonate (2.7 mg) under an argon atmosphere, and the mixture was stirred at room temperature for 3 hours. The reaction mixture was added with 2-naphthalenethiol (6.4 mg) and potassium carbonate (5.4 mg), and the mixture was stirred at room temperature for 3 hours. The reagents were supplemented twice in the same manner so that the starting material should substantially completely react. The reaction mixture was added with distilled water and ethyl acetate, the layers were separated, and then the organic layer was washed with distilled water and saturated brine. The organic layer was dried over anhydrous sodium sulfate and filtered, then the filtrate was concentrated under reduced pressure, and the resulting residue was purified by preparative thin layer chromatography (toluene:ethyl acetate=6:1) to obtain a thioether compound (7.3 mg).

(2) By using the compound obtained in (1) mentioned above (7.3 mg) as a starting material, the compound shown in Table 1 (4.2 mg) was obtained in the same manner as that of Example 1, (3).

Examples 159 to 162

Preparation methods of the compounds represented by the formula (C) having R defined in Table 2 are shown below.

[Formula 24]

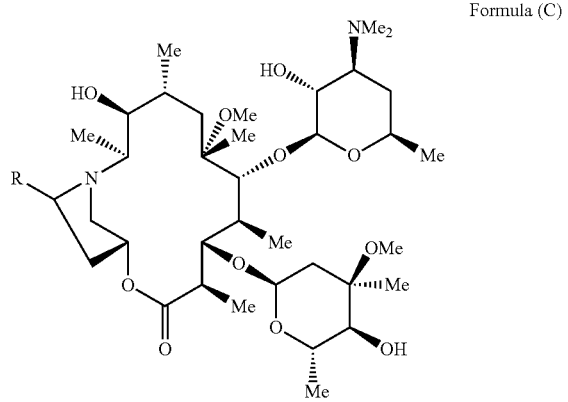

Formula (C)

TABLE 2

| Example | R | ESI MS (M + H) | $^1$H-NMR, CDCl$_3$, δ (ppm) |
|---|---|---|---|
| 159 | ![structure with O-CH2CH2-imidazole-pyridine] | 904.4 | (600 M Hz): 0.91 (d, J = 7.34 Hz, 3H) 1.02 (d, J = 6.88 Hz, 3H) 1.08 (d, J = 7.34 Hz, 3H) 1.13 (d, J = 7.34 Hz, 3H) 1.20-1.23 (m, 1H) 1.22 (d, J = 6.42 Hz, 3H) 1.26 (s, 3H) 1.29 (d, J = 5.96 Hz, 3H) 1.34 (s, 3H) 1.37 (d, J = 14.67 Hz, 1H) 1.59 (dd, J = 15.13, 5.04 Hz, 1H) 1.65 (d, J = 12.84 Hz, 1H) 1.76 (d, J = 14.21 Hz, 1H) 1.94-2.05 (m, 1H) 2.21 (d, J = 10.09 Hz, 1H) 2.20-2.24 (m, 1H) 2.28 (s, 6H) 2.33-2.48 (m, 3H) 2.82-2.88 (m, 1H) 2.88-2.93 (m, 1 H) 2.96-3.06 (m, 3H) 3.07-3.13 (m, 2H) 3.16-3.22 (m, 1H) 3.24-3.29 (m, 1H) 3.27 (s, 3H) 3.33 (s, 3H) 3.33-3.39 (m, 1H) 3.46-3.54 (m, 2 H) 3.58 (d, J = 9.63 Hz, 1H) 3.66-3.37 (m, 1H) 3.76 (d, J = 6.42 Hz, 1 H) 3.77-3.81 (m, 1H) 3.98-4.07 (m, 1H) 4.09-4.20 (m, 2H) 4.50 (d, J = 6.88 Hz, 1H) 4.88 (d, J = 9.63 Hz, 1H) 4.92-4.96 (m, 1H) 4.97-5.05 (m, 1H) 7.30 (dd, J = 7.79, 4.58 Hz, 1H) 7.36 (d, J = 1.38 Hz, 1H) 7.61 (d, J = 1.38 Hz, 1H) 8.09 (ddd, J = 7.91, 2.06, 1.95 Hz, 1H) 8.46 (dd, J = 4.81, 1.60 Hz, 1H) 8.95-8.98 (m, 1H) |
| 160 | ![structure with O-CH2CH2CH2-imidazole-pyridine] | 918.5 | (600 M Hz): 0.97 (d, J = 7.34 Hz, 3H) 1.04 (d, J = 6.42 Hz, 3H) 1.09 (d, J = 7.34 Hz, 3H) 1.15-1.21 (m, 1H) 1.17 (d, J = 7.34 Hz, 3H) 1.22 (d, J = 5.96 Hz, 3H) 1.26 (s, 3H) 1.29 (d, J = 5.96 Hz, 3H) 1.35 (s, 3H) 1.39 (d, J = 14.67 Hz, 1H) 1.60 (dd, J = 15.13, 5.04 Hz, 1H) 1.65 (d, J = 12.84 Hz, 1H) 1.80 (d, J = 14.67 Hz, 1H) 1.99-2.11 (m, 3H) 2.21 (d, J = 10.09 Hz, 1H) 2.23-2.28 (m, 1H) 2.28 (s, 6H) 2.38 (d, J = 15.13 Hz, 1H) 2.39-2.45 (m, 2H) 2.88-2.94 (m, 2H) 2.99-3.09 (m, 3H) 3.12-3.17 (m, 2H) 3.16-3.21 (m, 1H) 3.27-3.31 (m, 1H) 3.29 (s, 3H) 3.30-3.34 (m, 1H) 3.33 (s, 3H) 3.38-3.43 (m, 1H) 3.46-3.53 (m, 3H) 3.60 (d, J = 10.09 Hz, 1H) 3.77 (d, J = 6.88 Hz, 1H) 4.00-4.08 (m, 1H) 4.12 (td, J = 6.76, 2.06 Hz, 2H) 4.51 (d, J = 7.34 Hz, 1H) 4.91 (d, J = 10.09 Hz, 1H) 4.95 (d, J = 4.58 Hz, 1H) 5.02-5.04 (m, 1H) 7.27-7.32 (m, 2H) 7.56 (s, 1H) 8.09 (dt, J = 7.79, 1.83 Hz, 1H) 8.46 (dd, J = 4.81, 1.60 Hz, 1H) 8.97 (d, J = 2.29 Hz, 1H) |
| 161 | ![structure with O-(CH2)4-imidazole-pyridine] | 932.5 | (600 M Hz): 0.96 (d, J = 7.34 Hz, 3H) 1.03 (d, J = 6.88 Hz, 3H) 1.10 (d, J = 7.34 Hz, 3H) 1.16 (d, J = 7.34 Hz, 3H) 1.21-1.24 (m, 1H) 1.23 (d, J = 5.96 Hz, 3H) 1.26 (s, 3H) 1.29 (d, J = 5.96 Hz, 3H) 1.35 (s, 3H) 1.39 (d, J = 14.67 Hz, 1H) 1.56-1.67 (m, 4H) 1.78 (d, J = 14.67 Hz, 1H) 1.88-1.98 (m, 2H) 1.98-2.05 (m, 1 H) 2.21 (d, J = 10.09 Hz, 1H) 2.22-2.26 (m, 1H) 2.27 (s, 6H) 2.37 (d, J = 15.13 Hz, 1H) 2.39-2.44 (m, 2H) 2.85-2.93 (m, 2H) 2.96-3.00 (m, 1H) 3.01-3.05 (m, 1H) 3.05-3.09 (m, 1H) 3.11-3.16 (m, 2H) 3.17-3.22 (m, 1H) 3.26-3.33 (m, 2H) 3.28 (s, 3H) 3.33 (s, 3 H) 3.41-3.46 (m, 1H) 3.48-3.56 (m, 3H) 3.60 (d, J = 10.09 Hz, 1 H) 3.77 (d, J = 6.88 Hz, 1H) 4.00-4.10 (m, 3H) 4.52 (d, J = 7.34 Hz, 1H) 4.90 (d, J = 9.63 Hz, 1H) 4.95 (d, J = 4.58 Hz, 1H) 4.99-5.04 (m, 1H) 7.28-7.31 (m, 2H) 7.55-7.56 (m, 1H) 8.09 (dt, J = 7.79, 1.83 Hz, 1H) 8.47 (dd, J = 4.81, 1.60 Hz, 1H) 8.95-8.98 (m, 1H) |

TABLE 2-continued

| Example | R | ESI MS (M + H) | $^1$H-NMR, CDCl$_3$, δ (ppm) |
|---|---|---|---|
| 162 | (naphthyl-propyl-O-CMe$_2$- group) | 901.5 | (600 M Hz): 0.97 (d, J = 7.34 Hz, 3H) 1.06 (d, J = 6.42 Hz, 3H) 1.09 (d, J = 7.34 Hz, 3H) 1.17 (d, J = 7.34 Hz, 3H) 1.19-1.24 (m, 1H) 1.23 (d, J = 5.96 Hz, 3H) 1.26 (s, 3H) 1.30 (d, J = 5.96 Hz, 3H) 1.35 (s, 3H) 1.39 (d, J = 15.13 Hz, 1H) 1.60 (dd, J = 15.13, 5.04 Hz, 1H) 1.62-1.67 (m, 1H) 1.85 (d, J= 15.13 Hz, 1H) 2.00-2.10 (m, 3 H) 2.22 (d, J = 10.09 Hz, 1H) 2.23-2.26 (m, 1H) 2.29 (s, 6H) 2.38 (d, J = 15.13 Hz, 1H) 2.40-2.46 (m, 2H) 2.85-2.96 (m, 2H) 3.01-3.11 (m, 3H) 3.13-3.23 (m, 5H) 3.26-3.30 (m, 1H) 3.29 (s, 3H) 3.32-3.37 (m, 1H) 3.34 (s, 3H) 3.46-3.66 (m, 5H) 3.77 (d, J = 6.88 Hz, 1H) 4.01-4.09 (m, 1H) 4.52 (d, J = 7.34 Hz, 1H) 4.92 (d, J = 10.09 Hz, 1H) 4.95 (d, J = 4.58 Hz, 1H) 5.00-5.06 (m, 1H) 7.33-7.36 (m, 1H) 7.39 (d, J = 7.79 Hz, 1H) 7.44-7.53 (m, 2H) 7.71 (d, J = 8.25 Hz, 1H) 7.85 (d, J = 8.71 Hz, 1H) 8.07 (d, J = 8.25 Hz, 1 H) |

Example 159

(1) By using the compound obtained in Reference Example 1 (1.27 g) and the compound obtained in Reference Example 44 (1.27 g) as starting materials, a cyclized compound (192 mg) was obtained in the same manners as those of Example 1, (1) and (2).
(2) By using the compound obtained in (1) mentioned above (181 mg) as a starting material, an adduct compound (154 mg) was obtained in the same manners as those of Example 87, Example 13, (2), and Example 107, (3).
(3) The compound obtained in (2) mentioned above (24 mg) was dissolved in tetrahydrofuran (0.5 ml), the solution was added with a 1 M solution of tetrabutylammonium fluoride in tetrahydrofuran (116 µl), and the mixture was stirred at room temperature for 12 hours. The reaction mixture was added with a 1 M solution of tetrabutylammonium fluoride in tetrahydrofuran (19 µl), and the mixture was stirred at 60° C. for 2 hours. The reaction mixture was concentrated under reduced pressure, and the resulting residue was purified by silica gel column chromatography (chloroform to chloroform:methanol:28% aqueous ammonia=10:1:0.1) and preparative thin layer chromatography (chloroform:methanol:28% aqueous ammonia=10:1:0.1) to obtain the compound shown in Table 2 (8.7 mg).

Example 160

(1) By using the compound obtained in Reference Example 1 (1.12 g) and the compound obtained in Reference Example 45 (1.16 g) as starting materials, a cyclized compound (150 mg) was obtained in the same manners as those of Example 1, (1) and (2).
(2) By using the compound obtained in (1) mentioned above (85 mg) as a starting material, the compound shown in Table 2 (5.4 mg) was obtained in the same manners as those of Example 87, Example 13, (2), Example 107, (3), Example 1, (3), and Example 159, (3).

Example 161

(1) By using the compound obtained in Reference Example 1 (3.48 g), and the compound obtained in Reference Example 46 (2.76 g) as starting materials, a cyclized compound (660 mg) was obtained in the same manners as those of Example 1, (1) and (2).
(2) By using the compound obtained in (1) mentioned above (440 mg) as a starting material, an adduct compound (290 mg) was obtained in the same manners as those of Example 87, Example 13, (2), and Example 107, (3).
(3) By using the compound obtained in (2) mentioned above (24 mg) as a starting material, the compound shown in Table 2 (9.8 mg) was obtained in the same manner as that of Example 159, (3).

Example 162

(1) By using the compound obtained in Reference Example 1 (2.02 g) and the compound obtained in Reference Example 47 (1.48 g) as starting materials, a cyclized compound (73 mg) was obtained in the same manners as those of Example 1, (1) and (2).
(2) By using the compound obtained in (1) mentioned above (26 mg) as a starting material, the compound shown in Table 2 (7.4 mg) was obtained in the same manners as those of Example 1, (3) and Example 159, (3).

Examples 163 to 166

Preparation methods of the compounds represented by the formula (D) having R defined in Table 3 are shown below.

[Formula 25]

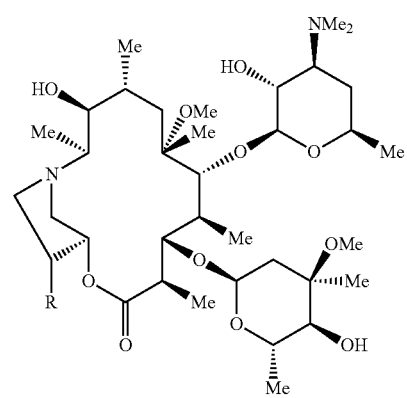

Formula (D)

TABLE 3

| Example | R | ESI MS (M + H) | $^1$H-NMR, CDCl$_3$, δ (ppm) |
|---|---|---|---|
| 163 | —H | 703 | (400 M Hz): 0.82 (d, J = 7.3 Hz, 3H) 0.89 (d, J = 7.1 Hz, 3H) 0.99 (d, J = 7.3 Hz, 3H) 1.03 (d, J = 6.8 Hz, 3H) 1.09 (d, J = 7.6 Hz, 3H) 1.17-1.35 (m, 10H) 1.54-1.88 (m, 4H) 1.91-2.65 (m, 7H) 2.29 (s, 3H) 2.30 (s, 3H) 2.68-3.29 (m, 11H) 3.37 (s, 3H) 3.45-3.50 (m, 1H) 3.80-3.91 (m, 2H) 4.01-4.14 (m, 1H) 4.48-4.57 (m, 1H) 4.75-4.86 (m, 1H) 4.94-5.02 (m, 1H) |
| 164 | benzyloxy-substituted group (PhCH$_2$O—, with stereochemistry) | 809.6 | (600 M Hz): 0.89 (d, J = 7.34 Hz, 3H) 1.04 (d, J = 6.88 Hz, 3H) 1.07 (d, J = 7.79 Hz, 3H) 1.21 (d, J = 5.96 Hz, 3H) 1.20-1.24 (m, 1H) 1.23 (d, J = 6.88 Hz, 3H) 1.24 (s, 3H) 1.26 (d, J = 5.96 Hz, 3H) 1.29 (s, 3H) 1.36 (dd, J = 14.67, 3.67 Hz, 1H) 1.50 (dd, J = 15.13, 5.04 Hz, 1H) 1.61-1.66 (m, 1H) 1.99 (dd, J = 14.67, 7.34 Hz, 1H) 2.06-2.18 (m, 3H) 2.28 (s, 6H) 2.33 (d, J = 15.13 Hz, 1H) 2.41-2.47 (m, 1H) 2.63 (dd, J = 10.55, 4.58 Hz, 1H) 2.73 (t, J = 6.88 Hz, 1H) 2.85-2.91 (m, 2H) 2.92-3.01 (m, 2H) 3.20-3.27 (m, 2H) 3.32 (s, 3H) 3.33 (s, 3H) 3.36 (dd, J = 10.55, 6.42 Hz, 1H) 3.47-3.55 (m, 1H) 3.77 (d, J = 6.42 Hz, 1H) 3.81 (dd, J = 6.42, 1.83 Hz, 1H) 3.83 (d, J = 8.71 Hz, 1H) 3.90 (t, J = 5.04 Hz, 1H) 3.96-4.03 (m, 1H) 4.48 (d, J = 7.34 Hz, 1H) 4.56 (d, J = 3.67 Hz, 2H) 4.70 (d, J = 5.04 Hz, 1H) 4.86 (d, J = 3.67 Hz, 1H) 7.15-7.40 (m, 5H) |
| 165 | HO— (with stereochemistry) | 719.4 | (600 M Hz): 0.89 (d, J = 6.88 Hz, 3H) 1.04 (d, J = 6.88 Hz, 3H) 1.09 (d, J = 7.34 Hz, 3H) 1.21-1.22 (m, 3H) 1.22-1.27 (m, 1H) 1.22-1.24 (m, 3H) 1.26 (s, 3H) 1.29 (d, J = 6.42 Hz, 3H) 1.33 (s, 3H) 1.37 (dd, J = 14.21, 2.75 Hz, 1H) 1.59 (dd, J = 15.13, 5.04 Hz, 1H) 1.62-1.67 (m, 1H) 2.07 (dd, J = 14.67, 8.25 Hz, 1H) 2.11-2.16 (m, 1H) 2.18 (d, J = 10.55 Hz, 1H) 2.27-2.30 (m, 1H) 2.29 (s, 6H) 2.39 (d, J = 14.67 Hz, 1H) 2.42-2.48 (m, 1H) 2.50 (dd, J = 10.55, 4.58 Hz, 1H) 2.79 (t, J = 7.11 Hz, 1H) 2.86-2.90 (m, 1H) 2.90 (d, J = 10.99 Hz, 1H) 2.97-3.04 (m, 2H) 3.17-3.22 (m, 1H) 3.24 (dd, J = 10.09, 7.34 Hz, 1H) 3.33 (s, 3H) 3.36 (s, 3H) 3.39 (dd, J = 10.55, 5.96 Hz, 1H) 3.47-3.54 (m, 1H) 3.77 (dd, J = 7.34, 1.83 Hz, 1H) 3.81 (d, J = 6.88 Hz, 1H) 3.99-4.07 (m, 2H) 4.12 (t, J = 5.27 Hz, 1H) 4.50 (d, J = 7.34 Hz, 1H) 4.62 (d, J = 3.67 Hz, 1H) 4.81 (d, J = 4.58 Hz, 1H) |
| 166 | PhCH$_2$O—CH$_2$—C(—)(—) (benzyloxymethyl gem-dimethyl group) | 823.5 | (600 M Hz): 0.84 (d, J = 7.34 Hz, 3H) 1.00 (d, J = 6.88 Hz, 6H) 1.19 (d, J = 7.34 Hz, 3H) 1.22 (d, J = 6.42 Hz, 3H) 1.22-1.25 (m, 1H) 1.27-1.31 (m, 1H) 1.28 (s, 3H) 1.29 (d, J = 6.42 Hz, 3H) 1.32 (s, 3H) 1.57-1.60 (m, 1H) 1.61-1.66 (m, 1H) 1.97-2.04 (m, 1H) 2.05-2.11 (m, 1H) 2.14 (d, J = 10.55 Hz, 1H) 2.29 (s, 6H) 2.38 (d, J = 15.59 Hz, 1H) 2.38-2.42 (m, 2H) 2.43-2.49 (m, 1H) 2.59 (t, J = 10.09 Hz, 1H) 2.74 (q, J = 6.88 Hz, 1H) 2.88-2.94 (m, 2H) 3.03-3.09 (m, 2H) 3.12 (t, J = 9.86 Hz, 1H) 3.18 (dd, J = 10.32, 7.11 Hz, 1H) 3.25-3.27 (m, 1H) 3.29 (s, 3H) 3.37 (s, 3H) 3.40 (dd, J =9.17, 5.96 Hz, 1H) 3.51 (t, J = 8.71 Hz, 1H) 3.53-3.57 (m, 1H) 3.91 (d, J = 5.04 Hz, 1H) 3.97 (dd, J = 8.02, 2.98 Hz, 1H) 4.08-4.14 (m, 1H) 4.40 (d, J = 12.38 Hz, 1H) 4.51-4.55 (m, 2H) 4.67 (d, J = 4.58 Hz, 1H) 5.08-5.15 (m, 1H) 7.24-7.38 (m, 5H) |

Example 163

(1) By using the lactonization precursor obtained in Example 1, (1) (225 mg) wherein the steric configuration of the asymmetric carbon atom on the pyrrolidine ring is S as a starting material, a cyclized compound (155 mg) was obtained in the same manner as that of Example 1, (2).

(2) By using the compound obtained in (1) mentioned above (155 mg) as a starting material, the compound shown in Table 3 (44.4 mg) was obtained in the same manner as that of Example 1, (3).

Example 164

(1) By using the compound obtained in Reference Example 1 (467 mg) and the compound obtained in Reference Example 48 (640 mg) as starting materials, a cyclized compound (81 mg) was obtained in the same manners as those of Example 1, (1) and (2).

(2) By using the compound obtained in (1) mentioned above (30 mg) as a starting material, the compound shown in Table 3 (19 mg) was obtained in the same manner as that of Example 1, (3).

Example 165

By using the compound obtained in Example 164, (1) (38 mg) as a starting material, the compound shown in Table 3 (7.0 mg) was obtained in the same manners as those of Example 11 and Example 1, (3).

Example 166

By using the compound obtained in Reference Example 1 (220 mg) and the compound obtained in Reference Example 49 (190 mg) as starting materials, the compound shown in Table 3 (4.8 mg) was obtained in the same manner as that of Example 1.

Examples 167 and 168

Preparation methods of the compounds represented by the formula (E) having R defined in Table 4 are shown below.

[Formula 26]

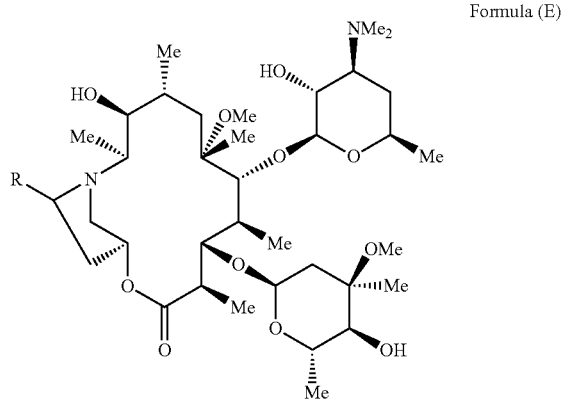

Formula (E)

TABLE 4

| Example | R | ESI MS (M + H) | $^1$H-NMR, CDCl$_3$, δ (ppm) |
|---|---|---|---|
| 167 | (structure: -CH(CH₃)-O-CH₂CH₂-N-imidazole-pyridinyl) | 904.4 | (600 M Hz): 0.98 (d, J = 6.88 Hz, 3H) 1.03 (d, J = 7.34 Hz, 3H) 1.10 (d, J = 6.88 Hz, 3H) 1.20 (d, J = 7.34 Hz, 3H) 1.23 (d, J = 5.96 Hz, 3H) 1.23-1.26 (m, 1H) 1.26 (s, 3H) 1.28 (d, J = 5.96 Hz, 3H) 1.38 (s, 3H) 1.61 (dd, J = 15.13, 5.04 Hz, 1H) 1.64-1.67 (m, 1H) 1.70-1.75 (m, 1H) 1.94-2.02 (m, 1H) 2.05-2.14 (m, 1H) 2.17 (d, J = 10.55 Hz, 1H) 2.28 (s, 6H) 2.30-2.34 (m, 1H) 2.35 (d, J = 15.13 Hz, 1H) 2.40-2.49 (m, 1H) 3.04 (t, J = 9.86 Hz, 6H) 3.18 (dd, J = 10.09, 7.34 Hz, 1H) 3.23-3.29 (m, 2H) 3.30 (s, 3H) 3.33 (s, 3H) 3.37-3.42 (m, 1H) 3.45-3.50 (m, 1H) 3.50-3.55 (m, 1H) 3.65-3.73 (m, 2H) 3.83 (d, J = 5.04 Hz, 1H) 4.01-4.06 (m, 1H) 4.06-4.12 (m, 1H) 4.12-4.16 (m, 2H) 4.47 (d, J = 7.34 Hz, 1H) 4.78 (d, J = 4.59 Hz, 1H) 4.99-5.04 (m, 1H) 7.29 (dd, J = 8.02, 4.81 Hz, 1H) 7.36 (s, 1H) 7.60 (d, J = 0.92 Hz, 1H) 8.10 (dt, J = 7.79, 1.83 Hz, 1H) 8.46 (dd, J = 4.81, 1.60 Hz, 1H) 8.98 (d, J = 1.38 Hz, 1H) |
| 168 | (structure: naphthyl-CH₂CH₂CH₂-O-) | 901.4 | (600 M Hz): 1.03 (dd, J = 7.11, 3.44 Hz, 6H) 1.18 (d, J = 6.88 Hz, 3H) 1.20-1.23 (m, 1H) 1.21 (d, J = 6.88 Hz, 3H) 1.23 (d, J = 5.96 Hz, 3H) 1.24-1.26 (m, 1H) 1.26 (s, 3H) 1.29 (d, J = 6.42 Hz, 3H) 1.40 (s, 3H) 1.61 (dd, J = 15.13, 5.04 Hz, 1H) 1.64-1.67 (m, 1H) 1.78 (d, J = 14.21 Hz, 1H) 1.99-2.05 (m, 2H) 2.05-2.09 (m, 1H) 2.09-2.14 (m, 1H) 2.17 (d, J = 10.55 Hz, 1H) 2.28 (s, 6H) 2.36 (d, J = 15.13 Hz, 1H) 2.38-2.42 (m, 1H) 2.42-2.48 (m, 1 H) 3.00 (d, J = 11.00 Hz, 1H) 3.04 (t, J = 10.09 Hz, 1H) 3.08-3.17 (m, 5H) 3.15 (t, J = 7.57 Hz, 1H) 3.20 (dd, J = 10.09, 7.34 Hz, 1H) 3.27-3.30 (m, 1 H) 3.32 (s, 3H) 3.33-3.35 (m, 1H) 3.33 (s, 3H) 3.40-3.48 (m, 2H) 3.49-3.57 (m, 1H) 3.80-3.85 (m, 1H) 3.86 (d, J = 5.04 Hz, 1H) 4.04-4.08 (m, 1 H) 4.07-4.13 (m, 1H) 4.46 (d, J = 7.34 Hz, 1H) 4.79 (d, J = 4.58 Hz, 1H) 5.04-5.10 (m, 1H) 7.33 (d, J = 6.88 Hz, 1H) 7.38 (d, J = 7.79 Hz, 1H) 7.46 (t, J = 7.34 Hz, 1H) 7.52 (t, J = 6.88 Hz, 1H) 7.71 (d, J = 8.25 Hz, 1H) 7.84 (d, J = 7.79 Hz, 1H) 8.06 (d, J = 8.71 Hz, 1H) | stirred at room temperature for 1 hour. The reaction mixture was added with saturated aqueous ammonium chloride and ethyl acetate, the layers were separated, and the organic layer was dried over anhydrous sodium sulfate, and filtered. The filtrate was concentrated under reduced pressure, and the resulting residue was purified by silica gel column chromatography (hexane:acetone:triethylamine=200:10:0.2 to 60:10:0.2) to obtain a cyclized compound (36 mg).

(3) By using the compound obtained in (2) mentioned above (36 mg) as a starting material, the compound shown in Table 4 (3.6 mg) was obtained in the same manners as those of Example 87, Example 13, (2), Example 107, (3), and Example 1, (3).

Example 168

By using the compound obtained in Reference Example 1 (2.02 g) and the compound obtained in Reference Example 47

Example 167

(1) By using the compound obtained in Reference Example 1 (1.27 g) and the compound obtained in Reference Example 44 (1.27 g) as starting materials, a lactonization precursor (165 mg) was obtained in the same manner as that of Example 1, (1).

(2) 4-Dimethylaminopyridine (321 mg) and 2-methyl-6-nitrobenzoic anhydride (109 mg) were dissolved in acetonitrile (20 ml), the solution was added dropwise with a solution of the compound obtained in (1) mentioned above (129 mg) in a mixed solution of acetonitrile and tetrahydrofuran (9:1, 20 ml) at room temperature, and the mixture was (1.48 g) as starting materials, the compound shown in Table 4 (5.8 mg) was obtained in the same manners as those of Example 1, (1), Example 167, (2), and Example 1, (3).

Examples 169 to 195

Preparation methods of the compounds represented by the formula (F) having $R^{1F}$ and $R^{2F}$ defined in Table 5 are shown below.

[Formula 27]

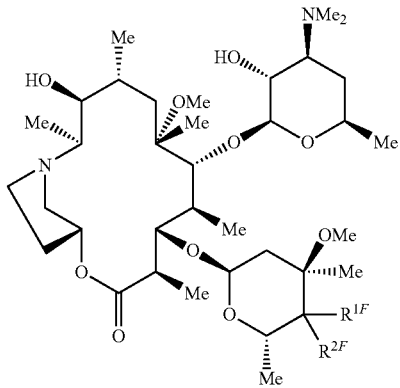

Formula (F)

TABLE 5

| Example | Reference Example | $R^{1F}$ | $R^{2F}$ | ESI MS (M + H) | $^1$H-NMR, CDCl$_3$, δ (ppm) |
|---|---|---|---|---|---|
| 169 | | H$_2$N— (wedge) | —H | 702.3 | (300 M Hz): 0.94-0.99 (m, 6H) 1.09 (d, J = 7.5 Hz, 3H) 1.15 (d, J = 7.2 Hz, 3H) 1.20-1.25 (m, 7H) 1.29 (d, J = 6.3 Hz, 3H) 1.37 (s, 3H) 1.44-1.67 (m, 4H) 1.75-1.85 (m, 1H) 1.96-2.06 (m, 1H) 2.21-2.29 (m, 8H) 2.35-2.59 (m, 5H) 2.80-3.08 (m, 4H) 3.17-3.23 (m, 3H) 3.29 (s, 3H) 3.31 (s, 3H) 3.44-3.51 (m, 1H) 3.61 (d, J = 9.7 Hz, 1H) 3.76 (d, J = 7.5 Hz, 1H) 4.02 (dq, J = 9.3 Hz, J = 6.3 Hz, 1H) 4.47 (d, J = 7.2 Hz, 1 H) 4.90-4.98 (m, 2H) |
| 170 | | H$_2$N⋯ (dashed) | —H | 702.2 | (300 M Hz): 0.90-1.30 (m, 25H) 1.55-2.30 (m, 19H) 2.80-3.15 (m, 4H) 3.22-3.40 (m, 9H) 3.55-3.75 (m, 3H) 4.60-4.73 (m, 2H) 4.92-4.99 (m, 2H) |
| 171 | | HO⋯ (dashed) | —H | 703.3 | (300 M Hz): 0.94-0.99 (m, 6H) 1.10 (d, J = 7.5 Hz, 3H) 1.16 (d, J = 7.2 Hz, 3H) 1.19-1.22 (m, 7H) 1.25 (d, J = 6.6 Hz, 3H) 1.37 (s, 3H) 1.44 (d, J = 15.6 Hz, 1H) 1.60-2.11 (m, 6H) 2.24-2.29 (m, 7H) 2.43-2.60 (m, 4H) 2.81-3.07 (m, 5H) 3.17-3.25 (m, 3H) 3.29 (s, 3H) 3.31 (s, 3H) 3.42-3.49 (m, 1H) 3.63 (d, J = 9.6 Hz, 1 H) 3.71 (d, J = 7.8 Hz, 1H) 4.48 (d, J = 7.2 Hz, 1H) 4.56 (q, J = 6.9 Hz, 1H) 4.93-4.98 (m, 2H) |
| 172 | | indole-CH$_2$-NH-CH$_2$CH$_2$-NH-C(O)-O— | —H | 918.7 | (600 M Hz): 0.96 (d, J = 6.88 Hz, 3H) 0.99 (d, J = 6.42 Hz, 3H) 1.10 (d, J = 7.34 Hz, 3H) 1.14-1.20 (m, 12H) 1.21-1.28 (m,1H) 1.35 (s, 3H) 1.41 (d, J = 15.13 Hz, 1H) 1.64 (dd, J = 15.13, 4.58 Hz, 1H) 1.74-1.85 (m, 2H) 1.98-2.05 (m, 1H) 2.23-2.30 (m, 1H) 2.41 (s, 6H) 2.42-2.62 (m, 5H) 2.80-2.89 (m, 3H) 2.91-3.00 (m, 2H) 3.03-3.08 (m, 1H) 3.16-3.21 (m, 2H) 3.30 (s, 3H) 3.31-3.35 (m, 3H) 3.34 (s, 3H) 3.61-3.64 (m, 1H) 3.65-3.71 (m, 1H) 3.76 (d, J = 7.34 Hz, 1H) 3.87-3.90 (m, 2H) 4.30-4.36 (m, 1H) 4.52 (d, J = 9.63 Hz, 1H) 4.56 (d, J = 7.34 Hz, 1H) 4.94-4.99 (m, 2H) 5.45 (br. s., 1H) 6.52 (br. s., 1H) 7.00 (d, J = 7.34 Hz, 1 H) 7.19-7.20 (m, 1H) 7.42 (s, 1H) 7.57 (d, J = 8.25 Hz, 1H) 9.32 (br. s., 1H) |

| Example | Reference Example | R^1F | R^2F | ESI MS (M + H) | 1H-NMR, CDCl3, δ (ppm) |
|---|---|---|---|---|---|
| 173 | | benzimidazol-4-yl-CH2-NH-CH2CH2-NH-C(=O)-O-tBu | H | 919.7 | (600 M Hz): 0.94-1.00 (m, 6H) 1.09-1.21 (m, 16H) 1.35 (s, 3H) 1.44-1.48 (m, 1H) 1.51-1.67 (m, 2H) 1.77-1.84 (m, 1H) 1.98-2.04 (m, 1H) 2.22-2.26 (m, 1H) 2.27 (s, 6H) 2.40-2.49 (m, 2H) 2.50-2.59 (m, 3H) 2.81-2.87 (m, 3H) 2.89-2.99 (m, 2H) 3.03-3.07 (m, 1H) 3.16-3.22 (m, 3H) 3.29 (s, 3H) 3.32 (s, 3H) 3.33-3.40 (m, 2H) 3.52-3.58 (m, 1H) 3.62-3.65 (m, 1H) 3.74 (d, J = 7.79 Hz, 1H) 4.16 (s, 2H) 4.33-4.39 (m, 1H) 4.47 (d, J = 6.42 Hz, 1H) 4.55 (d, J = 9.63 Hz, 1H) 4.93 (d, J = 4.58 Hz, 1H) 4.94-4.97 (m, 1H) 6.98 (s, 1H) 7.10 (br. s., 1H) 7.18-7.22 (m, 1H) 8.06 (br. s., 1H) |
| 174 | | tBu-O-C(=O)-NH-azetidin-3-yl; N-CH(Me)-(2-methoxyphenyl) | H | 935.6 | (600 M Hz): 0.95 (d, J = 6.88 Hz, 3H) 0.98 (d, J = 6.42 Hz, 3H) 1.10 (d, J = 7.34 Hz, 3H) 1.12-1.17 (m, 13H) 1.20 (d, J = 5.96 Hz, 3H) 1.35 (s, 3H) 1.45 (d, J = 15.59 Hz, 1H) 1.56-1.84 (m, 3H) 1.94-2.03 (m, 1H) 2.21-2.29 (m, 1H) 2.32 (s, 6H) 2.37-2.49 (m, 2H) 2.50-2.62 (m, 3H) 2.76-3.00 (m, 3H) 3.00-3.08 (m, 1H) 3.13-3.24 (m, 3H) 3.28 (s, 3H) 3.31 (s, 3H) 3.48-3.80 (m, 8H) 3.82 (s, 3H) 4.26-4.37 (m, 2H) 4.44-4.52 (m, 2H) 4.91 (d, J = 5.04 Hz, 1H) 4.92-4.97 (m, 1H) 6.85 (d, J = 8.25 Hz, 1H) 6.93 (t, J = 7.57 Hz, 1H) 7.16-7.22 (m, 1H) 7.37 (d, J = 7.34 Hz, 1H) |
| 175 | | 3-HO-C6H4-CH(Me)-NH-CH2CH2-NH-C(=O)-O-tBu | H | 909 | mixture of diastereomers, (400 M Hz): 0.95-1.02 (m, 6H) 1.04-1.46 (m, 19H) 1.56-2.10 (m, 3H) 2.22-2.33 (m, 1H) 2.35-2.52 (m, 9H) 2.52-2.67 (m, 3H) 2.57-3.10 (m, 7H) 3.12-3.24 (m, 3H) 3.29 (s, 3H) 3.32-3.40 (m 5H) 3.58-3.67 (m, 2H) 3.68-3.78 (m, 4H) 4.30-4.40 (m, 1H) 4.46-4.53 (m, 2H) 4.93-5.00 (m, 1H) 5.00-5.05 and 5.36-5.42 (m, 1H) 6.68-6.76 (m, 2H) 6.86-6.92 (m, 1H) 7.09-7.16 (m, 1H) |
| 176 | | tBu-O-C(=O)-NH-CH2CH2-N(Et)-CH(Me)-(2-methoxyphenyl) | H | 951.4 | (300 M Hz): 0.91-0.99 (m, 9H) 1.09-1.25 (m, 16H) 1.29 (d, J = 6.9 Hz, 3H) 1.35 (s, 3H) 1.44-1.55 (m, 2H) 1.63 (dd, J =15.0 Hz, J = 5.1 Hz, 1H) 1.78-1.85 (m, 1H) 1.96-2.05 (m, 1H) 2.23-2.28 (m, 7H) 2.35-2.63 (m, 9H) 2.81-3.07 (m, 4H) 3.15-3.25 (m, 5H) 3.30 (s, 3H) 3.31 (s, 3H) 3.56-3.64 (m, 2H) 3.76 (d, J = 8.1 Hz, 1H) 3.85 (s, 3H) 4.31-4.41 (m, 2H) 4.48-4.54 (m, 2H) 4.91-4.97 (m, 2H) 5.56-5.62 (m, 1H) 6.85-6.94 (m, 2H) 7.15-7.29 (m, 2H) |
| 177 | | 3-HO-C6H4-CH(Me)-NH-CH2CH2-NH- | HO-(stereo)-Me | 895 | mixture of diastereomers, (400 M Hz): 0.96 (d, J = 7.1 Hz, 3H) 0.99 (d, J = 6.8 Hz, 3H) 1.07 (d, J = 7.3 Hz, 3H) 1.11-1.18 (m, 13H) 1.31-1.38 (m, 6H) 1.43 (dd, J = 14.9, 5.9 Hz, 1H) 1.59-1.66 (m, 1H) 1.76-1.87 (m, 1H) 1.87-2.10 (m, 3H) 2.21-2.31 (m, 1H) 2.32-3.09 (m, 18H) 2.40 (s, 6H) 3.17-3.21 (m, 2H) 3.27-3.35 (m, 7H) 3.46-3.57 (m, 1H) 3.59-3.78 (m, 3H) 4.30-4.37 (m, 1H) 4.41 (dd, J = 7.1, 3.9 Hz, 1H) 4.91-4.98 (m, 2H) 6.68-6.82 (m, 3H) 7.17 (q, J = 7.8 Hz, H) |

TABLE 5-continued

| Example | Reference Example | R1F | R2F | ESI MS (M + H) | 1H-NMR, CDCl3, δ (ppm) |
|---|---|---|---|---|---|
| 178 | | | | 927 | (300 M Hz): 0.96 (d, J = 6.6 Hz, 6H) 1.09 (d, J = 6.5 Hz, 3H) 1.10 (s, 3H) 1.13 (d, J = 7.1 Hz, 3H) 1.19 (d, J = 6.6 Hz, 3H) 1.24 (d, J = 6.0 Hz, 3H) 1.25-1.35 (m, 1H) 1.42 (s, 3H) 1.52 (d, J = 15.1 Hz, 1H) 1.66-1.88 (m, 4H) 1.95-2.08 (m, 2H) 2.09 (d, J = 15.7 Hz, 1H) 2.23-2.30 (m, 1H) 2.30 (s, 6H) 2.40-2.66 (m, 7H) 2.75-2.98 (m, 6H) 3.00-3.09 (m, 1H) 3.14-3.23 (m, 2H) 3.22 (s, 3H) 3.27 (s, 3H) 3.33 (dd, J = 11.2, 6.6 Hz, 1H) 3.47 (dd, J = 11.3, 3.2 Hz, 1H) 3.54-3.74 (m, 4H) 4.42 (d, J = 6.1 Hz, 1H) 4.60 (q, J = 6.3 Hz, 1H) 4.76-4.97 (m, 4H) 7.58 (d, J = 8.8 Hz, 2H) 8.22 (d, J = 8.8 Hz, 2H) |
| 179 | | | | 803 | (400 M Hz): 0.95 (d, J = 7.1 Hz, 3H) 0.98 (d, J = 6.6 Hz, 3H) 1.09 (d, J = 7.6 Hz, 3H) 1.14 (s, 3H) 1.16 (d, J = 6.6 Hz, 6H) 1.22 (d, J = 6.1 Hz, 3H) 1.22-1.25 (m, 1H) 1.37 (s, 3H) 1.47 (d, J = 15.1 Hz, 1H) 1.61-1.84 (m, 2H) 1.93 (dd, J = 14.9, 5.1 Hz, 1H) 1.95-2.03 (m, 1H) 2.07 (d, J = 14.9 Hz, 1H) 2.22 (s, 6H) 2.30 (s, 6H) 2.34-2.59 (m, 7H) 2.66-2.72 (m, 2H) 2.76-3.08 (m, 5H) 3.15-3.24 (m, 3H) 3.28 (s, 3H) 3.30 (s, 3H) 3.47-3.56 (m, 1H) 3.63 (d, J = 9.7 Hz, 1H) 3.76 (d, J = 8.0 Hz, 1H) 4.30 (q, J = 6.3 Hz, 1H) 4.43 (d, J = 7.1 Hz, 1H) 4.88-4.98 (m, 2H) |
| 180 | | | | 732 | (400 M Hz): 0.96 (d, J = 7.1 Hz, 3H) 0.98 (d, J = 6.8 Hz, 3H) 1.10 (d, J = 7.3 Hz, 3H) 1.14 (s, 3H) 1.16 (d, J = 6.3 Hz, 6H) 1.22 (d, J = 6.1 Hz, 3H) 1.22-1.26 (m, 1H) 1.37 (s, 3H) 1.47 (d, J = 14.9 Hz, 1H) 1.60-1.85 (m, 2H) 1.94 (dd, J = 14.9, 5.1 Hz, 1H) 1.96-2.04 (m, 1H) 2.08 (d, J = 15.1 Hz, 1H) 2.28-2.32 (m, 1H) 2.29 (s, 6H) 2.42-2.60 (m, 5H) 2.78-3.08 (m, 1H) 3.16-3.24 (m, 3H) 3.28 (s, 3H) 3.30 (s, 3H) 3.44-3.54 (m, 1H) 3.64 (d, J = 9.5 Hz, 1H) 3.76 (d, J = 8.0 Hz, 1H) 4.35 (q, J = 6.3 Hz, 1H) 4.43 (d, J = 7.3 Hz, 1H) 4.92-4.99 (m, 2H) |
| 181 | | | | 788 | (400 M Hz): 0.92 (t, J = 7.1 Hz, 3H) 0.96 (d, J = 7.1 Hz, 3H) 0.98 (d, J = 6.8 Hz, 3H) 1.10 (d, J = 7.3 Hz, 3H) 1.14 (s, 3H) 1.16 (d, J = 6.3 Hz, 6H) 1.22 (d, J = 6.1 Hz, 3H) 1.22-1.26 (m, 1H) 1.37 (s, 3H) 1.47 (d, J = 15.6 Hz, 1H) 1.59-1.83 (m, 2H) 1.92 (dd, J = 14.9, 5.1 Hz, 1H) 1.96-2.05 (m, 1H) 2.08 (d, J = 14.9 Hz, 1H) 2.24-2.29 (m, 1H) 2.30 (s, 6H) 2.41-2.62 (m, 7H) 2.76-3.08 (m, 5H) 3.14-3.24 (m, 3H) 3.28 (s, 3H) 3.30 (s, 3H) 3.52-3.60 (m, 1H) 3.63 (d, J = 9.7 Hz, 1H) 3.75 (d, J = 8.0 Hz, 1H) 4.35 (q, J = 6.6 Hz, 1H) 4.42 (d, J = 7.3 Hz, 1H) 4.91-4.97 (m, 2H) |
| 182 | | | | 776 | (400 M Hz): 0.95 (d, J = 7.1 Hz, 3H) 0.98 (d, J = 6.8 Hz, 3H) 1.09 (d, J = 7.3 Hz, 3H) 1.15 (d, J = 7.1 Hz, 3H) 1.18 (s, 3H) 1.21 (d, J = 6.6 Hz, 3H) 1.23 (d, J = 6.1 Hz, 3H) 1.24-1.29 (m, 1H) 1.40 (s, 3H) 1.50 (d, J = 15.1 Hz, 1H) 1.63-1.71 (m, 1H) 1.76-1.91 (m, 2H) 1.96-2.07 (m, 1H) 2.10 (d, J = 15.1 Hz, 1H) 2.27-2.31 (m, 1H) 2.30 (s, 6H) 2.41-2.70 (m, 7H) 2.74-2.85 (m, 3H) 2.87-2.98 (m, 2H) 3.01-3.09 (m, 1H) 3.16-3.22 (m, 2H) 3.29 (s, 3H) 3.30 (s, 3H) 3.56-3.75 (m, 5H) 4.42-4.51 (m, 2H) 4.89-4.97 (m, 2H) |

TABLE 5-continued

| Example | Reference Example | R^1F | R^2F | ESI MS (M + H) | ¹H-NMR, CDCl₃, δ (ppm) |
|---|---|---|---|---|---|
| 183 | | (H₂N-CH₂-CH₂-NH-C(CH₃)₂-) | (HO⋯C(CH₃)₂-) | 775 | (400 M Hz): 0.96 (d, J = 7.1 Hz, 3H) 0.98 (d, J = 6.8 Hz, 3H) 1.10 (d, J = 7.3 Hz, 3H) 1.13-1.19 (m, 6H) 1.15 (s, 3H) 1.22 (d, J = 6.1 Hz, 3H) 1.22-1.26 (m, 1H) 1.37 (s, 3H) 1.48 (d, J = 14.9 Hz, 1H) 1.60-1.84 (m, 2H) 1.93 (dd, J = 14.9, 5.1 Hz, 1H) 1.96-2.05 (m, 1H) 2.08 (d, J = 14.4 Hz, 1H) 2.27-2.31 (m, 1H) 2.30 (s, 6H) 2.42-2.59 (m, 5H) 2.64-2.70 (m, 2H) 2.75-3.08 (m, 7H) 3.15-3.24 (m, 3H) 3.28 (s, 3H) 3.30 (s, 3H) 3.47-3.58 (m, 1H) 3.63 (d, J = 9.5 Hz, 1H) 3.75 (d, J = 8.3 Hz, 1H) 4.34 (q, J = 6.6 Hz, 1H) 4.42 (d, J = 7.1 Hz, 1H) 4.92-4.98 (m, 2H) |
| 184 | | (Me₂N-CH₂-CH₂-NH-C(CH₃)₂-) | (HO⋯C(CH₃)₂-) | 831 | (400 M Hz): 0.94-1.02 (m, 12H) 1.09 (d, J =7.6 Hz, 3H) 1.13 (s, 3H) 1.15 (d, J = 6.3 Hz, 6H) 1.22 (d, J = 6.1 Hz, 3H) 1.24-1.26 (m, 1H) 1.37 (s, 3H) 1.47 (d, J = 14.9 Hz, 1H) 1.60-1.86 (m, 2H) 1.94 (dd, J = 14.9, 5.1 Hz, 1H) 1.96-2.04 (m, 1H) 2.08 (d, J = 14.6 Hz, 1H) 2.28-2.31 (m, 1H) 2.30 (s, 6H) 2.38-2.58 (m, 11H) 2.62-2.67 (m, 2H) 2.76-3.08 (m, 5H) 3.15-3.24 (m, 3H) 3.28 (s, 3H) 3.30 (s, 3H) 3.46-3.56 (m, 1H) 3.63 (d, J = 9.8 Hz, 1H) 3.76 (d, J = 8.0 Hz, 1H) 4.29 (q, J = 6.6 Hz, 1H) 4.43 (d, J = 7.3 Hz, 1H) 4.91-4.99 (m, 2H) |
| 185 | | (pyrrolidine-CH₂-CH₂-NH-C(CH₃)₂-) | (HO⋯C(CH₃)₂-) | 829 | (400 M Hz): 0.96 (d, J = 7.3 Hz, 3H) 0.98 (d, J = 6.8 Hz, 3H) 1.09 (d, J = 7.3 Hz, 3H) 1.14 (s, 3H) 1.16 (d, J = 6.6 Hz, 6H) 1.22 (d, J = 6.1 Hz, 3H) 1.22-1.25 (m, 1H) 1.37 (s, 3H) 1.47 (d, J = 14.6 Hz, 1H) 1.62-1.84 (m, 6H) 1.93 (dd, J = 14.9, 5.1 Hz, 1H) 1.97-2.04 (m, 1H) 2.07 (d, J = 15.1 Hz, 1H) 2.26-2.29 (m, 1H) 2.30 (s, 6H) 2.41-2.59 (m, 11H) 2.71-2.76 (m, 2H) 2.77-3.08 (m, 5H) 3.15-3.24 (m, 3H) 3.28 (s, 3H) 3.30 (s, 3H) 3.50-3.58 (m, 1H) 3.63 (d, J = 9.5 Hz, 1H) 3.76 (d, J = 8.0 Hz, 1H) 4.32 (q, J = 6.6 Hz, 1H) 4.42 (d, J = 7.1 Hz, 1H) 4.91-4.97 (m, 2H) |
| 186 | | (piperazine-C(CH₃)₂-) | (HO⋯C(CH₃)₂-) | 801 | (400 M Hz): 0.95 (d, J = 7.3 Hz, 3H) 0.98 (d, J = 6.6 Hz, 3H) 1.09 (d, J = 7.6 Hz, 3H) 1.11 (s, 3H) 1.15 (d, J = 6.3 Hz, 6H) 1.16 (d, J = 6.8 Hz, 3H) 1.23 (d, J = 6.1 Hz, 3H) 1.22-1.26 (m, 1H) 1.36 (s, 3H) 1.46 (d, J = 14.9 Hz, 1H) 1.62-1.85 (m, 2H) 1.91-2.06 (m, 3H) 2.10 (d, J = 14.9 Hz, 1H) 2.25-2.29 (m, 1H) 2.30 (s, 6H) 2.41-2.64 (m, 7H) 2.76-3.08 (m, 9H) 3.14-3.24 (m, 3H) 3.28 (s, 3H) 3.31 (s, 3H) 3.37-3.46 (m, 1H) 3.63 (d, J = 9.5 Hz, 1H) 3.75 (d, J = 7.8 Hz, 1H) 4.16 (q, J = 6.6 Hz, 1H) 4.41 (d, J = 7.3 Hz, 1H) 4.92-4.99 (m, 2H) |
| 187 | | (1-benzyl-pyrrolidin-3-yl-NH-C(CH₃)₂-) | (HO⋯C(CH₃)₂-) | 891 | mixture of diastereomers, (400 M Hz): 0.96 (d, J = 7.1 Hz, 3H) 0.98 (d, J = 6.8 Hz, 3H) 1.07-1.26 (m, 16H) 1.36 (s, 3H) 1.44-1.85 (m, 4H) 1.86-1.94 (m, 1H) 1.96-2.18 (m, 3H) 2.26-2.30 (m, 1H) 2.27 (s, 3H) 2.28 (s, 3H) 2.36-2.85 (m, 10H) 2.86-3.08 (m, 3H) 3.15-3.24 (m, 3H) 3.27 (s, 3H) 3.30 (s, 3H) 3.46-3.66 (m, 4H) 3.74 (d, J = 7.1 Hz, 1H) 4.29-4.36 (m, 1H) 4.40 (d, J = 7.1 Hz, 1H) 4.91-4.97 (m, 2H) 7.25-7.34 (m, 5H) |

TABLE 5-continued

| Example | Reference Example | R<sup>1F</sup> | R<sup>2F</sup> | ESI MS (M + H) | <sup>1</sup>H-NMR, CDCl<sub>3</sub>, δ (ppm) |
|---|---|---|---|---|---|
| 188 | 53 | 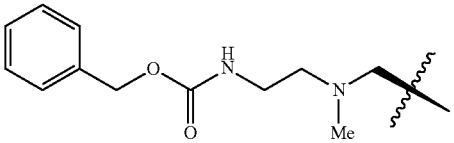 | 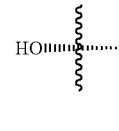 | 923 FAB MASS | (400 M Hz): 0.96 (d, J = 7.3 Hz, 3H) 0.99 (d, J = 7.1 Hz, 3H) 1.09 (d, J = 7.3 Hz, 3H) 1.10 (s, 3H) 1.16 (d, J =6.8 Hz, 6H) 1.23 (d, J = 6.1 Hz, 3H) 1.22-1.24 (m, 1H) 1.36 (s, 3H) 1.46 (d, J = 15.1 Hz, 1H) 1.62-1.70 (m, 1H) 1.74-1.85 (m, 1H) 1.92 (dd, J = 14.9, 4.9 Hz, 1H) 1.96-2.12 (m, 3H) 2.26-2.31 (m, 1H) 2.30 (s, 6H) 2.35 (s, 3H) 2.41-2.76 (m, 6H) 2.77-3.09 (m, 5H) 3.15-3.44 (m, 6H) 3.27 (s, 3H) 3.31 (s, 3H) 3.63 (d, J = 9.7 Hz, 1H) 3.74 (d, J = 8.0 Hz, 1H) 4.17 (q, J = 6.6 Hz, 1H) 4.40 (d, J = 7.1 Hz, 1H) 4.90-5.04 (m, 3 H) 5.09 (s, 2H) 7.30-7.37 (m, 5H) |
| 189 | 52 | 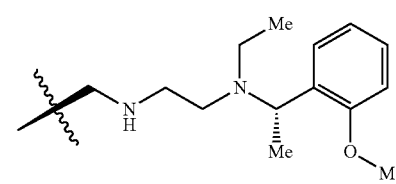 | 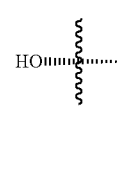 | 937 | (400 M Hz): 0.92-1.00 (m, 9H) 1.07-1.30 (m, 19H) 1.36 (s, 3H) 1.46 (d, J = 15.1 Hz, 1H) 1.55-1.85 (m, 2H) 1.90-1.21 (m, 3H) 2.28 (s, 6H) 2.28-2.32 (m, 2H) 2.41-2.69 (m, 10H) 2.76-3.08 (m, 5H) 3.15-3.23 (m, 3H) 3.28 (s, 3H) 3.31 (s, 3H) 3.40-3.50 (m, 1H) 3.63 (d, J = 9.7 Hz, 1H) 3.76 (d, J = 7.8 Hz, 1H) 3.81 (s, 3H) 4.24 (q, J = 6.3 Hz, 1 H) 4.33-4.44 (m, 2H) 4.92-4.97 (m, 2H) 6.86 (d, J = 8.0 Hz, 1H) 6.90-6.93 (m, 1H) 7.18-7.34 (m, 2H) |
| 190 |  | 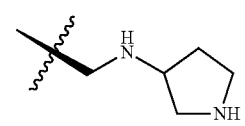 | 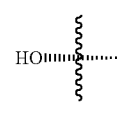 | 801 | mixture of diastereomers, (400 M Hz): 0.96 (d, J = 7.1 Hz, 3H) 0.98 (d, J = 6.8 Hz, 3H) 1.07-1.11 (m, 3H) 1.13-1.15 (m, 13H) 1.36-1.40 (m, 3H) 1.42-1.56 (m, 2H) 1.62-1.70 (m, 1H) 1.75-2.12 (m, 8H) 2.26-2.34 (m, 7 H) 2.41-2.59 (m, 5H) 2.64-2.72 (m, 1H) 2.76-3.09 (m, 8H) 3.16-3.25 (m, 3H) 3.28 (s, 3H) 3.30 (s, 3H) 3.50-3.60 (m, 1H) 3.64 (d, J = 9.7 Hz, 1H) 3.75 (d, J = 8.3 Hz, 1H) 4.34-4.43 (m, 2H) 4.90-4.97 (m, 2H) |
| 191 |  | 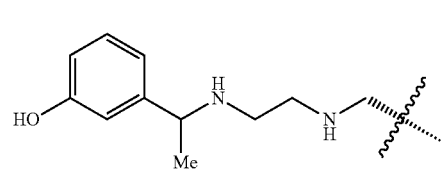 | 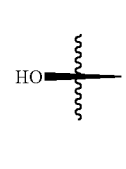 | 895 | mixture of diastereomers, (400 M Hz): 0.93-1.01 (m, 6H) 1.10 (d, J = 7.3 Hz, 3H) 1.13-1.39 (m, 19H) 1.47 (dd, J = 14.7, 7.1 Hz, 1H) 1.50-2.98 (m, 27H) 2.29 (s, 6H) 3.01-3.10 (m, 1H) 3.16-3.22 (m, 2H) 3.31-3.34 (m, 3H) 3.46-3.57 (m, 1H) 3.61-3.78 (m, 3 H) 4.37-4.48 (m, 2H) 4.85-4.90 (m, 1H) 4.98-5.04 (m, 1H) 6.67-6.90 (m, 3 H) 7.11-7.17 (m, 1H) |
| 192 |  | 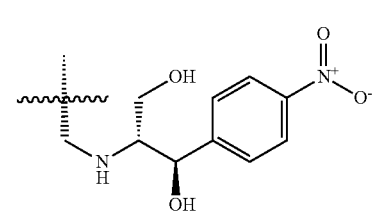 | 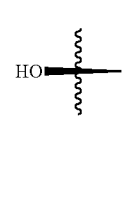 | 927 FAB MASS | (400 M Hz): 0.95 (d, J =7.3 Hz, 3H) 0.98 (d, J =6.6 Hz, 3H) 1.09 (d, J =7.3 Hz, 3H) 1.15 (d, J =7.1 Hz, 3H) 1.18 (s, 3H) 1.21 (d, J = 6.1 Hz, 3H) 1.22 (d, J = 6.8 Hz, 3H) 1.23-1.26 (m, 1H) 1.36 (s, 3H) 1.44 (d, J = 14.9 Hz, 1H) 1.61-1.68 (m, 1H) 1.76-1.86 (m, 2 H) 1.90-2.05 (m, 3H) 2.24-2.29 (m, 2H) 2.28 (s, 6H) 2.40-2.69 (m, 7H) 2.80-2.97 (m, 4H) 3.01-3.08 (m, 1H) 3.14-3.25 (m, 4 H) 3.26 (s, 3H) 3.33 (s, 3H) 3.45 (dd, J = 11.2, 3.4 Hz, 1H) 3.45-3.53 (m, 1H) 3.57 (d, J = 9.8 Hz, 1H) 3.68 (dd, J = 11.2, 3.7 Hz, 1 H) 3.73 (d, J = 7.6 Hz, 1H) 4.37-4.44 (m, 2 H) 4.81-4.85 (m, 2H) 4.93-4.99 (m, 1H) 7.58 (d, J = 8.8 Hz, 2H) 8.21 (d, J = 8.8 Hz, 2H) |

TABLE 5-continued

| Example | Reference Example | R$^{1F}$ | R$^{2F}$ | ESI MS (M + H) | $^1$H-NMR, CDCl$_3$, δ (ppm) |
|---|---|---|---|---|---|
| 193 | 52 | (structure: N-CH2CH2-N(Et)-CH(Me)-C6H4(2-OMe), with NH linker) | HO— (wedge) | 937 | (400 M Hz): 0.93-1.02 (m, 9H) 1.09-1.29 (m, 19H) 1.38 (s, 3H) 1.47 (d, J = 15.1 Hz, 1H) 1.61-1.68 (m, 1H) 1.75-2.05 (m, 3H) 2.20-2.26 (m, 2H) 2.27 (s, 6H) 2.40-2.65 (m, 10H) 2.73 (d, J = 12.9 Hz, 1H) 2.80-3.10 (m, 4H) 3.15-3.23 (m, 3H) 3.30 (s, 3H) 3.34 (s, 3H) 3.56-3.66 (m, 2H) 3.76 (d, J = 7.8 Hz, 1H) 3.80 (s, 3H) 4.36 (q, J = 6.8 Hz, 1H) 4.44-4.53 (m, 2H) 4.81 (d, J = 4.9 Hz, 1H) 4.92-4.99 (m, 1H) 6.84 (d, J = 7.6 Hz, 1H) 6.89-6.95 (m, 1H) 7.16-7.22 (m, 1H) 7.33 (dd, J = 7.8, 1.7 Hz, 1H) |
| 194 | 54 | (structure: NH-CH(Me)-C6H4(2-OMe)) | HO— (wedge) | 866.3 | (500 M Hz): 0.97 (d, J = 7.1 Hz, 3H) 1.01 (d, J = 6.7 Hz, 3H) 1.08-1.24 (m, 16H) 1.36 (d, J = 6.7 Hz, 3H) 1.39 (s, 3H) 1.44-1.69 (m, 9H) 1.83 (m, 1H) 1.97-2.08 (m, 2H) 2.20-2.28 (m, 2H) 2.30 (s, 3H) 2.47-2.64 (m, 5H) 2.68 (d, J = 12.8 Hz, 1H) 2.86 (m, 1H) 2.94-3.00 (m, 2H) 3.07 (m, 1H) 3.18-3.26 (m, 3H) 3.30 (s, 3H) 3.35 (s, 3H) 3.57-3.69 (m, 2H) 3.79 (d, J = 7.4 Hz, 1H) 3.83 (s, 3H) 4.05 (q, J = 6.7 Hz, 1H) 4.47 (q, J = 6.6 Hz, 1H) 4.51 (d, J = 7.2 Hz, 1H) 4.83 (m, 1H) 4.98 (m, 1H) 6.86-6.97 (m, 2H) 7.19-7.31 (m, 2H) |
| 195 |  | (structure: C6H4(2-OMe)-CH2-NH-) | HO— (wedge) | 852 | (500 M Hz): 0.97 (d, J = 7.1 Hz, 3H) 1.01 (d, J = 6.6 Hz, 3H) 1.11-1.22 (m, 16H) 1.39 (s, 3H) 1.45-1.65 (m, 9H) 1.82 (m, 1H) 2.01 (m, 1H) 2.12 (m, 1H) 2.22-2.28 (m, 2H) 2.29 (s, 3H) 2.46-2.62 (m, 4H) 2.69 (d, J = 12.6 Hz, 1H) 2.76 (d, J = 12.6 Hz, 1H) 2.85 (m, 1H) 2.96 (m, 1H) 3.07 (m, 1H) 3.18-3.25 (m, 3H) 3.30 (s, 3H) 3.36 (s, 3H) 3.56-3.62 (m, 3H) 3.71-3.82 (m, 3H) 3.83 (s, 3H) 4.45 (q, J = 6.5 Hz, 1H) 4.49 (d, J = 7.2 Hz, 1H) 4.83 (m, 1H) 4.98 (m, 1H) 6.86-6.94 (m, 2H) 7.21-7.27 (m, 2H) |

Example 169

(1) The compound obtained in Example 1, (2) (4.25 g) was dissolved in tetrahydrofuran (42.5 ml), the solution was added with ethanol (170 ml) and 1 N hydrochloric acid (21.3 ml), and the mixture was stirred at room temperature for 3 hours. The reaction mixture was neutralized with 1 N aqueous sodium hydroxide, and then concentrated under reduced pressure, the residue was added with distilled water and ethyl acetate, and the layers were separated. The organic layer was dried over anhydrous magnesium sulfate, and filtered, then the filtrate was concentrated under reduced pressure, and the resulting residue was purified by silica gel column chromatography (hexane:acetone=10:1 to 6:1) to obtain a 4"-hydroxy compound (2.67 g).

(2) N-Chlorosuccinimide (1.46 g) was dissolved in chloroform (60 ml), and the solution was cooled to −20° C. The solution was added with dimethyl sulfide (1.0 ml), the mixture was stirred for 20 minutes, and then added with a solution of the compound obtained in (1) mentioned above (1.7 g) in chloroform (25 ml), and the mixture was stirred for 10 minutes. The mixture was added with triethylamine (2.67 ml), the mixture was further stirred for 30 minutes, and then added with saturated aqueous sodium hydrogencarbonate, the mixture was warmed to room temperature, and added with chloroform, and the layers were separated. The organic layer was washed with saturated brine, dried over anhydrous magnesium sulfate, and filtered, then the filtrate was concentrated under reduced pressure, and the resulting residue was purified by silica gel column chromatography (hexane:acetone=30:1 to 10:1) to obtain a 4"-ketone compound (1.41 g).

(3) The compound obtained in (2) mentioned above (70 mg) was dissolved in a mixed solvent of methanol and tetrahydrofuran (3:1, 2.8 ml), the solution was added with ammonium acetate (87 mg) and sodium cyanoborohydride (5.2 mg), and the mixture was stirred overnight at room temperature. The reaction mixture was added with saturated aqueous sodium hydrogencarbonate and chloroform, the layers were separated, and then the organic layer was washed with saturated brine. The organic layer was dried over anhydrous sodium sulfate and filtered, then the filtrate was concentrated under reduced pressure, and the resulting residue was purified by silica gel column chromatography (chloroform:methanol=50:1 to 20:1) and silica gel column chromatography (NH-form, toluene:ethyl acetate=50:1 to 10:1) to obtain an amine compound (8.0 mg) of which steric configuration of the 4"-position is S, and an epimer mixture (13.3 mg).

(4) By using the amine compound (8.0 mg) of which steric configuration of the 4"-position is S obtained in (3) mentioned above as a starting material, the compound shown in Table 5 (4.3 mg) was obtained in the same manner as that of Example 1, (3).

Example 170

(1) The epimer mixture obtained in Example 169, (3) (13.3 mg) was dissolved in methylene chloride (0.26 ml), the solution was added with (9-9H-fluorenyl)methyl 2,5-dioxopyrrolidin-1-ylcarbonate (7.2 mg) and triethylamine (3.8 µl), the mixture was stirred at room temperature for 3 days. The reaction mixture was concentrated under reduced pressure, and the resulting residue was purified by preparative thin layer chromatography (hexane:ethyl acetate:methanol:28% aqueous ammonia=50:10:1:1) to obtain ((9-9H-fluorenyl(methoxy)carbonylamino compound (8.3 mg) of which steric configuration of the 4"-position is R.
(2) The compound obtained in (1) mentioned above (8.3 mg) was dissolved in piperidine (0.2 ml), and the solution was stirred at room temperature for 15 minutes. The reaction mixture was concentrated under reduced pressure, and the resulting residue was purified by preparative thin layer chromatography (chloroform:methanol:28% aqueous ammonia=30:1:0.1) to obtain an amine compound (5.3 mg) of which steric configuration of the 4"-position is R.
(3) By using the compound obtained in (2) mentioned above (5.3 mg) as a starting material, the compound shown in Table 5 (2.9 mg) was obtained in the same manner as that of Example 1, (3).

Example 171

(1) The compound obtained in Example 169, (2) (50 mg) was dissolved in ethanol (4.0 ml), the solution was added with Raney nickel slurry (0.5 ml), and the mixture was stirred at room temperature for 16 hours under a hydrogen atmosphere of 3.7 kgt/cm$^2$. The reaction mixture was filtered through Celite, then the filtrate was added with saturated brine and ethyl acetate, the layers were separated, and the organic layer was dried over anhydrous sodium sulfate, and filtered. The filtrate was concentrated under reduced pressure, and the resulting residue was purified by preparative thin layer chromatography (hexane:acetone:triethylamine=30:10:0.2) to obtain a hydroxy compound (21.2 mg) of which steric configuration of the 4"-position is R.
(2) By using the compound obtained in (1) mentioned above (21.2 mg) as a starting material, the compound shown in Table 5 (10.6 mg) was obtained in the same manner as that of Example 1, (3).

Example 172

(1) The compound obtained in Example 169, (1) (200 mg) and 1,1'-carbonyldiimidazole (105 mg) were dissolved in a mixed solvent of tetrahydrofuran and dimethylformamide (2:1, 2 ml), the solution was added with sodium hydride (15.5 mg), and the mixture was stirred at room temperature for 0.5 hour. The reaction mixture was added with distilled water and ethyl acetate, the layers were separated, and then the organic layer was washed with saturated brine, dried over anhydrous sodium sulfate, and filtered. The filtrate was concentrated under reduced pressure, and the resulting residue was purified by silica gel column chromatography (hexane:acetone=10:1) to obtain an imidazolide compound (220 mg).
(2) The compound obtained in (1) mentioned above (20 mg) was dissolved in tetrahydrofuran (0.3 ml), the solution was added with ethylenediamine (6 mg), and the mixture was stirred at room temperature for 5 hours. The reaction mixture was concentrated under reduced pressure, and the resulting residue was purified by silica gel column chromatography (chloroform:methanol:28% aqueous ammonia=10:1:0.1) to obtain an amine compound (21.6 mg).
(3) The compound obtained in (2) mentioned above (9.7 mg) was dissolved in chloroform (2 ml), the solution was added with 6-indolecarboxyaldehyde (1.4 mg) and sodium triacetoxyborohydride (3 mg), and the mixture was stirred at room temperature for 2 days. The reaction mixture was added with saturated aqueous sodium hydrogencarbonate and chloroform, the layers were separated, and then the organic layer was dried over anhydrous sodium sulfate, and filtered. The filtrate was concentrated under reduced pressure, and the resulting residue was purified by silica gel column chromatography (chloroform:methanol:28% aqueous ammonia=20:1:0.1) to obtain an adduct compound.
(4) By using the compound obtained in (3) mentioned above as a starting material, the compound shown in Table 5 (3.2 mg) was obtained in the same manner as that of Example 1, (3).

Example 173

By using the compound obtained in Example 172, (2) (11 mg) and 1H-benzimidazol-6-ylcarboxyaldehyde (1.6 mg) obtained by the method described in the patent document (International Patent Publication WO03/014116) as starting materials, the compound shown in Table 5 (3.7 mg) was obtained in the same manners as those of Example 172, (3) and Example 1, (3).

Example 174

By using the compound obtained in Example 172, (1) (15 mg) and the compound obtained in Reference Example 50 (25 mg) as starting materials, the compound shown in Table 5 (5.1 mg) was obtained in the same manners as those of Example 172, (2) and Example 1, (3).

Example 175

By using the compound obtained in Example 172, (1) (52.5 mg) and the compound obtained in Reference Example 51 as starting materials, the compound shown in Table 5 (13.9 mg) was obtained in the same manners as those of Example 172, (2) and Example 1, (3).

Example 176

By using the compound obtained in Example 172, (1) (30 mg) and the compound obtained in Reference Example 52 as starting materials, the compound shown in Table 5 (15.4 mg) was obtained in the same manners as those of Example 172, (2) and Example 1, (3).

Example 177

(1) Sodium hydride (6.97 mg) was suspended in tetrahydrofuran (1.8 ml), the suspension was added with trimethylsulfoxonium iodide (63.9 mg), and the mixture was stirred at room temperature for 2 hours. The compound obtained in Example 169, (2) (180 mg) was dissolved in a mixed solvent of dimethyl sulfoxide and tetrahydrofuran (2:1, 2.7 ml), the solution was added to the reaction mixture, and the mixture was stirred for 3 hours. The reaction mixture was added with saturated aqueous ammonium chloride and ethyl acetate, the layers were separated, the organic layer was concentrated under reduced pressure, and the resulting residue was purified by silica gel column chromatography (hexane:acetone=25:1 to 10:1) to obtain a 4"-epoxy compound (176 mg).
(2) By using the compound obtained in (1) mentioned above (176 mg) as a starting material, a deprotected compound (143 mg) was obtained in the same manner as that of Example 1, (3).
(3) The compound obtained in (2) mentioned above (13.6 mg), potassium iodide (15.8 mg), and the compound obtained in Reference Example 51 (17.2 mg) were dissolved in ethanol (200 μl), and the solution was stirred at 100° C. for 5 minutes, and further stirred at 120° C. for 15 minutes under microwave irradiation. The solution was added with distilled water and ethyl acetate, the layers were separated, the organic layer was concentrated under reduced pressure, and the resulting residue was purified by silica gel column chromatography (ethyl acetate:methanol:28% aqueous ammonia=30:1:0.1 to 10:1:0.1, then chloroform:methanol:28% aqueous ammonia=20:1:0.1 to 10:1:0.1) to obtain the compound shown in Table 5 (8.0 mg).

In Examples 178 to 189, the compounds shown in Table 5 were synthesized in the same manner as that of Example 177, (3) by using the compound obtained in Example 177, (2) and corresponding amine reagents.

Example 190

The compound obtained in Example 187 (18.9 mg) was dissolved in a mixed solvent of dioxane and distilled water (5:1, 378 μl), the solution was added with 5% palladium-carbon (30 mg) under an argon atmosphere, and then the mixture was stirred at room temperature for 19 hours and 30 minutes under a hydrogen atmosphere of 1 atm. The reaction mixture was filtered through Celite, then the filtrate was concentrated under reduced pressure, and the resulting residue was purified by preparative thin layer chromatography (chloroform:methanol:28% aqueous ammonia=5:1:0.1) to obtain the compound shown in Table 5 (10.4 mg).

Example 191

(1) Trimethylsulfonium tetrafluoroborate (133.4 mg) was suspended in tetrahydrofuran (7.2 ml), the suspension was cooled to −20° C., and then added with a 0.5 N solution of potassium bis(trimethylsilyl)amide in toluene (1.55 ml), and the mixture was stirred for 2 hours with warming to 0° C. Then, the reaction mixture was cooled to −78° C., added with a solution of the compound obtained in Example 169, (2) (180 mg) in ethylene glycol dimethyl ether (810 μl), and the mixture was stirred for 2 hours. The reaction mixture was added with saturated aqueous ammonium chloride and chloroform, the layers were separated, and the organic layer was dried over anhydrous magnesium sulfate, and filtered. The filtrate was concentrated under reduced pressure, and the resulting residue was purified by silica gel column chromatography (hexane:acetone=40:1 to 20:1) to obtain a 4"-epoxy compound (128.7 mg).
(2) By using the compound obtained in (1) mentioned above (128.7 mg) as a starting material, a deprotected compound (96.5 mg) was obtained in the same manner as that of Example 1, (3).
(3) By using the compound obtained in (2) mentioned above (13.6 mg) and the compound obtained in Reference Example 51 (17.2 mg) as starting materials, the compound shown in Table 5 (3.7 mg) was obtained in the same manner as that of Example 177, (3).

In Examples 192 to 195, the compounds shown in Table 5 were synthesized in the same manner as that of Example 177, (3) by using the compound obtained in Example 191, (2) and corresponding amine reagents.

Examples 196 to 203

Preparation methods of the compounds represented by the formula (G) having R defined in Table 6 are shown below.

[Formula 28]

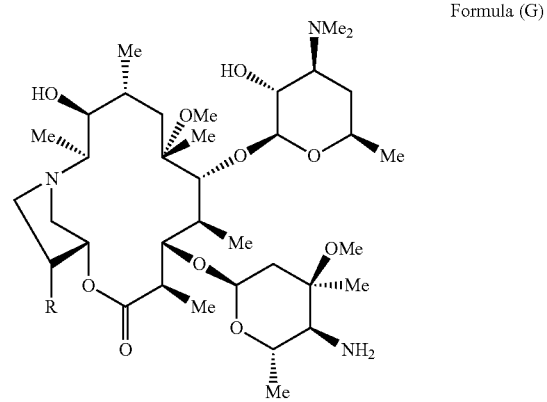

Formula (G)

TABLE 6

| Example | R | ESI MS (M + H) | $^1$H-NMR, CDCl$_3$, δ (ppm) |
|---|---|---|---|
| 196 | ![benzyloxy group] | 822.5 | (600 M Hz): 0.93 (d, J = 7.34 Hz, 3H) 1.00 (d, J = 6.88 Hz, 3H) 1.06-1.10 (m, 3H) 1.13-1.17 (m, 3H) 1.19-1.24 (m, 6H) 1.19-1.22 (m, 1 H) 1.29 (d, J = 6.42 Hz, 3H) 1.36 (s, 3H) 1.38-1.42 (m, 1H) 1.47-1.69 (m, 2H) 2.17-2.24 (m, 2H) 2.30 (br. s., 6H) 2.38 (d, J = 15.13 Hz, 1H) 2.43-2.55 (m, 3H) 2.71-2.78 (m, 1H) 2.78-2.91 (m, 3H) 2.91-3.00 (m, 2H) 3.10-3.14 (m, 1H) 3.15-3.25 (m, 2H) 3.29 (s, 3 H) 3.30 (s, 3H) 3.35-3.43 (m, 1H) 3.48 (t, J = 8.71 Hz, 1H) 3.56-3.60 (m, 1H) 3.61-3.65 (m, 1H) 3.75-3.78 (m, 1H) 3.99-4.04 (m, 1H) 4.45-4.56 (m, 3H) 4.91-4.95 (m, 1H) 5.01-5.07 (m, 1H) 7.27-7.37 (m, 5H) |

TABLE 6-continued

| Example | R | ESI MS (M + H) | ¹H-NMR, CDCl₃, δ (ppm) |
|---|---|---|---|
| 197 | naphthalen-2-yloxy-methyl group | 858.3 | (600 M Hz): 0.93 (d, J = 6.88 Hz, 3H) 1.05 (d, J = 6.42 Hz, 3H) 1.08 (d, J = 7.34 Hz, 3H) 1.11 (d, J = 7.79 Hz, 3H) 1.20 (s, 3H) 1.20-1.23 (m, 1H) 1.23 (d, J = 5.96 Hz, 3H) 1.28 (d, J = 5.96 Hz, 3H) 1.37 (s, 3H) 1.42-1.47 (m, 1H) 1.48-1.67 (m, 2H) 2.22 (d, J = 9.17 Hz, 1H) 2.23-2.26 (m, 1H) 2.30 (br. s., 6H) 2.34 (d, J = 15.13 Hz, 1H) 2.43-2.52 (m, 1H) 2.53-2.60 (m, 1H) 2.69-2.76 (m, 1H) 2.77-2.82 (m, 1H) 2.83-2.89 (m, 2H) 2.96-3.05 (m, 3H) 3.15-3.17 (m, 1H) 3.19-3.23 (m, 1H) 3.23-3.27 (m, 1H) 3.26 (s, 3H) 3.31 (s, 3H) 3.50-3.56 (m, 1H) 3.59 (d, J = 10.09 Hz, 1H) 3.78 (d, J = 7.34 Hz, 1H) 3.97-4.04 (m, 1H) 4.11 (t, J = 8.25 Hz, 1H) 4.23-4.28 (m, 1H) 4.50 (d, J = 7.34 Hz, 1H) 4.91 (d, J = 4.58 Hz, 1H) 5.18 (d, J = 5.04 Hz, 1H) 7.11 (dd, J = 8.71, 2.29 Hz, 1H) 7.15 (d, J = 2.75 Hz, 1H) 7.32 (dd, J = 15.13, 0.92 Hz, 1H) 7.42 (t, J = 7.57 Hz, 1H) 7.73 (dd, J = 10.32, 8.48 Hz, 3H) |
| 198 | 3-chlorophenoxymethyl group | 842.6 | (600 M Hz): 0.94 (d, J = 6.88 Hz, 3H) 1.03 (d, J = 6.42 Hz, 3H) 1.08 (d, J = 7.34 Hz, 3H) 1.11 (d, J = 6.88 Hz, 3H) 1.18-1.26 (m, 7H) 1.28 (d, J = 6.42 Hz, 3H) 1.36 (s, 3H) 1.44 (d, J = 15.13 Hz, 1H) 1.52-1.56 (m, 1H) 1.63-1.69 (m, 1H) 2.21-2.27 (m, 2H) 2.30 (s, 6H) 2.36 (d, J = 15.13 Hz, 1H) 2.44-2.54 (m, 2H) 2.62-2.69 (m, 1H) 2.74-2.86 (m, 3H) 2.90-3.04 (m, 3H) 3.15-3.25 (m, 3H) 3.28 (s, 3H) 3.30 (s, 3H) 3.51-3.56 (m, 1H) 3.58 (d, J = 9.63 Hz, 1H) 3.77 (d, J = 7.34 Hz, 1H) 3.97 (t, J = 8.48 Hz, 1H) 3.98-4.04 (m, 1H) 4.11 (dd, J = 8.94, 7.57 Hz, 1H) 4.49 (d, J = 7.34 Hz, 1H) 4.91 (d, J = 5.04 Hz, 1H) 5.12 (dd, J = 6.42, 4.58 Hz, 1H) 6.75-6.78 (m, 1H) 6.88 (t, J = 2.06 Hz, 1H) 6.90-6.93 (m, 1H) 7.18 (t, J = 8.02 Hz, 1H) |
| 199 | (E)-3-(quinolin-4-yl)acrylamide group | 898 FAB MASS | (300 M Hz): 0.97 (d, J = 6.87 Hz, 3H) 1.05 (d, J = 6.59 Hz, 3H) 1.14 (d, J = 7.42 Hz, 3H) 1.18 (d, J = 7.14 Hz, 3H) 1.18-1.27 (m, 10H) 1.30 (d, J = 6.32 Hz, 3H) 1.39 (s, 3H) 1.45-1.72 (m, J 3H) 2.18-2.34 (m, 8H) 2.39 (d, J = 15.1 Hz, 1H) 2.42-2.58 (m, 3H) 2.72-3.00 (m, 3H) 3.01-3.12 (m, 1H) 3.15-3.35 (m, 9H) 3.35-3.46 (m, 1H) 3.46-3.58 (m, 1H) 3.63 (d, J = 9.34 Hz, 1H) 3.77 (d, J = 7.69 Hz, 1H) 3.95-4.08 (m, 1H) 4.47 (d, J = 4.40 Hz, 1H) 4.44-4.57 (m, 1H) 4.75-4.84 (m, 1H) 4.91 (d, J = 4.67 Hz, 1H) 4.52 (br s, 1H) 6.57 (d, J = 15.4 Hz, 1H) 7.48 (d, J = 4.40 Hz, 1H) 7.57-7.66 (m, 1H) 7.71-7.80 (m, 1H) 8.14 (d, J = 8.52 Hz, 1H) 8.18 (d, J = 8.79 Hz, 1H) 8.38 (d, J = 15.4 Hz, 1H) 8.91 (d, J = 4.40 Hz, 1H) |
| 200 | 1-(4-(pyridin-3-yl)phenyl)-2-oxo-propyl group | 912 FAB MASS | (300 M Hz): 0.89 (d, J = 6.59 Hz, 3H) 0.92 (d, J = 7.14 Hz, 3H) 1.09 (d, J = 7.14 Hz, 3H) 1.15 (d, J = 7.14 Hz, 3H) 1.18-1.31 (m, 10H) 1.35 (s, 3H) 1.38-1.72 (m, 3H) 2.16-2.31 (m, 8H) 2.38 (d, J = 15.1 Hz, 1H) 2.40-2.53 (m, 2H) 2.67-2.82 (m, 2H) 2.67-2.82 (m, 2H) 2.82-3.02 (m, 2H) 3.10-3.24 (m, 1H) 3.28 (each s, 6H) 3.45-3.67 (m, 4H) 3.74 (d, J = 7.69 Hz, 1H) 3.94-4.06 (m, 1H) 4.26-4.38 (m, 1H) 4.47 (d, J = 7.14 Hz, 1H) 4.58-4.65 (m, 1H) 4.90 (d, J = 4.67 Hz, 1H) 5.44 (br s, 1H) 7.33-7.42 (m, 3H) 7.59 (d, J = 7.97 Hz, 1H) 7.84-7.91 (m, 1H) 8.60 (d, J = 8.52 Hz, 1H) 8.18 (dd, J = 1.37 Hz, J = 4.95 Hz, 1H) 8.85 (d, J = 2.47 Hz, 1H) |
| 201 | (E)-3-(isoquinolin-6-yl)acrylamide group | 898 FAB MASS | (300 M Hz): 0.97 (d, J = 7.14 Hz, 3H) 1.05 (d, J = 6.59 Hz, 3H) 1.13 (d, J = 7.42 Hz, 3H) 1.17 (d, J = 7.14 Hz, 3H) 1.18-1.27 (m, 7H) 1.29 (d, J = 6.04 Hz, 3H) 1.38 (s, 3H) 1.45-1.72 (m, 3H) 2.16-2.35 (m, 8H) 2.49 (d, J = 15.1 Hz, 1H) 2.40-2.57 (m, 3H) 2.74-3.002 (m, 2H) 3.01-3.11 (m, 1H) 3.16-3.26 (m, 3H) 3.29 (s, 3H) 3.31 (s, 3H) 3.35-3.45 (m, 1H) 3.46-3.58 (m, 1H) 3.63 (d, J = 9.62 Hz, 1H) 3.77 (d, J = 7.42 Hz, 1H) 3.96-4.07 (m, 1H) 4.43-4.57 (m, 2H) 4.75-4.83 (m, 1H) 4.91 (d, J = 4.40 Hz, 1H) 5.83 (br s, 1H) 6.51 (d, J = 15.4 Hz, 1H) 7.43 (dd, J = 4.40 Hz, J = 8.52 Hz, 1H) 7.81 (d, J = 15.4 Hz, 1H) 7.82-7.91 (m, 2H) 8.08 (d, J = 9.62 Hz, 1H) 8.17 (d, J = 7.69 Hz, 1H) 8.92 (dd, J = 1.65 Hz, J = 4.40 Hz, 1H) |
| 202 | 4-(pyridin-3-yl)benzamide group | 898 | (300 M Hz): 0.98 (d, J = 6.87 Hz, 3H) 1.06 (d, J = 6.59 Hz, 3H) 1.13 (d, J = 7.14 Hz, 3H) 1.18 (d, J = 7.14 Hz, 3H) 1.19-1.27 (m, 7H) 1.30 (d, J = 6.32 Hz, 3H) 1.39 (s, 3H) 1.46-1.72 (m, 3H) 2.23 (d, J = 9.34 Hz, 1H) 2.25-2.34 (m, 7H) 2.39 (d, J = 14.8 Hz, 1H) 2.43-2.58 (m, 3H) 2.75-3.01 (m, 3H) 3.02-3.13 (m, 1H) 3.16-3.27 (m, 3H) 3.30 (s, 3H) 3.32 (s, 3H) 3.40-3.58 (m, 2H) 3.63 (d, J = 10.2 Hz, 1H) 3.78 (d, J = 8.24 Hz, 1H) 3.95-4.08 (m, 1H) 4.48 (d, J = 7.14 Hz, 1H) 4.50-4.62 (m, 1H) 4.80-4.88 (m, 1H) 4.91 (d, J = 4.67 Hz, 1H) 6.20-6.32 (m, 1H) 7.40 (dd, J = 3.02 Hz, J = 7.97 Hz, 1H) 7.66 (d, J = 8.24 Hz, 1H) 7.83-7.94 (m, 3H) 8.63 (dd, J = 1.65 Hz, J = 4.95 Hz, 1H) 8.86 (d, J = 2.47 Hz, 1H) |

TABLE 6-continued

| Example | R | ESI MS (M + H) | $^1$H-NMR, CDCl$_3$, δ (ppm) |
|---|---|---|---|
| 203 | (pyridyl-phenyl-CH$_2$CH$_2$C(=O)NH-) | 926 FAB MASS | (400 M Hz): 0.90-0.98 (m, 6H) 1.10 (d, J = 7.3 Hz, 3H) 1.15 (d, J = 7.1 Hz, 3H) 1.20-1.27 (m, 7H) 1.29 (d, J = 6.1 Hz, 3 H) 1.36 (s, 3H) 1.47 (m, 1H) 1.53 (dd, J = 4.9, 15.2 Hz, 1H) 1.65 (m, 1H) 2.18-2.56 (m, 14H) 2.63-2.83 (m, 2H) 2.90 (m, 1H) 2.95-3.06 (m, 3H) 3.13-3.35 (m, 11H) 3.52 (m, 1H) 3.60 (m, 1H) 3.71 (d, J = 7.1 Hz, 1H) 3.74 (d, J = 7.1 Hz, 1H) 4.01 (m, 1H) 4.34 (m, 1H) 4.46 (d, J = 7.1 Hz, 1H) 4.60 (m, 1 H) 4.90 (m, 1H) 5.46 (m, 1H) 7.29-7.38 (m, 3H) 7.52 (m, 2 H) 7.86 (m, 1H) 8.58 (m,1H) 8.82 (m, 1H) |

Example 196

(1) The compound obtained in Example 9, (1) (1.0 g) was dissolved in a mixed solvent of ethanol and tetrahydrofuran (4:1, 25 ml), the solution was added with 1 N hydrochloric acid (2.5 ml), and the mixture was stirred at room temperature for 140 minutes. The reaction mixture was neutralized with 10% aqueous sodium hydroxide, and then added with ethyl acetate and saturated aqueous sodium hydrogencarbonate, and the layers were separated. The organic layer was dried over anhydrous magnesium sulfate, and filtered. The filtrate was concentrated under reduced pressure, and the resulting residue was purified by silica gel column chromatography (hexane:acetone:triethylamine=100:10: 0.2) to obtain a 4"-hydroxy compound (752 mg).

(2) By using the compound obtained in (1) mentioned above (752 mg) as a starting material, a 4"-ketone compound (693 mg) was obtained in the same manner as that of Example 169, (2).

(3) By using the compound obtained in (2) mentioned above (226 mg) as a starting material, the compound shown in Table 6 (33 mg) was obtained in the same manners as those of Example 169, (3) and Example 1, (3).

Example 197

(1) By using the compound obtained in Example 13, (1) (840 mg) and β-naphthol (225 mg) as starting materials, an ether compound (959 mg) was obtained in the same manner as that of Example 29, (1).

(2) By using the compound obtained in (1) mentioned above (959 mg) as a starting material, a 4"-ketone compound (447 mg) was obtained in the same manners as those of Example 169, (1) and (2).

(3) By using the compound obtained in (2) mentioned above (59 mg) as a starting material, the compound shown in Table 6 (2.6 mg) was obtained in the same manners as those of Example 169, (3) and Example 1, (3).

Example 198

(1) By using the compound obtained in Example 83, (1) (702 mg) as a starting material, a 4"-ketone compound (221 mg) was obtained in the same manners as those of Example 169, (1) and (2).

(2) By using the compound obtained in (1) mentioned above (221 mg) as a starting material, the compound shown in Table 6 (4.3 mg) was obtained in the same manners as those of Example 169, (3) and Example 1, (3).

Example 199

(1) By using the compound obtained in Example 123, (1) (79 mg) as a starting material, the compound shown in Table 6 (4 mg) was obtained in the same manners as those of Example 169, (1) to (3) and Example 1, (3).

Example 200

By using the compound obtained in Example 124, (1) (59 mg) as a starting material, the compound shown in Table 6 (2.2 mg) was obtained in the same manners as those of Example 169, (1) to (3) and Example 1, (3).

Example 201

By using the compound obtained in Example 125, (1) (78 mg) as a starting material, the compound shown in Table 6 (4.2 mg) was obtained in the same manners as those of Example 169, (1) to (3) and Example 1, (3).

Example 202

By using the compound obtained in Example 129, (1) (70 mg) as a starting material, the compound shown in Table 6 (3.0 mg) was obtained in the same manners as those of Example 169, (1) to (3) and Example 1, (3).

Example 203

By using the compound obtained in Example 128, (1) (59 mg) as a starting material, the compound shown in Table 6 (2.2 mg) was obtained in the same manners as those of Example 169, (1) to (3) and Example 1, (3).

Examples 204 to 212

Preparation methods of the compounds represented by the formula (H) having $R^{1H}$ and $R^{2H}$ defined in Table 7 are shown below.

[Formula 29]

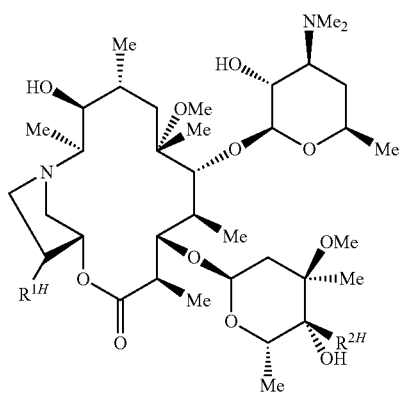

Formula (H)

TABLE 7

| Example | R[1H] | R[2H] | ESI MS (M + H) $^1$H-NMR, CDCl$_3$, δ (ppm) |
|---|---|---|---|
| 204 | benzyloxy-dimethyl group | N-(2-piperidinoethyl)amino group | 963.8 (600 M Hz): 0.93 (d, J = 7.34 Hz, 3H) 0.96 (d, J = 6.88 Hz, 3H) 1.08 (d, J = 7.34 Hz, 3H) 1.10-1.17 (m, 9H) 1.17-1.26 (m, 1H) 1.21 (d, J = 6.42 Hz, 3H) 1.35 (s, 3H) 1.42 (br. s., 2 H) 1.47 (d, J = 15.13 Hz, 1H) 1.50-1.67 (m, 5H) 1.92 (dd, J = 14.90, 5.27 Hz, 1H) 2.06 (d, J = 15.13 Hz, 1H) 2.22-2.50 (m, 11H) 2.28 (s, 6H) 2.50-2.58 (m, 1H) 2.58-2.63 (m, 1H) 2.63-2.73 (m, 2H) 2.76-2.87 (m, 2H) 2.88-3.07 (m, 3H) 3.12-3.23 (m, 3H) 3.27 (s, 3H) 3.29 (s, 3H) 3.36-3.58 (m, 3H) 3.61 (d, J = 9.63 Hz, 1H) 3.74 (d, J = 8.25 Hz, 1H) 4.27-4.34 (m, 1 H) 4.41 (d, J = 7.34 Hz, 1H) 4.50 (s, 2H) 4.65-4.70 (m, 1H) 4.93 (d, J = 4.58 Hz, 1H) 7.23-7.36 (m, 5H) |
| 205 | benzyloxy-dimethyl group | N-(2-pyrrolidinoethyl)amino group | 949.6 (600 M Hz): 0.93 (d, J = 6.88 Hz, 3H) 0.96 (d, J = 6.42 Hz, 3H) 1.08 (d, J = 7.34 Hz, 3H) 1.11-1.16 (m, 9H) 1.18-1.26 (m, 1H) 1.21 (d, J = 6.42 Hz, 3H) 1.35 (s, 3H) 1.47 (d, J = 14.67 Hz, 1H) 1.60-1.66 (m, 1H) 1.76 (br. s., 4H) 1.92 (dd, J = 14.90, 5.27 Hz, 1H) 2.06 (d, J = 14.67 Hz, 1H) 2.22-2.33 (m, 2 H) 2.29 (s, 6H) 2.41-2.65 (m, 11H) 2.69-2.75 (m, 2H) 2.76-3.07 (m, 5H) 3.13-3.23 (m, 3H) 3.27 (s, 3H) 3.29 (s, 3H) 3.36-3.56 (m, 3H) 3.61 (d, J = 9.17 Hz, 1H) 3.74 (d, J = 7.79 Hz, 1H) 4.28-4.33 (m, 1H) 4.41 (d, J = 7.34 Hz, 1H) 4.50 (s, 2H) 4.66-4.70 (m, 1H) 4.93 (d, J = 4.58 Hz, 1H) 7.23-7.36 (m, 5H) |
| 206 | benzyloxy-dimethyl group | N-[2-(diethylamino)ethyl]amino-dimethyl group | 951.7 (600 M Hz): 0.89-1.03 (m, 12H) 1.08 (d, J = 7.34 Hz, 3H) 1.11-1.17 (m, 9H) 1.18-1.27 (m, 1H) 1.21 (d, J = 5.96 Hz, 3H) 1.35 (s, 3 H) 1.47 (d, J = 14.67 Hz, 1H) 1.57-1.67 (m, 1H) 1.93 (dd, J = 14.90, 5.27 Hz, 1H) 2.06 (d, J = 15.13 Hz, 1H) 2.23-2.32 (m, 2H) 2.28 (s, 6H) 2.34-2.68 (m, 13H) 2.75-3.07 (m, 5H) 3.12-3.23 (m, 3H) 3.27 (s, 3H) 3.29 (s, 3H) 3.37-3.55 (m, 3H) 3.61 (d, J = 9.17 Hz, 1H) 3.75 (d, J = 8.25 Hz, 1H) 4.25-4.32 (m, 1H) 4.41 (d, J = 7.34 Hz, 1H) 4.50 (s, 2H) 4.66-4.71 (m, 1H) 4.93 (d, J = 5.04 Hz, 1H) 7.24-7.36 (m, 5H) |

TABLE 7-continued

| Example | R1H | R2H | ESI MS (M + H) 1H-NMR, CDCl3, δ (ppm) |
|---|---|---|---|
| 207 | benzyl ether-C(Me)- | -C(Me)(Me)-NH-CH2CH2-pyrrolidine | 949.7 (600 M Hz): 0.92 (d, J = 7.34 Hz, 3H) 1.00 (d, J = 6.88 Hz, 3H) 1.07 (d, J = 7.34 Hz, 3H) 1.12-1.14 (m, 1H) 1.12-1.17 (m, 4H) 1.12-1.14 (m, 3H) 1.14-1.15 (m, 3H) 1.14-1.16 (m, 3H) 1.21 (d, J = 5.96 Hz, 3H) 1.35 (s, 3H) 1.40 (d, J = 14.67 Hz, 1H) 1.62-1.67 (m, 1H) 1.76-1.79 (m, 1H) 1.95 (dd, J = 14.90, 5.27 Hz, 1H) 2.06 (d, J = 14.21 Hz, 1H) 2.17-2.25 (m, 1H) 2.31 (s, 6H) 2.43 (d, J = 13.76 Hz, 1H) 2.45-2.61 (m, 4H) 2.47-2.53 (m, 4H) 2.70-2.75 (m, 3H) 2.77-2.82 (m, 2H) 2.86 (dd, J = 9.40, 6.19 Hz, 1H) 2.89 (d, J =13.30 Hz, 1H) 2.92-3.00 (m, 2H) 3.09-3.15 (m, 1 H) 3.18 (d, J = 11.46 Hz, 1H) 3.22 (dd, J = 10.32, 7.11 Hz, 1H) 3.28 (s, 3H) 3.48 (t, J = 8.48 Hz, 1H) 3.52-3.56 (m, 1H) 3.58 (d, J = 9.63 Hz, 1H) 3.63 (dd, J = 9.17, 6.88 Hz, 1H) 3.77 (d, J = 7.34 Hz, 1H) 4.28 (q, J = 6.27 Hz, 1H) 4.45 (d, J = 7.34 Hz, 1H) 4.47-4.54 (m, 2H) 4.96 (d, J = 4.58 Hz, 1H) 5.03 (dd, J = 6.42, 4.58 Hz, 1H) 7.26-7.37 (m, 5H) |
| 208 | benzyl ether-C(Me)- | Me-CH2-N(Me-CH2-)-CH2CH2-NH-C(Me)- | 951.7 (600 M Hz): 0.92 (d, J = 7.34 Hz, 3H) 0.99-1.02 (m, 6H) 1.07 (d, J = 7.34 Hz, 3H) 1.12-1.16 (m, 12H) 1.22 (d, J = 6.42 Hz, 3H) 1.22-1.26 (m, 1H) 1.35 (s, 3H) 1.40 (d, J = 14.21 Hz, 1H) 1.64 (d, J = 11.46 Hz, 1H) 1.95 (dd, J = 14.90, 5.27 Hz, 1H) 2.03-2.09 (m, 1H) 2.17-2.24 (m, 1H) 2.30 (s, 6H) 2.37 (d, J = 13.30 Hz, 1H) 2.44-2.54 (m, 9 H) 2.62-2.68 (m, 2H) 2.73 (t, J = 9.17 Hz, 1H) 2.80 (dd, J = 11.46, 4.13 Hz, 2H) 2.84-2.90 (m, 2H) 2.91-3.00 (m, 2H) 3.11-3.14 (m, 1H) 3.18 (d, J = 11.92 Hz, 1H) 3.22 (dd, J = 10.32, 7.11 Hz, 1H) 3.28 (s, 3H) 3.29 (s, 3H) 3.48 (t, J = 8.71 Hz, 1H) 3.50-3.55 (m, 1H) 3.58 (d, J = 9.17 Hz, 1H) 3.63 (dd, J = 8.71, 6.88 Hz, 1H) 3.77 (d, J = 7.34 Hz, 1H) 4.27 (q, J = 6.42 Hz, 1H) 4.46 (d, J = 7.34 Hz, 1H) 4.47-4.53 (m, 2H) 4.75-4.85 (m, 1H) 4.96 (d, J = 4.58 Hz, 1H) 5.03 (dd, J = 6.19, 4.36 Hz, 1H) 7.26-7.37 (m, 5H) |
| 209 | HO-CH2-C(Me)- | Me-CH2-N(Me-CH2-)-CH2CH2-NH-C(Me)- | 861.6 (600 M Hz) 0.95 (d, J = 7.34 Hz, 3H) 0.99-1.02 (m, 9H) 1.11 (d, J = 7.34 Hz, 3H) 1.14 (s, 3H) 1.15 (d, J = 6.42 Hz, 3H) 1.17 (d, J = 6.88 Hz, 3H) 1.22 (d, J = 5.96 Hz, 3H) 1.23-1.27 (m, 1H) 1.36 (s, 3H) 1.47 (d, J = 14.67 Hz, 1H) 1.64 (d, J = 13.30 Hz, 1H) 1.95 (dd, J = 14.67, 5.50 Hz, 1H) 2.03-2.08 (m, 1H) 2.23-2.28 (m, 1H) 2.30 (s, 6H) 2.35-2.43 (m, 2H) 2.42-2.57 (m, 8H) 2.62-2.67 (m, 2H) 2.70 (t, J = 8.94 Hz, 1H) 2.77 (dd, J = 11.92, 5.04 Hz, 1H) 2.80-2.91 (m, 4H) 2.97-3.03 (m, 1H) 3.15-3.19 (m, 1H) 3.19-3.24 (m, 2H) 3.28 (s, 3H) 3.30 (s, 3 H) 3.46-3.54 (m, 1H) 3.64 (d, J = 9.63 Hz, 1H) 3.70 (dd, J = 10.55, 5.96 Hz, 1H) 3.78 (d, J = 7.34 Hz, 1H) 3.81 (dd, J = 10.55, 7.34 Hz, 1H) 4.27 (q, J = 6.27 Hz, 1H) 4.45 (d, J = 7.34 Hz, 1H) 4.95 (d, J = 5.04 Hz, 1 H) 5.06 (dd, J = 6.65, 4.81 Hz, 1H) |
| 210 | 2-naphthyl-O-CH(Me)- | Me-N(Me)-C(Me)- | 916.5 (600 M Hz): 0.92 (d, J = 7.34 Hz, 3H) 1.00-1.28 (m, 19H) 1.35 (s, 3H) 1.39-1.46 (m, 1 H) 1.59-1.69 (m, 1H) 1.89-2.07 (m, 3H) 2.17-2.26 (m, 1H) 2.30 (s, 6H) 2.35 (s, 6H) 2.39-2.62 (m, 2H) 2.65-2.90 (m, 5H) 2.94-3.06 (m, 3H) 3.10-3.34 (m, 3H) 3.24 (s, 3 H) 3.30 (s, 3H) 3.37-3.47 (m, 1H) 3.55-3.61 (m, 1H) 3.77 (d, J = 7.34 Hz, 1H) 4.06-4.18 (m, 2H) 4.21-4.29 (m, 1H) 4.43 (d, J = 7.34 Hz, 1H) 4.96 (d, J = 5.04 Hz, 1H) 5.13-5.20 (m, 1H) 7.07-7.16 (m, 2H) 7.28-7.33 (m, 1H) 7.37-7.44 (m, 1H) 7.68-7.78 (m, 3H) |

TABLE 7-continued

| Example | R$^{1H}$ | R$^{2H}$ | ESI MS (M + H) | $^1$H-NMR, CDCl$_3$, δ (ppm) |
|---|---|---|---|---|
| 211 | naphthalen-2-yloxy group attached via CH(CH$_3$)- linker | -CH(CH$_3$)CH$_2$N(Et)CH$_2$CH$_2$-(pyrrolidin-1-yl) | 985.7 | (600 M Hz): 0.92 (d, J = 7.34 Hz, 3H) 1.00-1.26 (m, 19H) 1.35 (s, 3H) 1.45 (d, J = 14.67 Hz, 1H) 1.60-1.80 (m, 6H) 1.89-2.04 (m, 2 H) 2.20-2.26 (m, 1H) 2.29 (s, 6H) 2.38-2.61 (m, 9H) 2.68-2.91 (m, 7H) 2.94-3.05 (m, 3 H) 3.13-3.30 (m, 3H) 3.24 (s, 3H) 3.29 (s, 3 H) 3.49-3.55 (m, 1H) 3.58 (d, J = 10.09 Hz, 1H) 3.77 (d, J = 7.34 Hz, 1H) 4.08-4.13 (m, 1H) 4.21-4.29 (m, 2H) 4.43 (d, J = 7.34 Hz, 1H) 4.93 (d, J = 4.58 Hz, 1H) 5.13-5.19 (m, 1H) 7.08-7.15 (m, 2H) 7.28-7.34 (m, 1H) 7.38-7.44 (m, 1H) 7.69-7.77 (m, 2H) |
| 212 | 3-chlorophenoxy group attached via CH(CH$_3$)- linker | -CH(NMe$_2$)- | 900.9 | (600 M Hz): 0.93 (d, J = 7.34 Hz, 3H) 1.02 (d, J = 6.88 Hz, 3H) 1.07 (d, J = 7.79 Hz, 3H) 1.09-1.12 (m, 3H) 1.15 (d, J = 6.42 Hz, 3H) 1.22 (d, J = 5.96 Hz, 3H) 1.22-1.25 (m, 1H) 1.25 (s, 3H) 1.34 (s, 3H) 1.43 (d, J = 15.13 Hz, 2H) 1.64 (d, J = 10.55 Hz, 1H) 1.94-1.98 (m, 1H) 2.05-2.08 (m, 1H) 2.19-2.25 (m, 1H) 2.29 (s, 6H) 2.36 (s, 6H) 2.40-2.48 (m, 1H) 2.51 (t, J = 7.11 Hz, 1H) 2.60-2.66 (m, 1H) 2.71-2.81 (m, 2H) 2.73-2.81 (m, 2H) 2.81-2.85 (m, 1H) 2.89-2.93 (m, 1H) 2.93-2.97 (m, 1H) 2.97-3.02 (m, 1H) 3.13-3.16 (m, 1H) 3.20 (dd, J = 10.32, 7.11 Hz, 1H) 3.23 (d, J = 11.92 Hz, 1H) 3.26 (s, 3H) 3.29 (s, 3H) 3.38-3.45 (m, 1H) 3.58 (d, J = 9.17 Hz, 1H) 3.76 (d, J = 7.34 Hz, 1H) 3.95 (t, J = 8.48 Hz, 1H) 4.10 (dd, J = 8.94, 7.11 Hz, 1H) 4.12-4.15 (m, 1H) 4.42 (d, J = 7.34 Hz, 1H) 4.96 (d, J = 5.04 Hz, 1H) 5.11 (dd, J = 6.42, 4.58 Hz, 1H) 6.74-6.77 (m, 1H) 6.86-6.88 (m, 1H) 6.89-6.92 (m, 1H) 7.17 (t, J = 8.25 Hz, 1H) |

Example 204

(1) By using the compound obtained in Example 10, (1) (1.0 g) as a starting material, a 4"-epoxy compound (108 mg) was obtained in the same manners as those of Example 169, (1), (2), Example 177, (1), and Example 1, (3).

(2) The compound obtained in (1) mentioned above (100 mg) and N-(2-aminoethyl)piperazine (68.4 mg) were dissolved in ethanol (1.5 ml), the solution was added with pyridinium chloride (2.8 mg), and the mixture was stirred at 80° C. for 16 hours. The reaction mixture was concentrated under reduced pressure, and then the resulting residue was purified by silica gel column chromatography (chloroform:methanol:28% aqueous ammonia=10:1:0.1) to obtain the compound shown in Table 7 (117.6 mg).

Example 205

By using the compound obtained in Example 204, (1) (60 mg) and N-(2-aminoethyl)pyrrolidine (41 mg) as starting materials, the compound shown in Table 7 (51.7 mg) was obtained in the same manner as that of Example 204, (2).

Example 206

By using the compound obtained in Example 204, (1) (60 mg) and N,N-diethylethylenediamine (41.7 mg) as starting materials, the compound shown in Table 7 (65.5 mg) was obtained in the same manner as that of Example 204, (2).

Example 207

(1) By using the compound obtained in Example 196, (2) (693 mg) as a starting material, an epoxy compound (444 mg) was obtained in the same manners as those of Example 177, (1) and Example 1, (3).

(2) By using the compound obtained in (1) mentioned above (80 mg) and 142-aminoethyl)pyrrolidine (54.7 mg) as starting materials, the compound shown in Table 7 (63 mg) was obtained in the same manner as that of Example 204, (2).

Example 208

By using the compound obtained in Example 207, (1) (80 mg) and N,N-diethylethylenediamine (55.7 mg) as starting materials, the compound shown in Table 7 (59 mg) was obtained in the same manner as that of Example 204, (2).

Example 209

The compound obtained in Example 208 (21 mg) was dissolved in tetrahydrofuran (0.5 ml), the solution was added with 20% palladium hydroxide-carbon (22 mg), and the mixture was stirred at 55° C. for 50 hours under a hydrogen atmosphere of 1 atm. The reaction mixture was filtered, then the filtrate was concentrated under reduced pressure, and the resulting residue was purified by preparative thin layer chromatography (chloroform:methanol:28% aqueous ammonia=10:1:0.1) to obtain the compound shown in Table 7 (5.3 mg).

Example 210

(1) By using the compound obtained in Example 197, (2) (200 mg) as a starting material, an epoxy compound (190 mg) was obtained in the same manner as that of Example 177, (1).

(2) By using the compound obtained in (1) mentioned above (30 mg), and 50% aqueous dimethylamine (49.2 μl) as starting materials, the compound shown in Table 7 (9 mg) was obtained in the same manners as those of Example 204, (2) and Example 1, (3).

Example 211

By using the compound obtained in Example 210, (1) (30 mg) and 1-(2-aminoethyl)pyrrolidine (69.2 μl) as starting materials, the compound shown in Table 7 (6 mg) was obtained in the same manners as those of Example 204, (2) and Example 1, (3).

Example 212

(1) By using the compound obtained in Example 198, (1) (55 mg) as a starting material, an epoxy compound (41 mg) was obtained in the same manner as that of Example 177, (1).

(2) By using the compound obtained in (1) mentioned above (41 mg) and 50% aqueous dimethylamine (69 μl) as starting materials, the compound shown in Table 7 (27 mg) was obtained in the same manners as those of Example 204, (2) and Example 1, (3).

Example 213

A preparation method of the compound represented by formula (I) is shown below.

Example 213

By using the compound obtained in Example 197, (2) (59 mg) as a starting material, the compound represented by the formula (I) (0.8 mg) was obtained in the same manners as those of Example 169, (3) and Example 1, (3).

MS (ESI) m/z=858.4 [M+H]$^+$ $^1$H-NMR (600 MHz, CDCl$_3$) δ (ppm): 0.94 (d, J=7.34 Hz, 3H), 1.05 (d, J=6.42 Hz, 3H), 1.10 (d, J=6.88 Hz, 3H), 1.10-1.14 (m, 1H), 1.13 (d, J=3.21 Hz, 3H), 1.19-1.21 (m, 3H), 1.20-1.22 (m, 1H), 1.22 (d, J=6.88 Hz, 3H), 1.25 (s, 3H), 1.28-1.32 (m, 1H), 1.37 (s, 3H), 1.53-1.60 (m, 2H), 2.00 (d, J=15.13 Hz, 1H), 2.20-2.26 (m, 1H), 2.29 (br, s, 6H), 2.30-2.34 (m, 1H), 2.46-2.54 (m, 1H), 2.55-2.61 (m, 1H), 2.70-2.76 (m, 1H) 2.81-2.92 (m, 3H), 2.98-3.05 (m, 2H), 3.14-3.18 (m, 1H) 3.18-3.24 (m, 1H), 3.26 (d, J=11.92 Hz, 1H), 3.29 (s, 3H), 3.30 (s, 3H), 3.45-3.49 (m, 1H), 3.60 (d, J=10.09 Hz, 1H), 3.77 (d, J=6.42 Hz, 1H 4.11 (t, J=8.48 Hz, 1H), 4.25 (dd, J=8.71, 7.34 Hz, 1H), 4.55-4.63 (m, 2H), 4.95 (d, J=4.58 Hz, 1H), 5.16-5.20 (m, 1H), 7.11 (dd, J=8.71, 2.29 Hz, 1H), 7.13-7.15 (m, 1H), 7.32 (t, J=7.57 Hz, 1H), 7.42 (t, J=7.57 Hz, 1H), 7.69-7.78 (m, 3H)

Examples 214 to 220

Preparation methods of the compounds represented by the formula (J) having R defined in Table 8 are shown below.

[Formula 30]

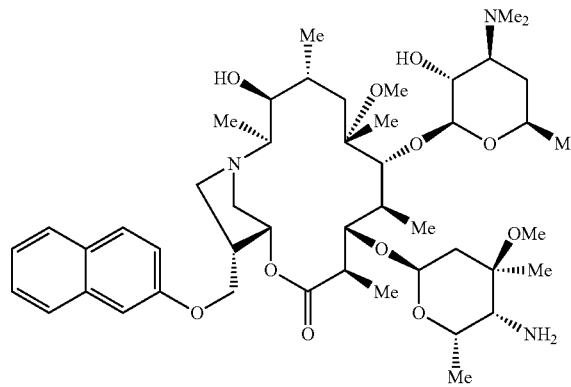

Formula (I)

[Formula 31]

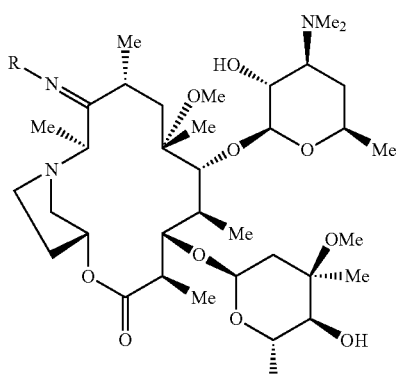

Formula (J)

TABLE 8

| Example | R | ESI MS (M + H) | ¹H-NMR, CDCl₃, δ (ppm) |
|---|---|---|---|
| 214 | HO-C(CH₃)₂- (structure) | 716.4 | (600 M Hz): 1.05-1.31 (m, 22H) 1.41 (s, 3H) 1.51-1.68 (m, 2H) 1.85-2.20 (m, 5H) 2.28 (s, 6H) 2.33-2.48 (m, 2H) 2.70-2.89 (m, 5H) 2.96-3.05 (m, 1H) 3.22-3.28 (m, 1H) 3.25 (s, 3H) 3.32 (s, 3H) 3.33-3.39 (m, 1H) 3.46-3.54 (m, 1H) 3.64-3.78 (m, 3H) 3.98-4.06 (m, 1H) 4.47 (d, J = 6.88 Hz, 1H) 4.78-4.82 (m, 1H) 5.08-5.15 (m, 1H) |
| 215 | benzyl-O-C(=O)-CH₂-O-C(CH₃)₂- (structure) | 864.6 | (600 M Hz): 1.24 (m, 25H) 1.49-1.67 (m, 2H) 1.85-2.23 (m, 5H) 2.28 (s, 6H) 2.32-2.49 (m, 2H) 2.69-2.90 (m, 5H) 2.96-3.04 (m, 1H) 3.10-3.38 (m, 2H) 3.18 (s, 3H) 3.32 (s, 3H) 3.42-3.56 (m, 1H) 3.62-3.73 (m, 3H) 3.97-4.07 (m, 1 H) 4.59-4.74 (m, 3H) 4.82-4.87 (m, 1H) 5.03-5.10 (m, 1 H) 5.12-5.20 (m, 2H) 7.27-7.40 (m, 5H) |
| 216 | (structure with pyridyl-imidazole-propyl-NH-C(=O)-CH₂-O-) | 958.8 | (600 M Hz): 1.01-.131 (m, 22H) 1.40 (s, 3H) 1.47-1.73 (m, 3H) 1.87-2.24 (m, 5H) 2.27 (s, 6H) 2.31-2.45 (m, 2 H) 2.69-3.02 (m, 4H) 3.17-3.34 (m, 2H) 3.22 (s, 3H) 3.32 (s, 3H) 3.43-3.79 (m, 9H) 3.95-4.08 (m, 3H) 4.43-4.55 (m, 3H) 4.82-4.89 (m, 1H) 4.89-4.97 (m, 1H) 6.40-6.51 (m, 1H) 7.24-7.30 (m, 1H) 7.41 (s, 1H) 7.60 (s, 1H) 8.03-8.11 (m, 1H) 8.41-8.47 (m, 1H) 8.90-9.01 (m, 1H) |
| 217 | (quinoline-propyl-NH-C(=O)-CH₂-O- structure) | 942.9 | (600 M Hz): 0.90-1.30 (m, 22H) 1.40 (s, 3H) 1.49-1.67 (m, 3H) 1.98-2.43 (m, 9H) 2.69-2.85 (m, 1H) 2.97-3.34 (m, 9H) 3.32 (s, 3H) 3.35-3.78 (m, 12H) 3.91-4.03 (m, 2H) 4.38-4.59 (m, 4H) 4.76-4.87 (m, 2H) 7.28-7.34 (m, 1H) 7.50-7.58 (m, 1H) 7.64-7.72 (m, 1H) 8.02-8.12 (m, 2H) 8.76-8.81 (m, 1H) |
| 218 | (structure with -O-CH₂-C(=O)-NH-CH₂CH₂-imidazole-pyridyl) | 944.5 | (600 M Hz): 0.97-1.30 (m, 22H) 1.36 (s, 3H) 1.50-1.78 (m, 3H) 1.84-1.98 (m, 2H) 2.12-2.23 (m, 1 H) 2.27 (s, 6H) 2.32-2.46 (m, 2H) 2.59-2.91 (m, 3 H) 2.94-3.03 (m, 1H) 3.10 (s, 3H) 3.15-3.27 (m, 2 H) 3.31 (s, 3H) 3.42-3.85 (m, 9H) 3.96-4.03 (m, 1 H) 4.15-4.27 (m, 2H) 4.41-4.57 (m, 3H) 4.85 (d, J = 4.59 Hz, 1H) 4.88-4.93 (m, 1H) 6.52-6.62 (m, 1H) 7.26-7.29 (m, 1H) 7.45 (s, 1H) 7.64 (s, 1H) 8.04-8.10 (m, 1H) 8.42-8.46 (m, 1H) 8.94 (d, J = 1.83 Hz, 1H) |
| 219 | (structure with -O-CH₂-C(=O)-NH-(CH₂)₃-imidazole-pyridyl) | 972.6 | (600 M Hz): 1.00-1.33 (m, 22H) 1.39 (s, 3H) 1.43-2.02 (m, 9H) 2.14-2.21 (m, 1H) 2.27 (s, 6H) 2.34-2.45 (m, 2H) 2.66-2.88 (m, 3H) 2.97-3.04 (m, 1H) 3.15-3.39 (m, 4H) 3.20 (s, 3H) 3.32 (s, 3H) 3.44-3.55 (m, 2H) 3.57-3.77 (m, 4H) 3.97-4.07 (m, 4H) 4.42-4.50 (m, 3H) 4.84-4.95 (m, 2H) 6.33-6.45 (m, 1H) 7.26-7.32 (m, 2H) 7.50-7.57 (m, 1H) 8.04-8.12 (m, 1H) 8.42-8.49 (m, 1H) 8.91-8.98 (m, 1H) |
| 220 | (structure with -O-CH₂-C(=O)-NH-(CH₂)₄-imidazole-pyridyl) | 986.6 | (600 M Hz): 1.04-1.31 (m, 22H) 1.32-1.43 (m, 2H) 1.40 (s, 3H) 1.49-1.73 (m, 8H) 1.83-1.93 (m, 2H) 2.28 (s, 6H) 2.32-2.47 (m, 2H) 2.75-2.87 (m, 2H) 2.96-3.03 (m, 1H) 3.13-3.43 (m, 6H) 3.20 (s., 3H) 3.30-3.32 (m, 4H) 3.44-3.79 (m, 5H) 3.93-4.05 (m, 3H) 4.43-4.49 (m, 3H) 4.82-4.87 (m, 1H) 4.95-5.05 (m, 1H) 6.31-6.40 (m, 1H) 7.26-7.31 (m, 2H) 7.53 (s, 1H) 8.03-8.12 (m, 1H) 8.42-8.48 (m, 1H) 8.95 (s., 1H) |

Example 214

(1) By using the compound obtained in Example 1, (2) (12.0 g) as a starting material, a 4"-hydroxy compound (7.77 g) was obtained in the same manner as that of Example 196, (1).

(2) The compound obtained in (1) mentioned above (7.77 g) was dissolved in chloroform (250 ml), and the solution was added with pyridine (9.7 ml). The reaction mixture was added with triphosgene (5.64 g) under ice cooling, after 5 minutes, the mixture was added with benzyl alcohol (9.84 ml), and the mixture was stirred at the same temperature for 30 minutes and at room temperature for 1 hour. The reaction mixture was added with saturated aqueous sodium hydrogencarbonate and chloroform, the layers were separated, and the organic layer was washed with saturated brine, then dried over anhydrous magnesium sulfate, and filtered. The filtrate was concentrated under reduced pressure, and the resulting residue was purified by silica gel column chromatography (hexane:acetone:triethylamine=100:10:0.2) to obtain a crude product. By using the resulting crude product as a starting material, a 4"-O-benzyloxycarbonyl compound (4.82 g) was obtained in the same manner as that of Example 1, (3).

(3) The compound obtained in (2) mentioned above (4.52 g) was dissolved in acetone (54 ml), the solution was added with acetic anhydride (764 µl), and the mixture was stirred for 4 hours under reflux by heating. The mixture was cooled to room temperature, and then added with saturated aqueous sodium hydrogencarbonate, and acetone was evaporated under reduced pressure. The resulting aqueous layer was extracted with chloroform, the organic layer was washed with saturated brine, dried over anhydrous magnesium sulfate, and filtered. The filtrate was concentrated under reduced pressure, and the resulting residue was purified by silica gel column chromatography (chloroform:methanol:28% aqueous ammonia=20:1:0.1) to obtain a 2'-O-acetyl compound (3.8 g).

(4) By using the compound obtained in (3) mentioned above (3.8 g) as a starting material, a crude product of 9-ketone compound was obtained in the same manner as that of Example 169, (2). The resulting crude product was added with methanol (30 ml), and the mixture was stirred for 4 hours under reflux by heating. The reaction mixture was cooled to room temperature, and then concentrated under reduced pressure, the resulting residue was dissolved in methanol (5 ml), the solution was added with 5% palladium-carbon (20 g), and the mixture was stirred overnight under a hydrogen atmosphere of 1 atm. The reaction mixture was filtered, then the filtrate was concentrated under reduced pressure, and the resulting residue was purified by silica gel column chromatography (chloroform:methanol:28% aqueous ammonia=20:1:0.1) to obtain a deprotected compound (1.1 g).

(5) The compound obtained in (4) mentioned above (1.1 g) was dissolved in methanol (5 ml), the solution was added with imidazole (641 mg) and hydroxylamine hydrochloride (534 mg), and the mixture was stirred for 4 hours under reflux by heating. The reaction mixture was cooled to room temperature, and then added with saturated aqueous sodium hydrogencarbonate and chloroform, and the layers were separated. The organic layer was washed with saturated brine, then dried over anhydrous magnesium sulfate, and filtered. The filtrate was concentrated under reduced pressure, and the resulting residue was purified by silica gel column chromatography (chloroform:methanol:28% aqueous ammonia=20:1:0.1 to 10:1:0.1) to obtain the compound shown in Table 8 (850 mg).

Example 215

The compound obtained in Example 214 (850 mg) was dissolved in tetrahydrofuran (8.5 ml), the solution was added with 18-crown-6-ether (1.57 g), benzyl bromoacetate (563 µl) and potassium hydroxide (333 mg), and the mixture was stirred at room temperature for 30 minutes. The reaction mixture was added with chloroform and saturated brine, the layers were separated, and the organic layer was dried over anhydrous magnesium sulfate, and filtered. The filtrate was concentrated under reduced pressure, and the resulting residue was purified by silica gel column chromatography (chloroform:methanol:28% aqueous ammonia=20:1:0.1 to 10:1:0.1) to obtain the compound shown in Table 8 (510 mg).

Example 216

(1) By using the compound obtained in Example 215 (510 mg) as a starting material, a 2'-O-acetyl compound (496 mg) was obtained in the same manner as that of Example 214, (3).

(2) The compound obtained in (1) mentioned above (496 mg) was dissolved in tetrahydrofuran (2.0 ml), the solution was added with 5% palladium-carbon (496 mg), and the mixture was stirred at room temperature for 1.5 hours under a hydrogen atmosphere of 1 atm. The reaction mixture was filtered, and then concentrated under reduced pressure to obtain a carboxylic acid (133 mg).

(3) The compound obtained in (2) mentioned above (20 mg) was dissolved in chloroform (0.5 ml), the solution was added with 3-(4-pyridin-3-yl-1H-imidazol-1-yl)propan-1-amine (24.8 mg) obtained by the method described in the literature (Bioorganic & Medicinal Chemistry, 2006, vol. 14, pp. 3697-3711) and 1-ethyl-3-(3-dimethylaminopropyl)carbodiimide hydrochloride (23.5 mg), and the mixture was stirred at room temperature for 2 hours. The reaction mixture was added with chloroform and saturated brine, the layers were separated, and the organic layer was dried over anhydrous magnesium sulfate, and then filtered. The filtrate was concentrated under reduced pressure, and the resulting residue was added with methanol (5 ml), and the reaction mixture was stirred for 6 hours under reflux by heating, and then concentrated under reduced pressure. The resulting residue was purified by preparative thin layer chromatography (chloroform:methanol:28% aqueous ammonia=10:1:0.1) to obtain the compound shown in Table 8 (3.0 mg).

Example 217

By using the compound obtained in Example 216, (2) (25 mg) and the compound obtained in Reference Example 55 (28.5 mg) as starting materials, the compound shown in Table 8 (0.36 mg) was obtained in the same manner as that of Example 216, (3).

Example 218

By using the compound obtained in Example 216, (2) (20 mg) and 2-(4-pyridin-3-yl-1H-imidazol-1-yl)ethanamine (23.1 mg) obtained by the method described in the literature (Bioorganic & Medicinal Chemistry, 2006, vol. 14, pp. 3697-

3711) as starting materials, the compound shown in Table 8 (2.8 mg) was obtained in the same manner as that of Example 216, (3).

Example 219

By using the compound obtained in Example 216, (2) (20 mg) and 4-(4-pyridin-3-yl-1H-imidazol-1-yl)butan-1-amine (26.5 mg) obtained by the method described in the literature (Bioorganic & Medicinal Chemistry, 2006, vol. 14, pp. 3697-3711) as starting materials, the compound shown in Table 8 (2.1 mg) was obtained in the same manner as that of Example 216, (3).

Example 220

The compound obtained in Example 216, (2) (20 mg) and 5-(4-pyridin-3-yl-1H-imidazol-1-yl)pentan-1-amine (28.2 mg) obtained in the same manner as that of the method described in the literature (Bioorganic & Medicinal Chemistry, 2006, vol. 14, pp. 3697-3711) as starting materials, the compound shown in Table 8 (1.2 mg) was obtained in the same manner as that of Example 216, (3).

Examples 221 to 225

Preparation methods of the compounds represented by the formula (K) having R defined in Table 9 are shown below.

[Formula 32]

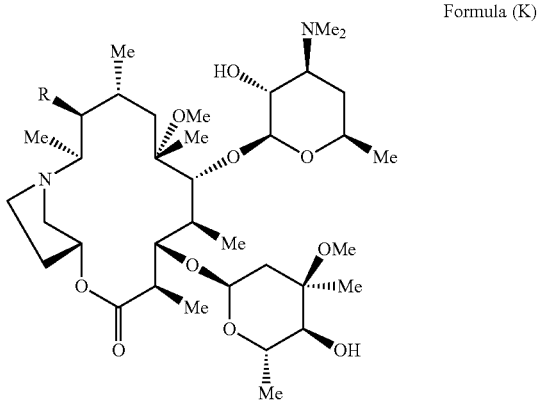

Formula (K)

TABLE 9

| Example | R | ESI MS (M + H) | $^1$H-NMR, CDCl$_3$, δ (ppm) |
|---|---|---|---|
| 221 | quinolin-4-yl-propyl-NH-C(O)-O- | 915 | (300 M Hz): 0.93-1.34 (m, 25H) 1.36-2.45 (m, 15H) 2.29 (s, 6H) 2.66-2.78 (m, 1H) 2.88-3.38 (m, 9H) 3.19 (s, 3H) 3.33 (s, 3H) 3.43-3.57 (m, 1H) 3.68-3.84 (m, 2H) 3.99-4.09 (m, 1H) 4.54 (d, J = 7.4 Hz, 1H) 4.67-4.95 (m, 3H) 5.10-5.22 (m, 1H) 7.22-7.27 (m, 1H) 7.56 (t, J = 8.5 Hz, 1H) 7.70 (t, J = 6.9 Hz, 1H) 8.00 (d, J = 8.5 Hz, 1H) 8.11 (d, J = 8.2 Hz, 1H) 8.80 (d, J = 4.7 Hz, 1H) |
| 222 | -O-C(O)-NH-propyl-N(imidazole-pyridin-3-yl) | 931 | (400 M Hz): 0.96-1.01 (m, 3H) 1.04 (d, J = 6.6 Hz, 3H) 1.09 (d, J = 7.3 Hz, 3H) 1.15 (d, J = 7.1 Hz, 3H) 1.20 (d, J = 5.9 Hz, 3H) 1.24-1.28 (m, 4H) 1.25 (s, 3H) 1.31 (s, 3H) 1.40-1.66 (m, 2H) 1.76-1.92 (m, 3H) 1.98-2.09 (m, 2H) 2.17-2.25 (m, 6H) 2.28 (s, 6H) 2.69-2.81 (m, 1H) 2.95-3.45 (m, 8H) 3.20 (s, 3H) 3.34 (s, 3H) 3.46-3.56 (m, 1H) 3.74 (d, J = 6.4 Hz, 1H) 3.76-3.83 (m, 1H) 3.99-3.10 (m, 3H) 4.55 (d, J = 7.1 Hz, 1H) 4.67-4.73 (m, 1H) 4.79-4.84 (m, 1H) 4.96-5.19 (m, 2H) 7.27-7.34 (m, 2H) 7.57 (s, 1H) 8.06-8.11 (m, 1H) 8.47 (dd, J = 4.9, 1.7 Hz, 1H) 8.96 (d, J = 1.5 Hz, 1H) |
| 223 | -O-C(O)-NH-ethyl-N(imidazole-pyridin-3-yl) | 917 | (400 M Hz): 0.97-1.02 (m, 6H) 1.08 (d, J = 7.6 Hz, 3H) 1.14 (d, J = 7.1 Hz, 3H) 1.21 (d, J = 6.1 Hz, 3H) 1.22-1.26 (m, 3H) 1.24 (s, 3H) 1.30 (s, 3H) 1.37-1.45 (m, 1H) 1.56 (dd, J = 15.1, 4.9 Hz, 1H) 1.60-1.68 (m, 1H) 1.74-2.51 (m, 8H) 2.29 (s, 6H) 2.72-2.81 (m, 1H) 2.85-3.65 (m, 9H) 3.19 (s, 3H) 3.33 (s, 3H) 3.70-3.76 (m, 2H) 4.01-4.22 (m, 3H) 4.52 (d, J = 7.3 Hz, 1H) 4.67 (d, J = 8.5 Hz, 1H) 4.82 (d, J = 4.1 Hz, 1H) 4.99-5.25 (m, 2H) 7.26-7.32 (m, 2H) 7.53 (s, 1H) 8.05-8.10 (m, 1H) 8.47 (dd, J = 5.6, 1.5 Hz, 1H) 8.93-8.96 (m, 1H) |
| 224 | 3-(furan-3-yl)benzyl-NH-C(O)-O- | 902 | (400 M Hz): 0.96-1.18 (m, 18H) 1.24 (s, 3H) 1.24-1.27 (m, 1H) 1.29 (s, 3H) 1.43-1.85 (m, 4H) 2.00-2.51 (m, 7H) 2.28 (s, 6H) 2.65-2.76 (m, 1H) 2.92-3.38 (m, 6H) 3.15 (s, 3H) 3.33 (s, 3H) 3.44-3.56 (m, 1H) 3.72 (d, J = 5.6 Hz, 1H) 3.77-3.85 (m, 1H) 3.94-4.06 (m, 1H) 4.27-4.43 (m, 2H) 4.53 (d, J = 7.1 Hz, 1H) 4.69-4.82 (m, 2H) 5.04-5.23 (m, 2H) 6.68 (s, 1H) 7.14 (d, J = 7.3 Hz, 1H) 7.28-7.33 (m, 1H) 7.35-7.39 (m, 2H) 7.46 (s, 1H) 7.71 (s, 1H) |

TABLE 9-continued

| Example | R | ESI MS (M + H) | $^1$H-NMR, CDCl$_3$, δ (ppm) |
|---|---|---|---|
| 225 | (furan-3-yl phenyl ethyl carbamate structure) | 916 | (400 M Hz): 0.93-0.97 (m, 3H) 1.03 (d, J = 6.3 Hz, 3H) 1.08 (d, J 7.3 Hz, 3H) 1.14 (d, J = 7.1 Hz, 3H) 1.21 (d, J = 6.1 Hz, 3H) 1.23-1.27 (m, 4H) 1.25 (s, 3H) 1.29 (s, 3H) 1.39-1.87 (m, 4H) 1.99-2.51 (m, 7H) 2.29 (s, 6H) 2.69-2.87 (m, 3H) 2.91-3.57 (m, 9H) 3.18 (s, 3H) 3.34 (s, 3H) 3.74 (d, J = 5.9 Hz, 1H) 3.75-3.83 (m, 1H) 4.00-4.10 (m, 1H) 4.53 (d, J = 7.1 Hz, 1H) 4.69 (d, J = 7.1 Hz, 1H) 4.75-4.83 (m, 2H) 5.03-5.17 (m, 1H) 6.67-6.71 (m, 1H) 7.08 (d, J = 7.3 Hz, 1H) 7.26-7.37 (m, 3H) 7.46-7.49 (m, 1H) 7.72 (s, 1H) |

Example 221

(1) The compound obtained in Example 214, (3) (146.2 mg) and 1,4-diazabicyclo[2.2.2]octane (186.6 mg) were dissolved in pyridine (439 μl), the solution was added with allyl isocyanate (438 μl), and the mixture was stirred at 100° C. for 10 minutes under microwave irradiation. The reaction mixture was added with distilled water and ethyl acetate, the layers were separated, the organic layer was concentrated under reduced pressure, and the resulting residue was purified by silica gel column chromatography (chloroform:methanol=100:1 to 50:1) to obtain a 9-O-carbamoyl compound (61.7 mg).

(2) The compound obtained in (1) mentioned above (61.7 mg), tris(dibenzylideneacetone)dipalladium(0) (11.7 mg), and the compound obtained in Reference Example 33 (53.4 mg) were dissolved in dioxane (610 μl), the solution was added successively with dicyclohexylmethylamine (54.7 μl) and a 0.44 N solution of tri-t-butylphosphine in dioxane (58.3 μl), and the mixture was stirred at 100° C. for 10 minutes under microwave irradiation. The reaction mixture was filtered, then the filtrate was concentrated under reduced pressure, and the resulting residue was purified by preparative thin layer chromatography (hexane:acetone:triethylamine=10:20:0.4) to obtain a coupled compound (24.3 mg) as a mixture of isomers for the double bond.

(3) The compound obtained in (2) mentioned above (24.3 mg) was dissolved in methanol (486 μl), and the solution was stirred at 50° C. for 22 hours. The reaction mixture was concentrated under reduced pressure, and the resulting residue was purified by preparative thin layer chromatography (chloroform:methanol:28% aqueous ammonia=10:1:0.1) to obtain a 2'-hydroxy compound (15.1 mg) as a mixture of isomers for the double bond.

(4) The compound obtained in (3) mentioned above (15.1 mg) was dissolved in a mixed solvent of dioxane and distilled water (5:1, 0.3 ml), the solution was added with 5% palladium-carbon (22.7 mg) under an argon atmosphere, and then the mixture was stirred at room temperature for 2 days under a hydrogen atmosphere of 1 atm. The reaction mixture was filtered through Celite, then the filtrate was concentrated under reduced pressure, and the resulting residue was purified by preparative thin layer chromatography (chloroform:methanol:28% aqueous ammonia=5:1:0.1) to obtain the compound shown in Table 9 (7.4 mg).

Example 222

(1) The compound obtained in Example 169, (1) (2.67 g) and 4-dimethylaminopyridine (35 mg) were dissolved in methylene chloride (26.7 ml), the solution was added with triethylamine (799 μl) and acetic anhydride (542 μl), and the mixture was stirred at room temperature for 19 hours. The reaction mixture was added with saturated aqueous ammonium chloride and chloroform, the layers were separated, and the organic layer was dried over anhydrous magnesium sulfate, and filtered. The filtrate was concentrated under reduced pressure, and the resulting residue was purified by silica gel column chromatography (hexane:acetone:triethylamine=200:10:0.2) to obtain a 4"-O-acetyl compound (1.68 g).

(2) By using the compound obtained in (1) mentioned above (1.68 g) as a starting material, a deprotected compound (1.24 g) was obtained in the same manner as that of Example 1, (3).

(3) By using the compound obtained in (2) mentioned above (1.24 g) as a starting material, a 2'-O-acetyl compound (1.19 mg) was obtained in the same manner as that of Example 214, (3).

(4) The compound obtained in (3) mentioned above (500 mg) and carbonyldiimidazole (309 mg) were dissolved in pyridine (5 ml), and the mixture was stirred at 50° C. for 2 hours. The reaction mixture was cooled to room temperature, then the solution was added with ethyl acetate, and the mixture was washed successively with saturated aqueous ammonium chloride, distilled water, and saturated brine. The organic layer was dried over anhydrous magnesium sulfate, and filtered, and the filtrate was concentrated under reduced pressure to obtain a 9-O-imidazolylcarbonyl compound (632 mg).

(5) The compound obtained in (4) mentioned above (159.2 mg) and 3-(4-pyridin-3-yl-1H-imidazol-1-yl)propan-1-amine (331 mg) obtained by the method described in the literature (Bioorganic & Medicinal Chemistry, 2006, vol. 14, pp. 3697-3711) were dissolved in pyridine (318.4 μl), and the mixture was stirred at room temperature for 25 hours. The reaction mixture was added with distilled water and ethyl acetate, the layers were separated, the organic layer was concentrated under reduced pressure, and the resulting residue was purified by preparative thin layer chromatography (chloroform:methanol:28% aqueous ammonia=10:1:0.1) to obtain a 9-O-carbamoyl compound (133 mg).

(6) The compound obtained in (5) mentioned above (70 mg) was dissolved in a mixed solvent of methanol and distilled water (3:1, 1.65 ml), the solution was added with potassium carbonate (95.3 mg), and the mixture was stirred at room temperature for 39 hours, and at 35° C. for 6 hours. The reaction mixture was added with distilled water and ethyl acetate, the layers were separated, the organic layer was concentrated under reduced pressure, and the resulting residue was purified by preparative thin layer chromatography (chloroform:methanol:28% aqueous ammonia=7:1:0.1) to obtain the compound shown in Table 9 (47 mg).

Example 223

By using the compound obtained in Example 222, (4) (100 mg) and 2-(4-pyridin-3-yl-1H-imidazol-1-yl)ethanamine (193.4 mg) obtained by the method described in the literature (Bioorganic & Medicinal Chemistry, 2006, vol. 14, pp. 3697-3711) as starting materials, the compound shown in Table 9 (29.9 mg) was obtained in the same manners as those of Example 222, (5) and (6).

Example 224

(1) By using the compound obtained in Example 222, (4) (100 mg) and the compound obtained in Reference Example 56 (178.1 mg) as starting materials, a 9-O-carbamate compound (80 mg) was obtained in the same manner as that of Example 222, (5).
(2) By using the compound obtained in (1) mentioned above (80 mg) as a starting material, the compound shown in Table 9 (44.7 mg) was obtained in the same manner as that of Example 222, (6).

Example 225

(1) By using the compound obtained in Example 222, (4) (100 mg) and the compound obtained in Reference Example 57 (192.5 mg) as starting materials, a 9-O-carbamate compound (86.7 mg) was obtained in the same manner as that of Example 222, (5).
(2) By using the compound obtained in (1) mentioned above (86.7 mg) as a starting material, the compound shown in Table 9 (46.6 mg) was obtained in the same manner as that of Example 222, (6).

Example 226

A preparation method of the compound represented by the formula (L) is shown below.

[Formula 33]

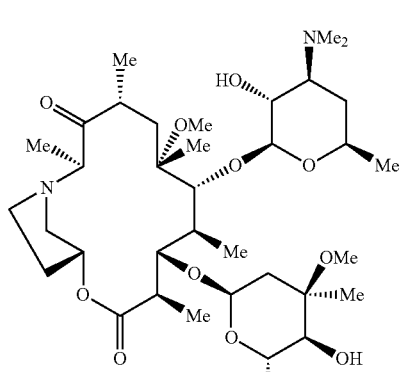

Formula (L)

Example 226

(1) N-Chlorosuccinimide (152 mg) was dissolved in toluene (6 ml), and the solution was cooled to −25° C. The solution was added with dimethyl sulfide (279 μl), the mixture was stirred for 15 minutes, and then added with a solution of the compound obtained in Example 214, (3) (100 mg) in toluene (1 ml), and the mixture was stirred for 15 minutes. The reaction mixture was added with triethylamine (317 μl), the mixture was further stirred for 10 minutes, then warmed to room temperature, and added with saturated aqueous sodium hydrogencarbonate and ethyl acetate, and the layers were separated. The organic layer was concentrated under reduced pressure, and the resulting residue was purified by silica gel column chromatography (hexane:acetone:triethylamine=30:10:0.2 to 20:10:0.2) to obtain a 9-ketone compound (118.2 mg).

(2) By using the compound obtained in (1) mentioned above (118.2 mg) as a starting material, a methanol solution of 2'-hydroxy compound was obtained in the same manner as that of Example 221, (3). The reaction mixture was added with 5% palladium-carbon (100 mg) under an argon atmosphere, and the mixture was stirred at room temperature for 2 hours under a hydrogen atmosphere of 1 atm. The reaction mixture was filtered through Celite, then the filtrate was concentrated under reduced pressure, and the resulting residue was purified by silica gel column chromatography (chloroform:methanol:28% aqueous ammonia=40:1:0.1 to 15:1:0.1) to obtain a compound represented by the formula (L) (49.8 mg).

MS (ESI) m/z=701 [M+H]$^+$ $^1$H-NMR (300 MHz, CDCl$_3$) δ (ppm): 1.05 (d, J=6.6 Hz, 3H), 1.08 (d, J=7.4 Hz, 3H), 1.13 (d, J=7.1 Hz, 3H), 1.20-1.33 (m, 10H), 1.24 (s, 3H), 1.36 (s, 3H), 1.55 (dd, J=15.4, 4.7 Hz, 1H), 1.60-1.69 (m, 2H), 1.85-2.29 (m, 5H), 2.29 (s, 6H), 2.37 (d, J=15.1 Hz, 1H), 2.39-2.51 (m, 1H), 2.62-2.82 (m, 5H), 2.95-3.05 (m, 2H), 3.14 (s, 3H), 3.19-3.29 (m, 1H), 3.34 (s, 3H), 3.43-3.55 (m, 1H), 3.66 (d, J=7.7 Hz, 1H), 3.74 (d, J=7.1 Hz, 1H), 3.84 (q, J=6.9 Hz, 1H), 3.95-4.06 (m, 1H), 4.45 (d, J=7.4 Hz, 1H), 4.79 (d, J=4.7 Hz, 1H), 5.10-5.16 (m, 1H)

Examples 227 to 229

Preparation methods of the compounds represented by the formula (M) having $R^{1M}$ and $R^{2M}$ defined in Table 10 are shown below.

[Formula 34]

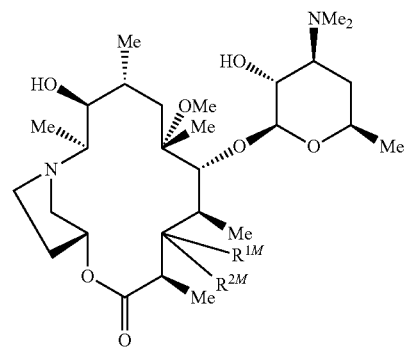

Formula (M)

TABLE 10

| Example | R$^{1M}$ | R$^{2M}$ | ESI MS (M + H) | $^1$H-NMR, CDCl$_3$, δ (ppm) |
|---|---|---|---|---|
| 227 | HO-C(CH$_3$)$_2$-CH$_2$- (structure) | -CH$_2$-H (structure) | 545 FAB MASS | (400 M Hz): 1.12 (d, J = 7.1 Hz, 6H) 1.09 (d, J = 7.1 Hz, 3H) 1.20-1.24 (m, 2H) 1.24 (d, J = 6.6 Hz, 3H) 1.26 (d, J = 6.1 Hz, 3H) 1.34 (s, 3H) 1.63-1.70 (m, 1H) 1.79-2.10 (m, 3H) 2.25 (s, 6H) 2.36-2.53 (m, 2H) 2.57-2.69 (m, 2 H) 2.76 (dd, J = 12.0, 4.2 Hz, 1H) 2.90 (dd, J = 15.1, 7.8 Hz, 1H) 2.98-3.07 (m, 1H) 3.09-3.16 (m, 2H) 3.18-3.22 (m, 1H) 3.20 (s, 3H) 3.26 (dd, J = 10.3, 7.6 Hz, 1H) 3.46 (d, J = 9.8 Hz, 1H) 3.49-3.58 (m, 1H) 3.68-3.75 (m, 1H) 3.79 (d, J = 1.7 Hz, 1H) 4.47 (d, J = 7.6 Hz, 1H) 5.01-5.06 (m, 1H) |
| 228 | 3-pyridyl-CH$_2$-C(O)-O- structure | -CH$_2$-H structure | 664 | (300 M Hz): 0.91 (d, J = 6.9 Hz, 3H) 0.95 (d, J = 7.1 Hz, 3H) 1.00 (d, J = 6.9 Hz, 3H) 1.11 (d, J = 7.4 Hz, 3H) 1.14 (d, J = 6.0 Hz, 3H) 1.19-1.25 (m, 2H) 1.26 (s, 3H) 1.55-1.64 (m, 1H) 1.75-1.87 (m, 1H) 1.91-2.06 (m, 1H) 2.13-2.23 (m, 1H) 2.29 (s, 6H) 2.31-2.42 (m, 1H) 2.55 (q, J = 7.1 Hz, 1H) 2.65-2.87 (m, 3H) 2.99-3.26 (m, 7H) 3.26 (s, 3H) 3.71 (d, J = 3.3 Hz, 2H) 3.79 (d, J = 4.4 Hz, 1H) 3.94 (d, J = 7.1 Hz, 1H) 4.93 (d, J = 10.7 Hz, 1H) 4.98-5.04 (m, 1H) 7.29 (dd, J = 8.0, 4.9 Hz, 1H) 7.71-7.76 (m, 1H) 8.52-8.56 (m, 2H) |
| 229 | O=C-O- structure | O=C-O- structure | 543 | (300 M Hz): 0.95 (d, J = 7.3 Hz, 3H) 0.98 (d, J = 6.9 Hz, 3H) 1.22-1.26 (m, 1H) 1.24 (d, J = 6.0 Hz, 3H) 1.25 (d, J = 6.6 Hz, 3H) 1.30 (d, J = 7.7 Hz, 3H) 1.34 (s, 3H) 1.50 (dd, J = 15.1, 1.9 Hz, 1H) 1.62-171 (m, 1H) 1.81-1.94 (m, 1H) 1.98-2.11 (m, 1H) 2.18-2.25 (m, 1H) 2.27 (s, 6H) 2.40-2.55 (m, 3H) 2.76 (dd, J = 15.1, 9.9 Hz, 1H) 2.91 (s, 3H) 2.94-3.10 (m, 2H) 3.14-3.25 (m, 3H) 3.47-3.65 (m, 2H) 3.82 (q, J = 6.9 Hz, 1H) 4.31 (d, J = 7.1 Hz, 1H) 4.35 (d, J = 8.5 Hz, 1H) 5.01-5.07 (m, 1H) |

Example 227

The compound obtained in Example 1 (372.7 mg) was dissolved in a mixed solvent of methanol and ethanol (1:1, 1.38 ml), the solution was added with 1 N hydrochloric acid (1.38 ml), and the mixture was stirred at room temperature for 4 hours and 30 minutes, then warmed to 50° C., and further stirred for 2 hours. The reaction mixture was ice-cooled, and added with 2.5 N aqueous sodium hydroxide, the mixture was then added with saturated aqueous sodium hydrogencarbonate and chloroform, and the layers were separated. The organic layer was dried over anhydrous magnesium sulfate, and filtered, then the filtrate was concentrated under reduced pressure, and the resulting residue was purified by silica gel column chromatography (ethyl acetate:methanol:28% aqueous ammonia=30:1:0.1, and then chloroform:methanol:28% aqueous ammonia=10:1:0.1 to 5:1:0.1) to obtain the compound shown in Table 10 (316.7 mg).

Example 228

(1) By using the compound obtained in Example 227 (296.9 mg) as a starting material, a 2'-O-acetyl compound (319.8 mg) was obtained in the same manner as that of Example 214, (3).
(2) The compound obtained in (1) mentioned above (319.8 mg) was dissolved in dimethylformamide (1.76 ml), the solution was added with imidazole (167 mg) and triethylchlorosilane (210.1 μl), and the reaction mixture was stirred at room temperature for 24 hours and 30 minutes. The reaction mixture was added with distilled water and ethyl acetate, the layers were separated, the organic layer was concentrated under reduced pressure, and the resulting residue was purified by silica gel column chromatography (hexane:acetone:triethylamine=50:10:0.2 to 20:10:0.2) to obtain a 9-O-triethylsilyl compound (304.9 mg).
(3) The compound obtained in (2) mentioned above (50 mg) was dissolved in chloroform (1 ml), the solution was added with 3-pyridylacetic acid hydrochloride (99.2 mg), 1-ethyl-3-(3-dimethylaminopropyl)carbodiimide hydrochloride (109.3 mg), triethylamine (49.7 μl), and 4-dimethylaminopyridine (21.8 mg), and the mixture was stirred at room temperature for 24 hours. The reaction mixture was added with saturated aqueous ammonium chloride and ethyl acetate, the layers were separated, the organic layer was washed successively with saturated aqueous sodium hydrogencarbonate and saturated brine, dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain a 3-O-acyl compound (16.8 mg).
(4) The compound obtained in (3) mentioned above (16.8 mg) was dissolved in methanol (336 μl), and the reaction mixture was stirred at 40° C. for 12 hours and 30 minutes, at 50° C. for 3 hours and 30 minutes, and at 60° C. for 1 hour and 30 minutes. The reaction mixture was concentrated, and added with ethanol (300 μl) and 1 N hydrochloric acid (300 μl), and the mixture was stirred at room temperature for 4 hours. The reaction mixture was added with saturated aqueous sodium hydrogencarbonate and ethyl acetate, the layers were separated, the organic layer was concentrated under reduced pressure, and the resulting residue was purified by preparative thin layer chromatography (chloroform:methanol:28% aqueous ammonia=10:1:0.1) to obtain the compound shown in Table 10 (13.4 mg).

Example 229

(1) By using the compound obtained in Example 228, (2) 100 mg) as a starting material, a 3-ketone compound (48.9 mg) was obtained as a mixture of isomers in the same manner as that of Example 226, (1).
(2) By using the compound obtained in (1) mentioned above (48.9 mg) as a starting material, the compound shown in Table 10 (28.6 mg) was obtained in the same manner as that of Example 228, (4).

Examples 230 and 231

Preparation methods of the compounds represented by the formula (N) having R defined in Table 11 are shown below.

[Formula 35]

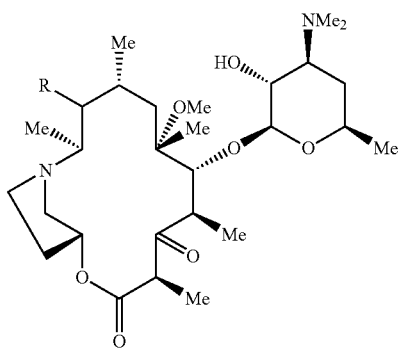

Formula (N)

(2) By using the compound obtained in (1) mentioned above (19.3 mg) as a starting material, a 2'-O-acetyl compound (18.4 mg) was obtained in the same manner as that of Example 214, (3).

(3) By using the compound obtained in (2) mentioned above (18.4 mg) as a starting material, and methylene chloride solvent instead of toluene, a 3-ketone compound was obtained as a crude product in the same manner as that of Example 226, (1). The resulting crude product was added with methanol (368 µl), the reaction mixture was stirred at room temperature for 25 hours, and then concentrated under reduced pressure, and the resulting residue was purified by preparative thin layer chromatography (chloroform:methanol:28% aqueous ammonia=10:1:0.1) to obtain the compound shown in Table 11 (12.4 mg).

Example 231

By using the compound obtained in Example 225, (1) (86.6 mg) as a starting material, the compound shown in Table 11 (3.4 mg) was obtained in the same manners as those of Example 230, (1), Example 214, (3), and Example 230, (3).

TABLE 11

| Example | R | ESI MS (M + H) | $^1$H-NMR, CDCl$_3$, δ (ppm) |
|---|---|---|---|
| 230 | ![structure] | 742 | (300 M Hz): 0.93 (d, J = 6.6 Hz, 3H) 1.06 (d, J = 6.6 Hz, 3H) 1.14 (d, J = 5.8 Hz, 3H) 1.20-1.31 (m, 1H) 1.22 (s, 3H) 1.28 (d, J = 6.7 Hz, 3H) 1.40 (d, J = 7.4 Hz, 3H) 1.47-2.18 (m, 4H) 2.32 (s, 6H) 2.35-2.42 (m, 1H) 2.45-2.60 (m, 2H) 2.83-3.31 (m, 5H) 3.10 (s, 3H) 3.43-3.59 (m, 2H) 3.89 (q, J = 7.1 Hz, 1H) 4.04-4.14 (m, 1H) 4.30-4.45 (m, 3H) 4.55-4.63 (m, 1H) 4.78-4.82 (m, 1H) 4.93-5.13 (m, 2H) 6.68 (s, 1H) 7.16 (d, J = 7.4 Hz, 1H) 7.29-7.43 (m, 3H) 7.45-7.49 (m, 1H) 7.72 (s, 1H) |
| 231 | ![structure] | 756 | (400 M Hz): 0.87 (d, J = 6.3 Hz, 3H) 1.02 (d, J = 6.6 Hz, 3H) 1.16 (d, J = 6.1 Hz, 3H) 1.22 (s, 3H) 1.22-1.25 (m, 1H) 1.29 (d, J = 6.8 Hz, 3H) 1.40 (d, J = 7.3 Hz, 3H) 1.46-2.16 (m, 4H) 2.35 (s, 6H) 2.78-3.30 (m, 7H) 3.12 (s, 3H) 3.38-3.62 (m, 4H) 3.90 (q, J = 6.8 Hz, 1H) 4.40 (d, J = 7.6 Hz, 1H) 4.47-4.55 (m, 1H) 4.67-4.75 (m, 1H) 4.82 (s, 1H) 5.03-5.13 (m, 1H) 6.68-6.70 (m, 1H) 7.09 (d, J = 7.1 Hz, 1H) 7.28-7.37 (m, 3H) 7.47-7.49 (m, 1H) 7.72 (s, 1H) |

Example 230

(1) The compound obtained in Example 224, (1) (87.3 mg) was dissolved in ethanol (323 µl), the solution was added with 1 N hydrochloric acid (323 µl), and the mixture was stirred at room temperature for 22 hours and at 50° C. for 2 days. The reaction mixture was added with 2.5 N aqueous sodium hydroxide and ethyl acetate, the layers were separated, and the organic layer was concentrated under reduced pressure to obtain a 3-hydroxy compound as a crude product. The resulting crude product was added with methanol (2 ml), the reaction mixture was stirred at room temperature for 30 hours, and then concentrated under reduced pressure, and the resulting residue was purified by preparative thin layer chromatography (chloroform:methanol:28% aqueous ammonia=10:1:0.1) to obtain a 3,2'-dihydroxy compound (19.3 mg).

Example 232

A preparation method of the compound represented by the formula (O) is shown below.

[Formula 36]

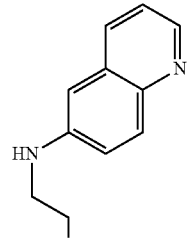

Formula (O)

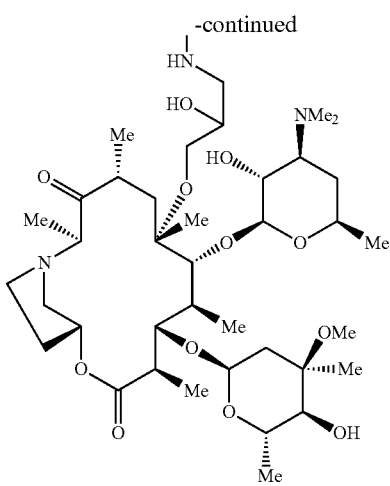

Example 232

(1) By using the compound obtained in Reference Example 58 (200 mg) and the compound obtained in Reference Example 60 (98 mg) as starting materials, a cyclized compound (96 mg) was obtained in the same manners as those of Example 1, (1) and (2).

(2) The compound obtained in (1) mentioned above (57 mg) was dissolved in a mixed solution of tetrahydrofuran and distilled water (2:1, 3 ml), the solution was added with 4 wt % aqueous osmium tetroxide (68 μl) and N-methylmorpholine N-oxide (31.5 mg), and the mixture was stirred at room temperature for 30 minutes. The reaction mixture was added with sodium hydrogensulfite, the mixture was made basic with 10% aqueous sodium hydroxide, and extracted with chloroform. The organic layer was dried over anhydrous magnesium sulfate, and filtered. The filtrate was concentrated under reduced pressure, the resulting residue was dissolved in chloroform (1 ml), the solution was added with 36% aqueous formaldehyde (13.4 μl) and sodium triacetoxyborohydride (22.8 mg), and the mixture was stirred at room temperature for 1 hour. The reaction mixture was added with saturated aqueous sodium hydrogencarbonate and chloroform, the layers were separated, and then the organic layer was dried over anhydrous sodium sulfate, and filtered. The filtrate was concentrated under reduced pressure, and the resulting residue was purified by silica gel column chromatography (hexane:acetone:triethylamine=100:10:0.2 to 30:10:0.2) to obtain a diol compound (31 mg).

(3) The compound obtained in (2) mentioned above (31 mg) was dissolved in chloroform (1 ml), the solution was added with triethylamine (79 μl), 4-dimethylaminopyridine (34.7 mg), and p-toluenesulfonyl chloride (10.8 mg), and the mixture was stirred at room temperature for 1 hour. The reaction mixture was added with p-toluenesulfonyl chloride (27 mg), and the mixture was stirred at room temperature for 4 hours. The mixture was added with saturated aqueous sodium hydrogencarbonate and ethyl acetate, the layers were separated, and then the organic layer was dried over anhydrous magnesium sulfate, and filtered. The filtrate was concentrated under reduced pressure, the resulting residue was dissolved in methanol (1 ml), the solution was added with potassium carbonate (7.9 mg), and the mixture was stirred at room temperature for 4 hours. The reaction mixture was added with ethyl acetate, the mixture was washed with saturated aqueous sodium hydrogencarbonate, and then the organic layer was dried over anhydrous magnesium sulfate, and filtered. The filtrate was concentrated under reduced pressure, and the resulting residue was purified by silica gel column chromatography (hexane:acetone:triethylamine=200:10:0.2 to 100:10:0.2) to obtain an epoxy compound (20 mg).

(4) By using the compound obtained in (3) mentioned above (17 mg) as a starting material, a deprotected compound (8.2 mg) was obtained in the same manner as that of Example 1, (3).

(5) The compound obtained in (4) mentioned above (6.0 mg) and the compound obtained in Reference Example 59 (15 mg) were dissolved in ethanol (0.2 ml), and the solution was stirred for 16 hours under reflux by heating. The reaction mixture was concentrated under reduced pressure, and the resulting residue was purified by preparative thin layer chromatography (chloroform:methanol:28% aqueous ammonia=10:1:0.1) to obtain the compound represented by the formula (O) (2.6 mg).

MS (ESI) m/z=932.7 [M+H]$^+$ $^1$H-NMR (600 MHz, CDCl$_3$): 0.90-0.99 (m, 6H), 1.05-1.30 (m, 16H), 1.34-1.38 (m, 3H), 1.41-1.52 (m, 1H), 1.62-1.67 (m, 1H), 1.77-1.82 (m, 1H), 1.95-2.03 (m, 1H), 2.12-2.22 (m, 2H), 2.27 (s, 6H), 2.29-2.57 (m, 5H), 2.59-2.76 (m, 2H), 2.78-3.07 (m, 7H), 3.16-3.25 (m, 3H), 3.23-3.30 (m, 3H), 3.43-3.52 (m, 2H), 3.68-3.78 (m, 3H), 3.82-4.09 (m, 4H), 4.40-4.45 (m, 1H), 4.72-4.83 (m, 1H), 4.89-4.98 (m, 1H), 6.66-6.68 (m, 1H), 7.11-7.16 (m, 1H), 7.20-7.25 (m, 1H), 7.83 (dd, J=9.17, 2.75 Hz, 1H), 7.89 (d, J=7.79 Hz, 1H), 8.53-8.60 (m, 1H)

Examples 233 to 390

Preparation methods of the compounds represented by the formula (P) having R defined in Table 12 are shown below.

[Formula 37]

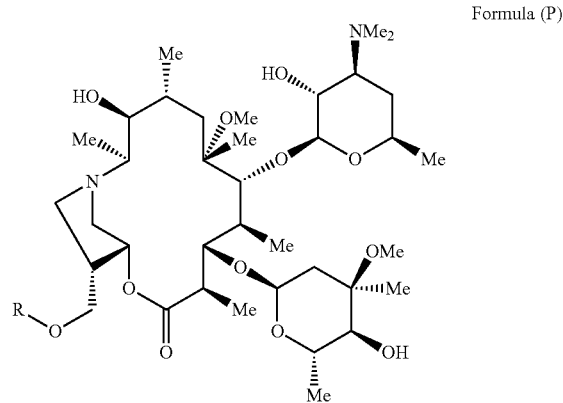

Formula (P)

TABLE 12
| Example | R | ESI MS (M + H) |
|---|---|---|
| 233 | 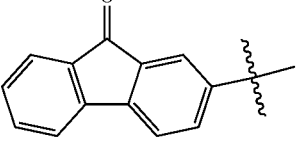 | 911.6 |
| 234 | 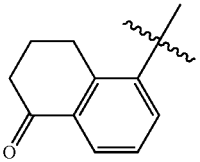 | 877.7 |
| 235 | 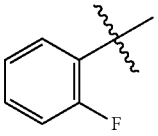 | 827.7 |
| 236 | 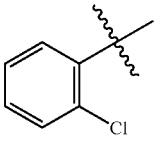 | 843.6 |
| 237 | 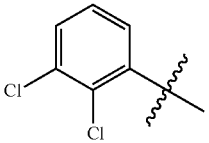 | 877.6 |
| 238 | 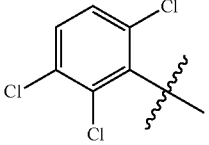 | 911.6 |
| 239 | 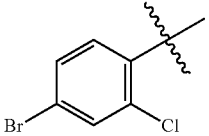 | 921.6 |
| 240 | 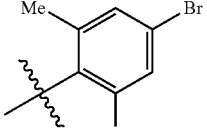 | 935.6 |
| 241 | 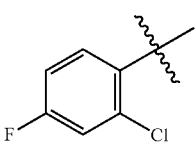 | 861.6 |
TABLE 12-continued
| Example | R | ESI MS (M + H) |
|---|---|---|
| 242 | 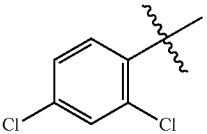 | 877.6 |
| 243 | 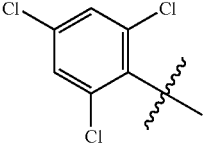 | 911.6 |
| 244 | 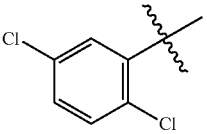 | 877.6 |
| 245 | 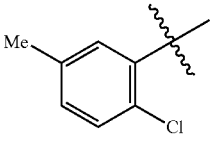 | 857.7 |
| 246 | 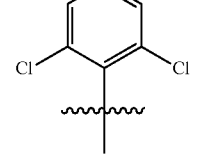 | 877.6 |
| 247 | 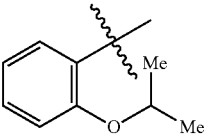 | 867.7 |
| 248 | 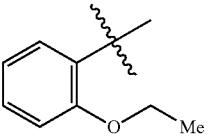 | 853.7 |
| 249 | 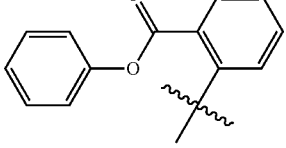 | 929.8 |
| 250 | 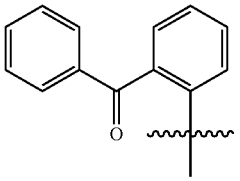 | 913.7 |

TABLE 12-continued

| Example | R | ESI MS (M + H) |
|---|---|---|
| 251 | 2-acetylphenyl | 851.7 |
| 252 | 2-propionylphenyl | 865.7 |
| 253 | 2-(trifluoromethyl)phenyl | 877.7 |
| 254 | 2-isopropylphenyl | 851.8 |
| 255 | 2-methylphenyl | 823.7 |
| 256 | 2,3-dimethylphenyl | 837.8 |
| 257 | 2,3,5-trimethylphenyl | 851.8 |
| 258 | 2,3,6-trimethylphenyl | 851.8 |
| 259 | 3,5-dimethylphenyl (X position) | 851.8 |
| 260 | 2-(1-methylethyl)-4-methylphenyl | 865.8 |
| 261 | 2-benzylphenyl | 899.7 |
| 262 | 2-methylphenyl (CH linker) | 837.7 |
| 263 | 2-ethylphenyl | 851.8 |
| 264 | 3,5-difluorophenyl | 845.7 |
| 265 | 3,4,5-trimethylphenyl | 851.8 |
| 266 | 4-bromophenyl | 887.6 |
| 267 | 4-fluorophenyl | 827.8 |
| 268 | 4-chloro-2-bromophenyl | 921.7 |

TABLE 12-continued
| Example | R | ESI MS (M + H) |
|---|---|---|
| 269 | 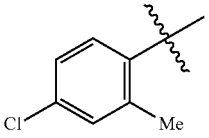 | 857.7 |
| 270 | 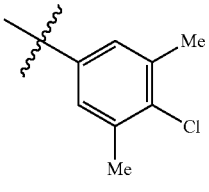 | 871.8 |
| 271 | 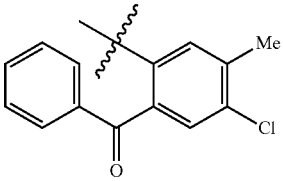 | 961.8 |
| 272 | 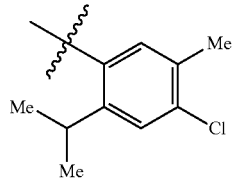 | 899.8 |
| 273 | 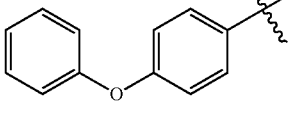 | 901.8 |
| 274 | 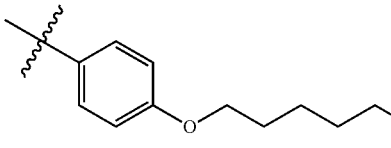 | 923.8 |
| 275 | 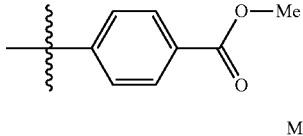 | 867.7 |
| 276 | 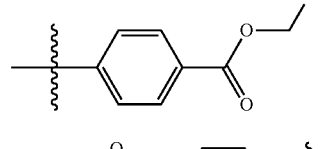 | 881.7 |
| 277 | 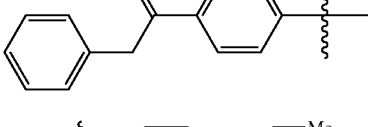 | 927.8 |
| 278 | 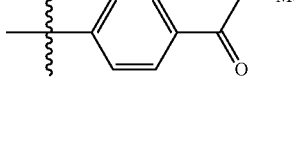 | 865.8 |
| 279 | 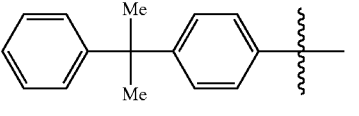 | 927.8 |
| 280 | 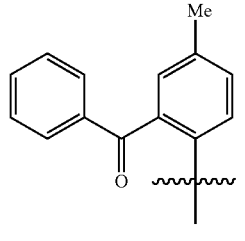 | 927.8 |
| 281 | 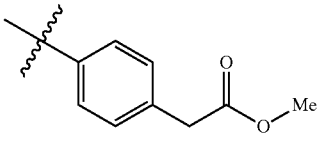 | 881.8 |
| 282 | 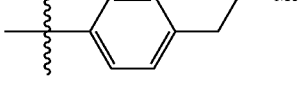 | 851.8 |
| 283 | 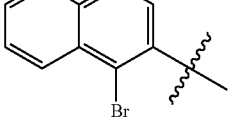 | 937.7 |
| 284 | 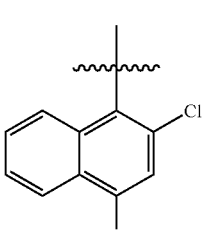 | 927.7 |
| 285 | 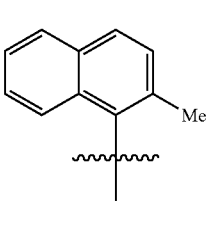 | 873.8 |
| 286 | 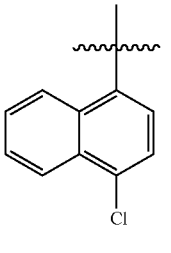 | 893.7 |

TABLE 12-continued

| Example | R | ESI MS (M + H) |
|---|---|---|
| 287 | naphthyl-OMe | 889.8 |
| 288 | 6-bromonaphthyl | 937.7 |
| 289 | 4-methylcoumarin-7-yl | 891.7 |
| 290 | 6-methoxycoumarin-7-yl | 907.7 |
| 291 | coumarin-7-yl | 877.7 |
| 292 | 2,3-dimethoxyphenyl | 869.7 |
| 293 | 2-benzoyl-4-methoxyphenyl | 943.8 |

TABLE 12-continued

| Example | R | ESI MS (M + H) |
|---|---|---|
| 294 | 2-acetyl-5-methoxyphenyl | 881.7 |
| 295 | 2,6-diisopropylphenyl | 893.8 |
| 296 | 3-methoxy-4-(ethoxycarbonylmethyl)phenyl | 925.8 |
| 297 | 2,4-difluorophenyl | 845.7 |
| 298 | 2,3-difluorophenyl | 845.7 |
| 299 | 2-bromo-4-fluorophenyl | 905.7 |
| 300 | fluoren-2-yl | 897.8 |
| 301 | 3,4,8-trimethylcoumarin-7-yl | 919.8 |
| 302 | 2-acetyl-4-fluorophenyl | 869.8 |

TABLE 12-continued
| Example | R | ESI MS (M + H) |
|---|---|---|
| 303 | 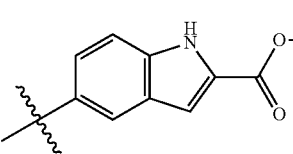 | 920.8 |
| 304 | 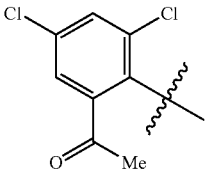 | 919.7 |
| 305 | 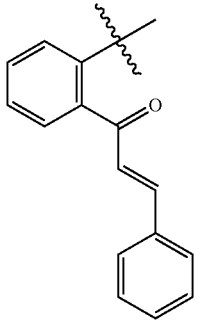 | 939.8 |
| 306 | 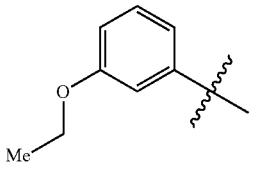 | 853.8 |
| 307 | 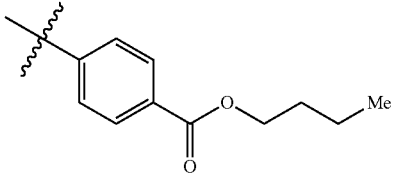 | 909.8 |
| 308 | 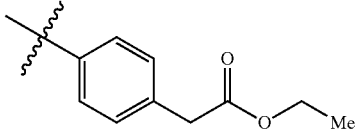 | 895.8 |
| 309 | 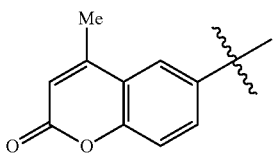 | 891.7 |
| 310 | 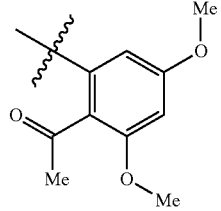 | 911.8 |
| 311 | 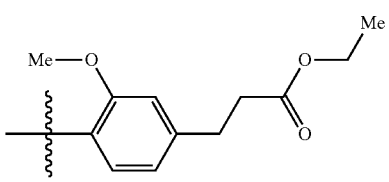 | 939.8 |
| 312 | 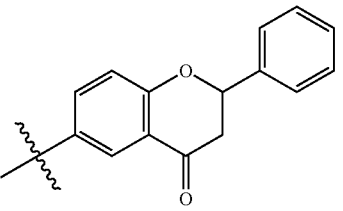 | 955.8 |
| 313 | 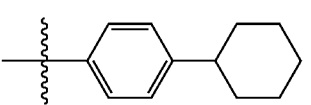 | 891.6 |
| 314 | 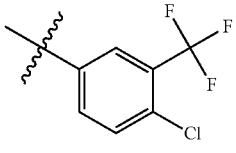 | 911.5 |
| 315 | 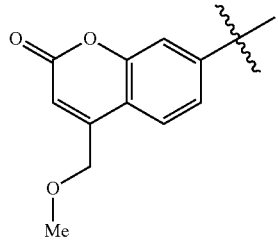 | 921.5 |
| 316 | 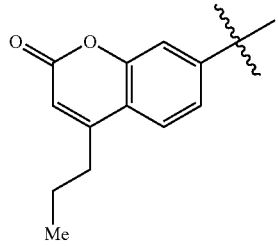 | 919.5 |

TABLE 12-continued

| Example | R | ESI MS (M + H) |
|---|---|---|
| 317 | | 881.6 |
| 318 | | 889.6 |
| 319 | | 895.5 |
| 320 | | 889.6 |
| 321 | | 895.6 |
| 322 | | 925.6 |
| 323 | | 863.6 |
| 324 | | 943.6 |
| 325 | | 841.6 |
| 326 | | 899.5 |
| 327 | | 911.5 |
| 328 | | 933.5 |
| 329 | | 893.5 |
| 330 | | 947.7 |
| 331 | | 861.5 |
| 332 | | 961.6 |

TABLE 12-continued

| Example | R | ESI MS (M + H) |
|---|---|---|
| 333 | 4-methoxy-2-propanoylphenyl | 895.6 |
| 334 | pentafluorophenyl | 899.5 |
| 335 | 2,6-difluorophenyl | 845.5 |
| 336 | 2-(methylthio)phenyl | 855.5 |
| 337 | 2-(methoxycarbonyl)phenyl | 867.6 |
| 338 | 4-acetyl-2-methylphenyl | 865.6 |
| 339 | 3-acetoxyphenyl | 867.5 |
| 340 | 3-benzoylphenyl | 913.6 |

TABLE 12-continued

| Example | R | ESI MS (M + H) |
|---|---|---|
| 341 | 4-acetyl-3-methylphenyl (with 2-Me) | 865.6 |
| 342 | 4-bromo-2,6-dimethylphenyl | 915.5 |
| 343 | 4-bromo-3,5-dimethylphenyl | 915.5 |
| 344 | 4-iodophenyl | 935.4 |
| 345 | 4-propoxyphenyl | 867.6 |
| 346 | 4-butoxyphenyl | 881.6 |
| 347 | 4-(methylthio)phenyl | 855.5 |
| 348 | 4-(1,1-dimethylpropyl)phenyl | 879.7 |
| 349 | 4-(1-methylethyl)phenyl | 851.6 |
| 350 | 4-(1-methylpropyl)phenyl | 865.6 |

TABLE 12-continued

| Example | R | ESI MS (M + H) |
|---|---|---|
| 351 | 4-benzylphenyl | 899.6 |
| 352 | 4-ethylphenyl | 837.6 |
| 353 | 4-(1H-1,2,4-triazol-1-yl)phenyl | 876.6 |
| 354 | 3-(methoxycarbonyl)naphthalen-2-yl | 917.6 |
| 355 | 5,7-dichloroquinolin-8-yl | 928.5 |
| 356 | quinolin-5-yl | 860.6 |
| 357 | 3-acetyl-4,5-dimethoxyphenyl | 911.6 |
| 358 | 2-(N,N-diethylcarbamoyl)phenyl | 908.6 |

TABLE 12-continued

| Example | R | ESI MS (M + H) |
|---|---|---|
| 359 | 3,5-di-tert-butyl-5-methylphenyl | 935.7 |
| 360 | 4-bromo-2-fluorophenyl | 905.5 |
| 361 | 2-iodophenyl | 935.4 |
| 362 | 2-(methoxycarbonyl)-4-methylphenyl | 881.6 |
| 363 | 4-methoxy-2-methylphenyl | 853.6 |
| 364 | 4-acetyl-2-(methoxycarbonyl)phenyl | 909.6 |
| 365 | 3-methyl-4-fluorophenyl | 841.5 |
| 366 | 2,5-difluorophenyl | 845.5 |

TABLE 12-continued

| Example | R | ESI MS (M + H) |
|---|---|---|
| 367 | 3-CF3-4-F-phenyl | 895.5 |
| 368 | 3-Me-4-SMe-phenyl | 869.6 |
| 369 | 3-F-4-Br-phenyl | 905.4 |
| 370 | 4'-Br-biphenyl-4-yl | 963.5 |
| 371 | 7-propyl-quinolin-8-yl | 902.6 |
| 372 | 3-Cl-4-Me-phenyl | 857.5 |
| 373 | 3-Me-4-Br-phenyl | 901.5 |
| 374 | 2-acetyl-5-fluoro-phenyl | 869.5 |
| 375 | 5,7-dimethyl-quinolin-8-yl | 888.6 |
| 376 | 4-(3-methoxy-3-oxopropanoyl)phenyl | 909.5 |
| 377 | 4-heptanoylphenyl | 921.6 |
| 378 | 5-bromo-2-acetyl-phenyl | 929.4 |
| 379 | 2-acetyl-4-chloro-phenyl | 885.5 |
| 380 | 2,6-dimethyl-3-(ethoxycarbonyl)phenyl | 895.6 |
| 381 | 2-oxo-1,2,3,4-tetrahydroquinolin-6-yl | 878.6 |
| 382 | 2-oxo-1,2,3,4-tetrahydroquinolin-7-yl | 878.6 |
| 383 | 2-(3-phenylpropanoyl)phenyl | 941.6 |

TABLE 12-continued

| Example | R | ESI MS (M + H) |
|---|---|---|
| 384 | 3-Cl, 4-F phenyl with methyl | 861.5 |
| 385 | 4-CF₃ phenyl with methyl | 877.5 |
| 386 | 4-C(Me)₃ phenyl with methyl | 865.6 |
| 387 | 3,4-diF phenyl with methyl | 845.5 |
| 388 | 4-OCF₃ phenyl with methyl | 893.5 |
| 389 | 3-Me, 4-Cl phenyl with methyl | 857.5 |
| 390 | 3,5-diMe phenyl with methyl | 837.5 |

In Examples 233 to 390, the compounds shown in Table 12 were synthesized in the same manner as that of Example 29 by using corresponding phenol reagents.

Examples 391 to 474

Preparation methods of the compounds represented by the formula (Q) having R defined in Table 13 are shown below.

[Formula 38]

Formula (Q)

TABLE 13

| Example | Reference Example | R | ESI MS (M + H) | $^1$H-NMR, CDCl$_3$, δ (ppm) |
|---|---|---|---|---|
| 391 | | benzoxazol-4-yloxymethyl | 850.6 | (500 MHz): 0.91 (d, J = 6.88 Hz, 3H) 1.03 (d, J = 6.88 Hz, 3H) 1.06-1.11 (m, 6H) 1.17-1.27 (m, 7H) 1.29 (d, J = 6.12 Hz, 3H) 1.36 (s, 3H) 1.41-1.48 (m, 1H) 1.54-1.70 (m, 2H) 2.19-2.27 (m, 2H) 2.30 (s, 6H) 2.36 (d, J = 14.91 Hz, 1H) 2.40-2.58 (m, 2H) 2.71-3.06 (m, 8H) 3.13-3.28 (m, 3H) 3.29 (s, 3H) 3.31 (s, 3H) 3.44-3.53 (m, 1H) 3.56-3.62 (m, 1H) 3.73-3.78 (m, 1H) 3.99-4.09 (m, 1H) 4.30-4.37 (m, 1H) 4.43-4.50 (m, 2H) 4.89 (d, J = 4.59 Hz, 1H) 5.15-5.21 (m, 1H) 6.83 (d, J = 8.41 Hz, 1H) 7.18 (d, J = 8.03 Hz, 1H) 7.27-7.32 (m, 1H) 8.02 (s, 1H) |

TABLE 13-continued

| Example | Reference Example | R | ESI MS (M + H) | ¹H-NMR, CDCl₃, δ (ppm) |
|---|---|---|---|---|
| 392 | 61 | | 971.7 | (600 MHz): 0.93 (d, J = 7.34 Hz, 3H) 1.01 (d, J = 6.42 Hz, 3H) 1.04-1.10 (m, 6H) 1.16-1.23 (m, 1H) 1.21 (d, J = 6.42 Hz, 3H) 1.24 (s, 3H) 1.28 (d, J = 5.96 Hz, 3H) 1.28 (s, 9H) 1.35 (s, 3H) 1.41 (d, J = 14.67 Hz, 1H) 1.54-1.67 (m, 2H) 2.18-2.24 (m, 1H) 2.28 (s, 6H) 2.35 (d, J = 15.13 Hz, 1H) 2.38-2.45 (m, 1H) 2.50 (t, J = 7.57 Hz, 1H) 2.65-2.72 (m, 1H) 2.74-2.86 (m, 3H) 2.93-3.02 (m, 4H) 3.11-3.15 (m, 1H) 3.16-3.25 (m, 2H) 3.27 (s, 3H) 3.30 (s, 3H) 3.43-3.50 (m, 1H) 3.57 (d, J = 9.17 Hz, 1H) 3.74 (d, J = 7.34 Hz, 1H) 3.99-4.08 (m, 2H) 4.21 (dd, J = 9.17, 6.88 Hz, 1H) 4.45 (d, J = 6.88 Hz, 1H) 4.89 (d, J = 4.58 Hz, 1H) 5.05 (s, 2H) 5.12 (dd, J = 6.19, 4.36 Hz, 1H) 6.82-6.85 (m, 1H) 6.86-6.90 (m, 1H) 6.96 (d, J = 2.29 Hz, 1H) 7.26-7.31 (m, 1H) 7.32-7.38 (m, 2H) 7.40-7.43 (m, 2H) |
| 393 | 62 | | 971.9 | (600 MHz): 0.92 (d, J = 7.34 Hz, 3H) 1.01 (d, J = 6.42 Hz, 3H) 1.04-1.09 (m, 6H) 1.19-1.23 (m, 1H) 1.21 (d, J = 6.42 Hz, 3H) 1.23-1.25 (m, 12H) 1.28 (d, J = 6.42 Hz, 3H) 1.35 (s, 3H) 1.41 (d, J = 15.13 Hz, 1H) 1.53-1.67 (m, 2H) 2.19-2.23 (m, 1H) 2.28 (s, 6H) 2.34 (d, J = 15.13 Hz, 1H) 2.38-2.45 (m, 1H) 2.48 (t, J = 7.57 Hz, 1H) 2.65 (m, 2H) 2.77-2.86 (m, 2H) 2.91-3.03 (m, 4H) 3.11-3.15 (m, 1H) 3.16-3.24 (m, 2H) 3.27 (s, 3H) 3.30 (s, 3H) 3.43-3.51 (m, 1H) 3.57 (d, J = 9.17 Hz, 1H) 3.74 (d, J = 7.34 Hz, 1H) 3.98-4.06 (m, 2H) 4.18 (dd, J = 9.17, 7.34 Hz, 1H) 4.45 (d, J = 6.88 Hz, 1H) 4.88 (d, J = 4.58 Hz, 1H) 5.07 (s, 2H) 5.10 (dd, J = 6.19, 4.36 Hz, 1H) 6.83 (d, J = 8.25 Hz, 1H) 6.92 (dd, J = 8.48, 2.52 Hz, 1H) 6.94 (d, J = 2.29 Hz, 1H) 7.26-7.31 (m, 1H) 7.33-7.38 (m, 2H) 7.40-7.44 (m, 2H) |
| 394 | | | 865.7 | (600 MHz): 0.94 (d, J = 7.34 Hz, 3H) 1.04 (d, J = 6.88 Hz, 3H) 1.06-1.09 (m, 6H) 1.19-1.25 (m, 7H) 1.28 (d, J = 6.42 Hz, 3H) 1.33-1.36 (m, 3H) 1.34 (s, 9H) 1.43 (d, J = 14.67 Hz, 1H) 1.54-1.67 (m, 2H) 2.19-2.25 (m, 2H) 2.29 (s, 6H) 2.34 (d, J = 15.13 Hz, 2H) 2.40-2.48 (m, 1H) 2.51-2.56 (m, 1H) 2.70-2.92 (m, 5H) 2.92-3.03 (m, 3H) 3.13-3.17 (m, 1H) 3.17-3.24 (m, 1H) 3.28 (s, 3H) 3.29 (s, 3H) 3.30-3.33 (m, 1H) 3.44-3.51 (m, 1H) 3.58 (d, J = 10.09 Hz, 1H) 3.75 (d, J = 7.34 Hz, 1H) 3.97-4.06 (m, 2H) 4.14 (t, J = 8.25 Hz, 1H) 4.46 (d, J = 7.34 Hz, 1H) 4.89 (d, J = 4.58 Hz, 1H) 5.14 (dd, J = 6.19, 4.36 Hz, 1H) 6.83-6.89 (m, 2H) 7.13-7.19 (m, 1H) 7.25-7.28 (m, 1H) |
| 395 | 63 | | 862.7 | (500 MHz): 0.95 (d, J = 7.13 Hz, 3H) 1.00 (d, J = 7.13 Hz, 3H) 1.03-1.08 (m, 6H) 1.19-1.31 (m, 10H) 1.37 (s, 3H) 1.42-1.47 (m, 1H) 1.52-1.71 (m, 2H) 2.19-2.54 (m, 5H) 2.31 (s, 6H) 2.67-3.07 (m, 8H) 3.15-3.34 (m, 3H) 3.29 (s, 3H) 3.30 (s, 3H) 3.44-3.52 (m, 1H) 3.56-3.60 (m, 1H) 3.74-3.76 (m, 1H) 3.98-4.04 (m, 1H) 3.99-4.00 (m, 3H) 4.10-4.15 (m, 1H) 4.24-4.29 (m, 1H) 4.46 (d, J = 7.13 Hz, 1H) 4.87 (d, J = 4.66 Hz, 1H) 5.16-5.21 (m, 1H) 6.39 (d, J = 3.02 Hz, 1H) 6.59 (d, J = 7.95 Hz, 1H) 6.90 (d, J = 3.02 Hz, 1H) 6.94 (t, J = 7.82 Hz, 1H) 7.17 (d, J = 7.40 Hz, 1H) |
| 396 | | | 894.7 | (500 MHz): 0.94 (d, J = 7.13 Hz, 3H) 1.03 (d, J = 6.86 Hz, 3H) 1.08 (d, J = 7.68 Hz, 3H) 1.10 (d, J = 7.13 Hz, 3H) 1.20-1.32 (m, 13H) 1.36 (s, 3H) 1.43 (d, J = 14.81 Hz, 1H) 1.54-1.61 (m, 1H) 1.64-1.73 (m, 1H) 2.18-2.28 (m, 1H) 2.31 (s, 6H) 2.36 (d, J = 14.81 Hz, 1H) 2.40-2.70 (m, 3H) 2.75-3.06 (m, 5H) 3.12-3.25 (m, 6H) 3.29 (s, 3H) 3.31 (s, 3H) 3.44-3.54 (m, 3H) 3.58 (d, J = 9.60 Hz, 1H) 3.75 (d, J = 7.40 Hz, 1H) 3.82-3.87 (m, 4H) 3.94-4.14 (m, 3H) 4.46 (d, J = 7.13 Hz, 1H) 4.89 (d, J = 4.66 Hz, 1H) 5.11-5.16 (m, 1H) 6.40-6.45 (m, 2H) 6.50-6.54 (m, 1H) 7.16 (t, J = 8.50 Hz, 1H) |

TABLE 13-continued

| Example | Reference Example | R | ESI MS (M + H) | $^1$H-NMR, CDCl$_3$, δ (ppm) |
|---|---|---|---|---|
| 397 | 64 | (benzyl piperazine carboxylate linked to 3-phenoxy group) | 1027.8 | (500 MHz): 0.94 (d, J = 7.26 Hz, 3H) 1.03 (d, J = 6.88 Hz, 3H) 1.06-1.12 (m, 6H) 1.15-1.33 (m, 10H) 1.36 (s, 3H) 1.43 (d, J = 14.52 Hz, 1H) 1.53-1.69 (m, 2H) 2.20-2.27 (m, 2H) 2.29 (s, 6H) 2.33-2.47 (m, 2H) 2.49-2.55 (m, 1H) 2.59-2.68 (m, 1H) 2.73-2.87 (m, 3H) 2.89-3.05 (m, 4H) 3.09-3.27 (m, 6H) 3.29 (s, 3H) 3.31 (s, 3H) 3.43-3.52 (m, 1H) 3.58 (d, J = 10.32 Hz, 1H) 3.61-3.68 (m, 5H) 3.75 (d, J = 7.64 Hz, 1H) 3.93-4.13 (m, 3H) 4.46 (d, J = 7.26 Hz, 1H) 4.89 (d, J = 4.59 Hz, 1H) 5.11-5.15 (m, 1H) 5.16 (s, 2H) 6.41-6.45 (m, 2H) 6.50-6.53 (m, 1H) 7.16 (t, J = 8.60 Hz, 1H) 7.30-7.39 (m, 5H) |
| 398 | 65 | (benzyloxy-methylphenyl-oxy group) | 894.7 | (600 MHz): 0.93 (d, J = 7.34 Hz, 3H) 1.01 (d, J = 6.88 Hz, 3H) 1.04-1.10 (m, 6H) 1.15-1.26 (m, 1H) 1.18-1.23 (m, 6H) 1.24 (s, 3H) 1.28 (d, J = 6.42 Hz, 3H) 1.35 (s, 3H) 1.42 (d, J = 15.13 Hz, 1H) 1.48-1.68 (m, 2H) 2.18-2.25 (m, 1H) 2.28 (br. s, 6H) 2.35 (d, J = 15.13 Hz, 1H) 2.38-2.47 (m, 1H) 2.51 (t, J = 7.11 Hz, 1H) 2.57 (q, J = 7.79 Hz, 2H) 2.66-2.74 (m, 1H) 2.74-2.88 (m, 3H) 2.92-3.04 (m, 4H) 3.11-3.16 (m, 1H) 3.16-3.25 (m, 2H) 3.28 (s, 3H) 3.30 (s, 3H) 3.43-3.51 (m, 1H) 3.58 (d, J = 9.63 Hz, 1H) 3.75 (d, J = 7.34 Hz, 1H) 3.97-4.07 (m, 2H) 4.19 (dd, J = 9.17, 7.34 Hz, 1H) 4.46 (d, J = 7.34 Hz, 1H) 4.89 (d, J = 4.58 Hz, 1H) 5.04 (s, 2H) 5.12 (dd, J = 5.96, 4.13 Hz, 1H) 6.69 (dd, J = 8.25, 1.83 Hz, 1H) 6.76 (d, J = 1.83 Hz, 1H) 6.83 (d, J = 7.79 Hz, 1H) 7.26-7.30 (m, 1H) 7.35 (t, J = 7.57 Hz, 2H) 7.41 (d, J = 7.79 Hz, 2H) |
| 399 | 66 | (benzyl piperidine carboxylate linked to 3-phenoxy group) | 1026.8 | (500 MHz): 0.94 (d, J = 7.26 Hz, 3H) 1.01-1.11 (m, 9H) 1.18-1.26 (m, 7H) 1.29 (d, J = 6.12 Hz, 3H) 1.36 (s, 3H) 1.43 (d, J = 14.91 Hz, 1H) 1.53-1.69 (m, 4H) 1.80-1.88 (m, 2H) 2.18-2.26 (m, 2H) 2.28 (s, 6H) 2.36 (d, J = 14.91 Hz, 1H) 2.39-2.55 (m, 2H) 2.59-2.68 (m, 2H) 2.72-3.05 (m, 10H) 3.14-3.26 (m, 4H) 3.29 (s, 3H) 3.30 (s, 3H) 3.45-3.52 (m, 1H) 3.58 (d, J = 9.56 Hz, 1H) 3.75 (d, J = 7.26 Hz, 1H) 3.94-4.14 (m, 3H) 4.46 (d, J = 7.26 Hz, 1H) 4.89 (d, J = 4.59 Hz, 1H) 5.11-5.18 (m, 3H) 6.71-6.79 (m, 3H) 7.18-7.23 (m, 1H) 7.29-7.40 (m, 5H) |
| 400 | 67 | (3-(2-hydroxypropan-2-yl)phenoxy group) | 867.8 | (600 MHz): 0.89 (d, J = 7.34 Hz, 3H) 1.01 (d, J = 6.88 Hz, 3H) 1.07 (d, J = 7.34 Hz, 3H) 1.11 (d, J = 7.34 Hz, 3H) 1.19-1.25 (m, 1H) 1.21 (d, J = 5.96 Hz, 3H) 1.24 (s, 3H) 1.28 (d, J = 6.42 Hz, 3H) 1.35 (s, 3H) 1.47 (d, J = 15.13 Hz, 1H) 1.51-1.71 (m, 8H) 2.19-2.27 (m, 2H) 2.29 (br. s, 6H) 2.36 (d, J = 15.59 Hz, 1H) 2.39-2.47 (m, 1H) 2.50-2.58 (m, 1H) 2.61-2.70 (m, 1H) 2.75 (t, J = 8.71 Hz, 1H) 2.78-2.85 (m, 2H) 2.89-3.03 (m, 4H) 3.14-3.24 (m, 3H) 3.28 (s, 3H) 3.29 (s, 3H) 3.43-3.50 (m, 1H) 3.57 (d, J = 10.09 Hz, 1H) 3.74 (d, J = 7.79 Hz, 1H) 3.98-4.05 (m, 1H) 4.05-4.09 (m, 1H) 4.11-4.16 (m, 1H) 4.45 (d, J = 7.34 Hz, 1H) 4.88 (d, J = 4.58 Hz, 1H) 5.11 (dd, J = 6.65, 5.27 Hz, 1H) 6.74-6.78 (m, 1H) 6.98 (d, J = 8.25 Hz, 1H) 7.13-7.16 (m, 1H) 7.22 (t, J = 7.79 Hz, 1H) |
| 401 | 68 | (3-(piperidin-1-yl)phenoxy group) | 892.7 | (600 MHz): 0.94 (d, J = 7.34 Hz, 3H) 1.03 (d, J = 6.88 Hz, 3H) 1.07 (d, J = 7.34 Hz, 3H) 1.10 (d, J = 7.34 Hz, 3H) 1.18-1.27 (m, 7H) 1.29 (d, J = 6.42 Hz, 3H) 1.36 (s, 3H) 1.43 (d, J = 14.67 Hz, 1H) 1.54-1.61 (m, 4H) 1.63-1.72 (m, 4H) 2.20-2.27 (m, 2H) 2.30 (s, 6H) 2.37 (d, J = 14.67 Hz, 1H) 2.41-2.55 (m, 2H) 2.60-2.68 (m, 1H) 2.74-3.05 (m, 7H) 3.12-3.17 (m, 4H) 3.18-3.24 (m, 2H) 3.28 (s, 3H) 3.31 (s, 3H) 3.45-3.52 (m, 1H) 3.59 (d, J = 9.63 Hz, 1H) 3.75 (d, J = 7.34 Hz, 1H) 3.93-4.13 (m, 3H) 4.46 (d, J = 6.88 Hz, 1H) 4.89 (d, J = 4.58 Hz, 1H) 5.12-5.16 (m, 1H) 6.34-6.37 (m, 1H) 6.43-6.46 (m, 1H) 6.52-6.56 (m, 1H) 7.12 (t, J = 8.02 Hz, 1H) |

TABLE 13-continued

| Example | Reference Example | R | ESI MS (M + H) | $^1$H-NMR, CDCl$_3$, δ (ppm) |
|---|---|---|---|---|
| 402 | 69 | 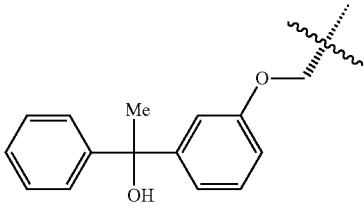 | 929.5 | (600 MHz): 0.83-0.92 (m, 3H) 0.97-1.03 (m, 3H) 1.06-1.14 (m, 6H) 1.14-1.20 (m, 1H) 1.20-1.23 (m, 3H) 1.23-1.26 (m, 3H) 1.27-1.30 (m, 3H) 1.33-1.39 (m, 3H) 1.43-1.68 (m, 3H) 1.89-1.95 (m, 3H) 2.14-2.32 (m, 7H) 2.32-2.46 (m, 2H) 2.48-2.58 (m, 1H) 2.60-2.68 (m, 1H) 2.69-2.87 (m, 3H) 2.87-3.04 (m, 4H) 3.06-3.24 (m, 3H) 3.27-3.29 (m, 3H) 3.30-3.31 (m, 3H) 3.41-3.51 (m, 3H) 3.54-3.62 (m, 1H) 3.71-3.77 (m, 1H) 3.97-4.15 (m, 3H) 4.41-4.47 (m, 1H) 4.85-4.91 (m, 1H) 5.07-5.12 (m, 1H) 6.71-6.77 (m, 1H) 6.81-6.85 (m, 1H) 7.12-7.24 (m, 3H) 7.27-7.32 (m, 2H) 7.39-7.46 (m, 2H) |
| 403 | | 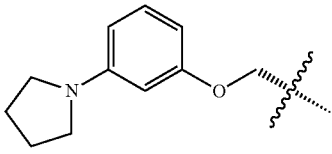 | 878.5 | (500 MHz): 1.03 (d, J = 6.86 Hz, 3H) 1.08 (d, J = 7.40 Hz, 3H) 1.11 (d, J = 7.13 Hz, 3H) 1.23 (d, J = 6.03 Hz, 3H) 1.25 (s, 3H) 1.27-1.45 (m, 8H) 1.49-1.66 (m, 2H) 1.94-2.02 (m, 4H) 2.18-2.69 (m, 6H) 2.31 (s, 6H) 2.77-3.06 (m, 9H) 3.13-3.34 (m, 7H) 3.28 (s, 3H) 3.31 (s, 3H) 3.45-3.53 (m, 1H) 3.59 (d, J = 8.78 Hz, 1H) 3.76 (d, J = 7.40 Hz, 1H) 3.92-4.14 (m, 3H) 4.45-4.49 (m, 1H) 4.88-4.92 (m, 1H) 5.11-5.16 (m, 1H) 6.13-6.20 (m, 2H) 6.23-6.28 (m, 1H) 7.05-7.10 (m, 1H) |
| 404 | | 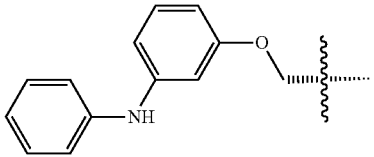 | 900.4 | (500 MHz): 0.93 (d, J = 6.88 Hz, 3H) 1.03 (d, J = 6.88 Hz, 3H) 1.07-1.13 (m, 6H) 1.20-1.27 (m, 7H) 1.29 (d, J = 6.12 Hz, 3H) 1.36 (s, 3H) 1.41-1.47 (m, 1H) 1.54-1.71 (m, 2H) 2.19-2.27 (m, 2H) 2.30 (s, 6H) 2.36 (d, J = 14.91 Hz, 1H) 2.39-2.56 (m, 2H) 2.62-2.69 (m, 1H) 2.75-3.05 (m, 9H) 3.14-3.26 (m, 4H) 3.29 (s, 3H) 3.31 (s, 3H) 3.45-3.53 (m, 1H) 3.58 (d, J = 9.56 Hz, 1H) 3.76 (d, J = 7.26 Hz, 1H) 3.95-4.13 (m, 3H) 4.47 (d, J = 7.26 Hz, 1H) 4.88-4.91 (m, 1H) 5.10-5.14 (m, 1H) 6.44-6.47 (m, 1H) 6.57-6.60 (m, 1H) 6.64-6.67 (m, 1H) 6.93 (t, J = 7.45 Hz, 1H) 7.07-7.11 (m, 2H) 7.13 (t, J = 8.03 Hz, 1H) 7.24-7.29 (m, 2H) |
| 405 | | 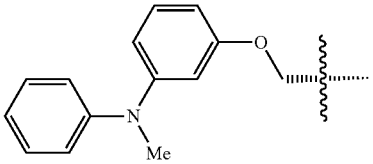 | 914.6 | (500 MHz): 0.94 (d, J = 7.13 Hz, 3H) 1.03 (d, J = 6.58 Hz, 3H) 1.06 (d, J = 7.40 Hz, 3H) 1.11 (d, J = 6.88 Hz, 3H) 1.17-1.24 (m, 4H) 1.25 (s, 3H) 1.29 (d, J = 6.03 Hz, 3H) 1.36 (s, 3H) 1.42 (d, J = 14.81 Hz, 1H) 1.54-1.71 (m, 2H) 2.19-2.26 (m, 2H) 2.30 (s, 6H) 2.37 (d, J = 15.08 Hz, 1H) 2.40-2.53 (m, 2H) 2.59-2.67 (m, 1H) 2.74-3.05 (m, 7H) 3.13-3.26 (m, 3H) 3.28 (s, 3H) 3.30 (s, 3H) 3.32 (s, 3H) 3.45-3.52 (m, 1H) 3.58 (d, J = 9.87 Hz, 1H) 3.75 (d, J = 7.40 Hz, 1H) 3.93 (t, J = 8.50 Hz, 1H) 4.00-4.11 (m, 2H) 4.47 (d, J = 7.13 Hz, 1H) 4.90 (d, J = 4.66 Hz, 1H) 5.09-5.13 (m, 1H) 6.44-6.48 (m, 1H) 6.49-6.52 (m, 1H) 6.54-6.58 (m, 1H) 6.96-7.01 (m, 1H) 7.04-7.08 (m, 2H) 7.13 (t, J = 8.09 Hz, 1H) 7.26-7.30 (m, 2H) |
| 406 | | 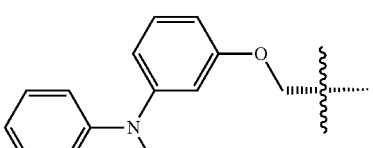 | 928.6 | (600 MHz): 0.94 (d, J = 7.34 Hz, 3H) 1.02 (d, J = 6.88 Hz, 3H) 1.06 (d, J = 7.34 Hz, 3H) 1.11 (d, J = 6.88 Hz, 3H) 1.18-1.26 (m, 10H) 1.29 (d, J = 5.96 Hz, 3H) 1.36 (s, 3H) 1.42 (d, J = 14.67 Hz, 1H) 1.55-1.60 (m, 1H) 1.63-1.68 (m, 1H) 2.21-2.26 (m, 2H) 2.30 (s, 6H) 2.37 (d, J = 14.67 Hz, 1H) 2.40-2.53 (m, 2H) 2.58-2.66 (m, 1H) 2.75-2.86 (m, 3H) 2.90-3.04 (m, 4H) 3.14-3.24 (m, 3H) 3.28 (s, 3H) 3.32 (s, 3H) 3.46-3.51 (m, 1H) 3.58 (d, J = 9.63 Hz, 1H) 3.75 (q, J = 7.03 Hz, 2H) 3.92 (t, J = 8.48 Hz, 1H) 4.00-4.10 (m, 2H) 4.46 (d, J = 6.88 Hz, 1H) 4.90 (d, J = 5.04 Hz, 1H) 5.09-5.13 (m, 1H) 6.42-6.48 (m, 2H) 6.50-6.54 (m, 1H) 6.97 (t, J = 7.34 Hz, 1H) 7.01-7.05 (m, 2H) 7.12 (t, J = 8.02 Hz, 1H) 7.25-7.29 (m, 2H) |

TABLE 13-continued

| Example | Reference Example | R | ESI MS (M + H) | $^1$H-NMR, CDCl$_3$, δ (ppm) |
|---|---|---|---|---|
| 407 | 70 | (3-(1-phenylvinyl)phenoxy methyl) | 911.6 | (600 MHz): 0.93 (d, J = 7.34 Hz, 3H) 1.02 (d, J = 6.42 Hz, 3H) 1.05 (d, J = 7.79 Hz, 3H) 1.09 (d, J = 6.88 Hz, 3H) 1.18-1.23 (m, 1H) 1.22 (d, J = 5.96 Hz, 3H) 1.24 (s, 3H) 1.28 (d, J = 6.42 Hz, 3H) 1.35 (s, 3H) 1.42 (d, J = 15.13 Hz, 1H) 1.56-1.59 (m, 1H) 1.61-1.67 (m, 1H) 2.19-2.25 (m, 1H) 2.28 (br. s., 6H) 2.36 (d, J = 15.13 Hz, 1H) 2.39-2.45 (m, 1H) 2.45-2.53 (m, 1H) 2.59-2.67 (m, 1H) 2.71-2.87 (m, 3H) 2.89-3.04 (m, 4H) 3.12-3.16 (m, 1H) 3.16-3.24 (m, 2H) 3.27 (s, 3H) 3.31 (s, 3H) 3.43-3.51 (m, 1H) 3.57 (d, J = 9.17 Hz, 1H) 3.74 (d, J = 7.34 Hz, 1H) 3.93-3.98 (m, 1H) 3.99-4.05 (m, 1H) 4.08-4.13 (m, 1H) 4.45 (d, J = 6.88 Hz, 1H) 4.88 (d, J = 4.58 Hz, 1H) 5.11 (dd, J = 5.50, 4.58 Hz, 1H) 5.42-5.46 (m, 2H) 6.81-6.91 (m, 3H) 7.22 (t, J = 7.79 Hz, 1H) 7.26-7.35 (m, 5H) |
| 408 | | (4-(diethylamino)-2-(oxymethyl)benzaldehyde) | 908.5 | (600 MHz): 0.95 (d, J = 7.34 Hz, 3H) 1.02-1.07 (m, 6H) 1.10 (d, J = 7.34 Hz, 3H) 1.18-1.27 (m, 13H) 1.29 (d, J = 6.42 Hz, 3H) 1.37 (s, 3H) 1.46 (d, J = 14.67 Hz, 1H) 1.55-1.60 (m, 1H) 1.63-1.68 (m, 1H) 2.20-2.28 (m, 1H) 2.29 (s, 6H) 2.36 (d, J = 15.13 Hz, 1H) 2.39-2.53 (m, 2H) 2.69-2.85 (m, 4H) 2.89-3.05 (m, 4H) 3.16-3.27 (m, 3H) 3.29 (s, 3H) 3.30 (s, 3H) 3.37-3.50 (m, 5H) 3.58 (d, J = 9.63 Hz, 1H) 3.75 (d, J = 7.34 Hz, 1H) 4.08 (s, 3H) 4.45 (d, J = 6.88 Hz, 1H) 4.89 (d, J = 4.58 Hz, 1H) 5.09-5.17 (m, 1H) 6.03 (d, J = 2.29 Hz, 1H) 6.26-6.30 (m, 1H) 7.71 (d, J = 8.71 Hz, 1H) 10.10 (s, 1H) |
| 409 | | (3-(dibutylamino)phenoxy methyl) | 936.6 | (500 MHz): 0.91-0.99 (m, 6H) 1.01-1.14 (m, 9H) 1.20-1.39 (m, 20H) 1.41 (d, J = 14.91 Hz, 1H) 1.50-1.62 (m, 5H) 1.64-1.73 (m, 1H) 2.18-2.40 (m, 3H) 2.32 (s, 6H) 2.41-2.56 (m, 2H) 2.60-2.70 (m, 1H) 2.76-3.05 (m, 7H) 3.13-3.26 (m, 6H) 3.28 (s, 3H) 3.31 (s, 3H) 3.45-3.53 (m, 1H) 3.59 (d, J = 9.56 Hz, 1H) 3.76 (d, J = 7.26 Hz, 1H) 3.92-4.15 (m, 3H) 4.47 (d, J = 7.26 Hz, 1H) 4.90 (d, J = 4.59 Hz, 1H) 5.11-5.17 (m, 1H) 6.11-6.29 (m, 3H) 7.07 (t, J = 8.22 Hz, 1H) |
| 410 | 71 | (2-(3-(hydroxydiphenylmethyl)phenyl)ethyl) | 991.8 | (600 MHz): 0.86 (d, J = 6.88 Hz, 3H) 1.00 (d, J = 6.88 Hz, 3H) 1.08 (d, J = 7.79 Hz, 3H) 1.10 (d, J = 6.88 Hz, 3H) 1.15-1.20 (m, 1H) 1.21 (d, J = 6.42 Hz, 3H) 1.24 (s, 3H) 1.28 (d, J = 6.42 Hz, 3H) 1.36 (s, 3H) 1.45-1.66 (m, 3H) 2.18-2.21 (m, 1H) 2.22 (br. s., 6H) 2.32-2.43 (m, 2H) 2.49-2.55 (m, 1H) 2.56-2.63 (m, 1H) 2.72 (t, J = 9.17 Hz, 1H) 2.76-2.83 (m, 2H) 2.86-3.04 (m, 4H) 3.11-3.22 (m, 3H) 3.28 (s, 3H) 3.31 (s, 3H) 3.41-3.49 (m, 1H) 3.57 (d, J = 10.09 Hz, 1H) 3.74 (d, J = 7.34 Hz, 1H) 3.97-4.04 (m, 2H) 4.05-4.11 (m, 1H) 4.44 (d, J = 7.34 Hz, 1H) 4.89 (d, J = 4.58 Hz, 1H) 5.06 (dd, J = 6.65, 5.27 Hz, 1H) 6.75 (d, J = 7.34 Hz, 1H) 6.78 (dd, J = 8.02, 2.06 Hz, 1H) 7.05 (s, 1H) 7.17 (t, J = 8.02 Hz, 1H) 7.21-7.33 (m, 10H) |
| 411 | 72 | (3-(1-cyclopropyl-1-hydroxyethyl)phenoxy methyl) | 893.3 | (600 MHz): 0.85-0.92 (m, 3H) 1.01 (d, J = 6.88 Hz, 3H) 1.06-1.13 (m, 6H) 1.19-1.21 (m, 1H) 1.22 (d, J = 5.96 Hz, 3H) 1.24 (s, 3H) 1.28 (d, J = 5.96 Hz, 3H) 1.35 (s, 3H) 1.45 (d, J = 7.79 Hz, 3H) 1.45-1.48 (m, 1H) 1.51-1.67 (m, 2H) 2.18-2.26 (m, 1H) 2.26-2.33 (m, 11H) 2.36 (d, J = 16.05 Hz, 1H) 2.38-2.46 (m, 1H) 2.49-2.58 (m, 1H) 2.61-2.69 (m, 1H) 2.72-2.77 (m, 1H) 2.78-2.85 (m, 2H) 2.88-3.04 (m, 4H) 3.13-3.24 (m, 3H) 3.28 (s, 3H) 3.30 (s, 3H) 3.43-3.50 (m, 1H) 3.57 (d, J = 9.63 Hz, 1H) 3.74 (d, J = 7.34 Hz, 1H) 3.96-4.06 (m, 1H) 4.06-4.16 (m, 2H) 4.43-4.47 (m, 1H) 4.89 (d, J = 5.04 Hz, 1H) 5.11 (dd, J = 6.42, 5.50 Hz, 1H) 6.74-6.78 (m, 1H) 7.05-7.09 (m, 1H) 7.15-7.19 (m, 1H) 7.19-7.24 (m, 1H) |

TABLE 13-continued

| Example | Reference Example | R | ESI MS (M + H) | $^1$H-NMR, CDCl$_3$, δ (ppm) |
|---|---|---|---|---|
| 412 | 73 | 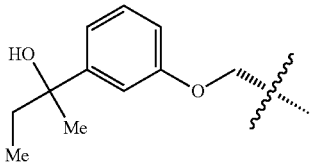 | 881.5 | (600 MHz): 0.74-0.82 (m, 3H) 0.85-0.90 (m, 3H) 1.01 (d, J = 6.88 Hz, 3H) 1.06-1.13 (m, 6H) 1.18-1.21 (m, 1H) 1.22 (d, J = 5.04 Hz, 3H) 1.24 (s, 3H) 1.28 (d, J = 6.42 Hz, 3H) 1.35 (s, 3H) 1.42-1.50 (m, 1H) 1.51 (d, J = 5.04 Hz, 3H) 1.53-1.68 (m, 2H) 1.73-1.87 (m, 2H) 2.18-2.26 (m, 1H) 2.29 (br. s., 6H) 2.36 (d, J = 15.13 Hz, 1H) 2.38-2.46 (m, 1H) 2.50-2.57 (m, 1H) 2.60-2.70 (m, 1H) 2.75 (q, J = 8.41 Hz, 1H) 2.78-2.84 (m, 2H) 2.88-2.97 (m, 2H) 2.97-3.04 (m, 2H) 3.13-3.23 (m, 3H) 3.27-3.29 (m, 3H) 3.29-3.31 (m, 3H) 3.42-3.50 (m, 1H) 3.57 (d, J = 10.09 Hz, 1H) 3.74 (d, J = 7.79 Hz, 1H) 3.95-4.17 (m, 3H) 4.43-4.47 (m, 1H) 4.88 (d, J = 5.50 Hz, 1H) 5.09-5.14 (m, 1H) 6.72-6.77 (m, 1H) 6.87-6.95 (m, 1H) 7.05-7.13 (m, 1H) 7.18-7.24 (m, 1H) |
| 413 | 74 | 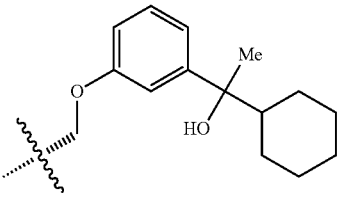 | 935.6 | (600 MHz): 0.85-0.92 (m, 3H) 0.94-1.01 (m, 4H) 1.01 (d, J = 6.42 Hz, 3H) 1.05-1.18 (m, 8H) 1.19-1.26 (m, 7H) 1.27-1.31 (m, 3H) 1.35 (d, J = 5.04 Hz, 3H) 1.39-1.46 (m, 1H) 1.46-1.51 (m, 3H) 1.51-1.78 (m, 7H) 2.18-2.25 (m, 1H) 2.28 (br. s., 6H) 2.35 (d, J = 15.13 Hz, 1H) 2.38-2.47 (m, 1H) 2.48-2.59 (m, 1H) 2.60-2.69 (m, 1H) 2.71-2.86 (m, 3H) 2.88-3.03 (m, 4H) 3.10-3.24 (m, 3H) 3.26-3.33 (m, 6H) 3.41-3.52 (m, 1H) 3.57 (d, J = 10.09 Hz, 1H) 3.71-3.77 (m, 1H) 3.94-4.18 (m, 3H) 4.45 (d, J = 8.71 Hz, 1H) 4.85-4.92 (m, 1H) 5.08-5.15 (m, 1H) 6.71-6.77 (m, 1H) 6.85-6.93 (m, 1H) 6.99-7.10 (m, 1H) 7.17-7.23 (m, 1H) |
| 414 | 75 | 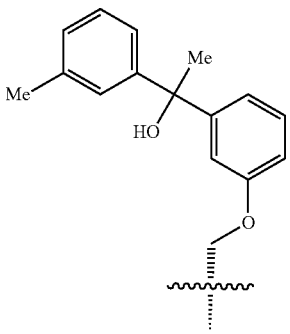 | 943.6 | (600 MHz): 0.84-0.92 (m, 3H) 0.98-1.03 (m, 3H) 1.06-1.14 (m, 6H) 1.14-1.19 (m, 1H) 1.19-1.23 (m, 3H) 1.24 (s, 3H) 1.28 (d, J = 6.42 Hz, 3H) 1.36 (d, J = 5.50 Hz, 3H) 1.44-1.69 (m, 3H) 1.90 (s, 3H) 2.16-2.34 (m, 10H) 2.34-2.47 (m, 2H) 2.49-2.58 (m, 1H) 2.59-2.67 (m, 1H) 2.67-2.86 (m, 3H) 2.86-3.04 (m, 4H) 3.09-3.24 (m, 3H) 3.26-3.32 (m, 6H) 3.41-3.51 (m, 1H) 3.54-3.61 (m, 1H) 3.71-3.77 (m, 1H) 3.96-4.16 (m, 3H) 4.45 (d, J = 6.42 Hz, 1H) 4.89 (d, J = 4.58 Hz, 1H) 5.07-5.12 (m, 1H) 6.71-6.77 (m, 1H) 6.81-6.86 (m, 1H) 6.98-7.07 (m, 1H) 7.10-7.20 (m, 3H) 7.20-7.29 (m, 2H) |
| 415 | 76 | 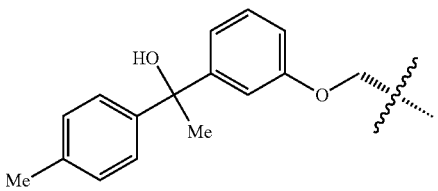 | 943.5 | (600 MHz): 0.84-0.92 (m, 3H) 0.98-1.04 (m, 3H) 1.05-1.14 (m, 6H) 1.14-1.20 (m, 1H) 1.21 (d, J = 6.42 Hz, 3H) 1.24 (s, 3H) 1.28 (d, J = 6.42 Hz, 3H) 1.36 (d, J = 5.50 Hz, 3H) 1.44-1.69 (m, 3H) 1.90 (s, 3H) 2.15-2.33 (m, 10H) 2.34-2.46 (m, 2H) 2.49-2.58 (m, 1H) 2.59-2.67 (m, 1H) 2.67-2.87 (m, 3H) 2.88-3.06 (m, 4H) 3.07-3.24 (m, 3H) 3.25-3.35 (m, 6H) 3.40-3.50 (m, 1H) 3.53-3.61 (m, 1H) 3.69-3.78 (m, 1H) 3.97-4.15 (m, 3H) 4.40-4.48 (m, 1H) 4.89 (d, J = 4.58 Hz, 1H) 5.06-5.12 (m, 1H) 6.70-6.76 (m, 1H) 6.82 (d, J = 7.79 Hz, 1H) 7.07-7.21 (m, 4H) 7.27-7.35 (m, 2H) |
| 416 | 77 | 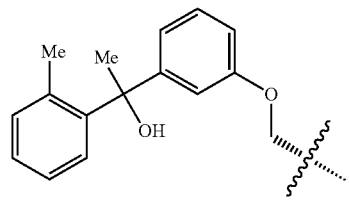 | 943.6 | (600 MHz): 0.83-0.90 (m, 3H) 1.00 (d, J = 6.88 Hz, 3H) 1.07-1.16 (m, 6H) 1.16-1.20 (m, 1H) 1.20-1.26 (m, 6H) 1.27-1.30 (m, 3H) 1.34-1.38 (m, 3H) 1.44-1.50 (m, 1H) 1.52-1.67 (m, 2H) 1.87-1.91 (m, 3H) 1.99-2.02 (m, 3H) 2.15-2.31 (m, 7H) 2.32-2.44 (m, 2H) 2.49-2.58 (m, 1H) 2.58-2.76 (m, 2H) 2.76-3.04 (m, 6H) 3.07-3.24 (m, 3H) 3.28 (s, 3H) 3.31 (s, 3H) 3.39-3.51 (m, 1H) 3.58 (d, J = 10.09 Hz, 1H) 3.70-3.77 (m, 1H) 3.98-4.06 (m, 2H) 4.07-4.15 (m, 1H) 4.41-4.47 (m, 1H) 4.89 (d, J = 5.04 Hz, 1H) 5.05-5.12 (m, 1H) 6.60-6.69 (m, 1H) 6.70-6.75 (m, 1H) 7.04-7.24 (m, 5H) 7.60-7.68 (m, 1H) |

TABLE 13-continued

| Example | Reference Example | R | ESI MS (M + H) | $^1$H-NMR, CDCl$_3$, δ (ppm) |
|---|---|---|---|---|
| 417 | | 3-(2-methylpropyl? ethyl)phenoxy group (Me-CH2CH2-C6H4-O-) | 851 | (400 MHz): 0.93 (t, J = 7.33 Hz, 3H) 0.94 (d, J = 7.32 Hz, 3H) 1.03 (d, J = 6.84 Hz, 3H) 1.06 (d, J = 7.32 Hz, 3H) 1.10 (d, J = 7.08 Hz, 3H) 1.19-1.27 (m, 1H) 1.22 (d, J = 6.10 Hz, 3H) 1.25 (s, 3H) 1.29 (d, J = 6.34 Hz, 3H) 1.36 (s, 3H) 1.43 (d, J = 14.65 Hz, 1H) 1.57 (dd, J = 15.38, 4.88 Hz, 1H) 1.59-1.70 (m, 3H) 2.18-2.58 (m, 8H) 2.30 (s, 6H) 2.59-2.88 (m, 4H) 2.90-3.06 (m, 4H) 3.14-3.25 (m, 3H) 3.29 (s, 3H) 3.31 (s, 3H) 3.43-3.53 (m, 1H) 3.58 (d, J = 9.77 Hz, 1H) 3.75 (d, J = 7.57 Hz, 1H) 3.93-4.08 (m, 2H) 4.12 (dd, J = 8.79, 7.33 Hz, 1H) 4.46 (d, J = 7.08 Hz, 1H) 4.89 (d, J = 4.64 Hz, 1H) 5.14 (dd, J = 6.11, 4.15 Hz, 1H) 6.67-6.73 (m, 2H) 6.76 (d, J = 7.33 Hz, 1H) 7.14-7.20 (m, 1H) |
| 418 | | 3-(1-methylethyl)phenoxy group | 851 | (400 MHz): 0.94 (d, J = 7.33 Hz, 3H) 1.03 (d, J = 6.84 Hz, 3H) 1.06 (d, J = 7.56 Hz, 3H) 1.10 (d, J = 7.08 Hz, 3H) 1.19-1.27 (m, 13H) 1.29 (d, J = 6.10 Hz, 3H) 1.36 (s, 3H) 1.43 (d, J = 14.65 Hz, 1H) 1.57 (dd, J = 15.14, 4.88 Hz, 1H) 1.62-1.70 (m, 1H) 2.18-2.56 (m, 6H) 2.30 (s, 6H) 2.59-2.71 (m, 1H) 2.73-3.07 (m, 8H) 3.14-3.26 (m, 3H) 3.29 (s, 3H) 3.31 (s, 3H) 3.44-3.53 (m, 1H) 3.58 (d, J = 9.52 Hz, 1H) 3.75 (d, J = 7.32 Hz, 1H) 3.94-4.08 (m, 2H) 4.12 (dd, J = 9.03, 7.32 Hz, 1H) 4.46 (d, J = 7.32 Hz, 1H) 4.89 (d, J = 4.39 Hz, 1H) 5.14 (dd, J = 6.44, 4.39 Hz, 1H) 6.70 (dd, J = 8.05, 2.44 Hz, 1H) 6.75 (t, J = 1.71 Hz, 1H) 6.82 (d, J = 7.57 Hz, 1H) 7.19 (t, J = 7.82 Hz, 1H) |
| 419 | | 3-ethynylphenoxy group | 833 | (400 MHz): 0.94 (d, J = 7.08 Hz, 3H) 1.03 (d, J = 6.59 Hz, 3H) 1.07 (d, J = 7.57 Hz, 3H) 1.10 (d, J = 7.08 Hz, 3H) 1.19-1.25 (m, 1H) 1.22 (d, J = 6.10 Hz, 3H) 1.25 (s, 3H) 1.29 (d, J = 6.10 Hz, 3H) 1.37 (s, 3H) 1.44 (d, J = 14.65 Hz, 1H) 1.57 (dd, J = 15.14, 5.13 Hz, 1H) 1.62-1.69 (m, 1H) 2.20-2.54 (m, 4H) 2.30 (s, 6H) 2.60-3.06 (m, 9H) 3.14-3.26 (m, 3H) 3.29 (s, 3H) 3.31 (s, 3H) 3.43-3.53 (m, 1H) 3.59 (d, J = 9.52 Hz, 1H) 3.75 (d, J = 7.33 Hz, 1H) 3.94-4.07 (m, 2H) 4.12 (dd, J = 9.04, 7.57 Hz, 1H) 4.46 (d, J = 7.32 Hz, 1H) 4.89 (d, J = 4.64 Hz, 1H) 5.13 (dd, J = 6.44, 4.39 Hz, 1H) 6.85-6.91 (m, 1H) 6.98-7.02 (m, 1H) 7.07 (d, J = 7.57 Hz, 1H) 7.22 (t, J = 8.06 Hz, 1H) |
| 420 | | 3-(trifluoromethoxy)phenoxy group | 893 | (400 MHz): 0.94 (d, J = 7.06 Hz, 3H) 1.03 (d, J = 7.06 Hz, 3H) 1.05 (d, J = 7.79 Hz, 3H) 1.10 (d, J = 7.07 Hz, 3H) 1.19-1.27 (m, 1H) 1.22 (d, J = 5.84 Hz, 3H) 1.25 (s, 3H) 1.29 (d, J = 6.33 Hz, 3H) 1.37 (s, 3H) 1.45 (d, J = 14.62 Hz, 1H) 1.57 (dd, J = 15.35, 5.12 Hz, 1H) 1.63-1.71 (m, 1H) 2.20-2.53 (m, 6H) 2.30 (s, 6H) 2.61-3.05 (m, 8H) 3.15-3.26 (m, 3H) 3.29 (s, 3H) 3.31 (s, 3H) 3.43-3.53 (m, 1H) 3.59 (d, J = 9.74 Hz, 1H) 3.75 (d, J = 7.55 Hz, 1H) 3.95-4.07 (m, 2H) 4.09-4.17 (m, 1H) 4.46 (d, J = 7.06 Hz, 1H) 4.89 (d, J = 4.63 Hz, 1H) 5.13 (dd, J = 6.33, 4.62 Hz, 1H) 6.74 (s, 1H) 6.78-6.84 (m, 2H) 7.27 (t, J = 8.28 Hz, 1H) |
| 421 | | 3-cyanophenoxy group | 834 | (400 MHz): 0.94 (d, J = 7.31 Hz, 3H) 1.04 (d, J = 6.58 Hz, 3H) 1.08 (d, J = 7.55 Hz, 3H) 1.12 (d, J = 7.07 Hz, 3H) 1.19-1.27 (m, 1H) 1.23 (d, J = 6.09 Hz, 3H) 1.25 (s, 3H) 1.30 (d, J = 6.33 Hz, 3H) 1.37 (s, 3H) 1.46 (d, J = 14.86 Hz, 1H) 1.58 (dd, J = 15.10, 4.87 Hz, 1H) 1.63-1.71 (m, 1H) 2.19-2.54 (m, 6H) 2.30 (s, 6H) 2.61-3.05 (m, 8H) 3.15-3.28 (m, 3H) 3.29 (s, 3H) 3.32 (s, 3H) 3.43-3.53 (m, 1H) 3.59 (d, J = 9.50 Hz, 1H) 3.75 (d, J = 7.55 Hz, 1H) 3.97-4.08 (m, 2H) 4.14 (dd, J = 8.77, 7.07 Hz, 1H) 4.46 (d, J = 7.31 Hz, 1H) 4.90 (d, J = 4.39 Hz, 1H) 5.13 (dd, J = 6.33, 4.39 Hz, 1H) 7.09-7.15 (m, 2H) 7.23 (d, J = 7.55 Hz, 1H) 7.37 (t, J = 8.04 Hz, 1H) |

TABLE 13-continued

| Example | Reference Example | R | ESI MS (M + H) | ¹H-NMR, CDCl₃, δ (ppm) |
|---|---|---|---|---|
| 422 | | | 877 | (400 MHz): 0.94 (d, J = 7.31 Hz, 3H) 1.04 (d, J = 6.82 Hz, 3H) 1.06 (d, J = 7.55 Hz, 3H) 1.09 (d, J = 7.07 Hz, 3H) 1.19-1.27 (m, 1H) 1.22 (d, J = 6.09 Hz, 3H) 1.25 (s, 3H) 1.29 (d, J = 6.33 Hz, 3H) 1.37 (s, 3H) 1.45 (d, J = 14.86 Hz, 1H) 1.57 (dd, J = 15.10, 4.87 Hz, 1H) 1.62-1.70 (m, 1H) 2.18-2.54 (m, 6H) 2.30 (s, 6H) 2.62-3.06 (m, 8H) 3.15-3.27 (m, 3H) 3.29 (s, 3H) 3.31 (s, 3H) 3.43-3.52 (m, 1H) 3.59 (d, J = 9.75 Hz, 1H) 3.75 (d, J = 7.55 Hz, 1H) 3.98-4.07 (m, 2H) 4.16 (t, J = 7.55 Hz, 1H) 4.45 (d, J = 7.06 Hz, 1H) 4.89 (d, J = 4.63 Hz, 1H) 5.14 (dd, J = 6.34, 4.39 Hz, 1H) 7.03-7.08 (m, 1H) 7.11 (s, 1H) 7.19 (d, J = 7.79 Hz, 1H) 7.38 (t, J = 8.03 Hz, 1H) |
| 423 | | | 867 | (400 MHz): 0.93 (d, J = 7.31 Hz, 3H) 1.03 (d, J = 6.58 Hz, 3H) 1.09 (d, J = 7.55 Hz, 3H) 1.11 (d, J = 6.82 Hz, 3H) 1.19-1.27 (m, 1H) 1.22 (d, J = 6.09 Hz, 3H) 1.25 (s, 3H) 1.29 (d, J = 6.09 Hz, 3H) 1.37 (s, 3H) 1.46 (d, J = 14.86 Hz, 1H) 1.58 (dd, J = 15.10, 4.87 Hz, 1H) 1.62-1.71 (m, 1H) 2.19-2.58 (m, 6H) 2.30 (s, 6H) 2.62-3.07 (m, 8H) 3.14-3.26 (m, 3H) 3.29 (s, 3H) 3.31 (s, 3H) 3.43-3.53 (m, 1H) 3.59 (d, J = 9.74 Hz, 1H) 3.76 (d, J = 7.31 Hz, 1H) 3.91 (s, 3H) 3.99-4.08 (m, 2H) 4.17 (dd, J = 8.01, 7.06 Hz, 1H) 4.47 (d, J = 7.06 Hz, 1H) 4.90 (d, J = 4.39 Hz, 1H) 5.14 (dd, J = 6.44, 4.39 Hz, 1H) 7.05-7.11 (m, 1H) 7.33 (t, J = 7.79 Hz, 1H) 7.54-7.58 (m, 1H) 7.61-7.66 (m, 1H) |
| 424 | | | 823 | (400 MHz): 0.94 (d, J = 7.31 Hz, 3H) 1.03 (d, J = 6.82 Hz, 3H) 1.07 (d, J = 7.55 Hz, 3H) 1.10 (d, J = 7.31 Hz, 3H) 1.19-1.27 (m, 1H) 1.22 (d, J = 6.09 Hz, 3H) 1.25 (s, 3H) 1.29 (d, J = 6.34 Hz, 3H) 1.36 (s, 3H) 1.43 (d, J = 15.10 Hz, 1H) 1.57 (dd, J = 15.10, 4.87 Hz, 1H) 1.63-1.72 (m, 1H) 2.19-2.55 (m, 6H) 2.28 (s, 3H) 2.30 (s, 6H) 2.59-2.70 (m, 1H) 2.71-2.88 (m, 3H) 2.90-3.07 (m, 4H) 3.13-3.26 (m, 3H) 3.28 (s, 3H) 3.31 (s, 3H) 3.43-3.54 (m, 1H) 3.59 (d, J = 9.74 Hz, 1H) 3.75 (d, J = 7.55 Hz, 1H) 3.95 (t, J = 9.01 Hz, 1H) 3.99-4.08 (m, 1H) 4.10 (dd, J = 9.01, 7.31 Hz, 1H) 4.46 (d, J = 7.06 Hz, 1H) 4.89 (d, J = 4.62 Hz, 1H) 5.13 (dd, J = 6.33, 4.38 Hz, 1H) 6.78 (d, J = 8.53 Hz, 2H) 7.06 (d, J = 8.04 Hz, 2H) |
| 425 | | | 863 | (400 MHz): 0.94 (d, J = 7.08 Hz, 3H) 1.03 (d, J = 6.84 Hz, 3H) 1.07 (d, J = 7.57 Hz, 3H) 1.10 (d, J = 7.08 Hz, 3H) 1.19-1.27 (m, 1H) 1.22 (d, J = 6.11 Hz, 3H) 1.25 (s, 3H) 1.29 (d, J = 6.11 Hz, 3H) 1.36 (s, 3H) 1.43 (d, J = 14.65 Hz, 1H) 1.58 (dd, J = 14.89, 4.88 Hz, 1H) 1.63-1.70 (m, 1H) 1.73-1.82 (m, 4H) 2.17-2.57 (m, 6H) 2.30 (s, 6H) 2.59-3.06 (m, 12H) 3.14-3.25 (m, 3H) 3.28 (s, 3H) 3.32 (s, 3H) 3.44-3.53 (m, 1H) 3.58 (d, J = 10.01 Hz, 1H) 3.75 (d, J = 7.32 Hz, 1H) 3.94 (t, J = 9.04 Hz, 1H) 3.98-4.14 (m, 2H) 4.46 (d, J = 7.08 Hz, 1H) 4.90 (d, J = 4.39 Hz, 1H) 5.12 (dd, J = 6.35, 4.39 Hz, 1H) 6.59 (d, J = 2.44 Hz, 1H) 6.64 (dd, J = 8.30, 2.68 Hz, 1H) 6.95 (d, J = 8.3 Hz, 1H) |
| 426 | | | 849 | (400 MHz): 0.94 (d, J = 7.08 Hz, 3H) 1.03 (d, J = 6.59 Hz, 3H) 1.07 (d, J = 7.57 Hz, 3H) 1.10 (d, J = 7.08 Hz, 3H) 1.19-1.27 (m, 1H) 1.23 (d, J = 5.86 Hz, 3H) 1.25 (s, 3H) 1.29 (d, J = 6.35 Hz, 3H) 1.36 (s, 3H) 1.43 (d, J = 14.64 Hz, 1H) 1.57 (dd, J = 14.90, 4.89 Hz, 1H) 1.63-1.70 (m, 1H) 2.01-2.11 (m, 2H) 2.19-2.55 (m, 6H) 2.30 (s, 6H) 2.59-2.70 (m, 1H) 2.72-3.05 (m, 11H) 3.13-3.25 (m, 3H) 3.28 (s, 3H) 3.31 (s, 3H) 3.44-3.53 (m, 1H) 3.59 (d, J = 9.52 Hz, 1H) 3.75 (d, J = 7.32 Hz, 1H) 3.92-4.07 (m, 2H) 4.10 (dd, J = 9.27, 7.32 Hz, 1H) 4.46 (d, J = 7.08 Hz, 1H) 4.89 (d, J = 4.40 Hz, 1H) 5.13 (dd, J = 6.35, 4.15 Hz, 1H) 6.66 (dd, J = 8.05, 2.19 Hz, 1H) 6.77 (d, J = 2.20 Hz, 1H) 7.09 (d, J = 8.31 Hz, 1H) |

TABLE 13-continued

| Example | Reference Example | R | ESI MS (M + H) | $^1$H-NMR, CDCl$_3$, δ (ppm) |
|---|---|---|---|---|
| 427 | | 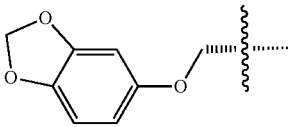 | 853 | (400 MHz): 0.94 (d, J = 7.06 Hz, 3H) 1.03 (d, J = 6.82 Hz, 3H) 1.08 (d, J = 7.31 Hz, 3H) 1.12 (d, J = 7.06 Hz, 3H) 1.19-1.27 (m, 1H) 1.23 (d, J = 6.09 Hz, 3H) 1.25 (s, 3H) 1.29 (d, J = 6.09 Hz, 3H) 1.36 (s, 3H) 1.43 (d, J = 15.10 Hz, 1H) 1.58 (dd, J = 15.10, 4.87 Hz, 1H) 1.63-1.72 (m, 1H) 2.18-2.68 (m, 7H) 2.30 (s, 6H) 2.75-3.07 (m, 7H) 3.14-3.25 (m, 3H) 3.29 (s, 3H) 3.32 (s, 3H) 3.43-3.53 (m, 1H) 3.59 (d, J = 9.50 Hz, 1H) 3.75 (d, J = 7.60 Hz, 1H) 3.91 (t, J = 8.80 Hz, 1H) 3.98-4.09 (m, 2H) 4.47 (d, J = 7.31 Hz, 1H) 4.90 (d, J = 4.39 Hz, 1H) 5.11 (dd, J = 6.09, 4.38 Hz, 1H) 5.90 (s, 2H) 6.31 (dd, J = 8.53, 2.44 Hz, 1H) 6.46 (d, J = 2.43 Hz, 1H) 6.69 (d, J = 8.28 Hz, 1H) |
| 428 | | 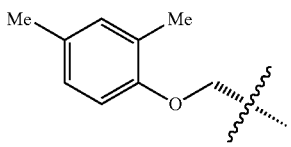 | 837 | (400 MHz): 0.94 (d, J = 7.06 Hz, 3H) 1.04 (d, J = 8.28 Hz, 3H) 1.06 (d, J = 7.80 Hz, 3H) 1.09 (d, J = 7.30 Hz, 3H) 1.19-1.27 (m, 1H) 1.22 (d, J = 6.08 Hz, 3H) 1.25 (s, 3H) 1.29 (d, J = 6.33 Hz, 3H) 1.36 (s, 3H) 1.43 (d, J = 14.85 Hz, 1H) 1.57 (d, J = 15.10, 4.87 Hz, 1H) 1.62-1.71 (m, 1H) 2.14 (s, 3H) 2.20-2.55 (m, 6H) 2.24 (s, 3H) 2.30 (s, 6H) 2.63-3.06 (m, 8H) 3.13-3.26 (m, 3H) 3.28 (s, 3H) 3.31 (s, 3H) 3.43-3.53 (m, 1H) 3.58 (d, J = 9.50 Hz, 1H) 3.75 (d, J = 7.31 Hz, 1H) 3.93-4.14 (m, 3H) 4.46 (d, J = 7.31 Hz, 1H) 4.89 (d, J = 4.38 Hz, 1H) 5.14 (dd, J = 6.09, 4.14 Hz, 1H) 6.72 (d, J = 9.02 Hz, 1H) 6.90-6.95 (m, 2H) |
| 429 | | 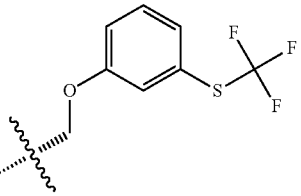 | 909 | (400 MHz): 0.94 (d, J = 7.06 Hz, 3H) 1.03 (d, J = 7.30 Hz, 3H) 1.06 (d, J = 7.80 Hz, 3H) 1.10 (d, J = 7.06 Hz, 3H) 1.19-1.27 (m, 1H) 1.23 (d, J = 5.84 Hz, 3H) 1.25 (s, 3H) 1.29 (d, J = 6.33 Hz, 3H) 1.37 (s, 3H) 1.45 (d, J = 14.85 Hz, 1H) 1.57 (dd, J = 15.10, 4.87 Hz, 1H) 1.63-1.72 (m, 1H) 2.18-2.54 (m, 6H) 2.30 (s, 6H) 2.62-3.06 (m, 8H) 3.15-3.27 (m, 3H) 3.29 (s, 3H) 3.31 (s, 3H) 3.43-3.53 (m, 1H) 3.59 (d, J = 9.75 Hz, 1H) 3.75 (d, J = 7.31 Hz, 1H) 3.97-4.07 (m, 2H) 4.14 (d, J = 8.77, 7.31 Hz, 1H) 4.46 (d, J = 7.07 Hz, 1H) 4.89 (d, J = 4.63 Hz, 1H) 5.14 (dd, J = 6.33, 4.39 Hz, 1H) 6.98-7.03 (m, 1H) 7.21-7.24 (m, 1H) 7.23 (d, J = 7.55 Hz, 1H) 7.32 (t, J = 8.04 Hz, 1H) |
| 430 | 78 | 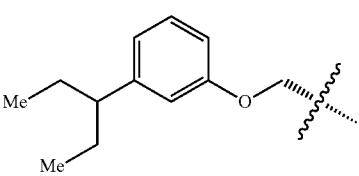 | 879 FAB MASS | (400 MHz): 0.77 (t, J = 7.3 Hz, 6H) 0.94 (d, J = 7.3 Hz, 3H) 1.04 (d, J = 6.6 Hz, 3H) 1.05 (d, J = 7.1 Hz, 3H) 1.09 (d, J = 7.1 Hz, 3H) 1.16-1.26 (m, 7H) 1.29 (d, J = 6.3 Hz, 3H) 1.36 (s, 3H) 1.44 (d, J = 14.4 Hz, 1H) 1.48-1.73 (m, 6H) 2.19-2.34 (m, 9H) 2.36 (d, J = 14.9 Hz, 1H) 2.39-2.57 (m, 2H) 2.60-2.71 (m, 1H) 2.73-2.88 (m, 3H) 2.90-3.05 (m, 4H) 3.16-3.26 (m, 3H) 3.29 (s, 3H) 3.30 (s, 3H) 3.43-3.52 (m, 1H) 3.58 (d, J = 9.3 Hz, 1H) 3.75 (d, J = 7.6 Hz, 1H) 3.97 (dd, J = 9.0, 7.6 Hz, 1H) 4.03 (dq, J = 9.3, 6.3 Hz, 1H) 4.12 (dd, J = 9.0, 7.6 Hz, 1H) 4.46 (d, J = 7.1 Hz, 1H) 4.89 (d, J = 4.4 Hz, 1H) 5.15 (dd, J = 4.4, 6.3 Hz, 1H) 6.65-6.75 (m, 3H) 7.18 (t, J = 7.8 Hz, 1H) |
| 431 | 79 | 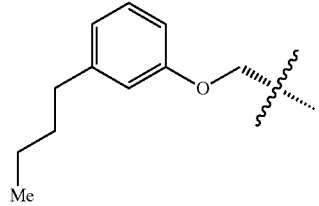 | 865 FAB MASS | (400 MHz): 0.92 (d, J = 7.3 Hz, 3H) 0.94 (d, J = 7.1 Hz, 3H) 1.03 (d, J = 6.6 Hz, 3H) 1.08 (d, J = 7.6 Hz, 3H) 1.10 (d, J = 7.3 Hz, 3H) 1.15-1.40 (m, 15H) 1.43 (d, J = 14.6 Hz, 1H) 1.53-1.69 (m, 4H) 2.19-2.28 (m, 2H) 2.29 (s, 6H) 2.37 (d, J = 15.3 Hz, 1H) 2.37-2.55 (m, 2H) 2.57 (t, J = 7.6 Hz, 2H) 2.60-2.70 (m, 1H) 2.73-2.88 (m, 3H) 2.90-3.05 (m, 4H) 3.18 (br s, 1H) 3.20 (dd, J = 10.2, 7.3 Hz, 1H) 3.23 (d, J = 11.7 Hz, 1H) 3.29 (s, 3H) 3.31 (s, 3H) 3.32 (br s, 1H) 3.43-3.53 (m, 1H) 3.58 (d, J = 9.7 Hz, 1H) 3.75 (d, J = 7.3 Hz, 1H) 3.98 (dd, J = 9.0, 7.6 Hz, 1H) 4.02 (dq, J = 9.3, 6.3 Hz, 1H) 4.06 (t, J = 7.1 Hz, 1H) 4.47 (d, J = 7.3 Hz, 1H) 4.85 (br s, 1H) 4.89 (d, J = 4.6 Hz, 1H) 5.14 (dd, J = 6.3, 4.4 Hz, 1H) 6.67-6.73 (m, 2H) 6.76 (d, J = 7.6 Hz, 1H) 7.17 (t, J = 8.5 Hz, 1H) |

TABLE 13-continued

| Example | Reference Example | R | ESI MS (M + H) | ¹H-NMR, CDCl₃, δ (ppm) |
|---|---|---|---|---|
| 432 | 80 | 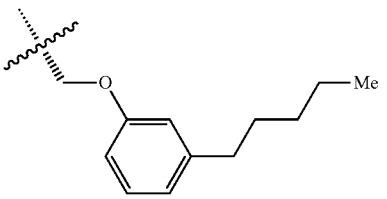 | 879 FAB MASS | (400 MHz): 0.89 (d, J = 7.1 Hz, 3H) 0.94 (d, J = 7.1 Hz, 3 H) 1.03 (d, J = 6.6 Hz, 3H) 1.08 (d, J = 7.6 Hz, 3H) 1.10 (d, J = 7.1 Hz, 3H) 1.16-1.35 (m, 14H) 1.43 (d, J = 14.9 Hz, 1H) 1.53-1.70 (m, 4H) 2.18-2.27 (m, 2H) 2.29 (s, 6H) 2.36 (d, J = 15.1 Hz, 1H) 2.38-2.47 (m, 1H) 2.48-2.59 (m, 3 H) 2.60-2.70 (m, 1H) 2.73-2.88 (m, 3H) 2.91-3.05 (m, 4H) 3.15 (br s, 1H) 3.20 (dd, J = 10.5, 7.3 Hz, 1H) 3.23 (d, J = 11.7 Hz, 1H) 3.29 (s, 3H) 3.31 (s, 3H) 3.34 (br s, 1H) 3.43-3.52 (m, 1H) 3.59 (d, J = 9.5 Hz, 1H) 3.75 (d, J = 7.3 Hz, 1H) 3.93-4.00 (m, 1H) 4.04 (dq, J = 9.3, 6.3 Hz, 1H) 4.12 (dd, J = 9.3, 7.6 Hz, 1H) 4.46 (d, J = 7.3 Hz, 1H) 4.84 (br s, 1H) 4.90 (d, J = 4.6 Hz, 1H) 5.14 (dd, J = 6.1, 4.1 Hz, 1H) 6.67-6.73 (m, 2H) 6.77 (d, J = 7.8 Hz, 1H) 7.17 (dt, J = 1.0, 8.5 Hz, 1H) |
| 433 | | 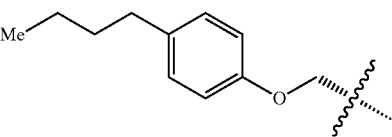 | 865 | (400 MHz): 0.90 (t, J = 7.31 Hz, 3H) 0.93 (d, J = 5.60 Hz, 3H) 1.02 (d, J = 6.82 Hz, 3H) 1.06 (d, J = 7.31 Hz, 3H) 1.06 (d, J = 7.31 Hz, 3H) 1.22 (d, J = 6.09 Hz, 3H) 1.24 (s, 3H) 1.24 (d, J = 5.35 Hz, 3H) 1.29 (d, J = 6.09 Hz, 3H) 1.33 (d, J = 7.58 Hz, 1H) 1.35 (s, 3H) 1.42 (d, J = 14.6 Hz, 1H) 1.50-1.59 (m, 2H) 1.63-1.66 (m, 2H) 2.28-2.29 (m, 1H) 2.29 (s, 6H) 2.40 (d, J = 15.1 Hz, 1H) 2.39-2.54 (m, 4H) 2.60-3.01 (m, 8H) 3.15 (d, J = 4.38 Hz, 1H) 3.23-3.24 (m, 2H) 3.27 (s, 3H) 3.31 (s, 3H) 3.39-3.46 (m, 1H) 3.57 (d, J = 2.92 Hz, 1H) 3.75 (d, J = 6.65 Hz, 1H) 3.95 (t, J = 7.79 Hz, 1H) 4.02 (dd, J = 9.26, 2.92 Hz, 1H) 4.45 (d, J = 7.06 Hz, 1H) 4.88 (d, J = 4.38 Hz, 1H) 5.12 (dd, J = 6.33, 4.38 Hz, 1H) 6.78-6.79 (m, 2H) 7.04-7.06 (m, 1H) |
| 434 | | 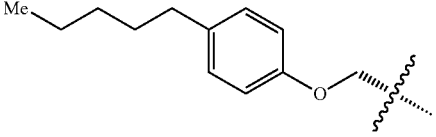 | 879 | (400 MHz): 0.88 (t, J = 7.31 Hz, 3H) 0.93 (d, J = 5.60 Hz, 3H) 1.02 (d, J = 6.82 Hz, 3H) 1.06 (d, J = 7.31 Hz, 3H) 1.06 (d, J = 7.31 Hz, 3H) 1.22 (d, J = 6.09 Hz, 3H) 1.24 (s, 3H) 1.24 (d, J = 5.35 Hz, 3H) 1.29 (d, J = 6.09 Hz, 3H) 1.33 (d, J = 7.58 Hz, 1H) 1.35 (s, 3H) 1.42 (d, J = 14.6 Hz, 1H) 1.50-1.59 (m, 2H) 1.63-1.66 (m, 2H) 2.28-2.29 (m, 1H) 2.29 (s, 6H) 2.40 (d, J = 15.1 Hz, 1H) 2.39-2.54 (m, 4H) 2.60-3.01 (m, 8H) 3.15 (d, J = 4.38 Hz, 1H) 3.23-3.24 (m, 2H) 3.27 (s, 3H) 3.31 (s, 3H) 3.39-3.46 (m, 1H) 3.57 (d, J = 2.92 Hz, 1H) 3.75 (d, J = 6.65 Hz, 1H) 3.95 (t, J = 7.79 Hz, 1H) 4.02 (dd, J = 9.26, 2.92 Hz, 1H) 4.45 (d, J = 7.06 Hz, 1H) 4.88 (d, J = 4.38 Hz, 1H) 5.12 (dd, J = 6.33, 4.38 Hz, 1H) 6.78-6.79 (m, 2H) 7.04-7.06 (m, 1H) |
| 435 | | 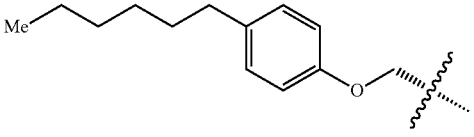 | 893 | (400 MHz): 0.86 (t, J = 6.82 Hz, 3H) 0.94 (d, J = 7.06 Hz, 3H) 1.03 (d, J = 6.58 Hz, 3H) 1.06 (d, J = 7.31 Hz, 3H) 1.07 (d, J = 7.31 Hz, 3H) 1.22 (d, J = 6.09 Hz, 3H) 1.24 (s, 3H) 1.24 (d, J = 5.35 Hz, 3H) 1.29 (d, J = 6.09 Hz, 6H) 1.33 (d, J = 7.58 Hz, 1H) 1.35 (s, 3H) 1.42 (d, J = 14.6 Hz, 1H) 1.50-1.59 (m, 2H) 1.63-1.66 (m, 2H) 2.26-2.28 (m, 1H) 2.29 (s, 6H) 2.40 (d, J = 15.1 Hz, 1H) 2.39-2.54 (m, 4H) 2.60-3.01 (m, 8H) 3.15 (d, J = 4.38 Hz, 1H) 3.23-3.24 (m, 2H) 3.27 (s, 3H) 3.31 (s, 3H) 3.39-3.46 (m, 1 H) 3.57 (d, J = 2.92 Hz, 1H) 3.75 (d, J = 6.65 Hz, 1H) 3.95 (t, J = 7.79 Hz, 1H) 4.02 (dd, J = 9.26, 2.92 Hz, 1H) 4.45 (d, J = 7.06 Hz, 1H) 4.88 (d, J = 4.38 Hz, 1H) 5.12 (dd, J = 6.33, 4.38 Hz, 1H) 6.79-6.81 (m, 2H) 7.04-7.05 (m, 1H) |
| 436 | | 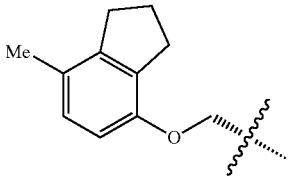 | 863 | (400 MHz): 0.94 (d, J = 7.06 Hz, 3H) 1.03 (d, J = 6.82 Hz, 3H) 1.07 (d, J = 7.31 Hz, 3H) 1.09 (d, J = 6.82 Hz, 3H) 1.22 (d, J = 6.09 Hz, 3H) 1.25 (s, 3H) 1.25-1.30 (m, 1H) 1.29 (d, J = 6.33 Hz, 3H) 1.36 (s, 3H) 1.42 (d, J = 14.6 Hz, 1H) 1.57 (dd, J = 15.10, 5.12 Hz, 1H) 1.64-1.67 (m, 1H) 2.02-2.08 (m, 2H) 2.19 (s, 3H) 2.22-2.27 (m, 2H) 2.30 (s, 6H) 2.36 (d, J = 15.1 Hz, 1H) 2.42-2.54 (m, 2H) 2.64-2.67 (m, 1H) 2.73-2.88 (m, 7H) 2.93-3.04 (m, 4H) 3.15 (d, J = 4.38 Hz, 1H) 3.19-3.23 (m, 2H) 3.28 (s, 3H) 3.31 (s, 3H) 3.45-3.48 (m, 1H) 3.58 (d, J = 7.31 Hz, 1H) 3.75 (d, J = 7.31 Hz, 1H) 3.96-4.06 (m, 2H) 4.09-4.13 (m, 1H) 4.46 (d, J = 7.31 Hz, 1H) 4.89 (d, J = 4.63 Hz, 1H) 5.13 (dd, J = 6.09, 4.38 Hz, 1H) 6.59 (d, J = 8.04 Hz, 1H) 6.90 (d, J = 8.04 Hz, 1H) |

TABLE 13-continued

| Example | Reference Example | R | ESI MS (M + H) | $^1$H-NMR, CDCl$_3$, δ (ppm) |
|---|---|---|---|---|
| 437 | | 4-chloroindan-7-yloxy group | 883 | (400 MHz): 0.93 (d, J = 7.31 Hz, 3H) 1.03 (d, J = 6.82 Hz, 3H) 1.07 (d, J = 7.31 Hz, 3H) 1.09 (d, J = 6.82 Hz, 3H) 1.22 (d, J = 6.09 Hz, 3H) 1.25 (s, 3H) 1.25-1.30 (m, 1H) 1.29 (d, J = 6.33 Hz, 3H) 1.36 (s, 3H) 1.43 (d, J = 14.9 Hz, 1H) 1.57 (dd, J = 15.10, 5.12 Hz, 1H) 1.64-1.67 (m, 1H) 2.04-2.08 (m, 2H) 2.20-2.27 (m, 2H) 2.30 (s, 6H) 2.36 (d, J = 15.1 Hz, 1H) 2.42-2.54 (m, 2H) 2.65-2.72 (m, 1H) 2.73-2.88 (m, 7H) 2.93-3.04 (m, 4H) 3.15 (d, J = 4.38 Hz, 1H) 3.19-3.23 (m, 2H) 3.28 (s, 3H) 3.31 (s, 3H) 3.45-3.51 (m, 1H) 3.58 (d, J = 7.31 Hz, 1H) 3.75 (d, J = 7.31 Hz, 1H) 3.96-4.06 (m, 2H) 4.11 (t, J = 11.45, 1H) 4.46 (d, J = 7.31 Hz, 1H) 4.89 (d, J = 4.63 Hz, 1H) 5.13 (dd, J = 6.09, 4.38 Hz, 1H) 6.61 (d, J = 8.52 Hz, 1H) 7.05 (d, J = 8.53 Hz, 1H) |
| 438 | 81 | 3-cyclopropylphenoxy group | 849 FAB MASS | (400 MHz): 0.66-0.72 (m, 2H) 0.90-0.98 (m, 5H) 1.04 (d, J = 6.6 Hz, 3H) 1.07 (d, J = 7.3 Hz, 3H) 1.10 (d, J = 7.1 Hz, 3H) 1.17-1.28 (m, 7H) 1.29 (d, J = 6.1 Hz, 1H) 1.37 (s, 3H) 1.42 (d, J = 15.1 Hz, 1H) 1.58 (dd, J = 15.1, 4.9 Hz, 1H) 1.65-1.74 (m, 1H) 1.82-1.90 (m, 1H) 2.17-2.29 (m, 2H) 2.32 (s, 6H) 2.36 (d, J = 14.9 Hz, 1H) 2.42-2.57 (m, 2H) 2.58-2.70 (m, 1H) 2.71-3.07 (m, 7H) 3.13-3.26 (m, 3H) 3.28 (s, 3H), 3.31 (s, 3H) 3.44-3.54 (m, 1H) 3.59 (d, J = 10.0 Hz, 1H) 3.71 (d, J = 7.3 Hz, 1H) 3.93-3.99 (m, 1H) 4.03 (dq, J = 9.3, 6.3 Hz, 1H) 4.12 (dd, J = 9.0, 7.3 Hz, 1H) 4.47 (d, J = 7.3 Hz, 1H) 4.89 (d, J = 4.4 Hz, 1H) 5.14 (dd, J = 6.3, 4.1 Hz, 1H) 6.58-6.62 (m, 1H) 6.63-6.69 (m, 2H) 7.14 (t, J = 8.0 Hz, 1H) |
| 439 | | 3-(pentafluoroethyl)phenoxy group | 927 | (400 MHz): 0.94 (d, J = 7.31 Hz, 3H) 1.04 (d, J = 4.90 Hz, 3H) 1.05 (d, J = 4.38 Hz, 3H) 1.09 (d, J = 7.06 Hz, 3H) 1.22 (d, J = 5.85 Hz, 3H) 1.25 (s, 3H) 1.29 (d, J = 6.09 Hz, 3H) 1.36 (s, 3H) 1.45 (d, J = 14.6 Hz, 1H) 1.57 (dd, J = 15.10, 4.87 Hz, 1H) 1.66 (d, J = 12.7 Hz, 1H) 2.18-2.27 (m, 2H) 2.29 (s, 3H) 2.36 (d, J = 15.1 Hz, 1H) 2.39-2.44 (m, 2H) 2.64-2.78 (m, 2H) 2.79-2.87 (m, 2H) 2.89-3.05 (m, 4H) 3.15-3.26 (m, 3H) 3.29 (s, 3H) 3.31 (s, 3H) 3.48 (dd, J = 9.74, 4.38 Hz, 1H) 3.58 (d, J = 6.09 Hz, 1H) 3.75 (d, J = 7.55 Hz, 1H) 3.97-4.06 (m, 2H) 4.16 (t, J = 8.77 Hz, 1H) 4.45 (d, J = 7.06 Hz, 1H) 4.89 (d, J = 4.63 Hz, 1H) 5.14 (dd, J = 6.33, 4.38 Hz, 1H) 7.07 (m, 1H) 7.16 (d, J = 7.55 Hz, 1H) 7.40 (t, J = 7.79 Hz, 1H) |
| 440 | | 2-methyl-2-phenoxypropyl group | 809.6 | (600 MHz): 0.96 (d, J = 7.34 Hz, 3H) 1.01 (d, J = 6.88 Hz, 3H) 1.10 (d, J = 7.34 Hz, 3H) 1.16 (d, J = 7.34 Hz, 3H) 1.17-1.21 (m, 1H) 1.22 (d, J = 5.96 Hz, 3H) 1.24 (s, 3H) 1.29 (d, J = 6.42 Hz, 3H) 1.37 (s, 3H) 1.48 (d, J = 14.67 Hz, 1H) 1.56 (dd, J = 15.13, 4.58 Hz, 1H) 1.63-1.67 (m, 1H) 2.20-2.29 (m, 2H) 2.28 (s, 6H) 2.35-2.47 (m, 2H) 2.38 (d, J = 14.67 Hz, 1H) 2.53-2.59 (m, 1H) 2.59-2.65 (m, 1H) 2.70 (dd, J = 12.15, 5.73 Hz, 1H) 2.81-2.88 (m, 1H) 2.91-2.96 (m, 1H) 2.96-3.07 (m, 2H) 3.12 (t, J = 8.48 Hz, 1H) 3.17-3.25 (m, 3H) 3.29 (s, 3H) 3.31 (s, 3H) 3.42-3.49 (m, 1H) 3.63 (d, J = 9.63 Hz, 1H) 3.74 (d, J = 7.79 Hz, 1H) 3.89-3.93 (m, 1H) 3.95-3.99 (m, 1H) 3.99-4.05 (m, 1H) 4.43 (d, J = 7.34 Hz, 1H) 4.81 (dd, J = 5.27, 2.98 Hz, 1H) 4.88 (d, J = 4.58 Hz, 1H) 6.83-6.96 (m, 3H) 7.21-7.29 (m, 2H) |

TABLE 13-continued

| Example | Reference Example | R | ESI MS (M + H) | $^1$H-NMR, CDCl$_3$, δ (ppm) |
|---|---|---|---|---|
| 441 | | 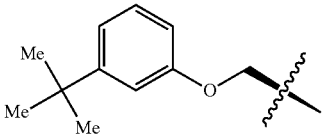 | 865.8 | (600 MHz): 0.96 (d, J = 7.34 Hz, 3H) 1.01 (d, J = 6.42 Hz, 3H) 1.09 (d, J = 7.34 Hz, 3H) 1.16 (d, J = 6.88 Hz, 3H) 1.19-1.22 (m, 1H) 1.22 (d, J = 5.96 Hz, 3H) 1.24 (s, 3H) 1.28-1.30 (m, 3H) 1.29 (s, 9H) 1.37 (s, 3H) 1.48 (d, J = 15.13 Hz, 1H) 1.56 (dd, J = 15.13, 5.04 Hz, 1H) 1.62-1.67 (m, 1H) 2.25-2.29 (m, 2H) 2.28 (s, 6H) 2.38 (d, J = 15.13 Hz, 1H) 2.38-2.46 (m, 2H) 2.53-2.59 (m, 1H) 2.59-2.65 (m, 1H) 2.71 (dd, J = 11.92, 5.96 Hz, 1H) 2.83-2.89 (m, 1H) 2.90-2.97 (m, 1H) 2.97-3.02 (m, 1H) 3.02-3.07 (m, 1H) 3.13 (t, J = 8.48 Hz, 1H) 3.16-3.24 (m, 3H) 3.29 (s, 3H) 3.31 (s, 3H) 3.43-3.49 (m, 1H) 3.63 (d, J = 9.63 Hz, 1H) 3.74 (d, J = 8.25 Hz, 1H) 3.88-3.92 (m, 1H) 3.95-4.00 (m, 1H) 4.00-4.06 (m, 1H) 4.43 (d, J = 7.34 Hz, 1H) 4.81 (dd, J = 5.50, 2.75 Hz, 1H) 4.88 (d, J = 4.58 Hz, 1H) 6.66-6.69 (m, 1H) 6.88-6.91 (m, 1H) 6.96-6.98 (m, 1H) 7.19 (t, J = 8.02 Hz, 1H) |
| 442 | | 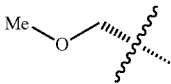 | 747.4 | (600 MHz): 0.94 (d, J = 6.88 Hz, 3H) 1.00 (d, J = 6.88 Hz, 3H) 1.12 (d, J = 7.34 Hz, 3H) 1.16 (d, J = 6.88 Hz, 3H) 1.18-1.22 (m, 1H) 1.23 (d, J = 5.96 Hz, 3H) 1.25 (s, 3H) 1.30 (d, J = 5.96 Hz, 3H) 1.37 (s, 3H) 1.44 (d, J = 15.13 Hz, 1H) 1.55-1.68 (m, 2H) 2.20-2.25 (m, 1H) 2.29 (s, 6H) 2.36-2.54 (m, 4H) 2.73 (t, J = 9.17 Hz, 1H) 2.80 (dd, J = 11.69, 4.36 Hz, 1H) 2.83-3.04 (m, 5H) 3.13-3.24 (m, 3H) 3.28 (s, 3H) 3.33 (s, 3H) 3.33 (s, 3H) 3.38 (t, J = 8.71 Hz, 1H) 3.46-3.52 (m, 1H) 3.54 (dd, J = 9.17, 6.42 Hz, 1H) 3.60 (d, J = 9.17 Hz, 1H) 3.76 (d, J = 7.34 Hz, 1H) 4.01-4.07 (m, 1H) 4.48 (d, J = 7.34 Hz, 1H) 4.91 (d, J = 4.58 Hz, 1H) 5.02 (dd, J = 6.19, 4.36 Hz, 1H) |
| 443 | | 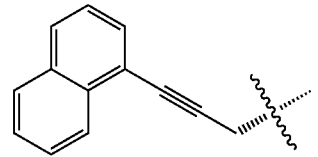 | 867 | (400 MHz): 0.97 (d, J = 7.3 Hz, 3H) 1.05 (d, J = 6.8 Hz, 3H) 1.14 (d, J = 7.1 Hz, 3H) 1.15 (d, J = 7.5 Hz, 3H) 1.20-1.27 (m, 7H) 1.30 (d, J = 6.3 Hz, 3H) 1.38 (s, 3H) 1.44-1.49 (m, 1H) 1.58 (dd, J = 4.8, 15.1 Hz, 1H) 1.65-1.72 (m, 1H) 1.72-2.20 (m, 1H) 2.15-2.63 (m, 13H) 2.68-2.80 (m, 2H) 2.78-3.08 (m, 7H) 3.12-3.35 (m, 9H) 3.45-3.54 (m, 1H) 3.60-3.67 (m, 1H) 3.74-3.79 (m, 1H) 4.02-4.08 (m, 1H) 4.49 (d, J = 7.1 Hz, 1H) 4.88-4.95 (m, 1H) 5.10-5.17 (m, 1H) 7.35-7.45 (m, 1H) 7.47-7.61 (m, 3H) 7.75-7.85 (m, 2H) 8.25-8.29 (m, 1H) |
| 444 | | 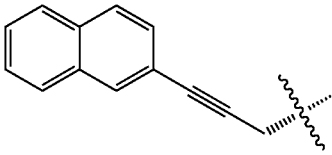 | 867 | (400 MHz): 0.97 (d, J = 7.1 Hz, 3H) 1.04 (d, J = 6.8 Hz, 3H) 1.14 (d, J = 7.6 Hz, 3H) 1.16 (d, J = 7.1 Hz, 3H) 1.20-1.27 (m, 7H) 1.30 (d, J = 6.1 Hz, 3H) 1.37 (s, 3H) 1.42-1.49 (m, 1H) 1.58 (dd, J = 4.8, 15.1 Hz, 1H) 1.64-1.68 (m, 1H) 1.68-1.80 (m, 2H) 2.16-2.69 (m, 14H) 2.80-3.08 (m, 7H) 3.12-3.34 (m, 9H) 3.45-3.53 (m, 1H) 3.60-3.67 (m, 1H) 3.74-3.82 (m, 1H) 4.01-4.09 (m, 1H) 4.49 (d, J = 7.0 Hz, 1H) 4.89-4.96 (m, 1H) 5.05-5.14 (m, 1H) 7.40-7.48 (m, 3H) 7.73-7.83 (m, 3H) 7.84-7.93 (m, 1H) |
| 445 | | 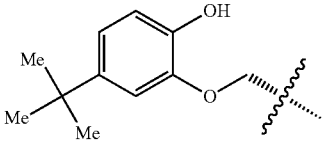 | 881.8 | (600 MHz): 0.94 (d, J = 6.88 Hz, 3H) 1.00-1.06 (m, 6H) 1.10 (d, J = 7.34 Hz, 3H) 1.16-1.21 (m, 1H) 1.21 (d, J = 5.96 Hz, 3H) 1.24 (s, 3H) 1.28 (d, J = 5.96 Hz, 3H) 1.28 (s, 9H) 1.36 (s, 3H) 1.44 (d, J = 14.21 Hz, 1H) 1.52-1.60 (m, 1H) 1.64 (d, J = 11.46 Hz, 1H) 2.21 (d, J = 10.09 Hz, 1H) 2.28 (s, 6H) 2.36 (d, J = 14.67 Hz, 1H) 2.39-2.45 (m, 1H) 2.47-2.53 (m, 1H) 2.65-2.78 (m, 2H) 2.79-2.85 (m, 2H) 2.86-2.97 (m, 2H) 2.97-3.04 (m, 2H) 3.14-3.21 (m, 2H) 3.25 (d, J = 11.46 Hz, 1H) 3.28 (s, 3H) 3.29 (s, 3H) 3.43-3.51 (m, 1H) 3.60 (d, J = 9.63 Hz, 1H) 3.75 (d, J = 7.79 Hz, 1H) 3.98-4.05 (m, 1H) 4.07-4.18 (m, 2H) 4.44 (d, J = 7.34 Hz, 1H) 4.86 (d, J = 4.58 Hz, 1H) 5.18 (dd, J = 6.42, 4.13 Hz, 1H) 6.80-6.84 (m, 1H) 6.86-6.90 (m, 2H) |

TABLE 13-continued

| Example | Reference Example | R | ESI MS (M + H) | $^1$H-NMR, CDCl$_3$, δ (ppm) |
|---|---|---|---|---|
| 446 | | 2-methyl-4-tert-butyl-phenoxy group | 881.7 | (600 MHz): 0.93 (d, J = 7.34 Hz, 3H) 1.00-1.04 (m, 6H) 1.09 (d, J = 7.34 Hz, 3H) 1.18-1.21 (m, 1H) 1.22 (d, J = 6.42 Hz, 3H) 1.23 (s, 3H) 1.26 (s, 9H) 1.28 (d, J = 6.42 Hz, 3H) 1.35 (s, 3H) 1.44 (d, J = 15.13 Hz, 1H) 1.53-1.58 (m, 1H) 1.64 (d, J = 13.30 Hz, 1H) 2.21 (d, J = 10.09 Hz, 1H) 2.28 (s, 6H) 2.35 (d, J = 15.59 Hz, 1H) 2.38-2.49 (m, 2H) 2.64-2.72 (m, 2H) 2.77-2.83 (m, 2H) 2.83-2.93 (m, 2H) 2.97-3.03 (m, 2H) 3.15-3.25 (m, 3H) 3.28 (s, 3H) 3.29 (s, 3H) 3.43-3.50 (m, 1H) 3.59 (d, J = 9.17 Hz, 1H) 3.73 (d, J = 7.34 Hz, 1H) 3.98-4.04 (m, 1H) 4.05-4.18 (m, 2H) 4.44 (d, J = 6.88 Hz, 1H) 4.86 (d, J = 4.59 Hz, 1H) 5.15 (dd, J = 6.65, 4.36 Hz, 1H) 6.77-6.80 (m, 1H) 6.80-6.84 (m, 1H) 6.96 (d, J = 2.29 Hz, 1H) |
| 447 | | 4-ethyl-2-hydroxyphenoxy group | 853.7 | (600 MHz): 0.94 (d, J = 7.34 Hz, 3H) 1.03 (d, J = 6.88 Hz, 3H) 1.05 (d, J = 7.34 Hz, 3H) 1.10 (d, J = 6.88 Hz, 3H) 1.16-1.26 (m, 1H) 1.19 (t, J = 7.57 Hz, 3H) 1.22 (d, J = 6.42 Hz, 3H) 1.24 (s, 3H) 1.28 (d, J = 5.96 Hz, 3H) 1.36 (s, 3H) 1.45 (d, J = 15.59 Hz, 1H) 1.51-1.69 (m, 2H) 2.20 (d, J = 10.55 Hz, 1H) 2.28 (br. s., 6H) 2.36 (d, J = 14.67 Hz, 1H) 2.38-2.46 (m, 2H) 2.46-2.52 (m, 1H) 2.56 (q, J = 7.49 Hz, 2H) 2.65-2.77 (m, 2H) 2.77-2.85 (m, 2H) 2.85-2.97 (m, 2H) 2.97-3.04 (m, 2H) 3.14-3.22 (m, 2H) 3.24 (d, J = 11.92 Hz, 1H) 3.28 (s, 3H) 3.30 (s, 3H) 3.43-3.51 (m, 1H) 3.60 (d, J = 9.17 Hz, 1H) 3.75 (d, J = 7.34 Hz, 1H) 3.98-4.05 (m, 1H) 4.06-4.12 (m, 1H) 4.12-4.18 (m, 1H) 4.45 (d, J = 6.88 Hz, 1H) 4.86 (d, J = 5.04 Hz, 1H) 5.18 (dd, J = 6.42, 4.13 Hz, 1H) 6.66-6.72 (m, 2H) 6.82 (d, J = 7.79 Hz, 1H) |
| 448 | | 3-(piperazin-1-yl)phenoxy group | 893.8 | (500 MHz): 0.94 (d, J = 7.13 Hz, 3H) 1.03 (d, J = 6.86 Hz, 3H) 1.06-1.13 (m, 6H) 1.18-1.27 (m, 7H) 1.29 (d, J = 6.31 Hz, 3H) 1.36 (s, 3H) 1.44 (d, J = 14.81 Hz, 1H) 1.54-1.61 (m, 1H) 1.63-1.69 (m, 1H) 2.20-2.28 (m, 2H) 2.31 (s, 6H) 2.37 (d, J = 14.81 Hz, 1H) 2.42-2.56 (m, 2H) 2.60-2.69 (m, 1H) 2.74-2.87 (m, 3H) 2.90-3.07 (m, 7H) 3.12-3.26 (m, 7H) 3.29 (s, 3H) 3.31 (s, 3H) 3.44-3.53 (m, 1H) 3.58 (d, J = 9.87 Hz, 1H) 3.75 (d, J = 7.40 Hz, 1H) 3.94-4.06 (m, 2H) 4.07-4.14 (m, 1H) 4.46 (d, J = 7.13 Hz, 1H) 4.87-4.91 (m, 1H) 5.10-5.16 (m, 1H) 6.39-6.42 (m, 1H) 6.43-6.46 (m, 1H) 6.51-6.57 (m, 1H) 7.15 (t, J = 8.23 Hz, 1H) |
| 449 | | 3-(4-methylpiperazin-1-yl)phenoxy group | 907.8 | (500 MHz): 0.94 (d, J = 7.13 Hz, 3H) 1.07 (d, J = 7.40 Hz, 9H) 1.18-1.27 (m, 7H) 1.29 (d, J = 6.03 Hz, 3H) 1.36 (s, 3H) 1.42 (d, J = 14.53 Hz, 1H) 1.54-1.73 (m, 2H) 2.19-2.40 (m, 2H) 2.32 (s, 6H) 2.35 (s, 3H) 2.42-2.70 (m, 7H) 2.74-3.05 (m, 7H) 3.12-3.25 (m, 7H) 3.28 (s, 3H) 3.31 (s, 3H) 3.44-3.53 (m, 1H) 3.58 (d, J = 9.87 Hz, 1H) 3.75 (d, J = 7.40 Hz, 1H) 3.93-4.14 (m, 3H) 4.46 (d, J = 7.13 Hz, 1H) 4.89 (d, J = 4.39 Hz, 1H) 5.11-5.16 (m, 1H) 6.38-6.42 (m, 1H) 6.42-6.46 (m, 1H) 6.51-6.56 (m, 1H) 7.15 (t, J = 8.23 Hz, 1H) |
| 450 | | 3-(piperidin-4-yl)phenoxy group | 892.8 | (500 MHz): 0.94 (d, J = 7.13 Hz, 3H) 1.03 (d, J = 6.86 Hz, 3H) 1.07-1.12 (m, 6H) 1.19-1.26 (m, 7H) 1.29 (d, J = 6.03 Hz, 3H) 1.37 (s, 3H) 1.42-1.69 (m, 5H) 1.80-1.86 (m, 2H) 2.19-2.27 (m, 2H) 2.29 (s, 6H) 2.34-2.46 (m, 2H) 2.50-2.86 (m, 8H) 2.90-3.05 (m, 4H) 3.14-3.26 (m, 4H) 3.29 (s, 3H) 3.31 (s, 3H) 3.44-3.51 (m, 1H) 3.57-3.60 (m, 1H) 3.75 (d, J = 7.40 Hz, 1H) 3.96-4.06 (m, 2H) 4.10-4.15 (m, 1H) 4.46 (d, J = 7.13 Hz, 1H) 4.88-4.91 (m, 1H) 5.11-5.15 (m, 1H) 6.71-6.74 (m, 1H) 6.75-6.77 (m, 1H) 6.79-6.82 (m, 1H) 7.20 (t, J = 7.95 Hz, 1H) |

TABLE 13-continued

| Example | Reference Example | R | ESI MS (M + H) | $^1$H-NMR, CDCl$_3$, δ (ppm) |
|---|---|---|---|---|
| 451 | | (3-(1-methylpiperidin-4-yl)phenoxy)methyl group | 906.7 | (500 MHz): 0.94 (d, J = 7.26 Hz, 3H) 1.03 (d, J = 6.50 Hz, 3H) 1.07 (d, J = 7.64 Hz, 3H) 1.10 (d, J = 7.26 Hz, 3H) 1.19-1.24 (m, 4H) 1.25 (s, 3H) 1.29 (d, J = 6.50 Hz, 3H) 1.36 (s, 3H) 1.43 (d, J = 14.52 Hz, 1H) 1.54-1.69 (m, 2H) 1.78-1.87 (m, 3H) 2.03-2.11 (m, 2H) 2.19-2.27 (m, 2H) 2.29 (s, 6H) 2.33 (s, 3H) 2.34-2.54 (m, 3H) 2.61-2.69 (m, 1H) 2.75-3.05 (m, 10H) 3.13-3.26 (m, 3H) 3.29 (s, 3H) 3.31 (s, 3H) 3.44-3.52 (m, 1H) 3.59 (d, J = 9.56 Hz, 1H) 3.75 (d, J = 7.26 Hz, 1H) 3.93-3.99 (m, 1H) 4.00-4.07 (m, 1H) 4.09-4.14 (m, 1H) 4.46 (d, J = 7.26 Hz, 1H) 4.90 (d, J = 4.59 Hz, 1H) 5.11-5.15 (m, 1H) 6.70-6.74 (m, 1H) 6.76 (br. s., 1H) 6.80-6.83 (m, 1H) 7.20 (t, J = 7.84 Hz, 1H) |
| 452 | | (4-carboxy-3-methylphenoxy)methyl group | 868.3 | (600 MHz): 0.94 (d, J = 7.34 Hz, 3H) 1.04 (d, J = 6.88 Hz, 3H) 1.07 (d, J = 7.34 Hz, 3H) 1.09 (d, J = 7.34 Hz, 3H) 1.19-1.27 (m, 1H) 1.22 (s, 3H) 1.24 (d, J = 5.96 Hz, 3H) 1.28 (d, J = 6.42 Hz, 3H) 1.36 (s, 3H) 1.44 (d, J = 15.13 Hz, 1H) 1.55 (dd, J = 14.67, 5.04 Hz, 1H) 1.74 (d, J = 10.55 Hz, 1H) 2.18-2.26 (m, 1H) 2.36 (d, J = 14.67 Hz, 1H) 2.43 (s, 6H) 2.46-2.53 (m, 1H) 2.58 (s, 3H) 2.63-2.76 (m, 2H) 2.78-3.07 (m, 7H) 3.13-3.19 (m, 1H) 3.20-3.31 (m, 2H) 3.28 (s, 3H) 3.32 (s, 3H) 3.47-3.55 (m, 1H) 3.57 (d, J = 10.09 Hz, 1H) 3.71-3.77 (m, 1H) 3.94-4.07 (m, 2H) 4.10-4.15 (m, 1H) 4.50 (d, J = 7.34 Hz, 1H) 4.87 (d, J = 4.58 Hz, 1H) 5.13 (dd, J = 6.42, 4.58 Hz, 1H) 6.65-6.74 (m, 2H) 7.92 (d, J = 9.17 Hz, 1H) |
| 453 | | (3-(1-phenylethyl)phenoxy)methyl group | 913.5 | (600 MHz): 0.89-0.94 (m, 3H) 1.01 (d, J = 6.42 Hz, 3H) 1.05-1.10 (m, 6H) 1.18-1.21 (m, 1H) 1.21 (d, J = 5.96 Hz, 3H) 1.24 (s, 3H) 1.28 (d, J = 5.96 Hz, 3H) 1.35 (s, 3H) 1.42 (d, J = 14.67 Hz, 1H) 1.57 (dd, J = 15.13, 5.04 Hz, 1H) 1.59-1.62 (m, 3H) 1.64 (d, J = 12.84 Hz, 1H) 2.19-2.25 (m, 1H) 2.26-2.31 (m, 6H) 2.36 (d, J = 15.13 Hz, 1H) 2.38-2.46 (m, 1H) 2.47-2.54 (m, 1H) 2.57-2.65 (m, 1H) 2.72-2.86 (m, 3H) 2.88-3.04 (m, 4H) 3.12-3.17 (m, 1H) 3.17-3.24 (m, 2H) 3.27 (s, 3H) 3.30-3.32 (m, 3H) 3.43-3.51 (m, 1H) 3.57 (d, J = 9.63 Hz, 1H) 3.74 (d, J = 7.34 Hz, 1H) 3.91-3.95 (m, 1H) 3.99-4.13 (m, 3H) 4.45 (d, J = 7.34 Hz, 1H) 4.88 (d, J = 4.58 Hz, 1 H) 5.10 (dd, J = 5.96, 4.58 Hz, 1H) 6.69 (dd, J = 7.79. 2.29 Hz, 1H) 6.74 (s, 1H) 6.78 (d, J = 8.25 Hz, 1H) 7.13-7.19 (m, 2H) 7.19-7.23 (m, 2H) 7.24-7.29 (m, 2H) |
| 454 | | (4-(diethylamino)-2-(hydroxymethyl)phenoxy)methyl group | 910.5 | (500 MHz): 0.95 (d, J = 7.13 Hz, 3H) 1.01-1.10 (m, 9H) 1.13-1.19 (m, 6H) 1.20-1.27 (m, 7H) 1.29 (d, J = 6.03 Hz, 3H) 1.36 (s, 3H) 1.40-1.46 (m, 1H) 1.53-1.70 (m, 2H) 2.19-2.39 (m, 2H) 2.32 (s, 6H) 2.41-2.55 (m, 2H) 2.68-3.07 (m, 8H) 3.15-3.38 (m, 7H) 3.28 (s, 3H) 3.30 (s, 3H) 3.45-3.53 (m, 1 H) 3.59 (d, J = 9.05 Hz, 1H) 3.75 (d, J = 7.40 Hz, 1H) 3.98-4.07 (m, 2H) 4.13-4.19 (m, 1H) 4.52 (d, J = 4.39 Hz, 3H) 4.85-4.90 (m, 1H) 5.15-5.20 (m, 1H) 6.18-6.25 (m, 2H) 7.06 (d, J = 8.23 Hz, 1H) |
| 455 | | styryl group | 805 FAB MASS | (300 MHz): 0.97 (d, J = 7.14 Hz, 3H) 1.05 (d, J = 6.59 Hz, 3H) 1.13 (d, J = 7.14 Hz, 3H) 1.14 (d, J = 7.42 Hz, 3H) 1.19-1.27 (m, 1H) 1.24 (d, J = 7.14 Hz, 3H) 1.25 (s, 3H) 1.30 (d, J = 6.32 Hz, 3H) 1.38 (s, 3H) 1.46 (d, J = 15.11 Hz, 1H) 1.58 (dd, J = 15.11 4.95 Hz, 1H) 1.62-1.72 (m, 1H) 2.18-2.62 (m, 5H) 2.31 (s, 6H) 2.82-3.29 (m, 9H) 3.30 (s, 3H) 3.32 (s, 3H) 3.45-3.56 (m, 1H) 3.62 (d, J = 9.62 Hz, 1H) 3.79 (d, J = 7.14 Hz, 1H) 3.99-4.10 (m, 1H) 4.49 (d, J = 7.14 Hz, 1H) 4.91 (d, J = 4.67 Hz, 1H) 5.00 (t, J = 5.22 Hz, 1H) 6.27 (dd, J = 15.93, 7.97 Hz, 1H) 6.41 (d, J = 15.93 Hz, 1H) 7.17-7.24 (m, 1H) 7.26-7.39 (m, 4H) |
| 456 | | phenethyl group | 807 FAB MASS | (400 MHz): 0.95 (d, J = 7.30 Hz, 3H) 1.02 (d, J = 6.57 Hz, 3H) 1.10 (d, J = 7.55 Hz, 3H) 1.17 (d, J = 7.06 Hz, 3H) 1.19-1.27 (m, 1H) 1.23 (d, J = 6.09 Hz, 3H) 1.26 (s, 3 H) 1.30 (d, J = 6.09 Hz, 3H) 1.36 (s, 3H) 1.38 (d, J = 16.80 Hz, 1H) 1.52-1.88 (m, 4H) 2.02-2.61 (m, 7H) 2.30 (s, 6H) 2.77-3.25 (m, 3H) 3.28 (s, 3H) 3.33 (s, 3H) 3.45-3.54 (m, 1H) 3.62 (d, J = 9.50 Hz, 1H) 3.77 (d, J = 7.06 Hz, 1H) 4.00-4.09 (m, 1H) 4.49 (d, J = 7.31 Hz, 1H) 4.89-4.97 (m, 2H) 7.14-7.22 (m, 3H) 7.27-7.32 (m, 2H) |

| Example | Reference Example | R | ESI MS (M + H) | $^1$H-NMR, CDCl$_3$, δ (ppm) |
|---|---|---|---|---|
| 457 | | 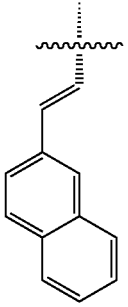 | 855 | (400 MHz): 0.99 (d, J = 7.08 Hz, 3H) 1.07 (d, J = 6.58 Hz, 3H) 1.13 (d, J = 7.08 Hz, 3H) 1.17 (d, J = 7.57 Hz, 3H) 1.19-1.27 (m, 1H) 1.Z4 (d, J = 4.64 Hz, 3H) 1.25 (s, 3H) 1.31 (d, J = 6.35 Hz, 3H) 1.40 (s, 3H) 1.48 (d, J = 14.90 Hz, 1H) 1.53-1.73 (m, 3H) 2.20-2.39 (m, 3H) 2.23 (s, 6H) 2.42-2.62 (m, 2H) 2.87-3.35 (m, 9H) 3.31 (s, 6H) 3.45-3.56 (m, 1H) 3.63 (d, J = 9.76 Hz, 1H) 3.80 (d, J = 7.08 Hz, 1H) 4.00-4.10 (m, 1H) 4.51 (d, J = 7.08 Hz, 1H) 4.91 (d, J = 4.64 Hz, 1H) 5.04 (t, J = 4.89 Hz, 1H) 6.40 (dd, J = 15.87. 8.55 Hz, 1 H) 6.57 (d, J = 15.87 Hz, 1H) 7.39-7.48 (m, 2H) 7.61 (dd, J = 8.54, 1.71 Hz, 1H) 7.69 (s, 1H) 7.76-7.82 (m, 3H) |
| 458 | | 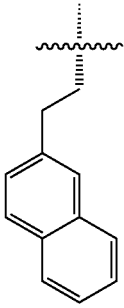 | 857 FAB MASS | (400 MHz): 0.95 (d, J = 7.31 Hz, 3H) 1.01 (d, J = 6.57 Hz, 3H) 1.12 (d, J = 7.30 Hz, 3H) 1.16 (d, J = 7.31 Hz, 3H) 1.19-1.27 (m, 1H) 1.23 (d, J = 6.09 Hz, 3H) 1.25 (s, 3 H) 1.31 (d, J = 6.09 Hz, 3H) 1.37 (s, 3H) 1.39 (d, J = 15.06 Hz, 1H) 1.54-1.98 (m, 4H) 2.05-2.56 (m, 5H) 2.30 (s, 6H) 2.68-2.77 (m, 2H) 2.81-3.25 (m, 9H) 3.29 (s, 3H) 3.33 (s, 3H) 3.45-3.55 (m, 1H) 3.63 (d, J = 9.75 Hz, 1H) 3.78 (d, J = 7.06 Hz, 1H) 3.99-4.09 (m, 1H) 4.49 (d, J = 7.06 Hz, 1H) 4.92 (d, J = 4.39 Hz, 1H) 4.97 (t, J = 4.14 Hz, 1H) 7.31 (dd, J = 8.52, 1.70 Hz, 1H) 7.39-7.48 (m, 2H) 7.60 (s, 1H) 7.75-7.82 (m, 3H) |
| 459 | | 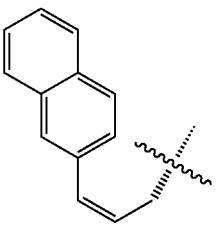 | 869 | (300 MHz): 0.75 (d, J = 7.14 Hz, 3H) 0.90 (d, J = 7.14 Hz, 3H) 0.93 (d, J = 5.49 Hz, 3H) 1.21 (d, J = 6.04 Hz, 3H) 1.18-1.36 (m, 16H) 1.25 (s, 3H) 1.52 (dd, J = 15.4, J = 5.22 Hz, 1H) 1.58-1.74 (m, 1H) 2.06-2.18 (m, 1H) 2.27 (d, J = 15.1 Hz, 1H) 2.33 (s, 3H) 2.35-2.60 (m, 4H) 2.68-3.03 (m, 6H) 3.04-3.10 (m, 1H) 3.11-3.21 (m, 1H) 3.23 (s, 3H) 3.25 (s, 3H) 3.41-3.52 (m, 1H) 3.68 (d, J = 7.42 Hz, 1H) 3.93-4.04 (m, 1H) 4.43 (d, J = 7.14 Hz, 1H) 4.81 (d, J = 4.40 Hz, 1H) 4.88-4.96 (m, 1H) 5.62-5.73 (m, 1H) 6.59 (d, J = 11.8 Hz, 1H) 7.37-7.48 (m, 3H) 7.70 (s, 1 H) 7.74-7.87 (m, 3H) |
| 460 | | 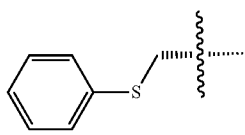 | 825 | (300 MHz): 0.94 (d, J = 7.14 Hz, 3H) 0.99 (d, J = 6.87 Hz, 3H) 1.12 (d, J = 7.42 Hz, 3H) 1.16 (d, J = 7.14 Hz, 3H) 1.23 (d, J = 6.04 Hz, 3H) 1.26 (s, 3H) 1.30 (d, J = 6.32 Hz, 3H) 1.36 (s, 3H) 1.42 (d, J = 14.8 Hz, 1H) 1.59 (dd, J = 15.1, 4.95 Hz, 1H) 1.61-1.70 (m, 1H) 2.16-2.26 (m, 1H) 2.30 (s, 6H) 2.33-2.57 (m, 3H) 2.77-3.06 (m, 7H) 3.08-3.15 (m, 1 H) 3.16-3.25 (m , 2H) 3.28 (s, 3H) 3.33 (s, 3H) 3.43-3.55 (m, 1H) 3.60 (d, J = 9.34 Hz, 1H) 3.77 (d, J = 7.42 Hz, 1H) 3.99-4.10 (m, 1H) 4.48 (d, J = 7.14 Hz, 1H) 4.92 (d, J = 4.67 Hz, 1H) 4.96-5.03 (m, 1H) 7.18-7.22 (m , 1H) 7.24-7.38 (m, 4H) |
| 461 | | 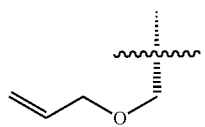 | 773 | (400 MHz): 0.94 (d, J = 7.07 Hz, 3H) 1.01 (d, J = 6.82 Hz, 3H) 1.11 (d, J = 7.55 Hz, 3H) 1.16 (d, J = 7.06 Hz, 3H) 1.19-1.27 (m, 1H) 1.23 (d, J = 6.09 Hz, 3H) 1.26 (s, 3H) 1.30 (d, J = 6.09 Hz, 3H) 1.36 (s, 3H) 1.43 (d, J = 14.61 Hz, 1H) 1.56-1.69 (m, 2H) 2.20-2.57 (m, 7H) 2.29 (s, 6H) 2.74 (t, J = 9.25 Hz, 1H) 2.78-3.07 (m, 6H) 3.11-3.24 (m, 3H) 3.28 (s, 3H) 3.33 (s, 3H) 3.35-3.51 (m, 2H) 3.56-3.64 (m, 2H) 3.76 (d, J = 7.55 Hz, 1H) 3.94-4.08 (m, 3H) 4.47 (d, J = 7.31 Hz, 1H) 4.73-4.93 (m, 2H) 5.03 (dd, J = 6.09, 4.14 Hz, 1H) 5.15-5.20 (m, 1H) 5.22-5.30 (m, 1H) 5.84-5.94 (m, 1H) |

TABLE 13-continued

| Example | Reference Example | R | ESI MS (M + H) | $^1$H-NMR, CDCl$_3$, δ (ppm) |
|---|---|---|---|---|
| 462 | | 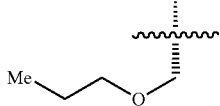 | 775 FAB MASS | (400 MHz): 0.90 (t, J = 7.31 Hz, 3H) 0.94 (d, J = 7.06 Hz, 3H) 1.01 (d, J = 6.82 Hz, 3H) 1.11 (d, J = 7.55 Hz, 3H) 1.15 (d, J = 6.82 Hz, 3H) 1.19-1.27 (m, 1H) 1.23 (d, J = 5.85 Hz, 3H) 1.25 (s, 3H) 1.30 (d, J = 6.09 Hz, 3H) 1.36 (s, 3H) 1.43 (d, J = 15.10 Hz, 1H) 1.51-1.70 (m, 4H) 2.20-2.57 (m, 7H) 2.30 (s, 6H) 2.73 (t, J = 9.25 Hz, 1H) 2.77-3.07 (m, 6H) 3.10-3.25 (m, 3H) 3.28 (s, 3H) 3.30-3.65 (m, 6H) 3.33 (s, 3H) 3.76 (d, J = 7.30 Hz, 1H) 3.98-4.09 (m, 1H) 4.48 (d, J = 7.30 Hz, 1H) 4.89-4.95 (m, 1H) 4.99-5.06 (m, 1H) |
| 463 | | 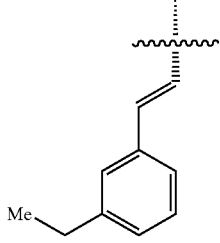 | 833 | (400 MHz): 0.97 (d, J = 7.06 Hz, 3H) 1.05 (d, J = 6.82 Hz, 3H) 1.13 (d, J = 6.82 Hz, 3H) 1.15 (d, J = 7.31 Hz, 3H) 1.19-1.27 (m, 10H) 1.30 (d, J = 6.09 Hz, 3H) 1.38 (s, 3H) 1.46 (d, J = 14.85 Hz, 1H) 1.58 (dd, J = 15.10, 4.87 Hz, 1H) 1.62-1.73 (m, 1H) 2.19-2.50 (m, 4H) 2.30 (s, 6H) 2.53-2.68 (m, 3H) 2.83-3.36 (m, 9H) 3.30 (s, 3H) 3.32 (s, 3H) 3.45-3.55 (m, 1H) 3.62 (d, J = 9.50 Hz, 1H) 3.79 (d, J = 7.07 Hz, 1H) 4.00-4.10 (m, 1H) 4.50 (d, J = 7.30 Hz, 1H) 4.92 (d, J = 4.38 Hz, 1H) 5.00 (t, J = 4.87 Hz, 1H) 6.26 (dd, J = 15.83, 8.28 Hz, 1H) 6.39 (d, J = 15.83 Hz, 1H) 7.04-7.08 (m, 1H) 7.15-7.26 (m, 3H) |
| 464 | | 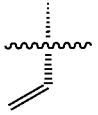 | 729 FAB MASS | (400 MHz): 0.95(d, J = 7.1 Hz, 3H) 1.02 (d, J = 6.8 Hz, 3H) 1.12 (d, J = 7.6 Hz, 3H) 1.16 (d, J = 7.1 Hz, 3H) 1.20-1.27 (m, 7H) 1.30 (d, J = 6.3 Hz, 3H) 1.37 (s, 3H) 1.43 (d, J = 14.1 Hz, 1H) 1.59 (dd, J = 15.1, 5.1 Hz) 1.62-1.69 (m, 1H) 2.17-2.28 (m, 1H) 2.29 (s, 6H) 2.38 (d, J = 15.3 Hz, 1H) 2.40-2.57 (m, 2H) 2.70-2.83 (m, 6H) 2.85-3.06 (m, 2H) 3.11-3.16 (m, 1H) 3.18-3.25 (m, 2H) 3.29 (s, 3H) 3.33 (s, 3H) 3.45-3.54 (m, 1H) 3.60 (d, J = 8.8 Hz, 1H) 3.78 (d, J = 7.3 Hz, 1 H) 4.05 (dq, J = 9.3, 6.1 Hz, 1H) 4.49 (d, J = 7.3 Hz, 1H) 4.92 (d, J = 4.6 Hz, 1H) 4.93-4.97 (m, 1H) 5.02 (s, 1H) 5.05 (dd, J = 8.5, 1.7 Hz, 1H) 5.88 (ddd, J = 10.5, 8.5, 8.3 Hz, 1H) |
| 465 | | 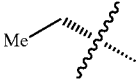 | 731 FAB MASS | (400 MHz): 0.87 (t, J = 7.3 Hz, 3H) 0.94 (d, J = 7.3 Hz, 3H) 1.02 (d, J = 6.8 Hz, 3H) 1.11 (d, J = 7.6 Hz, 3H) 1.17 (d, J = 7.1 Hz, 3H) 1.19-1.27 (m, 7H) 1.30 (d, J = 6.1 Hz, 3H) 1.33-1.56 (m, 6H) 1.59 (dd, J = 3.7, 10.7 Hz) 1.62-1.68 (m, 1H) 1.90-2.02 (m, 1H) 2.14-2.33 (m, 8H) 2.35-2.55 (m, 3H) 2.74-3.07 (m, 6H) 3.10 (d, J = 4.4 Hz, 1H) 3.16 (d, J = 11.7 Hz, 1H) 3.21 (dd, J = 7.3, 10.5 Hz, 1H) 3.28 (s, 3H) 3.33 (s, 3H) 3.36 (br s 1H) 3.44-3.54 (m, 1H) 3.61 (d, J = 8.8 Hz, 1H) 3.77 (d, J = 7.1 Hz, 1H) 4.04 (dq, J = 9.3, 6.3 Hz, 1H) 4.49 (d, J = 7.3 Hz, 1H) 4.90-4.96 (m, 2H) |
| 466 | | 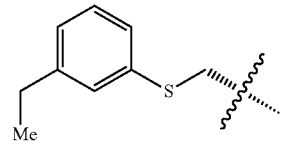 | 853.5 | (400 MHz): 0.94 (d, J = 7.1 Hz, 3H) 0.99 (d, J = 6.8 Hz, 3H) 1.11 (d, J = 7.3 Hz, 3H) 1.19-1.28 (m, 10H) 1.30 (d, J = 6.3 Hz, 3H) 1.36 (s, 3H) 1.41 (d, J = 14.4 Hz, 1H) 1.60 (dd, J = 15.1, 1.0 Hz, 1H) 1.69 (d, J = 12.7 Hz, 1H) 2.16-2.28 (m, 2H) 2.32 (s, 6H) 2.34-2.55 (m, 4H) 2.62 (q, J = 7.8 Hz, 2H) 2.78-3.07 (m, 7H) 3.08-3.16 (m, 2H) 3.19-3.23 (m, 2H) 3.29 (s, 3 H) 3.42 (s, 3H) 3.44-3.54 (m, 1H) 3.60 (d, J = 10.0 Hz, 1H) 3.78 (d, J = 7.1 Hz, 1H) 402 (dq, J = 9.0, 6.1 Hz, 1H) 4.48 (d, J = 7.1 Hz, 1H) 4.92 (d, J = 4.6 Hz, 1H) 5.97-6.02 (m, 1H) 7.02 (d, J = 7.6 Hz, 1H) 7.13-7.23 (m, 3H) |
| 467 | | 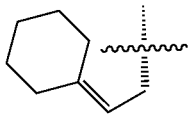 | 811 | (400 MHz): 0.94 (d, J = 7.31 Hz, 3H) 0.95-1.69 (m, 10H) 1.02 (d, J = 6.82 Hz, 3H) 1.12 (d, J = 7.55 Hz, 3H) 1.17 (d, J = 7.06 Hz, 3H) 1.23 (d, J = 5.85 Hz, 3H) 1.26 (s, 3H) 1.30 (d, J = 6.09 Hz, 3H) 1.36 (s, 3H) 2.00-2.57 (m, 13H) 2.30 (s, 6H) 2.72-3.37 (m, 8H) 3.29 (s, 3H) 3.34 (s, 3H) 3.44-3.55 (m, 3H) 3.61 (d, J = 9.74 Hz, 1H) 3.78 (d, J = 7.06 Hz, 1H) 3.99-4.10 (m, 1H) 4.50 (d, J = 7.31 Hz, 1H) 4.87-5.03 (m, 3H) |
| 468 | | 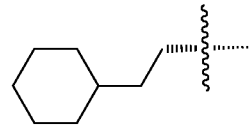 | 813 FAB MASS | (400 MHz): 0.78-1.75 (m, 19H) 0.94 (d, J = 7.31 Hz, 3H) 1.02 (d, J = 6.57 Hz, 3H) 1.11 (d, J = 7.31 Hz, 3H) 1.17 (d, J = 6.82 Hz, 3H) 1.23 (d, J = 6.09 Hz, 3H) 1.26 (s, 3H) 1.30 (d, J = 6.09 Hz, 3H) 1.36 (s, 3H) 1.93-2.07 (m, 1H) 2.08-2.57 (m, 6 H) 2.30 (s, 6H) 2.74-3.35 (m, 8H) 3.28 (s, 3H) 3.34 (s, 3H) 3.44-3.55 (m, 1H) 3.61 (d, J = 9.74 Hz, 1H) 3.77 (d, J = 7.07 Hz, 1H) 4.00-4.11 (m, 1H) 4.49 (d, J = 7.31 Hz, 1H) 4.88-4.96 (m, 2H) |

TABLE 13-continued

| Example | Reference Example | R | ESI MS (M + H) | $^1$H-NMR, CDCl$_3$, δ (ppm) |
|---|---|---|---|---|
| 469 | | (phenylacetylene group) | 802 | (400 MHz): 0.97 (d, J = 7.23 Hz, 3H) 1.04 (d, J = 6.81 Hz, 3H) 1.07 (d, J = 7.50 Hz, 3H) 1.16 (d, J = 7.10 Hz, 3H) 1.22 (d, J = 7.31 Hz, 3H) 1.25 (s, 3H) 1.30 (d, J = 6.20 Hz, 1H) 1.38 (s, 3H) 1.44 (d, J = 14.0 Hz, 1H) 1.58 (dd, J = 15.2, 4.90 Hz, 1H) 1.64-1.67 (m, 1H) 2.21-2.26 (m, 2H) 2.29 (s, 6H) 2.38 (d, J = 6.90 Hz, 1H) 2.42-2.46 (m, 1H) 2.56-2.61 (m, 1H) 2.90 (dd, J = 11.9, 3.90 Hz, 1H) 2.95-3.05 (m, 5H) 3.14-3.30 (m, 6H) 3.30 (s, 3H) 3.31 (s, 3H) 3.47-3.51 (m, 1H) 3.66 (d, J = 8.70 Hz, 1H) 3.79 (d, J = 7.30 Hz, 1H) 4.02-4.06 (m, 1H) 4.47 (d, J = 7.20 Hz, 1H) 4.90 (d, J = 4.60 Hz, 1H) 5.10 (dd, J = 5.30, 4.10 Hz, 1H) 7.24-7.30 (m, 3H) 7.36-7.41 (m, 2H) |
| 470 | | (cyclopentylidenemethyl group) | 797 FAB MASS | (500 MHz): 0.94 (d, J = 7.2 Hz, 3H) 1.02 (d, J = 6.7 Hz, 3H) 1.12 (d, J = 7.4 Hz, 3H) 1.16 (d, J = 7.1 Hz, 3H) 1.19-1.27 (m, 8H) 1.30 (d, J = 6.2 Hz, 3H) 1.36 (s, 3H) 1.38 (d, J = 15.3 Hz, 1H) 1.55-1.69 (m, 7H) 2.00-2.27 (m, 8H) 2.30 (s, 6H) 2.38 (d, J = 15.0 Hz, 1H) 2.41-2.56 (m, 2H) 2.73-3.07 (m, 6H) 3.08-3.13 (m, 1H) 3.17 (dd, J = 11.7, 7.3 Hz, 1H) 3.22 (dd, J = 10.2, 7.3 Hz, 1H) 3.28 (s, 3H) 3.34 (s, 3H) 3.46-3.53 (m, 1H) 3.62 (d, J = 9.7 Hz, 1H) 3.78 (d, J = 7.0 Hz, 1H) 4.05 (dq, J = 9.1, 6.3 Hz, 1H) 4.49 (d, J = 7.2 Hz, 1H) 4.89-4.95 (m, 2H) 5.13-5.19 (m, 1H) |
| 471 | | (2-cyclopentylethyl group) | 799 FAB MASS | (500 MHz): 0.94 (d, J = 7.0 Hz, 3H) 1.01-1.08 (m, 4H) 1.11 (d, J = 7.4 Hz, 3H) 1.17 (d, J = 7.1 Hz, 3H) 1.20-1.27 (m, 10H) 1.30 (d, J = 6.2 Hz, 3H) 1.34-1.39 (m, 4H) 1.43-1.54 (m, 3H) 1.55-1.63 (m, 3H) 1.64-1.78 (m, 5H) 1.97-2.10 (m, 1H) 2.13-2.27 (m, 2H) 2.30 (s, 6H) 2.38 (d, J = 15.1 Hz, 1H) 2.42-2.49 (m, 2H) 2.75-3.06 (m, 6H) 3.08-3.13 (m, 1H) 3.16 (d, J = 11.8 Hz, 1H) 3.21 (dd, J = 10.2, 7.2 Hz, 1H) 3.28 (s, 3H) 3.34 (s, 3H) 3.46-3.56 (m, 1H) 3.62 (d, J = 9.0 Hz, 1H) 3.77 (d, J = 7.0 Hz, 1H) 4.05 (dq, J = 9.1, 6.2 Hz, 1H) 4.49 (d, J = 7.2 Hz, 1H) 4.90-4.97 (m, 2H) |
| 472 | | (styryl group) | 804 | (400 MHz): 0.95 (d, J = 7.00 Hz, 3H) 0.98 (d, J = 6.41 Hz, 3H) 1.07 (d, J = 7.50 Hz, 3H) 1.16 (d, J = 7.10 Hz, 3H) 1.22 (d, J = 7.31 Hz, 3H) 1.25 (s, 3H) 1.30 (d, J = 6.20 Hz, 1H) 1.38 (s, 3H) 1.44 (d, J = 14.6 Hz, 1H) 1.58 (dd, J = 15.1, 4.90 Hz, 1H) 1.63-1.68 (m, 1H) 1.68-1.87 (m, 2H) 2.21-2.28 (m, 2H) 2.30 (s, 6H) 2.38 (d, J = 15.1 Hz, 1H) 2.41-2.46 (m, 1H) 2.54-2.60 (m, 1H) 2.78-3.05 (m, 12H) 3.09-3.26 (m, 6H) 3.30 (s, 3H) 3.33 (s, 3H) 3.46-3.52 (m, 1H) 3.62 (d, J = 9.80 Hz, 1H) 3.78 (t, J = 7-40 Hz, 1H) 4.02-4.08 (m, 1H) 4.49 (d, J = 7.20 Hz, 1H) 4.92 (d, J = 4.70 Hz, 1H) 4.99 (dd, J = 6.00, 4.50 Hz, 1H) 5.78 (dd, J = 11.5, 10.1 Hz, 1H) 6.54 (d, J = 11.6 Hz, 1H) 7.14-7.37 (m, 5H) |
| 473 | | (3-methylbenzyloxymethyl group) | 835 FAB MASS | (400 MHz): 0.95 (d, J = 7.06 Hz, 3H) 1.01 (d, J = 6.58 Hz, 3H) 1.10 (d, J = 7.30 Hz, 3H) 1.16 (d, J = 7.07 Hz, 3H) 1.19-1.27 (m, 10H) 1.30 (d, J = 6.09 Hz, 3H) 1.36 (s, 3H) 1.38 (d, J = 14.85 Hz, 1H) 1.55-1.87 (m, 4H) 2.00-2.58 (m, 7H) 2.30 (s, 6H) 2.63 (q, J = 7.55 Hz, 2H) 2.79-3.24 (m, 9H) 3.28 (s, 3H) 3.33 (s, 3H) 3.44-3.54 (m, 1H) 3.62 (d, J = 9.98 Hz, 1H) 3.77 (d, J = 7.06 Hz, 1H) 4.00-4.09 (m, 1H) 4.49 (d, J = 7.06 Hz, 1H) 4.90-4.97 (m, 2H) 6.96-7.05 (m, 3H) 7.20 (t, J = 7.55 Hz, 1H) |
| 474 | | (2-(tert-butoxy)ethoxymethyl group) | 833.2 | (600 MHz): 0.93 (d, J = 6.88 Hz, 3H) 1.00 (d, J = 6.42 Hz, 3H) 1.09 (d, J = 7.34 Hz, 3H) 1.15 (d, J = 6.88 Hz, 3H) 1.18 (s, 9H) 1.22 (d, J = 5.96 Hz, 3H) 1.25 (s, 3H) 1.29 (d, J = 6.42 Hz, 3H) 1.35 (s, 3H) 1.37-1.72 (m, 3H) 2.17-2.54 (m, 11H) 2.69-2.90 (m, 4H) 2.91-3.04 (m, 3H) 3.11-3.24 (m, 3H) 3.27 (s, 3H) 3.32 (s, 3H) 3.42-3.54 (m, 6H) 3.56-3.65 (m, 3H) 3.75 (d, J = 7.34 Hz, 1H) 3.99-4.06 (m, 1H) 4.47 (d, J = 6.88 Hz, 1H) 4.90 (d, J = 4.58 Hz, 1H) 4.99-5.04 (m, 1H) |

In Examples 391 to 439, the compounds shown in Table 13 were synthesized in the same manner as that of Example 29 by using corresponding phenol reagents.

Example 440

By using the compound obtained in Example 23, (1) (30 mg) and phenol (5.3 mg) as starting materials, the compound shown in Table 13 (13.5 mg) was obtained in the same manner as that of Example 29.

Example 441

By using the compound obtained in Example 23, (1) (40 mg) and 3-t-butylphenol (11.2 mg) as starting materials, the compound shown in Table 13 (22.4 mg) was obtained in the same manner as that of Example 29.

Example 442

(1) By using the compound obtained in Reference Example 1 (437 mg) and the compound obtained in Reference Example 82 (185 mg) as starting materials, a cyclized compound (226 mg) was obtained in the same manners as those of Example 1, (1) and (2).
(2) By using the compound obtained in (1) mentioned above (70 mg) as a starting material, the compound shown in Table 13 (39 mg) was obtained in the same manner as that of Example 1, (3).

Example 443

(1) By using the compound obtained in Example 156, (1) (20 mg) and 1-iodonaphthalene (27 µl) as starting materials, a 1-naphthylethynyl compound (14 mg) was obtained in the same manner as that of Example 157, (1).
(2) By using the compound obtained in (1) mentioned above (14 mg) as a starting material, the compound shown in Table 13 (8 mg) was obtained in the same manner as that of Example 1, (3).

Example 444

(1) By using the compound obtained in Example 156, (1) (20 mg) and 2-bromonaphthalene (38 mg) as starting materials, a 2-naphthylethynyl compound (6 mg) was obtained in the same manner as that of Example 157, (1).
(2) By using the compound obtained in (1) mentioned above (6 mg) as a starting material, the compound shown in Table 13 (3 mg) was obtained in the same manner as that of Example 1, (3).

Example 445

By using the compound obtained in Example 392 (27.5 mg) as a starting material, the compound shown in Table 13 (10.8 mg) was obtained in the same manner as that of Example 87.

Example 446

By using the compound obtained in Example 393 (27.6 mg) as a starting material, the compound shown in Table 13 (15.1 mg) was obtained in the same manner as that of Example 87.

Example 447

By using the compound obtained in Example 398 (40 mg) as a starting material, the compound shown in Table 13 (20.2 mg) was obtained in the same manner as that of Example 87.

Example 448

The compound obtained in Example 397 (130 mg) was dissolved in tetrahydrofuran (2.0 ml), the solution was added with 5% palladium-carbon (130 mg), and the mixture was stirred at room temperature for 16 hours under a hydrogen atmosphere of 1 atm. The reaction mixture was filtered, then the filtrate was concentrated under reduced pressure, the resulting residue was dissolved in tetrahydrofuran (1.0 ml), the solution was added with 5% palladium-carbon (40 mg), and the mixture was stirred at room temperature for 12 hours under a hydrogen atmosphere of 1 atm. The reaction mixture was filtered, then the filtrate was concentrated under reduced pressure, and the resulting residue was purified by preparative thin layer chromatography (chloroform:methanol:28% aqueous ammonia=10:1:0.1) to obtain the compound shown in Table 13 (5.7 mg).

Example 449

By using the compound obtained in Example 13, (1) (30 mg) and 3-(4-methylpiperazin-1-yl)phenol (10 mg) as starting materials, the compound shown in Table 13 (9 mg) was obtained in the same manner as that of Example 29.

Example 450

By using the compound obtained in Example 399 (30 mg) as a starting material, the compound shown in Table 13 (13.9 mg) was obtained in the same manner as that of Example 448.

Example 451

By using the compound obtained in Example 450 (10 mg) as a starting material, the compound shown in Table 13 (6.9 mg) was obtained in the same manner as that of Example 14.

Example 452

(1) By using the compound obtained in Example 13, (1) ((50 mg) and the compound obtained in Reference Example 83 (22.5 mg) as starting materials, an ether compound (65.6 mg) was obtained in the same manner as that of Example 29.
(2) By using the compound obtained in (1) mentioned above (30 mg) as a starting material, a triol compound (8.1 mg) was obtained in the same manner as that of Example 80, (2).
(3) By using a compound obtained in the same manner as that of (2) mentioned above (12 mg) as a starting material, the compound shown in Table 13 (9.8 mg) was obtained in the same manner as that of Example 448.

Example 453

By using the compound obtained in Example 407 (28 mg) as a starting material, the compound shown in Table 13 (23.5 mg) was obtained in the same manner as that of Example 448.

Example 454

The compound obtained in Example 408 (20 mg) was dissolved in methanol (0.5 ml), the solution was added with sodium borohydride (2.0 mg) under ice cooling, and the mixture was stirred for 2 hours. The mixture was added with saturated aqueous sodium hydrogencarbonate and ethyl acetate, the layers were separated, and the organic layer was dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 13 (10.3 mg).

Example 455

(1) By using the compound obtained in Reference Example 1 (1.77 g) and the compound obtained in Reference Example 84 (2.40 g) as starting materials, a lactonization precursor (1.26 g) was obtained in the same manner as that of Example 1, (1).

(2) 4-Dimethylaminopyridine (577 mg) and 2-methyl-6-nitrobenzoic anhydride (814 mg) were dissolved in chloroform (150 ml), the solution was warmed to 50° C., and then added dropwise with a solution of the compound obtained in (1) mentioned above (1.03 g) in chloroform (50 ml) over 30 minutes, and the mixture was stirred at the same temperature for 3 hours. The reaction mixture was left to cool to room temperature, and then washed successively with saturated aqueous ammonium chloride and saturated aqueous sodium hydrogencarbonate, and the organic layer was dried over anhydrous magnesium sulfate, and filtered. The filtrate was concentrated under reduced pressure, and the resulting residue was purified by silica gel column chromatography (hexane:acetone=70:1 to 30:1) to obtain a cyclized compound (323 mg).

(3) By using the compound obtained in (2) mentioned above (30 mg) and iodobenzene (25.2 μl) as starting materials, the compound shown in Table 13 (9 mg) was obtained in the same manners as those of Example 144, (1) and Example 1, (3).

Example 456

The compound obtained in Example 455 (6.9 mg) was dissolved in a mixed solvent of methanol and ethyl acetate (3:1, 140 μl), the solution was added with 5% palladium-carbon (3.5 mg), and the mixture was stirred at room temperature for 3 hours under a hydrogen atmosphere of 1 atm. The reaction mixture was filtered, then the filtrate was concentrated under reduced pressure, and the resulting residue was purified by preparative thin layer chromatography (ethyl acetate:methanol:28% aqueous ammonia=10:1:0.1) to obtain the compound shown in Table 13 (4.9 mg).

Example 457

By using the compound obtained in Example 455, (2) (36.8 mg) and 2-bromonaphthalene (56.8 mg) as starting materials, the compound shown in Table 13 (3.2 mg) was obtained in the same manners as those of Example 146, (1) and Example 1, (3).

Example 458

By using the compound obtained in Example 457 (8.8 mg) as a starting material, the compound shown in Table 13 (5.7 mg) was obtained in the same manner as that of Example 456.

Example 459

The compound obtained in Example 444 (6.5 mg) was dissolved in 1,4-dioxane (0.5 ml), the solution was added with the Lindlar catalyst (6.6 mg), and the mixture was stirred at room temperature for 13 hours under a hydrogen atmosphere of 1 atm. The reaction mixture was filtered, then the filtrate was concentrated under reduced pressure, and the resulting residue was purified by preparative thin layer chromatography (ethyl acetate:methanol:28% aqueous ammonia=8:1:0.1) to obtain the compound shown in Table 13 (4.3 mg).

Example 460

By using the compound obtained in Example 13, (2) (25 mg) and thiophenol (9.6 μl) as starting materials, the compound shown in Table 13 (13.5 mg) was obtained in the same manners as those of Example 158, (1) and Example 1, (3).

Example 461

(1) The compound obtained in Example 13, (1) (50 mg), 1,4-bis(diphenylphosphino)butane (4 mg), and allyl t-butylcarbonate (78.4 μl) obtained by the method described in the literature (Journal of Organic Chemistry, 2003, vol. 68, p. 8847) were dissolved in tetrahydrofuran (1 ml), the solution was added with tris(dibenzylideneacetone)dipalladium(0), and the mixture was stirred at 70° C. for 2 hours. The reaction mixture was left to cool, and then filtered, the filtrate was concentrated under reduced pressure, and the resulting residue was purified by silica gel column chromatography (hexane:acetone=50:1 to 10:1) to obtain an allyl compound (45.7 mg).

(2) By using the compound obtained in (1) mentioned above (45.7 mg) as a starting material, the compound shown in Table 13 (19.9 mg) was obtained in the same manner as that of Example 1, (3).

Example 462

By using the compound obtained in Example 461 (12.3 mg) as a starting material, the compound shown in Table 13 (10.3 mg) was obtained in the same manner as that of Example 456.

Example 463

By using the compound obtained in Example 455, (2) (30 mg) and 1-bromo-3-ethylbenzene (20.7 mg) as starting materials, the compound shown in Table 13 (16 mg) was obtained in the same manners as those of Example 144, (1) and Example 1, (3).

Example 464

By using the compound obtained in Example 455, (2) (45 mg) as a starting material, the compound shown in Table 13 (25 mg) was obtained in the same manner as that of Example 1, (3).

Example 465

By using the compound obtained in Example 464 (14.4 mg) as a starting material, the compound shown in Table 13 (12.2 mg) was obtained in the same manner as that of Example 456.

Example 466

By using the compound obtained in Example 13, (2) (25 mg) and the compound obtained in Reference Example 85

(16.8 μl) as starting materials, the compound shown in Table 13 (8.7 mg) was obtained in the same manners as those of Example 158 and Example 1, (3).

Example 467

(1) The compound obtained in Example 142, (2) (50 mg) was dissolved in methylene chloride (1 ml), the solution was added with methylenecyclohexane (22.1 μl) and the second generation Grubbs catalyst (15.6 mg), and the mixture was stirred for 3 hours and 30 minutes under reflux by heating. The reaction mixture was filtered, then the filtrate was concentrated under reduced pressure, and the resulting residue was purified by silica gel column chromatography (hexane:ethyl acetate=30:1 to 10:1) to obtain a coupled compound (48.2 mg).
(2) By using the compound obtained in (1) mentioned above (48.2 mg) as a starting material, the compound shown in Table 13 (32.3 mg) was obtained in the same manner as that of Example 1, (3).

Example 468

By using the compound obtained in Example 467 (18 mg) as a starting material, the compound shown in Table 13 (13.6 mg) was obtained in the same manner as that of Example 456.

Example 469

(1) By using the compound obtained in Reference Example 1 (663 mg) and the compound obtained in Reference Example 86 (355 mg) as starting materials, a cyclized compound (120 mg) was obtained in the same manners as those of Example 1, (1) and (2).
(2) By using the compound obtained in (1) mentioned above (100 mg) and iodobenzene (190 mg) as starting materials, a phenylethynyl compound (42 mg) was obtained in the same manner as that of Example 157, (1).
(3) By using the compound obtained in (2) mentioned above as a starting material, the compound shown in Table 13 (27 mg) was obtained in the same manner as that of Example 1, (3).

Example 470

By using the compound obtained in Example 142, (2) (40 mg) and methylenecyclopentane (15.5 μl) as starting materials, the compound shown in Table 13 (15.6 mg) was obtained in the same manner as that of Example 467.

Example 471

By using the compound obtained in Example 470 (14.0 mg) as a starting material, the compound shown in Table 13 (11.9 mg) was obtained in the same manner as that of Example 456.

Example 472

A solution of the compound obtained in Example 469 (25 mg) in ethanol (2 ml) was added with quinoline (0.002 ml) and the Lindlar catalyst (25 mg), and the mixture was stirred for 3 hours and 30 minutes under a hydrogen atmosphere. The reaction mixture was filtered through Celite, then the filtrate was concentrated under reduced pressure, and the resulting residue was purified by preparative thin layer chromatography (chloroform:methanol:28% aqueous ammonia=20:1:0.1) to obtain the compound shown in Table 13 (19 mg).

Example 473

By using the compound obtained in Example 463 (12.4 mg) as a starting material, the compound shown in Table 13 (8.9 mg) was obtained in the same manner as that of Example 456.

Example 474

(1) The compound obtained in Example 461, (1) (48 mg) was dissolved in a mixed solution of tetrahydrofuran and distilled water (2:1, 6 ml), the solution was added with 4 wt % aqueous osmium tetroxide (110 μl) and N-methylmorpholine N-oxide (25 mg), and the mixture was stirred at room temperature for 1 hour. The reaction mixture was added with saturated aqueous sodium hydrogencarbonate and then sodium hydrogensulfite, and then the mixture was stirred, and then extracted with ethyl acetate. The organic layer was dried over anhydrous magnesium sulfate, and filtered. The filtrate was concentrated under reduced pressure to obtain a diol compound (11 mg).
(2) The compound obtained in (1) mentioned above (11 mg) was dissolved in chloroform, the solution was added with 90% lead tetraacetate (6.5 mg) under ice cooling, and the mixture was stirred for 10 minutes. The reaction mixture was added with saturated aqueous sodium hydrogencarbonate and diethyl ether, the layers were separated, and then the organic layer was washed with saturated brine, dried over anhydrous sodium sulfate, and filtered. The filtrate was concentrated under reduced pressure, and the resulting residue was dissolved in tetrahydrofuran (0.5 ml), the solution was added with sodium borohydride (9 mg) and methanol (0.5 ml), and the mixture was stirred for 10 minutes. The reaction mixture was added with saturated aqueous sodium hydrogencarbonate and ethyl acetate, the layers were separated, and then the organic layer was washed with saturated brine, dried over anhydrous magnesium sulfate, and filtered. The filtrate was concentrated under reduced pressure to obtain a hydroxy compound (9 mg).
(3) The compound obtained in (2) mentioned above (9 mg) was dissolved in methylene chloride (1 ml), the solution was added with di-t-butyl dicarbonate (4 mg) and magnesium perchlorate (0.2 mg), and the mixture was heated to 40° C. for 1 hour. The mixture was further added with di-t-butyl dicarbonate (10 mg) and magnesium perchlorate (0.5 mg) 3 times with intervals of 2 hours. The reaction mixture was added with distilled water and chloroform, the layers were separated, and then the organic layer was dried over anhydrous magnesium sulfate, and filtered. The filtrate was concentrated under reduced pressure, and the resulting residue was purified by silica gel column chromatography (hexane:acetone:triethylamine=50:10:0.2) to obtain a t-butyl ether compound (10 mg).
(4) By using the compound obtained in (3) mentioned above (10 mg) as a starting material, the compound shown in Table 13 (2.2 mg) was obtained in the same manner as that of Example 1, (3).

Examples 475 to 479

Preparation methods of the compounds represented by the formula (R) having $X^{1R}$ and $X^{2R}$ defined in Table 14 are shown below.

[Formula 39]

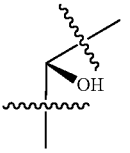

Formula (R)

TABLE 14

| Example | $X^{1R}$ | $X^{2R}$ | ESI MS (M + H) | $^1$H-NMR, CDCl$_3$, δ (ppm) |
|---|---|---|---|---|
| 475 | 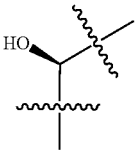 | 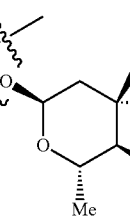 | 707.5 | (600 MHz): 1.00 (d, J = 7.34 Hz, 3H) 1.06 (d, J = 6.42 Hz, 3H) 1.11 (d, J = 7.34 Hz, 3H) 1.18-1.26 (m, 2H) 1.21 (d, J = 6.42 Hz, 3H) 1.25 (d, J = 5.96 Hz, 3H) 1.30 (s, 9H) 1.33 (s, 3H) 1.61-1.67 (m, 3H) 2.24 (s, 6H) 2.36-2.42 (m, 1H) 2.43-2.49 (m, 1H) 2.56-2.63 (m, 2H) 2.94-3.13 (m, 6H) 3.17-3.26 (m, 2H) 3.18 (s, 3H) 3.40-3.45 (m, 1H) 3.49-3.55 (m, 1H) 3.70-3.73 (m, 1H) 3.75-3.78 (m, 1H) 3.97 (dd, J = 9.17, 7.34 Hz, 1H) 4.14 (dd, J = 9.17, 6.88 Hz, 1H) 4.45 (d, J = 7.34 Hz, 1H) 5.16 (t, J = 4.13 Hz, 1H) 6.68-6.72 (m, 1H) 6.90-6.92 (m, 1H) 6.97-6.99 (m, 1H) 7.21 (t, J = 7.79 Hz, 1H) |
| 476 | 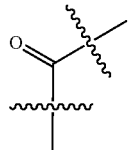 | 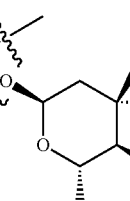 | 863.7 | (600 MHz): 1.03-1.08 (m, 6H) 1.11 (d, J = 6.88 Hz, 3H) 1.19-1.22 (m, 6H) 1.21-1.24 (m, 1H) 1.23 (s, 3H) 1.27 (d, J = 6.42 Hz, 3H) 1.29 (s, 9H) 1.35 (s, 3H) 1.51-1.65 (m, 3H) 2.12-2.22 (m, 2H) 2.27 (s, 6H) 2.28-2.32 (m, 1H) 2.34 (d, J = 15.13 Hz, 1H) 2.39-2.45 (m, 1H) 2.62-2.72 (m, 2H) 2.74-2.82 (m, 2H) 2.89 (t, J = 8.48 Hz, 1H) 2.94-3.02 (m, 2H) 3.06 (t, J = 8.48 Hz, 1H) 3.13 (s, 3H) 3.23 (dd, J = 10.32, 7.11 Hz, 1H) 3.30 (s, 3H) 3.44-3.51 (m, 1H) 3.66 (d, J = 7.34 Hz, 1H) 3.70 (d, J = 7.34 Hz, 1H) 3.83 (q, J = 6.57 Hz, 1H) 3.96-4.03 (m, 2H) 4.09-4.13 (m, 1H) 4.43 (d, J = 6.88 Hz, 1H) 4.79 (d, J = 4.58 Hz, 1H) 5.23-5.28 (m, 1H) 6.65-6.72 (m, 1H) 6.87-6.91 (m, 1H) 6.95-6.99 (m, 1H) 7.19 (t, J = 8.02 Hz, 1H) |
| 477 | 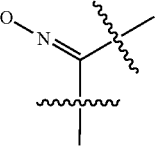 | 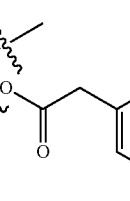 | 878.5 | (600 MHz): 1.03-1.06 (m, 6H) 1.13 (d, J = 6.88 Hz, 3H) 1.15 (d, J = 6.88 Hz, 3H) 1.21-1.24 (m, 1H) 1.22 (d, J = 6.42 Hz, 3H) 1.23 (s, 3H) 1.27-1.29 (m, 3H) 1.29 (s, 9H) 1.41 (s, 3H) 1.52-1.67 (m, 3H) 2.10-2.25 (m, 3H) 2.28 (s, 6H) 2.34 (d, J = 15.13 Hz, 1H) 2.39-2.46 (m, 1H) 2.64-2.69 (m, 1H) 2.71-2.81 (m, 2H) 2.92 (d, J = 12.38 Hz, 1H) 2.98-3.06 (m, 2H) 3.07-3.14 (m, 1H) 3.20 (s, 3H) 3.24 (dd, J = 10.09, 7.34 Hz, 1H) 3.30 (s, 3H) 3.34-3.40 (m, 1H) 3.45-3.52 (m, 1H) 3.62-3.76 (m, 3H) 3.97-4.05 (m, 2H) 4.08-4.13 (m, 1H) 4.45 (d, J = 6.88 Hz, 1H) 4.81 (d, J = 4.58 Hz, 1H) 5.22-5.25 (m, 1H) 6.66-6.69 (m, 1H) 6.88-6.90 (m, 1H) 6.95-6.98 (m, 1H) 7.13-7.17 (m, 1H) |
| 478 | 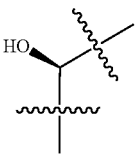 | 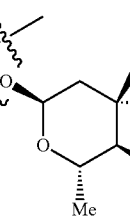 | 826.4 | (600 MHz): 0.86 (d, J = 6.88 Hz, 3H) 0.94 (d, J = 6.88 Hz, 3H) 1.05 (d, J = 6.42 Hz, 3H) 1.10-1.14 (m, 6H) 1.15-1.19 (m, 1H) 1.19-1.23 (m, 1H) 1.26 (s, 3H) 1.30 (s, 9H) 1.56-1.61 (m, 1H) 2.11-2.18 (m, 1H) 2.28 (s, 6H) 2.31-2.38 (m, 1H) 2.59-2.65 (m, 1H) 2.65-2.71 (m, 1H) 2.73-2.80 (m, 1H) 2.91 (t, J = 9.40 Hz, 1H) 2.98-3.14 (m, 6H) 3.17 (dd, J = 10.32, 7.11 Hz, 1H) 3.25 (s, 3H) 3.27 (d, J = 11.92 Hz, 1H) 3.66-3.74 (m, 2H) 3.79 (d, J = 3.67 Hz, 1H) 3.93 (d, J = 6.88 Hz, 1H) 3.97 (dd, J = 9.17, 7.34 Hz, 1H) 4.12 (dd, J = 9.17, 7.34 Hz, 1H) 4.92 (d, J = 10.09 Hz, 1H) 5.14-5.18 (m, 1H) 6.68-6.72 (m, 1H) 6.90-6.92 (m, 1H) 6.97-7.00 (m, 1H) 7.2 (t, J = 8.02 Hz, 1H) 7.29 (dd, J = 7.56, 5.27 Hz, 1H) 7.70-7.74 (m, 1H) 8.52-8.55 (m, 2H) |

TABLE 14-continued

| Example | $X^{1R}$ | $X^{2R}$ | ESI MS (M + H) | $^1$H-NMR, CDCl$_3$, δ (ppm) |
|---|---|---|---|---|
| 479 | (structure) | (structure) | 705.4 | (600 MHz): 0.94 (d, J = 7.34 Hz, 3H) 1.03 (d, J = 6.88 Hz, 3H) 1.16 (d, J = 6.88 Hz, 3H) 1.18-1.24 (m, 1H) 1.20 (d, J = 7.34 Hz, 3H) 1.23 (d, J = 5.96 Hz, 3H) 1.29 (s, 9H) 1.31 (s, 3H) 1.43-1.48 (m, 1H) 1.63-1.69 (m, 1H) 2.19-2.25 (m, 1H) 2.27 (s, 6H) 2.42-2.49 (m, 1H) 2.68-2.74 (m, 1H) 2.74-2.82 (m, 2H) 2.86 (t, J = 9.17 Hz, 1H) 2.90 (s, 3H) 2.90-2.95 (m, 1H) 2.99-3.04 (m, 1H) 3.14-3.23 (m, 3H) 3.48-3.56 (m, 2H) 3.58-3.64 (m, 1H) 4.05 (dd, J = 9.17, 6.88 Hz, 1H) 4.18 (t, J = 8.71 Hz, 1H) 4.28 (d, J = 7.34 Hz, 1H) 4.37 (d, J = 7.34 Hz, 1H) 5.23 (dd, J = 6.19, 3.90 Hz, 1H) 6.72 (dd, J = 8.02, 2.52 Hz, 1H) 6.90-6.92 (m, 1H) 6.96-6.99 (m, 1H) 7.22 (t, J = 7.79 Hz, 1H) |

Example 475

(1) By using the compound obtained in Example 13, (1) (2.0 g) and 3-t-butylphenol (559 mg) as starting materials, an ether compound (2.0 g) was obtained in the same manner as that of Example 29, (1).

(2) By using the compound obtained in (1) mentioned above (770 mg) as a starting material, the compound shown in Table 14 (274 mg) was obtained in the same manner as that of Example 227.

Example 476

(1) By using the compound obtained in Example 475, (1) (768 mg) as a starting material, a 4″-hydroxy compound (461 mg) was obtained in the same manner as that of Example 169, (1).

(2) By using the compound obtained in (1) mentioned above (306 mg) as a starting material, the compound shown in Table 14 (37.1 mg) was obtained in the same manners as those of Example 214, (2), (3) and (4).

Example 477

By using the compound obtained in Example 476 (27.2 mg) as a starting material, the compound shown in Table 14 (15.9 mg) was obtained in the same manner as that of Example 214, (5).

Example 478

(1) By using the compound obtained in Example 475 (231 mg) as a starting material, a 2′-O-acetyl and 9-O-triethyl-silyl compound (132 mg) was obtained in the same manners as those of Example 214, (3) and Example 228, (2).

(2) By using the compound obtained in (1) mentioned above (39.7 mg) as a starting material, the compound shown in Table 14 (8.5 mg) was obtained in the same manners as those of Example 228, (3) and (4).

Example 479

By using the compound obtained in Example 478, (1) (25.8 mg) as a starting material, the compound shown in Table 14 (8.0 mg) was obtained in the same manners as those of Example 169, (2) and Example 228, (4).

Examples 480 to 507

Preparation methods of the compounds represented by the formula (S) having R and X defined in Table 15 are shown below.

[Formula 40]

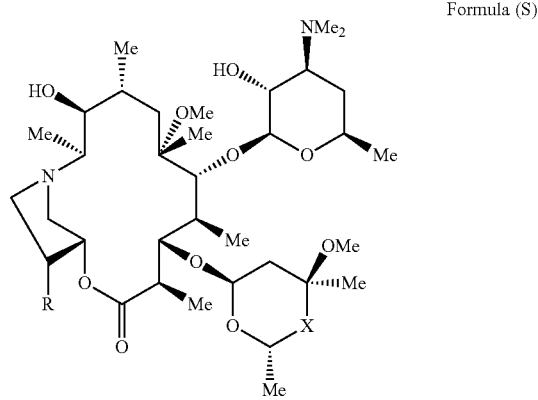

Formula (S)

TABLE 15

| Example | R | X | ESI MS (M + H) | ¹H-NMR, CDCl₃, δ (ppm) |
|---|---|---|---|---|
| 480 | 2-Br-C₆H₄-O-CH₂- | epoxide (dimethyl oxirane) | 899.5 | (500 MHz): 0.94 (d, J = 7.40 Hz, 3H) 1.02-1.09 (m, 12H) 1.14 (d, J = 6.86 Hz, 3H) 1.15-1.26 (m, 4H) 1.34 (s, 3H) 1.41 (d, J = 15.08 Hz, 1H) 1.61-1.68 (m, 1H) 1.86-1.92 (m, 1H) 2.19-2.28 (m, 3H) 2.29 (s, 6H) 2.45-2.57 (m, 2H) 2.62 (d, J = 4.11 Hz, 1H) 2.70-3.05 (m, 7H) 3.13-3.28 (m, 3H) 3.28 (s, 3H) 3.30 (s, 3H) 3.41-3.49 (m, 1H) 3.57-3.61 (m, 1H) 3.83 (d, J = 6.58 Hz, 1H) 4.06-4.20 (m, 2H) 4.53 (d, J = 7.40 Hz, 1H) 4.75-4.81 (m, 1H) 5.02- 5.06 (m, 1H) 5.15-5.19 (m, 1H) 6.82 (d, J = 1.37 Hz, 1H) 6.91 (dd, J = 8.36, 1.23 Hz, 1H) 7.23-7.27 (m, 1H) 7.51(dd, J = 7.82, 1.51 Hz, 1H) |
| 481 | 2-Br-C₆H₄-O-CH₂- | -C(OH)(CH₃)-CH₂-N(Me)₂ | 944.9 | (500 MHz): 0.93 (d, J = 6.88 Hz, 3H) 0.99-1.06 (m, 6H) 1.08-1.17 (m, 9H) 1.19-1.28 (m, 4H) 1.35 (s, 3H) 1.43 (d, J = 14.91 Hz, 1H) 1.62-1.68 (m, 1H) 1.90-2.09 (m, 2H) 2.19-2.27 (m, 1H) 2.30 (s, 6H) 2.36 (s, 6H) 2.41-2.53 (m, 2H) 2.65-3.05 (m, 9H) 3.12-3.31 (m, 3H) 3.26 (s, 3H) 3.30 (s, 3H) 3.38-3.46 (m, 1H) 3.57 (d, J = 9.56 Hz, 1H) 3.75 (d, J = 7.64 Hz, 1H) 4.04-422 (m, 3H) 4.42 (d, J = 6.88 Hz, 1H) 4.96 (d, J = 4.97 Hz, 1H) 5.12-5.19 (m, 1H) 6.79-6.84 (m, 1H) 6.89-6.93 (m, 1H) 7.22-7.25 (m, 1H) 7.49-7.53(m, 1H) |
| 482 | 2-Br-C₆H₄-O-CH₂- | -C(OH)(CH₃)-CH₂-NH-CH₂CH₂-pyrrolidinyl | 1013.7 | (500 MHz): 0.93 (d, J = 7.26 Hz, 3H) 1.03 (dd, J = 6.88, 5.35 Hz, 6H) 1.09-1.16 (m, 9H) 1.18-1.27 (m, 4H) 1.35 (s, 3H) 1.44 (d, J = 14.52 Hz, 1H) 1.64-1.67 (m, 1H) 1.74-1.82 (m, 4H) 1.90-2.06 (m, 2H) 2.21-2.27 (m, 2H) 2.29 (s, 6H) 2.39-2.61 (m, 8H) 2.62-3.05 (m, 10H) 3.13-3.24 (m, 3H) 3.25 (s, 3H) 3.29 (s, 3H) 3.49-3.59 (m, 2H) 3.75 (d, J = 7.26 Hz, 1H) 4.06-4.11 (m, 1H) 4.15-4.20 (m, 1H) 4.24-4.30 (m, 1H) 4.42 (d, J = 7.26 Hz, 1H) 4.94 (d, J = 4.59 Hz, 1H) 5.13-5.17 (m, 1H) 6.79-6.84 (m, 1H) 6.89-6.93 (m, 1H) 7.22-7.26 (m, 1H) 7.49-7.53 (m, 1H) |
| 483 | 2-Br-C₆H₄-O-CH₂- | -C(OH)(CH₃)-CH₂-NH-CH₂CH₂-N(Et)-CH(Me)-(2-OMe-C₆H₄) | 1121.7 | (600 MHz): 0.89-0.96 (m, 6H) 0.99-1.04 (m, 6H) 1.05-1.13 (m, 9H) 1.14-1.22 (m, 1H) 1.16 (d, J = 6.42 Hz, 3H) 1.27 (d, J = 6.88 Hz, 3H) 1.34 (s, 3H) 1.42 (d, J = 15.13 Hz, 1H) 1.59 (d, J = 13.30 Hz, 1H) 1.93 (dd, J = 14.67, 5.50 Hz, 1H) 2.03 (d, J = 14.67 Hz, 1H) 2.18-2.24 (m, 1H) 2.27 (s, 6H) 2.27-2.31 (m, 1H) 2.37-2.70 (m, 9H) 2.71-2.78 (m, 1H) 2.78-2.86 (m, 3H) 2.88-3.03 (m, 3H) 3.11-3.16 (m, 1H) 3.16-3.20 (m, 1H) 3.24 (d, J = 13.75 Hz, 1H) 3.24 (s, 3H) 3.28 (s, 3H) 3.41-3.48 (m, 1H) 3.56 (d, J = 9.63 Hz, 1H) 3.75 (d, J = 7.34 Hz, 1H) 3.79 (s, 3H) 4.07 (t, J = 8.48 Hz, 1H) 4.14-4.24 (m, 2H) 4.31-4.39 (m, 1H) 4.41 (d, J = 7.34 Hz, 1H) 4.94 (d, J = 4.58 Hz, 1H) 5.14 (dd, J = 6.42, 4.58 Hz, 1H) 6.77-6.82 (m, 1H) 6.84 (d, J = 8.25 Hz, 1H) 6.88-6.94 (m, 2H) 7.17-7.25 (m, 2H) 7.28-7.31 (m, 1H) 7.50 (dd, J = 7.79, 1.38 Hz, 1H) |

TABLE 15-continued

| Example | R | X | ESI MS (M + H) | ¹H-NMR, CDCl₃, δ (ppm) |
|---|---|---|---|---|
| 484 | (3-ethylphenoxy methyl group) | (2-hydroxy-2-methyl-3-(dimethylamino)propyl with gem-dimethyl) | 894.8 | (600 MHz): 0.93 (d, J = 7.34 Hz, 3H) 1.02 (d, J = 6.42 Hz, 3H) 1.06 (d, J = 7.34 Hz, 3H) 1.08-1.12 (m, 1H) 1.10 (d, J = 7.34 Hz, 3H) 1.11 (s, 3H) 1.14 (d, J = 6.42 Hz, 3H) 1.19-1.25 (m, 6H) 1.34 (s, 3H) 1.41 (d, J = 14.67 Hz, 1H) 1.60-1.67 (m, 1H) 1.91-1.99 (m, 2H) 2.06 (d, J = 15.13 Hz, 1H) 2.16-2.25 (m, 1H) 2.30 (br. s., 6H) 2.36 (s, 6H) 2.40-2.48 (m, 1H) 2.49-2.55 (m, 1H) 2.57-2.67 (m, 3 ) 2.70-2.86 (m, 4H) 2.90-3.02 (m, 3H) 3.11-3.16 (m, 1H) 3.17-3.24 (m, 2H) 3.26 (s, 3H) 3.29 (s, 3H) 3.37-3.45 (m, 1H) 3.57 (d, J = 9.63 Hz, 1H) 3.76 (d, J = 6.88 Hz, 1H) 3.96 (t, J = 8.48 Hz, 1H) 4.09-4.16 (m, 2H) 4.42 (d, J = 6.88 Hz, 1H) 4.96 (d, J = 5.04 Hz, 1H) 5.12 (dd, J = 6.19, 4.36 Hz, 1H) 6.67-6.71 (m, 1H) 6.72 (s,1H) 6.77 (d, J = 7.34 Hz, 1 H) 7.16 (t, J = 7.79 Hz, 1H) |
| 485 | (3-ethylphenoxy methyl group) | (2-hydroxy-3-(2-pyrrolidin-1-ylethylamino)propyl with gem-dimethyl) | 963.9 | (600 MHz): 0.92 (d, J = 7.34 Hz, 3H) 1.02 (d, J = 6.88 Hz, 3H) 1.06 (d, J = 7.34 Hz, 3H) 1.09 (d, J = 6.88 Hz, 3H) 1.12 (s, 3H) 1.14 (d, J = 6.42 Hz, 3H) 1.17-1.25 (m, 7H) 1.35 (s, 3H) 1.42 (d, J = 14.21 Hz, 1H) 1.60-1.66 (m, 1H) 1.76 (br. s, 4H) 1.93 (dd, J = 14.90, 5.27 Hz, 1H) 2.00-2.06 (m, 1H) 2.18-2.25 (m, 1H) 2.29 (s, 6H) 2.38-2.68 (m, 11 H) 2.69-3.03 (m, 10H) 3.11-3.16 (m, 1 H) 3.18-3.24 (m, 2H) 3.25 (s, 3H) 3.28 (s, 3H) 3.49-3.55 (m, 1H) 3.57 (d, J = 11.00 Hz, 1H) 3.76 (d, J = 7.34 Hz, 1H) 3.96 (t, J = 8.48 Hz, 1H) 4.09-4.14 (m, 1 H) 4.27 (q, J = 6.11 Hz, 1H) 4.43 (d, J = 7.34 Hz, 1H) 4.94 (d, J = 4.58 Hz, 1H) 5.12 (dd, J = 6.42, 4.13 Hz, 1H) 6.67-6.71 (m, 1H) 6.71-6.73 (m, 1H) 6.77 (d, J = 7.34 Hz, 1H) 7.17 (t, J = 7.79 Hz, 1 H) |
| 486 | (3-ethylphenoxy methyl group) | (2-hydroxy-3-methylbutyl with gem-dimethyl) | 837.6 | (500 MHz): 0.89-0.99 (m, 6H) 1.04 (d, J = 6.50 Hz, 3H) 1.06-1.14 (m, 6H) 1.15-1.30 (m, 10H) 1.32-1.45 (m, 4H) 1.58-1.78 (m, 2H) 2.03-2.10 (m, 1H) 2.18-2.26 (m, 2H) 2.30 (s, 6 H) 2.43-2.70 (m, 5H) 2.77-3.05 (m, 6 H) 3.14-3.27 (m, 3H) 3.29 (s, 3H) 3.30 (s, 3H) 3.41-3.49 (m, 1H) 3.60 (d, J = 9.56 Hz, 1H) 3.73 (d, J = 6.88 Hz, 1H) 3.95-4.00 (m, 1H) 4.09-4.15 (m, 1H) 4.51-4.58 (m, 2H) 4.98 (d, J = 5.35 Hz, 1H) 5.12-5.17 (m, 1H) 6.68-6.74 (m, 2 H) 6.77-6.80 (m, 1H) 7.18 (t, J = 7.84 Hz, 1H) |

TABLE 15-continued

| Example | R | X | ESI MS (M + H) | $^1$H-NMR, CDCl$_3$, δ (ppm) |
|---|---|---|---|---|
| 487 | 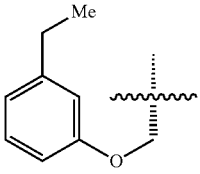 | 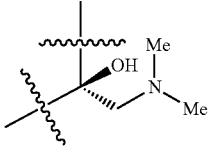 | 894.8 | (600 MHz): 0.93 (d, J = 6.88 Hz, 3H) 1.02 (d, J = 6.42 Hz, 3H) 1.05-1.11 (m, 6H) 1.13-1.24 (m, 13H) 1.36 (s, 3H) 1.43 (d, J = 14.67 Hz, 1H) 1.51 (dd, J = 15.13. 5.50 Hz, 1H) 1.65 (d, J = 13.75 Hz, 1H) 2.17 (d, J = 14.21 Hz, 1H) 2.20-2.24 (m, 2H) 2.26 (s, 6H) 2.36 (s, 6H) 2.46-2.58 (m, 2H) 2.58-2.67 (m, 3H) 2.69 (d, J = 14.21 Hz, 1H) 2.74-2.88 (m, 3H) 2.90-3.04 (m, 3H) 3.13 (d, J = 3.67 Hz, 1H) 3.18 (dd, J = 10.55, 7.34 Hz, 1H) 3.22 (d, J = 11.92 Hz, 1H) 3.27 (s, 3H) 3.34 (s, 3H) 3.53 (d, J = 10.09 Hz, 1H) 3.67-3.74 (m, 1H) 3.78 (d, J = 7.34 Hz, 1H) 3.93-3.99 (m, 1H) 4.11 (dd, J = 8.71, 7.34 Hz, 1H) 4.52-4.59 (m, 2H) 4.79 (d, J = 4.58 Hz, 1H) 5.12 (dd, J = 6.19, 4.36 Hz, 1H) 6.67-6.71 (m, 1H) 6.72 (s, 1H) 6.77 (d, J = 7.34 Hz, 1H) 7.17 (t, J = 7.79 Hz, 1H) |
| 488 | 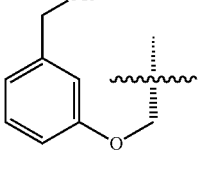 | 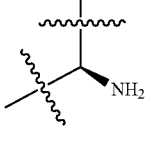 | 836.7 | (500 MHz): 0.94 (d, J = 6.88 Hz, 3H) 1.03 (d, J = 6.50 Hz, 3H) 1.06-1.12 (m, 6H) 1.17-1.27 (m, 10H) 1.28 (d, J = 6.50 Hz, 3H) 1.36 (s, 3H) 1.43 (d, J = 15.29 Hz, 1H) 1.48-1.68 (m, 2H) 2.20-2.27 (m, 2H) 2.30 (s, 6H) 2.36 (d, J = 14.91 Hz, 1H) 2.44-2.69 (m, 5H) 2.75-2.89 (m, 3H) 2.91-3.05 (m, 3H) 3.13-3.26 (m, 3H) 3.28 (s, 3H) 3.30 (s, 3H) 3.50-3.60 (m, 2H) 3.77 (d, J = 7.26 Hz, 1H) 3.95-4.15 (m, 3H) 4.49 (d, J = 7.26 Hz, 1H) 4.91 (d, J = 4.97 Hz, 1H) 5.12-5.16 (m, 1H) 6.68-6.80 (m, 3H) 7.15-7.20 (m, 1H) |
| 489 | 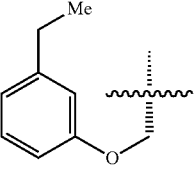 | 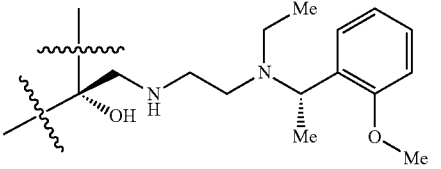 | 1071.7 | (600 MHz): 0.90-0.97 (m, 6H) 1.02 (d, J = 6.88 Hz, 3H) 1.04-1.14 (m, 12H) 1.17 (d, J = 5.96 Hz, 3H) 1.18-1.20 (m, 1H) 1.22 (t, J = 7.79 Hz, 3H) 1.27 (d, J = 6.88 Hz, 3H) 1.35 (s, 3H) 1.42 (d, J = 15.13 Hz, 1H) 1.60-1.68 (m, 1H) 1.93 (dd, J = 14.90. 5.27 Hz, 1H) 2.00-2.06 (m, 1H) 2.18-2.24 (m, 1H) 2.27 (s, 6H) 2.28-2.31 (m, 1H) 2.38-2.67 (m, 11H) 2.72-2.86 (m, 4H) 2.90-3.03 (m, 3H) 3.11-3.24 (m, 3H) 3.25 (s, 3H) 3.28 (s, 3H) 3.40-3.50 (m, 1H) 3.57 (d, J = 10.09 Hz,1H) 3.77 (d, J = 6.88 Hz, 1H) 3.80 (s, 3H) 3.93-4.00 (m, 1H) 4.11 (dd, J = 9.17, 7.34 Hz, 1H) 4.18-4.24 (m, 1H) 4.33-4.38 (m, 1H) 4.43 (d, J = 7.79 Hz, 1H) 4.95 (d, J = 5.04 Hz, 1H) 5.12 (dd, J = 6.19, 4.36 Hz, 1H) 6.67-6.71 (m, 1H) 6.71-6.73 (m, 1H) 6.77 (d, J = 7.34 Hz, 1H) 6.85 (d, J = 8.25 Hz, 1H) 6.92 (t, J = 6.8 Hz, 1H) 7.14-7.22 (m, 2H) 7.30 (d, J = 7.79 Hz, 1H) |

TABLE 15-continued

| Example | R | X | ESI MS (M + H) | ¹H-NMR, CDCl₃, δ (ppm) |
|---|---|---|---|---|
| 490 | (structure: MeO-CH(Me)-) | (carbamate structure with Me, OMe aryl group) | 995.6 | (600 MHz): 0.91-0.96 (m, 6H) 1.01 (d, J = 6.42 Hz, 3H) 1.11-1.21 (m, 16H) 1.27-1.32 (m, 3H) 1.35 (s, 3H) 1.41-1.45 (m, 1H) 1.49-1.55 (m, 1H) 1.62-1.67 (m, 1H) 2.19-2.24 (m, 1H) 2.25 (s, 6H) 2.37-2.67 (m, 9H) 2.70-3.01 (m, 6H) 3.18 (m, 3H) 3.24-3.27 (m, 1H) 3.29 (s, 3H) 3.321 (s, 3H) 3.33 (s, 3H) 3.38 (t, J = 8.71 Hz, 1H) 3.54 (dd, J = 8.94, 6.65 Hz, 1H) 3.59-3.67 (m, 2H) 3.77 (d, J = 7.34 Hz, 1H) 3.85 (s, 3H) 4.33-4.40 (m, 2H) 4.53 (d, J = 10.09 Hz, 1H) 4.55 (d, J = 6.88 Hz, 1H) 4.95 (d, J = 5.04 Hz, 1H) 5.00-5.03 (m, 1H) 5.49-5.53 (m, 1H) 6.87 (d, J = 8.71 Hz, 1H) 6.92 (d J = 7.57 Hz, 1H) 7.21 (t, J = 7.57 Hz, 1H) 7.28 (d, J = 5.50 Hz, 1H) |
| 491 | (structure: HO-CH₂-CH(OH)-) | (carbamate structure with Me, OMe aryl group) | 1025.7 | (600 MHz): 0.90-0.97 (m, 6H) 1.01-1.06 (m, 3H) 1.08-1.33 (m, 19H) 1.34 (s, 3H) 1.36-1.41 (m, 1H) 1.45-1.72 (m, 5H) 2.14-2.22 (m, 2H) 2.26 (s, 6H) 2.40-2.67 (m, 5H) 2.83-3.02 (m, 4H) 3.09-3.32 (m, 5H) 3.29 (s, 3H) 3.31 (s, 3H) 3.40-3.46 (m, 2H) 3.59-3.71 (m, 6H) 3.76-3.79 (m, 1H) 3.85 (s, 3H) 4.32-4.41 (m, 2H) 4.50-4.57 (m, 2H) 4.93-5.01 (m, 2H) 5.46-5.52 (m, 1H) 6.85-6.96 (m, 2H) 7.19-7.31 (m, 2H) |
| 492 | (structure: HO-CH₂-) | (carbamate structure with Me, OMe aryl group) | 995.6 | (600 MHz): 0.94 (d, J = 6.88 Hz, 6H) 1.02 (d, J = 6.88 Hz, 3H) 1.09-1.21 (m, 17H) 1.24-1.33 (m, 4H) 1.34 (s, 3H) 1.38 (d, J = 15.13 Hz, 1H) 1.49-1.70 (m, 3H) 1.77-1.84 (m, 1H) 2.15-2.30 (m, 2H) 2.26 (s, 6H) 2.37-2.68 (m, 6H) 2.79-3.04 (m, 5H) 3.08-3.34 (m, 5H) 3.29 (s, 3H) 3.31 (s, 3H) 3.58-3.70 (m, 5H) 3.76-3.80 (m, 1H) 3.85 (s, 3H) 4.32-4.41 (m, 2H) 4.50-4.59 (m, 2H) 4.93-4.98 (m, 2H) 5.46-5.52 (m, 1H) 6.84-6.95 (m, 2H) 7.18-7.31 (m, 2H) |
| 493 | (structure: HO-CH₂-) | (carbamate structure with Me, OMe aryl group) | 981.7 | (600 MHz): 0.90 (t, J = 7.11 Hz, 3H) 0.95 (d, J = 6.88 Hz, 3H) 0.99 (d, J = 6.42 Hz, 3H) 1.09-1.23 (m, 13H) 1.25 (s, 3H) 1.29 (d, J = 6.88 Hz, 3H) 1.34 (s, 3H) 1.42-1.74 (m, 3H) 2.15-2.72 (m, 9H) 2.82-2.91 (m, 1H) 2.95-3.07 (m, 6H) 3.07-3.31 (m, 9H) 3.32 (s, 3H) 3.33 (s, 3H) 3.55-3.61 (m, 2H) 3.66 (d, J = 9.63 Hz, 1H) 3.69-3.75 (m, 2H) 3.77 (d, J = 7.34 Hz, 1H) 3.89 (s, 3H) 4.29-4.39 (m, 2H) 4.52 (d, J = 9.17 Hz, 1H) 4.60 (d, J = 6.88 Hz, 1H) 4.68-4.73 (m, 1H) 4.93 (d, J = 4.13 Hz, 1H) 5.59-5.66 (m, 1H) 6.86-6.94 (m, 2H) 7.18-7.24 (m, 1H) 7.25-7.29 (m, 1H) |

TABLE 15-continued

| Example | R | X | ESI MS (M + H) | $^1$H-NMR , CDCl$_3$, δ (ppm) |
|---|---|---|---|---|
| 494 | (allyl group) | (carbamate structure) | 991 | (400 MHz): 0.90-0.96 (m, 6H) 1.02 (d, J = 6.8 Hz, 3H) 1.11-1.21 (m, 16H) 1.30 (d, J = 6.9 Hz, 3H) 1.35 (s, 3H) 1.40 (d, J = 14.6 Hz, 1H) 1.49-1.56 (m, 1H) 1.65 (dd, J = 15.5, 5.1 Hz, 1H) 2.08-2.23 (m, 2H) 2.25 (s, 6H) 2.37-2.70 (m, 7H) 2.76 (t, J = 9.3 Hz, 1H) 2.82-3.06 (m, 3H) 3.08-3.27 (m, 4H) 3.29 (s, 3H) 3.32 (s, 3H) 3.59-3.70 (m, 2H) 3.78 (d, J = 6.8 Hz, 1H) 3.85 (s, 3H) 4.31-4.41 (m, 2H) 4.53 (d, J = 9.7 Hz, 1H) 4.56 (d, J = 7.1 Hz, 1H) 4.91-5.05 (m , 4H) 5.47-5.53 (m , 1H) 5.69-5.81 (m, 1H) 6.87 (d, J = 7.8 Hz, 1H) 6.92 (br t, J = 7.5 Hz, 1H) 7.22 (br t, J = 7.5 Hz, 1H) 7.24 (d, J = 7.5 Hz,1H) |
| 495 | (Me-substituted group) | (carbamate structure) | 993 | (400 MHz): 0.90 (t, J = 7.3 Hz, 3H) 0.94 (d, J = 7.1 Hz, 3H) 1.02 (d, J = 6.8 Hz, 3H) 1.12 (d, J = 7.5 Hz, 3H) 1.14-1.22 (m, 13H) 1.26 (d, J = 6.6 Hz, 3H) 1.30 (d, J = 6.6 Hz, 3H) 1.35 (s, 3H) 1.41-1.68 (m, 2H) 2.01-2.24 (m, 2H) 2.26 (s, 6H) 2.38-2.67 (m, 7H) 2.74-3.11 (m, 4H) 3.14-3.30 (m, 8H) 3.28 (s,3H) 3.32 (s, 3H) 3.59-3.71 (m, 2H) 3.78 (d, J = 7.0 Hz, 1H) 3.85 (s, 3H) 4.31-4.43 (m, 2H) 4.53 (d, J = 10.0 Hz, 1H) 4.57 (d, J = 7.3 Hz, 1H) 4.89-4.98 (m, 2H) 5.49 (br s, 1H) 6.87 (d, J = 8.0 Hz, 1H) 6.92 (br t, J = 7.6 Hz, 1H) 7.22 (br t, J = 7.4 Hz, 1H) 7.24 (d, J = 7.5 Hz, 1H) |
| 496 | (vinyl group) | (carbamate structure) | 977 FAB MASS | (400 MHz): 0.94 (t, J = 7.1 Hz, 3H) 0.96 (d, J = 7.4 Hz, 3H) 1.02 (d, J = 6.8 Hz, 3H) 1.10-1.24 (m, 16H) 1.30 (d, J = 7.1 Hz, 1H) 1.36 (s, 3H) 1.43 (d, J = 14.9 Hz, 1H) 1.48-1.56 (m, 1H) 1.64 (dd, J = 15.3, 5.1 Hz, 1H) 2.15-2.24 (m, 1H) 2.26 (s, 6H) 2.36-2.68 (m, 7H) 2.70-2.84 (m, 2H) 2.87-3.07 (m, 5H) 3.09-3.28 (m, 5H) 3.30 (s, 3H) 3.32 (s, 3H) 3.35-3.44 (m, 1H) 3.60 (d, J = 9.5 Hz, 1H) 3.62-3.72 (m, 1H) 3.78 (d, J = 6.8 Hz, 1H) 3.85 (s, 3H) 4.31-4.42 (m, 2H) 4.50-4.59 (m, 2H) 4.92-4.98 (m, 2H) 5.01-5.09 (m, 2H) 5.48-5.54 (m, 1H) 5.84-5.94 (m, 1H) 6.88 (d, J = 8.0 Hz, 1H) 7.93 (t, J = 7.6 Hz, 1H) 7.19-7.31 (m, 2H) |
| 497 | (Me-substituted group) | (carbamate structure) | 979 FAB MASS | (400 MHz): 0.88 (t, J = 7.3 Hz, 3H) 0.90-0.98 (m, 6H) 1.03 (d, J = 6.6 Hz, 3H) 1.09-1.22 (m, 16H) 1.25-1.59 (m, 10H) 1.64 (dd, J = 15.1, 5.3 Hz, 1H) 1.90-2.04 (m, 1H) 2.12-2.23 (m, 1H) 2.27 (s, 6H) 2.37-2.72 (m, 7H) 2.74-3.34 (m, 17H) 3.62 (d, J = 10.0 Hz, 1H) 3.78 (d, J = 6.8 Hz, 1H) 3.85 (s, 3H) 4.30-4.45 (m, 2H) 4.52 (d, J = 9.7 Hz, 1H) 4.57 (d, J = 7.3 Hz, 1H) 4.91-4.99 (m, 2H) 5.56 (br s, 1H) 6.88 (d, J = 8.0 Hz, 1H) 6.93 (t, J = 7.6 Hz, 1H) 7.18-7.34 (m, 2H) |

TABLE 15-continued

| Example | R | X | ESI MS (M + H) | $^1$H-NMR, CDCl$_3$, δ (ppm) |
|---|---|---|---|---|
| 498 | (allyl acetate group) | (carbamate with N-ethyl, N-[(1-(2-methoxyphenyl)ethyl)] ethylenediamine) | 1049 | (400 MHz): 0.90-0.97 (m, 6H) 1.02 (d, J = 6.5 Hz, 3H) 1.10-1.21 (m, 13H) 1.30 (d, J = 6.8 Hz, 3H) 1.35 (s, 3H) 1.43 (d, J = 14.9 Hz, 1H) 1.47-1.70 (m, 2H) 2.07 (s, 3H) 2.19-2.18 (m, 7H) 2.43 (d, J = 14.7 Hz, 1H) 2.38-2.68 (m, 5H) 2.74-2.83 (m, 2H) 2.85-3.03 (m, 4H) 3.10-3.15 (m, 1H) 3.16-3.32 (m, 3H) 3.29 (s, 3H) 3.32 (s, 3H) 3.59-3.71 (m, 2H) 3.60 (d, J = 10.0 Hz, 1H) 3.62-3.71 (m, 1H) 3.78 (d, J = 7.0 Hz, 1H) 3.85 (s, 3H) 4.31-4.42 (m, 2H) 4.48-4.59 (m, 4H) 4.90-4.98 (m, 2H) 4.48-4.54 (m, 1H) 5.49 (br s, 1H) 5.60 (dt, J = 15.4. 6.6 Hz, 1H) 5.83 (dd, J = 15.4, 7.9 Hz, 1H) 6.87 (d, J = 8.3 Hz, 1H) 6.93 (t, J = 7.3 Hz, 1H) 7.22 (t, J = 7.6 Hz, 1H) 7.27-7.31 (m, 1H) |
| 499 | (allyl alcohol group) | (same as above) | 1007 | (400 MHz): 0.90-0.97 (m, 6H) 1.03 (d, J = 6.7 Hz, 3H) 1.10-1.23 (m, 13H) 1.31 (d, J = 6.8 Hz, 3H) 1.35 (s, 3H) 1.42 (d, J = 14.8 Hz, 1H) 1.48-1.56 (m, 1H) 1.65 (dd, J = 15.0, 5.0 Hz, 1H) 2.16-2.25 (m, 1H) 2.26 (s, 6H) 2.43 (d, J = 15.1 Hz, 1H) 2.48-2.68 (m, 4H) 2.73-2.81 (m, 2H) 2.87-3.05 (m, 4H) 3.09-3.15 (m, 1H) 3.16-3.30 (m, 4H) 3.30 (s, 3H) 3.32 (s, 3H) 3.60 (d, J = 9.6 Hz, 1H) 3.62-3.71 (m, 1H) 3.79 (d, J = 7.0 Hz, 1H) 3.85 (s, 3H) 4.12 (d, J = 5.5 Hz, 1H) 4.32-4.42 (m, 2H) 4.52 (d, J = 9.8 Hz, 1H) 4.57 (d, J = 7.1 Hz, 1H) 4.93 (br t, J = 4.6 Hz, 1H) 4.96 (d, J = 4.9 Hz, 1H) 5.50 (br s, 1H) 5.67 (dt, J = 15.5, 5.7 Hz, 1H) 5.77 (dd, J = 15.6, 7.8 Hz, 1H) 6.87 (d, J = 8.2 Hz, 1H) 6.93 (t, J = 7.3 Hz, 1H) 7.22 (t, J = 7.4 Hz, 1H) 7.29 (d, J = 7.3 Hz, 1H) |
| 500 | (hydroxypropyl group) | (same as above) | 1009 | (400 MHz): 0.90-0.97 (m, 6H) 1.02 (d, J = 6.6 Hz, 3H) 1.11 (d, J = 7.3 Hz, 3H) 1.13-1.21 (m, 10H) 1.30 (d, J = 6.8 Hz, 3H) 1.34 (s, 3H) 1.38 (d, J = 14.8 Hz, 1H) 1.41-1.61 (m, 5H) 1.65 (dd, J = 15.1, 5.1 Hz, 1H) 2.02-2.12 (m, 1H) 2.13-2.22 (m, 1H) 2.26 (s, 6H) 2.36-2.68 (m, 5H) 2.77-3.06 (m, 6H) 3.08-3.12 (m, 1H) 3.15-3.32 (m, 4H) 3.28 (s, 3H) 3.31 (s, 3H) 3.63 (d, J = 6.1 Hz, 1H) 3.59-3.71 (m, 1H) 3.78 (d, J = 6.8 Hz, 1H) 3.84 (s, 3H) 3.35-4.41 (m, 2H) 4.46 (d, J = 9.7 Hz, 1H) 4.48 (d, J = 7.3 Hz, 1H) 4.57 (d, J = 7.1 Hz, 1H) 4.85-5.01 (m, 2H) 5.51 (br s, 1H) 6.87 (d, J = 8.3 Hz, 1H) 6.92 (t, J = 7.6 Hz, 1H) 7.22 (t, J = 7.6 Hz, 1H) 7.26-7.30 (m, 1H) |

TABLE 15-continued

| Example | R | X | ESI MS (M + H) | $^1$H-NMR, CDCl$_3$, δ (ppm) |
|---|---|---|---|---|
| 501 | (HO-CH$_2$- group) | (carbamate linker with Me, OMe aryl) | 981 | (400 MHz) 0.93 (t, J = 9.0 Hz, 3H) 0.95 (d, J = 7.0 Hz, 3H) 1.01 (d, J = 6.6 Hz, 3H) 1.12 (d, J = 7.4 Hz, 3H) 1.14-1.21 (m, 10H) 1.30 (d, J = 6.7 Hz, 3H) 1.35 (s, 3H) 1.47 (d, J = 14.9 Hz, 1H) 1.49-1.56 (m, 1H) 1.64 (dd, J = 15.1, 5.1 Hz, 1H) 2.23-2.29 (m, 1H) 2.25 (s, 6H) 2.32-2.67 (m, 5H) 2.71 (d, J = 8.8 Hz, 1H) 2.76-2.93 (m, 3H) 2.97-3.03 (m, 1H) 3.15-3.30 (m, 4H) 3.30 (s, 3H) 3.32 (s, 3H) 3.58-3.84 (m, 3H) 3.78 (d, J = 6.8 Hz, 1H) 3.85 (s, 3H) 3.30-4.43 (m, 2H) 4.53 (d, J = 9.3 Hz, 2H) 4.93 (d, J = 4.8 Hz, J = 1H) 5.03-5.09 (m, 1H) 5.55 (br s, 1H) 6.87 (d, J = 8.1 Hz, 1H) 6.92 (t, J = 7.6 Hz, 1H) 7.21 (t, J = 7.6 Hz, 1H) 7.28 (d, J = 7.6 Hz, 1H) |
| 502 | (piperidinyl-ethyl) | (same core) | 1062.9 | (400 MHz): 0.94-0.98 (m, 6H) 1.02 (d, J = 6.8 Hz, 3H) 1.12 (d, J = 7.6 Hz, 3H) 1.13-1.84 (m, 33H) 1.99-2.10 (m, 1H) 2.11-2.70 (m, 20H) 2.73-3.06 (m, 6H) 3.07-3.41 (m, 11H) 3.62 (d, J = 9.8 Hz, 1H) 3.63-3.72 (m, 1H) 3.77 (d, J = 6.8 Hz, 1H) 3.85 (s, 3H) 4.30-4.44 (m, 2H) 4.52 (d, J = 9.8 Hz, 1H) 4.57 (d, J = 7.1 Hz, 1H) 4.90-4.99 (m, 2H) 5.51 (br s, 1H) 6.87 (d, J = 8.3 Hz, 1H) 6.92 (t, J = 7.6 Hz, 1H) 7.18-7.33 (m, 2H) |
| 503 | (cis-nitrile alkenyl) | (same core) | 1016.7 | (400 MHz): 0.87-1.06 (m, 9H) 1.08-1.40 (m, 23H) 1.42 (d, J = 15.1 Hz, 1H) 1.64 (dd, J = 14.9, 5.1 Hz, 1H) 2.12-2.77 (m, 17H) 2.78-3.17 (m, 8H) 3.18-3.37 (m, 10H) 3.60 (d, J = 9.8 Hz, 1H) 3.63-3.73 (m, 1H) 3.78 (d, J = 6.8 Hz, 1H) 3.85 (s, 3H) 4.24-4.40 (m, 1H) 4.52 (d, J = 9.8 Hz, 1H) 4.57 (d, J = 7.1 Hz, 1H) 4.85-4.94 (m, 1H) 4.97 (d, J = 4.9 Hz, 1H) 5.35 (d, J = 11.0 Hz, 1H) 6.42-6.52 (m, 1H) 6.88 (d, J = 8.3 Hz, 1H) 6.94 (t, J = 7.6 Hz, 1H) 7.18-7.37 (m, 2H) |
| 504 | (nitrile alkyl) | (same core) | 1018.7 | (400 MHz): 0.90-1.08 (m, 9H) 1.09-1.45 (m, 25H) 1.46-1.75 (m, 5H) 2.02-2.75 (m, 17H) 2.76-3.05 (m, 6H) 3.07-3.37 (m, 11H) 3.61 (d, J = 9.5 Hz, 1H) 3.64-3.73 (m, 1H) 3.77 (d, J = 6.8 Hz, 1H) 3.86 (s, 3H) 4.29-4.39 (m, 1H) 4.52 (d, J = 9.8 Hz, 1H) 4.55-4.62 (m, 1H) 4.89-5.02 (m, 2H) 6.90 (d, J = 8.3 Hz, 1H) 6.92-7.00 (m, 1H) 7.18-7.37 (m, 2H) |
| 505 | (nitrile alkenyl) | (same core) | 1002.6 | (400 MHz): 0.88-0.99 (m, 6H) 1.02 (d, J = 7.1 Hz, 3H) 1.12 (d, J = 6.6 Hz, 3H) 1.13-1.40 (m, 21H) 1.50 (d, J = 14.4 Hz, 1H) 1.64 (dd, J=15.1, 5.1 Hz, 1H) 2.19-2.33 (m, 7H) 2.35-2.70 (m, 7H) 2.76 (dd, J = 9.5, 3.7 Hz, 1H) 2.79-2.93 (m, 4H) 2.98-3.07 (m, 1H) 3.14-3.42 (m, 12H) 3.57 (d, J = 10.0 Hz, 1H) 3.59-3.70 (m, 1H) 3.76 (d, J = 7.3 Hz, 1H) 3.85 (s, 3H) 4.30-4.42 (m, 1H) 4.53 (d, J = 9.8 Hz, 1H) 4.54-4.59 (m, 1H) 4.94 (d, J = 4.6 Hz, 1H) 5.02-5.07 (m, 1H) 5.37 (d, J = 11.0 Hz, 1H) 5.57-5.65 (m, 1H) 6.89 (d, J = 7.6 Hz, 1H) 6.90-6.98 (m, 1H) 7.19-7.33 (m, 2H) |

TABLE 15-continued

| Example | R | X | ESI MS (M+H) | $^1$H-NMR, CDCl$_3$, δ (ppm) |
|---|---|---|---|---|
| 506 | (cyanoethyl group) | (carbamate linker with N-ethyl, methyl-CH-(2-methoxyphenyl)) | 1004 FAB MASS | (400 MHz): 0.87-0.99 (m, 6H) 1.03 (d, J = 6.6 Hz, 3H) 1.12 (d, J = 7.6 Hz, 3H) 1.13-1.37 (m, 21H) 1.40 (d, J = 15.6 Hz, 1H) 1.65 (dd, J = 15.4, 5.4 Hz, 1H) 1.71-1.82 (m, 1H) 1.88-1.98 (m, 1H) 2.15-2.73 (m, 14H) 2.78-3.02 (m, 6H) 3.08-3.14 (m, 1H) 3.15-3.35 (m, 10H) 3.61 (d, J = 9.5 Hz, 1H) 3.63-3.72 (m, 1H) 3.77 (d, J = 7.3 Hz, 1H) 3.86 (s, 3H) 4.30-4.42 (m, 1H) 4.53 (d, J = 9.8 Hz, 1H) 4.57 (d, J = 6.8 Hz, 1H) 4.93-5.02 (m, 2H) 6.88 (d, J = 8.1 Hz, 1H) 6.90-6.98 (m, 1H) 7.19-7.37 (m, 2H) |
| 507 | (allyl group) | (aminomethyl-OH linker with N-ethyl, methyl-CH-(2-methoxyphenyl)) | 977 | (400 MHz): 0.87 (d, J = 7.08 Hz, 3H) 0.90 (s, 3H) 0.94 (d, J = 6.59 Hz, 3H) 1.02 (s, 3H) 1.04 (d, J = 7.57 Hz, 3H) 1.10 (s, 3H) 1.12 (d, J = 6.59 Hz, 3H) 1.19 (m, 1H) 1.21 (d, J = 6.84 Hz, 3H) 1.28 (s, 3H) 1.33 (d, J = 14.6 Hz, 1H) 1.54 (m, 1H) 1.89 (dd, J = 14.7, 5.37 Hz, 1H) 1.99-2.15 (m, 2H) 2.18-2.26 (m, 3H) 2.23 (s, 3H) 2.34-2.59 (m, 8H) 2.67-2.98 (m, 10H) 3.04 (d, J = 3.91 Hz, 1H) 3.11 (d, J = 8.79 Hz, 1H) 3.15 (dd, J = 10.3, 7.32 Hz, 1H) 3.21 (s, 3H) 3.23 (s, 3H) 3.41 (m, 1H) 3.44 (d, J = 9.77 Hz, 1H) 3.72 (m, 1H) 3.73 (s, 3H) 4.16 (dd, J = 12.7, 6.10 Hz, 1H) 4.30 (dd, J = 13.7, 6.84 Hz, 1H) 4.41 (d, J = 7.08 Hz, 1H) 4.85-4.97 (m, 4H) 5.62-5.74 (m, 1H) 6.79 (d, J = 8.30 Hz, 1H) 6.86 (t, J = 7.57 Hz, 1H) 7.14 (dt, J = 7.32, 1.71 Hz, 1H) 7.24 (dd, J = 7.57, 1.47 Hz, 1H) |

Example 480

By using the compound obtained in Example 82, (1) (890 mg) as a starting material, the compound shown in Table 15 (230 mg) was obtained in the same manners as those of Example 169, (1), (2), Example 177, (1) and Example 1, (3).

Example 481

The compound obtained in Example 480 (70 mg), 50% aqueous dimethylamine (1 ml) and pyridine hydrochloride (3 mg) were dissolved in ethanol (1.0 ml), and the solution was stirred overnight at 80° C. The reaction mixture was concentrated under reduced pressure, and the resulting residue was purified by preparative thin layer chromatography (chloroform:methanol:28% aqueous ammonia=10:1:0.1) to obtain the compound shown in Table 15 (52 mg).

Example 482

By using the compound obtained in Example 480 (70 mg) and 1-(2-aminoethyl)pyrrolidine (195 µl) as starting materials, the compound shown in Table 15 (43 mg) was obtained in the same manner as that of Example 481.

Example 483

By using the compound obtained in Example 480 (15 mg) and the compound obtained in Reference Example 52 (18.5 mg) as starting materials, the compound shown in Table 15 (16.8 mg) was obtained in the same manner as that of Example 481.

Example 484

(1) By using the compound obtained in Example 13, (1) (2.0 g) and 3-ethylphenol (454 mg) as starting materials, an ether compound (2.04 g) was obtained in the same manner as that of Example 29.
(2) By using the compound obtained in (1) mentioned above (2.03 g) as a starting material, a 4"-OH compound (1.21 g) was obtained in the same manner as that of Example 169, (1).
(3) By using the compound obtained in (2) mentioned above (1.2 g) as a starting material, a 4"-ketone compound (1.2 g) was obtained in the same manner as that of Example 169, (2).
(4) By using the compound obtained in (3) mentioned above (300 mg) as a starting material, a 4"-epoxide compound (171.9 mg) was obtained in the same manners as those of Example 177, (1) and Example 1, (3).
(5) By using the compound obtained in (4) mentioned above (50 mg) and 50% aqueous dimethylamine (58.3 µl) as starting materials, the compound shown in Table 15 (35.8 mg) was obtained in the same manner as that of Example 481.

Example 485

By using the compound obtained in Example 484, (4) (30 mg) and 1-(2-aminoethyl)pyrrolidine (20.2 mg) as starting materials, the compound shown in Table 15 (20.2 mg) was obtained in the same manner as that of Example 481.

Example 486

(1) The compound obtained in Example 484, (3) (100 mg) was dissolved in tetrahydrofuran (1.5 ml), the solution was added with L-Selectride (470 µl) at −78° C., and the mixture was warmed to room temperature, and stirred overnight. The reaction mixture was added with saturated aqueous sodium hydrogencarbonate and ethyl acetate, the layers were separated, and the organic layer was dried over anhydrous magnesium sulfate, and filtered. The filtrate was concentrated under reduced pressure, and the resulting residue was purified by preparative thin layer chromatography (hexane:acetone:triethylamine=30:10:0.2) to obtain an epihydroxyl compound (14 mg).
(2) By using the compound obtained in (1) mentioned above (14 mg) as a starting material, the compound shown in Table 15 (5.3 mg) was obtained in the same manner as that of Example 1, (3).

Example 487

(1) By using the compound obtained in Example 484, (3) (300 mg) as a starting material, a 4"-epoxide compound (165.4 mg) was obtained in the same manners as those of Example 191, (1) and Example 1, (3).
(2) By using the compound obtained in (1) mentioned above (50 mg) and 50% aqueous dimethylamine (58.3 µl) as starting materials, the compound shown in Table 15 (35.8 mg) was obtained in the same manner as that of Example 481.

Example 488

By using the compound obtained in Example 484, (3) (30 mg) as a starting material, the compound shown in Table 15 (2.0 mg) was obtained in the same manners as those of Example 169, (3) and Example 1, (3).

Example 489

The compound obtained in Example 484, (4) (10 mg), the compound obtained in Reference Example 52 (13.1 mg), and pyridine hydrochloride (0.3 mg) were dissolved in ethanol (0.25 ml), and the mixture was stirred at 120° C. for 70 minutes and at 150° C. for 15 minutes under microwave irradiation. The reaction mixture was concentrated under reduced pressure, and the resulting residue was purified by preparative thin layer chromatography (ethyl acetate:methanol:28% aqueous ammonia=10:1:0.1) to obtain the compound shown in Table 15 (8.1 mg).

Example 490

(1) By using the compound obtained in Example 442, (1) (227 mg) as a starting material, a 4"-hydroxy compound (95 mg) was obtained in the same manner as that of Example 169, (1).
(2) By using the compound obtained in (1) mentioned above (50 mg) and the compound obtained in Reference Example 52 (21 mg) as starting materials, the compound shown in Table 15 (44 mg) was obtained in the same manners as those of Example 172, (1), (2), and Example 1, (3).

Example 491

(1) By using the compound obtained in Reference Example 1 (593.6 mg) and the compound obtained in Reference Example 87 (250 mg) as starting materials, a lactonization precursor (509.4 mg) was obtained in the same manner as that of Example 1, (1).
(2) By using the compound obtained in (1) mentioned above (500 mg) as a starting material, an imidazolide compound (78.1 mg) was obtained in the same manners as those of Example 1, (2), Example 169, (1), and Example 172, (1).
(3) The compound obtained in (2) mentioned above (78.0 mg) was dissolved in tetrahydrofuran (0.5 ml), the solution was added with the compound obtained in Reference Example 52 (19.5 mg), and the reaction mixture was concentrated under reduced pressure, and left overnight. The resulting residue was purified by silica gel column chromatography (hexane:acetone:triethylamine=30:10:0.2) to obtain a carbamate compound (77.5 mg).
(4) The compound obtained in (3) mentioned above (72.0 mg) was dissolved in tetrahydrofuran (7 ml), the solution was added successively with distilled water (3.5 ml), N-methylmorpholine N-oxide (34.6 mg), and 4 wt % aqueous osmium tetroxide, and the mixture was stirred at room temperature for 3 hours. The reaction mixture was added with saturated aqueous sodium hydrogencarbonate, aqueous sodium hydrogenthiosulfate, and ethyl acetate, the layers were separated, the organic layer was dried over anhydrous magnesium sulfate and filtered, and the filtrate was concentrated under reduced pressure to obtain a crude product (68.7 mg).
(5) By using the compound obtained in (4) mentioned above (8.0 mg) as a starting material, the compound shown in Table 15 (2.0 mg) was obtained in the same manner as that of Example 1, (3).

Example 492

(1) The compound obtained in Example 491, (4) (60 mg) was dissolved in chloroform (2.0 ml), the solution was added with 90% lead tetraacetate (35.4 mg) under ice cooling, and the mixture was stirred for 15 minutes. The reaction mixture was added with saturated aqueous sodium hydrogencarbonate and diethyl ether, the layers were separated, and the resulting organic layer was washed with saturated brine, then dried over anhydrous magnesium sulfate, and filtered. The resulting residue was dissolved in tetrahydrofuran (0.5 ml), the solution was added with methanol (0.5 ml) and sodium borohydride (3.6 mg) under ice cooling, and the mixture was stirred for 30 minutes. The reaction mixture was added with saturated aqueous sodium hydrogencarbonate and ethyl acetate, the layers were separated, and the organic layer was washed with saturated brine, dried over anhydrous magnesium sulfate, and filtered. The filtrate was concentrated under reduced pressure, and the resulting residue was purified by silica gel column chromatography (hexane:acetone:triethylamine=50:10:0.2) to obtain a hydroxyethyl compound (35 mg).
(2) By using the compound obtained in (1) mentioned above (15 mg) as a starting material, the compound shown in Table 15 (2.7 mg) was obtained in the same manner as that of Example 1, (3).

Example 493

(1) The compound obtained in Example 23, (1) (65 mg) was dissolved in chloroform (3 ml), the solution was added with t-butyldimethylsilyl chloride (18.2 mg), triethylamine (25.3 µl), and 4-dimethylaminopyridine (3.7 mg), and the mixture was stirred at room temperature for 3 hours. The reaction mixture was added with t-butyldimethylsilyl chloride (18.2 mg), triethylamine (25.3 µl), and 4-dimethylaminopyridine (3.7 mg), and the mixture was further stirred overnight at room temperature. The reaction mixture was added with distilled water and chloroform, the layers were separated, and the organic layer was concentrated under reduced pressure. The resulting residue was purified by silica gel column chromatography (hexane:acetone:triethylamine=110:10:0.2) to obtain a silyl compound (23.5 mg).

(2) By using the compound obtained in (1) mentioned above (65 mg) as a starting material, a crude product of imidazolide compound was obtained in the same manners as those of Example 169, (1) and Example 172, (1), and by using the crude product of the imidazolide compound and the compound obtained in Reference Example 52 (8.7 mg) as starting materials, a carbamate compound (26.2 mg) was obtained in the same manner as that of Example 172.

(3) By using the compound obtained in (2) mentioned above (25 mg) as a starting material, the compound shown in Table 15 (7.6 mg) was obtained in the same manner as that of Example 1, (3).

Example 494

(1) By using the compound obtained in Example 142, (2) (100 mg) as a starting material, an imidazolide compound (70 mg) was obtained in the same manners as those of Example 169, (1) and Example 172, (1).

(2) By using the compound obtained in (1) mentioned above (67 mg) and the compound obtained in Reference Example 52 (28 mg) as starting materials, a carbamate compound (61 mg) was obtained in the same manner as that of Example 172, (2).

(3) By using the compound obtained in (2) mentioned above (58 mg) as a starting material, the compound shown in Table 15 (43 mg) was obtained in the same manner as that of Example 1, (3).

Example 495

By using the compound obtained in Example 494 (25 mg) as a starting material, the compound shown in Table 15 (20 mg) was obtained in the same manner as that of Example 13, (5).

Example 496

(1) By using the compound obtained in Example 455, (2) (227 mg) and the compound obtained in Reference Example 52 (91 mg) as starting materials, a carbamate compound (212 mg) was obtained in the same manners as those of Example 169, (1) and Example 172.

(2) By using the compound obtained in (1) mentioned above (39.6 mg) as a starting material, the compound shown in Table 15 (25 mg) was obtained in the same manner as that of Example 1, (3).

Example 497

By using the compound obtained in Example 496 (20 mg) as a starting material, the compound shown in Table 15 (17.1 mg) was obtained in the same manner as that of Example 456.

Example 498

(1) The compound obtained in Example 496, (1) (50 mg) was dissolved in methylene chloride (1 ml), the solution was added with the second generation Grubbs catalyst (13 mg) and cis-1,4-diacetoxy-2-butene (15 µl), and the mixture was stirred for 16 hours under reflux by heating. The reaction mixture was added with the second generation Grubbs catalyst (10.5 mg) and cis-1,4-diacetoxy-2-butene (13 µl), and the mixture was further stirred for 25 hours under reflux by heating. The reaction mixture was concentrated under reduced pressure, and the resulting residue was purified by preparative thin layer chromatography (hexane:ethyl acetate=4:1), and then further purified by preparative thin layer chromatography (chloroform:methanol=10:1) to obtain a coupled compound (23 mg).

(2) By using the compound obtained in (1) mentioned above (32 mg) as a starting material, the compound shown in Table 15 (21 mg) was obtained in the same manner as that of Example 1, (3).

Example 499

The compound obtained in Example 498 (14 mg) was dissolved in methanol (1 ml), the solution was added with sodium hydrogencarbonate (3.4 mg), and the mixture was stirred at room temperature for 28 hours. The reaction mixture was added with distilled water, the mixture was extracted with ethyl acetate, and the organic layer was washed with saturated brine, then dried over anhydrous sodium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 15 (16 mg).

Example 500

The compound obtained in Example 499 (13.5 mg) was dissolved in a mixed solvent of methanol and ethyl acetate (1:1, 2 ml), the solution was added with 5% palladium-carbon (7 mg) under an argon atmosphere, and then the mixture was stirred at room temperature for 3 hours under a hydrogen atmosphere of 1 atm. The reaction mixture was filtered, then the filtrate was concentrated under reduced pressure, and the resulting residue was purified by preparative thin layer chromatography (chloroform:methanol:28% aqueous ammonia=10:1:0.1) to obtain the compound shown in Table 15 (10 mg).

Example 501

(1) By using the compound obtained in Example 13, (1) (100 mg) as a starting material, a 4"-hydroxy compound (70 mg) was obtained in the same manner as that of Example 169, (1).

(2) The compound obtained in (1) mentioned above (29 mg) was dissolved in dimethylformamide (150 µl), the solution was added with t-butyldimethylsilyl chloride (6.8 mg) and imidazole (6.2 mg), and the mixture was stirred at 60° C. for 2.5 hours. The reaction mixture was further added with t-butyldimethylsilyl chloride (6.8 mg) and imidazole (6.2 mg), the mixture was stirred at 60° C. for 2.5 hours, and then added with distilled water, and the mixture was extracted with ethyl acetate. The organic layer was washed successively with distilled water and saturated brine, then dried over anhydrous sodium sulfate and filtered, the filtrate was concentrated under reduced pressure, and the resulting residue was purified by preparative thin layer chromatography (hexane:acetone=3:1) to obtain a silyl compound (15 mg).

(3) By using the compound obtained in (2) mentioned above (24 mg) and the compound obtained in Reference Example 52 (9 mg) as starting materials, the compound shown in Table 15 (14 mg) was obtained in the same manners as those of Example 172, (1), (2) and Example 1, (3).

Example 502

(1) The compound obtained in Example 491, (4) (64 mg) was dissolved in chloroform (1 ml), the solution was added with lead tetraacetate (33.9 mg), and the mixture was stirred for 25 minutes. The reaction mixture was added with saturated aqueous sodium hydrogencarbonate and ethyl acetate, the layers were separated, and the resulting organic layer was washed with saturated brine, then dried over anhydrous sodium sulfate, and filtered. The filtrate was concentrated under reduced pressure, and the resulting residue was purified by silica gel column chromatography (chloroform to chloroform:methanol:28% aqueous ammonia=50:1:0.1) to obtain an aldehyde compound (32 mg).

(2) The compound obtained in (1) mentioned above (10.5 mg) was dissolved in a mixed solvent of chloroform and ethanol (3:1, 150 μl), the solution was added with piperidine (4.2 μl), acetic acid (7.4 μl), and sodium triacetoxyborohydride (9.1 mg), and the mixture was stirred at room temperature for 30 minutes. The reaction mixture was added with saturated aqueous sodium hydrogencarbonate, the mixture was extracted with ethyl acetate, the organic layer was dried over anhydrous sodium sulfate and filtered, and then the filtrate was concentrated under reduced pressure to obtain an amine compound (10.9 mg).

(3) By using the compound obtained in (1) mentioned above (10.9 mg) as a starting material, the compound shown in Table 15 (5.4 mg) was obtained in the same manner as that of Example 1, (3).

Example 503

(1) The compound obtained in Example 494, (1) (20 mg) was dissolved in methylene chloride (400 μl), the solution was added with acrylonitrile (27.2 μl) and the second generation Hoveyda-Grubbs catalyst (2.0 mg), the mixture was stirred for 3 hours under microwave irradiation, then added with acrylonitrile (27.2 μl) and the second generation Hoveyda-Grubbs catalyst (2.0 mg), and the mixture was stirred at 100° C. for 2 hours. The reaction mixture was concentrated under reduced pressure, and the resulting residue was purified by preparative thin layer chromatography (hexane:acetone:28% aqueous ammonia=70:30:0.2) to obtain a coupled compound (5.3 mg).

(2) By using the compound obtained in (1) mentioned above (8.5 mg) as a starting material, the compound shown in Table 15 (4.3 mg) was obtained in the same manner as that of Example 1, (3).

Example 504

By using the compound obtained in Example 503 (5.5 mg) as a starting material, the compound shown in Table 15 (1.3 mg) was obtained in the same manner as that of Example 456.

Example 505

(1) By using the compound obtained in Example 496, (1) (64 mg) as a starting material, a coupled compound (9.4 mg) was obtained in the same manner as that of Example 503, (1).

(2) By using the compound obtained in (1) mentioned above (9.4 mg) as a starting material, the compound shown in Table 15 (3.9 mg) was obtained in the same manner as that of Example 1, (3).

Example 506

By using the compound obtained in Example 505 (5.6 mg) as a starting material, the compound shown in Table 15 (4.7 mg) was obtained in the same manner as that of Example 456.

Example 507

(1) By using the compound obtained in Example 142, (2) (168.5 mg) as a starting material, a 4"-hydroxy compound (121 mg) was obtained in the same manner as that of Example 169, (1).

(2) By using the compound obtained in (1) mentioned above (40 mg) as a starting material, a deprotected compound (19 mg) was obtained in the same manners as those of Example 169, (2), Example 177, (1), and Example 1, (3).

(3) By using the compound obtained in (2) mentioned above (19 mg) and the compound obtained in Reference Example 52 (17 mg) as starting materials, the compound shown in Table 15 (13 mg) was obtained in the same manner as that of Example 177, (3).

Examples 508 to 515

Preparation methods of the compounds represented by the formula (T) having R defined in Table 16 are shown below.

[Formula 41]

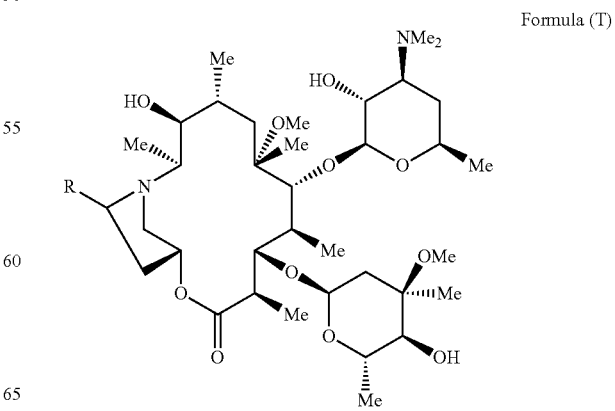

Formula (T)

TABLE 16

| Example | R | ESI MS (M + H) | $^1$H-NMR, CDCl$_3$, δ (ppm) |
|---|---|---|---|
| 508 | benzyl-O-C(CH$_3$)$_2$- | 823.6 | (600 MHz): 0.90 (d, J = 7.34 Hz, 3H) 1.01 (d, J = 6.42 Hz, 3H) 1.04 (d, J = 7.34 Hz, 3H) 1.14 (d, J = 7.34 Hz, 3H) 1.18-1.23 (m, 1H) 1.21 (d, J = 5.96 Hz, 3H) 1.24 (s, 3H) 1.28 (d, J = 5.96 Hz, 3H) 1.33 (s, 3H) 1.35 (d, J = 15.13 Hz, 1H) 1.58 (dd, J = 15.13, 5.04 Hz, 1H) 1.62-1.66 (m, 1H) 1.79-1.84 (m, 1H) 1.97-2.04 (m, 1H) 2.16-2.24 (m, 2H) 2.28 (s, 6H) 2.36 (d, J = 14.67 Hz, 1H) 2.36-2.45 (m, 2H) 2.78-2.85 (m, 1H) 2.89 (dd, J = 11.92, 4.13 Hz, 1H) 2.97-3.26 (m, 8H) 3.26 (s, 3H) 3.33 (s, 3H) 3.38 (t, J = 8.71 Hz, 1H) 3.47-3.53 (m, 1H) 3.57 (d, J = 10.09 Hz, 1H) 3.74 (d, J = 6.88 Hz, 1H) 4.00-4.06 (m, 1H) 4.46 (d, J = 11.46 Hz, 1H) 4.50 (d, J = 6.88 Hz, 1H) 4.53-4.57 (m, 1H) 4.89 (d, J = 10.09 Hz, 1H) 4.92 (d, J = 4.58 Hz, 1H) 4.99-5.02 (m, 1H) 7.23-7.36 (m, 5H) |
| 509 | benzyl-O-CH(CH$_3$)- (stereo) | 823.6 | (600 MHz): 0.92-0.99 (m, 3H) 1.07 (d, J = 7.34 Hz, 3H) 1.11 (d, J = 6.42 Hz, 3H) 1.16 (d, J = 6.88 Hz, 3H) 1.17-1.20 (m, 1H) 1.21 (d, J = 6.42 Hz, 3H) 1.21-1.24 (m, 1H) 1.23 (s, 3H) 1.29 (d, J = 6.42 Hz, 3H) 1.37 (s, 3H) 1.54 (dd, J = 15.13, 4.58 Hz, 1H) 1.61-1.66 (m, 1H) 1.93-2.11 (m, 3H) 2.27 (s, 6H) 2.27-2.31 (m, 1H) 2.33-2.45 (m, 4H) 2.36 (d, J = 15.13 Hz, 1H) 2.71-2.78 (m, 1H) 2.95-3.01 (m, 1H) 3.12-3.28 (m, 5H) 3.25 (s, 3H) 3.30 (s, 3H) 3.31-3.48 (m, 3H) 3.69 (d, J = 8.25 Hz, 1H) 3.75-3.80 (m, 1H) 3.98-4.05 (m, 1H) 4.38 (d, J = 7.34 Hz, 1H) 4.44-4.50 (m, 2H) 4.85 (d, J = 5.04 Hz, 1H) 5.03-5.06 (m, 1H) 7.23-7.34 (m, 5H) |
| 510 | HO-C(CH$_3$)$_2$- | 733.5 | (600 MHz): 0.98 (d, J = 7.34 Hz, 3H) 1.03 (d, J = 6.42 Hz, 3H) 1.08 (d, J = 7.34 Hz, 3H) 1.15 (d, J = 7.34 Hz, 3H) 1.16-1.21 (m, 1H) 1.21 (d, J = 5.96 Hz, 3H) 1.24 (s, 3H) 1.28 (d, J = 5.96 Hz, 3H) 1.35 (s, 3H) 1.52 (d, J = 14.67 Hz, 1H) 1.57 (dd, J = 15.13, 5.04 Hz, 1H) 1.64 (d, J = 10.09 Hz, 1H) 1.93 (dd, J = 14.44, 4.81 Hz, 1H) 2.07-2.14 (m, 1H) 2.18-2.24 (m, 1H) 2.28 (s, 6H) 2.29-2.45 (m, 3H) 2.37 (d, J = 15.13 Hz, 1H) 2.81 (dd, J = 14.67, 9.63 Hz, 1H) 2.84-2.90 (m, 2H) 2.90-2.95 (m, 1H) 2.99-3.04 (m, 1H) 3.07-3.13 (m, 1H) 3.17-3.25 (m, 2H) 3.29 (s, 3H) 3.32 (s, 3H) 3.33 (d, J = 11.92 Hz, 1H) 3.43-3.51 (m, 2H) 3.61 (d, J = 9.63 Hz, 1H) 3.68 (dd, J = 10.77, 3.90 Hz, 1H) 3.75 (d, J = 7.34 Hz, 1H) 3.98-4.06 (m, 1H) 4.47 (d, J = 7.34 Hz, 1H) 4.87-4.93 (m, 2H) 4.97-5.02 (m, 1H) |
| 511 | HO-CH$_2$-C(CH$_3$)- (stereo) | 733.6 | (600 MHz): 0.79-0.94 (m, 6H) 1.09 (d, J = 7.79 Hz, 3H) 1.16 (d, J = 7.34 Hz, 3H) 1.18-1.23 (m, 1H) 1.22 (d, J = 5.96 Hz, 3H) 1.24 (s, 3H) 1.29 (d, J = 5.96 Hz, 3H) 1.38 (s, 3H) 1.55 (dd, J = 15.13, 5.04 Hz, 1H) 1.59-2.27 (m, 8H) 2.27 (s, 6H) 2.37 (d, J = 15.59 Hz, 1H) 2.39-2.46 (m, 1H) 2.71-2.77 (m, 1H) 3.01 (t, J = 9.63 Hz, 1H) 3.10-3.22 (m, 2H) 3.23 (s, 3H) 3.32 (s, 3H) 3.32-3.48 (m, 3H) 3.69 (d, J = 8.25 Hz, 1H) 3.88-3.93 (m, 1H) 3.99-4.07 (m, 1H) 4.37 (d, J = 6.88 Hz, 1H) 4.88 (d, J = 4.58 Hz, 1H) 5.04-5.11 (m, 1H) |
| 512 | PhO-CH$_2$-C(CH$_3$)- | 809.6 | (600 MHz): 0.78 (d, J = 7.34 Hz, 3H) 0.87-0.96 (m, 3H) 1.02 (d, J = 7.34 Hz, 3H) 1.14 (d, J = 7.34 Hz, 3H) 1.20-1.26 (m, 7H) 1.29 (d, J = 6.42 Hz, 3H) 1.35 (s, 3H) 1.52 (dd, J = 15.36, 4.81 Hz, 1H) 1.58-1.70 (m, 3H) 1.75-2.05 (m, 1H) 2.23-2.36 (m, 3H) 2.31 (s, 6H) 2.40-2.63 (m, 5H) 2.74-2.84 (m, 1H) 2.99 (t, J = 9.40 Hz, 1H) 3.01-3.32 (m, 5H) 3.26 (s, 3H) 3.32 (s, 3H) 3.40-3.50 (m, 1H) 3.73 (d, J = 7.79 Hz, 1H) 4.02-4.09 (m, 1H) 4.08-4.20 (m, 1H) 4.41 (d, J = 7.34 Hz, 1H) 4.47-4.51 (m, 1H) 4.74-4.80 (m, 1H) 4.85-4.92 (m, 1H) 6.86-6.94 (m, 3H) 7.23-7.28 (m, 2H) |
| 513 | 3-(tBu)-C$_6$H$_4$-O-CH$_2$-C(CH$_3$)- | 865.7 | (600 MHz): 0.79 (d, J = 7.34 Hz, 3H) 0.86-0.92 (m, 3H) 1.04 (d, J = 7.79 Hz, 3H) 1.12 (d, J = 7.34 Hz, 3H) 1.19-1.24 (m, 1H) 1.22 (s, 3H) 1.21-1.24 (m, 3H) 1.29 (s, 9H) 1.28-1.30 (m, 3H) 1.35 (s, 3H) 1.52 (dd, J = 15.13, 5.04 Hz, 1H) 1.58-1.72 (m, 3H) 1.79-1.95 (m, 1H) 2.21-2.29 (m, 2H) 2.30 (s, 6H) 2.34 (d, J = 15.13 Hz, 1H) 2.39-2.53 (m, 4H) 2.55-2.62 (m, 1H) 2.78-2.86 (m, 1H) 3.00 (t, J = 9.40 Hz, 1H) 3.03-3.24 (m, 2H) 3.23 (dd, J = 10.09, 7.34 Hz, 2H) 3.26 (s, 3H) 3.33 (s, 3H) 3.42-3.50 (m, 1H) 3.73 (d, J = 7.79 Hz, 1H) 4.02-4.09 (m, 1H) 4.11-4.18 (m, 1H) 4.40 (d, J = 7.34 Hz, 1H) 4.45-4.49 (m, 1H) 4.75-4.80 (m, 1H) 4.87-4.94 (m, 1H) 6.68-6.72 (m, 1H) 6.91-6.97 (m, 2H) 7.18 (t, J = 8.25 Hz, 1H) |
| 514 | PhO-CH$_2$-C(CH$_3$)- (stereo) | 809.6 | (600 MHz): 0.87-0.92 (m, 3H) 0.99-1.06 (m, 3H) 1.13-1.18 (m, 6H) 1.18-1.23 (m, 1H) 1.22 (d, J = 6.42 Hz, 3H) 1.24 (s, 3H) 1.30 (d, J = 5.96 Hz, 3H) 1.35 (s, 3H) 1.48-1.54 (m, 1H) 1.56 (dd, J = 15.13, 5.04 Hz, 1H) 1.62-1.75 (m, 2H) 2.13-2.47 (m, 7H) 2.28 (s, 6H) 2.52-2.58 (m, 1H) 2.61-2.69 (m, 1H) 2.83-2.90 (m, 1H) 3.00 (t, J = 9.17 Hz, 1H) 3.04-3.11 (m, 1H) 3.21 (dd, J = 10.32, 7.11 Hz, 1H) 3.20-3.39 (m, 3H) 3.28 (s, 3H) 3.32 (s, 3H) 343-3.50 (m, 1H) 3.74 (d, J = 8.25 Hz, 1H) 3.79-3.91 (m, 1H) 4.01-4.08 (m, 1H) 442 (d, J = 7.34 Hz, 1H) 4.56-4.62 (m, 1H) 4.87-4.92 (m, 1H) 4.94-4.98 (m, 1H) 6.87-6.95 (m, 3H) 7.23-7.30 (m, 2H) |

TABLE 16-continued

| Example | R | ESI MS (M + H) | ¹H-NMR, CDCl₃, δ (ppm) |
|---|---|---|---|
| 515 | (3,3-dimethyl-butyl-substituted phenoxy methyl group with Me, Me, Me substituents) | 865.7 | (600 MHz): 0.88-0.95 (m, 3H) 1.00-1.07 (m, 3H) 1.15 (d, J = 7.34 Hz, 3H) 1.17 (d, J = 6.88 Hz, 3H) 1.18-1.22 (m, 1H) 1.22 (d, J = 5.96 Hz, 3H) 1.24 (s, 3H) 1.29 (s, 9H) 1.29-1.31 (m, 3H) 1.35 (s, 3H) 1.48-1.55 (m, 1H) 1.56 (dd, J = 15.13, 4.58 Hz, 1H) 1.62-1.78 (m, 2H) 2.09-2.22 (m, 1H) 2.23-2.32 (m, 2H) 2.28 (s, 6H) 2.33-2.74 (m, 6H) 2.83-2.89 (m, 1H) 3.00 (t, J = 8.94 Hz, 1H) 3.04-3.14 (m, 1H) 3.14-3.34 (m, 3H) 3.20 (dd, J = 10.09, 7.34 Hz, tH) 3.28 (s, 3H) 3.32 (s, 3H) 3.43-3.50 (m, 1H) 3.74 (d, J = 7.79 Hz, 1H) 3.77-3.89 (m, 1H) 4.01-4.07 (m, 1H) 4.42 (d, J = 7.34 Hz, 1H) 4.56-4.63 (m, 1H) 4.86-4.93 (m, 1H) 4.93-4.97 (m, 1H) 6.73 (dd, J = 8.02. 2.06 Hz, 1H) 6.91-6.94 (m, 1H) 6.95-6.98 (m, 1H) 7.21 (t, J = 8.02 Hz, 1H) |

Example 508

(1) By using the compound obtained in Reference Example 1 (5.30 g) and the compound obtained in Reference Example 88 (3.36 g) as starting materials, a cyclized compound (890 mg) was obtained in the same manners as those of Example 1, (1) and (2).

(2) By using the compound obtained in (1) mentioned above (106 mg) as a starting material, the compound shown in Table 16 (23.7 mg) was obtained in the same manner as that of Example 1, (3).

Example 509

(1) By using the compound obtained in Reference Example 1 (8.38 g) and the compound obtained in Reference Example 89 (5.31 g) as starting materials, a cyclized compound (2.90 g) was obtained in the same manners as those of Example 1, (1) and (2).

(2) By using the compound obtained in (1) mentioned above (74.9 mg) as a starting material, the compound shown in Table 16 (24.0 mg) was obtained in the same manner as that of Example 1, (3).

Example 510

By using the compound obtained in Example 508 (15.0 mg) as a starting material, the compound shown in Table 16 (3.5 mg) was obtained in the same manner as that of Example 87.

Example 511

By using the compound obtained in Example 509 (12.2 mg) as a starting material, the compound shown in Table 16 (2.3 mg) was obtained in the same manner as that of Example 87.

Example 512

(1) By using the compound obtained in Example 508, (1) (550 mg) as a starting material, a debenzylated compound (398 mg) was obtained in the same manner as that of Example 87.

(2) By using the compound obtained in (1) mentioned above (40 mg) and phenol (7.0 mg) as starting materials, the compound shown in Table 16 (4.4 mg) was obtained in the same manners as those of Example 29, (1) and Example 80, (2).

Example 513

By using the compound obtained in Example 512, (1) (40 mg) and 3-t-butylphenol (11.2 mg) as starting materials, the compound shown in Table 16 (6.7 mg) was obtained in the same manners as those of Example 29, (1) and Example 80, (2).

Example 514

(1) By using the compound obtained in Example 509, (1) (1.1 g) as a starting material, a debenzylated compound (570 mg) was obtained in the same manner as that of Example 87.

(2) By using the compound obtained in (1) mentioned above (60 mg) and phenol (10.6 mg) as starting materials, the compound shown in Table 16 (17 mg) was obtained in the same manner as that of Example 29.

Example 515

By using the compound obtained in Example 514, (1) (60 mg) and 3-t-butylphenol (16.8 mg) as starting materials, the compound shown in Table 16 (19 mg) was obtained in the same manner as that of Example 29.

Examples 516 to 520

Preparation methods of the compounds represented by the formula (U) having $X^{1U}$ and $X^{2U}$ defined in Table 17 are shown below.

[Formula 42]

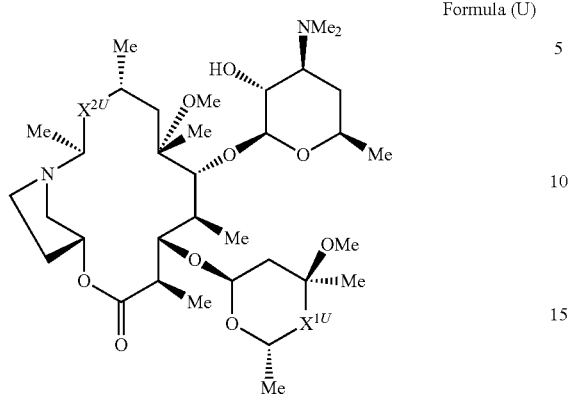

Formula (U)

TABLE 17

| Example | X$^{1u}$ | X$^{2u}$ | ESI MS (M + H) | $^1$H-NMR, CDCl$_3$, δ (ppm) |
|---|---|---|---|---|
| 516 |  |  | 950.8 | (600 MHz): 0.96 (t, J = 6.88 Hz, 3H) 1.06-1.10 (m, 6H) 1.13 (d, J = 6.42 Hz, 9H) 1.15-1.27 (m, 8H) 1.28 (d, J = 6.88 Hz, 3H) 1.41 (s, 3H) 1.60-1.65 (m, 1H) 1.85-1.95 (m, 3H) 2.04 (d, J = 14.67 Hz, 3H) 2.27-2.32 (m, 1H) 2.29 (s, 6H) 2.42-2.89 (m, 13H) 3.25-3.30 (m, 7H) 3.33-3.43 (m, 1H) 3.49-3.57 (m, 1H) 3.68-3.80 (m, 3H) 3.81 (s, 3H) 4.21 (q, J = 6.42 Hz, 1H) 4.36 (q, J = 6.88 Hz, 1H) 4.46 (d, J = 7.34 Hz, 1H) 4.83 (d, J = 4.58 Hz, 1H) 5.11-5.15 (m, 1H) 6.84-6.87 (m, 1H) 6.91-6.95 (m, 1H) 7.18-7.22 (m, 1H) 7.30-7.33 (m, 1H) |
| 517 |  |  | 949.6 | (500 MHz): 0.89-0.97 (m, 3H) 1.05 (d, J = 6.88 Hz, 3H) 1.07-1.24 (m, 16H) 1.26 (d, J = 6.88 Hz, 3H) 1.30 (d, J = 6.50 Hz, 3H) 1.35 (s, 3H) 1.47-1.70 (m, 6H) 1.88-2.32 (m, 4H) 2.25 (s, 6H) 2.37-2.83 (m, 11H) 2.95-3.03 (m, 1H) 3.15 (s, 3H) 3.21-3.28 (m, 3H) 3.31 (s, 3H) 3.63-3.71 (m, 2H) 3.72-3.77 (m, 1H) 3.84 (s, 3H) 4.29-4.41(m, 2H) 4.52 (d, J = 9.94 Hz, 2H) 4.80-4.85 (m, 1H) 5.12-5.17 (m, 1H) 5.45-5.51 (m, 1H) 6.85-6.95 (m, 2H) 7.19-7.24 (m, 1H) 7.25-7.30 (m, 1H) |
| 518 |  |  | 965.0 | (600 MHz): 0.88-0.96 (m, 3H) 1.03-1.22 (m, 22H) 1.26-1.34 (m, 3H) 1.40 (s, 3H) 1.45-1.80 (m, 3H) 1.85-1.96 (m, 1H) 2.01-2.19 (m, 3H) 2.25 (s, 6H) 2.21-2.31 (m, 2H) 2.35-2.91 (m, 11H) 3.16-3.28 (m, 3H) 3.24 (s, 3H) 3.30 (s, 3H) 3.65-3.79 (m, 3H) 3.83 (s, 3H) 4.29-4.42 (m, 2H) 4.47-4.58 (m, 2H) 4.79-4.86 (m, 1H) 5.08-5.18 (m, 1H) 5.37-5.50 (m, 1H) 6.82-6.88 (m, 1H) 6.88-6.95 (m, 1H) 7.16-7.23 (m, 1H) 7.26-7.31 (m, 1H) |
| 519 |  |  | 935.6 | (600 MHz): 0.96 (t, J = 7.11 Hz, 3H) 1.04 (d, J = 6.42 Hz, 3H) 1.06-1.30 (m, 24H) 1.34 (s, 3H) 1.57-1.70 (m, 2H) 1.86-1.94 (m, 2H) 2.02-2.25 (m, 4H) 2.28 (s, 6H) 2.31 (d, J = 13.75 Hz, 1H) 2.41-2.77 (m, 13H) 2.81 (d, J = 13.76 Hz, 1H) 2.96-3.02 (m, 1H) 3.19 (s, 3H) 3.25-3.31 (m, 2H) 3.49-3.55 (m, 1H) 3.69 (d, J = 7.34 Hz, 1H) 3.79-3.87 (m, 2H) 3.81 (s, 3H) 4.22 (q, J = 6.27 Hz, 1H) 4.36 (q, J = 6.88 Hz, 1H) 4.45 (d, J = 7.34 Hz, 1H) 4.77-4.81 (m, 1H) 5.14-5.19 (m, 1H) 6.86 (d, J = 7.34 Hz, 1H) 6.91-6.95 (m, 1H) 7.18-7.22 (m, 1H) 729-7.33 (m, 1H) |

TABLE 17-continued

| Example | X$^{1u}$ | X$^{2u}$ | ESI MS (M + H) | $^1$H-NMR, CDCl$_3$, δ (ppm) |
|---|---|---|---|---|
| 520 | (structure with carbamate, N-ethyl, methoxyphenyl group) | (H$_2$N- substituted structure) | 950.6 | (600 MHz): 0.90-1.39 (m, 32H) 1.42-2.11 (m, 6H) 2.25 (s, 6H) 2.32-2.93 (m, 11H) 3.05-3.28 (m, 7H) 3.31 (s, 3H) 3.59-3.77 (m, 4H) 3.84 (s, 3H) 4.33-4.41 (m, 3H) 4.48-4.57 (m, 2H) 4.88-4.92 (m, 1H) 4.96-5.01 (m, 1H) 5.47-5.55 (m, 1H) 6.84-6.95 (m, 2H) 7.18-7.31 (m, 2H) |

Example 516

(1) By using the compound obtained in Example 1, (2) (2.0 g) as a starting material, a deprotected compound (220 mg) was obtained in the same manners as those of Example 169, (1), (2), Example 177, (1), and Example 1, (3).
(2) By using the compound obtained in (1) mentioned above (200 mg) as a starting material, an acetyl compound (200 mg) was obtained in the same manner as that of Example 214, (3).
(3) By using the compound obtained in (2) mentioned above (200 mg) as a starting material, a crude product of 9-ketone compound was obtained in the same manner as that of Example 169, (2). The resulting compound was added with methanol (10 ml), and the solution was stirred overnight at room temperature. The reaction mixture was further stirred for 2 hours under reflux by heating, cooled to room temperature, and then concentrated under reduced pressure, and the resulting residue was purified by silica gel column chromatography (chloroform:methanol:28% aqueous ammonia=50:1:0.1 to 20:1:0.1) to obtain a 9-ketone and 2"-free compound (157.5 mg).
(4) By using the compound obtained in (3) mentioned above (35 mg) and the compound obtained in Reference Example 52 (51.5 mg) as starting materials, an aminomethyl compound (16.9 mg) was obtained in the same manner as that of Example 481.
(5) By using the compound obtained in (4) mentioned above (15 mg) as a starting material, the compound shown in Table 17 (6.8 mg) was obtained in the same manner as that of Example 214, (5).

Example 517

(1) By using the compound obtained in Example 176 (220 mg) as a starting material, an acetyl compound (224 mg) was obtained in the same manner as that of Example 214, (3).
(2) By using the compound obtained in (1) mentioned above (223 mg) as a starting material, the compound shown in Table 17 (14.3 mg) was obtained in the same manner as that of Example 516, (3).

Example 518

By using the compound obtained in Example 517 (15 mg) as a starting material, the compound shown in Table 17 (4.4 mg) was obtained in the same manner as that of Example 214, (5).

Example 519

By using the compound obtained in Example 516, (3) (130 mg) and the compound obtained in Reference Example 52 (191.4 mg) as starting materials, the compound shown in Table 17 (19.8 mg) was obtained in the same manner as that of Example 481.

Example 520

(1) The compound obtained in Example 517 (20 mg) was dissolved in ethanol (600 μl), the solution was added with hydrazine monohydrate (30 μl), and the mixture was stirred at 100° C. for 10 hours. The reaction mixture was added with distilled water and ethyl acetate, the layers were separated, and the organic layer was dried over anhydrous magnesium sulfate, and filtered. The filtrate was concentrated under reduced pressure to obtain a crude product (22 mg).
(2) The compound obtained in (1) mentioned above (5.0 mg) was dissolved in methanol (100 μl), the solution was added with water (50 μl), and the mixture was stirred at −20° C. The reaction mixture was added with 3 N hydrochloric acid (3 μl) and aqueous sodium nitrite (20 μl), and then added with 3 N hydrochloric acid to maintain the mixture at pH 3. The reaction mixture was further added with aqueous sodium nitrite (20 μl), and the mixture was stirred for 1 hour while the mixture was maintained at pH 3 by adding 3 N hydrochloric acid. The reaction mixture was added with potassium carbonate under ice cooling and thereby made alkaline, the solution was added with sodium borohydride (1.0 mg), and the mixture was stirred. The reaction mixture was stirred for 30 minutes while the mixture was maintained at pH 4 by adding 1 N hydrochloric acid. The reaction mixture was added with saturated aqueous sodium hydrogencarbonate and chloroform, the layers were separated, and the organic layer was dried over anhydrous magnesium sulfate, and filtered. The filtrate was concentrated under reduced pressure, and the resulting residue was purified by preparative thin layer chromatography (chloroform:methanol:28% aqueous ammonia=10:1:0.1) to obtain the compound shown in Table 17 (1.3 mg).

Example 521

A preparation method of the compound represented by the formula (Y) wherein R is hydrogen atom is shown below.

333

[Formula 43]

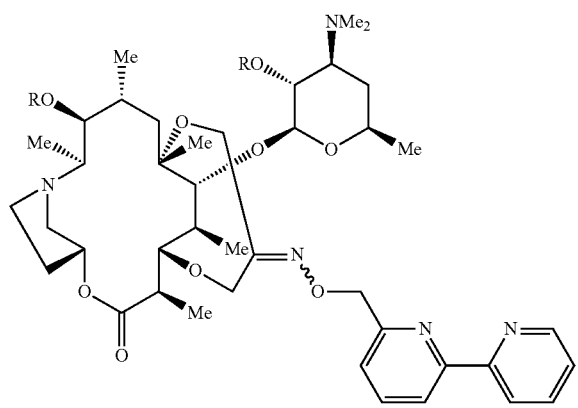

Formula (Y)

Example 521

(1) The compound represented by the formula V (2.64 g), which was obtained by the method described in the patent document (US2006/0142214), was dissolved in tetrahydrofuran (80 ml), the solution was added with a 1.06 M solution of lithium triethylborohydride in tetrahydrofuran (19.8 ml) at −30° C., and the mixture was stirred for 1 hour. The reaction mixture was added with saturated aqueous ammonium chloride and ethyl acetate, the layers were separated, and then the organic layer was dried over anhydrous magnesium sulfate, and filtered. The filtrate was concentrated under reduced pressure, the resulting residue was dissolved in ethylene glycol (50 ml) and pyridine (10 ml), and the solution was concentrated under reduced pressure with heating on an oil bath at 130° C. The resulting residue was dissolved in ethyl acetate and distilled water, the layers were separated, and then the organic layer was dried over anhydrous magnesium sulfate, and filtered. The filtrate was concentrated under reduced pressure, and the resulting residue was purified by silica gel column chromatography (chloroform:methanol:28% aqueous ammonia=20:1:0.1) to obtain a 9-hydroxyl compound (1.41 g).

(2) By using the compound obtained in (1) mentioned above (1.85 g) as a starting material, the compound represented by the formula W (260 mg) was obtained in the same manner as that of Reference Example 1.

(3) By using the compound obtained in (2) mentioned above (250 mg) and the compound obtained in Reference Example 2 (164 mg) as starting materials, the compound represented by the formula X wherein X is =CH₂ (43 mg) was obtained in the same manners as those of Example 1, (1) and (2).

(4) The compound obtained in (3) mentioned above (25.4 mg) was dissolved in a mixed solution of tetrahydrofuran and distilled water (2:1, 1.5 ml), the solution was added with 4 wt % aqueous osmium tetroxide (40 µl) and N-methylmorpholine N-oxide (18 mg), and the mixture was stirred at room temperature for 1 hour. The reaction mixture was added with saturated aqueous sodium hydrogencarbonate and then added with sodium hydrogensulfite, the mixture was stirred, and then extracted with ethyl acetate. The organic layer was dried over anhydrous magnesium sulfate, and filtered. The filtrate was concentrated under reduced pressure, the resulting crude product was dissolved in chloroform, the solution was added with 90% lead tetraacetate (23 mg) under ice cooling, and the mixture was stirred for 10 minutes. The reaction mixture was added

334 with saturated aqueous sodium hydrogencarbonate and diethyl ether, the layers were separated, and then the organic layer was washed with saturated brine, dried over anhydrous sodium sulfate, and filtered. The filtrate was concentrated under reduced pressure, and the resulting residue was purified by silica gel column chromatography (chloroform:methanol:28% aqueous ammonia=20:1:0.1) to obtain a compound represented by the formula X wherein X is =O (11 mg).

(5) The compound obtained in (4) mentioned above (11 mg) was dissolved in acetonitrile (0.5 ml), the solution was added with a solution of O-(2,2'-bipyridin-6-ylmethyl)hydroxylamine (5.4 mg) obtained in Reference Example 90 and 1 N hydrochloric acid (30 µl) in ethanol (1 ml), and the mixture was stirred at room temperature for 1 hour. The reaction mixture was added with saturated aqueous sodium hydrogencarbonate and ethyl acetate, the layers were separated, and then the organic layer was dried over anhydrous magnesium sulfate, and filtered. The filtrate was concentrated under reduced pressure, and the resulting residue was purified by silica gel column chromatography (hexane:acetone:triethylamine=50:10:0.2) to obtain a compound represented by the formula Y wherein R is triethylsilyl (12.5 mg).

(6) By using the compound obtained in (5) mentioned above (12.5 mg) as a starting material, a compound represented by the formula Y wherein R is hydrogen atom (2.2 mg) was obtained in the same manner as that of Example 1, (3).

[Formula 44]

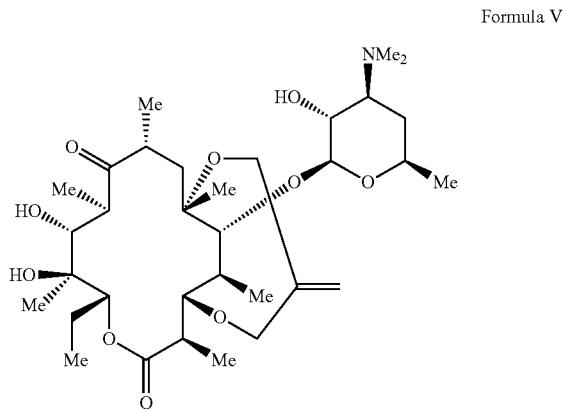

Formula V

[Formula 45]

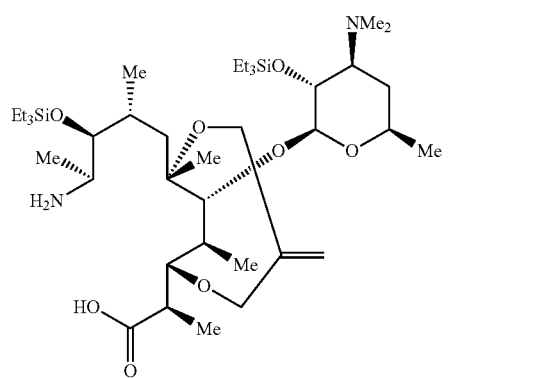

Formula W

335

-continued

[Formula 46]

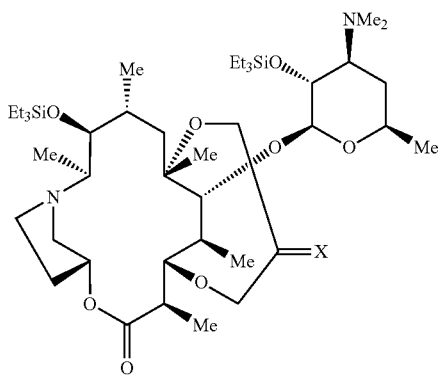

Formula X

Example 522

A preparation method of the compound represented by the formula (Z) is shown below.

[Formula 47]

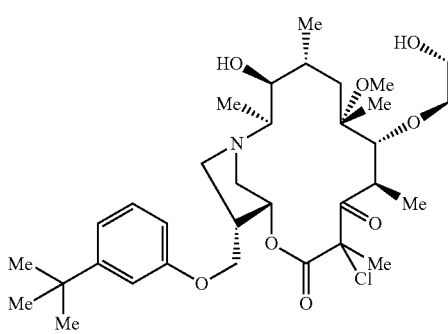

Formula (Z)

Example 522

By using the compound obtained in Example 478, (1) (86.6 mg) as a starting material, the compound represented by the formula (Z) (18.9 mg) was obtained in the same manners as those of Example 226, (1) and Example 228, (4).

Example 523

A preparation method of the compound represented by the formula (AA) is shown below.

336

[Formula 48]

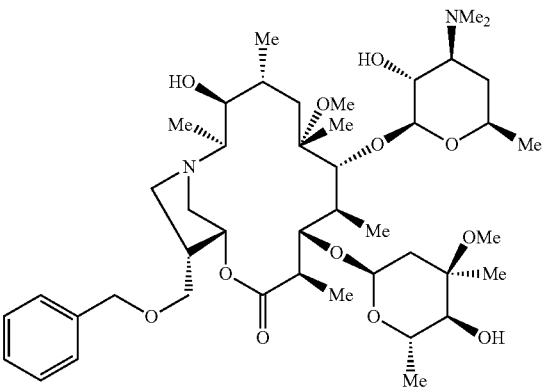

Formula (AA)

Example 523

By using the compound obtained in Reference Example 91 (100 mg) and the compound obtained in Reference Example 10 (88 mg) as starting materials, the compound represented by the formula (AA) (8.6 mg) was obtained in the same manner as that of Example 1.

Example 524

A preparation method of the compound represented by the formula (AB) is shown below.

[Formula 49]

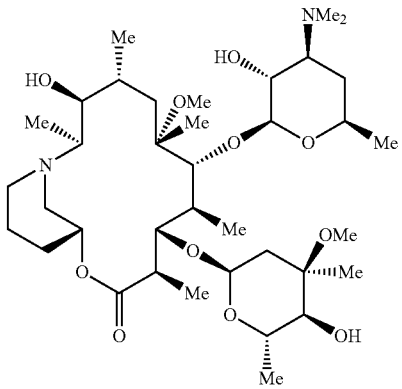

Formula (AB)

Example 524

(1) By using the compound obtained in Reference Example 1 (8 g) and the compound obtained in Reference Example 92 (13.3 g) as starting materials, a lactonization precursor (1.61 g) wherein the steric configuration of the asymmetric carbon atom on the piperidine ring was R, and a lactonization precursor (1.23 g) wherein the steric configuration of the asymmetric carbon atom on the piperidine ring was S were obtained in the same manner as that of Example 1, (1).

(2) By using the lactonization precursor (1.61 g) obtained in (1) mentioned above wherein the steric configuration of the asymmetric carbon atom on the piperidine ring was R as a starting material, a cyclized compound (286 mg) was obtained in the same manner as that of Example 1, (2).

(3) By using the compound obtained in (2) mentioned above (50 mg) as a starting material, the compound represented by the formula (AB) (34 mg) was obtained in the same manner as that of Example 1, (3).

Example 525

A preparation method of the compound represented by the formula (AC) is shown below.

[Formula 50]

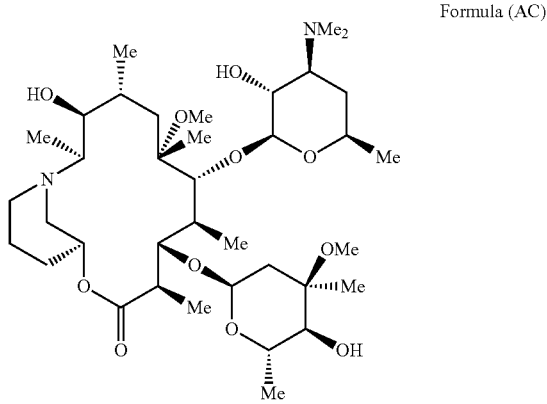

Formula (AC)

Example 525

(1) By using the lactonization precursor (1.22 g) obtained in Example 524, (1) wherein the steric configuration of the asymmetric carbon atom on the piperidine ring was S as a starting material, a cyclized compound (40.7 mg) was obtained in the same manner as that of Example 1, (2).
(2) By using the compound obtained in (1) mentioned above (40.7 mg) as a starting material, the compound represented by the formula (AC) (13 mg) was obtained in the same manner as that of Example 1, (3).

Example 526

A preparation method of the compound represented by the formula (AD) is shown below.

[Formula 51]

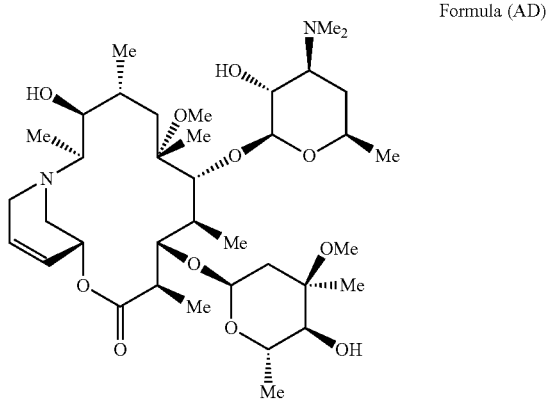

Formula (AD)

Example 526

(1) The compound obtained in Reference Example 1 (5.0 g) was dissolved in chloroform (50 ml), the solution was added with 30% aqueous sodium hydroxide (25 ml) and allyl bromide (440 μl), and the mixture was stirred at room temperature for 27 hours. The layers of the reaction mixture were separated, the organic layer was washed successively with 20% aqueous ammonium chloride and saturated brine, then dried over anhydrous sodium sulfate, and filtered. The filtrate was concentrated under reduced pressure, and the resulting residue was purified by silica gel column chromatography (ethyl acetate:methanol=20:1 to 8:1) to obtain an allyl compound (1.32 g).
(2) By using the compound obtained in (1) mentioned above (1.27 g) and epoxybutene (1.03 g) as starting materials, a lactonization precursor (439 mg) was obtained in the same manner as that of Example 1, (1).
(3) By using the compound obtained in (2) mentioned above (427 mg) as a starting material, a cyclized lactone compound (228 mg) was obtained in the same manner as that of Example 1, (2).
(4) The compound obtained in (3) mentioned above (30 mg) was dissolved in methylene chloride (10 ml), the solution was added with the second generation Grubbs catalyst (3.6 mg), and the mixture was stirred for 23 hours under reflux by heating. The reaction mixture was concentrated under reduced pressure, and the resulting residue was purified by preparative thin layer chromatography (hexane:ethyl acetate=3:1) to obtain a cyclized compound (14.9 mg).
(5) By using the compound obtained in (4) mentioned above (14.7 mg) as a starting material, the compound represented by the formula (AD) (9.5 mg) was obtained in the same manner as that of Example 1, (3).

Test Example 1 (In Vitro Antibacterial Activity)

In vitro antibacterial activities of the compounds of the present invention against various test bacteria were measured according to the microbroth dilution method (CLSI method). The test bacteria used are shown in Table 18. As Comparative agent 1, clarithromycin was used, and the results for typical exemplary compounds are shown as MIC values (minimum inhibitory concentration, μg/ml) in Table 19.

TABLE 18

| Test bacteria | Symbols of bacteria |
|---|---|
| H. influenzae ATCC 43095 | A |
| S. pneumoniae ATCC 49619 | B |
| S. pneumoniae ATCC 700904 | C |

TABLE 19

| Compound | A | B | C |
|---|---|---|---|
| Comparative agent 1 | 4 | 0.03 | >128 |
| Example1 | 0.5 | 0.12 | >128 |
| Example31 | 4 | 0.5 | 4 |
| Example35 | 16 | 0.25 | 2 |
| Example52 | 4 | 0.12 | 4 |
| Example56 | 2 | 0.12 | 1 |

TABLE 19-continued

| Compound | A | B | C |
|---|---|---|---|
| Example58 | 4 | 0.5 | 4 |
| Example62 | 4 | 0.25 | 4 |
| Example71 | 4 | 0.12 | 8 |
| Example72 | 2 | 0.25 | 4 |
| Example74 | 4 | 0.25 | 8 |
| Example75 | 2 | 0.12 | 1 |
| Example76 | 2 | 0.12 | 2 |
| Example77 | 2 | 0.25 | 1 |
| Example78 | 8 | 0.25 | 0.5 |
| Example81 | 4 | 0.12 | 2 |
| Example83 | 2 | 0.25 | 4 |
| Example144 | 4 | 0.25 | 4 |
| Example157 | 4 | 0.06 | 1 |
| Example158 | 4 | 0.12 | 1 |
| Example169 | 0.25 | 0.06 | >128 |
| Example172 | 8 | 0.25 | 4 |
| Example174 | 16 | 0.25 | 2 |
| Example175 | 8 | 0.12 | 8 |
| Example176 | 8 | 0.03 | 0.25 |
| Example178 | 4 | 0.12 | 4 |
| Example184 | 2 | 0.03 | 4 |
| Example185 | 2 | 0.06 | 4 |
| Example187 | 8 | 0.12 | 4 |
| Example188 | 8 | 0.25 | 4 |
| Example189 | 4 | 0.06 | 0.25 |
| Example194 | 4 | 0.06 | 2 |
| Example196 | 2 | 0.12 | 8 |
| Example198 | 4 | 0.25 | 4 |
| Example212 | 4 | 1 | 4 |
| Example214 | 2 | 0.5 | >128 |
| Example401 | 8 | 0.5 | 2 |
| Example461 | 2 | 0.5 | 64 |
| Example473 | 1 | 0.12 | 1 |
| Example479 | 8 | 1 | 16 |
| Example507 | 8 | 0.12 | 0.5 |
| Example511 | 2 | 0.5 | >128 |
| Example516 | 4 | 0.06 | 0.25 |
| Example521 | 8 | 0.12 | 8 |
| Example522 | 16 | 8 | >16 |
| Example523 | 4 | 0.12 | >128 |
| Example525 | 0.5 | 0.25 | >128 |

Industrial Applicability

The compounds of the present invention have potent antibacterial activity against various microorganisms, and even against *Hemophilus influenzae*, erythromycin resistant pneumococci and the like, against which sufficient antibacterial activity cannot be obtained with conventional macrolide antibiotics, and therefore, they can be used as medicaments for prophylactic and/or therapeutic treatment of various microbial infectious diseases.

What is claimed is:

1. A 10a-azalide compound represented by the formula (I):

[Formula 1]

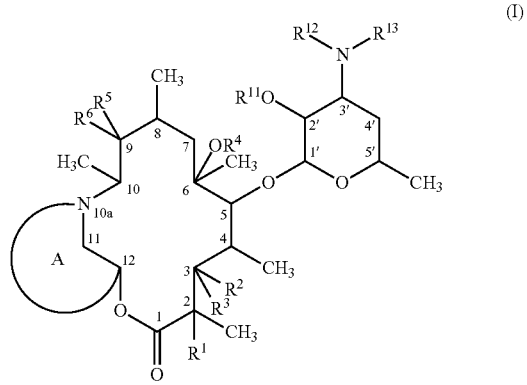

(I)

{wherein, in the formula, $R^1$ is:
a hydrogen atom, or
a halogen atom,
$R^2$ and $R^3$ combine together to represent an oxo group, or one of them is a hydrogen atom, and the other is:
a hydroxyl group,
a protected hydroxyl group,
a group represented by the formula —$X^{031}$—$R^{031}$, or a group represented by the formula (II):

[Formula 2]

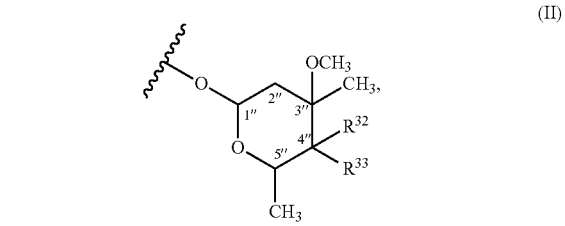

(II)

wherein $X^{031}$ is:
a group represented by the formula —O—,
a group represented by the formula —OCO—, or
a group represented by the formula —OCON($R^{20}$)—,
$R^{031}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A,
the group A is a group consisting of hydroxyl group, a halogen atom, a $C_{1-6}$ alkyl group, a $C_{1-6}$ haloalkyl group, a $C_{1-6}$ alkoxy group, a $C_{2-7}$ alkoxycarbonyl group, a nitro group, a saturated heterocyclic group and a $C_{1-11}$ acyl group,
one of $R^{32}$ and $R^{33}$ is a hydrogen atom, and the other is:
a hydrogen atom,
a hydroxyl group,
a protected hydroxyl group,
an amino group,
a protected amino group,
a group represented by the formula —$X^{331}$—$R^{331}$,
a group represented by the formula —$X^{331}$-$A^{331}$-$X^{332}$—$R^{331}$,
a group represented by the formula —$X^{331}$-$A^{331}$-$X^{332}$-$A^{332}$-$X^{333}$—$R^{331}$, or
a group represented by the formula —$X^{331}$-$A^{331}$-$X^{332}$-$A^{332}$-$X^{333}$-$A^{333}$-$X^{334}$—$R^{331}$,
wherein $X^{331}$ is:
a group represented by the formula —O—,
a group represented by the formula —OCO—,
a group represented by the formula —OCON($R^{20}$)—,
a group represented by the formula —N($R^{20}$)—, or
a group represented by the formula —N($R^{20}$)CO—,
$R^{331}$ is:
a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, or one of $R^{32}$ and $R^{33}$ is a hydroxyl group, and the other is:
a group represented by the formula —$X^{335}$—$R^{332}$,
a group represented by the formula —$X^{335}$-$A^{334}$-$X^{336}$—$R^{332}$, or
a group represented by the formula —$X^{335}$-$A^{334}$-$X^{336}$-$A^{335}$-$X^{337}$—$R^{332}$,
wherein $X^{335}$ is:
a single bond,
a group represented by the formula —$CH_2N(R^{20})$—,
a group represented by the formula —$CH_2N(R^{20})CO$—,
a group represented by the formula —$CH_2N(R^{20})CO_2$—,
a group represented by the formula —$CH_2N(R^{20})CON(R^{21})$—,
a group represented by the formula —$CH_2O$—, or
a group represented by the formula —$CH_2S(O)_p$—,
$R^{332}$ is:
a $C_{1-6}$ alkyl group which may be substituted with 1 to 3 groups selected from the group consisting of "an amino group, a hydroxyl group, an aryl group, a heterocyclic group, and a biaryl group (the aryl group, the heterocyclic group, and the biaryl group may be substituted with 1 to 3 substituents selected from the group A)",
a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A,
p is an integer of 0 to 2, or
$R^{32}$ and $R^{33}$ combine together to represent an oxo group,
an oxime group,
a protected oxime group,
a group represented by the formula (III)

[Formula 3]

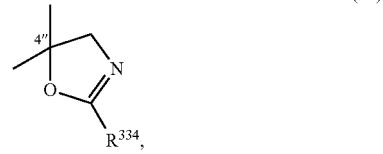

(III)

or
a group represented by the formula (IV)

[Formula 4]

(IV)

wherein $R^{334}$ is:
a group represented by the formula —OH or
a group represented by the formula —SH, or
one of $R^2$ and $R^3$ is a hydrogen atom, and the other may combine with $R^4$ to represent a group represented by the formula (V):

[Formula 5]

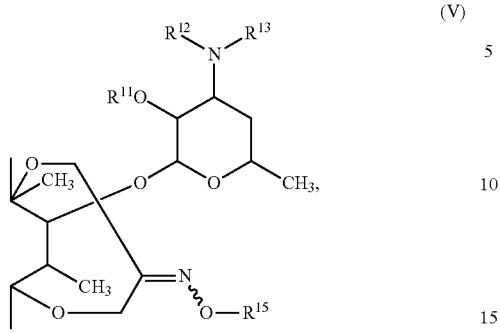

(V)

wherein $R^{15}$ is a $C_{1-6}$ alkyl group substituted with one biaryl group which may be substituted with 1 to 3 groups selected from the group A, $R^4$ is:

a hydrogen atom, a group represented by the formula —$R^{041}$, a group represented by the formula —$CH_2$—$CH(OH)$—$CH_2$—$NHR^{041}$, or a group represented by the formula —$CH_2$—$CH(OH)$—$CH_2$—$NH$-$A^{041}$-$X^{042}$—$R^{041}$, wherein $A^{041}$ is:

a divalent $C_{1-10}$ aliphatic hydrocarbon group, or a divalent heterocyclic group, and $R^{041}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, or $R^4$ may combine with $R^6$ to form cyclic carbonate [—$CO_2$—], one of $R^5$ and $R^6$ is a hydrogen atom, and the other is:

a hydrogen atom, a hydroxyl group, a protected hydroxyl group, an amino group, a protected amino group, a group represented by the formula —$X^{051}$—$R^{051}$, or a group represented by the formula —$X^{051}$-$A^{051}$-$X^{052}$—$R^{051}$, wherein $X^{051}$ is:

a group represented by the formula —O—, a group represented by the formula —$OCON(R^{22})$—, a group represented by the formula —$N(R^{22})$—, or a group represented by the formula —$N(R^{22})CO$—, and $R^{051}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, or $R^5$ and $R^6$ combine together to represent an oxo group, an oxime group, a protected oxime group, a group represented by the formula =N—$X^{053}$—$R^{052}$, or a group represented by the formula =N—$X^{053}$-$A^{052}$-$X^{054}$—$R^{052}$, wherein $X^{053}$ is:

a group represented by the formula —O—, or a group represented by the formula —CO—, and $R^{052}$ is:

a $C_{1-6}$ alkyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an aryl group, a heterocyclic group, and a biaryl group (the aryl group, the heterocyclic group, and the biaryl group may be substituted with 1 to 3 groups selected from the group A)", an aryl group which may be substituted with 1 to 3 groups selected from the group A, a heterocyclic group which may be substituted with 1 to 3 groups selected from the group A, or a biaryl group which may be substituted with 1 to 3 groups selected from the group A, the ring A is a group represented by the formula (VI)

[Formula 6]

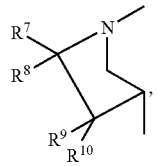

(VI)

or
a group represented by the formula (VII)

[Formula 7]

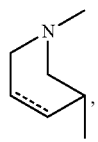

(VII)

wherein $R^7$ and $R^8$, which are the same or different, represent
a hydrogen atom, or
a group represented by the formula $—X^{071}—R^{071}$,
wherein $X^{071}$ is:
a single bond,
a group represented by the formula $-A^{072}-N(R^{27})—$,
a group represented by the formula $-A^{072}-N(R^{27})CO—$,
a group represented by the formula $-A^{072}-N(R^{27})CO_2—$,
a group represented by the formula $-A^{072}-N(R^{27})CON(R^{28})—$,
a group represented by the formula $-A^{072}-OCON(R^{27})—$,
a group represented by the formula $-A^{072}-O—$,
a group represented by the formula $-A^{072}-CO_2—$,
a group represented by the formula $—CO_2—$,
a group represented by the formula $-A^{072}-OCO—$,
a group represented by the formula $-A^{072}-OCO_2—$,
a group represented by the formula $-A^{072}-S(O)_t—$,
a group represented by the formula $-A^{072}-N(R^{27})SO_2—$,
a group represented by the formula $-A^{072}-SO_2N(R^{27})—$,
a group represented by the formula $-A^{072}-CON(R^{27})—$, or,
a group represented by the formula $—CON(R^{27})—$,
$A^{072}$ is:
a divalent $C_{1-10}$ aliphatic hydrocarbon group,
t is an integer of 0 to 2,
$R^{071}$ is:
a $C_{1-6}$ alkyl group which may be substituted with 1 to 3 groups selected from the group consisting of "an amino group, a hydroxyl group, an aryl group, a heterocyclic group, and a biaryl group (the aryl group, the heterocyclic group, and the biaryl group may be substituted with 1 to 3 groups selected from the group A)",
a $C_{2-6}$ alkenyl group which may be substituted with 1 to 3 groups selected from the group consisting of "an amino group, a hydroxyl group, an aryl group, a heterocyclic group, and a biaryl group (the aryl group, the heterocyclic group, and the biaryl group may be substituted with 1 to 3 groups selected from the group A)",
a $C_{2-6}$ alkynyl group which may be substituted with 1 to 3 groups selected from the group consisting of "an amino group, a hydroxyl group, an aryl group, a heterocyclic group, and a biaryl group (the aryl group, the heterocyclic group, and the biaryl group may be substituted with 1 to 3 groups selected from the group A)",
an aryl group which may be substituted with 1 to 3 groups selected from the group A,
a heterocyclic group which may be substituted with 1 to 3 groups selected from the group A, or
a biaryl group which may be substituted with 1 to 3 groups selected from the group A, and
$R^9$ and $R^{10}$, which are the same or different, represent
a hydrogen atom,
a hydroxyl group,
a protected hydroxyl group,
an amino group,
a protected amino group,
an azido group,
a halogen atom,
a group represented by the formula $—X^{091}—R^{091}$,
a group represented by the formula $—X^{091}-A^{091}-X^{092}—R^{091}$,
a group represented by the formula $—X^{091}-A^{091}-X^{092}-A^{092}-X^{093}—R^{091}$, or
a group represented by the formula $—X^{091}-A^{091}-X^{092}-A^{092}-X^{093}-A^{093}-X^{094}—R^{091}$,
wherein $X^{091}$ is:
a single bond,
a group represented by the formula $-A^{094}-N(R^{23})—$,
a group represented by the formula $-A^{094}-N(R^{23})CO—$,
a group represented by the formula $-A^{094}-N(R^{23})CO_2—$,
a group represented by the formula $-A^{094}-N(R^{23})CON(R^{24})—$,
a group represented by the formula $-A^{094}-OCON(R^{23})—$,
a group represented by the formula $-A^{094}-O—$,
a group represented by the formula $-A^{094}-CO_2—$,
a group represented by the formula $-A^{094}-OCO—$,
a group represented by the formula $-A^{094}-OCO_2—$,
a group represented by the formula $-A^{094}-S(O)_q—$,
a group represented by the formula $-A^{094}-N(R^{23})SO_2—$,
a group represented by the formula $-A^{094}-SO_2N(R^{23})—$, or
a group represented by the formula $-A^{094}-CON(R^{23})—$,
$A^{094}$ is:
a single bond,
a divalent $C_{1-10}$ aliphatic hydrocarbon group,
an arylene group, or
a divalent heterocyclic group,
$R^{091}$ is:
a $C_{1-6}$ alkyl group which may be substituted with 1 to 3 groups selected from the group consisting of "an amino group, a hydroxyl group, a $C_{3-8}$ cycloalkyl group, a $C_{3-8}$ cycloalkylidene group, a $C_{1-6}$ alkoxy group, a $C_{1-11}$ acyloxy group, a $C_{2-7}$ alkoxycarbonyl group, a $C_{1-11}$ acyl group, a cyano group, an aryl group, a heterocyclic group, and a biaryl group (the aryl group, the heterocyclic group, and the biaryl group may be substituted with 1 to 3 groups selected from the group A)", a $C_{2-6}$ alkenyl group which may be substituted with 1 to 3 groups selected from the group consisting of "an amino group, a hydroxyl group, a $C_{3-8}$ cycloalkyl group, a $C_{1-6}$ alkoxy group, a $C_{1-11}$ acyloxy group, a $C_{2-7}$ alkoxycarbonyl group, a cyano group, an aryl group, a heterocyclic group, and a biaryl group (the aryl group, the heterocyclic group, and the biaryl group may be substituted with 1 to 3 groups selected from the group A)", a $C_{2-6}$ alkynyl group which may be substituted with 1 to 3 groups selected from the group consisting of "an amino group, a hydroxyl group, a $C_{3-8}$ cycloalkyl group, a $C_{1-6}$ alkoxy group, a $C_{1-11}$ acyloxy group, a $C_{2-7}$ alkoxycarbonyl group, a cyano group, an aryl group, a heterocyclic group, and a biaryl group (the aryl group, the heterocyclic group, and the biaryl group may be substituted with 1 to 3 groups selected from the group A)", a $C_{3-8}$ cycloalkyl group which may be substituted with a $C_{1-6}$ alkyl group, an aryl group which may be substituted with 1 to 5 groups selected from the group B, a heterocyclic group which may be substituted with 1 to 5 groups selected from the group B, or a biaryl group which may be substituted with 1 to 5 groups selected from the group B, the group B is a group consisting of "a hydroxyl group, a halogen atom, a cyano group, a $C_{1-6}$ alkyl group, a $C_{1-6}$ hydroxyalkyl group, a $C_{2-6}$ alkynyl group, a $C_{3-8}$ cycloalkyl group, a $C_{1-6}$ haloalkyl group, a $C_{7-11}$ aralkyl group, a $C_{1-10}$ alkoxy group, a $C_{3-8}$ cycloalkoxy group, a $C_{1-6}$ haloalkoxy group, a $C_{7-11}$ aralkyloxy group, an aryloxy group, a $C_{1-11}$ acyloxy group, a $C_{1-6}$ alkylthio group, a $C_{1-6}$ haloalkylthio group, an adamantyl group, a carboxy group, a $C_{2-7}$ alkoxycarbonyl group, a $C_{2-7}$ alkylaminocarbonyl group, an aryloxycarbonyl group, a $C_{8-12}$ aralkyloxycarbonyl group, a $C_{1-11}$ acyl group, a $C_{1-11}$ haloacyl group, an amino group, a $C_{1-6}$ alkylamino group, a nitro group, a saturated heterocyclic group and a $C_{1-11}$ acylamino group", q is an integer of 0 to 2, and the bond indicated with lines including a broken line is a single bond or a double bond, $R^{11}$ is:
a hydrogen atom, or
a protective group of hydroxyl group, $R^{12}$ and $R^{13}$, which are the same or different, represent
a hydrogen atom,
a $C_{1-6}$ alkyl group, or
a protective group of amino group, $X^{332}$, $X^{333}$, $X^{334}$, $X^{336}$, $X^{337}$, $X^{042}$, $X^{052}$, $X^{054}$, $X^{092}$, $X^{093}$, and $X^{094}$ mentioned above, which are the same or different, represent a single bond,
a group represented by the formula —O—,
a group represented by the formula —OCO—,
a group represented by the formula —OCO$_2$—,
a group represented by the formula —OCON(R$^{25}$)—,
a group represented by the formula —S(O)$_r$—,
a group represented by the formula —SO$_2$N(R$^{25}$)—,
a group represented by the formula —OCS—,
a group represented by the formula —CO—,
a group represented by the formula —CO$_2$—,
a group represented by the formula —CON(R$^{25}$)—,
a group represented by the formula —CH=N—,
a group represented by the formula —CH=N—O—,
a group represented by the formula —C(R$^{25}$)=N—,
a group represented by the formula —C(R$^{25}$)=N—O—,
a group represented by the formula —C(R$^{25}$)=N—N(R$^{26}$)—,
a group represented by the formula —CH=N—N(R$^{25}$)—,
a group represented by the formula —CS—,
a group represented by the formula —C(S)O—,
a group represented by the formula —CSN(R$^{25}$)—,
a group represented by the formula —O—N=C(R$^{25}$)—,
a group represented by the formula —N=CH—,
a group represented by the formula —N(R$^{25}$)—,
a group represented by the formula —N(R$^{25}$)CO—,
a group represented by the formula —N(R$^{25}$)CS—,
a group represented by the formula —N(R$^{25}$)SO$_2$—,
a group represented by the formula —N(R$^{25}$)CO$_2$—, or
a group represented by the formula —N(R$^{25}$)CON(R$^{26}$)—, r is an integer of 0 to 2, $A^{331}$, $A^{332}$, $A^{333}$, $A^{334}$, $A^{335}$, $A^{051}$, $A^{052}$, $A^{091}$, $A^{092}$ and $A^{093}$ mentioned above, which are the same or different, represent a divalent $C_{1-10}$ aliphatic hydrocarbon group which may be substituted with a hydroxyl group or a $C_{1-6}$ alkoxy group, an arylene group which may be substituted with a hydroxyl group or a $C_{1-6}$ alkoxy group, or a divalent heterocyclic group which may be substituted with a hydroxyl group or a $C_{1-6}$ alkoxy group, and $R^{20}$, $R^{21}$, $R^{22}$, $R^{23}$, $R^{24}$, $R^{25}$, $R^{26}$, $R^{27}$ and $R^{28}$ mentioned above, which are the same or different, represent
a hydrogen atom, or
a $C_{1-6}$ alkyl group}, or a salt thereof.

2. The 10a-azalide compound or a salt thereof according to claim 1, wherein $R^2$ and $R^3$ combine together to represent an oxo group, or one of them is a hydrogen atom, and the other is:
a hydroxyl group,
a protected hydroxyl group,
a group represented by the formula —X$^{031}$—R$^{031}$, or a group represented by the formula (II),
the ring A is a group represented by the formula (VI),
$R^9$ and $R^{10}$, which are the same or different, represent:
a hydrogen atom,
a hydroxyl group,
a protected hydroxyl group,
an amino group,
a protected amino group,
an azido group,
a halogen atom,
a group represented by the formula —X$^{091}$—R$^{091}$,
a group represented by the formula —X$^{091}$-A$^{091}$-X$^{092}$—R$^{091}$,
a group represented by the formula —X$^{091}$-A$^{091}$-X$^{092}$-A$^{092}$-X$^{093}$—R$^{091}$, or
a group represented by the formula —X$^{091}$-A$^{091}$-X$^{092}$-A$^{092}$-X$^{093}$-A$^{093}$-X$^{094}$—R$^{091}$,
wherein X$^{091}$ is:
a single bond,
a group represented by the formula -A$^{094}$-N(R$^{23}$)—,
a group represented by the formula -A$^{094}$-N(R$^{23}$)CO—,
a group represented by the formula -A$^{094}$-N(R$^{23}$)CO$_2$—,
a group represented by the formula -A$^{094}$-N(R$^{23}$)CON(R$^{24}$)—,
a group represented by the formula -A$^{094}$-OCON(R$^{23}$)—,
a group represented by the formula -A$^{094}$-O—,
a group represented by the formula -A$^{094}$-CO$_2$—, a group represented by the formula -A$^{094}$-OCO—,
a group represented by the formula -A$^{094}$-OCO$_2$—,
a group represented by the formula -A$^{094}$-S(O)$_q$—,
a group represented by the formula -A$^{094}$-N(R$^{23}$)SO$_2$—,
a group represented by the formula -A$^{094}$-SO$_2$N(R$^{23}$)—, or
a group represented by the formula -A$^{094}$-CON(R$^{23}$)—,
A$^{094}$ is:
  a single bond,
  a divalent C$_{1-10}$ aliphatic hydrocarbon group,
  an arylene group, or
  a divalent heterocyclic group,
R$^{091}$ is:
  a C$_{1-6}$ alkyl group which may be substituted with 1 to 3 groups selected from the group consisting of "an amino group, a hydroxyl group, a C$_{1-6}$ alkoxy group, a C$_{2-7}$ alkoxycarbonyl group, a C$_{1-11}$ acyl group, a cyano group, an aryl group, a heterocyclic group, and a biaryl group (the aryl group, the heterocyclic group, and the biaryl group may be substituted with 1 to 3 groups selected from the group A)",
  a C$_{2-6}$ alkenyl group which may be substituted with 1 to 3 groups selected from the group consisting of "an amino group, a hydroxyl group, a C$_{1-6}$ alkoxy group, a C$_{2-7}$ alkoxycarbonyl group, a cyano group, an aryl group, a heterocyclic group, and a biaryl group (the aryl group, the heterocyclic group, and the biaryl group may be substituted with 1 to 3 groups selected from the group A)",
  a C$_{2-6}$ alkynyl group which may be substituted with 1 to 3 groups selected from the group consisting of "an amino group, a hydroxyl group, a C$_{1-6}$ alkoxy group, a C$_{2-7}$ alkoxycarbonyl group, a cyano group, an aryl group, a heterocyclic group, and a biaryl group (the aryl group, the heterocyclic group, and the biaryl group may be substituted with 1 to 3 groups selected from the group A)",
  a C$_{3-8}$ cycloalkyl group which may be substituted with a C$_{1-6}$ alkyl group,
  an aryl group which may be substituted with 1 to 5 groups selected from the group B',
  a heterocyclic group which may be substituted with 1 to 5 groups selected from the group B', or
  a biaryl group which may be substituted with 1 to 5 groups selected from the group B',
    the group B' is a group consisting of "a hydroxyl group, a halogen atom, a cyano group, a C$_{1-6}$ alkyl group, a C$_{3-8}$ cycloalkyl group, a C$_{1-6}$ haloalkyl group, a C$_{7-11}$ aralkyl group, a C$_{1-10}$ alkoxy group, a C$_{3-8}$ cycloalkoxy group, a C$_{1-6}$ haloalkoxy group, a C$_{7-11}$ aralkyloxy group, an aryloxy group, a C$_{1-11}$ acyloxy group, a C$_{1-6}$ alkylthio group, a C$_{1-6}$ haloalkylthio group, an adamantyl group, a C$_{2-7}$ alkoxycarbonyl group, a C$_{2-7}$ alkylaminocarbonyl group, an aryloxycarbonyl group, a C$_{1-11}$ acyl group, a C$_{1-11}$ haloacyl group, an amino group, a C$_{1-6}$ alkylamino group, a nitro group, a saturated heterocyclic group and a C$_{1-11}$ acylamino group", and
q is an integer of 0 to 2.

3. The 10a-azalide compound or a salt thereof according to claim 1, wherein one of R$^9$ and R$^{10}$ is a hydrogen atom, and the other is:
  a hydrogen atom,
  a hydroxyl group,
  a protected hydroxyl group,
  an amino group,
  a protected amino group,
  an azido group,
  a halogen atom,
  a group represented by the formula —X$^{091}$—R$^{091}$, or
  a group represented by the formula —X$^{091\text{-}A091}$-X$^{092}$—R$^{091}$.

4. The 10a-azalide compound or a salt thereof according to claim 1, wherein one of R$^9$ and R$^{10}$ is a hydrogen atom, and the other is:
  a hydrogen atom, or
  a group represented by the formula —X$^{091}$—R$^{091}$.

5. The 10a-azalide compound or a salt thereof according to claim 2, wherein one of R$^9$ and R$^{10}$ is a hydrogen atom, and the other is:
  a hydrogen atom, or
  a group represented by the formula —X$^{091}$—R$^{091}$.

6. The 10a-azalide compound or a salt thereof according to claim 1, wherein R$^9$ and R$^{10}$ both represent a hydrogen atom.

7. The 10a-azalide compound or a salt thereof according to claim 4, wherein X$^{091}$ is:
  a single bond,
  a group represented by the formula -A$^{094}$-N(R$^{23}$)—,
  a group represented by the formula -A$^{094}$-N(R$^{23}$)CO—,
  a group represented by the formula -A$^{094}$-N(R$^{23}$)CO$_2$—,
  a group represented by the formula -A$^{094}$-O—, or
  a group represented by the formula -A$^{094}$-S(O)$_q$—, and
A$^{094}$ is:
  a single bond, or
  a divalent C$_{1-10}$ aliphatic hydrocarbon group.

8. The 10a-azalide compound or a salt thereof according to claim 4, wherein
X$^{091}$ is:
  a single bond,
  a group represented by the formula -A$^{094}$-N(H)—,
  a group represented by the formula -A$^{094}$-N(H)CO—,
  a group represented by the formula -A$^{094}$-N(H)CO$_2$—,
  a group represented by the formula -A$^{094}$-O—, or
  a group represented by the formula -A$^{094}$-S—, and
A$^{094}$ is:
  a single bond, or
  a methylene group.

9. The 10a-azalide compound or a salt thereof according to claim 4, wherein X$^{091}$ is:
  a single bond,
  a group represented by the formula —CH$_2$—O—, or
  a group represented by the formula —CH$_2$—S—.

10. The 10a-azalide compound or a salt thereof according to claim 4, wherein R$^{091}$ is:
  a C$_{1-6}$ alkyl group which may be substituted with 1 to 3 groups selected from the group consisting of "a hydroxyl group, a C$_{3-8}$ cycloalkyl group, a C$_{3-8}$ cycloalkylidene group, a C$_{1-6}$ alkoxy group, a cyano group, an aryl group, a heterocyclic group, and a biaryl group (the aryl group may be substituted with 1 to 3 C$_{1-6}$ alkyl groups)",
  a C$_{2-6}$ alkenyl group which may be substituted with 1 to 3 groups selected from the group consisting of "a hydroxyl group, a C$_{1-11}$ acyloxy group, a cyano group, an aryl group, a heterocyclic group, and a biaryl group",
  a C$_{2-6}$ alkynyl group which may be substituted with 1 to 3 groups selected from the group consisting of "an aryl group, a heterocyclic group, and a biaryl group",
  an aryl group which may be substituted with 1 to 3 groups selected from the group consisting of the group C,
  a heterocyclic group which may be substituted with 1 to 3 groups selected from the group consisting of the group C, or a biaryl group which may be substituted with 1 to 3 groups selected from the group consisting of the group C, and the group C is a group consisting of "a hydroxyl group, a halogen atom, a cyano group, a $C_{1-6}$ alkyl group, a $C_{1-6}$ hydroxyalkyl group, a $C_{2-6}$ alkynyl group, a $C_{3-8}$ cycloalkyl group, a $C_{1-6}$ haloalkyl group, a $C_{7-11}$ aralkyl group, a $C_{1-10}$ alkoxy group, a $C_{3-8}$ cycloalkoxy group, a $C_{1-6}$ haloalkoxy group, a $C_{7-11}$ aralkyloxy group, an aryloxy group, a $C_{1-6}$ alkylthio group, a $C_{1-6}$ haloalkylthio group, an adamantyl group, a carboxy group, a $C_{2-7}$ alkoxycarbonyl group, an aryloxycarbonyl group, a $C_{1-11}$ acyl group, an amino group, a $C_{1-6}$ alkylamino group, a saturated heterocyclic group and a $C_{1-11}$ acylamino group".

11. The 10a-azalide compound or a salt thereof according to claim 4, wherein $R^{091}$ is:

a $C_{1-6}$ alkyl group which may be substituted with 1 to 3 groups selected from the group consisting of "a hydroxyl group, a cyano group, an aryl group, a heterocyclic group, and a biaryl group", a $C_{2-6}$ alkenyl group which may be substituted with 1 to 3 groups selected from the group consisting of "an aryl group, a heterocyclic group, and a biaryl group", a $C_{2-6}$ alkynyl group which may be substituted with 1 to 3 groups selected from the group consisting of "an aryl group, a heterocyclic group, and a biaryl group", an aryl group which may be substituted with 1 to 3 groups selected from the group C', a heterocyclic group which may be substituted with 1 to 3 groups selected from the group C', or a biaryl group which may be substituted with 1 to 3 groups selected from the group C', and the group C' is a group consisting of "a hydroxyl group, a halogen atom, a $C_{1-6}$ alkyl group, a $C_{3-8}$ cycloalkyl group, a $C_{7-11}$ aralkyl group, a $C_{1-10}$ alkoxy group, a $C_{3-8}$ cycloalkoxy group, a $C_{7-11}$ aralkyloxy group, an aryloxy group, a $C_{1-6}$ alkylthio group, an adamantyl group, an aryloxycarbonyl group, a $C_{1-11}$ acyl group, an amino group, a $C_{1-6}$ alkylamino group, and a $C_{1-11}$ acylamino group".

12. The 10a-azalide compound or a salt thereof according to claim 4, wherein $R^{091}$ is:

a $C_{1-6}$ alkyl group which may be substituted with one group selected from the group consisting of "an aryl group, and a biaryl group", a $C_{2-6}$ alkenyl group which may be substituted with one group selected from the group consisting of "an aryl group, and a biaryl group", a $C_{2-6}$ alkynyl group which may be substituted with one aryl group, an aryl group which may be substituted with 1 to 3 groups selected from the group consisting of "a hydroxyl group, a halogen atom, a $C_{1-6}$ alkyl group, a $C_{3-8}$ cycloalkyl group, a $C_{7-11}$ aralkyl group, a $C_{1-10}$ alkoxy group, a $C_{3-8}$ cycloalkoxy group, a $C_{7-11}$ aralkyloxy group, an aryloxy group, a $C_{1-6}$ alkylthio group, an adamantyl group, an aryloxycarbonyl group, a $C_{1-11}$ acyl group, an amino group, a $C_{1-6}$ alkylamino group, and a $C_{1-11}$ acylamino group", a heterocyclic group which may be substituted with one $C_{1-6}$ alkyl group, or a biaryl group which may be substituted with one group selected from the group consisting of "a hydroxyl group, a halogen atom, and a $C_{7-11}$ aralkyloxy group".

13. The 10a-azalide compound or a salt thereof according to claim 4, wherein $R^{091}$ is:

a $C_{1-6}$ alkyl group substituted with one biaryl group, a $C_{2-6}$ alkenyl group substituted with one aryl group, a $C_{2-6}$ alkynyl group substituted with one aryl group, an aryl group which may be substituted with one group selected from the group consisting of "a halogen atom, a $C_{1-6}$ alkyl group, a $C_{1-10}$ alkoxy group, a $C_{1-6}$ alkylamino group, and a $C_{7-11}$ aralkyloxy group", or a biaryl group.

14. The 10a-azalide compound or a salt thereof according to claim 1, wherein one of $R^9$ and $R^{10}$ is a hydrogen atom, and the other is:

a group represented by the formula —$X^{091}$-$A^{091}$-$X^{092}$—$R^{091}$, $X^{091}$ is:

a group represented by the formula -$A^{094}$-O—, $A^{094}$ is a divalent $C_{1-10}$ aliphatic hydrocarbon group, $A^{091}$ is an arylene group, and $X^{092}$ is a single bond, or a group represented by the formula —$N(R^{25})$—.

15. The 10a-azalide compound or a salt thereof according to claim 1, wherein one of $R^9$ and $R^{10}$ is a hydrogen atom, and the other is:

a group represented by the formula —$X^{091}$-$A^{091}$-$X^{092}$—$R^{091}$, $X^{091}$ is:

a group represented by the formula —$CH_2$—O—, $A^{091}$ is a phenylene group, and $X^{092}$ is a single bond, or a group represented by the formula —$N(R^{25})$—.

16. The 10a-azalide compound or a salt thereof according to claim 14, wherein $R^{091}$ is:

a $C_{1-6}$ alkyl group which may be substituted with 1 to 3 groups selected from the group consisting of "a hydroxyl group, a $C_{3-8}$ cycloalkyl group, and an aryl group (the aryl group may be substituted with 1 to 3 $C_{1-6}$ alkyl groups)", a $C_{2-6}$ alkenyl group which may be substituted with 1 to 3 aryl groups, an aryl group, or a heterocyclic group which may be substituted with 1 to 3 groups selected from the group consisting of "a $C_{1-6}$ alkyl group, and a $C_{8-12}$ aralkyloxycarbonyl group".

17. The 10a-azalide compound or a salt thereof according to claim 14, wherein $R^{091}$ is:

a $C_{1-6}$ alkyl group which may be substituted with 1 to 3 groups selected from the group consisting of "a hydroxyl group, a $C_{3-8}$ cycloalkyl group, and an aryl group (the aryl group may be substituted with 1 to 3 $C_{1-6}$ alkyl groups)", a $C_{2-6}$ alkenyl group which may be substituted with 1 to 3 aryl groups, or an aryl group.

18. The 10a-azalide compound or a salt thereof according to claim 1, wherein one of $R^2$ and $R^3$ is a hydrogen atom, and the other is:

a group represented by the formula (II).

19. The 10a-azalide compound or a salt thereof according to claim 18, wherein one of $R^{32}$ and $R^{33}$ is a hydrogen atom, and the other is:

a hydroxyl group, an amino group, or, a group represented by the formula —$X^{331}$-$A^{331}$-$X^{332}$—$R^{331}$, or one of $R^{32}$ and $R^{33}$ is a hydroxyl group, and the other is:
a group represented by the formula $-X^{335}-R^{332}$, or
a group represented by the formula $-X^{335}-A^{334}-X^{336}-R^{332}$.

20. The 10a-azalide compound or a salt thereof according to claim 18, wherein one of $R^{32}$ and $R^{33}$ is a hydrogen atom, and the other is a hydroxyl group.

21. The 10a-azalide compound or a salt thereof according to claim 19, wherein $X^{331}$ is:
a group represented by the formula $-OCON(H)-$,
$A^{331}$ is:
  a divalent $C_{1-10}$ aliphatic hydrocarbon group, or
  a divalent heterocyclic group,
$X^{332}$ is:
  a single bond, or
  a group represented by the formula $-N(R^{25})-$,
$X^{335}$ is:
  a group represented by the formula $)-CH_2N(R^{20})-$,
$A^{334}$ is:
  a divalent $C_{1-10}$ aliphatic hydrocarbon group which may be substituted with a hydroxyl group, or
  a divalent heterocyclic group, and
$X^{336}$ is:
  a single bond,
  a group represented by the formula $-N(R^{25})-$, or
  a group represented by the formula $-N(R^{25})CO_2-$.

22. The 10a-azalide compound or a salt thereof according to claim 21, wherein $R^{331}$ is:
a $C_{1-6}$ alkyl group substituted with one group selected from the group consisting of "an aryl group, and a heterocyclic group (the aryl group and the heterocyclic group may be substituted with one group selected from the group A)", and
$R^{332}$ is:
a $C_{1-6}$ alkyl group which may be substituted with one group selected from the group consisting of "a hydroxyl group, an aryl group, and a heterocyclic group (the aryl group and the heterocyclic group may be substituted with one group selected from the group A)", or
an aryl group which may be substituted with one group selected from the group A.

23. A medicament containing a substance selected from the group consisting of the 10a-azalide compound or a physiologically acceptable salt thereof according to claim 1 as an active ingredient.

24. The medicament according to claim 23, which is used for therapeutic treatment of a microbial infectious disease.

25. The medicament according to claim 23, which is used for therapeutic treatment of a bacterial infectious disease.

26. A method of therapeutic treatment of a microbial infection, comprising administering an effective amount of the medicament according to claim 23 to a mammal.

27. A method of therapeutic treatment of a bacterial infection, comprising administering an effective amount of the medicament according to claim 23 to a mammal.

* * * * *

UNITED STATES PATENT AND TRADEMARK OFFICE
CERTIFICATE OF CORRECTION

PATENT NO. : 8,293,715 B2
APPLICATION NO. : 12/671813
DATED : October 23, 2012
INVENTOR(S) : T. Sugimoto et al.

It is certified that error appears in the above-identified patent and that said Letters Patent is hereby corrected as shown below:

On Title Page, Item (56) References Cited, Foreign Patent Documents (column 2, line 9) of the printed patent, "CA 1 661 904 A1 5/2006" should be -- EP 1 661 904 A1 5/2006 --.

Signed and Sealed this
Fourteenth Day of May, 2013

Teresa Stanek Rea
*Acting Director of the United States Patent and Trademark Office*